(12) United States Patent
Baltes

(10) Patent No.: US 12,054,706 B2
(45) Date of Patent: *Aug. 6, 2024

(54) METHODS FOR TARGETED INSERTION OF DNA IN GENES

(71) Applicant: BLUEALLELE CORPORATION, Oakdale, MN (US)

(72) Inventor: Nicholas J. Baltes, Oakdale, MN (US)

(73) Assignee: BLUEALLELE CORPORATION, Oakdale, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/830,011

(22) Filed: Jun. 1, 2022

(65) Prior Publication Data

US 2023/0212553 A1    Jul. 6, 2023

Related U.S. Application Data

(63) Continuation of application No. 17/590,613, filed on Feb. 1, 2022, now Pat. No. 11,365,407, which is a continuation of application No. 17/366,290, filed on Jul. 2, 2021, now Pat. No. 11,254,930, which is a continuation of application No. 16/800,444, filed on Feb. 25, 2020, now Pat. No. 11,091,756, which is a continuation of application No. 16/601,144, filed on Oct. 14, 2019, now abandoned.

(60) Provisional application No. 62/864,432, filed on Jun. 20, 2019, provisional application No. 62/830,654, filed on Apr. 8, 2019, provisional application No. 62/746,497, filed on Oct. 16, 2018.

(51) Int. Cl.
| | |
|---|---|
| C12N 15/10 | (2006.01) |
| C12N 15/86 | (2006.01) |
| C12N 15/90 | (2006.01) |

(52) U.S. Cl.
CPC .......... *C12N 15/102* (2013.01); *C12N 15/86* (2013.01); *C12N 15/907* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | | |
|---|---|---|---|
| 6,228,639 | B1 | 5/2001 | Gaitanaris |
| 6,740,503 | B1 | 5/2004 | Harrington et al. |
| 7,005,299 | B1 | 2/2006 | Smith et al. |
| 9,255,250 | B2 | 2/2016 | Gregory et al. |
| 9,677,070 | B2 | 6/2017 | Allison et al. |
| 9,765,404 | B2 | 9/2017 | Sastry-Dent et al. |
| 10,240,115 | B2 | 3/2019 | Tang |
| 11,254,930 | B2 | 2/2022 | Baltes |
| 2004/0106566 | A1 | 6/2004 | Lin et al. |
| 2005/0064474 | A1 | 3/2005 | Umov |
| 2005/0208489 | A1 | 9/2005 | Carroll |
| 2012/0046349 | A1 | 2/2012 | Bell et al. |
| 2013/0280222 | A1 | 10/2013 | Kay et al. |
| 2014/0130205 | A1 | 5/2014 | Bhyri |
| 2016/0040155 | A1 | 2/2016 | Maizels et al. |
| 2016/0102322 | A1 | 4/2016 | Ravinder et al. |
| 2016/0281111 | A1 | 9/2016 | Cotta-Ramusino et al. |
| 2017/0073664 | A1 | 3/2017 | Mccafferty et al. |
| 2018/0023075 | A1 | 1/2018 | Liang et al. |
| 2018/0110877 | A1 | 4/2018 | Wilson et al. |
| 2018/0112213 | A1 | 4/2018 | Welstead et al. |
| 2018/0119123 | A1 | 5/2018 | Gori et al. |
| 2018/0273932 | A1 | 9/2018 | Bothmer et al. |
| 2018/0296603 | A1 | 10/2018 | Gori et al. |
| 2018/0362590 | A1 | 12/2018 | Monds et al. |
| 2019/0032089 | A1 | 1/2019 | Townes et al. |
| 2019/0032092 | A1 | 1/2019 | Gong et al. |
| 2019/0032156 | A1 | 1/2019 | Gong et al. |
| 2019/0093114 | A1 | 3/2019 | Bower et al. |
| 2019/0134221 | A1 | 5/2019 | Bumcrot et al. |
| 2019/0136210 | A1 | 5/2019 | Cotta-Ramusino et al. |
| 2019/0276850 | A1 | 9/2019 | Brinkmann et al. |
| 2019/0330603 | A1 | 10/2019 | Ahlfors et al. |
| 2019/0390189 | A1 | 12/2019 | Lee et al. |
| 2020/0040362 | A1* | 2/2020 | Carlo ................. C12N 15/111 |
| 2020/0231974 | A1 | 7/2020 | Jarvis et al. |
| 2020/0270617 | A1* | 8/2020 | Finn .................... A61K 48/005 |

FOREIGN PATENT DOCUMENTS

| | | |
|---|---|---|
| BR | 102014027 448 A2 | 9/2015 |
| CA | 2906747 A1 | 9/2014 |
| EP | 2893025 B1 | 7/2015 |
| EP | 3114227 A1 | 1/2017 |
| EP | 3122880 A2 | 2/2017 |
| EP | 3344771 A1 | 7/2018 |
| EP | 3375877 A1 | 9/2018 |
| EP | 3426784 A1 | 1/2019 |

(Continued)

OTHER PUBLICATIONS

Yew. et al.Human Gene therapy, 8:575-584 (Year: 1997).*
Blueallele, LLC in connection with PCT/US2019/058857 filed Oct. 30, 2019, "The International Search Report and the Written Opinion of the International Searching Authority, or the Declaration", 19 pages, mailed Jun. 23, 2020.
Robert, Francois, "Bidirectional terminators: an underestimated aspect of gene regulation", Curr Genet, vol. 64, pp. 389-391, 2018.
Ouyang et al., "CRISPR/Cas9-Targeted Deletion of Polyglutamine in Spinocerebellar Ataxia Type 3-Derived Induced Pluripotent Stem Cells", vol. 27, No. 11, pp. 756-770, 2018.
Blueallele, LLC in connection with PCTUS2019/056083 filed Oct. 14, 2019, "The International Search Report and the Written Opinion of the International Searching Authority, or the Declaration", 21 pages, mailed Dec. 19, 2019.

(Continued)

*Primary Examiner* — Anoop K Singh
(74) *Attorney, Agent, or Firm* — Carla Mouta-Bellum; Arrigo, Lee, Guttman & Mouta-Bellum, LLP

(57) ABSTRACT

Methods and compositions for modifying the coding sequence of endogenous genes using rare-cutting endonucleases and transposases. The methods and compositions described herein can be used to modify the coding sequence of endogenous genes.

10 Claims, 8 Drawing Sheets

Specification includes a Sequence Listing.

(56) References Cited

FOREIGN PATENT DOCUMENTS

| | | | |
|---|---|---|---|
| EP | 3556858 A2 | 10/2019 | |
| EP | 3592140 A1 | 1/2020 | |
| ES | 2653212 T3 | 2/2018 | |
| ES | 2699848 T3 | 2/2019 | |
| ES | 2730378 T3 | 11/2019 | |
| JP | 2020530769 A | 10/2020 | |
| WO | 2010097437 A1 | 9/2010 | |
| WO | 2013075008 A1 | 5/2013 | |
| WO | 2013169802 A1 | 11/2013 | |
| WO | 2015017866 A1 | 2/2015 | |
| WO | 2015089351 A1 | 6/2015 | |
| WO | 2015153780 A1 | 10/2015 | |
| WO | 2015173436 A1 | 11/2015 | |
| WO | 2016073990 A2 | 5/2016 | |
| WO | 2016109840 A2 | 7/2016 | |
| WO | 2016161380 A1 | 10/2016 | |
| WO | 2016172727 A1 | 10/2016 | |
| WO | 2016182959 A8 | 11/2016 | |
| WO | 2017048995 A1 | 3/2017 | |
| WO | 2017155408 A1 | 9/2017 | |
| WO | 2018009534 A1 | 1/2018 | |
| WO | 2018009562 A1 | 1/2018 | |
| WO | WO-2018131551 A1 * | 7/2018 | ......... A61K 31/7088 |
| WO | 2018195555 A1 | 10/2018 | |
| WO | 2018197020 A1 | 11/2018 | |
| WO | 2019005851 A1 | 1/2019 | |
| WO | 2019092505 A1 | 5/2019 | |
| WO | 2019113149 A1 | 6/2019 | |
| WO | 2019118875 A1 | 6/2019 | |
| WO | 2019157326 A1 | 8/2019 | |
| WO | 2019157326 A2 | 9/2019 | |
| WO | 2019178500 | 9/2019 | |
| WO | 2019183123 A1 | 9/2019 | |
| WO | 2019210216 A2 | 10/2019 | |
| WO | 020082042 A2 | 4/2020 | |
| WO | 2020082041 A1 | 4/2020 | |
| WO | 2020082046 A2 | 4/2020 | |
| WO | 2020082047 A1 | 4/2020 | |

OTHER PUBLICATIONS

Friedel et al., "Gene targeting using a promoterless gene trap vector ("targeted trapping") is an efficient method to mutate a large fraction of genes", PNAS, vol. 102, No. 37, pp. 13188-13193, Sep. 13, 2005.
Gilles et al., "Efficient CRISPR-mediated gene targeting and transgene replacement in the beetle Tribolium castaneum", The Company of Biologists, vol. 142, pp. 2832-2839, Jun. 29, 2015.
Hahm et al., "Construction of retroviral vectors with enhanced efficiency of transgene expression", Journal of Virological Methods, vol. 121, pp. 127-136, May 27, 2004.
Hildinger et al., "Design of 5' Untranslated Sequences in Retroviral Vectors Developed for Medical Use", Journal of Virology, vol. 73, No. 5, pp. 4083-4089, May 1999.
Intellia Therapeutics, "Q3 2018 Earnings and Corporate Development", Powerpoint, 23 pages, presented Oct. 31, 2018.
Ruan et al., "Highly efficient CRISPR/Cas9-mediated transgene knockin at the H11 locus in pigs", Scientific Reports, 10 pages, Sep. 18, 2015.
Suzuki et al., "In vivo genome editing via CRISPR/Cas9 mediated homology-independent targeted integration", Nature, vol. 540, 24 pages, Dec. 1, 2016.
Uno et al., "CRISPR/Cas9-induced transgene insertion and telomere-associated truncation of a single human chromosome for chromosome engineering in CHO and A9 cells", Scientific Reports, 10 pages, Oct. 6, 2017.
Yao et al., "Homology-mediated end joining-based targeted integration using CRISPR/Cas9", Cell Research, vol. 27, pp. 801-814, Apr. 6, 2017.
Sheng et al Canadian Journal of Microbiology, 445-454 (Year: 2014).
Ryu et al Plant Molecular Biology 54: 489-502 (Year: 2004).
Senis et al Nucleic acid Res. , 45(1), e3 (Year: 2016).
Kaiser Science, 317, 580 (Year: 2007).
Frank et al N. Engl. J Med. Jul. 9;361 (2): 161-9 (Year: 2009).
Edelstein Journal Gene Med., 597-602 (Year: 2004).
High Nature, 435, 577-579 (Year: 2005).
Ramirez Nature Methods, 5(5): 374-375 (Year: 2008).
Li Nature, Jul. 14,, 475, 7355, 217-221 (Year: 2011).
Christian Genetics, 757-761 (Year: 2010).
Hauschild PNAS, 108( 29), 12013-12017 (Year: 2011).
Hsu et al Nat Biotechnology. Sep;31 (9):827-32 (Year: 2013).
Lee et al., (Drug Discovery Today: Disease Models, vol. 20, 13-20 (Year: 2016).
Kosicki et al Nature Biotechnology, 36, 765-771 (Year: 2018).
Robert et al Curr Genetics, 64(2):389-391 (Year: 2018).
Cox et al , Nature Medicine 21 (2), 121-13 (Year: 2015).
Kuscu et al Nature biotechnology, 32(7), 677 (Year: 2014).
Kleinstiver Nature, 523, 481-485 (Year: 2015).
Pluta et al. (Acta Biochimica Polonica. Nov. 23, 2009. 54(4): 531-595) (Year: 2009).
Kurosaki et al. (Journal of Human Genetics (2011) 56, 727-733). (Year: 2011).
Yew et al. (Human Gene Therapy 8:575-584 (Mar. 20, 1997)). (Year: 1997).
Great Britain Search Report, issued Feb. 8, 2023, in connection with Great Britain Application No. GB2300487.2, 1 page.
Ohmori et al. "CRISPR/Cas9-mediated genome editing via postnatal administration of AAV vector cures haemophilia B mice", Sci Rep, Jun. 23, 2017, vol. 7, No. 1, article No. 4159 (11 pages).
Finn, Jonathan Ph.D. "Supra-therapeutic levels of transgene expression achieved in vivo by CRISPR/Cas9 mediated targeted gene insertion", 26thAnnual Congress of the European Society of Cell Therapy, Oct. 18, 2018, (14 pages).

* cited by examiner

SEQUENCE LISTING

<160> NUMBER OF SEQ ID NOS: 51

<210> SEQ ID NO 1
<211> LENGTH: 3527
<212> TYPE: DNA
<213> ORGANISM: Artificial Sequence

```
<220> FEATURE:
<223> OTHER INFORMATION: Construct

<400> SEQUENCE: 1
gtgcggctgc aagtgacccc aggctgggct cggccgggag gcggggagga gagaagggga      60
taccccatcc aacagccact ctaggcaaag gtccccggat cccggctgtg accacctccc     120
atcctgcccc caagccaccg gggtgcccgg cggccggagc ggacacggat ccccaccaca     180
ccagctgcct atgctgtccc ccagcccccc ttgcccaccc gccgcccct ccccgccgcc      240 cgcagctgct tgctcctcgg ttgtggatca tatttgagtt ctgggccgtg ccgcccgacc     300
tttcactttc ctttaacccg gcttctgttt ttgtttcaat tatgatttct gtcctctgga     360
cgcctgtgag taattttga acttctgct attttttaacc ccgaaactta caaaactcca     420
tttctcattt ctcttttcac tttgttgtgt tggttttcga ctcctcccct ccctgtctca     480
ctccccctcc tccctccct cctccctgtg gctgttgctt ttttccattc aatgtcctgt      540
gtcccccctc tcctcctcct cctcctcctc cccctccccc tctccctct cctcccggcc      600 cctctccctt cgctcccctc tcttcctccc aatcccgtgt ctcctttgat tttgttgtat     660
cttttttttt gatttccttt gtttcaattt tcgtgtaggg cagtagttcc gtaagtggaa     720
gcccagcccc ctcaacatct ggtaccagca ctccgcggcg gggccgccgc cagctccccc     780 agacccctc caccccccgg ccacacgtgt cctattcccc tgtgatccgt aaggccggcg      840
gctcggggcc cccgcagcag cagcagcagc agcagcagca gcagcagcag caggcggtgg     900
ccaggccggg ccgggcggcc accagcggcc ctcggaggta cccaggcccc acggccgagc     960
ctctggccgg agatcggccg cccacggggg gccacagcag cggccgctcg cccaggatgg    1020
agaggcgggt cccaggcccg gccgggagcg agtccccag ggcctgtcga cacgcgggg     1080 cccggtggcc ggcatctggc ccgcacgtgt ccgaggggcc cccgggtccc cggcaccatg    1140
gctactaccg gggctccgac tacgacgagg ccgatggccc gggcagcggg gcggcgagg     1200 aggccatggc cggggcctac gacgcgccac ccccgtacg acacgcgtcc tcgggcgcca    1260
ccgggcgctc gcccaggact ccccgggcct cgggcccggc ctgcgcctcg ccttctcggc    1320
acggccggcg actccccaac ggctactacc cggcgcacgg actggccagg ccccgcgggc    1380
cgggctccag gaagggcctg cacgaaccct acagcgagag tgacgatgat tggtgctaaa    1440
acttgtttat tgcagcttat aatggttaca aataaagcaa tagcatcaca aatttcacaa    1500
ataaagcatt tttttcactg cattctagtt gtggtttgtc caaactcatc aatgtatctt    1560
atcatgtctg gatctcccca gcatgcctgc tattctcttc caatcctcc ccttgctgt      1620 cctgccccac cccacccccc agaatagaat gacacctact cagacaatgc gatgcaattt    1680
cctcatttta ttaggaaagg acagtgggag tggcaccttc cagggtcaag gaaggcacgg    1740
gggaggggca acaacagat ggctggcaac tagaaggcac agtcagcacc agtcgtcgtc     1800
ggattcgctg tagggttcat ggagacccct ccgagcccca ggtcctcttg gccgggccaa    1860
gccgtgtgca gggtaatatc cattggggag cctccggcca tgccgagaag gtgaagcgca    1920
cgctggtcct gacgcccggg gggtgcgagg agacctccct gtcgcccggg aagacgcatg    1980
cctaacggga ggcggagcat cataagcacc agccatcgct tcctcgccac caccactgcc    2040
gggcccgtca gcttcgtcat agtcagaacc ccgataatat ccgtgatggc gaggccctgg    2100
aggtccttcg ctaacgtgtg gcccagaagc aggccaccgc gcacctccat ggcgacatgc    2160
tctaggactc tcgcttcttg caggtccagg aacccgccgc tccattcgcg ggcttcgccc    2220
```

```
actactgtgt ccacctgtcg gagggcggtc tccggcaagg ggttcagcgg ttgggcctgg    2280
atagcgccgc ggaccggagg tagcagcccg accgggtcgt gctaccgctt gctgttgctg    2340
ttgttgctgt tgctgctgtt gttgttgggg tggcccgcta cctcccgctt ttctaataac    2400
tggtgaataa ctcacatgtg ggcgcggagt ggatggtgtc tgagggagtt gccttctccc    2460 tcggcgggt gtagacgtac cagatgttga aggcgccggg ctcccgctta ctgaactact    2520
gtaaatgaat gagaaaaccg gtttagaaag tgcacagctg tcagggaagt caacacttca    2580
gtgagcatgt gaccatgtgg agtcagcttc ctgtttcgtg ctgcaatcgc ccgggcgagg    2640
tggcgcccgc ccggcccccc acgcaccca cgcacacacc ccacccgagg agccgcgcag    2700
aggccgcggg ggcccagcac agagggcccg ggagagggcc agccgggaga ccccagactc    2760
tggagaggcc agggctgggc cacaagggtg tcccgcagag accctcggcc aaaagagacc    2820
ctcctgggca gccacggcgc ccccaaccca gccccgatcc ccccacccac gacagggggct    2880 ctcgggtggg aggcagggag cagacaaacc acacagccaa gggatttgaa ttaactcagc    2940 cattttttgga gaactttggg gaacatgaaa aaaaaaaaa aaaaaaaaaa aaaaaacatt    3000
tttaaaagaa aaaacgggga gaaaaaaata gcttctattg atgagtttta tcatctcaat    3060
tgaatctttc ctttccctga tgaagacagc tggtggccga gtgcggcaaa gagccagaa    3120 ggaaccagaa tcccagtgcc ctacaccccac caccagacac actcacaccc acacacgttc    3180
tcagacacac acaagagtgc ttgccggtta taccaaaccc tactattact gcctgcagaa    3240
atcaatttaa aaaataata ataacaataa acaattttaa aaaggacaaa aaaattaatg    3300
attgagaaaa gaggcatttt tttctgacat ttggtcctgc ttgaaacaac aaaagaagaa    3360
gaaaaaccca ccatcaccac cgattccttt gcttcttttt tccttttttc ctaccttgtt    3420
tgaaaaccgt gggcttggga ctgtgaatta ttgcatgaca ttcaaaaaga aaaaaaaat    3480 aaaaaaagt tgaatcaaat ttctgtcctc tggacgcctg tgagtaa                   3527
```

<210> SEQ ID NO 2
<211> LENGTH: 703
<212> TYPE: DNA
<213> ORGANISM: Artificial Sequence
<220> FEATURE:
<223> OTHER INFORMATION: Construct

<400> SEQUENCE: 2

```
gtgcggctgc aagtgacccc aggctgggct cggccgggag gcggggagga gagaagggga     60
taccccatcc aacagccact ctaggcaaag gtccccggat cccggctgtg accacctccc    120
atcctgcccc caagccaccg gggtgcccgg cggccggagc ggacacggat ccccaccaca    180
ccagctgcct atgctgtccc cccagccccc ttgcccaccc gccgcccct cccgccgcc     240 cgcagctgct tgctcctcgg ttgtggatca tatttgagtt ctgggccgtg ccgcccgacc    300
tttcactttc ctttaacccg gcttctgtttt ttgtttcaat tatgatttct gtcctctgga    360
cgcctgtgag taattttttga aacttctgct attttttaacc ccgaaactta caaaactcca    420
tttctcattt ctcttttcac tttgttgtgt tggttttcga ctcctcccct cctgtctca     480 ctccccctcc tccctccct cctccctgtg gctgttgctt ttttccattc aatgtcctgt    540 gtccccctc tcctcctcct cctccctctc ccctcccc tcctccctct cctccggcc      600 cctctccctt cgctcccctc tcttcctccc aatcccgtgt ctccttgat tttgttgtat    660 cttttttttt gatttccttt gtttcaattt tcgtgtaggg cag                      703
```

<210> SEQ ID NO 3
<211> LENGTH: 736
<212> TYPE: DNA
<213> ORGANISM: Artificial Sequence
<220> FEATURE:
<223> OTHER INFORMATION: Construct

<400> SEQUENCE: 3

```
tagttccgta agtggaagcc agccccctc aacatctggt accagcactc cgcggcgggg      60
ccgccgccag ctcccccaga cccctccac ccccggcca cacgtgtcct attccctgt       120
gatccgtaag gccggcggct cggggccccc gcagcagcag cagcagcagc agcagcagca    180
gcagcagcag gcggtggcca ggccgggccg ggcggccacc agcggccctc ggaggtaccc    240
aggccccacg gccgagcctc tggccggaga tcggccgccc acggggggcc acagcagcgg    300
ccgctcgccc aggatggaga ggcgggtccc aggcccggcc cggagcgagt ccccagggc     360
ctgtcgacac ggcggggccc ggtggccggc atctggcccg cacgtgtccg aggggccccc    420
gggtccccgg caccatggct actaccgggg ctccgactac gacgaggccg atggcccggg    480
cagcggggc ggcgaggagg ccatggccgg ggcctacgac gcgccacccc ccgtacgaca     540
cgcgtcctcg ggcgccaccg ggcgctcgcc caggactccc cgggcctcgg gcccggcctg    600
cgcctcgcct tctcggcacg gccggcgact ccccaacggc tactaccccgg cgcacggact   660
ggccaggccc cgcggggccgg gctccaggaa gggcctgcac gaaccctaca gcgagagtga   720
cgatgattgg tgctaa                                                   736
```

<210> SEQ ID NO 4
<211> LENGTH: 135
<212> TYPE: DNA
<213> ORGANISM: Artificial Sequence
<220> FEATURE:
<223> OTHER INFORMATION: Construct

<400> SEQUENCE: 4

```
aacttgttta ttgcagctta taatggttac aaataaagca atagcatcac aaatttcaca    60
aataaagcat ttttttcact gcattctagt tgtggtttgt ccaaactcat caatgtatct   120
tatcatgtct ggatc                                                   135
```

<210> SEQ ID NO 5
<211> LENGTH: 208
<212> TYPE: DNA
<213> ORGANISM: Artificial Sequence
<220> FEATURE:
<223> OTHER INFORMATION: Construct

<400> SEQUENCE: 5

```
tccccagcat gcctgctatt ctcttcccaa tcctccccct tgctgtcctg ccccacccca    60
cccccagaa tagaatgaca cctactcaga caatgcgatg caatttcctc attttattag   120
gaaaggacag tgggagtggc accttccagg gtcaaggaag gcacggggga ggggcaaaca   180
acagatggct ggcaactaga aggcacag                                      208
```

<210> SEQ ID NO 6
<211> LENGTH: 736
<212> TYPE: DNA
<213> ORGANISM: Artificial Sequence
<220> FEATURE:
<223> OTHER INFORMATION: Construct

<400> SEQUENCE: 6

```
tcagcaccag tcgtcgtcgg attcgctgta gggttcatgg agacccttcc gagacccagg      60
tcctcttggc cgggccaagc cgtgtgcagg gtaatatcca ttggggagcc tccggccatg     120
ccgagaaggt gaagcgcacg ctggtcctga cgcccggggg gtgcgaggag acctccctgt     180
cgccccggaa gacgcatgcc taacgggagg cggagcatca taagcaccag ccatcgcttc     240
ctcgccacca ccactgccgg gcccgtcagc ttcgtcatag tcagaacccc gataatatcc     300
gtgatggcga ggccctggag gtccttcgct aacgtgtggc ccagaagcag gccaccgcgc     360
acctccatgg cgacatgctc taggactctc gcttcttgca ggtccaggaa cccgccgctc     420
cattcgcggg cttcgcccac tactgtgtcc acctgtcgga gggcggtctc cggcaagggg     480
ttcagcggtt gggcctggat agcgccgcgg accggaggta gcagcccgac cgggtcgtgc     540
taccgcttgc tgttgctgtt gttgctgttg ctgctgttgt tgttggggtg gcccgctacc     600
tcccgctttt ctaataactg gtgaataact cacatgtggg cgcggagtgg atggtgtctg     660
agggagttgc cttctccctc ggcggggtgt agacgtacca gatgttgaag gcgccgggct     720
cccgcttact gaacta                                                     736

<210> SEQ ID NO 7
<211> LENGTH: 110
<212> TYPE: DNA
<213> ORGANISM: Artificial Sequence
<220> FEATURE:
<223> OTHER INFORMATION: Construct

<400> SEQUENCE: 7
ctgtaaatga atgagaaaac cggtttagaa agtgcacagc tgtcagggaa gtcaacactt      60
cagtgagcat gtgaccatgt ggagtcagct tcctgtttcg tgctgcaatc                110

<210> SEQ ID NO 8
<211> LENGTH: 446
<212> TYPE: DNA
<213> ORGANISM: Artificial Sequence
<220> FEATURE:
<223> OTHER INFORMATION: Construct

<400> SEQUENCE: 8
gcccgggcga ggtggcgccc gcccggcccc ccacgcaccc cacgcacaca ccccacccga      60
ggagccgcgc agaggccgcg ggggcccagc acagagggcc cggagagggg ccagccggga     120
gaccccagac tctggagagg ccagggctgg gccacaaggg tgtcccgcag agaccctcgg     180
ccaaaagaga ccctcctggg cagccacggc gccccccaac cagccccgat ccccccaccc     240
acgacagggg ctctcgggtg ggaggcaggg agcagacaaa ccacacagcc aagggatttg     300
aattaactca gccattttg gagaactttg gggaacatga aaaaaaaaaa aaaaaaaaa      360 aaaaaaaca tttttaaaag aaaaacggg gagaaaaaa tagcttctat tgatgagttt      420
tatcatctca attgaatctt tcctttt                                         446

<210> SEQ ID NO 9
<211> LENGTH: 24
<212> TYPE: DNA
<213> ORGANISM: Artificial Sequence
<220> FEATURE:
<223> OTHER INFORMATION: Target site

<400> SEQUENCE: 9
tttctgtcct ctggacgcct gtga                                             24
```

<210> SEQ ID NO 10
<211> LENGTH: 2288
<212> TYPE: DNA
<213> ORGANISM: Artificial Sequence
<220> FEATURE:
<223> OTHER INFORMATION: Construct

<400> SEQUENCE: 10

| | | | | | |
|---|---|---|---|---|---|
| atttcattta | tcaggtgttc | agtgaatgct | tactatgtaa | cagcacagtt | atcagcactg | 60 |
| gggaaataga | tgagtaagat | aagatttgca | ctttcattag | cttacatgcc | ataaagaggg | 120 |
| aaataaagag | aacaccagat | gatgataagt | ttatgctgag | aattaaaatg | aagtgatgaa | 180 |
| ataatgggaa | tgtcaggtgg | ctactttttgg | tgggatggtc | aggaaaggca | tctctgggga | 240 |
| gataaatttt | aagctcagac | ctgagtgaaa | agaatgagcc | agccatggaa | acattatgtt | 300 |
| aactcacatg | gtagtttgaa | atgctttatc | tgatcaaagg | tacttatttt | tggtgacttt | 360 |
| caacaatatt | aagggtctat | aaaccaacac | tcatttgcat | aagaataact | accagtgaat | 420 |
| cttttttgtat | gataggtttt | ttgtttgttg | ttttttttgag | acagagtctc | gctctgtcgc | 480 |
| ccaggctgga | gtgcagtggc | gcgatcttgg | ctcactgcaa | cctctacctc | cccggttcaa | 540 |
| gtgattctcc | tgcctcagcc | tcccaaagta | gctgggatta | caggtgcctg | ccaccacgcc | 600 |
| tggctaattt | ttgtattttt | agtagagatg | gggtttcacc | gtgttgtcca | ggctcgtgtc | 660 |
| aaacttctga | cctcaagcca | tccacccgcc | tcggcctccc | aaagtgctgg | gattacaggt | 720 |
| gtgagccacc | actcctggcc | atgataggtt | attttgtgat | gaaaatacct | acctcttaat | 780 |
| ttgtctgata | aatttaaatt | ttatgtctag | atttcctaag | atcagcactt | ccatatttta | 840 |
| aagtaatctg | tatcagacta | actgctcttg | cattctttta | ataccagtga | ctactttgat | 900 |
| tcgtgaaaca | atgtatttc | cttatgaata | gttttctca | tggtgtattt | attcttttaa | 960 |
| gttttgtttt | ttaaatatac | ttcacttttg | aatgtttcag | acagcagcaa | aagcagcaac | 1020 |
| agcagcagca | gcagcagcag | caggggggacc | tatcaggaca | gagttcacat | ccatgtgaaa | 1080 |
| ggccagccac | cagttcagga | gcacttggga | gtgatctagg | tgatgctatg | agtgaagaag | 1140 |
| acatgcttca | gcagctgtg | accatgtctt | tagaaactgt | cagaaatgat | ttgaaaacag | 1200 |
| aaggaaaaaa | ataaaacttg | tttattgcag | cttataatgg | ttacaaataa | agcaatagca | 1260 |
| tcacaaattt | cacaaataaa | gcatttttt | cactgcattc | tagttgtggt | ttgtccaaac | 1320 |
| tcatcaatgt | atcttatcat | gtctggatct | ccccagcatg | cctgctattc | tcttcccaat | 1380 |
| cctcccccctt | gctgtcctgc | cccaccccac | ccccagaat | agaatgacac | ctactcagac | 1440 |
| aatgcgatgc | aatttcctca | ttttattagg | aaaggacagt | gggagtggca | ccttccaggg | 1500 |
| tcaaggaagg | cacggggggag | gggcaaacaa | cagatggctg | gcaactagaa | ggcacagcta | 1560 |
| cttcttgccc | tcggtcttca | ggtcgttgcg | cacggtctcc | aggctcatgg | tcacggcggc | 1620 |
| ctgcagcatg | tcctcctcgc | tcatggcgtc | gcccaggtcg | ctgcccaggg | cgccgctgct | 1680 |
| ggtggcgggg | cgctcgcagg | ggtggctgct | ctggccgctc | aggtcgccct | gctgctgctg | 1740 |
| ctgctgctgc | tgctgctgct | tctgctgctg | tctgtaaatg | aatgagaaaa | ccggtttaga | 1800 |
| aagtgcacag | ctgtcaggga | agtcaacact | tcagtgagca | tgtgaccatg | tggagtcagc | 1860 |
| ttcctgtttc | gtgctgcaat | cgtaaggcct | gctcaccatt | catcatgttc | gctaccttca | 1920 |
| cactttatct | gacatacgag | ctccatgtga | ttttttgcttt | acattattct | tcattccctc | 1980 |
| tttaatcata | ttaagaatct | taagtaaatt | tgtaatctac | taaatttccc | tggattaagg | 2040 |
| agcagttacc | aaaagaaaaa | aaaaaaaaaa | agctagatgt | ggtggctcac | atctgtaatc | 2100 |

```
ccagcactttgggaaaccaaggcaggagaggattgctagaacatttaatgaatactttaa    2160 cataataatttaaacttcacagtaatttgtacagtctccaaaaattccttagacatcatg    2220 gatattttctttttttgagatggagtcttgctctgtcactttgagacagagtctcgctc    2280 tgtcgccc                                                         2288
```

<210> SEQ ID NO 11
<211> LENGTH: 24
<212> TYPE: DNA
<213> ORGANISM: Artificial Sequence
<220> FEATURE:
<223> OTHER INFORMATION: Target site

<400> SEQUENCE: 11

```
tttgagacag agtctcgctc tgtc                                         24
```

<210> SEQ ID NO 12
<211> LENGTH: 60
<212> TYPE: DNA
<213> ORGANISM: Artificial Sequence
<220> FEATURE:
<223> OTHER INFORMATION: gRNA
<220> FEATURE:
<221> NAME/KEY: misc_feature
<222> LOCATION: (9)..(40)
<223> OTHER INFORMATION: n is a, c, g, or t

<400> SEQUENCE: 12

```
ctgataacnn nnnnnnnnn nnnnnnnnnn nnnnnnnnnn gtgaactgcc gagtaggtag    60
```

<210> SEQ ID NO 13
<211> LENGTH: 47
<212> TYPE: DNA
<213> ORGANISM: Vibrio cholerae

<400> SEQUENCE: 13

```
aattatcaat ttatgggtgt aattatcatt ttatggttgt atcaaca                47
```

<210> SEQ ID NO 14
<211> LENGTH: 258
<212> TYPE: DNA
<213> ORGANISM: Artificial Sequence
<220> FEATURE:
<223> OTHER INFORMATION: gRNA
<220> FEATURE:
<221> NAME/KEY: misc_feature
<222> LOCATION: (236)..(258)
<223> OTHER INFORMATION: n is a, c, g, or t

<400> SEQUENCE: 14

```
tattaatagc gccgcaattc atgctgcttg cagcctctga attttgttaa atgagggtta    60
gtttgactgt ataaatacag tcttgctttc tgaccctggt agctgctcac cctgatgctg   120
ctgtcaatag acaggatagg tgcgctccca gcaataaggg cgcggatgta ctgctgtagt   180
ggctactgaa tcaccccga tcaagggga accctccaaa aggtgggttg aaagtnnnnn    240
nnnnnnnnnn nnnnnnnn                                                258
```

<210> SEQ ID NO 15
<211> LENGTH: 20
<212> TYPE: DNA
<213> ORGANISM: Artificial Sequence
<220> FEATURE:
<223> OTHER INFORMATION: Target site

<400> SEQUENCE: 15

```
ccgcccgacc tttcactttc                                               20
```

<210> SEQ ID NO 16
<211> LENGTH: 20
<212> TYPE: DNA
<213> ORGANISM: Artificial Sequence
<220> FEATURE:
<223> OTHER INFORMATION: Target site

<400> SEQUENCE: 16

```
cccggatccc ggctgtgacc                                               20
```

<210> SEQ ID NO 17
<211> LENGTH: 2391
<212> TYPE: DNA
<213> ORGANISM: Artificial Sequence
<220> FEATURE:
<223> OTHER INFORMATION: Construct

<400> SEQUENCE: 17

```
atttcattta tcaggtgttc agtgaatgct tactatgtaa cagcacagtt atcagcactg    60
gggaaataga tgagtaagat aagatttgca ctttcattag cttacatgcc ataaagaggg   120
aaataaagag aacaccagat gatgataagt ttatgctgag aattaaaatg aagtgatgaa   180
ataatgggaa tgtcaggtgg ctacttttgg tgggatggtc aggaaaggca tctctgggga   240
gataaatttt aagctcagac ctgagtgaaa agaatgagcc agccatggaa acattatgtt   300
aactcacatg gtagtttgaa atgctttatc tgatcaaagg tacttatttt tggtgacttt   360
caacaatatt aagggtctat aaaccaacac tcatttgcat aagaataact accagtgaat   420
cttttttgtat gataggtttt ttgtttgttg tttttttgag acagagtctc gctctgtcgc   480
ccaggctgga gtgcagtggc gcgatcttgg ctcactgcaa cctctacctc cccggttcaa   540
gtgattctcc tgcctcagcc tcccaaagta gctgggatta caggtgcctg ccaccacgcc   600
tggctaattt ttgtattttt agtagagatg gggtttcacc gtgttgtcca ggctcgtgtc   660
aaacttctga cctcaagcca tccacccgcc tcggcctccc aaagtgctgg gattacaggt   720
gtgagccacc actcctggcc atgataggtt attttgtgat gaaaatacct acctcttaat   780
ttgtctgata aatttaaatt ttatgtctag atttcctaag atcagcactt ccatatttta   840
aagtaatctg tatcagacta actgctcttg cattctttta ataccagtga ctactttgat   900
tcgtgaaaca atgtatttc cttatgaata gttttctca tggtgtattt attctttaa   960
gttttgtttt ttaaatatac ttcacttttg aatgtttcag acagcagcaa aagcagcaac  1020
agcagcagca gcagcagcag caggggggacc tatcaggaca gagttcacat ccatgtgaaa  1080
ggccagccac cagttcagga gcacttggga gtgatctagg tgatgctatg agtgaagaag  1140
acatgcttca ggcagctgtg accatgtctt tagaaactgt cagaaatgat ttgaaaacag  1200
aaggaaaaaa ataaaacttg tttattgcag cttataatgg ttacaaataa agcaatagca  1260
tcacaaattt cacaaataaa gcatttttt cactgcattc tagttgtggt ttgtccaaac  1320
tcatcaatgt atcttatcat gtctggatct ccccagcatg cctgctattc tcttcccaat  1380
cctccccctt gctgtcctgc cccacccac ccccagaat agaatgacac ctactcagac  1440
aatgcgatgc aatttcctca ttttattagg aaaggacagt gggagtggca cttccaggg  1500
tcaaggaagg cacggggggag gggcaaacaa cagatggctg gcaactagaa ggcacagcta  1560
cttcttgccc tcggtcttca ggtcgttgcg cacggtctcc aggctcatgg tcacggcggc  1620
```

```
ctgcagcatg tcctcctcgc tcatggcgtc gcccaggtcg ctgcccaggg cgccgctgct      1680
ggtggcgggg cgctcgcagg ggtggctgct ctggccgctc aggtcgccct gctgctgctg      1740
ctgctgctgc tgctgctgct tctgctgctg tctgtaaatg aatgagaaaa ccggtttaga      1800
aagtgcacag ctgtcaggga agtcaacact tcagtgagca tgtgaccatg tggagtcagc      1860
ttcctgtttc gtgctgcaat cgtaaggcct gctcaccatt catcatgttc gctaccttca      1920
cactttatct gacatacgag ctccatgtga ttttgcttt acattattct tcattccctc       1980
tttaatcata ttaagaatct taagtaaatt tgtaatctac taaatttccc tggattaagg      2040
agcagttacc aaaagaaaaa aaaaaaaaaa agctagatgt ggtggctcac atctgtaatc      2100
ccagcacttt gggaaaccaa ggcaggagag gattgctaga acatttaatg aatactttaa      2160
cataataatt taaacttcac agtaatttgt acagtctcca aaaattcctt agacatcatg      2220
gatatttttc ttttttttgag atggagtctt gctcttttaa gctcagacct gagtgaaaag      2280
aatttgagac agagtctcgc tctgtcgcct ttcctaagat cagcacttcc atatttggtg      2340
actttcaaca atattaaggg tctataaacc aacactcatt tgcataagaa t               2391
```

<210> SEQ ID NO 18
<211> LENGTH: 20
<212> TYPE: DNA
<213> ORGANISM: Artificial Sequence
<220> FEATURE:
<223> OTHER INFORMATION: Target site

<400> SEQUENCE: 18

```
aatatggaag tgctgatctt                                                   20
```

<210> SEQ ID NO 19
<211> LENGTH: 1205
<212> TYPE: DNA
<213> ORGANISM: Artificial Sequence
<220> FEATURE:
<223> OTHER INFORMATION: Construct

<400> SEQUENCE: 19

```
tttaagctca gacctgagtg aaaagaattt gagacagagt ctcgctctgt cgcctttcct        60
aagatcagca cttccatatt ttaaagtaat ctgtatcaga ctaactgctc ttgcattctt       120
ttaataccag tgactacttt gattcgtgaa acaatgtatt ttccttatga atagttttttc      180 tcatggtgta tttattcttt taagttttgt ttttaaata tacttcactt ttgaatgttt       240
cagacagcag caaaagcagc aacagcagca gcagcagcag cagcagggg acctatcagg       300 acagagttca catccatgtg aaaggccagc caccagttca ggagcacttg ggagtgatct       360
aggtgatgct atgagtgaag aagacatgct tcaggcagct gtgaccatgt ctttagaaac       420
tgtcagaaat gatttgaaaa cagaaggaaa aaaataaaac ttgtttattg cagcttataa       480
tggttacaaa taaagcaata gcatcacaaa tttcacaaat aaagcatttt ttcactgca       540 ttctagttgt ggtttgtcca aactcatcaa tgtatcttat catgtctgga tctccccagc       600
atgcctgcta ttctcttccc aatcctcccc cttgctgtcc tgccccaccc cacccccag       660 aatagaatga cacctactca gacaatgcga tgcaatttcc tcattttatt aggaaaggac       720
agtgggagtg gcaccttcca gggtcaagga aggcacgggg gaggggcaaa caacagatgg       780
ctggcaacta gaaggcacag ctacttcttg ccctcggtct tcaggtcgtt gcgcacggtc       840
tccaggctca tggtcacggc ggcctgcagc atgtcctcct cgctcatggc gtcgcccagg       900
tcgctgccca gggcgccgct gctggtggcg gggcgctcgc aggggtggct gctctggccg       960
```

```
ctcaggtcgc cctgctgctg ctgctgctgc tgctgctgct gcttctgctg ctgtctgtaa    1020
atgaatgaga aaaccggttt agaaagtgca cagctgtcag ggaagtcaac acttcagtga    1080
gcatgtgacc atgtggagtc agcttcctgt ttcgtgctgc aatctttaag ctcagacctg    1140
agtgaaaaga atttgagaca gagtctcgct ctgtcgcctt tcctaagatc agcacttcca    1200
tattt                                                                 1205
```

<210> SEQ ID NO 20
<211> LENGTH: 1723
<212> TYPE: DNA
<213> ORGANISM: Artificial Sequence
<220> FEATURE:
<223> OTHER INFORMATION: Construct

<400> SEQUENCE: 20

```
atttcattta tcaggtgttc agtgaatgct tactatgtaa cagcacagtt atcagcactg      60
gggaaataga tgagtaagat aagatttgca ctttcattag cttacatgcc ataaagaggg     120
aaataaagag aacaccagat gatgataagt ttatgctgag aattaaaatg aagtgatgaa     180
ataatgggaa tgtcaggtgg ctactttttgg tgggatggtc aggaaaggca tctctgggga    240
gataaatttt aagctcagac ctgagtgaaa agaatgagcc agccatggaa acattatgtt     300
aactcacatg gtagtttgaa atgctttatc tgatcaaagg tacttatttt tggtgacttt     360
caacaatatt aagggtctat aaaccaacac tcatttgcat aagaataact accagtgaat     420 cttttttgtat gataggtttt ttgtttgttg tttttttgag acagagtctc gctctgtcgc    480
ccaggctgga gtgcagtggc gcgatcttgg ctcactgcaa cctctacctc cccggttcaa     540
gtgattctcc tgcctcagcc tcccaaagta gctgggatta caggtgcctg ccaccacgcc     600
tggctaattt ttgtattttt agtagagatg gggtttcacc gtgttgtcca ggctcgtgtc     660
aaacttctga cctcaagcca tccacccgcc tcggcctccc aaagtgctgg gattacaggt     720
gtgagccacc actcctggcc atgataggtt attttgtgat gaaaatacct acctcttaat     780
ttgtctgata aatttaaatt ttatgtctag aaatcctaag atcagcactt ccatattttta    840 aagtaatctg tatcagacta actgctcttg cattctttta ataccagtga ctactttgat    900
tcgtgaaaca atgtattttc cttatgaata gttttctca tggtgtattt attcttttaa      960 gttttgttt ttaaatatac ttcacttttg aatgtttcag acagcagcaa aagcagcaac     1020
agcagcagca gcagcagcag caggggggacc tatcaggaca gagttcacat ccatgtgaaa    1080
ggccagccac cagttcagga gcacttggga gtgatctagg tgatgctatg agtgaagaag    1140
acatgcttca ggcagctgtg accatgtctt tagaaactgt cagaaatgat ttgaaaacag    1200
aaggaaaaaa ataaaacttg tttattgcag cttataatgg ttacaaataa agcaatagca    1260
tcacaaattt cacaaataaa gcattttttt cactgcattc tagttgtggt ttgtccaaac    1320
tcatcaatgt atcttatcat gtctggatcg taaggcctgc tcaccattca tcatgttcgc    1380
taccttcaca ctttatctga catacgagct ccatgtgatt tttgctttac attattcttc    1440
attccctctt taatcatatt aagaatctta agtaaatttg taatctacta aatttccctg    1500
gattaaggag cagttaccaa aagaaaaaaa aaaaaaaag ctagatgtgg tggctcacat     1560
ctgtaatccc agcactttgg gaaaccaagg caggagagga ttgctagaac atttaatgaa    1620
tactttaaca taataattta aacttcacag taatttgtac agtctccaaa aattccttag    1680
acatcatgga tatttttctt ttttttgagat ggagtcttgc tct                     1723
```

```
<210> SEQ ID NO 21
<211> LENGTH: 19
<212> TYPE: DNA
<213> ORGANISM: Artificial Sequence
<220> FEATURE:
<223> OTHER INFORMATION: Primer

<400> SEQUENCE: 21
caaaggtgcc cttgaggtt                                                19

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
aggagaagtc tgccgttact                                               20

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
ggacaaacca caactagaat gc                                            22

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
taggaaagga cagtgggagt                                               20

<210> SEQ ID NO 25
<211> LENGTH: 24
<212> TYPE: DNA
<213> ORGANISM: Artificial Sequence
<220> FEATURE:
<223> OTHER INFORMATION: Primer

<400> SEQUENCE: 25
ccattatgtc tcagttgttc agtg                                          24

<210> SEQ ID NO 26
<211> LENGTH: 19
<212> TYPE: DNA
<213> ORGANISM: Artificial Sequence
<220> FEATURE:
<223> OTHER INFORMATION: Primer

<400> SEQUENCE: 26
ccagaccatc tcagacacc                                                19

<210> SEQ ID NO 27
<211> LENGTH: 18
<212> TYPE: DNA
<213> ORGANISM: Artificial Sequence
<220> FEATURE:
<223> OTHER INFORMATION: Primer
```

-continued

<400> SEQUENCE: 27
ggctgggctt ccacttac                                                     18

<210> SEQ ID NO 28
<211> LENGTH: 22
<212> TYPE: DNA
<213> ORGANISM: Artificial Sequence
<220> FEATURE:
<223> OTHER INFORMATION: Primer

<400> SEQUENCE: 28
gtggtttgtc caaactcatc aa                                                22

<210> SEQ ID NO 29
<211> LENGTH: 22
<212> TYPE: DNA
<213> ORGANISM: Artificial Sequence
<220> FEATURE:
<223> OTHER INFORMATION: Primer

<400> SEQUENCE: 29
agtaactctg cacttcccat tg                                                22

<210> SEQ ID NO 30
<211> LENGTH: 639
<212> TYPE: PRT
<213> ORGANISM: Scytonema hoffmanni

<400> SEQUENCE: 30

Met Ser Gln Ile Thr Ile Gln Ala Arg Leu Ile Ser Phe Glu Ser Asn
1               5                   10                  15

Arg Gln Gln Leu Trp Lys Leu Met Ala Asp Leu Asn Thr Pro Leu Ile
            20                  25                  30

Asn Glu Leu Leu Cys Gln Leu Gly Gln His Pro Asp Phe Glu Lys Trp
        35                  40                  45

Gln Gln Lys Gly Lys Leu Pro Ser Thr Val Val Ser Gln Leu Cys Gln
    50                  55                  60

Pro Leu Lys Thr Asp Pro Arg Phe Ala Gly Gln Pro Ser Arg Leu Tyr
65                  70                  75                  80

Met Ser Ala Ile His Ile Val Asp Tyr Ile Tyr Lys Ser Trp Leu Ala
                85                  90                  95

Ile Gln Lys Arg Leu Gln Gln Gln Leu Asp Gly Lys Thr Arg Trp Leu
            100                 105                 110

Glu Met Leu Asn Ser Asp Ala Glu Leu Val Glu Leu Ser Gly Asp Thr
        115                 120                 125

Leu Glu Ala Ile Arg Val Lys Ala Ala Glu Ile Leu Ala Ile Ala Met
    130                 135                 140

Pro Ala Ser Glu Ser Asp Ser Ala Ser Pro Lys Gly Lys Gly Lys
145                 150                 155                 160

Lys Glu Lys Lys Pro Ser Ser Ser Pro Lys Arg Ser Leu Ser Lys
            165                 170                 175

Thr Leu Phe Asp Ala Tyr Gln Glu Thr Glu Asp Ile Lys Ser Arg Ser
        180                 185                 190

Ala Ile Ser Tyr Leu Leu Lys Asn Gly Cys Lys Leu Thr Asp Lys Glu
    195                 200                 205

Glu Asp Ser Glu Lys Phe Ala Lys Arg Arg Gln Val Glu Ile Gln
    210                 215                 220

-continued

```
Ile Gln Arg Leu Thr Glu Lys Leu Ile Ser Arg Met Pro Lys Gly Arg
225                 230                 235                 240

Asp Leu Thr Asn Ala Lys Trp Leu Glu Thr Leu Leu Thr Ala Thr Thr
            245                 250                 255

Thr Val Ala Glu Asp Asn Ala Gln Ala Lys Arg Trp Gln Asp Ile Leu
        260                 265                 270

Leu Thr Arg Ser Ser Ser Leu Pro Phe Pro Leu Val Phe Glu Thr Asn
    275                 280                 285

Glu Asp Met Val Trp Ser Lys Asn Gln Lys Gly Arg Leu Cys Val His
290                 295                 300

Phe Asn Gly Leu Ser Asp Leu Ile Phe Glu Val Tyr Cys Gly Asn Arg
305                 310                 315                 320

Gln Leu His Trp Phe Gln Arg Phe Leu Glu Asp Gln Gln Thr Lys Arg
            325                 330                 335

Lys Ser Lys Asn Gln His Ser Ser Gly Leu Phe Thr Leu Arg Asn Gly
        340                 345                 350

His Leu Val Trp Leu Glu Gly Glu Lys Gly Glu Pro Trp Asn Leu
    355                 360                 365

His His Leu Thr Leu Tyr Cys Cys Val Asp Asn Arg Leu Trp Thr Glu
370                 375                 380

Glu Gly Thr Glu Ile Val Arg Gln Glu Lys Ala Asp Glu Ile Thr Lys
385                 390                 395                 400

Phe Ile Thr Asn Met Lys Lys Lys Ser Asp Leu Ser Asp Thr Gln Gln
            405                 410                 415

Ala Leu Ile Gln Arg Lys Gln Ser Thr Leu Thr Arg Ile Asn Asn Ser
        420                 425                 430

Phe Glu Arg Pro Ser Gln Pro Leu Tyr Gln Gly Gln Ser His Ile Leu
    435                 440                 445

Val Gly Val Ser Leu Gly Leu Glu Lys Pro Ala Thr Ala Val Val
450                 455                 460

Asp Ala Ile Ala Asn Lys Val Leu Ala Tyr Arg Ser Ile Lys Gln Leu
465                 470                 475                 480

Leu Gly Asp Asn Tyr Glu Leu Leu Asn Arg Gln Arg Gln Gln Gln
            485                 490                 495

Tyr Leu Ser His Glu Arg His Lys Ala Gln Lys Asn Phe Ser Pro Asn
        500                 505                 510

Gln Phe Gly Ala Ser Glu Leu Gly Gln His Ile Asp Arg Leu Leu Ala
    515                 520                 525

Lys Ala Ile Val Ala Leu Ala Arg Thr Tyr Lys Ala Gly Ser Ile Val
530                 535                 540

Leu Pro Lys Leu Gly Asp Met Arg Glu Val Val Gln Ser Glu Ile Gln
545                 550                 555                 560

Ala Ile Ala Glu Gln Lys Phe Pro Gly Tyr Ile Glu Gly Gln Lys
            565                 570                 575

Tyr Ala Lys Gln Tyr Arg Val Asn Val His Arg Trp Ser Tyr Gly Arg
        580                 585                 590

Leu Ile Gln Ser Ile Gln Ser Lys Ala Ala Gln Thr Gly Ile Val Ile
    595                 600                 605

Glu Glu Gly Lys Gln Pro Ile Arg Gly Ser Pro His Asp Lys Ala Lys
610                 615                 620

Glu Leu Ala Leu Ser Ala Tyr Asn Leu Arg Leu Thr Arg Arg Ser
625                 630                 635
```

```
<210> SEQ ID NO 31
<211> LENGTH: 642
<212> TYPE: PRT
<213> ORGANISM: Anabaena cylindrica

<400> SEQUENCE: 31
```

| | | | | | | | | | | | | | | |
|---|---|---|---|---|---|---|---|---|---|---|---|---|---|---|
| Met | Ser | Val | Ile | Thr | Ile | Gln | Cys | Arg | Leu | Val | Ala | Glu | Glu | Asp | Ser |
| 1 | | | | 5 | | | | | 10 | | | | | 15 | |

| Leu | Arg | Gln | Leu | Trp | Glu | Leu | Met | Ser | Glu | Lys | Asn | Thr | Pro | Phe | Ile |
| | | | 20 | | | | | 25 | | | | | 30 | | |

| Asn | Glu | Ile | Leu | Leu | Gln | Ile | Gly | Lys | His | Pro | Glu | Phe | Glu | Thr | Trp |
| | | | 35 | | | | | 40 | | | | | 45 | | |

| Leu | Glu | Lys | Gly | Arg | Ile | Pro | Ala | Glu | Leu | Leu | Lys | Thr | Leu | Gly | Asn |
| | 50 | | | | | 55 | | | | | 60 | | | | |

| Ser | Leu | Lys | Thr | Gln | Glu | Pro | Phe | Thr | Gly | Gln | Pro | Gly | Arg | Phe | Tyr |
| 65 | | | | | 70 | | | | | 75 | | | | | 80 |

| Thr | Ser | Ala | Ile | Thr | Leu | Val | Asp | Tyr | Leu | Tyr | Lys | Ser | Trp | Phe | Ala |
| | | | | 85 | | | | | 90 | | | | | 95 | |

| Leu | Gln | Lys | Arg | Arg | Lys | Gln | Gln | Ile | Glu | Gly | Lys | Gln | Arg | Trp | Leu |
| | | | 100 | | | | | 105 | | | | | 110 | | |

| Lys | Met | Leu | Lys | Ser | Asp | Gln | Glu | Leu | Glu | Gln | Glu | Ser | Gln | Ser | Ser |
| | | | 115 | | | | | 120 | | | | | 125 | | |

| Leu | Glu | Val | Ile | Arg | Asn | Lys | Ala | Thr | Glu | Leu | Phe | Ser | Lys | Phe | Thr |
| | 130 | | | | | 135 | | | | | 140 | | | | |

| Pro | Gln | Ser | Asp | Ser | Glu | Ala | Leu | Arg | Arg | Asn | Gln | Asn | Asp | Lys | Gln |
| 145 | | | | | 150 | | | | | 155 | | | | | 160 |

| Lys | Lys | Val | Lys | Lys | Thr | Lys | Lys | Ser | Thr | Lys | Pro | Lys | Thr | Ser | Ser |
| | | | | 165 | | | | | 170 | | | | | 175 | |

| Ile | Phe | Lys | Ile | Phe | Leu | Ser | Thr | Tyr | Glu | Glu | Ala | Glu | Glu | Pro | Leu |
| | | | 180 | | | | | 185 | | | | | 190 | | |

| Thr | Arg | Cys | Ala | Leu | Ala | Tyr | Leu | Leu | Lys | Asn | Asn | Cys | Gln | Ile | Ser |
| | | | 195 | | | | | 200 | | | | | 205 | | |

| Glu | Leu | Asp | Glu | Asn | Pro | Glu | Glu | Phe | Thr | Arg | Asn | Lys | Arg | Arg | Lys |
| | 210 | | | | | 215 | | | | | 220 | | | | |

| Glu | Ile | Glu | Ile | Glu | Arg | Leu | Lys | Asp | Gln | Leu | Gln | Ser | Arg | Ile | Pro |
| 225 | | | | | 230 | | | | | 235 | | | | | 240 |

| Lys | Gly | Arg | Asp | Leu | Thr | Gly | Glu | Glu | Trp | Leu | Glu | Thr | Leu | Glu | Ile |
| | | | | 245 | | | | | 250 | | | | | 255 | |

| Ala | Thr | Phe | Asn | Val | Pro | Gln | Asn | Glu | Asn | Glu | Ala | Lys | Ala | Trp | Gln |
| | | | 260 | | | | | 265 | | | | | 270 | | |

| Ala | Ala | Leu | Leu | Arg | Lys | Thr | Ala | Asn | Val | Pro | Phe | Pro | Val | Ala | Tyr |
| | | | 275 | | | | | 280 | | | | | 285 | | |

| Glu | Ser | Asn | Glu | Asp | Met | Thr | Trp | Leu | Lys | Asn | Asp | Lys | Asn | Arg | Leu |
| | 290 | | | | | 295 | | | | | 300 | | | | |

| Phe | Val | Arg | Phe | Asn | Gly | Leu | Gly | Lys | Leu | Thr | Phe | Glu | Ile | Tyr | Cys |
| 305 | | | | | 310 | | | | | 315 | | | | | 320 |

| Asp | Lys | Arg | His | Leu | His | Tyr | Phe | Gln | Arg | Phe | Leu | Glu | Asp | Gln | Glu |
| | | | | 325 | | | | | 330 | | | | | 335 | |

| Ile | Leu | Arg | Asn | Ser | Lys | Arg | Gln | His | Ser | Ser | Ser | Leu | Phe | Thr | Leu |
| | | | 340 | | | | | 345 | | | | | 350 | | |

| Arg | Ser | Gly | Arg | Ile | Ala | Trp | Leu | Pro | Gly | Glu | Glu | Lys | Gly | Glu | His |
| | | | 355 | | | | | 360 | | | | | 365 | | |

| Trp | Lys | Val | Asn | Gln | Leu | Asn | Phe | Tyr | Cys | Ser | Leu | Asp | Thr | Arg | Met |
| | 370 | | | | | 375 | | | | | 380 | | | | |

```
Leu Thr Thr Glu Gly Thr Gln Gln Val Val Glu Lys Val Thr Ala
385                 390                 395                 400

Ile Thr Glu Ile Leu Asn Lys Thr Lys Gln Lys Asp Asp Leu Asn Asp
                405                 410                 415

Lys Gln Gln Ala Phe Ile Thr Arg Gln Gln Ser Thr Leu Ala Arg Ile
            420                 425                 430

Asn Asn Pro Phe Pro Arg Pro Ser Lys Pro Asn Tyr Gln Gly Lys Ser
        435                 440                 445

Ser Ile Leu Ile Gly Val Ser Phe Gly Leu Glu Lys Pro Val Thr Val
    450                 455                 460

Ala Val Asp Val Val Lys Asn Lys Val Ile Ala Tyr Arg Ser Val
465             470                 475                 480

Lys Gln Leu Leu Gly Glu Asn Tyr Asn Leu Leu Asn Arg Gln Arg Gln
                485                 490                 495

Gln Gln Gln Arg Leu Ser His Glu Arg His Lys Ala Gln Lys Gln Asn
            500                 505                 510

Ala Pro Asn Ser Phe Gly Glu Ser Glu Leu Gly Gln Tyr Val Asp Arg
        515                 520                 525

Leu Leu Ala Asp Ala Ile Ile Ala Ile Ala Lys Lys Tyr Gln Ala Gly
    530                 535                 540

Ser Ile Val Leu Pro Lys Leu Arg Asp Met Arg Glu Gln Ile Ser Ser
545                 550                 555                 560

Glu Ile Gln Ser Arg Ala Glu Asn Gln Cys Pro Gly Tyr Lys Glu Gly
                565                 570                 575

Gln Gln Lys Tyr Ala Lys Glu Tyr Arg Ile Asn Val His Arg Trp Ser
            580                 585                 590

Tyr Gly Arg Leu Ile Glu Ser Ile Lys Ser Gln Ala Ala Gln Ala Gly
        595                 600                 605

Ile Ala Ile Glu Thr Gly Lys Gln Ser Ile Arg Gly Ser Pro Gln Glu
    610                 615                 620

Lys Ala Arg Asp Leu Ala Val Phe Thr Tyr Gln Glu Arg Gln Ala Ala
625                 630                 635                 640

Leu Ile

<210> SEQ ID NO 32
<211> LENGTH: 208
<212> TYPE: DNA
<213> ORGANISM: Artificial Sequence
<220> FEATURE:
<223> OTHER INFORMATION: Transposon left end

<400> SEQUENCE: 32
tacagtgaca aattatctgt cgtcggtgac agattaatgt cattgtgact atttaattgt      60
cgtcgtgacc catcagcgtt gcttaattaa ttgatgacaa attaaatgtc atcaatataa     120
tatgctctgc aattattata caaagcaatt aaaacaagcg gataaaagga cttgctttca     180
acccacccct aagtttaata gttactga                                        208

<210> SEQ ID NO 33
<211> LENGTH: 219
<212> TYPE: DNA
<213> ORGANISM: Artificial Sequence
<220> FEATURE:
<223> OTHER INFORMATION: Transposon right end

<400> SEQUENCE: 33
cgacagtcaa tttgtcatta tgaaaataca caaaagcttt ttcctatctt gcaaagcgac      60
```

-continued

```
agctaatttg tcacaatcac ggacaacgac atctattttg tcactgcaaa gaggttatgc    120
taaaactgcc aaagcgctat aatctatact gtataaggat tttactgatg acaataattt    180
gtcacaacga catataatta gtcactgtac acgtagaga                            219
```

<210> SEQ ID NO 34
<211> LENGTH: 394
<212> TYPE: PRT
<213> ORGANISM: Vibrio cholerae

<400> SEQUENCE: 34

```
Met Phe Leu Gln Arg Pro Lys Pro Tyr Ser Asp Glu Ser Leu Glu Ser
1               5                   10                  15

Phe Phe Ile Arg Val Ala Asn Lys Asn Gly Tyr Gly Asp Val His Arg
            20                  25                  30

Phe Leu Glu Ala Thr Lys Arg Phe Leu Gln Asp Ile Asp His Asn Gly
        35                  40                  45

Tyr Gln Thr Phe Pro Thr Asp Ile Thr Arg Ile Asn Pro Tyr Ser Ala
    50                  55                  60

Lys Asn Ser Ser Ala Arg Thr Ala Ser Phe Leu Lys Leu Ala Gln
65                  70                  75                  80

Leu Thr Phe Asn Glu Pro Pro Glu Leu Leu Gly Leu Ala Ile Asn Arg
                85                  90                  95

Thr Asn Met Lys Tyr Ser Pro Ser Thr Ser Ala Val Val Arg Gly Ala
            100                 105                 110

Glu Val Phe Pro Arg Ser Leu Leu Arg Thr His Ser Ile Pro Cys Cys
        115                 120                 125

Pro Leu Cys Leu Arg Glu Asn Gly Tyr Ala Ser Tyr Leu Trp His Phe
    130                 135                 140

Gln Gly Tyr Glu Tyr Cys His Ser His Asn Val Pro Leu Ile Thr Thr
145                 150                 155                 160

Cys Ser Cys Gly Lys Glu Phe Asp Tyr Arg Val Ser Gly Leu Lys Gly
                165                 170                 175

Ile Cys Cys Lys Cys Lys Glu Pro Ile Thr Leu Thr Ser Arg Glu Asn
            180                 185                 190

Gly His Glu Ala Ala Cys Thr Val Ser Asn Trp Leu Ala Gly His Glu
        195                 200                 205

Ser Lys Pro Leu Pro Asn Leu Pro Lys Ser Tyr Arg Trp Gly Leu Val
    210                 215                 220

His Trp Trp Met Gly Ile Lys Asp Ser Glu Phe Asp His Phe Ser Phe
225                 230                 235                 240

Val Gln Phe Phe Ser Asn Trp Pro Arg Ser Phe His Ser Ile Ile Glu
                245                 250                 255

Asp Glu Val Glu Phe Asn Leu Glu His Ala Val Val Ser Thr Ser Glu
            260                 265                 270

Leu Arg Leu Lys Asp Leu Leu Gly Arg Leu Phe Phe Gly Ser Ile Arg
        275                 280                 285

Leu Pro Glu Arg Asn Leu Gln His Asn Ile Ile Leu Gly Glu Leu Leu
    290                 295                 300

Cys Tyr Leu Glu Asn Arg Leu Trp Gln Asp Lys Gly Leu Ile Ala Asn
305                 310                 315                 320

Leu Lys Met Asn Ala Leu Glu Ala Thr Val Met Leu Asn Cys Ser Leu
                325                 330                 335

Asp Gln Ile Ala Ser Met Val Glu Gln Arg Ile Leu Lys Pro Asn Arg
```

```
              340                 345                 350
Lys Ser Lys Pro Asn Ser Pro Leu Asp Val Thr Asp Tyr Leu Phe His
            355                 360                 365

Phe Gly Asp Ile Phe Cys Leu Trp Leu Ala Glu Phe Gln Ser Asp Glu
            370                 375                 380

Phe Asn Arg Ser Phe Tyr Val Ser Arg Trp
385                 390

<210> SEQ ID NO 35
<211> LENGTH: 640
<212> TYPE: PRT
<213> ORGANISM: Vibrio cholerae

<400> SEQUENCE: 35

Met Gln Thr Leu Lys Glu Leu Ile Ala Ser Asn Pro Asp Asp Leu Thr
1               5                   10                  15

Thr Glu Leu Lys Arg Ala Phe Arg Pro Leu Thr Pro His Ile Ala Ile
            20                  25                  30

Asp Gly Asn Glu Leu Asp Ala Leu Thr Ile Leu Val Asn Leu Thr Asp
        35                  40                  45

Lys Thr Asp Asp Gln Lys Asp Leu Leu Asp Arg Ala Lys Cys Lys Gln
50                  55                  60

Lys Leu Arg Asp Glu Lys Trp Trp Ala Ser Cys Ile Asn Cys Val Asn
65                  70                  75                  80

Tyr Arg Gln Ser His Asn Pro Lys Phe Pro Asp Ile Arg Ser Glu Gly
            85                  90                  95

Val Ile Arg Thr Gln Ala Leu Gly Glu Leu Pro Ser Phe Leu Leu Ser
            100                 105                 110

Ser Ser Lys Ile Pro Pro Tyr His Trp Ser Tyr Ser His Asp Ser Lys
            115                 120                 125

Tyr Val Asn Lys Ser Ala Phe Leu Thr Asn Glu Phe Cys Trp Asp Gly
        130                 135                 140

Glu Ile Ser Cys Leu Gly Glu Leu Leu Lys Asp Ala Asp His Pro Leu
145                 150                 155                 160

Trp Asn Thr Leu Lys Lys Leu Gly Cys Ser Gln Lys Thr Cys Lys Ala
                165                 170                 175

Met Ala Lys Gln Leu Ala Asp Ile Thr Leu Thr Thr Ile Asn Val Thr
            180                 185                 190

Leu Ala Pro Asn Tyr Leu Thr Gln Ile Ser Leu Pro Asp Ser Asp Thr
        195                 200                 205

Ser Tyr Ile Ser Leu Ser Pro Val Ala Ser Leu Ser Met Gln Ser His
210                 215                 220

Phe His Gln Arg Leu Gln Asp Glu Asn Arg His Ser Ala Ile Thr Arg
225                 230                 235                 240

Phe Ser Arg Thr Thr Asn Met Gly Val Thr Ala Met Thr Cys Gly Gly
            245                 250                 255

Ala Phe Arg Met Leu Lys Ser Gly Ala Lys Phe Ser Ser Pro Pro His
            260                 265                 270

His Arg Leu Asn Ser Lys Arg Ser Trp Leu Thr Ser Glu His Val Gln
        275                 280                 285

Ser Leu Lys Gln Tyr Gln Arg Leu Asn Lys Ser Leu Ile Pro Glu Asn
290                 295                 300

Ser Arg Ile Ala Leu Arg Arg Lys Tyr Lys Ile Glu Leu Gln Asn Met
305                 310                 315                 320
```

-continued

Val Arg Ser Trp Phe Ala Met Gln Asp His Thr Leu Asp Ser Asn Ile
                325                 330                 335

Leu Ile Gln His Leu Asn His Asp Leu Ser Tyr Leu Gly Ala Thr Lys
        340                 345                 350

Arg Phe Ala Tyr Asp Pro Ala Met Thr Lys Leu Phe Thr Glu Leu Leu
            355                 360                 365

Lys Arg Glu Leu Ser Asn Ser Ile Asn Asn Gly Glu Gln His Thr Asn
370                 375                 380

Gly Ser Phe Leu Val Leu Pro Asn Ile Arg Val Cys Gly Ala Thr Ala
385                 390                 395                 400

Leu Ser Ser Pro Val Thr Val Gly Ile Pro Ser Leu Thr Ala Phe Phe
                405                 410                 415

Gly Phe Val His Ala Phe Glu Arg Asn Ile Asn Arg Thr Thr Ser Ser
            420                 425                 430

Phe Arg Val Glu Ser Phe Ala Ile Cys Val His Gln Leu His Val Glu
        435                 440                 445

Lys Arg Gly Leu Thr Ala Glu Phe Val Glu Lys Gly Asp Gly Thr Ile
    450                 455                 460

Ser Ala Pro Ala Thr Arg Asp Asp Trp Gln Cys Asp Val Val Phe Ser
465                 470                 475                 480

Leu Ile Leu Asn Thr Asn Phe Ala Gln His Ile Asp Gln Asp Thr Leu
                485                 490                 495

Val Thr Ser Leu Pro Lys Arg Leu Ala Arg Gly Ser Ala Lys Ile Ala
            500                 505                 510

Ile Asp Asp Phe Lys His Ile Asn Ser Phe Ser Thr Leu Glu Thr Ala
        515                 520                 525

Ile Glu Ser Leu Pro Ile Glu Ala Gly Arg Trp Leu Ser Leu Tyr Ala
    530                 535                 540

Gln Ser Asn Asn Asn Leu Ser Asp Leu Leu Ala Ala Met Thr Glu Asp
545                 550                 555                 560

His Gln Leu Met Ala Ser Cys Val Gly Tyr His Leu Leu Glu Glu Pro
                565                 570                 575

Lys Asp Lys Pro Asn Ser Leu Arg Gly Tyr Lys His Ala Ile Ala Glu
            580                 585                 590

Cys Ile Ile Gly Leu Ile Asn Ser Ile Thr Phe Ser Ser Glu Thr Asp
        595                 600                 605

Pro Asn Thr Ile Phe Trp Ser Leu Lys Asn Tyr Gln Asn Tyr Leu Val
    610                 615                 620

Val Gln Pro Arg Ser Ile Asn Asp Glu Thr Thr Asp Lys Ser Ser Leu
625                 630                 635                 640

<210> SEQ ID NO 36
<211> LENGTH: 352
<212> TYPE: PRT
<213> ORGANISM: Vibrio cholerae

<400> SEQUENCE: 36

Met Lys Leu Pro Thr Asn Leu Ala Tyr Glu Arg Ser Ile Asp Pro Ser
1               5                   10                  15

Asp Val Cys Phe Phe Val Val Trp Pro Asp Asp Arg Lys Thr Pro Leu
            20                  25                  30

Thr Tyr Asn Ser Arg Thr Leu Leu Gly Gln Met Glu Ala Ala Ser Leu
        35                  40                  45

Ala Tyr Asp Val Ser Gly Gln Pro Ile Lys Ser Ala Thr Ala Glu Ala
    50                  55                  60

```
Leu Ala Gln Gly Asn Pro His Gln Val Asp Phe Cys His Val Pro Tyr
 65                  70                  75                  80

Gly Ala Ser His Ile Glu Cys Ser Phe Ser Val Ser Phe Ser Ser Glu
                 85                  90                  95

Leu Arg Gln Pro Tyr Lys Cys Asn Ser Ser Lys Val Lys Gln Thr Leu
            100                 105                 110

Val Gln Leu Val Glu Leu Tyr Glu Thr Lys Ile Gly Trp Thr Glu Leu
        115                 120                 125

Ala Thr Arg Tyr Leu Met Asn Ile Cys Asn Gly Lys Trp Leu Trp Lys
130                 135                 140

Asn Thr Arg Lys Ala Tyr Cys Trp Asn Ile Val Leu Thr Pro Trp Pro
145                 150                 155                 160

Trp Asn Gly Glu Lys Val Gly Phe Glu Asp Ile Arg Thr Asn Tyr Thr
                165                 170                 175

Ser Arg Gln Asp Phe Lys Asn Asn Lys Asn Trp Ser Ala Ile Val Glu
            180                 185                 190

Met Ile Lys Thr Ala Phe Ser Ser Thr Asp Gly Leu Ala Ile Phe Glu
        195                 200                 205

Val Arg Ala Thr Leu His Leu Pro Thr Asn Ala Met Val Arg Pro Ser
210                 215                 220

Gln Val Phe Thr Glu Lys Glu Ser Gly Ser Lys Ser Lys Ser Lys Thr
225                 230                 235                 240

Gln Asn Ser Arg Val Phe Gln Ser Thr Ile Asp Gly Glu Arg Ser
                245                 250                 255

Pro Ile Leu Gly Ala Phe Lys Thr Gly Ala Ala Ile Ala Thr Ile Asp
            260                 265                 270

Asp Trp Tyr Pro Glu Ala Thr Glu Pro Leu Arg Val Gly Arg Phe Gly
        275                 280                 285

Val His Arg Glu Asp Val Thr Cys Tyr Arg His Pro Ser Thr Gly Lys
290                 295                 300

Asp Phe Phe Ser Ile Leu Gln Gln Ala Glu His Tyr Ile Glu Val Leu
305                 310                 315                 320

Ser Ala Asn Lys Thr Pro Ala Gln Glu Thr Ile Asn Asp Met His Phe
                325                 330                 335

Leu Met Ala Asn Leu Ile Lys Gly Gly Met Phe Gln His Lys Gly Asp
            340                 345                 350

<210> SEQ ID NO 37
<211> LENGTH: 199
<212> TYPE: PRT
<213> ORGANISM: Vibrio cholerae

<400> SEQUENCE: 37

Met Lys Trp Tyr Tyr Lys Thr Ile Thr Phe Leu Pro Glu Leu Cys Asn
 1               5                  10                  15

Asn Glu Ser Leu Ala Ala Lys Cys Leu Arg Val Leu His Gly Phe Asn
                 20                  25                  30

Tyr Gln Tyr Glu Thr Arg Asn Ile Gly Val Ser Phe Pro Leu Trp Cys
            35                  40                  45

Asp Ala Thr Val Gly Lys Lys Ile Ser Phe Val Ser Lys Asn Lys Ile
        50                  55                  60

Glu Leu Asp Leu Leu Lys Gln His Tyr Phe Val Gln Met Glu Gln
 65                  70                  75                  80

Leu Gln Tyr Phe His Ile Ser Asn Thr Val Leu Val Pro Glu Asp Cys
```

```
                        85                  90                  95

Thr Tyr Val Ser Phe Arg Arg Cys Gln Ser Ile Asp Lys Leu Thr Ala
                100                 105                 110

Ala Gly Leu Ala Arg Lys Ile Arg Arg Leu Glu Lys Arg Ala Leu Ser
                115                 120                 125

Arg Gly Glu Gln Phe Asp Pro Ser Ser Phe Ala Gln Lys Glu His Thr
        130                 135                 140

Ala Ile Ala His Tyr His Ser Leu Gly Glu Ser Ser Lys Gln Thr Asn
145                 150                 155                 160

Arg Asn Phe Arg Leu Asn Ile Arg Met Leu Ser Glu Gln Pro Arg Glu
                165                 170                 175

Gly Asn Ser Ile Phe Ser Ser Tyr Gly Leu Ser Asn Ser Glu Asn Ser
                180                 185                 190

Phe Gln Pro Val Pro Leu Ile
                195

<210> SEQ ID NO 38
<211> LENGTH: 230
<212> TYPE: PRT
<213> ORGANISM: Vibrio cholerae

<400> SEQUENCE: 38

Met Ala Thr Ser Leu Pro Thr Pro Ser Ala Ile Thr Thr Ser Ala Leu
1               5                   10                  15

Glu Tyr Ala Phe His Thr Pro Ala Arg Asn Leu Thr Lys Ser Arg Gly
                20                  25                  30

Lys Asn Ile His Arg Tyr Val Ser Val Lys Met Ser Lys Arg Ile Thr
            35                  40                  45

Val Glu Ser Thr Leu Glu Cys Asp Ala Cys Tyr His Phe Asp Phe Glu
        50                  55                  60

Pro Ser Ile Val Arg Phe Cys Ala Gln Pro Ile Arg Phe Leu Tyr Tyr
65                  70                  75                  80

Leu Asn Gly Gln Ser His Ser Tyr Val Pro Asp Phe Leu Val Gln Phe
                85                  90                  95

Asp Thr Asn Glu Phe Val Leu Tyr Glu Val Lys Ser Ala Tyr Ala Lys
                100                 105                 110

Asn Lys Pro Asp Phe Asp Val Glu Trp Glu Ala Lys Val Lys Ala Ala
                115                 120                 125

Thr Glu Leu Gly Leu Glu Leu Glu Leu Val Glu Glu Ser Asp Ile Arg
        130                 135                 140

Asp Thr Val Val Leu Asn Asn Leu Lys Arg Met His Arg Tyr Ala Ser
145                 150                 155                 160

Lys Asp Glu Leu Asn Asn Val His Asn Ser Leu Leu Lys Ile Ile Lys
                165                 170                 175

Tyr Asn Gly Ala Gln Ser Ala Arg Cys Leu Gly Glu Gln Leu Gly Leu
                180                 185                 190

Lys Gly Arg Thr Val Leu Pro Ile Leu Cys Asp Leu Ser Arg Cys
                195                 200                 205

Leu Leu Asp Thr Arg Leu Asp Lys Pro Leu Ser Leu Glu Ser Arg Phe
        210                 215                 220

Glu Leu Ala Ser Tyr Gly
225                 230

<210> SEQ ID NO 39
<211> LENGTH: 603
```

```
<212> TYPE: PRT
<213> ORGANISM: Vibrio cholerae

<400> SEQUENCE: 39
```

| | | | | | | | | | | | | | | |
|---|---|---|---|---|---|---|---|---|---|---|---|---|---|---|
| Met | Ala | Lys | Lys | Gly | Phe | Ser | Ser | Phe | His | Arg | Lys | Ala | Val | Ser | Ser |
| 1 | | | | 5 | | | | | 10 | | | | | 15 | |
| Gln | Asp | Thr | Leu | Glu | Ser | Ile | Glu | Leu | Val | Ser | Ser | Ala | Asn | Cys | Leu |
| | | | 20 | | | | | 25 | | | | | 30 | | |
| Glu | Ser | Val | Thr | Tyr | Gln | Asp | Ile | Ser | Ala | Phe | Pro | Glu | Thr | Ile | Ala |
| | | | 35 | | | | | 40 | | | | | 45 | | |
| Val | Glu | Ile | Asn | Phe | Arg | Leu | Ser | Ile | Leu | Arg | Phe | Leu | Ala | Arg | Lys |
| | 50 | | | | | 55 | | | | | 60 | | | | |
| Cys | Glu | Thr | Ile | Val | Ala | Lys | Ser | Ile | Glu | Pro | His | Arg | Val | Glu | Leu |
| 65 | | | | | 70 | | | | | 75 | | | | | 80 |
| Gln | Gln | Asn | Tyr | Ser | Arg | Lys | Ile | Pro | Ser | Ala | Ile | Thr | Ile | Tyr | Arg |
| | | | | 85 | | | | | 90 | | | | | 95 | |
| Trp | Trp | Leu | Ala | Phe | Arg | Lys | Ser | Asp | Tyr | Asn | Pro | Ile | Ser | Leu | Ala |
| | | | 100 | | | | | 105 | | | | | 110 | | |
| Pro | Asn | Ile | Lys | Asp | Arg | Gly | Asn | Arg | Glu | Thr | Lys | Val | Ser | Thr | Val |
| | | | 115 | | | | | 120 | | | | | 125 | | |
| Val | Asp | Ser | Ile | Met | Glu | Gln | Ala | Val | Glu | Arg | Val | Ile | Ser | Gly | Arg |
| | 130 | | | | | 135 | | | | | 140 | | | | |
| Lys | Val | Asn | Val | Ser | Ser | Ala | Tyr | Lys | Arg | Val | Arg | Arg | Lys | Val | Arg |
| 145 | | | | | 150 | | | | | 155 | | | | | 160 |
| Gln | Tyr | Asn | Leu | Thr | His | Gly | Thr | Lys | Tyr | Thr | Tyr | Pro | Lys | Tyr | Glu |
| | | | | 165 | | | | | 170 | | | | | 175 | |
| Ser | Val | Arg | Lys | Arg | Val | Lys | Lys | Thr | Pro | Phe | Glu | Leu | Leu | Ala |
| | | | 180 | | | | | 185 | | | | | 190 | | |
| Ala | Gly | Lys | Gly | Glu | Arg | Val | Ala | Lys | Glu | Phe | Arg | Arg | Met | Gly |
| | | | 195 | | | | | 200 | | | | | 205 | | |
| Lys | Lys | Ile | Leu | Thr | Ser | Ser | Val | Leu | Glu | Arg | Val | Glu | Ile | Asp | His |
| | 210 | | | | | 215 | | | | | 220 | | | | |
| Thr | Val | Val | Asp | Leu | Phe | Ala | Val | His | Glu | Glu | Tyr | Arg | Ile | Pro | Leu |
| 225 | | | | | 230 | | | | | 235 | | | | | 240 |
| Gly | Arg | Pro | Trp | Leu | Thr | Gln | Leu | Val | Asp | Cys | Tyr | Ser | Lys | Ala | Val |
| | | | | 245 | | | | | 250 | | | | | 255 | |
| Ile | Gly | Phe | Tyr | Leu | Gly | Phe | Glu | Pro | Pro | Ser | Tyr | Val | Ser | Val | Ser |
| | | | 260 | | | | | 265 | | | | | 270 | | |
| Leu | Ala | Leu | Lys | Asn | Ala | Ile | Gln | Arg | Lys | Asp | Asp | Leu | Ile | Ser | Ser |
| | | | 275 | | | | | 280 | | | | | 285 | | |
| Tyr | Glu | Ser | Ile | Glu | Asn | Glu | Trp | Leu | Cys | Tyr | Gly | Ile | Pro | Asp | Leu |
| | 290 | | | | | 295 | | | | | 300 | | | | |
| Leu | Val | Thr | Asp | Asn | Gly | Lys | Glu | Phe | Leu | Ser | Lys | Ala | Phe | Asp | Gln |
| 305 | | | | | 310 | | | | | 315 | | | | | 320 |
| Ala | Cys | Glu | Ser | Leu | Leu | Ile | Asn | Val | His | Gln | Asn | Lys | Val | Glu | Thr |
| | | | | 325 | | | | | 330 | | | | | 335 | |
| Pro | Asp | Asn | Lys | Pro | His | Val | Glu | Arg | Asn | Tyr | Gly | Thr | Ile | Asn | Thr |
| | | | 340 | | | | | 345 | | | | | 350 | | |
| Ser | Leu | Leu | Asp | Asp | Leu | Pro | Gly | Lys | Ser | Phe | Ser | Gln | Tyr | Leu | Gln |
| | | | 355 | | | | | 360 | | | | | 365 | | |
| Arg | Glu | Gly | Tyr | Asp | Ser | Val | Gly | Glu | Ala | Thr | Leu | Thr | Leu | Asn | Glu |
| | 370 | | | | | 375 | | | | | 380 | | | | |
| Ile | Arg | Glu | Ile | Tyr | Leu | Ile | Trp | Leu | Val | Asp | Ile | Tyr | His | Lys | Lys |
| 385 | | | | | 390 | | | | | 395 | | | | | 400 |

Pro Asn Gln Arg Gly Thr Asn Cys Pro Asn Val Ala Trp Lys Lys Gly
                405                 410                 415

Cys Gln Glu Trp Glu Pro Glu Glu Phe Ser Gly Ser Lys Asp Glu Leu
            420                 425                 430

Asp Phe Lys Phe Ala Ile Val Asp Tyr Lys Gln Leu Thr Lys Val Gly
        435                 440                 445

Ile Thr Val Tyr Lys Glu Leu Ser Tyr Ser Asn Asp Arg Leu Ala Glu
    450                 455                 460

Tyr Arg Gly Lys Lys Gly Asn His Lys Val Gln Phe Lys Tyr Asn Pro
465                 470                 475                 480

Glu Cys Met Ala Val Ile Trp Val Leu Asp Gly Asp Met Asn Glu Tyr
                485                 490                 495

Phe Thr Val Asn Ala Ile Asp Tyr Glu Tyr Ala Ser Arg Val Ser Leu
            500                 505                 510

Trp Gln His Lys Tyr Asn Met Lys Tyr Gln Ala Glu Leu Asn Ser Ala
        515                 520                 525

Glu Tyr Asp Glu Asp Lys Glu Ile Asp Ala Glu Ile Lys Ile Glu Glu
    530                 535                 540

Ile Ala Asp Arg Ser Ile Val Lys Thr Asn Lys Ile Arg Ala Arg Arg
545                 550                 555                 560

Arg Gly Ala Arg His Gln Glu Asn Ser Ala Arg Ala Lys Ser Ile Ser
                565                 570                 575

Asn Ala Asn Pro Ala Ser Ile Gln Lys His Glu Asp Glu Ile Val Ser
            580                 585                 590

Ala Asp Asn Asp Asp Trp Asp Ile Asp Tyr Val
        595                 600

<210> SEQ ID NO 40
<211> LENGTH: 330
<212> TYPE: PRT
<213> ORGANISM: Vibrio cholerae

<400> SEQUENCE: 40

Met Ser Glu Thr Arg Glu Ala Arg Ile Ser Arg Ala Lys Arg Ala Phe
1               5                   10                  15

Val Ser Thr Pro Ser Val Arg Lys Ile Leu Ser Tyr Met Asp Arg Cys
                20                  25                  30

Arg Asp Leu Ser Asp Leu Glu Ser Glu Pro Thr Cys Met Met Val Tyr
            35                  40                  45

Gly Ala Ser Gly Val Gly Lys Thr Thr Val Ile Lys Lys Tyr Leu Asn
        50                  55                  60

Gln Asn Arg Arg Glu Ser Glu Ala Gly Gly Asp Ile Ile Pro Val Leu
65                  70                  75                  80

His Ile Glu Leu Pro Asp Asn Ala Lys Pro Val Asp Ala Ala Arg Glu
                85                  90                  95

Leu Leu Val Glu Met Gly Asp Pro Leu Ala Leu Tyr Glu Thr Asp Leu
            100                 105                 110

Ala Arg Leu Thr Lys Arg Leu Thr Glu Leu Ile Pro Ala Val Gly Val
        115                 120                 125

Lys Leu Ile Ile Ile Asp Glu Phe Gln His Leu Val Glu Glu Arg Ser
    130                 135                 140

Asn Arg Val Leu Thr Gln Val Gly Asn Trp Leu Lys Met Ile Leu Asn
145                 150                 155                 160

Lys Thr Lys Cys Pro Ile Val Ile Phe Gly Met Pro Tyr Ser Lys Val

```
              165                 170                 175
Val Leu Gln Ala Asn Ser Gln Leu His Gly Arg Phe Ser Ile Gln Val
            180                 185                 190

Glu Leu Arg Pro Phe Ser Tyr Gln Gly Arg Gly Val Phe Lys Thr
        195                 200                 205

Phe Leu Glu Tyr Leu Asp Lys Ala Leu Pro Phe Glu Lys Gln Ala Gly
        210                 215                 220

Leu Ala Asn Glu Ser Leu Gln Lys Lys Leu Tyr Ala Phe Ser Gln Gly
225                 230                 235                 240

Asn Met Arg Ser Leu Arg Asn Leu Ile Tyr Gln Ala Ser Ile Glu Ala
                245                 250                 255

Ile Asp Asn Gln His Glu Thr Ile Thr Glu Glu Asp Phe Val Phe Ala
                260                 265                 270

Ser Lys Leu Thr Ser Gly Asp Lys Pro Asn Ser Trp Lys Asn Pro Phe
            275                 280                 285

Glu Glu Gly Val Glu Val Thr Glu Asp Met Leu Arg Pro Pro Pro Lys
        290                 295                 300

Asp Ile Gly Trp Glu Asp Tyr Leu Arg His Ser Thr Pro Arg Val Ser
305                 310                 315                 320

Lys Pro Gly Arg Asn Lys Asn Phe Phe Glu
                325                 330

<210> SEQ ID NO 41
<211> LENGTH: 105
<212> TYPE: DNA
<213> ORGANISM: Vibrio cholerae

<400> SEQUENCE: 41
tgttgatgca accataaagt gatatttaat aattatttat aatcagcaac ttaaccacaa        60
aacaaccata tattgatatc tcacaaaaca accataagtt gatat                      105

<210> SEQ ID NO 42
<211> LENGTH: 48031
<212> TYPE: DNA
<213> ORGANISM: Homo sapiens

<400> SEQUENCE: 42
gtgggggccg ttggctccag acaaataaac atggagtcca tcttccacga gaaagtgagt        60
gtccgcgttc ggtggggagc tgtctgccgc gcggtggcgg gcgtggagcg cggcatcacc       120
gcctctcgga gggctgggtg gggcccgagt cgcccccatg ccgatctcgc ccggcgaggg       180
gcgacgccgc agcctcccgc tcctcggct cgaggagggg agcatcacct acgcccctac        240 ttccccgcg gccccgccc tgggagccgg gaggagtat gggcggggcc ggggcgtct          300 cgggacacgg gagtggggtg gcgcccagtg ggtttgcttc tgcctttctc cgtcactttc       360
catcgctttt cggaggattc cttcacccct ccccaatcct tccctctccc tagggtctag       420
ctagagtcat ctctgggaca cctccctcaa cccctcctac cctaatcctg gcagaattaa       480
cttttcctcc tccggactgc tcaattctat attggagtct tccctacacg tagatctttg       540
gggtcttgtt cgtgtctttc ccctgcacta ggtccgcgag cctcccgagg gaggagacct       600
tggctcgccc actgtagggc ctgacattta ggaagtgaag taggaaaccc ggcgtgcccc       660
taaacaggga agtcgtcaca agagttttta ttacgggatg tttgggtttg gtttctttg       720 gtactcccat ctttccggag caggcggcca gctttgtttt taggtattag gagtggactg       780
ggatgatttt gttgtagtct gcctagcctg ctgtcccttt aactcttccg tgaccatgca       840
```

```
cttgaagata ctgtttgtga tatgtaaaga aactcctcgt ttctctcata ctattatcca    900
gccatttgtg tgtgagtgaa gccttcccca ggacagcttt ggcacatggt atcatgtttc    960
ataatagttt cgtgtttgga aagagttgct ggtaaggctg ttatttaata ggaggagcaa   1020 agggttttg ttttattaaa tacttataaa tgatcattta tcccagacat ttaaaattca    1080
cacacacaca acaaataaag caaagacaaa agaatacatt taccaaatgt aaatctgtag   1140 cataaattt ttttaatttt tattttaaag atggggtctc attctgtcac ccaggcaggt    1200
gtgcaatgga gagatcatgg ctcactgcag ccttgatctc ctaggcacaa gcgatcctcc   1260
cgcctctgcc tccagagtag ctgggactac aggtgcatat cgccagggcc aggtaatgtt   1320
tttgggagag acggggtctc gctgtgttgc ccaggctggt ctcgaactcc tggactcagg   1380
tgattctccc acctcggcct ctcgaagtgc tgtgattaca ggcgtgagcc actgtgcctg   1440
gaacaaattg ttaagtacaa tgcttttcat tgtagaaaac atctcggaaa cttttgaaat   1500
aggctgatgt tcagtggggg aggaaggact cagtcgtata gttgtcacta atttttgac    1560 ttgattgaca tgactcgtaa atcatagaca atagagattt ggttgcttgg ctgagtagag   1620
tgcgtgaaaa atacacacgt actttttttt tttttttttt gagatggagt ttggctcttg   1680
tcacccaggc tggagtgcaa tggcgccatc atggctcact gcaacctccg cctcccgtt    1740 caagcgattc tcctgcctca gtctcccag tagctgagat tacaggcgcc cgccaccacg     1800
cccagctaat ttttgtattt ttagtagaga cagggtttca ccatgttggc caggctggtc   1860
tccaactcct gacaggtggt ccgcccgcct cggcctccca aagtgctggg attacaggcg   1920
tgagccaccg cacccggcca tattttgtt attaattttc aaaggctttg gtgtgggacc    1980
acatttcaac atggaaggcc ttaaacatgt tccacactac ttcctgagaa ttagacaaga   2040
tttttaacaa tattgttacc tagttgggac acatttgtac tgacccatgg gatgaaaaaa   2100
agctgagtgc tagcctagtg aaaatctact tacccgaaag aaatccctct tagtctgggt   2160
gcagtggctc acaccagtgc tttgggaggc ccagacgggc ggatcatgag gtcagtagtt   2220
tgagaccagc ctggccaaca tggtgaaacc ccgtctctac taaaaataca aaaaattagc   2280
caggtgtggt ggcaggcgcc tgtaatccca ggtactctgg aggctgaggc aggagaattg   2340
cttgaacccg agaggcagag gttgcagtga gccgagaccg tgccactgca cttcagcctg   2400
ggcaacagag cgagactccg tctcaaaaaa agaaaagga aaaagagtc cctcttaatt     2460 atcagcatgt gtataggcct acagatactt caggaatacc tttaccatta tcatcaactt   2520
gtatctacat agcatgtgaa gattcaacaa tttagttttt tgggcgtcct caagagtacg   2580
cacctataac catatggccc aattgttaat ctcctataca gtccattctg ggaatgtttg   2640
ggcttactgt gccattttc cgttcactgc cttcccctct gcaatatacc tttaacccctt    2700 gctaggtcct gggtttggag agccagagaa ccaactttgg ccctaaagaa gctgtgtagg   2760
tagcaatatc tgcctacgaa gggccttgca accatttcct cttggaacct tggtttcctc   2820
tttctgagta gtcactttga gtacccttta ttaagttaga atgtaaaaac agtttctcac   2880
tgatatatct gcagtgcctg agagagggcc tggcacagag taagtactca ataaatattt   2940
gaatggggcc gggcgtggtg agacctgtct ctacaagaat gaacaaaatt agctgggcgt   3000
gttagcacat gcctgtagac ttgggaggct gaggtgggag gattgcatga gtctgggagg   3060
tcgaggctgt agtgagccat gatcgcacca ctgcactcca gcctagggga cagagcaaga   3120
tcctgtctca aagaaaaaaa atgtatatat ttgaatggat aaagagatgg ctttgagttt   3180
```

```
ctgagatata tatggtgctg tttatctaaa gtaaacaagt tttctgtaaa tattttaagg    3240
ctttgcaggc cagctgtagt ctctgtcaca cattcttatt tgtgcatgtt tttcccaacc    3300
atgtaaaaat gtaaagtgca ttcttagcta ctggggcagg ttgaatttgg cccatgggct    3360
agagtttgcc aaccctaac ttaaacctt gtactaactt tatgaccact actggatttt    3420
tgttgttgtt tgttttagtt ctggtgcctg ctttgttttt tttttttttt ttaatcctct    3480
tgctgatgtt tcttggtgca gttactgtgc catttgtatt ggtgctttta atgtaatgca    3540
aactggtaat aatatctaaa cttgctgggg ttgtacataa aattattgaa aagattgaaa    3600
agatgctgag cattgactct gtggcattca ttatgcccct ttgtgattgc tggattttag    3660
ccatctttag acatttgag ctttaggaga agccaaattc tgtataaatg acttgaagtg    3720
ctaatagcac aggttttgaa acctctgcct gggtttgagt ctcagctctg ccttttacta    3780
cctgtgtgat cctgagcaag ttacttagta tccctgtcct ctagtttcct cctctgtagt    3840
gtggggataa taacatagac ataacctgag agttagagtg tagagaaggc tccctggcag    3900
atagtgctgt agaagtactg gccattgcca ttactcaggt gcttgtgttt gctgaacctc    3960
atagtaaggg ctcggagagc actaagagga ggtgagaaat gctgctagat tgacagcttg    4020
tccccagata gcccattccc gagagcacct taggtttata cctgatttgt gttgtagtta    4080
gtagtgtctc tggtaatttg aactagtttc aggttggtct tgaaaacctg gggaggttgg    4140
gggtaaatga tttggtagca gttctctttt gtgattttat acattatctt tgtagaactg    4200
cagtttgcta attctctgag cccaacacaa tgaagtctgg gcctaaaatc atagaatttc    4260
ttttattttt ttttttgttt ttaatttatt tattccctcc ctccctcctt tcttcctttc    4320 ttcctttct ttcttctttt ccttccttcc ttccttcttt cttttctttc tttcttttct    4380
ttctttggag tctcactctg tcaccaggct ggagtgcagt ggcacgaact tcttcagag    4440 tctcactttg tcaccaggct ggagtgcagt ggcgcgaact cagctcactg caacctccgt    4500
ctcctgagtt caagagattc tcctgcctca gcctcccgag tagctgggac tataggcatg    4560
tgccaccatg cccagctaat tttcttattt ttagtagaga cgaggtttca ccatgttggc    4620
caggatggtc ttgatctctt gacctcgtga tccacctgcc tcagcctccc aaagtgcggg    4680
gattacaggc gtgagctacc acgcccagcc tattttttat ttttgaggc agagtctcac    4740 tctgtcaccc aggctggagt gcagtggtgc aatctcagct cactgcaacc tccgcctcct    4800
gggttcaggt gattctcctg ccttagcctc ctgagcacct gggactacag gcgcctgcca    4860
ccacacctgg ctaattctta tatttttagt agaggcgggg tttcaccatg ttggccaggc    4920
tggtctcgaa ctcctgatct caagtgatca acctgccttg gcctcccaaa gtgctggaat    4980
tacagccatg agccaccatg cccagccaaa tcatgagatt tcaataccgc tgaactttga    5040
ttatggcaaa gtgaacttct gctttgatta aagcttgatg agagaggtgg ctgggatag    5100 tttgagataa gggcaaggca ggaaaatgca taatcttacg tgggctcatt gtcattgtac    5160
aattcttttg gtccatgtgg aatttgatcc gtcctatgac ttaagttatg tttatttttg    5220
tttttatttt tatttattttt gtgtcttttt gagagacatg atgttgctct gtcacctggg    5280
ccagaataca gtggcacaat cttagctccg tgtagccttg aactcctggg ctcaagtgat    5340
cctcccacct cagcccctca aacagttgag attatagtat gaaccactgt gcctagcctt    5400 aagtgattt taaatttgta ctgaacagtt tgtcctttcc ttccattaaa tcatattaga    5460
agtacagaac ttgatatttc ctgtagcaat acagttttc tttgatgaag tttgatttca    5520
agtacttatt tttcataatt taaagctatt ttttatagag agaattttaa tcaaatattt    5580
```

```
ggatgtcact attgctatat atggtattaa gtatggtgac catagtttgt aaactccaaa    5640
ctgacagcaa gacaggaaat ttgtgttagc aaaggctttt ttcttactgt ttgaattttt    5700
taaaaattag atacaataca gagaggagca cacaaatcat taagagtaca gctcagcgaa    5760
ttttcacaca gtgaacatgt gtaaacagca agtaacaaaa gatttacctg catcctataa    5820
cctcccatta ttccctttc taggtactgt ctctccactg cattcccacc aaatataacc     5880
actatgctga attctgacat cataaatgag ttttgcctga ttttgagctt ttgtgactgg    5940
aagtgtacag tgtatatacc ctttcgattc tgtcctcttt agtttaccat tgtttgagaa    6000
atttatccat actgttccag aattaactac tgttaattat tgttaattaa ctactgttgt    6060
agttaattca tcctcattgt tatctagtat tcttttgtga gtaaacacaa tttccattct    6120
actgtgatcc cagctatcca tttgggtcgt ttccagtttg gggtccatta caaatagtaa    6180
tgctatctgt aatgctattt tgtattacta caaatagtaa tgctatttgt ggcacaaaaa    6240
tactgctttt gtgaacattc ttatacatgt cttttgatga atgtatgttt gcattgctgt    6300
tgtttacatt atgtacctag taatggaatt gctagatcat aggagatgta tatattaagc    6360
tttagtggat gcattacata attattagtt attattggtt ataccaattt atcctctcat    6420
cagtagtata caacagtttc tgtatctcta atctccaaca ttttagccat tttagagttt    6480
gtgtactaac acattgtggt tttaatttac atttccctga tgactaataa agttgagtac    6540
ctcttttgtg ttctttatag ccatttgact gtcttgtgaa gtgcttgttt gtcttgccta    6600
ttttctcttt ctttctttct ttttcttcct tccttccttt ctttctttct tctttctttc    6660
cttccttctt ttctttcttt ctgtctttct ttcttgtctt tcttgtcttt ctgtctttct    6720
tggtcttgcc ctgtcaccca tgctggagtg cagtggtgca gtctcagctt actgtagcct    6780
cgaccttttt ggggctcaag ttatcctcct ttctcagcct cccaagaagc tggactacaa    6840
gcacgcacca ccatgctcag ttaatttttt attttttgta gaaatggggt ttcaccatgt    6900
tgtccaggct ggtctcaaac ttctgggctc aagtaatcct cctgccttgg cctcccaaaa    6960
tgctgggatt acaggcatga gccaccgcag ccagccttgg ctattttca aaaggatata    7020 agtagaacat ctgtatatcc cttcaatttg catattattc agtaagagtt gcactctggt    7080
agtagaaata tataaggagg agaaagaagt ggaaacaaaa agtctattct catgagaaga    7140
cttgggggat agtgttctct ctagctccaa gctacttatt ccttacgaaa agttgaagat    7200
aaacttatct cagactgagg ctgtctcaat gttgtcttcc tattccatta tacacatata    7260
acccatattt ttttcaccag ctgaattttg ctcctagaaa attgattcat caggaaaaat    7320
atccgtcttg caaggtggtt ctctttagag tctgctgtgt gacatagctc aggacaaatt    7380
gtgtgatgtc agataggttg ggttaaggaa tagaccttat tggggaaaga gagaacttgg    7440
agggccaagg ttagcaggag aaggaaatgt tctctcatct gccgtcaatt cagggagggg    7500
caaacctggt gtctgtgttc acagggaggg atccatccat ctgtgattct cccttcttat    7560
caggtagcat gggaaagcta cactgttgcg gggaggaggg tcacacgcag gctacttagt    7620
accaggcacc ctggacttgg attcaggttg ccagttgtgt gagaaactgc ccagcacctg    7680
aaggccctga acccatgaga agttgtacct acctcccatg aggaggaatc ctgtcatccc    7740
atgggagctg agcttgggtg cagtccctct tgctggcttg tccaggagtg agctccaggg    7800
ttgtttggga cagttctgct cattgcttta cactgtgtat acattatctg tagagttcca    7860
tgaagagaac ttcagcactg taactgcaag ttttaacatg gaacagaatt tttctcacct    7920
```

-continued

```
gtattaattc ttaagatttg aagttctatc aacaagcatt tagattgtgt ggagattttt      7980
ttatttttat ttttggagac agagtcttgc tctgttaccc agactggagt ggcagtggca      8040
tggtcttggc tcactgcagg ctctacttcc tgggttcaag cgattctcat gcctcagtgt      8100
cctgattagc taggactaca ggtacacacc accatgctgg ctaattttg tatttttagt      8160
agagacgagg tttcaccgta ttggtcaggc tggtctcgaa ctcccagcct caagcagtcc      8220
acccacctcg gcctcccaaa ctgctgggat tacaggtgtg agccaccatg cttgactgac      8280
atcatcatgt taaaagaata aatgttctag ggagctgggc acagtgtcat gtttctgtag      8340
ttctagctgc tcgggaggct gaggcaggaa gatcccttga gcctggagt tcaagtccag       8400
cctgggcaac atagtgagat ctcttttttt aaataaataa ataactgttc tagggactaa      8460
aatttccttt caccattagt aatttactgt agaatctcca agaatgaact tattttaggt      8520
actgaaaatg agggagacta aatgttttat acagtagttt ttagtaaaat atgagatttg      8580
atgcatttga tagatgatgt ttgttttaaaa taattcttaa attttgatc atgtaattat      8640
agtttcatta atggtagatt tgtaaaataa atgttaccaa atgaaaatgc atgtacctat      8700
gttaattatc cttatctaaa gctgaaagtt cagttcaact atgttaaaac atagtagggg      8760
cctggcaggg tggctcttgc ctgtaatccc agaacttagg gaggccaagg tgggcagatc      8820
acgaggtcag gagatcgaga ccatcctggc taacattgtg aaaccgtatc gctactaaaa      8880
atacaaaaaa ttagccgggc atggcggtgg gcacctgtag tcgcagctac ttggtaggct      8940
gaggcaggag aatggcgtga actcaggagg cagagcttac agtgagccga gatcatgcca      9000
ctgcactcca ggctgggtga cagagcaaga ctccatctca aaaaaaaaaa aaaagttggc      9060
caggtgtggc ggctcacacc tgtaatccca gcacttttgg aggccgaggc aggcggatca      9120
caagatcagt agtttgagac cagcctggct aacagagtga aaccctgtat atactaaaaa      9180
tacaaaaatt agccaggcat ggtggtgcat gcctgtagtc ccagctactt gagaggctga      9240
ggcaggagaa tcacttgaac ccgggaggcg gaggttgtgg taagctgaga ttgctccact      9300
gcactccagc ctggacaaca gagcaagact ctgtctcaaa aaaaaaaaa attaatgatt       9360
aaattattta ggggagccgg cgcagtggc tcacgcctgt aatcccagca ctttgggagg       9420
ccaaggcggg cggatcacga ggtcaggaga tcaagaccat cctggctaac acaggatgaa      9480
accccgtctc tactaaaaat acaaaaattt agccgggcgt ggtggcgggt gcctgtagta      9540
ccagctactc gggaggctga ggcaggagaa tggcatgaac ccgggtggcg gagcttgcag      9600
tgagccaaga tagcgccact gcactccggc ctgggtgaaa gagtgagact ccgtctcaaa      9660
aaaaaaaaa aattatttag gggaagatac tatacaattc tgtttaacaa gtcacatttt       9720
aatttttct tttggaaata ttagcaagaa ggctcacttt gtgctcaaca ttgcctgaat       9780
aacttattgc aaggagaata ttttagccct gtggaattat cctcaattgc acatcagctg      9840
gatgaggagg agaggatgag aatgcagaaa ggaggagtta ctagtgaaga ttatcgcacg      9900
tttttacagg tactgatttt aaactcacta agtcacattt cttttttttt ttttttttg      9960
agacggagtc tcgccctgtt gcccatgctg gagtgcaatg gcgcgatctc ggctcactgc      10020
aacctctgcc tcccgggttc aagcgattct cctgcctcag cctcccaagt agctgggatt      10080
acaggcacac ggcactatgc ccggctaatt ttttgtatct tgttagaga tggggtttca       10140
ccatgttggt caggttggtc tcaaactcct gaccttatga tccacctgtc ttggcctccc      10200
aaagtgctgg gattataggt gtgagccacc acacccggct tacatttctt ttaaaaatgt      10260
ggataccatt tagaaaagga tgggccattc ttcctatagg gatctgactg gtgaattata      10320
```

```
actgtgctgt taactttgga aatgggaatg cacaagatat tgttttaaat atgcacgcta    10380
atgacagttt gtatccttct ttccccaccc ccacccttgc ttcaactacc tgtcaaaatt    10440
aacagcagcc ttctggaaat atggatgaca gtggtttttt ctctattcag gtaagtagtc    10500
acaagcatgt actatgtgtt gcttacatcc caggcaccgt ttcacagcct ttcaatagtc    10560
actgtaacaa ggcgaccttc ggaagttctt ctgtctacag agtatagatt atactctaga    10620
gtactagatt ttttttttct tgagacagag tctcgttctg tcacctaggc tggagtgcag    10680
tggcgtgatc ttggctcact gtagcctctg cctcccgggt tcaagcgatc ctcctgcctc    10740
agcctcccaa gtagctggga ttacaggcac ccgccaccac accagttaat atttgtattt    10800
ttagtagaga tagtggggtt tcaccgtgtt ggccagtctg gtctccaact cctgacctca    10860
gcctcccaaa gtgctgggat tacaggtgtg agccactgca cctggccaac tagagtacta    10920 gattttttata tagataaaca tgaaaggatt gtagaatctt catattagag tgggcatttt   10980
aaaaattcct tcttgagaaa gattaatttg catctggatg ctaataataa ccttaattct    11040
ggccgggcgc ggtggctcac acctgtaatc ccagcacttt ggggaggccg aggtgggcgg    11100
atcacgaggt caggagattg agaccatcct ggctaacatg gtgaaacccc gtctctacta    11160
aaaatacaaa aattagctgg acgtggtgac acgtgcctgt aatcccagct actcgggagg    11220
ctgaggcagg agaatcgctt gaaccaggga gtcgtaggtt gcagtgagcc aagatcgcgc    11280
cactgcactc tagcctggtg acagagcgag actccatctc aaagaaaaaa agaaatcctt    11340
aattctaata agtcacaatg tctcaaactt accatctgtt gggtaaattt gagaaaatgc    11400 ataccttgc taccatcctt ttaaatcagc ctaccagact ggatttcctt attatggttt     11460
gtggcttttg atttttttt tttaatgtat agctctcttt gaattctttg gtggttatat     11520
atatatgtac tcgcaagatt cttttatctg tgggtctttc attcttttc taacactgtg     11580 agttgtatcc agagtacttt cggaacctct cctgagcgac ctatctctgc agatatcttt    11640
gtttatgttt cccttgtact gccctcctgg actcttcctc atccaccagc atttccatct    11700
agtgctttac cgtgccactg ctaacaggta atggctactg cagggctgaa atcagaggcc    11760
agagtaggcc cagcacttgg cgtttcctat ttgtgccttg ctgctcttgg tgcctgttca    11820
tgtgtgccca ctaccttgca ctcaatttct gtctttgctg gtacctggct cacttgcttc    11880
tttgttggct accttggagg gcagatagtg aattttcaga aatttccctt ttttttgtcag   11940 acagattgaa ataaacaggt ttgcatttg tttttttctac aagcggcaag cccatgaccc    12000
tagaagtctg acatctatgg aaccttcagt ttaaatgccc agggagaact tattttggta    12060
gatatgattt ctgacattgc aggtagcaag ttgaatataa ttttttctaaa gtagcaccca   12120 cagcagccaa attatcagat gtatatagta gactagtttt aagaaaagca cttatgggta    12180
gaatatacat ctggattttt gaggcagttt tatttaggaa ttgtgtggtt ttctggaaca    12240
tctcagagac ctggtatgaa aagcactctt ctaatatata tgtgtttttt tttatggatt    12300
tagtgatata tctatacaca cacactttt aaaacctata gccggctggg cgtggtggct     12360
catgcctgta atcccagtac tttgggaggc ccaggcgggt ggatcacaag gtcaggagat    12420
tgagaccagc ctggccaaca aggtgaaacc ctgtctctac taaaaataca aaatagctg    12480 ggtgtggtgg cgtgtgcttg taatcccagc tactcgggag cctcaggagg agaatcgctt    12540
gaacctggga ggcggaggtt gcagcagcc gagatcgtgc cactatactc cagcctgggc    12600
gacagagcaa gactctgtca caaaaaaaa aaaaaaaacc tatagccttc tagagaaatt    12660
```

```
tatatatgaa gtacacaact aacatagcta cacttcctaa atttggaatg gagtggttta   12720
gcttatgaaa agttgctatt tttcttaaca ggttataagc aatgccttga aagtttgggg   12780
tttagaacta atcctgttca acagtccaga gtatcagagg ctcaggatcg atcctatgta   12840
agattctgtt ttgcatttca tacatttctt ttcccaaatt tgatttttaa agttgtaatt   12900
tcttaaagaa gagaaataca ttttgaatac ttttgttttg atgttccctg tttcattcac   12960
tcagactttc ctatttcacc tttgtgatgt ccatgagcat ctgccctgta gccttcctgg   13020 cacccccagtg tctgtggcag cacagagctg accccataag tggtgcatga ggccatcttg   13080
tggcacagca tcactaagct gctgcagaga cgttcatatg gttgtgtgat cttttaaaaa   13140
catcagtgac acttaactat aaatataatc ttaaattatc acaaatttta tataatattt   13200
gccagtagac aacataaata tgaattcaat atttcaagtt aatattgtct gttttctttt   13260
ttagaaatga aagatcattt atatgcaatt ataaggaaca ctggtttaca gttagaaaat   13320
taggaaaaca ggtaacattt cttaccctct cttgtctttt tttcttatat tgtaccccat   13380
ttaaaactaa aatgtgggcc aggtgtggtg gctcatgcca acagtttggg aggctgaggt   13440
ggggggatca cttgaagcca ggagtttgag accagcctgg gcaacaaagg gaggtcctgt   13500
ctcttaaaaa aaaaataaaa ataaaaataa aataaaataa aaaaaaaaac aaagagccag   13560
gcatggtggc tcacatctgt aattccagct tacttggaag gctgagtcag aaggatcact   13620
tgagctcagg agtttgaggc tgcagtgaac tatgattttg tcactgtacc ccagcctggg   13680
tgacagagta agactgttct ataaaacata aaaataaaaa aaatatattt aaaaattaaa   13740
aaaaaaaaag gattgctgac tttaaaatta ggaaactgac cagtaatgtg tgtgtgtgta   13800
gcatggttta tccttcttga tagatagaaa ttgtcatttt aaaagataat atcagttttc   13860
cttataaatt tatttgtgac aagtatatgc aatttaacta tatcataaga aaattctat    13920 attaaagata atacaaatgt ggttactttt aagtgggttt ttatgtgatg actatgttct   13980
gtcagttaat tattacattt atagatttgt atttagcata gtgctgtcac aaagcctgaa   14040
atagtgtcaa gcatgaataa agcattcaat tatgtttgct ttagtgtaag attattcatt   14100
atgattccaa aagccatgta atacgtacgt ctacagaaaa tcacttctat ttttttaaata   14160 aaacatgaaa tatgtcttga gcaagctatt ttaagaaaca atcatttaac gtccttgtta   14220
ttagaatttt gaatctttga aagagggtta ttgaaaacca gctaggacag taaaaaagaa   14280
taaactagtg atacatgcag caatatggat gaatctcaaa ataattatgc tgaaagaata   14340
acccacaaac aaaatactac ctgctgtatg gtatcattta ttaaaagtct agaaaagtgc   14400
agattcatct gtagtgatgg aaagcagatt gaccagcggt tgcctgggga cgagaaggct   14460
atggaggagt gagaggggag ggttacagag aggcacggga acatggcaa tgaggaatgt    14520 gttcactatc ttggttgtag taatggtttc atgggagtac agtatacaaa tgtgaaaaca   14580
tttcagaggc cagatgcagt ggctcatgcc tgtaatccca gcacttttgg aggccaaggc   14640
aggaggattg cttgagctca aggagttcag gaccagcctg gcaatggca caagacccca    14700 tctctaaaaa aaaatgaaa gaaaaaaaaa ttggctaggc gtggtgatgc atggccgtag    14760
tcccaggtgc tagggaggct gaggagggag cacagaggtc aagcctgcag tgaatcatga   14820
tcgtgctact gcactccagc ttgggtgaca gaaggagatc ctgtctcaaa aaaaagttt    14880 caaattatac actttaaata tgtgcagttt attatatgtc acttataccc caataaatct   14940 gttttttttta aaatgtaaat acaagccaaa aaaggtataa gtcaagaaaa tatattgaat   15000
taaatctgta agagataatt caaaaacaaa aaccctattg ttatctttta agtcacccaa   15060
```

```
atcaaatttg ggaaaagtca cctacttagc ttcatcctaa gttggttctt tctttctttc    15120
tttccttctt ttgagacgga ttcttgctct atcgcccagg ctggattgca gtggcgggat    15180
cttggctccc tgcaacctcc gccacctggg ttcaagcaat tctcttgtct cagcctccca    15240
aatagctgtg tctacagcca cgcaccacca cacccagcta ttttttgtat ttttagtaga    15300
gacggggttt cgccatgttg gtcaggctgg tcttgaactc ctgacctcag gtgatccgtc    15360
cgtctctgcc tctcaaagtg ctggggttac aggcgtgagc caccatgccg agccctaagt    15420
tggttctttc ttaaagttct tcctgaggag ccaagagcaa gttaaggaga tgtaacctag    15480
aagcttacag tggaggctag ctgggtgcag tggttcacgc ctgtaatccc agcactttag    15540
gaggctgagg caggagatc actgaggcca ggagcttgag agcagcttgg cccaacacag     15600
tgacaccttg tctctacaaa aaaaaaaaaa aaaaaggca gcttacagca gtagaggctg    15660
atgcgagtgg gaatcacctc taggtaaaaa ccagtgtagc gtactgctga gattatttaa    15720
cctctgggtt ttatttatgt gttttaaaa attatgatcc agtattttt acttttttt       15780 gtataaagta agcactgaat ttttaaggtt gtattaattt gcaaataaat gtctatctta    15840
ttattttgag agatttaaaa aatttagttt cttcaaaatt gcattttcac attttgaatt    15900
acgttatctt tgacaaatac agaagatgtc aaattttggt ttattttctt tggttctaat    15960 ttatatttt gttaaaaact atattttca ctatagactc tttctgtctc tcgaggtccc       16020
tgtataatga aaagaaggc tggaaaaagt attaacattg tcaaaatcca ggaaaagtag     16080
ttggtcatga tattgatcgt taactttaga aacttttgt atcttgtggg ttaaattagg      16140
attactatgt ggtagtgata atgatgtta attagggccg agtgcagtgg ctaacacctg      16200
taattccagc atgtagggag gctgaggtgg gaggatgtct tgaatccagg agtttgagac    16260
cagcctgtac aacatagtgt aagacccctt ctccacacaa aaaaattaga aaatttgtca    16320
agcatcttgg tgcacacctg tagtcccagc tgcttgggag gatgaagcga gagaatcact    16380
taagcccagg tgttcgaggc tgcagtgagc tatgattgca ccactgcact ccagactaga    16440
tgaccatctc ttttaaaaaa atgtgtttat atgttatatg tgatagtgct ttttaaaaac    16500
atttttaaat tatagagaca gggtctcact atgttacagc ccaggctggt ctcaaattcc    16560
tgggctcaag caatcctccc accttagcta acctcccaaa gtgctcggat tataggcatg     16620
agctgcatgc ccagctaatt tagtgatttt taaaaactga gctggtaatt ataaattctc     16680
ttcctggaac ttctgacttt ctcacaattg gaatcttttg acaaaaatta tcagtaatgg    16740
gaaaactttg tgtagttgtc attttcctc ccatcagtgt gatagatatg attggagtta      16800
tgttggactg atattttgaa aaagattta attatagcta ttaataaaga catttaaact     16860
actgactatg cattttatt cttttgggag ggtttaatgt ttatagttta aagcaaactg      16920 ttgttttaa aaagtatct aacagggccg gcgcggtgg ctcacacctg taatcccagc        16980
actttgggag gccaggcgg gcggatcaca aggtcaagag atcaagacca tcctggctaa     17040
catggtgaaa ccctgtctct actaaaaata caaaaaata gctgggtgtg gcggcgtgcg     17100
cctgtagtcc cagctactcg ggaggctgag gcaggaggat ggcatgaacc cgggaggcgg    17160
agcttgcagt gagccgagat cgcgccactg cactccagcc tgggcgacag agcaatactc    17220
tgtctaaaaa aaaaaaaaa aaaaaaaaaa gagtatttag cagaggccag gtgcagtggc    17280
tcatgtttgt aatcccagaa ctttgggagg ctgaggcggg cggatcattt gaggtcagga    17340
gtttgagacc agcctggcca atgtggcaaa tgtgctgtct ctaactaaaa atacaaaaat    17400
```

```
tagctgggtg tggtggtgca gacctgtagt cccagctact tgggaggctg aggcaggaga    17460
atcacttgaa cctgggaggc agaggttgca gtgatccgag atcatgccac tgcactccag    17520
cctgggttac agagtgagac tcttctcaaa aaaaaaaaaa agtatttaat agtgataaat    17580
ctgcagtatt ctcttgtagt ttttaagatc atattattca gtcaaagaaa agagctcaac    17640
ttgaaatatt tccagagttt aaacaatctt actaagcttt gatgggttgt atctattctt    17700
aacatgtgaa acttccttat tacctataat atacactaac ttaaatattg acaattttt    17760 tccagtggtt taacttgaat tctctcttga cgggtccaga attaatatca gatacatatc    17820
ttgcactttt cttggctcaa ttacaacagg aaggtaagta acggctgaac attttgtaat    17880
gttacctttc gaagtagtta ataaccagg cacattagat gacagtgtga taaaactgtt    17940
tttctggcag tggcagtgaa acaatcttta gttttgacgt ggtgataggc tgtgatttgg    18000
gtgacgctgt tcagttagag ttctcactga cacctggccc ttcctcttct gaggatgctg    18060
ctttctttgc agcccttcta agtaatggct ttttctttta tacatcacat atcacacggc    18120
tgagaggagg gatagatgtt tttcttcttt gcctcttcta ggccactgtt cttccttata    18180
aactccagtt tctttgaaat acatgcccct aacggctggg cacggtggct cacgcctgta    18240
atcccagcac tttgggaggc tgaggcaggc ggatcacgat gtcaggagat cgagaccatc    18300
ctggctaaca cggtgaaatc ctgtctctac taaaaataac aaaaaattag ccggggtgtg    18360
gtggcggacg cctgtagtcc gagctactcg ggaggctgag gcaggagaat ggcgtgaacc    18420
caggaggcgg agcttgcagt gagctgagat cgcgccactg ccctccagcc tgggcgacag    18480
agcgagactc cgtctcaaaa aaaaaagaa agaaaaaaa aagaaatac atgcccctag    18540 attaaactat cccttgtcct tttgcactca tccacaagtc tcttttcatc agtgatttta    18600
ggatctgact cgttgtcttt ttctctactt caactacttt tatcattctt aattatttct    18660
gtatcgtcaa tcaatccagt acctgcctct tagtttcaaa atcacttact cttgcttagc    18720
tattaccagt aatcataacc actgtcaaat ctcaattgca agcatattac tctttaacta    18780
ccacctccta tctttaaacc atgttttgtc tgttttttta ttccagccat tctttaaacc    18840
ctactgtggg gcccaagcat ttcctttata cgcattcttc ctttcttcta ctgcttattt    18900
tctgtaatcc gtcatcataa tcactccatt gcattcttca acgtgtttcc cctctctccc    18960
tccatcatac ttgaatgaca aaaatctcaa ccctggttaa accacatctt ggccttgtcc    19020
attcctgtac cagagtagct ggacgtggct aaaaaataac ataaacatg atgattggtt    19080 ttactttttt cttaaatgat ctatccatcc attcacccat ccatctatca aagtgactag    19140
gcctatttct gaagcccagg ctggagtgca gcagcataat cacagctcat tgcagctcca    19200
aactcctggg ctcaagtgat tctcttgcct tagcctgttg agtagctggg actacaggct    19260
tgtgctacca cacctagcta aggttttact ttaaatttat tataatcaca aaattcagat    19320
gagcctttag tgctgtctga tatttctact atgttttctt agtgatgtac cacccctcca a    19380 ggtgtttata aaaaattatg taccactctc caagaagttt ataaaaaata atgtgccacc    19440
ctccaaggtg actaatttca cagcttatgt ctttaaacct ttaagcactt tcctctccct    19500
tacacacctt ccttgtggct ttccgttaca ttctgctgag aacatagaag caattaaaat    19560
tatgttcttt ctaccagcaa atttatcaat ttgcttatat cttcacctgt gctttgagcc    19620
tatttaaata gatgaatggt cccctacctc taaccaaaac cagtccctca cttgtgggct    19680
ggatcccagc tcttctcacc tactcaagat gttcctgctt tcatctctcc actctcttat    19740
ataatcagtt ccccccccct ttttttgtaa tattcctata agcagtaaaa taagcttttt    19800
```

```
atttccattg attaaaaata aaaatcctct cttaattcca tgaaactcca gctgcctccc    19860 cattttatt ttttccttag gattgtctct agtgtgcctt ctccttttct tgaactctgc    19920
ctcctgggtt caagcgattc tcctgcctca acctcccgag tagctgggat tacaggcgtg    19980
caccaccatg accggctaat ttttttttt ttttttgag atggagtttc cctcttgttg    20040
ctccggctgg agtgcaatgg cgtgatctcg gctcaccgta acttctgcct cctgggttca    20100 agcgatttc ttgcctcagc ctcccgagta gctggattta caggcatgtg ccaccatgcc    20160
tggctaattt tgtatttag tagagatgga aggggtttct ccatgtttgt taggctggtc    20220
tccaactcct gacctcaggt gagccgccca cctcggcccc ctaaagtgct gggattacag    20280
gcatgagcca ctgcgcctgg ccccggctaa attttttttt tttttttttg tattttagt    20340 agagacaggg tttcaccata ttggccaggt tggtctcgaa ttcctggcct cgagtgatcc    20400
acctgcctca gcctcccaaa gtgctgggat tacaggcgtg agtcaccttg cctagccatc    20460
ttttagtaat ggtatttgga gatcacaatt tgagtgctgg catgcttatt gctgctgggt    20520
ttgttatgta gttattgtga attcacattt aggaatatag gttttttaat tctttgattt    20580
tagatacttg tatctttttt cttttatatt taaaaccttg gttcctgatg atatcccttc    20640
ttagaaaccc tgtctacctt tggccttcag cccaccatgc tgtggttttc ctaacttgct    20700
gcctgcactt ttcagattcc tttcatggat cttaaatatc atctgtaaat aagatctatg    20760
tgtcaataat taccaaactt ttatctttag tcttgacatc taccctgaac acctagcttt    20820
gactaactcc tagctttggc atctccactt ggaaatccaa aaagtgtttc aaactgaaca    20880
tgtctatgaa agacttattt ttttctctct atccatgcta tccatcaggt tttccatttc    20940
cataagggtg actcttgtac tctggttcct atatattata ccgacagagc agcccagagt    21000
gcttcttaac cagtgtaagg cctgttatgt cccaccctca ctctttgtcc ttcagtggct    21060
tcccagcaca cttagaataa aatctgaagt cttaggccgg gcttggtggc tcatgcctgc    21120
aatcccagca ctttgggagg atgaggggggc agatcacttg aggtcaggag ttgatgagac    21180
cagcctggcc aacatggtga aaccctgtct ctaccaaaaa atacaaaaat taactgggtg    21240
tggtgttgtg cacctgtagt cccagctact cgggaggctg agataggaga atcacttgaa    21300
cccgggaggc agaggttaca gcgagccaag atcataccac tgcactccag cctgggtgac    21360
agaacgagac tctcaaaaaa aaattaaaaa aaaaaatat gtgaagtctt gaataaaacc    21420
caagatcttt accatggccc ctgaacaggg cagagtatcc attcttcaga cactcttcat    21480
agaataccat ggtgagctgg catatttatt atacaataca gaaacaattt tactggcaga    21540
aaacacatta aaccgtctaa actctgaata cagttgtcct cataaaaaat gttcaacata    21600 ctatttgag gttttccatt aatagttctt ataatctttg tcccattatg tgttaatcca    21660
acaaaggata tccaataaca aacaccaaag tttaagaaaa atgtgctagg cgcggtggct    21720
cacacctgta atcccagcac tttgggaggc cgaggtgggc agatcacctg aggtcaggag    21780
ttcgagacca gcccagccaa catggtgaaa ccctgcctct cctaaaaata caaacattaa    21840
ctgggtgtgg tggtgggtgc ctgtaatccc agctactcag gaggctgagg caggagaatc    21900
gcttgaacct cctgggaggc agaggttgca gtgagctaat attgcaccac tgcactccag    21960
cctgggtgac agagtgagac tccatctcaa attaaaaaaa aaaaaaatt aatgatagag    22020 aaacttaaat cagttagatt gttttaggta tagcccatcc ttggttttg tgtgtagcat    22080 ctagcttggg gaaaccctgg atttctggaa tcatatttag acacagtcac actagactaa    22140
```

```
tgtaattctt ttgggatgca aaccacacgt ttgacacctt aaatagcttt taggtatttg   22200
gcttcccagc ccctattttt agttacaagg ggtgtacatg tgtgggtcag ggtgggggta   22260
gctctttccg cagatgatta gttttagcca tgttactagt tattgcacac attatctgtg   22320
tcctcacagc agccctgtga gtaagtgtat tagggttctc tagagggaca gaactaataa   22380
ggtagatgta tatatgaagg gtaatgtatt aaggagtatc gactcgtatg atcacaaggt   22440
gaagtcccac aataggctct ctgcaggctg aggaaccagg aagccagtcc aagtcccaaa   22500
acctcaaaag tagggaagct gacagtgcag ccttcagtct gtggcaaaag gcctgagagc   22560
ccctggcaaa ccactggtgt aagttcaaga gtccaaaaga tgaagaactt ggagtctgat   22620
gtttgagggc aggaagcatc cagcatggga gaaagatgaa ggctcagcaa gtctagtact   22680
tccacactct tatttctgcc tgctttattc tagctgagct ggcagctgat tagatggtga   22740
ccacccagtt tgagggtggg tctacctctc ccagttcact ggcttaaatg ttaatctcct   22800
ttggcaacac cctcgcagac acacccagaa acaataattt gtagccttca atccaatcaa   22860
gttgataata ttaaccatca caggaaggta ctagtatcat atgtttaaca gtagaaacca   22920
agacaaatgc agctaggaag tgggagaact gggatcagat gcaggcagtc tgattctaaa   22980
tcagttgctg ttacccactc tgacaacagt aagtgagtag cctgctcagt caagtactat   23040
attagtaggg ccctttacag acatatttat ttctcacagt cactcaatga gacggctctt   23100
ccagtcttac aatggagaaa gtgaggctca gagactttaa gtaacttacc ttagacgact   23160
ttactagtaa gtataagaat cattatttgg actaaagtct ttctgaatcc tcagcttgta   23220
tttttttcca gtgttctgtg ctgccttttt atctactagt gttttacatc aattttgaat   23280
ctctttacta actggttagg ttgattttg cctttttttt ttaggttatt ctatatttgt   23340
cgttaagggt gatctgccag attgcgaagc tgaccaactc ctgcagatga ttagggtcca   23400
acagatgcat cgaccaaaac ttattggaga agaattagca caactaaaag agcaaaggta   23460
aaaatgaggc ctgcagtatg gaatatatgg tagtatttca ttatgagaat taaattttca   23520
tgcttagatt gaatatgtgg tccttgtgtt gttggcgact ctattttgga ccttatattt   23580
tagtgaagtt tattagttta aacttgaatc aactctttga aatacttaaa tatattaact   23640
tagttagctg gtatggtata ttcctagcac ttcgggaggc tgaggcaggc tgattgcttc   23700
aacccaggag ttcagacca gcctgggcaa catggcaaaa cctcatctct acaaatagta   23760
caaaaattag ccagatgtgg tggtgtatgc ctatagtccc agctacttgg gaggcagagg   23820
aagaaggatc acctgaaact gggaggtag agactacagt gagccataat cacactaccg   23880
cactccagcc tggtcgagag agtcagaccc tgtctcaaaa aaaaaaaaa aaagaaacgg   23940 aaaaaaaaaa cttagttgga ttcaaattgc aacacaatca ttatattact agagcttatt   24000
tgccagaaaa cattttaagt tttgacttac ttaaagcctt tacattacaa atgcctttat   24060
gttatgtcta aaatagaaga ttggttgcag ttattaccag tgcttttgtt ctttagagtc   24120
cataaaacag acctggaacg agtgttagaa gcaaatgatg gctcaggaat gttagacgaa   24180
gatgaggagg attttcagag ggctctggca ctaagtcgcc aagaaattga catggaagat   24240
gaggaagcag atctccgcag ggctattcag ctaagtatgc aaggtaaaga cattctgatg   24300
tgtgttgtat tcattgctga agaattgatt ccaattattc ttagatttca tggaagttaa   24360
tgtactctta gaggtgtttt gacaattact gcagaagcaa tagctatata gtgggctttc   24420
cctttagatt tcttataatg gaaatcactt tttacaacct atattttatt aggagtagtt   24480 atattttac tcctggttat tttatttggt ttcaacactg tactaacaca atagtaaatt   24540
```

```
gtggttttaa tctttgtggg tatcagttga cccttatcca aatcagctgt tacataaata  24600
tgtgccatta gacactatgg aagggcctgg acagggaata taaactgatt ttacaaaaac  24660
ccaacattta ttggctatgc aacttaaacc gtaagcccac tttggtgggc ccagtttttt  24720
agtgatataa actatcaata gagaaaagcg aaaacatatc ccctagacaa tctaggcaaa  24780
gaaaaatgtt aagacatagc tcaaagtagc ttaattaaaa gtttgaagtg ggttttttgt  24840
tttatttttt tctaactcat atgtatttgc ttctactttc taatgaaatt atttatcagt  24900
tgatttcctt agatatctaa ataaaattga aatttcatta atgggaagat tattttttatc  24960 ctgaactttt cttgcctcta tgcatgcctc tgagtactcc atatggtgtg caatcccatt  25020
tttgattaat agagtcctgc tggattagca gggacagaaa tcagctttag atttcttttct  25080 tttttttttt tctttctttt ttttttttt tttttttgag tcagagtctc actgtcgccc  25140
agcctggagt gcagtgatct tggctcactg caacccctgc ctccgaggtt caagcgattc  25200
tcctgcctca gcctcctgag tagctgggac tacaggcgcc taccaccacg cccagctaat  25260
tttttgtact tttagtagag atagggtttt gcccttttgg ccaggctggt cttgaactcc  25320
tgacctcagg tgatccacct gccttggcct cccaaagtgc tgggattaca tgtgtgagcc  25380
accacgccca gccagaagag tagaatattc ttaaagagaa aacgttttaa aggcttactc  25440
aaatgagtat aaacaaacat attgttgctt gaattggtaa atacagtgat tggttttttgt  25500 tgtgttgtgt tttgttttca ggtagttcca gaaacatatc tcaagatatg acacagacat  25560
caggtacaaa tcttacttca gaagagcttc ggaagagacg agaagcctac tttgaaaagt  25620
aaagtagttg gtacaagtta aagtagcatg tttaatattt gctttggcta ttttgtctat  25680
ttgtaaatgg ttactgcctg aatcctgtga atatttgaat gtatttttta aaaatttaca  25740
gcaaatagga cgggcacggt ggcttacgcc tgtgatgcta gcagtttggg aggccaaggc  25800
gggcagattg cctgaggtca ggagttcgag accagcctgg gcaacacagt gaaaccccat  25860
ctctactaaa aatacaaaag aatcagctgg gcatggaagc gtgcgcctgt agtcccagct  25920
gcttgggagg ctgagccagg agaattgctt gaacccggga cgtggaggtt gcagtgagcc  25980
gagatcgcac cactgccctc cagactgggt gacagagtga gactccgtct ccaaaaatat  26040
atgtatatat ataaataa aataaaaat ttacggcaaa taacatgaaa caaaaaaacc  26100
ttgccccaat actggataaa ttttttaaac tgagtgaagg aaaccttata aaatttcatt  26160
tattaaaaga aaaatgaaat taggacaaga caagaagaat gccaattgat cctttggatg  26220
tacttcttgc ttacctgatt aaccctgcaa aattcctcta ccaatcagta cgaaaaacag  26280
ctttggaggt atgggagcgc attcccaaat agacgtggta gttcatttag ctgctcatgg  26340
ccgcttcagg cagtcctgta agcctgttag catcagggga atggatgcaa accataaatc  26400
tggatcaact cctaaaacct taccttgtgc ccagccttgt aagtgcttgc taaataggaa  26460
ttccaccata tgaaaataca ttcttttcaa gtaactatca ttcagacttt tgtcccccac  26520
tttttttttt taaagaaaaa taaaggctg gcacggtgg cttacgtctg taatcccacc  26580
attttaggag gccaaggcag gtggatcacc tgaggtcagg aattcaagac cagcctgacc  26640
aacatggtga aacctcatct ctactaaaaa tacaaaaatt agccgggcat ggtggtgggt  26700
gcctgtaatc ccagctactt gggaggctca gacaggagaa tcgcttgaat ctgggaggca  26760
gaagttgcag tgagctgaga taacgccatt gcactccagc ctgggggaca agagcgagac  26820 tcgtctcaa aaaaaagag aaagaaaact tcatgttaaa gattacaaga taaataatca  26880
```

```
gacccactga tcctaggtca gaaaacagag tcatagctca atctgactta ctatttgctg    26940
tatttcatcc attctgagat gcacatagtt tcacatttca atgtctctga aattgagaag    27000
catcttacag tcataattga cagtatatta gcagcaccta taaatattgg ctcattttac    27060
atttgatggt ataatgaaga aaatatttac ctttttttct gttttgtttt taagtcacaa    27120
ctcagaagta gatgaaggaa aattctgatc agctgacatc ctcttaatgt gagatatttc    27180
tagtctttat tcagtataga ttaatggcta attatatgtt aaatttcaaa gtagtgctta    27240
ttagtgcttt ttacttttaa gtttcaaaat taactttttt attataataa actccaaatt    27300
tatacaaaag tagaaaaact agcatactcc tgtttatgac ccagattcaa caaatactag    27360
cacacggcca atcttgcttt tttttttttt ttttttgag atggagtctt gctctgttgc     27420
ccaggctgga gtgcaatggc acaatttctg ctcactgcaa cctctgcctc ctgagttcaa    27480
gcgattctcc cacttcagcc tcccaagtag ctgggattac aggtacacac caccatgcct    27540
ggctaattct tgtattttta gtagacacgg gatttcacca tgtcgtccag gctggcctta    27600
aactcctgac ctcaagtgat ccacctgcct cggcctccca gagtgctggg attacaggca    27660
tgagccactg agcccggccc aatctcgttt tataatactc ccatctccca ttctttccac    27720
tgtcccacct gcaagtttgg attattttgt aacaaatctc aatcatcata ttattctata    27780
accatttta a tatgtgtctc taaaatatat tagctttatt tttaacatag ttaaatgcta    27840
ttgtcataaa ataataatca taataattaa ttgtaattct atatcatcaa ttatctagtt    27900
aatgtaaaaa ataaatctaa ggccaggcgc ggtggctcac acctgtaatc ccagcacttt    27960
gggaggctga ggtgggcaga tcacctgaga tcaggagttc aagaccagcc tgaccaacat    28020
ggagaaaccc catctctact aaaaatacaa aaaattagcc aggcgtggtg gcgcatgctt    28080
gtaatcccag ctacttgaga ggctgaggca ggagaatcac ttgaacccgg gaggcgaggt    28140
tgcggtgagc cgagatcgtg ccattgcact ctagcctggg caaaaagagt gaaactccat    28200
ctcaaataaa taaataaata aataataaaa aataacttaa atctacttaa ttagaaaaac    28260
taacattcta aaaatttat tttaagaaat atcaaaattg gctgggcacg gtggctcacg    28320
cctctaatcc ctgcactttg gaaggctgag gtgggcggat cacctgaggt caggagggtc    28380
aggagtacaa gaccagcctg gccaacatgg cgaaaccctg tctccactaa aaatacaaaa    28440
attagccagg catgatgatg ggcacctgta atcccagcta ctcaggaggc tgagacagaa    28500
gaatcgcttg aacccaggag gtagaggttg cagtgagctg agatcacccc actgcactcc    28560
agcctgggtg acagagtgaa actccgcctc aaaaaaaaaa aaaagagaaa agaaatatag    28620
aaattaaagc atacatggcc aggcgtagtg gctcatgtct gtaatcccag cactttggga    28680
ggctgaggca ggcagatcac ttgaggccat gagttcaaga ccaacctggc caacatggcg    28740
aaagcctgtc tctactaaaa atacaaaaaa attagttggg catggtggtg cacacctgta    28800
atcacagcta ctttggaggc tgaggcagga gaatcgtttg aacccagagg tggaggttgc    28860
agtgagccga gattgtgcca ctgcactcta tcctgggtga cagagcgaga tactgtctca    28920
aaagaaaaa  aaaaggctg  ggcgcggtag ttcatgcctg caatcccagc actttgggag    28980
gccgaggcag gcagattacg aagtcaggag atggagacca tcctggctaa tacagtgaaa    29040
ccccgtctct actaaaaaat acacaaaaat tagctgggtg tggtggcagg cacctgtagt    29100
cccagctact ctggaggctg aggcaggaga atggcatgaa cccggaggt ggagcttgca     29160
gtgagcagag atcacaccac tgcactccag tctgggcgac agagcgaggc tctgtctcaa    29220
aaaaaaaaa  gaaagcatac tctcacctcc ttcagtgact gatgttagta ttttggcaca    29280
```

```
ttcttttttct gtgacatata cacacttacc ttgtaagtgt tgtactcatt tcctatgaca   29340
gtaaatagtc tttgtaacag gctgcatgat atttcataaa atgaatggat gtggcataat   29400
ttatatgtga gccttttgaa ttctgctatt ataattaata ttgcaatgaa caattcttat   29460
attgcctcta cacctcaaat gtcttatcat ttcttctagt ttttctgagg atgtcagatt   29520
attgggttaa aggatatgaa cattttttaag gccttggaac agatttctaa attgctttcc   29580
agaataattc ccatgtgata ctttcaccat gtttatttca gactttttt tttttttttt    29640 tttgagacga aatctcactc tgtcacccag gctggagtgt agtggcatga tctcggctca   29700
ctgcaacctc cgcctcctga gtttaagcga ttattctgcc tcagcctccc aagtagctgc   29760
ggttacaggc aagtgcctcc atgcctggct aattttttgtg tcttttgtag acatggggtt   29820
tcaccatgtt gcccaggctg gtttcgaact cctgagctca ggcaatctgc ctacctcggc   29880
ctcccaaagt tctgggatta caggcgtgca ccaccgcgcc cagccatcag agtctttttt   29940
gtcaaaataa aatggtctaa agacatacat catagagaaa ctataataca aaatttacag   30000
gtatatctaa gaaaagaaaa gtatatttaa agcataaaaa taaactgctc ttttacttaa   30060
aattttttaa aaactggatt aaaaatatga aacttccaac aaattgagct ttttttttt     30120 tttttttctt ttttgagacg aggtctcgct tttgtcaccc agtctggagt gcagtggcgc   30180
gatctcggct cactgcaacc tccacctccc tggttcaagc aattcccctg cctcagcctc   30240
ccaagtagct gggattacag gcgcatgcca ccacgtcggg ctaattttt tgtatttta     30300 gtagagaggg ggtttcacca tgttggccag actggtctcg aactcctgat ctcaggcaat   30360
ctgccagcct gggtctccca acatgctggg attacaggca tgagccactg cactcggcct   30420 gaactttta tagtagtaac gataattcag taatgtccaa taatgactaa gtaagttata    30480
acaagtacaa tgtcagcaat aactagtgct ttttagtaaa cagggtcagg caaccttgta    30540 ccctttaaa aatgttcgaa tatcgatata cctccttcct acttggtgga ggattgattg    30600
aggaggaaag tgtgcagtga tggttaccag cttcagcctc ttggcttgac tttgcaaata   30660
ctggtgagaa tttggaaaga gcttgagaat atcttacata gtcacatgtt gctgagaaga   30720
gttaagaact aacttcttga tgttcatttt taacaatggc ttgcattcaa aaccttgtag   30780
agctcattag taggagctaa gaagctaata tttgcctttc actaaaattc ctgattactt   30840
agcctaggta gttcgttgtc tctctaggtt ctgtctttgg gagcttgggt ctaaggttat   30900
caagctaact cttcttccc tctcacccctt cccaaattga ccctggtgct gatttgttat   30960
tcatacgatt ttctagttt ctttttccct ttttgagtat ttgaagcttc atactgaata   31020
tagtaatcat agtattcatg cataaagaaa atcataaagt aattgcataa atgcataaag   31080
taatcatagt tttcatgcat taaaaaaact agttttggct gggcgctatg gctcacgctt   31140
gtaatcccag cactttcgga ggccaaggca ggcgaatcat ctgaggtcag gagttcgaga   31200
ctagcctggc caacatggcg aaaccctcttc tctactaaaa atacaaaaaa attagccgag   31260
tatggtggcg ggcgcctgta atcctagcta tttggcaggc tgaggcagga gaatcacttg   31320
aacctgggag gcagaggttg cagtgagccg aggttgtgcc attgcactac agcctaggcg   31380
acaagagcaa gactccatct caaaaaaaaa aaaaaaaaa aaaaaactcc ctattacaga    31440
ttcataattt atgagtcatt aaataatatt ttcaagccat gacattttt ccagcagtag    31500 tctctaaatc tgtttaccaa tcataaaacc ccaagcaaaa ctctactaca tcagctgtgt   31560
cactgtaaaa cctgccttaa ctcacagaag catgaaatta agcaatgtgt gtgaaactat   31620
```

```
tttataaact gtaaagtatt ccatacatac atgttggcag ttattaatgt cttctctagg    31680
tgtggctttg aaatggatgc agatgctttc tgttacaaaa aacataagtt gcaaatgttc    31740
tataacaagg agagacacaa atatcttcat ggacatggat tgctatgagt gtttgattgc    31800
ctaatacttg agccaccact tcagtgatat ggtataattt atcaaacagt gttgagaaac    31860
agaaactact ggggatgttt taaagaggaa aatacttaat atagaaatta ggggtttaca    31920
taatcttaag aaaggatgaa ggtgcagctc ttagccaggc ctccacagta ccacaaacca    31980
acttgcagga agagctgtaa ccactgcccc agttgggaca atgggtaatg aggatattaa    32040
atttaagaac atactgctat agcaatgatc cttggcatag aaagctgcca ccacaattgc    32100
ctagagatgg gaacatgaag tctggccccc attgcaacag cagtgaagca gaattttggg    32160
actggcatct cccaaatggc tttgcttgcc accagagaac aaccaaagtg gagggagatg    32220
gctaggcctc atttctgcct attttatttt attttttgag acggagtctt gtctgtcgcc    32280
caggctggag tgcagtagtg tgatctcggc tcactgcagc ctccgcctcc cagcttcaaa    32340
caattctcct gcctcagcct cctgagtagc tgggattaca ggcacccgcc actgtgccca    32400
gccaattttc ttattttag tagaggtggg gttttgccac gttggccagg ctggtcttga    32460
actcctgacc tcaggtgatc tgcccgcctc agcctcccaa agtgttgtga ttacaggtat    32520
gagccaccat gcctggccca tttctcccctt tttttttttt tttttttttt gaggtggagt    32580
ctcactctgt tgcccagact ggagtgcagt ggtgcaatct ggcgcattg caacctctgc    32640 ctcccagttt caagcaattc ttctgcttca gcctcctgag tagctgggac tacaggtgtg    32700
tagcaccaca cctggctaat ttttgttttt gttttgtttt ttttgagaca gagtctcact    32760
ctgtcaccca ggctggagtg tagtggcatg atctgggctc actacaacct ccgcctcccg    32820
ggttcaagca attctcctgc ctcagcctcc agagtagctg ggattacagg tgtgcgccaa    32880
cacacctggc taatttttt gtatttttaa tagagatggg gtttcaccat gttggccagg    32940
ctggtctcga actcctgacc tcgtgatccg cccgcctcgg cctcccaaag tgctgggatt    33000
acaggcatga gccaccgtgc ccagacaagg tttgtatttt tagtagagac agttttgcca    33060
tgttggccag gctggtcttg aactcctcac ctcaggtgat ccgcctgcct ggcctccca    33120 aagtgctggg attacaggcg caagccactg tgcctgaccc gtttctgctt tttaaagctc    33180
atgtgagcac ttaatttgta accagaatcc tacttgtaaa ataatctaag acatgtagct    33240
tttagctttg taacctctat aatattgatg gcacagtggg agtggatgct gagtaccact    33300
tgaacatgtt ccacctcagt gtcttcacag ctggaaggtg tctacattgt ttcaaggtgg    33360
acaattgatt tacttctcat ttttcataaa ctaaaagtag aataaaggct attcctctaa    33420
aattgctatc tcacctgtca ctcccttgca ttctcacata ccttcttgag tggaggggca    33480
gagggcatgg agtgatagca gatgtgccag gaattctcca taactcagtc cgtccctctt    33540
gtgctatgtt gcagcatcag gatttgctaa tgggaggata ctgcccttac gtgcatcatt    33600
agccatgcac actaaggtct tacacctaca cacaggtcag tattctggct cagagaccaa    33660
cagggagaaa ttgcagttct cattagttga actttctta ttgttcacag ttttaaaaca    33720
caaaattgag aggaactcta taaaaaatgt gccattctat taataattgt tgctggtaat    33780
ttaaaaatcc ttgttccttt tcaaattctt atataccttt ttttttaaa cacttgatct    33840 tagccaaaag accgagaagc aatcttttt tttttttttt tttttttaa cctatagctt    33900 ctcactgaga ttgtcagctg tttgtaagtt ttggttttg gttttctgtg tttgtattta    33960
catatatgaa atacagattg agtatcccctt atccaaaatg cttaagactg gaagtgtttt    34020
```

```
agatttgggg ttttttagga tttgtgaata tttgcactat acttaccagt taagcattcc   34080
aaatccaaaa tttcaaatct gaagtgttcc actgagcacc tcttttgagt atcatgttgg   34140
tgctcaaaaa gtttctgatt ttggagcatt tggatttctg attctcggat ttaggatgct   34200
tgacctgtaa tttcagattt acataaaagc agaaatagta cacagagctc cttatatcct   34260
tcacccagat tccccaatta ttggcctttc tgaaccattt gggaataata tgcagatatg   34320
attttccatt atgtctcagt tgttcagtgt atattttcta agtacaagaa tatattccta   34380
catatttaca tgataaccgt catgtttaaa cattttaaaa tggggatttg tattacattg   34440
tttctctttt tgaaaaaatt acagaggagc ttaatgcaat cagtattact taaaatctga   34500
taatgtgtgt taaatagtag ttttcattta tttcatttat caggtgttca gtgaatgctt   34560
actatgtaac agcacagtta tcagcactgg ggaaatagat gagtaagata agatttgcac   34620
tttcattagc ttacatgcca taaagaggga aataaagaga acaccagatg atgataagtt   34680
tatgctgaga attaaaatga agtgatgaaa taatgggaat gtcaggtggc tactttggt   34740 gggatggtca ggaaaggcat ctctggggag ataaatttta agctcagacc tgagtgaaaa   34800
gaatgagcca gccatggaaa cattatgtta actcacatgg tagtttgaaa tgctttatct   34860
gatcaaaggt acttattttt ggtgactttc aacaatatta agggtctata aaccaacact   34920
catttgcata agaataacta ccagtgaatc tttttgtatg ataggttttt tgtttgttgt   34980 tttttttgaga cagagtctcg ctctgtcgcc caggctggag tgcagtggcg cgatcttggc   35040
tcactgcaac ctctacctcc ccggttcaag tgattctcct gcctcagcct cccaaagtag   35100
ctgggattac aggtgcctgc caccacgcct ggctaatttt tgtattttta gtagagatgg   35160
ggtttcaccg tgttgtccag gctcgtgtca aacttctgac ctcaagccat ccacccgcct   35220
cggcctccca aagtgctggg attacaggtg tgagccacca ctcctggcca tgataggtta   35280
ttttgtgatg aaaataccta cctcttaatt tgtctgataa atttaaattt tatgtctaga   35340
tttcctaaga tcagcacttc catattttaa agtaatctgt atcagactaa ctgctcttgc   35400 attctttaa taccagtgac tactttgatt cgtgaaacaa tgtatttcc ttatgaatag   35460 tttttctcat ggtgtattta ttcttttaag ttttgttttt taaatatact tcacttttga   35520
atgtttcaga cagcagcaaa agcagcaaca gcagcagcag cagcagcagc aggggggacct   35580 atcaggacag agttcacatc catgtgaaag gccagccacc agttcaggag cacttgggag   35640
tgatctaggt aaggcctgct caccattcat catgttcgct accttcacac tttatctgac   35700
atacgagctc catgtgattt tgctttaca ttattcttca ttccctcttt aatcatatta   35760
agaatcttaa gtaaatttgt aatctactaa atttccctgg attaaggagc agttaccaaa   35820
agaaaaaaaa aaaaaaagc tagatgtggt ggctcacatc tgtaatccca gcactttggg   35880
aaaccaaggc aggagaggat tgctagaaca tttaatgaat actttaacat aataatttaa   35940
acttcacagt aatttgtaca gtctccaaaa attccttaga catcatggat attttttcttt   36000 ttttgagatg gagtcttgct ctgtcaccca ggctggagtg cagtgtcgcg atctcggctc   36060
actgcaagct ctgcttcctg ggttcatggc attctcctgc ctcagcctcc tgagtagctg   36120
ggactacagg cgcccgccac atcgcctggc taatttttg tattttagt agagacaggg   36180 tttcaccatg ttagccagga tggtctcaat ctcctgacct catgatccgc ccgcctcggc   36240
ctcccaaagt gctgggatta caggcgtgag ccatcacgtc cggccagaaa tcatgaatat   36300
tagtaggtga aaaataaaca catttttacca cctggaaaat gaaaaatact tgagtataat   36360
```

```
ctaaataaca atgggaagtg cagagttact ttccaggtct cggtttaaat atgtcttaaa   36420
ctttggccaa ttagtagtag aagttgagag aaaaagtaac tatctgacaa agaaattata   36480
agcagaatat ataaagaact cttaaaactg aataatcaga aaacaactca ataaaaggt    36540 gaaggatttg aaaagatatt tcaccaaata agacatagg atgacaaata agcacatgaa    36600
aagactctca gcatcactag tcacagggaa atgcacgata aaaccacagt gagacaccat   36660
ggcacccctg taggtatggc tttaatgaag aaataaaact gacaatacca agtgttggca   36720
aggatccaag cagctgagac tcatatactg ttaatgggaa tgtaaaagtg tacagctttg   36780
gaaaacagtt tggcattttt ttgataaatg tatacttagc catgtgatcc agcagtccca   36840
atcatgtata tataaccaaa agaaaagaaa acttaggttc ataaaaaac ttatatcaaa    36900 tgcttatagc tgaccaggca tggtggccca tgcctataat cccagcactt tgggaggccg   36960
aggttggcag atacctgaag tcaagtgttc gagaccagcc tggccaacat ggcaaaaccc   37020
tgtctctact taaaatacaa aaattagcca ggcgtgatgg caggcacctg tagtccagct   37080
attcaggagg ctgaggcagg agaatcacgt gaacccggga ggcagaggtt gcagtgagcc   37140
gagatcgtgc cactatactc cagcctgggt gacagagcaa aactctgtct caaaaaaaa    37200 aaaaaaaaa agggctggac acggtggctt acgcctgtta tcccggcact ttgggaggcc   37260
aaggctgatg gatcacctga ggtcaggagt tcaagaccag cctggccaac atggtgaaac   37320
cccatctcta ctaaaaatac aaaaatttgc tgggcatggt ggtgggcacc tgtaatccca   37380
ggaggctgag gcaggagaat cacttgaacc cgggaggcgg agattgcagt gagccaagat   37440
tgtgccattg aactccagcc tgggtgacaa gaccaaaact ccttctcaaa aaaaaaaag    37500 attatagcat ctttattcat cattgcccaa aattacaaac tgcctaaatg tagaccttca   37560
tttagttaat gaatgcacaa actgtggtat atccaaacaa ttgaataaaa aaaggaatga   37620
actggtactt ttttctattc ctcctgttta agtacagcca aaacacctca acatttgtat   37680
aaaacatgag ctgggctggg tgcggtggct cacacgtgta atcccagcac tttgggaggc   37740
tgaggcgggt ggatcaccta aggttgggag ttcaagaccg gtctgaccaa catggagaaa   37800
ccctgtctca actaaaaata caagattagt cgggcatggt ggcgcatgcc tgtaatccca   37860
gcttcttggg aggctgaggc aggagaattg cttgatcccg ggaagcgaag gttgcagtaa   37920
gctgagattg caccattgca ctccagcctg gcaacaaga gcaaaactct gtctcaaaaa    37980 gaaaaaaaa accattcagc tgaatctcaa aggcagagag aagacagact ggctagggac    38040
cttgaaccca gaggagcagt gtggtgggga gtggactgga ttttcttttt gcctcattta   38100
tcctggactt ggtgctggag aagctatggg ttcagaccaa gagaaaccc catgaaaagc    38160 ctgctctctc tagccaaaag aggcaaccta gcaagataaa aacctttaga taataagcac   38220
ttgactccag tcaaacaaaa cagaataaac tggccccatt caccctgtc agcaaaggcc    38280 aagtgggagc caagatatgt accccaacct ggaagtcata aggtacactt ctcccctttc   38340
ccagccaagg tggtgttaga gaaggctgac tggggagctg ggattctcat tccctccagg   38400
aggtgataac actcctttca catggtgtca gtggtcacag ggaggctgaa cttccaccca   38460
gtaatacata ggcatctctc tggctcctat atgggtgatg ttggagaaga ggccgagtag   38520
agaatccaga ctgttgctga cacccagcag taacaaggac acctccacaa tgtccgtgga   38580
ggccatgtgg agatcagtaa caaggcactg ctctccctcc cagtcagaga gatgtcagtg   38640
gaggactagg gggctagaac tcccatgtgc gttcagcagt aatccccatg accgccactc   38700
cttgacatca caggccttga agaaacctgg actttcactc ccctctggtt gtagcgaggt   38760
```

```
ggcactccct tttccctgtt gccagtgctg tgtcagtgga ggcttgctaa attggaagat   38820
gtaaataaga ttcacattct cataacataa taccccaaat tttcaggatt taattgaaaa   38880
tcactaagct gggcatggtg gctcacacct gtaatcccag cactttggga ggccaaggtg   38940
ggccaaacac ttaaggtcag gaattcaaga ccagcctggc cagcatggtg aaaccctgtc   39000
tctactaaaa atacaaaaat tagctgggcg tggtggcaca tgcctgtaat cccagctact   39060
gggaaggcta aggcaggaaa atcactggaa cctgggagac ggaggttgca gtgatccaag   39120
atcgcactag tgtactgcag cctgggcaac agagcaagac tccatctaaa tttgtgtcag   39180
gattcccaga aggagatgag aaagggtggg gctgaaaaaa attgaggaag aagtcatggc   39240
tgaaaatttc ccaaatttgg caaaagtcag aaacctacag attgaaaaag ctgaatgaag   39300
ctcaaatatg ataaactcaa agaagttcac acagagacac atcacagtca gatttctgaa   39360
cactgcagac aaaaaatgaa gatctcgaaa ttagcaagaa atgaccttac ctaagcaatt   39420
tgaatgacag cagatttccc atcagagatc ataaaggcca gaaggaaggg gtacatacaa   39480
cattttttct agtgctgaaa gacaaaaact ctaggctggg cacggtggca cacacctgta   39540
atcccagcac ttttggaggc tgaggcaggc agatcacctg aagtcaggag ttcgagacca   39600
gcctggccaa catggggaaa ccctgtctct actaaaaata caaaaattag ccaggtgtgg   39660
tggcacgcac ctataatcct agctacttgg gaggctgagg cagggaaatc gcttgaacct   39720
gggaggcgac ggttgcagtg agccaaggtc gcgccactgc actccagcct gggcagttga   39780
gcgagactcc atctcaaaaa aaaaaaaatt atccaggctt ggtggtgggc gcctatagtc   39840
ccagctactt gggaggctga ggcaagagaa ttggttgaac ccaggaggtg gaggttgcag   39900
tgagccaagc tcatgccact gtactccagc ctgggtgaca gagcgagacc ttgtctcaaa   39960
aaaaaaaaaa aaaaaaaaaa acaagaaaaa aactctaaac ccagagttac atatccagtg   40020
aaatatcctt caggagtgaa gggaaaatta acgatttgtc ttcaggagac ctaccctaaa   40080
agaatggcta aaggaatttc tctaaacaga aaagaaatga taaagaagt aattttggaa   40140 catcaggaag gaagaaagaa caataaaaag agtaaaatat gggtaaacac aatagacttt   40200
cccctccttt tgaattttct aaattgtatg atggttgaag caagaattat agcactgatt   40260
tggttttcag tatatatatt ggaaatattt aaggcattat gttacagatg aaggagggtc   40320
aaaggatata aagggaggta acctttctat atttcttttg tactgatgca ggcactttgg   40380
aaaataattt cactatttgt ttaaaaactg aacataccct gaccatatga catagcatct   40440
atactcctgg gcatttatcc cagagaaaca gaaatttatt tattttttttt ttagtattac   40500 actccgtaag tgctgtaata ctagcactta gggaggctga ggcaagcaga ttgcttgagc   40560
ccaggagttc aagaccagcc tgggcaatgc tgcacagtca aaaagaaaaa acaaacattt   40620
agaaaactat tttaaagtc tttaattgct gaatgcctct ttggctaata tttggaagat   40680
cattattatt attttcttt tttaggcaga gtcttgctct gtcactgagg ctggagtgca   40740
gtggcgccat ctcggcttac tgcaacctct gcctcccggg ttcacgccat tctcctgcct   40800
cagcctcccg agtagctggg actacaggcg tgtgccacca tgcccggcta atttttttgtg   40860 ttttagtag agatggggtt tcactatgtt agtcaggatg tctccatct cctaacctcg   40920 tgatccgccc acctcggctt cccaaaatgc tgggattaca ggcgtgagcc actgtgccca   40980
gcctggaaga tcattatttta gtcctacaac tgacacattg ttccactgac gcaattgccc   41040
aggctggtct tgaactcctg ggctcaagca atctgcctgc ctcggcctcc ctaagtgcta   41100
```

```
gtattacagg cttgagccac tgtgcccagc caaaaataga aatttatatt ctcacaaaaa   41160
catgtacatg aatgtttata gcagctttac ttgtcataat caaaaactgg aaacaaccaa   41220
aatgtcctac agtgaaacaa actgtagtac atccatagca tgtaatactc tactgtcagg   41280
attaaaaaga aacccactgt tggcacaggc agcaccgtgg ctggatctca ggggcattat   41340
gctgagtgca aaaaagcctc aaagggtctt acactgtatg attccacttg ttcaactaaa   41400
aatgacagct gtatagagat agagaacata ttagtggttt ccactagtta gagaaagtgg   41460
gtaaaagata ggtgggtggg aatataaatc gatagcaggg agatctttgt ggtattataa   41520
cacttctatg tcttgattgt agtggtggtg gttacatgaa tacacgtgtg ataaaatgcc   41580
atgtagaact acatataacg ttgtgccaat gtcaatatct aggttttagt ttgatcttta   41640
gttacataag atgtaactat tgggtgaaat tgggcaaaag agtacacgaa acctctctta   41700
aatatcttta caacttcctt tgaattgaca gttttttcaaa atagaaagtt gggttttttgt   41760 aaatacatga attgttgata tacacaacaa atctcaaatg cattatgcta cgtgaaagaa   41820
gccatattca aaaggctaca tacctactga tgccttttat atgacgtgca ggaaaagata   41880
aaactgtagg acagagaata tactggtggc tatctgggat taggaaatgg ggatcgacca   41940
caaaggggca gcatggggga attttctggg gcaatggaat ggttgtgtat cttgatggtg   42000
tatttgtcaa aatatataga actataaaag taaattttgc tttatatgta ttaaatcaaa   42060
aaaagaaact cgtgctcaaa tagaaataca ttttctgaga acttgccttt tgatgacttt   42120
gagaattttc tggaaatttt aaagaaatgt ggttttgttt cccaacaggt gatgctatga   42180
gtgaagaaga catgcttcag gcagctgtga ccatgtcttt agaaactgtc agaaatgatt   42240
tgaaaacaga aggaaaaaaa taatacccttt aaaaaataat ttagatattc atactttcca   42300
acattatcct gtgtgattac agcatagggt ccactttggt aatgtgtcaa agagatgagg   42360
aaataagact tttagcggtt tgcaaacaaa atgatgggaa agtggaacaa tgcgtcggtt   42420
gtaggactaa ataatgatct tccaaatatt agccaaagag gcattcagca attaaagaca   42480
tttaaaatag ttttctaaat gtttcttttt cttttttgag tgtgcaatat gtaacatgtc   42540
taaagttagg gcattttttct tggatctttt tgcagactag ctaattagct ctcgcctcag   42600 gcttttttcca tatagtttgt tttctttttc tgtcttgtag gtaagttggc tcacatcatg   42660
taatagtggc tttcatttct tattaaccaa attaaccttt caggaaagta tctctacttt   42720
cctgatgttg ataatagtaa tggttctaga aggatgaaca gttctcccctt caactgtata   42780 ccgtgtgctc cagtgttttc ttgtgttgtt ttctctgatc acaaccttttc tgctacctgg   42840 ttttcattat tttcccacaa ttcttttgaa agatggtaat ctttttctgag gtttagcgtt   42900 ttaagcccta cgatgggatc attatttcat gactggtgcg ttcctaaact ctgaaatcag   42960
ccttgcacaa gtacttgaga ataaatgagc atttttttaaa atgtgtgagc atgtgctttc   43020
ccagatgctt tatgaatgtc ttttcactta tatcaaaacc ttacagcttt gttgcaaccc   43080
cttcttcctg cgccttattt tttcctttct tctccaattg agaaaactag gagaagcata   43140
gtatgcaggc aagtctcctt ctgttagaag actaaacata cgtacccacc atgaatgtat   43200
gatacatgaa atttggcctt caattttaat agcagtttta tttttatttt tctcctatga   43260
ctggagcttt gtgttctctt tacagttgag tcatggaatg taggtgtctg cttcacatct   43320
tttagtaggt atagcttgtc aaagatggtg atctggaaca tgaaaataat ttactaatga   43380
aaatatgttt aaatttatac tgtgatttga cacttgcatc atgtttagat agcttaagaa   43440
caatggaagt cacagtactt agtggatcta taaataagaa agtccatagt tttgataaat   43500
```

```
attctctttta attgagatgt acagagagtt tcttgctggg tcaataggat agtatcattt    43560
tggtgaaaac catgtctctg aaattgatgt tttagtttca gtgttcccta tccctcattc    43620
tccatctcct tttgaagctc ttttgaatgt tgaattgttc ataagctaaa atccaagaaa    43680
tttcagctga caacttcgaa aattataata tggtatattg ccctcctggt gtgtggctgc    43740
acacatttta tcagggaaag ttttttgatc taggatttat tgctaactaa ctgaaaagag    43800
aagaaaaaat atctttatt tatgattata aatagcttt ttcttcgata taacagattt    43860
tttaagtcat tattttgtgc caatcagttt tctgaagttt cccttacaca aaggatagc    43920 tttatttaa aatctaaagt ttcttttaat agttaaaaat gtttcagaag aattataaaa    43980
ctttaaaact gcaagggatg ttggagttta gtactactcc ctcaagattt aaaaagctaa    44040
atattttaag actgaacatt tatgttaatt attaccagtg tgtttgtcat attttccatg    44100
gatatttgtt cattacctt ttccattgaa aagttacatt aaacttttca tacacttgaa    44160
ttgatgagct acctaatata aaatgagaa aaccaatatg cattttaaag ttttaactt    44220 agagtttata aagttcatat ataccctagt taaagcactt aagaaaatat ggcatgtttg    44280
acttttagtt cctagagagt ttttgttttt gtttttgttt tttttgaga cggagtcttg    44340 ctatgtctcc caggctggag ggcagtggca tgatctcggc tcactacaac ttccacctcc    44400
cgggttcaag caattctcct gcctcagcct ccagagtagc tgggattaca ggcgcccacc    44460
accacacccg gcagattttt gtattttgg tagagacgcg gtttcatcat gtttggccag    44520
gctggtctcg aactcctgac ctcaggtgat ccgcctgcct tggcctccca agtgttggg    44580 attacaggca tgagccactg cgcctggcca gctagagagt ttttaaagca gagctgagca    44640
cacactggat gcgtttgaat gtgtttgtgt agtttgttgt gaaattgtta catttagcag    44700
gcagatccag aagcactagt gaactgtcat cttggtgggg ttggcttaaa tttaattgac    44760
tgtttagatt ccattttctta attgattggc cagtatgaaa agatgccagt gcaagtaacc    44820
atagtatcaa aaagttaaa aattattcaa agctatagtt tatacatcag gtactgccat    44880
ttactgtaaa ccacctgcaa gaaagtcagg aacaactaaa ttcacaagaa ctgtcctgct    44940
aagaagtgta ttaaagattt ccattttgtt ttactaattg ggaacatctt aatgtttaat    45000
atttaaacta ttggtatcat ttttctaatg tataatttgt attactggga tcaagtatgt    45060
acagtggtga tgctagtaga agtttaagcc ttggaaatac cactttcata ttttcagatg    45120
tcatggattt aatgagtaat ttatgttttt aaaattcaga atagttaatc tctgatctaa    45180
aaccatcaat ctatgttttt tacggtaatc atgtaaatat ttcagtaata taaactgttt    45240
gaaaaggctg ctgcaggtaa actctatact aggatcttgg ccaaataatt tacaattcac    45300
agaatatttt atttaaggtg gtgcttttt ttttgtcct taaaacttga tttttcttaa    45360
ctttattcat gatgccaaag taaatgagga aaaaactca aaaccagttg agtatcattg    45420
cagacaaaac taccagtagt ccatattgtt taatattaag ttgaataaaa taatttat    45480 ttcagtcaga gcctaaatca catttgatt gtctgaattt ttgatactat ttttaaaatc    45540
atgctagtgg cggctgggcg tggtagctca cgcctgtaat cccagcattt gggaggccg    45600 aagtgggtgg atcacgaggt cgggagttcg agaccagctt ggccaaaatg gtgaaacccc    45660
atctgtacta aaaactacaa aaattagctg ggcgcggtgg caggtgcctg taatcccagc    45720
tacctgggag tctgaggcag gagaattgct tgaaccctgg cgacagagga tgcagtgagc    45780
caagatggtg ccactgtact ccagactggg cgacagagtg agactctgtc tcaaaaaaaa    45840
```

```
aaaaaaaatc atgctagtgc caagagctac taaattctta aaaccggccc attggacctg    45900
tacagataaa aaatagattc agtgcataat caaaatatga taattttaaa atcttaagta    45960
gaaaaataaa tcttgatgtt ttaaattctt acgaggattc aatagttaat attgatgatc    46020
tcccggctgg gtgcagtggc tcacgcctgt aatcccagca gttctggagg ctgaggtggg    46080
cgaatcactt caggccagga gttcaagacc agtctgggca acatggtgaa acctcgtttc    46140
tactaaaaat acaaaatta gccgggcgtg gttgcacaca cttgtaatcc cagctactca    46200
ggaggctaag aatcgcatga gcctaggagg cagaggttgc agagtgccaa gggctcacca    46260
ctgcattcca gcctgcccaa cagagtgaga cactgtttct gaaaaaaaaa aatatatata    46320
tatatatata tatgtgtgta tatatatatg tatatatata tgacttccta ttaaaaactt    46380
tatcccagtc gggggcagtg gctcacgcct gtaatcccaa cactttggga ggctgaggca    46440
ggtggatcac ctgaagtccg gagtttgaga ccagcctggc caacatggtg aaaccccatc    46500
tctactaaaa atacaaaact taagccaggt atggtggcgg gcacctgtaa tcccagttac    46560
ttgggaggct gaggcaggag aatcgtttaa acccaggagg tggaggttgc agtgagctga    46620
gatcgtgcca ttgcactcta gcctgggcaa caagagtaaa actccatctt aaaggtttgt    46680
ttgttttttt ttaatccgga aacgaagagg cgttgggccg ctattttctt tttctttctt    46740
tctttctttc ttttttttt tttctgagac ggagtctagc tctgctgccc aggctggagt    46800
acaatgacac gatgttggct cactgcaacc tccacctcct gggttcaagc gattctcctg    46860
cctcagcctc ccaagtacct gggattacag gcacctgcca ctacacctgg cgaatatttg    46920 tttttttag tagagacggg cttttaccat gttaggctgg tctcaaactc ctgacctcag    46980
gtgatctgcc tgccttggcc tcccaaagtg ctgggattac aggtgcaggc caccacaccc    47040
ggccttgggc cactgttttc aaagtgaatt gtttgttgta tcgagtcctt aagtatggat    47100
atatatgtga ccctaattaa gaactaccag attggatcaa ctaatcatgt cagcaatgta    47160 aataaccttta tttttcatat tcaaaataaa aactttcttt tatttctggc ccctttataa    47220
ccagcatctt tttgctttaa aaaatgacct ggctttgtat ttttttagtc ttaaacataa    47280
taaaaatatt tttgttctaa tttgctttca tgagtgaaga ttattgacat cgttggtaaa    47340
ttctagaatt ttgattttgt ttttttaattt gaagaaaatc tttgctatta ttatttttc    47400 caagtggtct ggcattttaa gaattagtgc taataacgta acttctaaat ttgtcgtaat    47460
tggcatgttt aatagcatat caaaaaacat tttaagcctg tggattcata gacaaagcaa    47520
tgagaaacat tagtaaaata taaatggata ttcctgatgc atttaggaag ctctcaattg    47580
tctcttgcat agttcaagga atgttttctg aatttttta atgcttttt ttttttgaa    47640 agaggaaaac atacatttt aaatgtgatt atctaatttt tacaacactg gctattagg    47700 aataactttt taaaaattac tgttctgtat aaatatttga aattcaagta cagaaaatat    47760
ctgaaacaaa aagcattgtt gtttggccat gatacaagtg cactgtggca gtgccgcttg    47820
ctcaggaccc agccctgcag cccttctgtg tgtgctccct cgttaagttc atttgctgtt    47880
attacacaca caggccttcc tgtctggtcg ttagaaaagc cgggcttcca aagcactgtt    47940
gaacacagga ttctgttgtt agtgtggatg ttcaatgagt tgtatttaa atatcaaaga    48000 ttattaaata aagataatgt ttgcttttct a                                  48031
```

<210> SEQ ID NO 43
<211> LENGTH: 300019
<212> TYPE: DNA
<213> ORGANISM: Homo sapiens

<400> SEQUENCE: 43

```
gatgtcccga gctgctatcc ccggctcggc ccgggcagcc gccttctgag cccccgaccc      60
gaggcgccga gccgccgccg cccgatgggc tgggccgtgg agcgtctccg cagtcgtagc     120
tccagccgcc gcgctcccag ccccggcagc ctcagcatca gcggcggcgg cggcggcggc     180
ggcgtcttcc gcatcgttcg ccgcagcgta acccggagcc ctttgctctt tgcagaatgg     240
cccgcttcgg agacgagatg ccggcccgct acggggagg aggctccggg gcagccgccg      300
gggtggtcgt gggcagcgga ggcgggcgag gagccggggg cagccggcag ggcgggcagc     360
ccggggcgca aaggatgtac aagcagtcaa tggcgcagag agcgcggacc atggcactct     420
acaaccccat ccccgtccga cagaactgcc tcacggttaa ccggtctctc ttcctcttca     480
gcgaagacaa cgtggtgaga aaatacgcca aaaagatcac cgaatggcca tatccttttg     540
cccgaacccc agcagcagct gcgcctcccc ctcctccctc cgcctcccct cttccaggct     600
gggagagaga cccgggggtt gatgggaggt ggggaggagg ggggtcttcc aggggctggg     660
agaggggca ccggaggag tgtgaaagaa tctctccacc ccgagctggg ttgagctacc       720
ctggaggctt gggaatgggt ttgtgggggg ctggggggtg ggcagcggag agtggatcct     780
tcccaaggac cgactctaga atgagatctg gggcctgggg tcgtgcagga gccttggtgg     840
gggctttcga gccaagtccg gagggttttgg agttctacgg agtgagcttg gagcgggctc    900
gggcctgggc gcttctggcc agggcagggg aactatgggg gccttggttg ggttttcttg     960
gccgtcgctc actggagtcc acgcagggga agctggacag cctctccact actgctttcc    1020
ccaaggtggg gggccgccgc acttttaggg cagggcgctt gggggctccc agggctaaga    1080
gcaagaggga gtccatgtgg ccttcacact gagaagccag cactggccga agtgagtacc    1140
ccagggtggg ccgctgttcc tatctggaga ggatagtgat gggctggggg gcgcttatgt    1200
ttccctcatg tgtgcaggtc ccattgcctt taaccgctga ttggggaacc tcatcatctt    1260
tgggggtgtc gagaaagaga tcccacttgc tttatctggg cccctggcct gggaagacct    1320
gatctggaca ctttcagtaa gaaagacagg gcaacagcaa atgaggtggt gggtccattt    1380
tagagcacca tgtccagctt ttcctacccc gagtagccga gagggaacac caggagaatc    1440
agcacccatg tggacatctt aggtaggtaa atgccttttta aatttttttt tttttaatca    1500
aagatccaga ggaaaaaggt gaagcccaca ttttcttctg tggagatgct atcaaaatgc    1560
agatcttctg tgtttcttta aatccctgcc tgcttgaaat aaaccttgag gagggcttaa    1620
catctatcga gatgtaggca ggcaagggtg ggtaattagt cgggctttct agcagttatc    1680
taagcatgac ccagattcca ggaggggga cacaccctgc tgcccaggct ggctggccac    1740
tgtgccatgc ccagatgtgc cgcttctccg cacagttcca accagctgcc ctctgtgtaa    1800
aaatgaacgg gctggatggg tccctggggc tcagcgatga gtcccctatc ccttttgtat    1860
gtggttttgc agttatagac taaacggggc tgggccctgt gtggtctccg ggggttgctg    1920
tttgaggagc atggcgggtg gtagagggac tcacttcagg ggggttcaaa atcgagcctg    1980
gcgcttggat cctgggtgct gggattgcaa cagagggcac tgaggttttg gagtgtgtga    2040
gtggtctact ttgagggtgg ggaaaattaa gaagttcagc agaggtgctt ttgaggggag    2100
catacctcta actacgatgc catctccgtt ggtgcccaaa gcaggtgcca ggtctttgct    2160
tcctaagttt cagactctta aagaggctgg ttcttaaggt tagcaattcc tcaccatccc    2220
aggcccattg aagtgctcag gggtggcttg attactctgc ctatcaacag agtgaggagt    2280
```

-continued

```
gggagtgcct tgcaggagga cagggtattc atgggtgcac acccagttag ctccaggagt    2340
gagagggctt tgctcggctg acaggtttcc tcattgaaaa tggctttaga tcgccttctg    2400
gagcctggat ttggagactt ctaagaggaa aggaaggagg tggggagccc ttctgctgtg    2460
tccttagctt acctctgtcc agcctgaatc ctgcagattg gagggctgtt ggggagagg     2520 gggattgcag tggcccctcg aaggggggaa tcgtgggaga gggaggcagg tgaattgcga    2580
gtgttgcttg ccacttcatc tattctctgg ccagctcgcc cggggctttc ttgctcttat    2640
gatgagtttg tgcattatgc tctctgcaga ctgttttttgt tctctttgac ccgaggtaac   2700
aaacacatta tacagcccta ctctggaagg gaaaactccc cacctcacaa tctgtcatcg    2760
agctgggtca tccaggactg agctttctct gtcctggatg gagcggaggg cggtggcggg    2820
gtgggtggga gggttggaga tgagagggga tggacagaga cctggggagg gaggtagtga    2880
ataaaagaat tcaggccagt gtaaagagaa agacacgtgg aatgtcagag tcacgatacc    2940
agggcagaac attctacttt ttaatctaaa tatttctgcc attaaaaaaa aatgtttcag    3000
catatcctga gagtgaaaaa aaaagtgtgt aggtacttaa ataaagtcta atatatgtac    3060
aggcaagtac atatattcag atgcatagat ttttacaaaa tgaacacacc cacgtatcca    3120
gcacccaggt cccgatcagt gccctggaag tccccctccc cataccgcct cctagttgct    3180
cccccaacaa gggtaccgct cacctgactt ctaaggttca ttttgcctct tttaaacatg    3240
taaatggagt cacacagtac gttcttttgc cactggcttc ttttgctcac atctgtgtat    3300
gtgactctac tacaatctat ccattctact gttgatgggc atttgtgtca tttctgtttg    3360
tgccactggg aacattcttg tgtcttctat tattttttttc ccacagttct cttagatagg    3420
agtggaatcg cccctgctac ttttttgatgc atgtgttgtg ggatgtgtat ttggaaatgg    3480
tgttgactaa ggggttgcagg tcgatatgga aagcaggttc ctccctgtct tgtttaagag    3540
aagtgagtga atgatccatg aacttgtcgg tatgctcaca gggcctaaga gtgctacttc    3600
caaatgtaaa ttctggcatg gtacactggt gaaggatgca gtcttgctttt ctccacactc    3660 ggggcaattt gtcactatga tttcttcctc tttcatccct cagtgggtca aacttgaagc    3720
catcaatgac aattaagaat cctcatttat ttcatttttt cccctcttcc taagtgagga    3780
aacccaaatg gaagtctttg atgttcaaat ttacattgcc gtgttttttct catgccaggc    3840 agcaagccgt cttgaccaca caccttggtt tcatgttttc attgactgga attgtgattc    3900
aaatagggcc atgagggtct ctgatgattg ccgaagagct cagatctgtc agctcaaaaa    3960
ggagcatctg tcagccttcc tagagttccc tccccactta atgccactca ctccttctac    4020
caagtgccaa ggtgaatgtc atctttccag ccctccctgt gccaccaggt ctcccactga    4080
acatgatgta gaaactcagg ccatcggagg aacactggaa gcaggtcagt gtattatcac    4140
gcacagttgc ctgaattaca cgtagaattc cagcttttca tccggtttgc agaaatctta    4200
acaagacacc taaagtcaca ttgacatcag gtgacatcac tttgcatctc gtggacattg    4260
gctgattggc actcctctca tttttttttt ttttttttt tttaagaaaa gctctctaaa    4320
gagaaacttt ctgcatgaga agcgctggga gacatgggag caggttatca gactcttggc    4380
ctgtcctgag agatagaatg ttctagaagg tactgccgta gagggcagga tggtgtcact    4440
tacgtgatcc ttgtactaga ccggcttggc tggtatttcc agaggagcaa aattctgcga    4500
agtaaaattt agcacggctt ttccaatggg agtattttca aaagggtgc aatttcttat     4560 ccacaattcc ccaatccaaa aagctccaaa accaaaagga cgagctcata tagaggtaaa    4620
acctaacctg aactgacttc agtttgaagt cttaatttac agttttcatt cattctactt    4680
```

```
ggtgtgcatt tgagtatgtt ttgcagcaga aatgttagat gtgcttgatg atgaggtgct    4740
gcttcagctc ctgactgtta ggtctgcatt gtagtcctgt caaactttca ggtgtatgga    4800
agttgtcttg ttaacaggat ggttctggtc cagcaggatt tgggtggggt ctgggattct    4860
gcttttctag ctagcttcta gggattcccc atgtggtaag ttcatgggct agggttggag    4920
tatccaggtt agatcataga gacatcttgt tatcattttt cttttcctta aaaatcaggt    4980
ttataggggc cgggtctggt ggttcacgcc tataatccca gcactttggg aggctgaggc    5040
cggtggatca tgaggtcagg agttcgagac cagcctggcc aacatggtga accccgtctc    5100 tactaaaaa tacaaaaatt agccaggcgt ggtattgtgc gtctataatc ccagctactc    5160
gggaggctgg caggagaatc atttgaacct gggaggcaga ggttgcagtg agccgagatt    5220
gcaccactgt actttttttt gagactctgt ctcaaaaaaa aaatagattt attgatgtat    5280
aatttatttg tagcaaaatt cacccttttg acatactggt ctgcaagctt tgacaaatgg    5340
atgtagttgt ggccaccacc caaatcaaga tatgggacag tttcatcaac cctaaaatac    5400
ccccacagtg cccctcttga gtcagcaccc cacttctcca gccccttcaa ccactgatct    5460
gttctccatc cctacagctt tgccttttgc cgaaggtcat ataaatgtaa tttcacagta    5520
tatagccttt tgaatgtgga ttcttttact cagactttga gattcattca tgctgttgcc    5580
tgtgacagta gcgccttcct ttttggtgtt gagcaggatt ccatgatatg gatgaccag    5640 agtttgcttc ccagccgaag gacattggga tgcttccagt ttcaatgatt atgaatagag    5700
ctgctataaa cattggctta tgggttttag tgggaacatt tcatttcata catttcattt    5760
ctcttgggta aattaaccca ggagtgagat tgctgagttg tgtggtaggt gtatgtttaa    5820
ttttataaga ggctctcaaa ctgttttcct aagtggttgt accattttac attcccatct    5880
ttgcaatgcg tctaaaagcc ctgagttctg aattccaaag cacgtctggc ctcgatggct    5940
taggattaag gatgtggatc tatggaaagg agtggaagta atagtgttaa atcccggtca    6000
gagaaataag aaagattaag gatgtcattc aaagctatgt gcctgcacta gagagagaga    6060 aagaagggt tctcttgggt gggttccac ccctccctgg tagttctacc attcccagg    6120 aaaaagtcaa gctctgaggc tgtgagaccc atgatcttta ccctgttctt caccactgca    6180
accccagtgt gtgggacaaa gcaggcgtcc tataaacgtt tgctgagcaa atgagaaaag    6240
gtacctgtct tcacccatta actaaattgt ataacatcta tctgatctac ccttgtgcca    6300
acgttttagg attttgatgg gttttagttg caggggggttg agagactgtc catgagatta    6360
tcagaccaat gaaagtttct gaaatgttag tgcttgagta gattggatgc agcggcccct    6420
tgagaatgaa gtcttcttc agggacttgg agtgggaggc atctgttggg tgcgtagggc    6480
ttatgcttcc ccctccctgt ttccccccca gtagcaagca cacatataca ctttctcagc    6540
aataaaaagc accgccggga aggtggactc catccagaaa tgatcagagc ctaagagccg    6600
tgcagtaacg catttccgag aatgccagct cagctcctga gaaagggcc ggatgggatg    6660 gtgcctgctc tgaaagaggg cagagaggag agggaaaaca ctccggactc tgggtcagac    6720
tggcccaggt tcacattatt caccagccat gttatcttgg caccagagc ctatttcttg    6780 acatgcatga tgaggatatt ccttctagta gcatctccct tggagggctc tcaggagatt    6840
aaatggggtc gtgcgtgaaa aatggccagc acagtctcca gcacagagaa aaaccccaaa    6900
acgccagagc cgtaatacta tggagtcatt taggttccag tgttctttt ttggaaaccg    6960 gccagaaaag aggctttctg ggtgggaatg ggagcgaagt gcccccccc accaccccct    7020
```

```
gcgactggtc agtgtggatt gattaacctg atcgtggcgc tctttaaagc cacctttgga    7080
cattttgcat tctccgttct ctctggaagc tttcagggga aaaaaaattc gtggccactt    7140
gacccatttt tctattccct tgagtctaag gtaaaaatta attctctttc tcctttggt     7200 ccctccctct ctctgtgggt gacaaggtga gggagtttta agtatataaa ttagcttccc    7260
tcttcccctt ttgcactccc tgtctcttcc tttggggccg gtcgagagtg cagcccagga    7320
tggccacccc aggtgtccac tgcaaactcc acagaaaaac tttgctcaac ttttggttta    7380
gaatttaggt accccctcc ccttccaaac tttggtcttc tttctcctca ctccctaaaa     7440
aaataggaaa acaaggaac attcctggcg agggaaccat gagtgggcac agcaacttag     7500
gtttcaaaaa ccactgggcc tcagttctta tctgagtagg gtgacccttc agccagggtt    7560
gcctgggact atcctgggtt tagcatctct ggaaactcac agtcctgggc aaactgggac    7620
gctggtcacc ctaatggtga gttcttaaca cctgagagag aagaatggtg caagagatgg    7680
tgccgttgac caagaagggg ggagagtcag ttacttattc cctctgaaaa gccaagactt    7740
tttattggaa tgaatgcagc ttttagaagc cgtctttaag gcagctaata caagagagat    7800
tccagctatg aagggaaatg cctgagttaa gtccggatca agttttgaca tctcgcttcg    7860
gtcagacacg gctttatctg ccgttcagac tgggagcagc cgtgagtctt ccttaaaggt    7920
gcctgttgct caggcggcac ctgcagttag aaattagcag cctcccaccc ccagccccca    7980
aataacagga ttcaagagtc ccctctctga agccatgagg gaaacccaac ttagtcaccc    8040
acttgccagt aaataatatt catgctgtta agttctgttc tcattttagg cctatgtgta    8100
aaaaatatat gtaattttaa actgattttt aaagtatttt catacgaaca gcatttgcag    8160
gagggcgaag tctggatgtt acctttttgt aaaagtggat ggatttgtct tcaatgagac    8220
tctggggcag acttaaaact tggcccgcag tggtgttaca tggattctga tcttccagag    8280
tctgtcacgt tcttttatct ccatgatctt tattatcttc tttattgaga atgatgggca    8340
tggtgtgtgt gggtgggagg gctatgctga ccatcactgc agtgaaatgt gttcgtggca    8400
tgttgtggcg tctgcatagg aatgtgtctg tttgattaac agcacaagca gtggaggctg    8460
taaggaggaa aagaggaggg aaggtgatat tggatgcagg ggagacatat agagcttggg    8520
aacagtccac cctggctgca aatctcagct ccagctcaca gttgtggagc ctcagtcttc    8580
tcctctgtaa aacggggaca gtagtcctat gtccgaggaa ttgtaagaag gttaaaagat    8640
actgtaccca gaaagcacat ggcatatata atcatcctgt gaagtagcca actcaatgaa    8700
ttttatttta tttatttga gtcagagtct cactctgtca cccaggctgg agtgcagtgg    8760
catgatcatg gctcactata gcctcgacct cctaggctca agcgatcctc ctgccttagc    8820
ctcccgagaa gctgggacta taggcatgca ccaccgtacc cagctttaac aacataaatt    8880
tatatatata tatatatata tatatatata tatatatata tatatatatt              8940 ttttttttt ttttttttt tttttttttt ttgagatgga gtttcattct tgttgcccag      9000
gctggagtgc aatggcgcga tctcggctca ctgcaacctc cgcctcccgg gttcaagcag    9060
gacgatgggc atttgggatg tttctagttt ggggtggggg attgtttgtt tgtttgctgt    9120
tatgaacaat gctgctgtaa ggaatcaata attttgaatg aatgaattcg aggtgttaat    9180
tttagtctgt gtacttggaa atctagcttc acctagaatc agctgagatt catcagcatt    9240
tatggcagga gctaagacat ttcacagctt actcatcatt ttctctaaga ggctgggtca    9300
accggttagc tcttggtcct gcttgtattc tgagagtcag aacctgtggt ttagacactg    9360
gcaattgata tggttgtaga gaagcagcat ggttgagttg agagcatgga ttctggagct    9420
```

```
aggtggctgg ggttcaaatc ccagctctac tagtcactgg ctgcgtgatc ttgggcaagt    9480
cacttaagtg ttctgtgctt cagtttccca gtctgtccca gtggtgattc taatagctcc    9540
atggggatcc taatagctcc tatctgggag gattaaatga gttaatacat ctgatgttta    9600
gagtggtgcc tgacacttag gaagcactat atgtgtttat acatggaaga gtggatagat    9660
ggatggactt atgtgggtgg ccatatttgg gcttctctga tccactgctg agaatagtgt    9720
gtggcacaca gtaggtgctg cataagtgtt aatattctgc tctttcttgc caagtctctc    9780
aactcccttg atctctgtta tttttggcgt ctgtgttgtt aacccattct tctgaatgat    9840
cagctgaatc actgttgctc caatatataa gccaaggaga acacaatcac aaggtctcat    9900
tgattgtcca tactagaatt ccatgattcc taggcccaag taggattttc cccacgtctc    9960
agcaatcctt cttccatgtt tctaatcttt ttctctcatt tgttatgccc cattgccaga   10020
ctctccaatc tccccacagc ttccccttcc tctaactata ctgtctctag tcttaccttc   10080
tccctaaggg caccgtcttt gaagacatca aatacttcag agcaccaaat ataggttagc   10140
ttctctgagg gccttacaag gacatggagt gtttgggtct tacacaaatt ggaatggtca   10200
gaaatgttta gagacttgag ttgtctttga aagagttgtc agaatgcaaa tttttgactt   10260
gtggcctgtt tctgatcaca acgcagtctt ttaagttatg gatcatagct ggatgtttgt   10320
ggtttagagg ggatggaggc atcctctgca gttagtgttg gatgtctggg tggatggatg   10380
gatggatgga tggatggatg gatggatgga tggatggttg aacagatgca tggatgagtg   10440
gatggatgga tggatgggat gaaggaagga aggaaggatg ggtgattgga gggtaggtgg   10500
gtggataagt agattggtag atgactcgat gggtgggtgg acaaatggat gggtgaatgg   10560
atgactggat ggatgactgg atggattggt gtatgagtga atatatggct ggatgaataa   10620
ataggcagat gactagactg gattgagggg taaaaatatg gatgactgga tgggtggatg   10680
agtggatgat agatggttga atgggtgggt ggatgggtgg atgttggata taagggtgta   10740
tggtagggta gctgtctatg tgtgggtctc cctgatattt ggtgttctgt ttgacttggg   10800
aatgaccaag tctctccgct taccacctta tttgtacctt ttccagtatc aagtgaattt   10860
tgcacacttt tgtaaaaatc aataagattg tatgtttagg actttgggag gccgaggcag   10920
gcagatcaca aggtcaggag atagagacca tcctggctaa cagggtgaag ccccatctct   10980
actaaaaata caaaaaatta gccaggcgtg gtggcgggca cctgtagtcc cagctacctg   11040
ggaggctgag gcaggagaat ggcatgaacc cgggaggtgg agcttgcagt gagccaagat   11100
catgccactg cactccagct tgggcgacag aacgagactc catctcaaaa taaataaata   11160
aataaatatt atatgcttag gttttaccta tgtaattaga aagctccttg agggtagggg   11220
acagtgattt gccttcctca catccccca aagttcctgc actatatcat gcataagtat   11280
ttaattgagt aatggtgagg aaagtaaaca gtgttattga acaaagatta ttaaaattct   11340
ggaaacacct ggttttgttt cagcactggg actgaaagtg gaattccttg gattttgctc   11400
cattggtgga taggatagca tgtggtggtg gactggtaga ctctttctct tccaagcaga   11460
ttgggtaaat gccccagatt cttacccact agtcagagat tacagattac tgattgatat   11520
ggtttttctc tgtgtcccca cccaaatctc atctcaaatt gtaataccca catgtcatgg   11580
gagggacctg gtgaaggtga ctggatcatg ggggtgattt cccccatgct gttcttgtga   11640
tagtgagttc tcatgagatc tgatggtttt aaacttgtgt gggcctcttt cctctctctc   11700
ctctcctgct gccatgtaag acgtgccttg ctttcccttt gccttctgcc atgatttgta   11760
```

```
agtttcctga ggcgtcccca gccatgcaga actgtgagtc aattgaacct cttttcttta    11820
taaattactt ttatagcagt gtgaaaacgg actaacacac tgatgtagca aggtccttta    11880
aggccccatg tgatctggtc cctgttttgt ctttgatctc atctctttca ttgtctacct    11940
tcctttcatt gtctattctg tctcagccct gctgaccatt ttactcacac ccatgtcatt    12000
tgcattacat gacattcctt ctgttcagca taagctattt cctctgcctg catcactgtt    12060
tctccaggtc tccccatggc taactccttc tcttcattta ggtctcagcc caaaagttac    12120
ctcctccaag aggcctatcc ttttcattta ctgaacatct catgtacaaa aagaatata     12180 aaatatatgt atactctctc atccacaaaa aaatctctga agacatttta atgtatttca    12240
tcccatacct ttttatgcat gtaaactttt aggaacacat ttccatgcca ctaggtatcc    12300
ttgaaaaaat aagggccacc atgtatagtt gcacaggttg tgcactgcac aaagatagca    12360
tgtcacatat cttaagtatc atggagcttg tatgtctact atttcagtac cccagctgat    12420
aaaagcttaa gtcttgtt ctagcaagat gaagctatta tgacaatttt tgacagagaa      12480 agggggtgttt tgtttaagtt cacaatcaga gaaatgggtg tcttgtttaa tttcacaacc   12540
agagaaaggg gtgtcttgtt taaattcata cagtggtgct gtatgggttg gtggcaaccc    12600
cagaaaagac tgttgttaat atctgataat gttccacttt atacgtgtat tatattcatg    12660
taacaatctc tggctgtttg ttttgccatt ataaataaca gtgcagtaaa catctttgtg    12720
tgtgaatctc tgtccaaggt tctgatagtt ttctgaatga aattcctgtc tatatatggc    12780
actccaagcc cataattgaa actctgctgt taccactttc tttgaatctg tagaaggaat    12840
tttgagaaca ggtgactggt atattcagga tgttgatgac aaggaacaga gaagaacag    12900 ttaaatggtt tggaattttt cctgggctgc atgtaaagca gtgcttttga actgggagca    12960 attttttcccc caaggggact tttggcaatg tctggagacg ttttggttg tcacgaatgt    13020 aggggagggg ggcaagatgc tactggcatc tggctggtag aaaccaggga tgcagttcag    13080
catcttaaaa tgcacaggac agcctttctc agtaaagaat tatccagctc caaatgtcag    13140
taataccaag gttgagaaat cttgatgtaa tcgatgtcat gggtttcttc aagaggagtg    13200
ggtggattta gggttttttgg gtgacttaaa tttaatttac agtttgtctt cctagctggg    13260
tgtctaagcc agctttctgt gaactttaga tcccacacaa gaagcaacag gcttgctacc    13320
gacagattcg ttgatgtaaa tatagatgag tgtatagaag gaaatctcac ccagagctgg    13380
aaaatgttgg aatgaaaact gcggcggcct ccccttctct ctccttcccc ttctgttgcc    13440
ctgtttgaaa atcgtgcctt actttctttg gtctcctggc atggtgaatg ctgctggtat    13500
ggactgtgtt tctatatccc cttgatcccc acacccttag gaacgtacag gagagagacc    13560
ctggagcata tcagcttaga gatggagggg aatgggaagg agtgcgttca ttcattcata    13620
aatgttgact gagcacctac tgtatgctag gtgaatggga ggacgtgagg gcagggaggt    13680
gacaaggttg gcttattctg ggctttgtga actatggtga ggattttgtt ttttttccaaa   13740 ggaaatggaa taaccactcc ttttttcccc ccgatatacc taaactttt gatttttcata    13800 acaaaaatgg gcttcctttt gtatatttgt tttgagacca gccgtttttc caccaacact    13860
gatcacactg cagtgagcat cctggtagag aagtctttgc acacttctgt cactgtttcc    13920
ctaggacaga ttcctggaaa tggtatggca aggttgtatg tcaggctttt gggccaggtt    13980
gcaagaaaca ggaagtctgt gcccttcaa attccaaggt cccctttccc tgacgacgtg     14040
gcccaatcag gcttgccctc ccttgatttt acatcttcac caatcagata agtgaaagtg    14100
aaatcctgtt gtggtatcct gtgcatttct ttggtgactt aagacataga gcatttcca    14160
```

```
gatctctgtg ggctgtttgg atatcctttc ctctgttttc tcaggcacat tctttaccga    14220
tgtctttgag ggattgagca agtttctgtt gaaattgagg catgtcatgg ctctgtgtgg    14280
ggcttgaggc agtccagtgt agtggaggga gggaggctgt ggagcctggc tgcctaggtt    14340
caaataccaa ctctgcttat ttccattcat atcattttag gcaaatcact tagcccctg    14400 ggcctgcctt tcctcatcag taaaagtggt ataacattag tgcctgcatt gtgggtggt    14460 tgtgaggaaa gcagcactca aaacagtacc tgacacacag tgggtgccaa ataagagtct    14520
gatgtattag tgttataggt atcggcctcc tccctcccca gtgcaatagt gtgtgtgcgc    14580
ctctgtgtac ctctgttggt gctgacaagc cctttttaaa atttagaggt gaggtctcac    14640
tctgtcccct aggctggagc acagtggtgc aatcatggct cactgcagcc tcaaccgcct    14700
gggctcaagc aatcctccca gcttagcctc ctgagtagtt gggactatcg gtgtgcacca    14760
ccacacctgg cccttagaca gccccttat ttcaaagcga aatggcagcc acaagattta    14820
gtgcaagctc tccaagcttt aggaccagct gcaactcctc taactgacca aacaggatcc    14880
cccatgtccc caaccccaa aacctgatga aaagcaaaca gaccattttc cacattcatg    14940
acggaaaggc ccttttcttg gctcctgccc ttgctcatgt caggatttca ctccatccct    15000
gataaagagg aagcaccatg tcccaggagg acatggaaac tctctgcttt gtggtgaata    15060
gttacagtaa cagtagctcc tctctgtggg gagcttatga gccctaagc tttatagaac    15120 tgccctggca gtttatgaga acttcatccc agccccaga gctcatggca cttattttg    15180 cccccagttt gcagatgtgc acactgagac tcagagagct aacactgctt gccaaggtca    15240
cacatctagc aaatggagaa actttatgag acaggtgaag gcacagcaag gataaaaacc    15300
cagagggaaa aatactcaag ttttctccgg gaaaccattt gcattccaga gaggttggtg    15360
tgcgagtggg caagagatgt cgcgggacga tggttaaggg acagagtctg agctcaacta    15420
ggactaggtt tcttccttc cttccttcct tcctttcttc cttccttctt cctttccttt    15480
gtctttctct ccctcccttc cttcttcctt tccttccttt cctttctctt tccctccctc    15540 cctccctcc ttcttccttc cttactcctt tccttccttc ctcctttcct tccttcctt    15600 tctcttcccc tccttccctc cctcccttct tccttccttt cttccttcc ttcctttttc    15660 ctttctcttt cctttctttc cttccttcc ttctctcctt cttccttctt ttctttctt    15720 cttttctctt tctttctttc tttctttctt tctttctttc tttctttcct ttctttctct    15780
ctctctctct ttcttccctt ctttctcctt cctccttcc ttcttttctt ttcttttcct    15840
ttcttttctt ttgttttttg agatgggagtc tcgctctgtt gcccaggctg gagtgcaatg    15900
gcacaatctc agctcactgc aacctctgcc tcccggttca agcaattttc ctgccttggc    15960
ctcccaagtg gctgggacta caggcacgcg ccaccacacc cagctaattt ttgcattttt    16020
agtagagatg gagtttcacc atgttggcca agctggtctc gacctcttga cctcgtgatc    16080
ctcctgcctc agcctcccaa agtgctggca ttacaggcgt gagctaccac gcctgggcta    16140
ggactaggtt tctatcggtg gtgtggcttt tgggaagcta cctaatctta accactctgt    16200
ttcgtcatct ataagataag cagtgtagca ttttcttgca ggaatgttgc aaggattaag    16260
tggatggtga ctgtaaaaca tcatgcgtgg cacatagtaa attctcagca ggtagtcatt    16320
gctggtcatt tacttttctc taatgaccag caagctctta atttcctcct tggcatgggc    16380
actgggacgt agatggacaa aacacagaga gaaataaaca cacggacaaa atccccgcc    16440 ctggtgtggc tgatattctg ggtggggaga gagagggagt ccaaggacca gataaacagg    16500
```

-continued

```
taaaggatag tttgagtgtg gtaagtacta aggctcaaaa ataaagatct cccaggtgat    16560
cttagctgca tttggaggtg acaggagata caactgagaa actgagatag gaggaaaccc    16620
aaggggagat gtgggcttga tttagggtga tctgaggagt aggagaagtc aggggctggt    16680
gtggggaggc tctgatggtt ctctctgggg agtgaagcag ggattcgttg gggagaccca    16740
aggggacagg tgaaggcccc tgaacaggtg gccagtgctg agaaaggaaa ggtggaggac    16800
ccaagtgagt tcctaatttc ttcattgctc ccctaaggtg tttgtctcac ccttggccat    16860
agtcttggat cacttacaga tgcagaccag gctgggctca atggcttgtg cctgtaatcc    16920
cagcactttg agaggctgaa cccaggagtt tgagagcagg ctgggcaaca tggtgaaacc    16980
ccgtctctac aaaaaaatac aaaaattggc cgagggtgtt ggcacatgcc tgtagtccca    17040
gctacttggg aggctgaggt aggaggatct cttgagcccg ggagacctat gctgccaaat    17100
aaggtaggca gtagccacac atggctattg caatttaga aattaattac aggccacatg     17160
tggtggctca cacctgtaat cccaacactt tgggaggccg aggcgggcag atcatgaggt    17220
caggagatcg agatcatcct ggccaacatg gtgaaacccc atctctacta aaatacaaa     17280 aattagctgg gcatggtggt gcacacccgc agtcccagct actcgggaga ctgaggcagg    17340
agaattgctt gaacccagga ggcagaggct gcagtgagct gagattgcac cactgcactc    17400
cagcctgggc aacagagaga gactccgtct caaaaaaaaa aaaaaaaaaa aaaaaagaa     17460 aagaaagaa attaattaca ataaaaacag tccctgagtt tcactggcca catttgaagt     17520
gcccgatgac cctgtgtggc ttagtgacca ctgtgctgaa tagtgcagat ctagagcatc    17580
ctactggaca tgttgccagg gtccctgaac caacagaatt agcatctcct gggagcttgt    17640
tggaaatgca gaatctcatc ccctacccca gacctgctca atcccaatct gctcttcagt    17700
gagattcctc aggtgatctt gactgcacct tctaatcact tggaagcttt aaaaatgctg    17760
aggctgggca cggtggctca cgtgtgtaat cccagcactt taagaggcca aggcgggtgg    17820
atcacctgag gtcagaagtt tgagaccagc ctggccaaca tggtgaaact ccatctctac    17880
taaaaattac aaaaattacc caggtgtggt ggcacacacc tgtagtccca gctacttggg    17940
aggctgaggc aggagaactg cttgaacctg ggaggtggag gttgcagtaa gctgagatgg    18000
cactgctgca ctccagcctg ggtgacagag tgggactctg tctcaaaaaa aaaaaaaaa     18060 aaaaaaaaa gaaagaaaa aggaaaatgc tgatgcccca agctccaccc ccacagatgc      18120
tggagagatt tgtccagggc ttcccctgga gtggggaatg tttgaaaact ccccaagggt    18180
ttctaaagtt cagccagagt tagcagaaag cccattaggt ggctaagcag gtagactgaa    18240
gttggagctg tgtgaccttg ggcaagccac ttaccctctc tgaaccacaa gctcccttct    18300
ctctaaaact agagacctgc tggcacctcc ctcccagggc tgtgagaagt aaatgatggg    18360
atgattcaaa gtgctgagta gggtcagatg cagtggctca cacctataat cctagcactt    18420
tgggacgctg aaatgggagg attgcttgaa gccaggagtt tgagaccagc ctgggcaaca    18480
tttaaacatt acccaggtgt agtggtgcat gcctgtagtc ctagctgctt gggaggccga    18540
ggtgggggga tcccttgagc ccaggagttc aaggctgcag tgaacaatga tggtgccact    18600
gcactccagc ctggggaca agagtgagac cctatttcta aaaagaaag aaacccaaaa      18660 tgctgagcga gtgccttgga ttgatagtaa gcagtgcctg tgtaataagc atgaatttta    18720
aaaaatgagg tcagcagcct tagagctaat ggttaatggg tttgggtgtg ggattttttt    18780 tttttttaatt tttaaaacat tgagataaaa ttcccataac ataaaattga ccattaacca    18840 tttttaaagtg tacagtttgg tggcattta tacactcagt gttgtgcaac catcacctct     18900
```

```
ctgtagttca aagaccccaa aaaggagacc ccgtactcac tgagcgctca ctccctgtct    18960
ctccccgctc ccccagcccc tggcaactac taatcttctg tctgtataga ttgacctatt    19020
ctgattttgg gggttttga actcgccttc cctggctgac aacctctcgc catccaggtg     19080
agactgtgtg aaagcccagc tccctgcatt tctgggtctt cctctcccca ctggggctg    19140 cccccacctg tttccccctc tgggcaccct ggttctactc atcagcctgg cttaatccca   19200
gcagcaggtc catgttctgc tctcctgtgg ctgccacaaa tgagaggttt catctcagct   19260
gggtttctcc tagttaaata tttaataaat aagacctaca acttgtgatg ctgggagtgt   19320
ttgatagtga aattaatgat ggggagagag tggcaggcgg cccacaggtc catgctggag   19380
ctgggatgag gcgccctggg caggcgtccg tgccactgat gcttgggaac cacggtgggc   19440
catgccatcc catttccccc agccagggcc tcttttttag cactgtgtcc agcacagggt   19500
agccacctga taaataagtg ttaaaagaaa gagaggctgc gtgtgtaggg aagaaggaag   19560
agacagagga gacaaagagg agacacagag agagagagag agatgagaga gaaagaaaag   19620
tggaaggtga gaaagagaca gagatggaag gggagagaag gacctggatg gaggaagtgc   19680
aaggaaggca atggtgaggg aaaagagaga gagacaaaga tggaagggat gaaggagagg   19740
gagagatatg gaggtagaga aagagagaca gaaagaagag agagaatatt gcttcttgta   19800
tcttcccctt ctcctgttat ccttgaccat cttattattt ttttctttt tctgtctctc     19860 cagttctcat ttccttaccc tcgccgtctt gccaactcgt catctctttt catttcctgt   19920
gtctatgtta tcttttaatt ttctgtctgg gtattttccc cttttctctt tctcagcata   19980
aactgttggt tggtgtatgt gtcttctttc tttttagtc tttaactgac gtgtgtgtgt    20040
atgtgtgtgt gtgagagaga gagagacaga cagacagaga gagagagaga gagacagaac   20100
aaacctagag agcagtgtag gaacatagat gaacatttta aagaccaaac catgaagcgt   20160
acacccattt tacccaggtc aagagccaca gggccaccat cagattctcc ctcatgctca   20220
tcctcaatca cagccactcc ttccctcctg gaggaaccac tattggagat tgtatgggaa   20280
ccattcgctt gctttcttgt gtggttgtac cacctaagta cgcatcctga agcaatatag   20340
tcagatatta tgtggttttg agttttatat gaataaaatc atgtgagagg agttgttttg   20400
tattttgctt cattggtttg cagttacctt tgtgagattt catcctcatt gtggtcactg   20460
cagctccttc atgatcttgt ttattcattg atgatgagca tgtgactttg ttctcttttg   20520
ggcactggca taagcagctt tgttggttgt ttatggattc tgctgctcgc ttgcaggggt   20580
ctctctggag cacatcgctc tgtgtgaaat tgttggatac taagatttgt acattttcac   20640
cttgactaaa cactgccaaa caattttcca aagtgcttgt gctaatttac actcctgccg   20700
gtggtgggtg agcattcaag atgcttcaca accttgccaa cacttggtat tgtcaggttt   20760
ttaagttata gcctttctca tggtgatttc tcattgtgat tttagtttgc atccccgat    20820 tgcaaattag agtgaacata gtttaaaata tttattgact attcaagctt gcttttttgt   20880
gaagtgcctc tacatgctct gtccattttt gattaggtca cttttaaaaa aaaatattg   20940 atttgtgggt gatccttaca tagcctggaa actgattctt catcattata tgttgtgcaa   21000
tattttctct tggcttggct tttgatcttt tttataatgt cttttgatca ccaacagttc   21060
ttaattttga tgtggttgat tttagaaatc ttttcctta gtttgtgg gctttgtatc     21120 ttatttaaga aaatcatttc taccctgagg ccatggatat atttatgtt atttctgaaa   21180 gttttacagt tgtgttcact gtatgtcttt aatcagcttg ggattgattt ttatatgtgg   21240
```

```
tggtaggtag gggtccaatt tccttttat tccataagaa ttgtcccagc atcatttatt    21300
aaaaagccca ttcttgcccc aatgatctgc aagacaacct cttgactgtt taacttttac   21360
cttctttcat ctggtctgtt tttatactca acctttgaag ccacaaatat ttattgagtg   21420
ccaactgtgt gccaggcact gagttacagt gacggatatg acagatgcaa tcatggcttt   21480
catggagttt acagtctggc aaggatgaca tgtaaatagt tattactact tataatttaa   21540
aatgttatag gccttgcaaa aagggacaag tctggcttgc tctaaaagaa acatgtgaaa   21600
caacatcttc cagggaagtg ctgataaact gagtctttag tgggcctctg ctattgtagg   21660
ggtgggaatg gtggaaaaga tgttttggcc cagggaaca gcatgtgcaa aggtcctgtg    21720
gaaggtgctt aggagtttga tatttatcct aaaggcactg tcaggctact gaagcagtaa   21780
tacaatgatt ttatgtctgt gaatagttcc actggttgct gcatggagaa tgtattggaa   21840
tacagcaaga ataaaaagcc atgagaccaa ttaggaaatg atttcactca ttcagggaag   21900
tgtgccttgg gctggcatgg tggctgtgga gatggaaatc attgatcaga ttaaaagaaa   21960
ttttgagctg gcatgatttt tcccctctct cccctctctc tatctctgtt tcttttctgg   22020
ttgtgttttc tgggtgagaa aagcagtttg tgatcctgcc aagggtatgt gctctggagg   22080
atgtatttgc cacagatggt ctttggaatt ctggccaaga gagtcactgg acagcccctg   22140
gcccccaggg tttctggagc caattcaaca atgactgttt attaacaaca gcaaggatga   22200
gttgctagcc tttccttcag agcacctttt aactgttacc ttactttgtt acccaaaccg   22260
acactatgga attggtgggg gagaagtgga agggttttta tctccatttt ttatagaacg   22320
ggggaagtta attggcactc ttgaaatcat acaaaagatg ttggtttcag gattggtttc   22380
tggactttca gcccaatccc aattactcaa gctcacacac ccaatcccca aacatactct   22440
tttgcaaata atttccctac tgaggtgctc ctggccaatt taaaaggtcc ccatttcctt   22500
gcctataaaa tgggaattaa agtaaaaata tctacctgtt gacttgctgt gaggtcagtg   22560
ggcctgacac atggtgtgga ctcattatat ttacctatgt gaatcccta gttccctta    22620 cttggaagag gtggaaaact caaaggggct taaacaagaa gtggggattg tattggctca   22680
tgagactgaa gagtctcagg agtgtccagc ttcaggcttg tttggatcta gggatcagat   22740
aacaccatta ggcctctgtt tctgtttctt ggctctactt tttgcagctg gctccattat   22800
ccatgactta gctgcacttc cagccctcca gtctgcccaa gaccatattc agagagagat   22860
tcttctctct ttttcagcta tcttcccgga attttcagca aatgctttct tgcttttgat   22920
tggctgttgc tgaggtcgtg tgctcatgcc agaaccaatc actgtgggga atgggaggt    22980 ggagaacggg gtgctctgat tggcttaggc ttgggtcaca tgactttatg gagttggggt   23040
ggagccaact tctccaagtg gggaagagca gtcttcttaa aggtgtatta ggatatgctt   23100
gctgctgtaa caagcaaccc ccaagtctgc agtagcttaa ggcaatacga atgtacttct   23160
cactcaccct aaatccaatc agataatcag caagtggcat tccatgtggt gatttcagga   23220
cccggctctt tccatctgtg gctccaccat cccctaagat cagaaagtcc ttcacttccg   23280
gcctgtagga aaagagtatg aaggctcaca caggaagttt tgggaggcca catatagaag   23340
tagtgaacct tacttctgcc tgcattctgt ggactgaat ttcatcccat ggtgtatgag    23400
agagggtccc agtaggaaac ggaagacaca gaccaagaat caaattaaga gatagcttaa   23460
gaatcaaatt aagagatagc ttacaaaggt gtgggccctt actgaaatag agaaggagga   23520
agagaggaag gaggcagaga cagagagaga ctgagactca caaagacaca cacacacaca   23580
cacacacaca cacacacaca cacacacaca caagttgaga gaaagaaggg gggagagaaa   23640
```

-continued

```
gagagagagg gagcatttcc taacaggaag ctggcagaat aaatgtcccc cattgtccaa    23700
agccagaggg ctgggagccc agtgagccca tccacacagg tcagcccccc atgtgacagt    23760
cctagaaggg taaagaagga aggagagtgg atttggggta atggaagaca gccaataccc    23820
atggtccatc tgactgcagg gggaactgag aaattcagtc catggagaag aaggtttagt    23880
ggacacgtca ctttgtcttt ttcacaaagt gaaactaggt tctcaggtgg aaaaaagaaa    23940
aagaaggttt gccttgctgc tattcttttt ttttttttga gacggagtct cactctgtca    24000
cccaagcggg agtgcagtgg cacgatctcg gctcactgga agctctgcct cctgggttca    24060
cgccattctc ctgcctcagc ctcccgagta gctgggacta caggcaccca ccaccacgcc    24120
cggctagttt ttttgtattt tagtagagac ggggtttcac tgctagccag gatggtctcg    24180
atctcctgac ctcgtgatcc gcccgcctca gcctcccaaa atgctgggat tacagacgtg    24240
agccaccgca cccggcctcc ttactgctat tcttattatt ggtggtagca gtggtggtga    24300
tggttattgg ttcttagttc cctctacatg ccagtatctg ctctcttctt tttttctccc    24360
ttacttcttt ccttgttctg caaattcttt ccctttaagt gaaaatcttt ccgtgttctc    24420
caagggagat aaattctatg ccaagcttga gtgtggggtc ctctgcttgg atagctgtct    24480
tctccaggag atgaggtaga actgagatag tgggggtctc tgcaggcagt ctgtgcccct    24540
ggcaagcccc tcaccttaac ctgaggctgg gtggggaaag atgccttgat ggagtcagaa    24600
cagaaagcaa gtgatcgctg cctgaaccaa gcagtcactt tcctggaggt gaaacctaga    24660
aacggtccct caggctgggt ccagggaggt ggacttgggt cccaggggca ggaagcaacc    24720
tgcccctcac ctgctcctac ctctttgtag cctatcttgg caaccagaag taggtataca    24780
agtgacgttg aagctgggca tgttaacaat ggtgtgagcc cgcctgactc caatctggtc    24840
cagctgtact ggccgtgcat cctcatctcc agccccagg gtcagcccag cggctgtaac    24900
aatggtctgt cccctcccg ccccacccac ttctttgaac tcctccaagg atctgtgatg    24960
atagggctgt cactgtctta gcttccacca ttcaagctta accggccttc ttcccctcca    25020
tggagaacgg aagagcaacc cctcattgcc tctggcagct gaccagcagg tccctgcctt    25080
ctgcccactc ccaggtctag acaatgaggt gagaggtag acaggaccaa gttccccagt    25140
gctgtcttct aggtccacct atcatgagag ccgtgattcc tagtttttat cacctctcc    25200 ccaactttgc cagctctcca cttctggcag tggtggctgc ccatgacttc accttcccgt    25260
gcctcagttt cctcatctgt aaaataagga cagccatggt aatgagagtt ctggtcaata    25320
tgccaggcac ctcgcttgca tcaatttagc tcatcctttc agtgccctga ggggtgggta    25380
ctgttatcat cccgtgtaac aaaaagagaa aaccgaaaca gagagagaga ctcactatct    25440
gaggtcttgc accctcaag caacaaaagt gggatttcag cctaggctat ctagattcgg    25500
agtccacggt ctcaatgaat aataacaaca ataataatat tgtcctaatc tgatgagttt    25560
ttgatcagat tcaatacaag agcataggca gaaaagctta gcccagtgcc cagcacatgg    25620
taagaactca gcatgttatt tataatagta ataaaccatt ttatgttatg taattatata    25680
ttcatagata aatatagttg actcttgaac aacatagggg ttggggcaat gacctcctgt    25740
gcagtcaaaa atgtgtgtgt aactttttt ctctattttt tagaaatttt aaaattagag    25800
acaaggtctc gcttttgttg ctcaggttga tctcgaactc ctgggctcaa gtgatcctcc    25860
tgcctcagcc tctcaaagtg ctaggattac aggtgtgagc cccgcaccc agcctgtgta    25920 taacttctga ctcccccaaa gcttaactac taacagtcta ttcttgacca gaagccttac    25980
```

```
cagtaacata aacagtcgat gaagacagat tttatatgtt atatgcatta tatactgtat    26040
tcttacaata aagtaagcta gggaggagaa agtattattt taagaaaatc ataaggaaga    26100
gaaaatatat ttactattca ttaattggaa agggatcatt ataaaggtct tcatcctcat    26160
tgtcttcaca ttaagtaggc tgaagaagag gaggagttgg tcttgttgtc tcaggggtgg    26220
cagaggtgga ggtggaaggg gaggccagaa agacaagcac gcttggtgta actgttattg    26280
gaaacaaatc tacataagtg gacccataaa attcaaacct gagttgttca ggggtcaact    26340
atatatgcta caaatacgta atatgctaat atagttgtat gttattgtta tagtacgggg    26400
atcagaaaat gttttctgca aaggattagc tagaaaatgt ctagtaaata ctgtctcttt    26460
gggaccactc tactctgcca ttatagcaaa ggcagctaca ggcaatacgt aaatgaatgg    26520
gcatggccat ttgccaataa aactttgttt acacaaacaa gccatgggcc agagtttgtc    26580
aacggctggt atagtatatg ttattatata ttagctttac ttttttctgtt gctttgttta    26640 tgttcttctt tgcccttcct ttcttaaagg ccagcctttc tttctctctg ttggtctgtc    26700
ttttaggaca gcatggcagg ccactgggac atgggctctc ctgactccag gcttgtttgt    26760
ctgataagac atgaagagtg aaggtggcag gactctgagc tcaggcctgt cctcctcctc    26820
ttccctctct tcgttttttc tttcctcttt cctctttctc tcccaagctc cagaagttgc    26880 catttttcctt tcccattgct gattttctct gccttgggag aaagcccgag aagatcactt    26940
ggaaaagccc acgagcatct ctggcctcac tcacccagct cctgccattg tctttactct    27000
tcctcagaca caccaggcac agtcctacct cagggccttt gcactggctg tttcctctgt    27060
ctgcattgtt cttctctcag gtgacctcat ggcttctccc tcctctcctt caggacttca    27120
ctcaaaggcc accttctcag catttgcctc ccgcccttct gccttatttt cccctttgga    27180
acttttcacc ttcttactta ctcatctgtc tgctatctgt caccctacat cactatgatc    27240
tccacaaggg aaggtgattt tattcgtttt ttgttctgtt ttgttgaaga tgaggttttg    27300
ctcttgttac ccaggctgga gtgtggtggc acgatctggg ctcactgcaa cctccacctc    27360
ccggattcaa gtgagtctcc tgcctcagcc tcctgagtag ctgggattac aggcacccac    27420
caccatgcct ggctaatttt tgtatttta gtacagatgg ggtttcacca tgttggccag    27480
gctgatctca aactcctgac ctcaggtgat ccacccacct cagccttcca aagtgctggg    27540
attactgtga gccaccacac ctgatctttt ggttttaccc accaatgtgg actagaacag    27600
cctagatcag caggtggcat gcagtaagca gttgataaat atgtgttgga tgagtgagca    27660
ctgtggcttc tgtcattctg ttgctcaata gcattcatct ggaaataacc acagtttgtt    27720
tatccattta cctgttgatt ggcatttctg ttgattctcg tttgggccat tatgaacaaa    27780
gctgctgtga aatacttata cctttgccca attcttcact tggtgaaccc ttataaatcc    27840
tttaggccag gtgtggtagc tcacgcttgt aaccccagca ctttgggaag ccgaggtagg    27900
aggatcgctg gaggccagga gttcaaaacc agcctgggta acatagcaag acccgtctct    27960
acaaaaaaat aaaaaattgg ctggacgtgg caatgcatgc ctgtagttcc agctacttag    28020
gaggctgagg tgggaagagt gcctgagccc aggagttcaa gaccgcagtg agtgatcgcg    28080
tcctgcactc caggctgggc gatagagtga gaccctgtct gtaaaaatga cagcaacaac    28140
aacaataata aaacctttag gtttcctctt aaaaggaaca tccttagagc ttttcctgac    28200
ccagcaactc accccaagtc tgaattagac ttcaccccat ttctttcata acatttatca    28260
caatgacatg tttattttgt gggggcgggt ggcattctgg ccagaactgt cgacttccag    28320
agtgaaaata cggaagaacc aaataaaaca caacacacac atttgcacag cagctcgagg    28380
```

```
gaggtgctta gttctttgag tttccaagaa cagagagacg aagatttgtc tggggaggaa   28440
aaatcaggga ctgcttcttg gaggaggtgg actgttgctg ccccatccac ccacacattt   28500
gcagatgtgg tgatgagaag atgactgtca cgaggtctct gagcccaggg ggcccatggt   28560
tgagtgcaaa gatagtgggg ttgacaaata atcgtcgtat aacaaaagaa aagccaccac   28620
agttgcataa tggaaaggcg gcttctatag aacattcaga tcatagttga aggcatgtca   28680
cactgtgtta ctcagaggcc actgtcagag ccaaaagtga gagtggatga gagtttgggc   28740
aggaaacaac tgaaccagat acagcatcac ctccatgagg gctcagcttt atctattttg   28800
tcttctgttg catccccagc ccttagaaca ctgcctggtc catctttgct gtgtgaataa   28860
taataaggaa cgatcgctgt gttgagtttg ggctgtgaat tcagacagtt tgctgctgca   28920
tacctgatta tgagtctcag ttttcctcct ccataaaatg ggcaaaacag tccttgcctc   28980
atggggctgt gcatttgttt agcaaacact gaaggagtat acatggtggc caaggcactc   29040
ttcaagacac aggaagcaga caaaagtccc tgccctctgg gagcttacat gctcatgggg   29100
agagatgtat gataagaaac aaaaatagta ggtaagttgc atagtacttt agaagattat   29160
aagggtaatg ggaagagaac agcagagaaa gggctgggga ggcagttgct gtattagata   29220
gagctttatc gaggcgatgg cattggagcc aagacttgag gaagctgtga ggatgtctag   29280
agaaagaagg aacagctggt gcaaaggccc tgaggtaggg gtatatgtga catgtgtgac   29340
agtgaggagg cagatgtggc tgaagccagt gagcaagaga gagggaaggt gcaaggataa   29400
ggacagagag gtgacgggac aggttttgga gggccttatg ggctgcgggg aggactttgg   29460
cttttgctct gagggagctg ggagccacgg agggcttttg agcagaggag ggacgtgacc   29520
tgactcagat attcataggc tcctctggct gctgtgaaaa gaacagactt tgaaggttgg   29580
gggcaggcag ggcagaagct ggggaattag gaaggaggtg acagtgttgg tcctggcagg   29640
taatagtggg ggtggaacca ggttgttgtc tgtggagata ataatgagtg gctggattct   29700
ggttataatt tttaagtttt tttattgtga taaaatgaat ttttttattg tgataaaatg   29760
aaatttacca ctttgaggtg tgcaattcca cagcacttac tacagtcacc ctgttatgca   29820
acagtcacct ctatttaatc tcagaacatt tcatcccccc taaaggaaac cctgcaccca   29880
ttagtagtta cttccagttt ctccctttcc ccagcttctg gaaactacta attctggata   29940
taagttgaaa gttgaccagt aggatttcta ggcagacagg tggtgagggc tcaatgcatt   30000
catgcacaga aagtactcag gtggcatatc ataggtgctc aaaactgaaa tggtgatgat   30060
gagttggcaa tgatggtgag tccttccaga atccctgctc tagtgctaaa ctgacctacc   30120
tggctgtgta gaattctcac ctgctggccg ggagggtggc agaaccagga tcccttctta   30180
cttccagtct ggcttgggtt agggataggg gaggaatgat cagaagaacc aagctagcac   30240
catctgttct ggaacatcat ccaactcttg tccagatttc ccagaactga gcaggaaaat   30300
gtccagggag gaacagtgca gctgatggaa gtcctggtaa gccctggccc cagcttcctg   30360
agctgctgtt gcaccaacta gcatttgttg gaccttcagt ctgagccaag atggcagctt   30420
cagaggaaga acaagaagtg tacaagtttc tttcatggtt gtgtccccgc ctccttatat   30480
agcctcatat aaacccctgc actatcccgt tactgtttgc ctctccctga aaagagtgta   30540
aaactccccc acttttttccc tacttttcac aatgtgtttt ggtttctaaa gatgaaactc   30600
ctttaattat gttctggttg taattttctg gctcctttta tttctcccctt acttgatgta   30660 ttattttccc ttgttccttc tgccccctgc ctccattgat gtttctcttc actgctatct   30720
```

```
agatttaatt ctcaactcct gccaagttca gggtgatagt gcaaaaagac atggaccatt   30780
tagtcttgaa ttcaggtccc acttctgaca ccttcaaagc tgctttactt tgggcaagtc   30840
atatgatctt cctgaggggg tatcctttac cttgttcagc taacatttct tgttttttctc  30900 tgggcacaga gtagagtgtc attttcccca cctccctgaa gttaggtatg gctgtgtgat   30960
ttggtttcat caatgaaatg tgaggggaag tgacgtgagt ccttccggac agaagcctta   31020
agggtgagca tgggattcac catgtttcct ttttcctgcc tccactgtca tggatgcaca   31080
aagatggacc ctctctcaaa gtaagtgctg gagagaggat gacatagatc agtccccatc   31140
ccacttcata gcatgagtag aaaaatagac ctggggtgtg ttcaaccact gagatctggg   31200
gattgtttgt tactgcagca ggacatagac taggctgact gtatacctca ttatctgcat   31260 tttgggctg atatctaatc acagtgtctc caggaagatt atgttgatgt atgttttagg    31320
gatggatatt catattttcc tataagggct caataggttt ggaaatgtca catgcatgta   31380
aacttctgat taacaaatat ttcttgcttt ccaatttctt cctatagtgc ttctaatttt   31440 cctgttttc aatcttgaat aaaatgtgag aagtgtttga cttctccttc gaggagatta   31500
atggtttcta aagcctgggg cattgattta gtcattctca acctccttgt ttctatgacc   31560 ttttttctc cttctctggt cacttagtgt ctgctaaggg gtgaaggaat gtctgtttta   31620
actcattgca ttttttttt ttttgagacg gagtctccct ctgttgccca ggctggagtg    31680
cagtggtgtg atgttggctc actgcaacct ctgcctcctg ggttcaagtg attcctctgc   31740
ctcagcatcc caagtagctg ggactacagg tgtctgccac cactcccggc taatttttgt   31800 attttttagta gagacggggt ttcaccatat tggccaggct ggtctcgaac tcctgacctt  31860
gtgatccgcc cgccttggcc tcccaaagtg ctgggattac aggcgtaagc caccacacct   31920
ggcaaactct ttgcattttt aactcttgac atcttcatct tctttttccc acctccctt    31980 tgcctgttcc tcccctgctc accccaccag ggagtttata atcaggttct agaacctgca   32040
atgtttttct gttgttgtct tccatcttcc ttgagtctta tgggaatcgg ccatagtcgc   32100
aaattaacaa atagctctga agcgcctcaa gcttggaggc atttcctttt gctcacctaa   32160
gcaagatcct ggagctgttg caaatatcct gcccccctact gtaaatctgt cttcatggtt  32220
gtaagagatt cagtcggggt cagtgaagac ccgagcagga gatcttggcc gaggctcctt   32280
gatgttctgt ctgcgctggg tgttgtcata ttgattaagc tcctgggact gctgccagca   32340
gcctctagga ttaaatcaat agagtttgca aaagtaaaag cttcttttgg agacacagaa   32400
tatgtgggtt tattttttaa tgataaagct tcaaggagaa tcttcatgga tggcagaacc   32460
agtgatggaa aaggcgaggc agacccaaat atttgggaa gtgcagtggg gagcaagtga    32520 gggaggttc attgggaggc cggggctttc cagaaaatct gtttaactgg agttgctaat    32580
gcaacagctc agagttagaa gtgaaggtgg aagatgcaag aaggactgcc gctgagatgt   32640
aaagagaaat gaaggagagg tggatccatt tgctcattca ataaacattt tgggaggcag   32700 ggggtgggg gggagcctgc catgtgcctg gaactgggat gtacatggtg gggacatgac    32760
agtgggcagg acagatgtgg ttcctcctgg ccctcctgga acttgtaaca ggaaaagaag   32820
gcataaaata aggaataggc aaatacagac ataattacta attgtggtaa gtgtttggga   32880
gaaaaccagc agggtcctgt gtttgtttcc tagggctgcc aggacaaatt gccatgaact   32940
atatggctta aaacaacata aatatattgt cacccagttc tgaaggctgg aagaccaaaa   33000
tcaaggcatc agcagtgctg agctcccttg gacggctcta gagaagaatg cttccttgat   33060
tcttccagtt tctggtagtt gttagcatac attggcttga ttggcttgtg gctgcatcac   33120
```

```
tgcagtctct gcctctgtct tcacatggcc ttctccttca tgtcagtgtc ttctcttcct   33180
cttctctctc tctcttttt tttttttgt cagggcctca ctctgtcacc ctgtacaaga   33240
gtacagcagt gcaattatag ctcactgcaa ctgctgcttc ccagcatcaa acaatcctcc   33300
cacctcagcc tcctgagcag ctgggactta caggcgtgca ccaccatact cagctaattt   33360
ttaaattttt gatagagatg ggatctcact atattgccca gactggtctt gaacttctgg   33420
gctcaagtga tcctccctcc tcagcctccc gaagtgctgg gattacaggt gtgagccact   33480
gcacctggcc tcttctgtct cttataagga tctttgtcga tggattttga gcccgtcaga   33540
taatccagga caatctcatc ttgagatctc taatttaatt atacttgcag aggccgtttt   33600
actaaataag gtcatggcca gaggctccag aggctaaagc atgggtatga ttgcaccact   33660
gcactttagg ctgggtgaca gagcaaggcc ccatctctga aaataaaat aaaataagta   33720 acctactaca ggccctttgc gtagaggata attagaagta caggggtacc acgtaagtga   33780
agacctgaag gttgttaagc acagagcaga gtgtgaacag aatgagacag agggaggaag   33840
agaatcccag gcagagggaa cagcatgtgc aaaggccctg ggaaggaac aagttcatca   33900 tgttaaaaat gagccagtgt agctagagtc tgatgagcaa agggactcac aggtgggaag   33960
acacccaaga agttggcaga gacaggtcac acaagacctt ctaggtcaag ttccggaggt   34020
gaactttatt ctcatgcaa tgagaagtcc tcagagaagc ttaagtggga tgggacagaa   34080
ctgctttact ttaaatatat atacatatat acaaacatat aatattacat atataagca   34140 tatatatgta tacatatata catatctatc tacctgtcta tatattttt agctgggcat   34200 ggtggctcac acctgtgatc ctagcacttt gggaggctga ggtgggagga tcacttgagc   34260
ccaggagttc aagaccagcc tgggcaacat agggagaccc catcactaca aataaaata   34320 aaaattaaaa attagctggg tgtgatagtg tgcacctgta gtcccagcta cccgggaggc   34380
tgaggtagga ggattgctgg agccccaaag gttgaggctc cagtaagccg tgattgtgcc   34440
cctgcactct agcttgagca acagagtgag atcctgtctc aataaaataa ttttttgtatt   34500 gaggtgaaat tcatgcaaca taagttaacc attttaaaat gagcaattca gtggcattca   34560
gcgcattcac aatattgtac aacctccacc tctttctagt gctgaaatat tttcatcacc   34620 accctccag aaaaccctgt atccatgagg cagttgctcc tcatcctccc ctcccggtat   34680 cccccaacc cccaccactc ctggtaacta caaatttgtt ttctgtttct atggatttac   34740
ctatactggc tctttcatat aaatgaattc aggcactgtg tgaccttcg tgtctggctt   34800 cttcacttaa gcataatgcc ctggcttctc tctggagaat gaaatggata gaccactttg   34860
gagtctactg agattataga tatttctgtg ggaagggaca gtggcttgac cttgggtggt   34920
gctgaagagg caatgctgag caggaggatt caaagtctaa tttcggaagt agaattggtg   34980
gggtctgatg atacatcagc tgtaggggga ggaagatgta ggaactggga aggtctctta   35040
gggtaacctt acctgattga gctccttact aggcagctgg tggtacaatt cataacaaag   35100
gttaatagag aaagagacat gggattaggg agggaatgga agagtttggg ccttggacac   35160
tgtagtggtt tgaatcctgt ccaccaaaaa ttcagatgca tttggaactt cagaacctga   35220
gacctcattt gaaagtagga tctttgcaga tgtcattgag tcaggattg agatgaggtc   35280 atcctggatt acagtggact cgagattcca tggtaagtgc ttttatatga aaggtacag   35340 gggagaaagt catgtggcaa tagaagcaga gaatggagtg ctgcagccac aagccaaaag   35400
acatgtagag gcaccaaaag cgggaagagg caaggaagga tcctccccta gagcctttga   35460
```

```
agggaaaccc cctaatttca gaaccttgcc tccaggatga cgagagaata aatttctgtt   35520
gttttaagcc acccaatctg tggcaatttg tcatgactgc cctaggagac taatatagac   35580
actcctatga gatgctctaa gaagacacag agtggtatag ctattgctaa gaccacacac   35640
tgtagcaggg aggaaatcaa atggagaaat gccccaactc cccctcctct ctgatctctt   35700
gctggtgcct cccgttggcc aagccaaccc agaaggcaga agatgtggtg gagggcagcg   35760
ttgcagggct tggatgatgc agtcacagaa gtcagccctg cctctaccag gatgccaaac   35820
agggcaatga gtggatattt tagggagaaa gggcaacaag agaatggcaa aatacatcga   35880
aatgcatgca agctctagaa agaggataga gatagataaa gggtgattac ctaggattaa   35940
gccccaggga agaccaacat ttagagattg gatagaaaaa gaggagcaaa aagggaagat   36000
tgagaagtag agaccaggag gataggagga aaactagaac aacattaaga agggcatggt   36060
caagtaatct gggcacagaa aaatggccct gggatttggc agcctggggg tctttggtga   36120
tcctctttgg aagagttttg gttgagtgat gggggctaga aaccagcctg gggagggtag   36180
gagaagaatg tgcagtgagg aagtggcagg aacacgtgaa ggcaactctt catgaagggg   36240
agtagagaaa ttggttggtg gctgaaggaa aattttcagt caagggtgga ggttttaatg   36300
atggaagaat attgatttct gtaaattggg tcattcccat ccattatacc aatatgcacg   36360
ggtgtcttct ctgatatagg atgctgggat tctcaaatgc ccatttgagt ttagcatcat   36420
gaatttaatg tcaccagccc agatagttga tctcattcag gaatgctcca ctgcccaggt   36480
atggggaagg caactagttg agttcatgca gggatggatt ttttccagga gagaaacagg   36540
aggcaagaaa gtgcgatata atcaacctat gtaaggttga caaggcagga gagggtcctg   36600
agaaatggcg gggtcagtgg gttgcagggc tcgatgggat ggacgttggt ttgcatttaa   36660
gggagttagt gagctgggag gtggttaaag aggaggtggt tcagccgggc gcggtggccc   36720
acacctgtaa tcgcagcact ttggggagcc gaggcgggcg gatcacaagg tcaggcgatc   36780
gagaccatcc tggctaacac ggtgaaaccc tgtctctact aaaaatacaa aaaaaaaaa   36840 aaaaattagc caggcgtggt ggcgggcgcc tgtagtccca gctactcagg agcctgaggc   36900
aggagaatgg cgtgaacccg ggaggcggag ctgctgtact ccagcctggg cgacagggcg   36960
agactccgtc tcaaaaaaaa aaaaaaaaa aaaaaaaaa gaggtggttc aagacaagga   37020
tgctggaaac aggtgttttg gaggtggctg gtgtagcttc tgagcatgca tagctggagt   37080
ggcttggagg agacattggt tattgatgaa gaggtaggga catcctccag tgatcaagga   37140
agcaggggac cagcatggac aatggtctct ccacagggaa attggaggtc atcaaatgtt   37200
aacaggttcc gtcggagtct tagctcccag cttctgtttt cctgtggatc tcaggatctt   37260
ggctgctggt gctacctctg actttggact tcccattgag cccagcagca ctgggaggga   37320
ccttcatggc attggctggt ttaaggaaga cttccttggc tttgctgact ttcttggggg   37380
ccttcttggc tacacctgct tttgagggag ccctcctcac ctcacctgac ttcttggggg   37440 cacctttttcc accttatctg agttgggaag gtctttctt gattctcttg ctttcttggg   37500
gcccttctca ctggtttttc tgggggccat gatggtggac atattccaga gctgagcttt   37560 cctttgttc ttaggaacta atttgaggct gccagtggcc ccaccttggt cttagagttg   37620
atggtctgca gggaatttcc aggttaaagg ttttttattt gtttgtttaa ttttgagaca   37680
gagtcttgct ctgtcaccca ggttggagtg cagcggcacg atcttggctc actgcagcct   37740
ccgcctcctg ggttcaaaca gttttcctgc ctcagcctcc taagtagctg ggattacaag   37800
cacgcaccac catgcccagc taactttgt attttttagtg gagacagggt ttcaccatgt   37860
```

```
tgaccaagct ggtctcaaac tcctgatctg aagtgatccg gccaccttgg cctcccaaag   37920
tgctgggatt acaggtgtga gccactgcgc ctgacctcca ggtttaagtt taaaccatga   37980
agtagatgga ctgtgtagag agagaccagg gaaatggagg attttactga ccactgaaca   38040
gggatgtcac tattgccaga gaggaaaagg attccccctt ggtagagtga acatataagg   38100
gaaagtggtt gaaaattgaa tcaggagaca gagacctcac accactcaga ggtccctaga   38160
gaactttact gacctagaaa aaagataaa cagggagaag gtcttcagtt cttgtttgga   38220
atctgacact gaagcatcct cactcctcac tctcttcccg accccgagag tctgaaattg   38280
attaatactt tttgtttaaa acttggcttg ttgttttgtt ttttctttct gttttcatca   38340
agggatcttt attttacttt tgtgtatttg tgtgttttcc atgagtcatg ttaattcttc   38400
catgtttaaa cttttttggcc cagaggaatt tatacattta aattatggat ttaatttcag   38460
aaggtacata cacacacaca cacacacact cactcatctc acttttttaaa aactgtaaaa   38520 tatagccctg taaatatcca gaaaatatct aatgtgggcc gggtatggtg gctcatgcct   38580
gtaatctcag cactttggga ggccgaggtg ggtggatcac ctgaggtcag gagttcgaga   38640
ctagcctggc caacgtggtg aaaccctatc ctcactaaaa ataaaaaaat tagctgggca   38700
tggtggcagg tgcctgtaat cccagctact cgggaggatg agacaggaga atcacttgaa   38760
cccaggaggc agaggctgca gtgagccgag atcaccccac tgcgcccag cctgggcgac   38820 agactgagac tctgtctcac aaaaaaaaaa aagaaaaga aaagtcagt gtgcatcccc   38880 tctgacatcc agcaacttca catcttggaa tttatgctgc aggaaaatta tcacaagtgc   38940
acaaggatgt atggtgagat agttattatt atcatttaa aagatagggt ctcactgtgt   39000
cacccaggct ggagtgcagt gaagtgatca cagctcactg cagccttgac cttctgggct   39060
cgagtgatcc tcgtgcctca gcctccccag tagctgggat tacaggtgtg agccaccatg   39120
cctggcatcc ccctttttt aaaaaaaggt tttaattatg aaagaatat gggcttgttg   39180 ttttgtgtgg ttttttaaaa gcttaaaaaa tgtgtagtgt gtcatttaga aggtgaaaag   39240
cccttacccc atcccacctc ccagagataa cctctgctag caatttcgtg tttgtctttc   39300
aaattttttc ccacacacat tctttgtact ggctgcttcc cctcctgggt tactcttctc   39360
ccagacagaa acagggctca ttcccttgcc tcctccagct tttattaaaa cattaacttc   39420
cctgtagctg gatgcagtgg ctcacgcctg taatcccagt gttttgggag gtggggaggc   39480
aggaggatag cttgagccca ggagtttgag actagcctgg gcaacatagc gagacccatc   39540
tctacaaata aataaataaa taaataaata aataaataaa taatgaaat ttaaagaga   39600 gagggaagga ctcttgaaaa ccgtccatat catgcttctc taaatggttg agggctcaga   39660
ggaaaaaaaa tcagcaattt cacatcacgg aatttattct gcagaaaaat tctcacagt   39720 gcacaaggat gcgtggtcag atgatgatga tgatgattat tattattatt attgaagaaa   39780
gtagcagcag cagcagcagt attttaaaag acagagtctc ggatgggcat ggtggctcac   39840
gcctgtaatc ccagcacttt gggaggttga ggtgggcaga tcacttgagg tcaggagttc   39900
gagaccagtc tggccaacat ggtgaaaccc caactctact aaaaatgcaa aaattagcca   39960
ggtatggtgg tgggtgcctg cagtcccagc taccagggag gctgaggcac gagaatagct   40020
tgaacccagg aaatggaggc tgcagtgagc caagatcgtg ccactgcact ccatgcactc   40080
cagcctgggt gctgacccag gttaggtgca agactccgtc ttaaaaaaa agaaaaggaa   40140 aaaaaaaaa aaaggacaga gcctcactgt gtcgcccagg gtaaagtgca atgagtaaag   40200
```

```
gcccatgatg ggaaccctga ggagagagtc aaggggaaag aaaaaaaaaa aagcaaaacc    40260
aaaatggaat ttaaaaaaaa tcaggtgcaa tttgcataac agaaaattaa ccattttaaa    40320
gtgaacggct ctgtggcatt tactgcactc caactgttat gtaactacca cctctgtcta    40380
gctccagaac attttcacca cccctaaagg agaccttgta cccattaagc agtctctctc    40440
cttctcccct ccccaccacc ttcctccagc ctctggcaac cacccatctg cattctgtct    40500
ctatggattt acctattcta ggtagtcaac aggatgagat atcccaaaag tccatccatg    40560
gatgaacaga taaaccaagt gtgatatgcc ttcctcagat attagtctgc cttaaaaagg    40620
aatgaaatac taatctttgc tacaacatag atgaacctca aaaatatgat gtggctggac    40680
acagtggctt acacctgtaa tcccagaact ttgggaggct gaggtgggcg gatcgcttga    40740
gcccaggtgt tcaagaccac cctgggtaac atagcaaaac tccatctcta caaaacaatt    40800
tacaaaaaac tagccaggtg tggtgacatg tgcctgtagt cccagctatt caggagactg    40860
aggcgagagg atcgattgag cccaggaggc cgaggctgca gtgagccatg atcataccac    40920
tgcactccag cctaggcaac agagtgagac cctatctcaa aaacaaaac aaaacaaaac    40980 aaaaaagttg atgctgagtg aaagaagcca gacacaaaag gcaacatcgt gtttaattcc    41040
atttacatga aatgtccaat gaagattttt tttggcaaca tttatttga gtataatatt    41100 cagtgagtgg accacacata tgcatgcact gcagtatgtt cttggaaaca tttcagattt    41160
gagaggtctg ttcagctatg atgacggtag gtattgtccc ttccctccct ccttgaagaa    41220
aaggaactaa ggctggacgc ggtggctcat gcctgtaatc ccagtacttt gggaggctga    41280
ggtgggcaga tcacttgagg tcaggagttc aagactagcc tggccaacat ggtgaaacca    41340
tgtctctact aaaaaataca aaaaattagc caggtatggt gctgcacgcc tgtagtccca    41400
gctactcggg aggctgaggc aggagaattg ctcgcaccca ggaggtggag gctgcagtca    41460
accgagattg caccattgca ctccagcctg ggtggcagag caagactctg tctcaaaaag    41520
aaaagagaag agaagagaaa agaaaagaaa ccaaaagaaa aggaaagaaa agaaaaggaa    41580
ccaagaccta gaagggcaaa ataggaaaaa gttggccggg cgcagtggct cacgcctgta    41640
atcccagcac tttgggaggc caaggtgggc agatacaaag gtcaggagat cgagaccacc    41700
ctggctaaca cggtgaaacc ccgtctctac taaaaatact aaaaattagc cgggcgcggt    41760
ggcaggcgcc tgtaatccca gctactcggg aggctgaggc aggagaatgg cgtgaacctg    41820
ggaggcggag cttgcagtga ccgagatag caccactgca gtctggcctg ggcgaaagag    41880
caagactcgg tctctaaaaa aaaaaaaaa aaaaaaattg gaaaagttat ttactattag    41940
cagcaattgt cataaagtaa tgaacattta ttgcatgatt acaatgagat aaattgtatc    42000
ctgtttttat aagcatatta agttttcttt tttaaaaaaa tgtatgtatt tatttatttt    42060
aagagatagg gtcttgctct gttgcccaga ctggagtgcc atggtatgat catagctcaa    42120
tgcagcctca aattcccagg ttcaagcaat cttcttgcct cagtctctcg agtagctagg    42180
actacaggca tgtgccaaca tgcctggcta gtttttcttat ttttaaatgt attttttgtag    42240 agacaggatc ttgctgtgtc gcccaggctg tcctcaaact cctggcctca gcgatcctc    42300 tgccttggcc tccaaaggg ctgagatgat aggcatctac ctctgcattt ggcccacatt    42360
aaattttcta gtcatcatgg gaaccaaaat aaacaatata aaacactcac attccttgag    42420
cacttactat atgcagggcc ctgtaataga ttattgtgtg tatcagctca ttccattctc    42480
acacaaccta tgaggttgat gctatttcct acctttata tatgaggaaa ctgaggctca    42540
gagaaggaaa ctgccttgcc caaggtcaag gccacgtctg atccccaaat cctttcaact    42600
```

```
cctctgcact actattttt  agtgcagata ttgccagttt tctaagcaga agcatgattt    42660
agcagccctg agtagacttc tcatttcaga accaaagtgt tggacattgt tggataatat    42720 gaaaacaaa  tgacacacaa acctatttga tactgttttt aattttctct tcatttgatt    42780
ttcctgatga catgattaat cttttttgcc tctaccctgt atgtgaaatg taggtctttg    42840
cagatgtctc agagagtgtt aatagttgct gctggttttg ttttctctcc ccggggattc    42900
ccatccctgg gtgcaagtga aattaaactt gtgcctcttt gccgctggcc gtggtgctga    42960
aaacatcccg ggcagcgcta gggttgccct tgttagcatg ccatccctgc taagagtctt    43020
aggctgatca gcgagtggag agatctttc  caggcttcat tttggttaga actgtgtgtt    43080
gaagatttta aagcccatgt ctgggaactg gagactgttt ggattgtttg aagttgaaat    43140
agtcatgaat aattcctact tgagatgggc ttatgagggc gtggactagc atgcaatggt    43200
tggcctttac taaactgtgg ccattggttg ggacttgggt gaggtgtaac ccatttggtc    43260
taatccatat ggttagggcc ccaagtgcac ctgcattcta ttttttttt  tttttaaata    43320 aaggcaaacc catctatctt ctaaccagga tagctcctga gtggtctttg ggaccacca     43380 gcttaaaagc atagactgtg ggctgggcac agtggctcat acctgtaatc ccagcacttt    43440
gaaaggccaa ggtgagagga tcgcttgagc ccaggagttc aagaccagcc taggcaacat    43500
ggtgagaccc tcatctctac aaaaatgtta aaagttagcc aggtgtgttg gcatgcacct    43560
atagtcccag ctactcagga ggctgaagtg ggtggatcgc ttgagcctgg gaggtcaagg    43620
ctacagtgag ctgtgatcgt gccactgtat ttcaccctgg gcaacagagc aagaccctaa    43680
ctcaaacaaa caaacaaaaa aaggcataga ctgtggagtt gggcagacct gggtgtgagc    43740
cccagctctg ccagtacctc ctatgtgacc ttgaaaattt gtttaatctc tctgagcctg    43800
gattttcttg tgtggaaaat gaggcttacc acagaaccca ccttgtagaa atgttgcaag    43860
gaattaactg aaacaaagtg cttaccacgg tatctgccca agaagcagt  tggaaacaag    43920 gcagctgtaa ttatggtcgc tgtgcttgtt aatggcccca taatagttga tcatattgca    43980
gagtgaaatt ggggtatgtg tttaatggac caaggaatat gtcttaaacc catatatcta    44040
gggttctggt accctctact cttttcctg  gtgattgtga tgagcatgga acttacatga    44100
aaatgaggtc tgtttggctt cttcacacaa gctcaatgac ctggctaact gctacaagta    44160 tctgttcct  tagaacccac ccatcagcag tccccatagt ggagacaagg tcacaaagag    44220
ttgacaaacc tgatttgatt tccgcaccaa ccacaggagg cttgaaatga gatgagggtg    44280
aagggcacca cagagggatg caaggattac ttggacactg caaggtcttg ctaagggatg    44340
ggaaccatca gccacgccca ctttgagaat ttccttcat  gttctgaatc tgaagagcaa    44400
ggtcctgttc tcagatgcaa gccctccttc ttccctacgc agagtcaaac ttggtctttt    44460
ccagggtcac atacagcctc tctctggggc ctctgcaggt cctgatcaat ttcattgtgt    44520
atagagctct gtgtctcctc acctgcctgc agggctgtct gctatcctga cttccgagag    44580
ccatttcgga agccagcttt tcctcccatc agggatgctt ctcttctttc agccccgcc     44640 ccgctttggc ctcctaggat ggctgatttt tctggatccc gctgacacag gtgctttctc    44700
tccgagccaa tcagggagca gaaaggctca gctcagctaa cagaggcatt gctcaccgca    44760
gctgtgagtt agaactcagg ctttctaaat cgggaggatc aggcatgact tgaggttggg    44820
ctgagaaagc ctcgcctgcc ccccagctcg actacccagt gaaaccttg  gcttctgcct    44880 cgggcgaggc atctcttacc atgccaagaa ctcagcagcc catctttctt tcatctgggc    44940
```

```
accaagtaca tcattgcata tttcaggggg tttcattgtg tccttaacat gctcatggag   45000
acttggcttg agatgaagtc ggggtttcta ggcagcagga cccatgtccc cttccttcat   45060
ttcctccacc ggtgatttttt gttttgtttt gttttgtttt gttttgtttt gttttgtttt   45120
tgagacggga tctcgttctg ttgtccaggc tggagtgcag tggcgttatc tcggctcact   45180
gcaaactctg cttcccgggt tcaggtgatt ctcctgcctc agcctcccaa gtagctgaga   45240
ttacaggcgt ctgccactat gcccagctaa ttttttgtatt tttagtagag acggggtttc   45300
accatgttgg ccaggctggt ctcgaactcc tgacctctgg tgatccaccc gcctcggcct   45360
cccaaagtgc tgggattaca ggtgtgagcc accgcaccag gcccttccac tggtgttttt   45420
tgagcatcta ctatatagag aatgctctcc tgggcacaga ggatgaagca gtgaacaaag   45480
tagacaaaaa atccccacgt gcatagagtg tgcagtctcg tgggagagac agggaacaag   45540
ataaagaagg aaaaaaatag cagatgcttg actggggacg gggactaaag aaagaaaaaa   45600
ataagcaggc taagggggtt gatggatgtg acctttgagt aaaggcctaa aggaagtgag   45660
ggagggagtc atgtggatgt ctggggaaag actattccag gagaatgaac agcaggtaca   45720
aaggcccctg ggtacaaatg tgcctgggga gtttggggaa taaaagggag gccggcgttg   45780
ctgtagctga gtgactaagg gagagaatag aggagatgag gggagggagg taatgggagc   45840
aggtcatgca ccttgctggt gctggaagga cttttgtttttt gcttttgagt gagatgggat   45900
ccatgggaag gctttgaata cttccacatg cattaggctg aaattttctt ttctgctttt   45960
gtcgcattcc aacattgctt ttatttcatc aaaatcttcg gtttcttctc aggctcttta   46020
cccaagtggg agcagaaggc tggtacccag ggctgttcag ttctcccccct ggggtcagaa   46080 cgtggaggag aaagcttgga ggagaaacag gaaccccccac ctctttctgg atgactcaaa   46140
accgcaatta cctgagctcc tcctcctatc cctgaaatag aggcacttag cacttcctaa   46200
acttcccggt gcacacaaat cccctggcga tctttttaaa tgcaggttct gactcagcag   46260
gtggatgcaa ggtctaaggc tgcattccta accggtgctg gttctgggac cacactttga   46320
gtagcaaggg tctgaggtca ttgttgcaga tgtccatctg gggcatgtct gtggacactt   46380 gcggggggtgc gggtgagcag agggagggggg gatgatgttg gaaaagcagt gtgagtatct   46440
gtgtttgata agaagtaaga aaatgaagca aggtgggaga gtagaacctc tttattttttg   46500 cctacgtgct aaggttttat tgccataccc agagagccct gggtctgaaa tccaggcaac   46560
actggccagt tgaaaccctg atattgcagc ccataaaagt gctgcatgct gcatggtgga   46620
cttctgggac tcttcctgga accttcagtg ccagagccgg tccaaaggaa gtcacatccc   46680
tgccattgag gggcaggaga ccagggaacc ggaggagtgg gatggcagaa gcgcgtgtaa   46740
ggaggctgag ttggcaggga gagaaagcga agtcagcttc aaatcatagc gagaggagac   46800
cagggaaggg cttggcgttg ctgctctgtg tacaaatatt gtctcttatt ttccaggctg   46860
cagggtgagg cagagtggag tatttgtgca acacagccca gctttgttct ctgggctcct   46920
aatgcctgtc agctcagagg cagaaagcca atcagagatg atcgtcggca aggccggctt   46980
ttgttggctc cccaaattgc cctgagtctc ggattttgct tttcagagtg tgctttcagc   47040
tggaggcaaa ggctgaagct ggtgacaaaa ggaagcctgg ttttcctggc tttccgagac   47100
ttttactgag ggggtttcta tttcagactc cgttttccca cctggaaagc aggttccact   47160
ctccctccgg cctggaaggg atggttttat ggtgcttcca aaatgccaaa cctaactcca   47220
gggcagaaga ggagactgaa accaattaat tttccaaagg ttagagctac gaggagggga   47280
gaggtttagc atggtcaagt tccccaagac atactaattg atctctctac agaatgcggg   47340
```

```
atttcagtgc ccccagggga cactcagcaa tgtttagaga ccacttgagg ttgtcatcac    47400
tggacaggag gggctgctac tggcatctag cacacacagg ccagggatac tgttgaacat    47460
gctgcagtgc ccagacagcc ccaccaagga gaatgatcca cccctaaacc tagtgctgag    47520
gttgggaaat cctgctccgg agtaaccaac accctatggc tttttcactc aagcagccgc    47580
ttctccagcg cttacacctc ctcagagatt gccagatcca tatgcagagc ctgttggcgt    47640
gggacacttc tgaggggtgt ggcagggaga cagcggacat tcccatttac cagctgatca    47700
gcaggttagg agctaatatg aaatgaacaa gatagaccct ccccacctgc cctgcagatc    47760
ctctggtggg acactaggga gggaggcctc ctaaacccaa atgacagttc ccaggatgca    47820 ggaggagtt tacctatgca aactggagag aatgcaaatg gggcatctag agatacttac    47880
tggacgaccc ctcccctgcc tcgggtcttg gaagaacaga ttctcagagg tctgccctga    47940
tcactgtaat ttttttttta ttgaggtaaa attaatataa cacaattaac cattttaaag    48000
tgacatttag ggctgggcac agtggctcat gcctgtaatc cccgcacttt gggaggctga    48060
ggaagaaagg tcgcccagga gttcaagacc accctgggca acaaagtaag actctgtctc    48120
ttacaaaaaa aaaattaggc acacatggtg ttgtgcacct gtagtcccag ctactcagga    48180
ggctgaggca ggaggatcgt ttgagcctag gaattcaagg ctgcggtgag ctatgatcat    48240
gccactgcac tccagcctgg gtgacagagc aaaattgtgt ttctttaaaa aaataaaagt    48300
aaaaataaat aagaaaagaa aggagagggg aggggagagg cgtttagtac actcacaatg    48360
ttgtgtaact gtcaccttca tctagttcta aaacattaag cagccactcc catttccctt    48420
gccattcccc aggaacaaca aatctgctgt ctgtctctgg atttgcctgt tcgggatatt    48480
tcatatacat ggaatcatac aatatggggt atttttatgtc tgcttctttc gcttggcata    48540
atgttttcaa ggttcattcc tgttctatca tgtatcagta cttcattcct tttttttttt    48600 ttttttgaa acgagttttt gcttttgttg cccaggctgg agtgcaatgg cacaatcttg    48660
gctcactgca acctccgcct cccgggttca agcaatcctc ctgcctcagc ctcctgagta    48720
gctgggatta caggcatgcg ccaccacacc cagctaattt tgtactttt ttagtagaga    48780 tggggtttct ccatgttggt catgctggtc ttgaactccc aacctcaggt gatctgcctg    48840
cctcggcctt ccaaagtgct gggattacag gcgtgagcca ctgcacccgg cctacttcat    48900 tccttttat ggctgaatac tattccattc tatgagtaga ccacattttg tttatccatt    48960
cacccactgg tgaaatttag gttgtttcca tcttttggct gttgtgaata gtgctgctgt    49020
gaatatttgt gtatgagtgt tcgttggaat acctgtctta cgatccttt gtgtttatac    49080 cttggagtgg agttactgtg tgtcacatgg taactctgtg attaactttt tgaggaacca    49140
aggaatggtt ttctatggca gttgcactgg tgttttttg ttgttgttgt ttttgttgtt    49200
gttgttttga gacagggtct cactcccatt gcccaggctg gagtgcagtg gtgcagtcat    49260
ggttcactgc agcctcaacc tcctggggct caagcaatcc tctctcctca gcctcccaag    49320
tagctggcac tacaggcctg cgccactatg cccggctaat ttttcatatt ttttgtagag    49380
atagagtctc agtttgttgc ctaggctggt ctcggactcc tgtgctcaag taatcctcct    49440
acctcggcct cccaaagtgc tgggattaca ggcatgagcc accgcatctg gccagctaca    49500 ccatttata ttcccaccag catgaggggtt tcaatttctt cacatcttca ccaacacttg    49560
ttttctgttt gtttgtttgt ttttaatagc tatcctagtg gatgtgaagc agtatcccgt    49620
tggggtttga tttgcacttc cctgatcact aatacccctca tgtacatatt ggccatttga    49680
```

```
ctgtcttctt tggagaaatg tctattccag cctcctgtcc attttttcaat tggattatct   49740 ttttgttgtt gtgttgtaaa tgttctctct ttattttttta tttttttgag acagagtctc   49800
gctctgtcgc ccaggctgga gtgcagtggc acgatcttgg ctcactgcaa gctccgcctc   49860
ccaggttcac gccattctcc tgcctcagcc tcccgagtag ctgggactac agatgcccgc   49920
taccacgccc ggctaatttt tgtattttt  ttagtagaga tagggtttca ccgtgttagc   49980
caggatggtc tcgatctcct gacctcatga tccacccgcc ttggcctccc aaagttctgg   50040
gattacaggc gtgagccacc acacctggcc gtaaatgttc tttatatagt actagaccct   50100
tatcagatac atgatttgca aatagcttct cctattctgt tacttgcctt ttaactttct   50160
tgataacgtc ctttgatgca caaaaggttt aaattttgat aaagcccagc atatctgttt   50220
tttcttctgt ggatcatgca ttaggtgtca aatctgatca taatgtttta tttatttatt   50280
tacttattta tttattattt tatttatttt tgagatggag tcttgctctg ttgcccaggc   50340
tagagtgcag tggcatgatc tcggctcact gcaacctcca cctcccaggt tcaagcgatt   50400
ctcctgcccc ggcctcccaa gtagctggga ctacaggtgt gtaccaccac gcctggctaa   50460 ttttttgtatt tttagtagag acagggtttc accatgttgg ccaggctggt ctcaaagtcc   50520
tgaccgcaag tgatccaccc accgcagcct ctatctattt ttaatttatc tcttttttttt   50580 tttttttttt tgagacaggg cctccttctg tcacccaggc tggagtgcag tggtatagtc   50640
attgtacact gcagcctcta cctcctcggc tcaagcaatt ctctcgcctc agcctcccaa   50700
gtacctggga ccacaggtgc ctgccatcat gctggccctg ccaccatatt tgaaattgca   50760
gccctgaccc cttccactgt ctatagtctt caccatctta ctacataaca tagcatatat   50820
gatgtactgt ataacatggt atatgcagtg tactgtatag catagtatac atgatgtagt   50880
catctcattt atttgcttct cctctgggaa gcaggaggaa gcttctcctc ttgtctgctt   50940
tgctctcaac tgtgtcccta gcccagaaca gagtctggca cacagcaggt actgaatgaa   51000
tatgtgttca gtgaatattg tgggtgagat agaaggtgaa tatccacatt tcccttaga   51060 agtcacctga tctgggtttg agatctgcag ggatctactc cagacaggag aacgaataat   51120
tccacctgtg ctgatgagtt ggaaggatct agagggcttg agatcttcc  actgggtca    51180 gtgggggtgg gtgcacctcc aacacccttc ttttctttga acaagatttt tccttaattc   51240
cccaatactc cctttgaata tatgatttta gccaccatca tagcgaattg catcgtcctc   51300
gcactggagc agcatctgcc tgatgatgac aagaccccga tgtctgaacg gctggtgagt   51360
gatgtctttt ctcagggtct tctccttggc tttagcagga cattaatttt tggggggagtg   51420 gagcagggca cagaggaggc tctcagtcct ggagcccaga gccagatcat gggaagccta   51480
aatttccttt tcatttttc  ttgaaccaga gtctcgctct gtcacccagg ctggagtgca   51540
gtggttcagt catagctcac tgcagcctcc acctcctggg ctcaagccat cctcccactg   51600
cagcctcctg agtagcaggg actacaggtg ccaccatgcc cagttaattt tcttattttt   51660
atcttttttt gtagagatgg ggatctcact aggttgctta ggctggtctc aaactgccca   51720
ctttggcatc tgacataatt tcaggcagta tactcaaatg aacattgtta atgttaataa   51780
ttatgtcttg gccagacact gtagctcatg cctgtaatcc cagcagtttg ggaggccaag   51840
gcaggtagat cacttgaggt caagagttcg agaccatcct gaccaacatg gtgaaagccc   51900
gtctctacta aaaaaataca aaattagctg gatatggtgg tgcacacctg taatcccagc   51960
tacttgggag gctgaggcag gagaatcgct tgaacccggg aggcagaggt tgcagtaagc   52020
caagatcgca ccattgcact ccagtctggg caacaggagt gaaactccat cttggtgggg   52080
```

```
gggaggcgaa aaaaaagaaa caagaatatt acaaaggata cagatgaaga gatgcaaagg    52140
gtgagatata ggagaagggt gtggctggca gcttctaggt agcttcagga gggggactgg    52200
tcaccagaaa gaccaaggca tgattcgagg gttgcgactt tcagcccac cccccaacct    52260
ctgggagggc agaggggctg aaaatcaagt tgatcaccaa cggtcaatga tttaaatcca    52320
aacctctaat catgccttgg ttttcccggt gaccaacccc catcctgaag ctacctagaa    52380
gctgccagcc atcagtcaat ccttagcctg caaaaagaca tcccttttgga gatcccaagg    52440
gttttaggag ctgtacacca ggaaacagtg tcaaagacca aacatacatt tcacaatgtc    52500
acagtcttct aaaaactata actagcctag caaacctatg atttctagat ctttgcattt    52560
tcacttaaaa taaagctaaa taaaaagcgt ccattgaaag actggtaagc aagtagaagt    52620
accagtggca agctaatgtg gaaaaaaaaa atcattcagg cagagtgaaa atgattgtag    52680
ctcgagaaac gttgctgtaa cagatgggaa acattcaca ttggggctct gatggagaag    52740
agcttgtagc ttaatttcaa atatgataga ttagcagctg gaagccagaa ccagccggag    52800
gttctgcaga ggaactggag gtgaggatac tggccactta tcagccagta cagaagtcct    52860
attccaaacc tttaacaatc tacatgccag ctgagaacca tcctaagggg tcagatttag    52920
gagtgaggtc aatgcacaag ctctagcctc aaataccttg aacgctgcat gtgacaagta    52980
aattctctaa accaatgctt tccattagaa ctttctgcag tcacagaaat gatctccatc    53040
tgccctgtcc aataggattg tcacttgaaa tgtagccagt gtgactgcag aactgtgttt    53100
tttatttat tgcatttaaa ttaattttaa ttgaaatagc cacatgtggc ctgtgactgt    53160
cgtattgaat aagacaggtg caaacaaata attctgttta gctgagtgat atgtgaggtt    53220
ggcccaaaag gaatgaagga ggaaggtgcc ttctctaggc attggctttg ctcgcaaaag    53280
gctttggaca agagaactct gcaagaggca gtgaggggtg gtgagtgcag gagggtcagg    53340
ggaagtgaga gggtgatagg tactgatttc taggtgggct ggttccctga tcttgtcaac    53400
atctgcccag cccaagacgc tgaccttgcc ttctctccct tccaggatga cacagaacca    53460
tacttcattg gaattttttg tttcgaggct ggaattaaaa tcattgccct tgggtttgcc    53520
ttccacaaag gctcctactt gaggaatggc tggaatgtca tggactttgt ggtggtgcta    53580
acggggtaag tggcgcgtgc tatacgcttt ggatttaact agctgaagga ttacgaggct    53640
tttggttggt gtggtccggg ccaggctcag gaaggctgag cccttgtgtt ctccctcccc    53700
ttgttatgcg cctgcctcct ttctgccaac accccacctc catgtctcag ctgtatatta    53760
cagcagatgc tttctgttac aattaaaata atagctcatt attgttggct gcttccagag    53820
tgctttatgc ccattctcta atttaatcct tgcaacaacc cactgaatta ggaaatatta    53880
atattcccat ctgaccactg aggaatcaga aactcagagt gtaacttgct taaggccacc    53940
cagcaagtaa gtgatggaac tgggagatga acagaagatt atgcattcca gaactcaagg    54000
ttttaagtgt tgtacgtgca tgggtctctt gatttgcttg aggatatctt gcttttattt    54060
caacttggtg aatgtttttt gagaatgtct gggtgcaagg gattgtgatt atgacaaagg    54120
agaaaagcaa gctaaataag gtacagttac tgtcttcaag gagttttcag atccatatat    54180
gatgaactgt ggttgaaatg tgtatatgct ttcctctaag cacctgtat gaggtagcac    54240
ttgctggtat aacaaaagat ccaaagctag gaaatgactt aaacacggca gaagtttatt    54300
tgtcactcat agaaaattca aaattgagct gggtgtggtg gtgcatgcct gtaatctcag    54360
cactttggga ggctgaggtg ggaggatcac ttgagctcag gagttcaaga ccagcttggg    54420
```

```
caacacagtg agaccacccc cccatctgta aaacataaaa taaaataaaa attaaccagg   54480
catggtggta catgcctggg agaattgctt gagctcagga gttggagggc acagtgagct   54540
atgatcatcc aaccgtgctc cagcctgggc aacagagcaa gaccccatct cgaaaaaaaa   54600
aagtccaaaa taattgttcc tagttgacag gctcatctcc tccaatgact gacgacccct   54660
gacccttgcc atattgtggc tcttcattgt cagcccacat catccaataa ctccatgctt   54720
gtctgtatca aaccaggaag gagaagtgag catagaaggt gatacttgga aaggtttatg   54780
agtttggaag gggtgtgacc catacctgtt ccattcatat cctattggct agaactcggt   54840
cacatgacca cacatcactg caagggaagc tgggaagtat cagattgtgc ttagaagaaa   54900
agggaaatgg atttggagaa tgacctacta gtctgtcagg gaccttaaaa acttttatta   54960
gattccagta gggacattag tatctggtac caatggctgg ttcctcctct tcccactctc   55020
tactctcctc tcagctaagt ctgggctctt ctattctaag acccttcttc actgacacc    55080 tttttcatag taatcattta caggatcata gctttccatg ttttgttgct gctccaggtt   55140
ctgtctctct tggcggatgt gatgggttgc agcacccaca ctgtgctggc cgggctctca   55200
caatgcagat ttgtttcaga gcaatgttgc ctctcacaga aggagctgtg gcctattggg   55260
ctgtttctgt agaggccttc agatgtcagc agtctgttgt aaggactctg ggctagctct   55320
catgggcttg ggtgttcaca gagggatctt tgttggctgt gctcacagtt cggtggcttg   55380
ggaccttggt gggttccaag ggcatattat ggtactgggc acttttctct tagtctacta   55440
ggaaactcat ctagaaacag cctagtggct aacttttta ttgttaaaa aatgtaaagc     55500 tgggcagggt ggctcatgcc tgtatcccag cacattggga ggccaaggtg ggaggattgc   55560
ttgggcccag gagtttgaga cgagcctgag caacatagca agaccacatc tccacaaaat   55620
aaaaattaaa agtgtataaa gctgggtaca gtggcacatg cctgtaaccc caattactca   55680
ggaggctgga gagagaggat tgcttgagcc taactagttt gagaccagct gggtaacct    55740 agcaagatcc catgcaaaac taagtagaga ataatagagc aaacacctgt gtatacattc   55800
atttattcaa tgactatta ttgaacactt ctgtgtgcca ggtcctgttc taggctctgg    55860
gacacagcag taaacaaaat agaaaaatcc cctgtcctca tggagctgag agtctactga   55920
tggagatgga cacaattgat gaatgaatct agtgtgtcag atggcggtga ggggtacaga   55980
ggaaaaataa agcaggggag ggatgggatg tgtggcaggc aggggtgagg ggtgctggaa   56040
gccagggaag acttcactgg gcatgtgaca tctgaatgaa aacctaaggg aggtgagtga   56100
gtgagccatg aggagagctg gaacagagtg tcaggcaaag gaacagcca gtgcaaaggc    56160 tctgaggctg gactgtatct gacatgtttg atcaacagta agaagaccca catggctaga   56220
gaaggtgacc agaagaatgg ggagaattgg ggatagagaa gtaatggagt aacctgctat   56280
caaaacacaa cctttctctt tttttttttt ttttttttttt tgacaagagt ctccctctgt   56340
cacccaggct ggagtgcagt ggtacaatct cagctcactg cagcctctgc ctcccagttt   56400
caagtgattc tcctgcctca gcctcccaag tagcttggat tacaggcgtg taccacaaca   56460
tctagctaat ttttgtattt ttagtagaga cgggtttacg ccatgttggc caggctggtc   56520
ttgaactcct gacctcaagt gatccacctg gcatggcctc ccaaagtgct gggattacag   56580
gcgtaagcca ctgtgcccag caaaacaaaa cctttctaac ctttctaatc cctgtttctt   56640
ccctccctag acccattcct ttctctccc catccagggg cactttcctg aattttatgt    56700
ttattatttg catttatgta ttcacacttt ggctgcctaa gtatataaga aatatatgct   56760 acctatttt acacttcaaa atatttttta aatagcatca gagtgagaat agtttacact    56820
```

```
ttgactacat gcatagataa gaaatatgtg ggctgggaat ggtggctcac acctgtaatc   56880
ctagcaattt tggaggcaaa gatggaagga ttactttagg ccagaagttt gagaccagcc   56940
tggccaatgt agtgaaaccc tgtctctaca aaatgaaata aaatgtaata aaatattcag   57000
ctgggcatgg tggtgtgctc ctgtggtccc agctactcag gaggccaagg cgggaggatc   57060
acttaagccc ataaggtcga cgctgtagtg agctatgact gcactccagc ttgggcaaca   57120
gagcaagacc ctgtccctaa aaaatgtttt ttgttgttgt tgttgttttt tgttttttg    57180 ttttttaat aaaggccagg tgtgatggct cacacttgta agcctagcac tttgagaggc   57240
cagggcagga agactgcttg agtccaggag tttaagacca gcctgggcaa catggtgaaa   57300
ccccatctat aaaaaaaatg caaaaaatta gccaggcatg atgacgcacg cctgtagtcc   57360
cagctactca ggaggctgag gtgggaggat cacgtgagcc caggaggtcg aggctgcagt   57420
gatccgtgat tgcaccactg cactccaggc tgggcaacaa agtaagacct tgtctcaaaa   57480
aaataaaata aaataaaaaa taaaaaaaag aaagagaaa gaaaaaaaga atatgtggt    57540 actgtttttc aaacttcaca tttctctaac ctgacttttg tgttcaacat gagataaatc   57600
tgattaataa aaatagtttc catgcatcca ttttcatgac tgcatagtat tctgtggtag   57660
gagtatgctg ccgtgtattt atctatttgg attgtttcca gctttgggct attttgaccc   57720
aaagtgtccc tgcttctcc caagtgagtt tctctagggc acgtacccag gagtggaact    57780
gctgagttgt atactgtgtg catcctcagc cccactaggt attgccaaat tgctctgcaa   57840
agtggttgtg ccaattcatg ctccctgggg gctggcttct gctggctgag gctggcttga   57900
ccttgctggc aggaaggagc cttaaaaatc cctgtgtggt tttttttgtt ttacttttat   57960
tttaagttta ggggtacaag tgcagatcta ttacatgggt aaactgtgt cttgggggtt    58020 tgttgtacag gttatttcat cacccacgta ttaagcctag tacccattag ttatttttct   58080
tgatcatctt cctcctcccg ccctccaccc tccaaaaggc cccagtgcgt gttgttcacc   58140
tctgtatgtc catgtgttat catcatttag cccccactta gaacacgcag tatttggttt   58200
tctgtttctg cattagtttg ctaaggataa tggcctccag ctccgtccgt gttcctgcaa   58260
aggacatgat cttgttcttt ttcttggctg catagtattc catggtgtat atgtaccaca   58320
ttttctttat ccagtctatc attgatgggc ttttgcagcc ctgttttttt tttttttca    58380 taataacacg gttatgggaa cacttaggga agctcatata ttattgagca gtgtgatggt   58440
taatattgag catcaacttg atcagcttga aggatgcaaa gtcttgttcc tgggtgtgtc   58500
tgtgagggtg ttgccaaagg agattaacat ttgagccggt gaactaggag aggcagactc   58560
acccccaatc tgtgtgggca ccatctaatc agctgccagt gtggccagaa taaaagcagg   58620
cagaagaagt tggaaagagt agacttgctg agtcttctgg ccttcatctt tgtcctgtgc   58680
tgaatgcttc ctgcccctcta aaatcagatt ccaagttctt cagcttttgg actcatggac   58740
ttacaccaat ggttagccag gagctctcag gcctttggcc acagactgaa ggctgcactg   58800
tcagcttccc tacttttgag gtttgaggac tctgacggat ccaccactgg cttccttgct   58860
cttcatcctt cagatgggct atcgtggac tttaccttgt gattgtgtga gtcaattctc    58920
cttataaact ccctttcata tatacatcta tcctgttagt tttgtccctc tgaagaacct   58980
tgactaatac agacacctag tgggtcccaa taagtgatca ttaaactgaa ggcagtcatt   59040
cagtaggtca gtttgtcact tgtgtttgta tctccctgct tacaacaagg tggccttttct   59100 tctagttttcc tgtcatctga tggaagagat tctagactca ttcctctaga ggagaaatac   59160
```

```
ttcatctaga acagataggt cctaagggtg agagctcatc gttgggatga atgaacccac    59220 tgaaattta tgcaagaaga aaattgtgta tatgtatatt ttttttttctg gtctgtagtt    59280 tttattagat tctcagggaa tcctgatcct atcatgaaga ccttctattc tagattgggt    59340
tcctttcaca tccccttctc ctttcttgtt gaattctcca tgcatttctt tcacttgctt    59400
ttcttgctct tatttctctg gtagtcagtt atccttttg tctggtggtt ctatctcctt     59460
caaatgaggc acattgctca aattttatta ctccaaattc caaggtgctg tttagtgtcc    59520
tgttgggttg taagctagga acagggaggg gaaagtaaaa cattctgcat gagctgggtg    59580
cagcgggcaa gcacctggaa ttccagctac tggaagctga ggtgggagga ttccctgagc    59640
ccaagggttt aaggccagcc tgggcaacaa agtgagattt tgtcttaaaa aaaaaaaaaa    59700
tcccagctgg gctctgtggc tcatacctgt aatcccagca ctttgggagg cagaggcggg    59760
cagatcgctt gaagtcagga gttccagacc agcctggcca acgtggtgaa accccatctg    59820
tactaaaaat acaaaaaaaa aaaaaaaaa gcctggcatg gtggtgtggt gtgcactggt     59880
aatcccagtt atttgggagg ctgaggcagc agaatcactt gaatccagga ggcagaggtt    59940
gcagtgagct gagattgtgc cactgcactc catcctggat gacagagtga gactctgtct    60000
caaaaaaaaa aaaaaaaga aagaaaaaac acgcgcgcac acacacac atcatgcaga       60060 cctagccttc tgccaatgtc aatggtagag aaacacagta gacacttaat tctatgtttc    60120
agagaggagg ggactcaaat atattaattt gacattgaga cagtgatgac tttaatgagt    60180
actttctttc ctttttttt tttttttttt cgggacagag tgcagtggtg ggattttggc    60240
tcactgtagc ctccacctcc tgggttccag cagttctcct gcctcagcct cctgagtagc    60300
tgggactaca ggcatgcact gctgtgcctg gctaattttt gtattttag tagagacggg     60360 gtttcacact atcagccaga ctggtctcga actccgacc tcaggtgatc tgcccacctc     60420
ggcctcccaa agtgctggga ttacaggcat gagccaccgt gcccggccta atgagtactt    60480
tctgattaac ctgttgccct ctcagattcc tgaagcaaac cacagcgtta aaacgtgatt    60540
cattttgtgt ggaccaccac ggtgtttacc ttcttcttgg gtgaagtttg gtggaaaaga    60600
tcttaccccg gacatctgtt tgttctttgt aactcagagc ctcagagaaa tcctaacttt    60660
ataatgttgt caaacccttg taaggcatgt ttttattgta tttgtgttct gatcatgaaa    60720
ctgaaaatgt gtaagaggaa gatttcagaa gcttggctgt atgtctgaga tgacagttct    60780
tttactgtca ttctcaaata tatataaata ttgaagagat caaataacac aaatcgtgca    60840
tgttaagaaa agagactgtg aacctcacca gagaggggtg agcacaattt ttttctttt     60900 ttattcacag ggttagcact gtccctttca cataataaat gctcagtaaa ataaatggtt    60960
gttaagccgg aaaagggtaa cacttctgat aatgagtgtc ctgggaaatt tactaagctg    61020
tttagaagat gggaccaaca cactgataga aatagtcaga tagtccagaa gtctatggca    61080
gatgccctga acatcagatg agatataaga cagagaagct ctgggtcttt gccagctctg    61140
acattttatg actctatgaa acggaaggtt cctttttaga agggtctata aactgtctca    61200
ggctttgggc cattttgttg aagatcagag gcaaggaaaa gacacaacta cacaggaacc    61260
atcagggaaa gatgttgttt tttggtcttg aagcatcatt gaatttttt ttttttttt     61320 gagacggagt ttttctcttg ttgcccaggc tagagtgcaa tggcatgatc tcggctcact    61380
gcaacctccg cctcccaggt tcaagtgatt ctcctgcctc agccttctga gtagctggga    61440
ttacaggcat gtaccaccaa gcccgggtaa tttttttgta tgtttagtag agacgaggtt    61500
tctccatgtt ggtcaggcta gtctccaagt cctgccctca ggtggtccgc ccacctctgt    61560
```

```
ctcccaaagt gctgagatta caagcgtgag ccaccgcacc gggccgcatc attggatttt    61620
aaggctccat ggattctggc aggtccagcc cttctgtttt actcacaaac aagtggtttg    61680
tccaaagtca cacagagatg gtggcaagag atctagaata agaaggtgtc ttcaagtcat    61740
ggagccagga accctggctt tttgggcaat ggaagtggta taaatgttta atatcacccc    61800
tcaggttctg ccactagagc ccagctctct cttccttcct cttgcccccct gactagccta   61860 tggcctcttt ccagagaata agaaagggat cctcagagaa taatcccagt tcctcgcttt    61920
ttattatata gttgaggaaa ccaagtctca gaggggtcag tgtcttgacc atacacctct    61980
catgtcctct ctccttttg attaattgaa taaatacatg tagttgcttc ttacctcctt     62040
tctttcttca cccctgcccc atgcacctgc tcttagttgc cttcacatgt aaacagcatt    62100
ccaacaacaa caacaaaaca caaccagcat tctaactcat gagaccagca acagttccta    62160
taaataccag cagcatttta ttttaatgtc tctctgcagt agtttctccc ctccatggat    62220
cagtcatcct tggtaccaaa aggattcccc actgtgacac aaatgctttt tgtcattctc    62280
agtgagttat accattgaga gagcatcgat cttttttattg ttcaaagctt ttggttgtca   62340
tgatatttgc tggaccatgt ttcaccagga accacatcac ttcctagcag caggagctat    62400
tttcttccat cttctaacaa caccagcagt gacagtgata ataatgatgt tagctgccat    62460
ggtcgttatt cttatcattt attgagtact tactatgtgc cagggactac attaagagtt    62520
ttatgtgtat tatcacattg agcctcgcta gcctttgtac agatgaatct gaggctcaga    62580
gaggttaagc tgctcacaag ggagtcacac agctggtaag gggtggatca ggatctcagc    62640
ctctctgcta ggacacttct ctaaacctag aataatactg ggcctgtgtt aagttcagca    62700
aagagctgta ttcaacccag tgtccttagg aatgtaatgc ctgttattaa caacagtggc    62760
aacattgata agctgaaact tatgaggtgc ttacaatatg atatactata tattatatac    62820
atacataggc acccacctat aatctcagca ctttaggagg ccaagtcagg aggatcactt    62880
gagcccagga gttcgagacc agcctgagca gcatagcaag atcctgtctc tgtaaaaagt    62940 ttatttttc agttggccag gtatgttggt acatgcctat agtcccagct aatgaggagg     63000
ctgaggcagg aggattgctt gagcccagga atttgaggct gcagtgaact atgatcacac    63060
cactgcactc cagcctgggt gacagagcaa gactgtctct aaaataaaa ataaaaataa     63120 aattatttca actctcaagg ttaaataaat actattatta ttcccattta cagatggagc    63180
aactgaggct caaagacatt aaatgcttac tgtcttagtc tgttttctgt tgcttatagc    63240
agaacacctg aaactgagta atttataaag aaaagcaat ttattcttta cagttatgga    63300
gactggaaag tttaagatca aggctgcatg agctataatg cacacacact attgcactcc    63360
aggctgggtg acagggtgag accccgtgtc aataaataat aatataaaat aaataaaaca    63420
aatttcaaca tgagttttgg aaggtttgaa atattcaagc cagagcatct gtctcataag    63480
tggtggaccc aggatttgaa ctaaggcaga tctggatcta gaacccatt tcttgaatcc     63540 tacgctattt ctctaaggtc aagtttgcca aggaaaataa acttgagaat ttgaatagag    63600
ctctctgaca tgggaagtca gggtgatcct tccttcccct ccctgatctt gggttccact    63660
atggctgggg gaaaacagga gcagaagaga tttcaagaaa tgagagattg gcctagcgcc    63720
atggttaaga cctggacttc agagtcagag gaagctcctc cctctatgac agtgagaatg    63780
tgggttgaac tcactgaacc tcagttttct cacctggaaa aagggagtaa aactagtgcc    63840
tagctcctag ggtttgcatc acacacgaaa gttggtgaac tgaaggaaaa aaacttaaat    63900
```

```
tcttgtgggg gagcatgtga tagatgctac aaattctcca tgccttattt acctagctta    63960
cgtctaagtt cacctgcagc ttcctcttgg tacactccca tctctctaca tctctgttgg    64020
agggcagtct ctggcatcac agagtttgct gagccagatg cttaacaacc tcggtagcat    64080
ccctcaacca gtgagctagg gagtcagtgt ataaataccc tggcttcccc attgctcagt    64140
gggaaaacac tgaaatatgt tatacagcat catagaggtg cctcagtaaa attgaatcct    64200
agttgttcac ataaaaccca ttcactagtg tacccttttac caatctctct cttcctcatt    64260
cctcacttgt aattccttgc attaccctccc aaattaacca ttggaccccta gttttttgcct    64320 tggggtctac tcggcgctaa ctcaaggagc ggaagttgga agcttagcgg gttacaggtt    64380
tcagcaccct ggacagctcc cagcacaccg tattgtgcta aaatgttctc ttccctccct    64440
ctgcctccag ctgggtgga gagggactga gtaaaggcca gatggccagg tgaccttgtt    64500
ccatactgag cttcttggcc atttttccctg tggggctgga aagaccttg ccatccatct    64560 ctccgcaggt ttgggggccg actgaggtct tgttttctcg aattgctatg acaaatgcca    64620
gcctgcctcc aagggcatc tgtcccactg cctctacagt ttgcatgcct aatgactcct    64680
ctcctctcac cagggcaggg aggtggctgc ctggtgggcc gcttgaagcc gggagaccaa    64740
gatcatgcca ctggactcgc aacaaaccga gactcttttt tttttttttt tttcctcgag    64800
acagggtctt gctctgttgc ccaggctgga gtgcagtggc gcgatcttgg ctcactgcag    64860
cctccgcctc ccaggttcaa gcactccac ctcagcctcc caagtagctg ggattacagg    64920
cgcacaccac catgcctggc taattttttgc attttttagta gagaggggggt ttcaccatgt    64980 tggccaggct gatctcgaac ttctcccctc aggtgatcca ctcgccttgg cctctcaaag    65040
tgctgggatt gcagctgtga gccaccatgc ctggccaaca aatagggact ctgtctcaaa    65100
aaataatttt ttttaaacat tgctttgcaa cccagctgct tcttgtgcag gcatctctaa    65160
atgaggacag ccagtctaca tagacacgta aggaagcata gtggttaaga cctggtctttt    65220 ggggttagag tggattccca acctgactcc actgtttcca agctgtgtga ccttgggcaa    65280
gttactgtac ctccctgaat cttccattttc ttcatctgga aaatgagagt agtagcatcc    65340
cctgacttgg tggggcatgg tggctgatgc ttgtaatcca aacactttggg gaagccaagg    65400 tgggtgaatc gcttaaactt gggagttcaa ggccattctg ggcaacatgg tgaaactcca    65460
tctctacaaa aacaaaacaa agcaaaaatt atctgggtgt gatagtgtgt gcctgtaatt    65520
ccagctactc aggaggctga ggtgggagaa tcacttgagc ccaggaggtc aagtctgcag    65580
tgagccgtgc ttgcaccact gcagtccaac agagcgagac cttgtctcaa acaaacaaaa    65640
caaaacacaa aacaacaaca aaatactacc accttatgga gttgttttca aggttcaatg    65700
agttaatgtc tgacccatgc tgggctgggt ttatggatgt tacttgccca gggacagtct    65760
gaagaaagag aaagtgatat agtccattgg gcctcagctt cctcatctgt ggaatgggaa    65820
taataattgc acctacctca aaaggtaaaa gtcagtgaga tacatataag gcattcagaa    65880
caaaaactgg cacagaataa gtgctcaatt atattagcta ttgtaagact aataactatc    65940
attataatga tgataataat tattactact tccccaggcc cagttccata gaccagttag    66000
ttaactgtag ggaacgtttg ctattattag ttgggttccc aatatctgac ctcccttttcc    66060 aatttaggga gaatcctccc cttttctataa agtactgctg gtctatggga tcccaccctc    66120
actaataagt tgaaggtgaa agggattcat tgtcaccca tcacctggta gtcagggcat    66180
gtgatttaaa caaccagggc caggcgcagt ggctcacgcc tgtaatccca gcactttggg    66240
acgccaaggc aggaggatag cttgagccaa gcccaggagt ttgagaccag actgggcaac    66300
```

```
atagtgagac ccctatctct taaaaatttt ttaattagct gggggtggta gcacaggctt    66360
gtagtccccg ctactcagga ggctgaggca ggaggattgc ttgagcccag gaggtcaagg    66420
ctgcagtgag ccgtgatagt gccactacac tccagcccag cctgggcaac agggcaagat    66480
cctgtctcaa aaacaaact aataaaaaac tcaaccagtc acgttttcct acccaggaat     66540
ttgaaaatgg accaagtgat ccaaacatga tggtttggac tctttcatgg cctcctgcta    66600
caggagaagg tcaggctggc tacattgttc ctgctgattt cccaaatccc ctcttctggc    66660
cccctgttga ttatctgagt ttcctaaaaa tccctttat gcctaagata gccggtcagt      66720
gtttggtttt gcaatcaaga acccagactg ggccaggcac ggtggcccac gcctgtaatc    66780
ccagcacttt gggaggccga ggcgggcaga tcatgagatc aggagatcga gaccatcctg    66840
gctaacgtgt gaaacccg tctctactaa aatacaaaa caaaaaaaaa aaattagcc         66900 aggcatgatg gcggtcacct gtagtcccag ctactgggga ggctgaggca ggagaatggc    66960
gtgaacccgg gaggcggagc ttgcagtgag ctgagatggc accactgcac tccagcctgg    67020
gcgacagaac gagactccgt caaaaaaaaa aaagaaaaa agaagaaccc agaacccaga     67080
ctgatcctga gacaaagatt tgagggcaac gaatcacgag gtcaggaaat cgagaccatc    67140
ctggctaaca tggtgaaacc ccgtctttat taaaaataca acaaattagc tgagcgtggt    67200
ggtgggcgcc tgtagtccca gctactcggg aggctgagga aggagaatgg cgtgaacctg    67260
ggaggcggag cttgcaataa gccaagatcg caccactgca ctccagcctg ggtgacagag    67320
caagactcca tctcaaaaaa aaaaaaaaaa aatttgagga caagtggttt gtttggcaat    67380
accaggaaac aggggaacag gatagtcaga aaagaaagag aaagctgggc atggtggctc    67440
actcctgtaa tctcagcact tgggaggcc aaggcaggtg gatcacctga ggtcaggagt      67500
ttgagaccag cctggccaac atggtgaaat cccgtctctg ctaaaaatat aaaaattagt    67560
cgggtgtggt ggcgtgcacc tataatcaaa ataaaataaa atcaggatat tttattttaa    67620
aactctgtct tagtgtaact catatttacc tcttctgtat gctcctttgc atcagttata    67680
tattgccata atacggctgt gtaacaaaca atccccaaga cccagtggct tataatgaca    67740
agcatttatt tagctcatga ttctgaaggg tggcagttta ggctgggccc agttgggtgc    67800
tttatctggt ctcagttgag ctcattcatg catctttggt cagctgcggg tcagctgggt    67860
ggctcttctg tttggctgtt agctggctgc agactggtcc aggatgacct cggctggaat    67920
gactgtgctc cactccctat ggtctttcac cctccagcag gctagcctga gctagttcac    67980
atggcagctt ttcatcctcc agcaggctag cctgagctag ttcacgtggc agcaatggga    68040
ttctaagaga aagaggaagt gttcagcctt cttaagggct agtcccagga atggcacaac    68100
atcgtgttgg ccactgttgt ccaaagcaag caatgaagct ggtccagatt caaggaatgg    68160
ggcaacagag cccatctggt atttacctgg ggccactggg gccccattcc tgttccctgg    68220
ggccttttgc cctgacttct gtgggccctc agagcatatt ttcagattcc tttccatccc    68280
tgaccctcag caatcaatgt agatgacgtg tcattactgt gtcacttgca cagagaaaag    68340
gaggaaaaaa tgtcagcaaa aactctgctg agagcagagg gcccatcata cagcaagctg    68400
gaaagaaaag tgggaatgat tacacagcct cctcagatgc ttccagcttt tatcaaatct    68460
cactgtgata tctgagttct gaaccctcac aggtggttgg cgtgcaaggg aagagatttc    68520
ttgtctgcca tgctgacatg cacagacacg caacctggct ccctctgtcc actgggcttt    68580
tggattttgt ttgttgaaat gttacccact cctgatcaga gctggatgga aacctggctc    68640
```

```
tgattccatt ggctcagggg ctcaggtggg ggcagaggcc aggctggttg ggtgtctatg    68700
tggagacctt aactcttctc cctcccgccc caactctttt tgtttctttt ttttttttt    68760 ttttttttg agatggggtt tcactcttgt tgcccaggct ggagtgcagt ggcgtgatct    68820
tggctcactg caacttctgc ctcctgggtt caagcaattc tcccacctca gcctcctgag    68880
tagctgggat tacaggagca cgccaccata cctggctaat ttttgtattt ttagtagaga    68940
cagggtttcg ccatgttggc caggctggtc ttgaactcct gacctcaggt gatcccccct    69000
cctcagcctc ccaaaatgct gggattagag gcgtgagcca ccacacctgg ccttttctt     69060 ttcttagctg cctccacctc tcttcccttc tgcagtgtta ggtttatgga aaccgaggcc    69120
ggcgtagaga tcaacttcag agagcatgaa ctgagcatct gctgggtctt agatccttta    69180
catagcttat catcttcaaa ccttctcaca gttctgtgtg gctagagcca ggatttggac    69240
acagctctgc cccactgtag aaccaggctt ccttctgtcc actgtcaaat tttagaggga    69300
gaaaataggg aaagggacac cagccttctc cacgagcagc ttctgcccac tcaccccagg    69360
gactttgcac atgctgtgtg cctgtgtctg agatatgctc cctcctctgt atctgcttaa    69420
ttcttaccca gacatgatac ataaagtatt taacatccag gtggcaggga caccagctaa    69480
cctgaaaaga ggttcccctg ttgtgccaca tgtgtactca ttgtttgctg cattgtgggg    69540
gcagtccagg ggccttgaag aggggccaag gtgccaaagg ggcactctca ggcctcaagg    69600
aagtacatgt ttactgatat gatactgtct cttcctccag gaaggaagcc ttccctgatc    69660
tccccactgc atgcccacta tgataccagt ttaggtcccc tctttatggc catctgtggc    69720
atcagtgtga atcctcttaa tgttgtctat ttggttaatc atctgtctcc ttcctctggg    69780
gggtaaagac agaaccacag agcctcgtgt agaacttgag aatggggttc agtaaaaatc    69840
tgttgaatgc ataaatgggt gattgagtga atgaatgaat gagtgaatga atgagtgagt    69900
ggatgaatga atgagtgaat gaatgagtga gtgaatgaat gaatgagtga attaatgaat    69960
gaattcatag ctgataatac aggcttcatg gcttttgtta ggcttgccca gacattgcta    70020
ggggatggac agaaggaaga agagctatac ttaattccag tcctgttgtt ctgtagcagg    70080
aggagaaaaa cagggactgc ccagcctgct ctgggtggat tcaggagcag ctgaggttcc    70140
tctcttattt gcaaacaggg aattcaaaaa gccccaacct cagaatcaca ctcgcctcag    70200
cagctgtacc agccaagggg acaatgtggg aagccttggg caccaggaat gctgagtgct    70260
tcgaaaaagc gaaggctcag ggaacaatcc ctgattttc attcccttgt cctttctgaa    70320
gaaacaggca aaggcaggcc aggcacggtg gctcacacct gtaatcccaa cactttagga    70380
ggccgaggct ggtgaatcac ttgaggtcag gagttcaaga ccagcgtagc caacatcatg    70440
aaatcccatc tctactaaaa atacaaaaat tagctgggtt tggtggtgca tccctgtaat    70500
ctcagctact cgggaggctg aggcatgaga atcacctgaa ctggggaggt ggaggttgca    70560
gtgagctgag tctgcgccac tgcactccag cctggatgac agagtgagac tccatcttaa    70620
aacaaaacaa aacaaaaaca agtaaagcct tgtgtgtttt taaattgtag gttcagcagc    70680
aaagctctgt aataaggagc tggaccctgc agtcagacag tcatgggctt ctccagtgcc    70740
cagccgagtg acccgaggga gttatgataa acaccaacat tcatccacaa tttgtaccta    70800
gtgctattct caatatcttg agtaaattat ctcatttaat cctccaggca catctttctt    70860
ggtaggtgcc gtcattgtcc ccagtgtaca tctgggaaaa tgaggacagg ctggcagagc    70920
acccttcctg ctcacctctg ctgctctgct gacctctggc aagactgttg tctctctgag    70980
cctcagtttc cccatctgaa aattggggcc tgtattagcc cgttctcaca ttgctataac    71040
```

```
gagatgcttg gctggggctg ggcgtgatgg cttatgcttg taatcccagc actttgggag    71100
gctgagttgg gcagattggg agtgtgagac cagcttgggc aatatagcaa gaccccatct    71160
cttctaaaaa aaaaaaaaaa ttagccaggc atggtgatat gcacctgtaa ttccagctac    71220
ccaggaggct gaggcaggag aattgcttga acccaggagg cagaggttgc agtgagccaa    71280
gattgcgcca ctgcactcca gcctgggaga cagagtgaga ctccatctca aaaacaaat     71340 tattttttaaa aaattaaaaa aaaaaatgcc tggctgggca cagtggctca cacccataat    71400
cccagtactt tgggaggcca aggtgggaag attgcttgag cccaggagtt ccagaccagc    71460
ctgggcaaca cagtgaaatc ctgtctctac taaaagtaca aaaattagcc aggtgtggtg    71520
gcacgcgcct gtggtcccag ctactcagga gggtgaggtg ggaggattgc ttaagcctgg    71580
gaggtcaagg ctgcagtgag caatgattat gccactgcac tccagcctgg gcgacagagt    71640
gagaccttgt aaaataata ataataataa taaataaata aaaccctga gactggggta     71700 atttataaag aaaagaggtt taattgactc acgattctgc aggctctaca gaaagcatgg    71760
cagcatctgc tcagcttctg ggaaggcctc aggaaactta caatcatggc agaaggtaaa    71820
gctggagcag gtgtcctcac atggccagaa caggaggaag agagagagtg gggagatgct    71880 acacacctt aaatgtccaa tctcacaaga actcactcac gatctcgaga atagcaccaa    71940
ggcggaaatc tgcccccatg atccaattac cttccaccag gccccacctc caacattggg    72000
gattacaatt cgccataaga tttggttgcg gacagacaca gatccaaagt acattaaaag    72060
taatggcaaa aaccacaatt acttttgcac caacctaata tctcaggggc tcattgtacc    72120
tatttcacag gacaaatgaa ggtatcagta ataacagtag cctgtagtcc cagctattca    72180
ggaggccgag acaggaggat cacttgaacc caggaggtcg aggctgcagt gagctatgat    72240
cacgccactg cactgcaccc tgggtgacag ggcgaaaact tatctctaaa aataataata    72300
acaacaacaa tagtgaacac agatataaca tgtgtgtggc caggctgtgc ccttagggct    72360
ttgcagggat tatttcattc actctcaatc tccccatttt acagatgaga aaactgacgt    72420
tcagaaaagc tagaggactt gccccaagcc acacggctag gaagtggtgg aattgggtt     72480 taaatgagga agcttgactt cagtgtcgaa gctcttaact gccacactca atacatggag    72540
tagaggttgc tgattctgtg attatctgat tctggaaagt aaagaccctg tttccagacg    72600
tttgctgctt gacttagttc ccaggggatg ccactggat gatgcagtgt tgcccaggag     72660
aggttagcta gacacactgc aaccattcca ttgctaatac ttatacttgc tcttgttctg    72720
ctgggtgcta tgcagggaag ggctgtctga gcccttgca agaattctcc cattggtgcc     72780
tcccagagat tctgaggttg gggcttttg catcccttat tagcagatga gacaccaaag    72840
cccaggtcaa taatctgacc tgcatccccc gcctaccagc cagaccaagg tcacttcccc    72900
acaatgcagg ccctgatcca aggctctggg tgcaaaccag tttccatgtc cctggggtc    72960 catcttcttc agctgacttt ttttttttt tttttttt gagacagcgt cttgctttgt        73020
tgccgaggct ggagtgcagt ggtgtgatca tggcttattg cagccttgac ctcccaggct    73080
caagcaatcc tcccacgtca gcctcctgag tagctaggac tatgggcaca cgccatgatg    73140
cctgggtaat ttttttttt ttttttttga cacagagtct cgcactgtag cccaggctgg    73200
agtgcagtgg cgcaatctcg gctcactgca agccccatct cccaggttca tgccattctc    73260
ctgcctcagc ctctcgagta gctgggatta caggtgcctg ctacctcgcc tggctaattt    73320
tttgtatttt tagtagagac ggggtttcac cgtgttagcc aggatggtct ccatctcctg    73380
```

```
acttcgtgat ccgcccacct cagcctccca aagcgctggg attacaggca tgagccagat   73440
gcctggctaa ttttaagtt tttttataaa ggcggggtct tgctatgttg cccaagctgg    73500
tctcaaactc ctggcctcaa aaagtcttcc tgcctcagcc tcccaaagtg ctaggattac   73560
agacatgagc cactgcaccc agcctgactt tttttctaac tgaaaaatta attatatata   73620
ttcatggagt acaatgggat gttctgatat atgtttacat ttttgaatga ttaaatcaag   73680
ccaattaaca tatccactac atcgcatact tattttttgt ggtgagaacg cttaaaatct   73740
actcttttag caattttgaa atatacaata ccttatgttg tatattacat tatgttgtat   73800
agtacgttga aacatacact acaatacgtt atcattaatt gtggtcacca tgctgtgcaa   73860
aagatctcta aaacgtattc ctcctgtctg actgaaactt tgtatccttt gcctaatatc   73920
tccccaatcc ctccaccacc agccctggt aaccaccatt ctctctgctt ccatgggttc    73980 aaattttta ttttttgaaa ttttaattt ttatttatt atttatttat ttatttattt      74040 attttgaga tggagtctcg ctctgtcacc cagtctggag tgcaatggtg ccatcttggc    74100
tcactgcaac ctccgcctcc tgggttcaag cgattctcca gcctcagcct cccgagtagc   74160
tggggttaca ggtgcttgcc accaggcccg gctaatttttt gtattttag tagagacggg   74220 gtttcaccat gttggctagg ctggtctgga actcctgacc tcagtgatc cacccacctc    74280 ggcctcccaa agtgctgaga ttacaagcgt tgagccactg cacctggcct aaaatttttt   74340 ttttttttt tttttttgag acggagtctc actctcttgc taggctggag tgcagtggca    74400
tgatctcagc ccactgcaac ctcagcctcc cgggttcaag cgattctcct gcctcagcct   74460
cctgagtagc tgggactaga ggtgtgcacc accacgccca gctaattttt gtattttag    74520 tagggacagg gtttcaccat gttggccagg atggtgtcaa tctcttgatc tcgtgatctg   74580
cctgcctcgg gcttccaaag tgatgggatt atgggccacc acgcccggcc tcaaatttttt 74640 tagagctcac atataagcga gattgtgtac tatttgcgtt tctgtgtctg gcttgtttca   74700
tcttagtata atgtcctcca ggttcatgca cgttgtcgca aaagatggaa tttgctcctt   74760
tttaaagact gaatagtact tcattgtgta catatacacg ccatattttc ttcatccatt   74820
cctttactga tggacatttg ggttgtacct gcatcttggc tattgtgaag agtgctgtca   74880
tgaacatggg tgtgcagctg actctgaggt gttagaggga ttacagctcc tccaaaagac   74940
caccgtcacc caaacctgct cctcctgccc tatttctgt ttaggtaaag gcggctttaa    75000 cccctgcag tgctctggcc tcagacctcc agatcttcct ctatgcctct atgcctcttt     75060
ttctccaccc cctgcatcca atctgttagc acatcttatt ggctctacct tcagaatcta   75120
cccagaatcc accacccacc tctcaccacc ttcacagccc caccccggtc cagccccat    75180 ctttgctggc ctggactaaa ccagttgccc ctccacccca atctggtctc ttaacttcag   75240
tccttgcccc accccagga ctgttcccca cacagcagcc agagggcacc tgtgagccac    75300
tgagtcagga cctggctcct ctttgctcac aacctcactt ggagaaaaag cccaaattct   75360
cctcacaggg acccacaaac tctgcccctg tgatccccca tccccctcta ttcccactct   75420
cctctccact cactcggctt cagctacaca agttccctgc tgtcccttac acaccaagca   75480
ctccccagcc tcagggcctt tgcacaggct gttccctctg cctggaacac tcttccccca   75540
gatatctgct tggctccccc ctcacttcct ttgggtcttt gctcaagtgt ccttctaaca   75600
tgtaactgcc tcacctgcac tgtgccaccc cactccccgc tctaggctt aatttccctc    75660 tacacccctg aagagcatct gccaagctat atttacttgt ttattggtta ttgccaatcc   75720
cctgccccca ctagaatgcc agctccatga gggcagggac ttctgtctgt tttgttcact   75780
```

```
gctattcccc cagagcctag aacacagcct ggcacatagt aagtattcac taaataattt    75840
gtaatatgaa ttgtgccagt aaaatcttcc aggggcatca agcccctgcc atgactaggt    75900
ggtaacatcc tcaccccctg tccatgtgct atctcctcct gacctgcttg tctcattgtt    75960
ctaatggtgg ctcacgcctg taatcccagc acttggggag gccgaggcgg gcagatacct    76020
gagttcagga gtttgagacc agcctggcca acatgatgaa accctgtctc tactaaaaat    76080
acaaaaatta gctgggcgtg gcattgcacg cctgtagtcc tagctactcg agaggctgag    76140
gcaggagaat cgcttgaacc cgggaggtgg aggttgcagt gagctgagat catgccattg    76200
caatccagcc tgggccacaa gagcgaaact ctgtctcaaa aaatatatat atatatttca    76260
ttgtggtaac atatgcataa cataaaatgt accattttt aagtgtttag ttgagcggcg    76320
ttaagtacat tcatattgtt gtgcaaccag gaccgccatc catctccaga acttttgcat    76380
cttgcaaaac tgaagctctg cccccaggaa actctcactc cccgctcccc cttcccctct    76440
ccccgactcc cccttccccc ctccccactc ccccacccct actccacact ccccactccc    76500
ccagcccctg gcaccgccg ttctagtttc tatctctgtg aatttggcta ctttgggtcc    76560
cccctgtgag tagaatcata cagtatttgt ctttttgtga ctggtttgtt tcgtggagca    76620
taatgtcctc cagtctcatc catattgtag catgagtcag aatttccttc ttttccaggc    76680
cgaatcgtat tccattgtgt ggatggacca cactttgctt atctgttcat ccagatgggc    76740
acttggcttc cacctttgg ctattgtaaa taatgctgct gtaaacctgt gtgtacaaat    76800
agctgagtcc ctgcttcaa ttcttttgga tatagaccca gaagtggaat tttttttaaa    76860
tcaagatttg acccactggg gcccttagag gtctcattgg ctctgaagct tttttttttt    76920 ttttttttg gacgctttga aactaaaaat aggagtgagg ggcacagtga gggggcaca    76980 catctctcgt gtcagcgttt tttaaaaaca ccccgggagg aagatgtgtg aaatccctcc    77040
cttccccccg ctcccacccc ctccaagatc tcaaaatacc tcttgtttta ggaagcggct    77100
gtgacatcag gcaggcagcg tgtggcatct gagacacaat atcgcaagtg gctgggagcc    77160
cagagaaacc aggacaggcg tgctggggat gtggactaga gatggagcta attttagtgg    77220
ctgaagaggc tgcaagaaga gagagaaaga ggggtgtgtg tgtgtgtgtg tgtgtgtgtg    77280
tgtgtgtgtg tgtacgcaca gtgatagagg ctggagggg agaaatgaca gataaatcag    77340
cttgggcaaa gaaagctaat gggcagagga gcgagaccca gctcagaagg tggtcagcaa    77400
atctaaagat gtgtgcccga gggtcaaggt ggtgggggga ttcataggca agtggtagag    77460
aggctattcc atttgcagag gctctctctg tttgaggcgt gattcacctg tgccgtcctc    77520
aaggccattc tgagaacacc actgttgttt tcctccttt atgagtaggg aaactgaggc    77580
attgaactgc ttctattctt cagtaagaag caggggaac atatggtaga agcaaagaaa    77640
tacaaacatg agggctctcg gggtctacgt gattggctgt gacatccatg agagcggatc    77700
gcaggttgaa ggaaacactg gtggcagaaa gtagctgaac atttggattt gggaatccca    77760
gtggacgtgg cgaaaattct ggcttttccc ttcacaggct gcggggccac tctgacctgc    77820
ggtttcctta tctgtgaaat ggaacgatgc cacctgtctc agcgttgttt tgaggatgcg    77880
aggagatgat ccgtgtaata tgcccactag ggggcctgct ccagggtaga ttctcagcaa    77940
atggtagtca tggttttgt tacatttggg gatattggca ggtaaaaagg aaatacttca    78000
ttcattccaa aattgctcac tgaggttcta ctatgtgcta ggccctgatg acacatcggt    78060
caacaagaca ggcctgcttt ctgcccttgt aaaacttcag ttcaactgca ttgcactcat    78120
```

```
cagcctaata atccaggtaa attgtgatga gaataacaac tagcatttac tatgagccct   78180
ttacaaatat taacccattt aatcttctaa agagcctata agataagagc tcttgccctg   78240
cgcagtggct cacgcctata atcccagcac gtcgtgaggc caaggcaggt ggatcacctg   78300
aggtcaggag ttcaagaata gcctgaccaa caggtgaaa  ccctgtctct gctaataata   78360
caaaaattag ccaggcatgg tggcaggtgc ctgtaatccc agctacttgg ctgaggtagg   78420
agaatcgctt gaacccagga ggcggaggtt gcagtgagtc gagatcactc cactgcactc   78480
caagagtgaa actctgtcac acacacaaaa aaaaacaacc tgttattatc cacattttac   78540
ctatgaggaa accgatgccc agagaggtta agtaactgtc caaggtcac  acagctacgg   78600
agtggtagag ctgggattca gacccaggag tgtgatccca gagtgtgtgt gtatgtttgt   78660
ttgtttgttt gtttgtttgt ttgttttttac cactgtgttt tcctgcttct gcaatagaag   78720
taatcaccag taacactgag cagttgttat gtgccatgcc cttaacacac atctccttgg   78780
atctttggaa agaatcctaa aagggttgtt tttcatgatc cacattttat ggagagagag   78840
agatcaaagc atagagagag gaagtaactt gcccaagatc ctgcagctga agactctagg   78900
gttgcaaatt tgggacggcc ctggaccctg cattccagct tctagcagct catagggga   78960
actctttatt tatttattta tttatttatt tattttattta tttatttga gatggagttt   79020
cgctcttctt gcccagcctg gaatgcaatg gcatgatctc ggctcactgc aacctccgcc   79080
tcctgggttc aagtgattct cctgcctcag cctcctgagt agctgagatt acaggcatat   79140
gccaccacgc ctggctaatt taattttttt tagtagagac ggggtttctc catgttggtc   79200
aggctggtct cgaactcctg acctcaggtg atccgcccat ctcggccccc caaagtgcta   79260
ggaatacagg cctgagccac cacgcatgcc ctgggggga  ccacttttat cggtgcattt   79320
cttccatttt ccctgtgtct gtgtaaagat aaacaccccc aagccccttg actatgaact   79380
gtgggccata attagttaat ggaaggtaaa tgttttagag acggaaattg ctgtgccatt   79440
tttcccccgct aggcattgtt gcctgcatgc taatgcaaca caatgtgcct tcttctgtc    79500
aggcattttt agacaaattc tattttccct aaaatatttt gccaaagaaa atagcaaatg   79560
gggaagacat tcagaggctc aggcagagag aggacaccat tcccttgggt ttaaacagaa   79620
tggcagagtg gataacagca cagatcttga gttaggtgga tgccaatttg tgatttattt   79680
cccagcaaac caagatgctg gctctctgtg tgcctcagtt tacttatttg tcaaatgagg   79740
agaataatgg tacctgtctc tcaccagctt accagttgcc tctttagcta tgtctaatct   79800
gctattaacc acgcccacta tgtctttaat tccaagtatt agaattgttt tcttcctaca   79860
agctgtctga tctttttttaa tcctgcttca tcttttgcag tattgttttc ctacagcagg   79920
atttctcaac cttggcacaa ttgacatttt gggctaggta attcttggcc gtgagctacc   79980
accctgtgct aagatactta gagcatccct ggcctctcac cctactaaat gccagtagca   80040
gcccctcccc agttgtggca gccaaaaatg gctcagacat tgccaaacga aatgtcccat   80100
ggagggtaga aacgccccca cttgagaatt gttctatagg tattttcaag catgtcttac   80160
atttctttaa gtataatatg caaagaaaa  ggctaaatct aaaaaaagcc cataatatgc   80220
gaagaatttt tataatcagt gtccaataac ttaagtatct aaaattgtta tggcttttt    80280
tctgctgtct cttgtttcct gtgattcctc attctggtgc cttgttttct tgaatgtctt   80340
gttatctttg gttgtgtgaa gctcattttc catgggacac tatttttgt  tttgttttgt   80400
tttgagacag agtctcgctt ggttgcccag gctggagtgc agtggtgcaa tatcagttca   80460
ctacaacctc agcctcccag gcccaaatga ttctcctgcc tcagcctcct gagtagctgg   80520
```

```
gattacaggc gtgtgccacc acacccagct aattttttg  tattttagt  agaggcaggg  80580
tttcaccacg ttggccaggc tggttttgaa ctcctgacct caagtgatca acccgcctcg  80640
gccccccaaa gtgctgggat tacaggtgtg agccaccgtg cccggcatcc atgggacact  80700
gttgaaggga gttcattgag gcctgcgatg aaggcgaacc ctccatggac aatttgcatt  80760
tactttttcc aggtgtctgg gaaactccca gtctaggacc atcttagact tttagaccaa  80820
caatgtgttg agaatttagg tcaccagtgt ctgcaaaagc cagcttgtgg ttataatttc  80880
tcaaaaactt ttgttttct  ccttttctgc aaagtgccaa agtaacttcc tcaaaaatct  80940
ctgggaatgg aaagacggga gtaaattaac ttcaggtttc ttacctgaaa gtgatagcct  81000
attggggccc catcctactt ggggagtggt gtgtctcctt tgagactttc taacacgtgt  81060
gtaccctgga ctttgcccca cccctgctcc ctaggaggcc ataaaacttg aagcagcagt  81120
tccatgggtt agacagatgc ccttggggca aaagtggttt taatgctctg gtagatgctc  81180
aggttacctc tgggaaattc ttgacttcac ttatttattt ggggctgata actactaatt  81240
gtcaggcctt tcttgtttca acaacatgga cttcagattt tatgcaggat tgtcatcgt  81300
tttcagcaag agagtcagtc ttattaccca gcttactgca ttagaaatag atgtctgggc  81360
caggcgcagt ggctcacacc tgtaatccca gctgtttggg aggctaaggt gggcggatca  81420
tgaggtcagg agttcgagac cagcctggcc aacatggtaa aacccatct  atactaaaga  81480
tagaaaaaat tagctgggtg tggtggtgcg tgcctgtaat cccagctact tgggaggctg  81540
aggcaggaga attgcttgaa cccgggaggc agaggttgca gtgagccaag atcgcaccac  81600
tgcactccag cctgggtgac aggacgagac tctgtctcaa aaaagaaat  agatgtctgt  81660
tgtgtggatt atttaaaaga gtagatggcc aagaactatg acttatgcct gtcatctcag  81720
cactttgaga ggctaaggtg gagggatcac ttgaggccat gagttagaga ccagcctggg  81780
aaacatagca agaccccat  ctctgcaaaa gtaaaataaa ataagttagt gtgcatgatg  81840
gtgcaggcat acctctagtc ctagctactc aggaggctga ggcaggagga tcacttgagc  81900
ctaggagttt gaggctacag tgatctatga tcatgccact gcactccagc ctgggtgaca  81960
gatcaagacc ctgcctctaa aacataaaaa taaatacaaa ttaagttaaa aaataaaata  82020
aataagtaat agaacatcca gcacagttct tggcatgcat tgactgttgt tgtttgtttg  82080
tttgtttgtt tgtgacggag tctcactctt gttgcccagg ctggagtgca atggcatgat  82140
cttggctcat cataacttcc acctcccagg ttcaggtgat tctcctactt cagcctcctg  82200
agtagctggg attacaggca cgtgccacca ctcctagctg ttttgttttg tttgtttgtt  82260
tgttttgtat ttttagtaga gatggggttt ctccaagttg gtcaggctgg tctcaaactc  82320
ctgacctcag gcgatctgcc agcctcggcc tcccaaagtg ctgagattac agacgtaagc  82380
caccacgcct ggccagctgt tttgattgtt aaatgaaggt ggtatgaaag ggaaggaaga  82440
acagtgacat ttgcaaggga cactccctgg agggcagggc aagggggctg tggaggggag  82500
aagtcagaga gtatgataca ggttgccttg ggtgatgttt tagattttag ccaacattgg  82560
caaagagcct catttatctc tcagagtagc tctggctact ggaaatgctg cacaacttca  82620
ggcggacttt ctagaagaaa actcttggcc aggtgcagtg actcacacct gtaatcccaa  82680
cactttggga ggctgaggca ggtggatcac ttgagctcaa gagtttgaga ccagactggg  82740
caacgtggca aaacctcatc tctacaaaaa aaatacaaa  aattaaccag gcgtggtggt  82800
gcatgcctgt atcccagcta cttgggaggc tgaggtggga ggattgcttg agcctgggga  82860
```

```
ggtggaggtg gtagtgagcc aagattgcac cactgcactc ccatttgagt gacagagcaa    82920
gaccttgtct caaaaaagaa aaaagaaaa gaaagaaaa gaaaattctc tctgggattc      82980
aatcctggcc cacacagcat tggcttcact tcacctcctt ctcccctgag atacacagca    83040
ccattccccc aagcttcatc aacttaatct ctgatctggg tgctgtgact tgtccccatt    83100
cctggccaga atttaaggta gggatgaacc cactagccct ccatcacgca ctctgccata    83160
aaagcacacc acgtgctgat tgctgtcttt ggtctccttt ctgccttgcc ctctagactc    83220
tgagctgctt ggagacagag gccagttttg tccatctcca aatcccctaa agtcctgtgg    83280
ccagcaagca ggtaggacat ctgaaagttc gtcagagagg gaattgcttt tctcttgaga    83340
tgcaactaga acaagaatct tattgacctg gagtagcttc aaggttgtaa gagtatgtgt    83400
cagggttctc caagaccact ctcaggtttg aaggtttgct aaaagggctc acggaccca     83460 gaaaagctgt gaaattcagt tatggtttat tacagtggaa gaatacagat aatacagatt    83520
aaaatctgca aagcaaaaga tgcacaaggc aatgtccagg ggagatcagg catgagcttc    83580
cagctgttca ctcccagtgg agttatgcaa acagtgctca attctcccag caatggtgtg    83640
tgacaatgta cagtgtaccg ccaaccagag aagctcacct gagccttggt gtccagggtt    83700
tttattgggg ctcagttaca ttgacatgga gcacccatgt gactgacttt aactgctggg    83760
tctccagcac actccaagat caaactgata ccgtgtgtcc cagggcccca gctgaacaca    83820
aacaggcagt caccatagat cccattgtga gcataagcta ccaggcatgg cccaaagccc    83880
tagatataca gatattcttt ccaggagcca gccaagggcc agtccttcct ttggaatatg    83940
cagagtttga actccccaac cccaaggagt taactctta ctacacagaa tataaatctc      84000
accaagtctt tcttcttgtc aagtcctctc aaggtgaccc attgctttta gcagtgtctt    84060
tgagaccctg cgtcatctgg ccttgaccca tatcacctgt gttatctctc cactctagct    84120
acattgaact tttcttttt gagatgtggt ctcactccat cacccaggct gaagtgcagt     84180
ggtacagtca cagctcactg cagcctcaaa ctcctgggct caagtgatcc tcccacctca    84240
gcctcctgag tagctgagcc cacaggtgca tgccattaca cccagctaat attttatttt    84300
ttagtaaaga tgggttctca ctatgttttcc caggttggtc tcaaactcct gggctcaagc    84360
agtcctccca tcttggcctc ccaaagtatt ggcattacag gggttagcca ccacatccag    84420
cccattgaac ttttttaagga tcccctagca tcctatactt tctgtcactg gatagccttg   84480
gaattatttt tccttctttt tgaaatactc ttcttctttc caccctttgc tgtcaagtct    84540
cagaataggc attatttcct ccaaaaaccc tctcctgacc ctccaaatct ggatgaggac    84600
acttcctttg cccagagagc acctgtttta atcctctcag gtggctataa taaaatacct    84660
taaactgggt ggcttataca cctcagaaat ttattttcca cagttctgga ggctgggaag    84720
atcaaggcac tgacagattt ggtgtctgat gagggccat ttcttgtttc gtagaagggg     84780
tcttcctact gcatctttcc atggtgaaaa gagttgaggc agctctctga aacctctttc    84840
atgagagcat gaatccctct gtcttcatga tctaatcacc tcccaaaggc cccacttcct    84900
aatatcttca cattggtgac taggtttcaa catatgaatt tgagaaagac acagacattc    84960
agaccatagc agtgctcttc caccaggttt tttatcccc tgtattataa ttgaggttta     85020
aattatctgc tttccttccc ttagattgta agctccatga gagcagggcc ctacccatcc    85080
agtcattgtc ctatccccca tgactacaac ttcctgggta cataattaat atttattata    85140
ttatgtagca aaggtatgct gccatactaa gagacccaaa aggccaccgg attaaaacct    85200
taaagaaaaa aaaataattt ctctcctata atagctgcaa ggttagccat gcaggttggc    85260
```

```
agggaagctc acttccacaa agtcactcag ggattcaggc tcctgttgcc ctcttctttt   85320
ctaccaccaa atgatcttca gcaccatttg cacaatcaaa acttaactgg tcttgaatag   85380
gcagaccttg aatttctgaa gtctcagacc caaaagtggc agctgtcact tccactgaca   85440
tatcactgat ggaaacttaa tcatgtgatc ataccaaact gctagggatg ctgggaaatg   85500
tagttttgtt gggaactcca tgacttggct aaaattccat tactgtagaa gatggtgggg   85560
gatggggag tggtggacat ccagtggttg ctaccatatt tattgaatca aattgtcaaa    85620
caggacctat ctgataaggg gttcttttcc agaattaact gaagtattaa atcaggggca   85680
aaggcatgtc acctcatctt tctctcccta tattggcttt ctaggctgt tataacagag    85740
taacatgaac ttggcggctt aaaacaacag aaatttattt tctcttagtt ctggaggcta   85800
gaagcctaaa atcaaggtgt cagcagagcc accttgacaa ctgctctagg aaagaattct   85860
tccttgcctc ttctggtggc tcctggcaac ccttggtatt cttttgtctgg catccacttc  85920
aatctctgcc tccatcttca tttgcctttt ttctctgtgt gtctatgtcc tttcctcttc   85980
ttagaaggat accagtcatt gaatttaggg cttactctaa atccaggatg atctcacctc   86040
aagatcctta attagttaca tctgcaaaga gcttatttca aaacaagatt gcattctgag   86100
gtttcggtaa acacgaattt gggggaaata gtattcaact caattcactg ctttacttaa   86160
gaaaagagac catgaagtga gcctccttct gcttgagaga gagagcgagc ctttctgtgc   86220
aataggtcaa tgaatggatg cagctgaatt ccacataact ttataaaaat agatggccag   86280
cccatggggt ttgctgaccc ctgcccaaaa attccaaagt caacagcagt ctcttttta    86340
atcatttctc tattttttaa tttattttta tttttatgtt gagatagagt cccgctctgt   86400
cgcccaggct ggagtgtagt agtctcggct cactgcaacc tctaccttcc agatacaagt   86460
gattctcctg cctcagtctc ctgagtggct aggagtacag gtgtccgcca ccatacccag   86520
ctaattttg tatttttaat agaaacaggg tttcaccatg ttggccaggc tggtctcgaa    86580
ctcctgacct caagtggtcc acccacctcg gcctcccaaa gtgctgggat tacaggcatg   86640
agccaccatg cccggccagg atttcttca ttttaacagc attcttactt gtcccacatc    86700
cattctatcc tgggtctaat tagataacaa aatctacaga tcttgtttaa ctgacattgt   86760
cctggggat acttttatc ttttgagaca aggtctcact ctgttaccca ggctggagtg     86820
cagtggcctg ataacagctc actgcagcct cgaccacctg ggttcaagcg atcctcccac   86880
ctcagcctcc agagtagctg gaaccacaga tgcatgccac cacacctggc taattttta    86940
atttcttgta gaggtgggt ctccctatgt taccaaaggc tggtctcaaa ctcctgggct    87000
caaaagagcc tcccacctta acctcccaaa gtgctgggat tacagatatg agccactgtt   87060
tccagccttg gaaatatagt ctaagaactg agtcaatagg cgattttgtc attgtgtgga   87120
catcatgtag agaacttaac acaaacctag atggtataaa ctactgcaca cctcagttat   87180
ggggcatacc ctattgcacc taggctgcaa acctgcacag caggttactg tcttgaatac   87240
tgtaggcagt tgtaacacaa tggtaagtat ttgtgtatct aaacatatct aggccgggca   87300
cggtggctca cgcctgtaat tccagatcac ctgaggtcag gagttcgagc ccagcctggc   87360
caacatggcg aaactccttc tttactgaaa atgcaaaaa ttagccaggt gtggtggcag    87420
gcacctgtaa tcccagctat tcgggaggct gaggcaggag aatcgcttga acctgggagg   87480
tggaggttgc agtgagctga gatcatgcca ctgcactcca gcctgggtga cagagcaaaa   87540
ctccatctca aaaaaataaa aaataaaaaa catatctaaa cagaaaaggt acagtaaaaa   87600
```

```
tacagttata accatatggg accaccattg tataggcagt ccgctgttga tcaaaacata   87660
tcaaaacatc gttatgtagc acatgactgt accataaacc acacggcttc aaacaaggga   87720
aatgtattct ctcactgttt tggaggccat aggtctgaaa tcgaggtgtc accagggtcc   87780
ctccaaagga tccggggggag gatccttcca ttggatttgg agttgcttca ctccagtctc   87840
tgcctcagtg gtgacagggc gttctcctct tccctctcaa agttccctct tctgctgtgt   87900
cataaggata catatgactg catttaggcc ccactcagaa aatccaggaa taaactcttg   87960
ccctcatatt cttaactaaa tcgtacctgc ataccttatt ttttctaaat aaggtagcat   88020
tccagggatt aggacatcaa cataacttct ggagggttca ctgttcaacc cactacagcc   88080
agaatgcgct ttgaattcag gttctgacat ctgggactgc ctcccacgta cacacaccac   88140
taccttgtac tgaatgcctg aagggttctg cccccacctc cactccccca aatatttgct   88200
gtggacctga gaaagctgac ttcatggaag cttcattcca ttgttctaag gacttttcat   88260
acattaacaa atgtcttctc tctatgggga aaaccacaga gaaatcaaga cagagtgggg   88320
ttaagtaact caccctgagga ggaacagtaa gtggcagagc caggattcaa accaacatgg   88380
ttttgcacag ttttgacatc atttgcaaca caaatattgt cacagatacc ttttttgagca   88440
tctactgtgc taaccgccag gaaggaaaag aacatgggc cggagagct cttgacaggg   88500
gacagggctg gccatggagg tctgtgtctt ggtggaagat gctatggttc tcttttttt   88560
tttttttttt tgagatggag tcttgctctg tcacccaggc tggagtgcag tagtgcaatc   88620
ttagctcaca gcaacctcca cctcccgggt tcaagcgatt ctcctgcctc agcctcccaa   88680
atatctggga ttataggcac acaccaccac gcccagctaa ttttttgtatt tttagtagag   88740
atggggtttc accatgtggg ccaggctggt ctcgatctcc tgaccttgtt gtgatccacc   88800
cgcctcggtc tcccaaagtg ctgggattac aggcatgagc caccacactg ggcaactatg   88860
gttctctttt aactccttgt gctgaaatta ttgcagaagc ccaggccagt tcatccccag   88920
aaagtgaggc ataaacaggc agagctctac agaaacagag aatccacgac tggtttgatg   88980
gaggctgcct cactacctac agaatgggct ctgggtggat tgttctatct ggggagccag   89040
cccacccacc agtctcagcc cttggcgact ctttcctgct gtcacagcag ctggacattc   89100
agaaaccgaa acatgacagc cttccctccc tgttcctgcc cagtggagtg aaacccctc   89160
gggacccaca taccgagcgt gcacagcagc acagagttgc acagttaaca cagcgcttct   89220
tctccagccc tccggatgca agctgacaga ttggcagctg gctgacttcc aaggtccagt   89280
gagttcttgg cagtcgcttt ctgacctgga cgagtggctg ccacctcctg gaacatcagg   89340
ctgccccctt ggggagaggg tgacggtctc tctggaaaga ctgtgagctt tgaggtggtc   89400
atcaaaagcc attcttggaa acattctttg agctgtaccg tgcaattcgg tcaccaattg   89460
cacgtatttg gatattaata tccgtatgtg gatattaaat tggttttggg ttttgttttg   89520
ttttgattgt ggcaaaatat acacaacaat cctcctgcct cagcctccca agtagctaca   89580
ggcatgcacc accatacccca gctaatttt ggatttttta aatttgtttg tttgttttg   89640
ttttttgaga tggagtgtag cactgttgcc tgggctggag tgcagtggcg cgatctcagc   89700
tcactgccac ctccgcctcc tggattcaag tgattctctt gcctcagcct cctgagtagc   89760
tgggattaca ggcgcccgcc aacacgccca gctaattttt tgtatttta gtagagatga   89820
ggttttacca tgtcggccag gcttgtctcg aactcctgac cttgtgatcc acccgcctca   89880
gcctcccaaa gtgctgggat tacaggtgtg agccaccgcg cccggccgat ttttgtagtt   89940
ttagtagaga cagggtttca ccatgttggc taggctggtc ccgaattcct gatctcaggt   90000
```

```
gatccaccgc ctcggcctcc cgaagtgcta ggattacagg catgagccac cgcacacagc    90060
ctaaatgctg tgcctcacgc ctgtaatccc aacactttgg taagctgagg ccagaggatt    90120
gcttgagccc aggagtttga daccagcctg ggcaacatag gaagacccca tctctataaa    90180
aaataaaaat aaattagcca ggcgtggtgg tgcaggcctg tggtcccagc tactcgggag    90240
gatgaggcag gaggatcgct tgagcccaag aggtcaaggc tgcagtgagc tgtgattgtg    90300
ccactgcact ccagcatggg tgaaagagca agaccttgtc tcaaaaaaaa ttaagcgaaa    90360
tttaaaattc tgtttctcac tcacacaggc tgcacttcaa gtgcttaatc atcccttgtg    90420
ggtggtggct atcatattgg acagcatgga tagagaatat ttttatcagc gtaggaagct    90480
tcatcagaga ggaccgctca gaggcctgtg gggaccagca cagtgcagta aagacacag     90540 gccagctggt gagagactgg tcttctgatc ccagatctgt ccctcacttg ctaggtgacc    90600
ttggacagct ccctcagtcc ctctggagtt ttctcttcat tgttaaatca ggaaattggc    90660
ctcagtgaat tctgaggccc catctacttt tttttttttt ttttttttt  tttttttaat    90720 tgagacagag tctcgctctg ttgaccaggc tggagtgcag tggcatgatc ttggctcact    90780
gtaacctccg cctcccaggt tcaagcaatt ctctgcctca tcctcccag tagctgggac     90840 tacaggcgtg caccaccatg cctgggtaat ttttgtgttt tcagtagaga ccgggttttg    90900
ccatgttggc caggctggtc tcaaactccc aaccttgagt gatcctccg cctcggcctc     90960 ccaaagtgct gggattacag gtgtgagcca ccacgcctgg cctcatctag ttctaaatgt    91020
tatgacccac tcagctctga agacaaggga ggaacatcct ctcagtctag ctctgacatg    91080
cagaagcctc tcaccctgtc ccccaggtca taaaggcagg cgtgttgtga agagcacaga    91140
atgggctgag aaaaatatgc agggattgcg tctatctccc ttccttccgc acgtttcctt    91200
gtcggcacca cctgcctcta ttccgcgccg cacacacacc cgccttctct ctgtctcgga    91260
ggaagacagg atcttccatc ccccaaatcc tgccctgatt cctactctga agcctctgcc    91320
ctgactcctt taagctccct gggaatacag cccatctcct atgccctcct catcccagta    91380
gttcctacct tccccaaaat cgctttggga aagtccccca atgagtaacc agctgtccta    91440
catgggcatc tcagaacttc tcttctgttg ttgttgttgt ttgttttgct tttgttttga    91500
gacaggatct ctcttttttca cccaggctcg agtgcagagg tgtgatctca gctcactgta    91560
gccttgacct cccaggctca ggcgatcctc cccctcagc ctctggaata gctgggacta     91620
caggcacacg ccaccacacc cgggcaaatt tttttagga cttttggtag aaatggagtt     91680
tcgccgtgtt gcccaggctg gtctctaact cctgggctca agcgatccgc ccactttggt    91740
ctctcaaagt gctgggacta cagacatgag ccaccacacc cggcagagct tctatttctt    91800
gagtgtgttc tcagccatgc taagacattt tctcttctca gcctgatgat gcttttggct    91860
tgtgtttctt tgttttaat taccccttcc cagtcgctgt catgggatca tgagggtctt    91920
ctgtccatct agatgacacc tttcttgtgc cacgtgtctc caacattccc tggttttaa    91980 accccttattg ctttcaagat actatccaag ctccttaatg tggcacattg tccttcgctg    92040
ctatctgcct gcttttttt  tgagacagag cctcgctcta ttgcctaggc tggagtgcag    92100
tggcgcaatc acagcttact ctgcagcctc gacttcttgg gctcaagcaa tcctcctgcc    92160
tcagccttct gagtagctgg gaccacaggc atgcaccatc atgcttggct aatttatttt    92220
tatttatttt tatagagaag gagtctccct atgttgccca ggctggtctc aaactcccgg    92280
actcaaagtt cattgcagtt tcaattttt  ccttggctca aggatcctcc cacttcagcc    92340
```

-continued

| | | | | | |
|---|---|---|---|---|---|
| tcctgagtag | ctgggactac | agacgggcac | caacacacct | ggctaatttt | tgtattttt | 92400 |
| gtagagatgg | ggtcccacta | tgttgcccag | gcttctatct | gcttttatct | caccttccac | 92460 |
| tcttccatcc | ttcctttctt | ttcttttatt | tcctttccct | tcccttgcct | tccttttctt | 92520 |
| tctttctttc | tttctttctt | tcttttcttc | tttctttctt | tcttttcttt | tctttctttc | 92580 |
| ttgacagagt | ctggctctgt | cacccagact | gaagtgcaat | ggcaagatct | tagctcactg | 92640 |
| caacctccac | ctcctgggtt | caagcaattc | tcctgtctca | gcctcccgag | tagctgagat | 92700 |
| tacaggtacc | tggcaccaca | cccggcaatt | ttttttttt | ttttagtaga | gacggggttt | 92760 |
| cgctatgttg | gccgggctgg | tcttgaactc | ctgacctcag | gtgatcctcc | cacctcagcc | 92820 |
| tcccaaagtg | ttgggattaa | caggtgtgag | ccactgtgcc | tggcctttt | ttttttttt | 92880 |
| ttttttttta | agacaggacc | ttgctctgtc | actcaggcca | gagtgcagtg | gcactataat | 92940 |
| cactttctgc | agccgtgacc | tcctgggctc | aagggatcct | cttgccttgg | cctccctagt | 93000 |
| agctgggact | acaggcatgt | gccaccacac | tggctaattt | ttaaaacttt | ttgtaggccg | 93060 |
| ggcacggtgg | ctcacacctg | taatcccagc | actttgggag | gccaaggcgg | gcggatcacg | 93120 |
| aggtcaggag | attgagacca | tcctggctaa | cacagtgaaa | ccccatctct | actgaaaata | 93180 |
| caaaaaatta | gccaggtatg | gtggcgggcg | cctgtagtcc | cagctactcg | ggaggctgag | 93240 |
| gcaggagaat | ggtgtgaacc | tgggaggcgg | agcttgcagt | gagctgagat | cacgccactg | 93300 |
| cactccagcc | tgggcgacag | agcgcgagac | accatctaaa | aaaaaaacaa | aaaaaaaaa | 93360 |
| caaaaaactt | tttgtagaga | tggattcttg | ctaggttgcc | caggctggtc | tcaagcttct | 93420 |
| aggctcaagc | agtcctcttg | cctgtgcctc | ccaaagcctt | gggattacag | gcgtgagccc | 93480 |
| ccacacctgg | tcctaaccca | ctttctgaac | ttccaaccac | accatttgt | cctaatattt | 93540 |
| aagtcacacc | ataacatgtc | ccacttcaga | aatgcctacc | aaagtagtct | tcaaatcttt | 93600 |
| ttaaatcagt | ggaccctttc | taccaaacaa | atgttatttt | ttaaatattt | attttagagt | 93660 |
| aatttagact | tttagaaagg | ttgtagctgg | gcgcagtggc | taacgcctgt | aatcccagca | 93720 |
| ctttgggagg | ccgagacagg | tagatcacct | gaggttgggc | gtttgagacc | agcctgggca | 93780 |
| acatggtgaa | accccgtctc | tactgaaaat | acgaaattag | tcaggtatgg | tggcacgcgc | 93840 |
| ctgtagtctc | agctactcgg | gaggctgagg | caggagaatt | gcttgaaccc | aggaggcgga | 93900 |
| ggttgcagtg | agctgagatc | gcgccactgc | actccagcct | gggtgacaga | gtgagactcc | 93960 |
| atctcaaaaa | aaaaaagaa | aagaaaaaa | agaaaggtta | taaatatatt | ataaagagtt | 94020 |
| cccacatacc | cttcacccag | tttctcctgt | tgtttgtatc | ttatattatc | accatatgct | 94080 |
| tgtcaatgct | aaggaattgc | tgggtgcaga | gtggcacatg | gctgcagtcc | cagatactca | 94140 |
| ggaggccaag | gcaggaggat | atcgcttgag | cccaggagtt | caagtctagc | ctgggcaaca | 94200 |
| cagtgagacc | tcttttctgc | aaaagaaaac | aaataaaaca | tctaaaaaag | aatacactgg | 94260 |
| aggcggcgtg | gaaacaagga | tctcatttgg | gagttgtctg | caatgttctg | agcaagcagt | 94320 |
| aacggaggcc | tcaagtcagg | gctgtggtca | tggaggtggg | gaggggtggt | tggtttcact | 94380 |
| atctgtgttg | acttaatttt | agatttgcag | actcaactga | gtatgaactt | taagagaaag | 94440 |
| agagaggcca | ggcacggtgg | gtcacacctg | taatcccagc | actttaggag | gccaagtggg | 94500 |
| gaaggccgct | tgagcccagg | agtttgacac | cagcctgggc | aacatagtga | gacccctgtc | 94560 |
| tctacaaaaa | aaaattttta | aattagccag | gcagggtgat | gtgtccctgt | aatcccagct | 94620 |
| actcaggaca | gtgaagcagg | aggatcattt | gagcccagaa | agttgaggct | gtagtgagct | 94680 |
| gtagttgcac | cattgtgctt | cagcctggga | gacaaagtga | gaccctgtct | caaaaaggag | 94740 |

```
aatgggaga  gagagagaga  gagagaagga  gaaagagaga  gaaagagaga  gagggaagtc   94800
aaggagaacc  ccacatttt   tgacatggtg  tattagtctc  ttctcacact  gctaataaag   94860
acatacctga  gactgggtaa  tttataaagg  aaagaggttt  aatgcactca  cagttccaca   94920
tggctgggga  ggcctcacaa  ccatggcaga  aggcaaagga  gaagtaaagg  catgtcttac   94980
atggcagcag  gcaagagagc  ttgtgccatt  tataaaacca  tcagatctca  tgagacttat   95040
tcactaccac  aagaacagta  tgggggaaac  tgccccatg   attcagttat  ctccacctgg   95100
cgccgccctt  gacacgtggg  gattattaca  attcaagttg  agatttgggt  gggaacacag   95160 ccaaaccta   tcacatgggc  aagtgaaagg  atgggtttgc  catcaaataa  aatggggaag   95220
gagactgact  aggtgggcag  attaggaact  cagctttcta  tgaagtgcct  actgatggat   95280
agagatattg  tgttggccat  ctattaggtt  ggtgcaaaag  taattgcggt  tttgccatta   95340
aaagtaatgg  caaaggaaat  aacctttgca  ccagcctaat  aggaattgga  gtctaaaatt   95400 caaaaaggt   aagtcagagc  tggagatcca  aaggcaggga  tcagcctcct  gtggaggcta   95460
tttaaggaac  tgaataaggg  catagatgca  ggagagcacc  caggactgag  cccagggctt   95520
actctccatc  attaaagagg  ttggggaaga  tgaggaggag  ccagcagaga  agactgaatt   95580
ggagcaaatc  agaagaatgt  gggtgctggc  tgtcatgcaa  ggaaagtgct  aagccatttc   95640
aagtatgagg  gaatgatcaa  tgatgtccac  tgatgctgat  gtgttgactc  aaatgaaaaa   95700
tgagaatcaa  ccattggatg  tagtggcatg  gagatctttc  gtgacctgag  ccagagctgc   95760
ttaggtgaag  aggtgaaggc  aagaggctac  tggaaggatt  actactagct  cttttaaaga   95820
gttctgctgt  gaagggtaga  ggaagagaga  tggggcatgt  gttagctggt  ggggaagtg   95880 gatttcagag  gtttgtttcc  cttaaaaaaa  aaaaaaaaa   gaaaaagaa   taagaaaaa    95940 aaaaaggcca  ggcacaatga  ctcacacctg  taatcccagc  attttgggag  gctgagacct   96000
cgggaatttg  agactagcct  ggacaacata  gtgagacccc  atctctacaa  aaaaaatttt   96060
tttttaatta  gctgggcatg  gtggtgcatg  cctgtggtcc  tagctacttg  ggaggctgag   96120
gtgagaggat  ctcttgagcc  tgggaggtcg  aggctgcagt  gagctatgat  cacaccactg   96180
cactccaggc  tggacaacag  agcaagaccc  tgtctcaaaa  aaaaaagatg  ggagacctaa   96240
cagcagattt  tatgctgata  ggaataacct  attagggag   aaaaacatga  ggatgctgga   96300
ggaagaagag  tgtcaggagg  acatctcttg  gtggacgaga  ggggatggca  tttggtgtac   96360
aggtggaagg  tttcactta   gatgacagca  cacacagtta  tctatagaaa  caggagaaaa   96420
tgcactatat  gggcatacat  gctgggaggt  agagagtaaa  taatagtggt  ggttgcttgt   96480
ggaaattctc  ttctaatgtt  tttatatttt  tatggtttat  caaggacaat  ttatattttt   96540
acagtttact  gcaaacaaca  agttctaatt  tattcaataa  ttatttgtgg  gtagaccgag   96600
tgcagtggtg  catgcctgta  atcctagcac  tttgggaagc  caaggtggga  ggattgcttg   96660
aactcctgat  tcacttctga  gcttgaatca  ggagttcgag  atcagcctaa  gcaacatggc   96720
aaaacactgt  ctctacacaa  aatacaaaaa  ctagccaggt  atagtggcat  gcacgtagtc   96780
ccagctattc  gggaggctaa  aacgggagga  tcatttgagc  cctgaaggtg  gaggttgcag   96840
tgagccaaga  gcgagccact  gcactccagc  ctgggtgata  gaataagacc  ctgcctcaaa   96900
aagaaattct  tattcttctt  cttcttatta  ttatttgagg  agacatttac  tttgtaccag   96960
gcgctgtgct  agatgctgga  gatacagaca  tcaacaatga  caaggctaag  tgcctggcgt   97020
atttgtactt  tgagtctaat  aaaagacatc  acacagacac  acaacacaca  cacacacaca   97080
```

```
cacaggattg tcaaaggatc aaccatttca catgtcaaga tcaggaatga tattggtcta    97140
ctactgcctt accatatctc ctaccatgac ctcatcttcc tcttgccaga ttttaagtct    97200
ttatacctca actcccagaa ctctcttcgc ctcacaccct atcacaatgt catccgtacc    97260
ccacggccaa tactccatca ttcgggaaag caaagttcca aagcgtcaag attgtatcaa    97320
tggacctgtc tctatggcaa cagtcctgaa tgagccaagc aaggtaaccc tggagatggc    97380
gtgaatgaga agtggcctg ttgccacgga gacgtgctga atgggaaggc ccccacgagc     97440
caggctatgt cacgaagccg aaacagtcag catgaagtcg gtatgtctat tttcaactcg    97500
gaattacaaa aatacatttt aatagagctc atgacccatc tccttcctcg tccctgcctc    97560 ccacccact cttcagcctt catcctacaa cacaatcgag cctcaccagg aacccttcaa      97620
acccctcaag gacaccttac tgttccttca gtacacagtc cccttcctgg gctgaggtgg    97680
tattcctttg accaactact gtctcccctt tgggaccaac agtattctca aaagccatga    97740
gcttatggga agaacattaa ctacattctt tggggcaaga acagttgctc acctgtgaac    97800
cagctcagct tgcatctgtg agaatgattg caatgggtag accagttctc catcaaagaa    97860
tggccctagc accccacaca cagtggtata atctgatcat gctggtgtat tgaacatata    97920
atgttagtgc cacatgaaag gaatttgtaa aaggacttag tgcctagaaa ggtaccttg     97980 aagatcttgg aatctctgaa acttacccag gttccttata ccctgctcaa agtattcctc    98040
catttatttc ttcattcatt agttcttttg tttcaccaca tatatatttt tgaaacgggg    98100
tctcactctg ttgcccaggc tagagtgcag tggcaagatc gtggctcact gcagcctcaa    98160
cctccccatc tcaagcagtc ctcccacctc agcttcctga gtagctggga caccacaggt    98220
acaagccacc acgccaggct aattcttgta attttttgtag agacggggtt ttgccatgtt   98280
gcccagtgta ttcgtttgtt ctcacattgc tataaagaac tacctgagac tgagtagttt    98340
ataaagaaaa gaggtttaat tgactcacgg ctccacaggc tgtgcggaag gcatggctga    98400
ggaggccaca ggaaacttgc aatcatggcg gaaaatgaag gggaaacaag cacatcttca    98460
catggtggca ggagagagag agtgaggggg ggagtgctac aaaaccaggt ctcacgagaa    98520
ctcactcact gtcatgagaa aagcaagggg gaaatctgct cccaggatcc aatcacctcc    98580
taccaggtcc ctcccccaac attggggatt acaattcaac atgagatctg ggtggggaca    98640
cagagccaaa ccatatcacc caggctggtc tctaactcct gagctcaagc aatctgcctg    98700
ccttggcctc ccaaagtgct aggattacag acgtgaacca tatttattaa gcattgttac    98760
agcaaagaga agcattgttg cagcataaca attggaagac tccattgatg gacgtctcca    98820
tcaacaagaa ctgtcggata aactatggta cacccatccc ttagcgtgtt atgaagtcat    98880
tacaaaaaga agaagcagat ctctgagtgt caataagagc tagtacttat agggtgtcta    98940
ctgtatacaa gtgctgttag aaagtgagta ttaactcatt taattcttgt aacaagcctg    99000
tgaggtggat tctttcatat ccccatttta cagagaagga aataggaatc tctatatcca    99060
agatatgtta tcaggtgaca aaagcagttt ttgaatggtg ccgccatttt ctcgtaagag    99120
caaatctgga agattccatg agaaattaat aattgtgttt gcctctgtag cggcaccctg    99180
aaagatttgg aagtaggtgt ggaaaggaaa cttactttct tgtgtctttc tgaatttgt     99240 actgtctacg cgttttgtct ttcacaaaac caaacagaaa atgaccattt ggtgcatttt    99300
gtgtgtcagg cattcttcta gtctagaaa gcacaggaga gcaaaatatt ttactgacga     99360
gaaaaatgag gcatggagaa gttaagtgac ttgcccaggt agcagagctg ggattccaca    99420
tcatagggtt tatacaggaa acaggtaaac agagctgtgc ttgtgtgtgg gtatgtgtgt    99480
```

```
acacatgcat acatgtgtgc atgtgtgtgt gtgtttgtgt gtgtgtgaat gtgcttgtgt   99540
gttgggagag ggaaatggca agagaagaac ctacagaagg tcagcaggaa ccaacccatg   99600
ttttgaggag tttggacttt atcctgaagg cacaagggag ccatggaagg atttagacaa   99660
ggggtggttg tgcttagctt tttatttaga aggatgactc tggctgaagg gtgatggccc   99720
agaatacagg tatatgtgaa ggactcctcc tgccctagta ggaggatgcc cacccaccct   99780
ctctgcccag tgcagtatca aagggcaaat tgggtacaga gaattctcac caagctgggt   99840
agaatccact ctgatgctgg ggagtggaca ctgaatgcac cagcctctcc tcctgctcaa   99900
tccctgaatt gaagctgttc cactaatgtt agggatcaga ttcccttcat atatatatat   99960
atatatatat atatatatat atatatatat ataaattttt tttttttgaga cagagtctcc  100020
ctctgtcacc caggctgaag cccattgtcg cgatcttggc tcactgcaac ctccacctcc  100080
caggttcaag caactcttgt tcctcagact cccaagtagc tgcgattaca ggcacccgcc  100140
accacacctg gctaattcta tattttttagt agagacaggg attcacctat gttggccagg  100200
ctggtcttga gctcctgggc tcaagtgatc agtctgcctc agcctcccaa agtgctagta  100260
ttacaggcat gagccaccat gcccgtcctt tttatattac ctttttttat agagatgtgg  100320
tttcactatg ttgaccaggc aggtcttaaa ctcctggcct caagcgatcc tcctcctca   100380
gcctcccaaa atgctaggat tacaggtgtg agccactgca tctgtccaga ctctgttctc  100440
cataaagctg gcatatggaa agagggaaga ccatccaggc aatatcgaag tcccattggt  100500
gctgatgtgg ctgctgagac cacatgaatg gatgcattct gactctgcca cctctcagct  100560
atgtgaccct gggccagtca gcaagtccct ctataactca gttttctcat ctgtaaaatg  100620
gcgtcaacag tagccaaccc cagcaaatac tgtgaaatat acagaacatc attataatgg  100680
tgaggatgat agagatgcta tgttatcaga atacctgggc ttgaaccagc tcccttctt   100740
gcaagctgtg tgacttggag ctgatgccca aacctctgtg ggcctcattt gtttcatctg  100800
ttcaatgggg ataataacac tcttacttca tacagttatg gaggatttat tgaaataatt  100860
gacatacagc tcttagaaca gtatccggct ccttgtaagc gctcaagaaa tattacagac  100920
tgttgataat aatgcaatac tactaccaat aatatggcca ggagcaatgg ctcacacctg  100980
taatcccagc actttaggag gcagaagcag gctgattgct tgagcacggg agttcgaggc  101040
cagcctgggt aacataggga gactctgtct ttacaaaaaa taaaaataaa aatacaaata  101100
attagccagg tatggtggtg catacctgta gttccagcta cttgggaggc tgaggtggga  101160
ggattgcttg agcccaggaa gttgaggcta cagtgagctg tgatcacacc actgcactcc  101220
agccagggca acagagtgag accctatctc aaaaataata ataatggccg ggcgcgctgg  101280
ctcatacctg taatcccagc actttgggag gccaaggcgg gcagatcact tgaggtcagg  101340
agtttgagac cagcctggcc aacatggtga aaccccatct actaaaaaca caaaaattag  101400
ccgggtgtgg tggcgggtg cctgtaatcc cagccactca ggaggctgag gcaggagaat   101460
cgcttgaacc cgggaggtgg aagttgcagt gagccgagat cacaccactg cactccagcc  101520
taggtgacac agtgagactc catctcaaat aataatatga gtaataataa taatatcatt  101580
tttatcatca ttcttactaa cagtctctca ctccttgccc tgcagttttg cctgttttct  101640
tggaataaca ctcttccaca cctttcccct cagggatggt tcacgtttag catcatgacc  101700
caccctggg gattagttag ctcatttctg gaaagcactt tggagctgta ggtgctttgc   101760
aggctggaaa catcacggga cttgtaccat atttaagcaa tgccagatta ttctgcctgg  101820
```

```
caggggagg acacagagga tacggccctg gtatcttttc tccctgccta cctcagcttt 101880
gctctgaacc attttctgtc ctgttcaggg cagcctgggc cacttgccac ttccagcttt 101940
ctcgggagag gatgccttcc tgatggcacg cctcttaaca cacacctggt gctgttgttg 102000
aaaaagcaac aattgactcc agcgccagca ctgagaggct tgtccttaaa attagcagga 102060
gctgttggaa ggtcgctgtt agctcttttg actggaacac actgttcccc aggtggcatg 102120
aggctgaata cagtgcaggg attggctctg ctctcaggtg gcctgctcca cgctcctgag 102180
ctccgggtgg aagctgtgac cattatttcc ttaacagaaa catatatagc agcattaact 102240 atgaaccttta ttactgtgtg tgtgtgtgtg tatatgtgta tatatatata tgcacatatg 102300
tgcatatgtg tgcctatgaa cctgttctga gcactttaca aatgtcaatg tattttatcc 102360
tcccaacaac ccattttata aataagactt gaggcacaga gaggttacgt tactgcccca 102420
agatcacaca gctggagagt ggtgaggcca agatttgaac atatgtacca ttgtaccata 102480
tgtaccaact ttttttttct ttttgggatg cattcttgct ctgtcaccca ggctggagag 102540
cagtggcatg accacggctc attacaacct caacctccag gttcaagcta tcctcccacc 102600
tcagcctctc aagtagctag gaccacaggt gcataccacc atgcccagct aatttaaagt 102660
ttttttttgt ttgtttgttt gtttgtttgc agagatgggg tctccttata ttacccaggc 102720
tggtctagaa ctcctaggtt caagcaatcc ccccacctcg gccttccaac atgctgggat 102780
tacaggcatg agccactgca cccaggtcct ccctccttat aaaggtcgcc aagcacaatc 102840
ttgtgagcct ggccctatcc acacccatac gcaacatggt gtgtatttt caaacaaaaa 102900 ctgaatgaac acctctggtt tgggttcccc tcacacttgt cccgggtttg ttgactctgt 102960
gttgtgggcc tagacaaagc agtgtctgga gctcctagac ccagggacca gacagtctgg 103020
gttcaaatcc tggctcttcc acttctgcct gagtgctctc tctgaacctg tctttcttta 103080
tctataaaat ggagataatt ttttaaact catcacttgg tcaaactgct ttgagcatgc 103140
aaatgagttc atatgtataa acctcttaga atgtcccagg caaagaacaa cacttccactc 103200 agatcaacat ttatttagca tctactgtgt acccatgact attctaggtg atgaggagac 103260
cctctggttc ttatgaggta gtgaggtggg ggagggtgag aaccctaaac attaacgatg 103320
gtgtgttcgc aggtgggaaa atcagtaaag tcgggtaaag ggaatttggg agtgctgtgc 103380
tcaagtcctg gccctgccac tttctggggt gcaagataca gcattgaata gggtggtcag 103440
ggtaggcctt attgggaaag tgatatttga gcagacgatc tagatgtcgg cacatattgc 103500
tactgtttga tggtactaat atgagtttga gtttcacttg caagtatata tatatatata 103560
tatatatata tatatatata tatatatgtg tgtgtgtgtg tgtatatata tatgtgtata 103620
tatatgtata tatgtgtgt tatatatgta tatatatatg tgtgtatata tgtatatata 103680
tgtatatata tgtatatata tgtgtgtata tatatgtgta tatatgtgta tatatatata 103740
tgaaatttgg tccatttatt tatgctgatc aattaattga tgttgaaatt ataattgaat 103800
gttttattaa taaacagata cccacatact attttttcag aaattgttag gttttggggt 103860
tttctttaga ttttgattat tttatttgc ttaattttct tttttctttt ttttaatttt 103920 attttttccat aagttattgg ggtacaggtg gtatttggtt gcatgagtaa gttcttcagt 103980
ggagatttgt gagaacctgg tgcacccatc acccgggcag tatacactgc accatatttg 104040
ttgtctgtta tccagtgctc acctcctact cttcccccca agtctctaaa gtccattgta 104100
ccattatttt actcacccac attctttggc ctgagatgct gagtggtcat gactcccaga 104160
tcccttcttg tttctgtatc aaagatcttt actaagatcc tggcctaggg aacctattcc 104220
```

```
ctttcctcat ccccaatggg agaaggggct tcttccccag cttatttgcc aactcatagg    104280
aaaggtatga aggagaggac tgtagttgtc ttgaagctgg tcagatgttg aagagatgat    104340
aatatttgct gatcaagaga gacaaagcaa tgctggaaga agaggctgtg ttagttaaca    104400
ccagctgcaa taaccaataa aaccaaaaat ctctggctta agagtatgca tgagtgagaa    104460
atcaacttct aaagtacaac tggtggccgg atgtggtggc ttatgcctgt aattctagca    104520
ctttgggagg ctgtggtggg agggtcgctt gaccccagta gtttaacgcc aacctgggca    104580
acacagtgag acaccatctc tactaaaaat aaaaaataat aaagtgaaac tggtgagggg    104640
tgcaatgagg tggagtggtg ggtgactcaa atatggctcg actccatgca gtcactcagg    104700
gatccaggct gttggaggct ctccctgctt aaacatgtgg cttccaaggt tgttctaaga    104760
gcctacattg agacagcagc tggggaaaag ggaaagtgga gtgggaggta cttatgaggg    104820
ttcctggaag tggtgaacaa cacttctgcc tgcattctat tgggtggaat ttagtcatgt    104880
ggcccaggct agctgcatgg gaggctggga aatgtagtct ctgattaggc tgccatttcc    104940
cagtcccact tgtgaatctt tagtgggaag ctcaccatgt ttgcaccagg gattcagtct    105000
acctcccact catgcctcaa ctatgtatca ggcactgtcg taagtacttt acatatcagc    105060
ctacctaatg caaacaacta ctcagtgggt gctttattgg tcacatgtat tagtgagaac    105120
atggaaaccc agagccgtta aatatcttgc ccaaggtcac acagctagga agtggcagag    105180
ttggaatttg aatccaggaa atctggctgc agagcccac  gcttagtata aattcattgt    105240
agtttagaaa gaggcagaag gaccctaaaa ttggcataat ccattttttg gtccctaagg    105300
aactgactga attgactact tgtaaaagtg agtcctggac aggcaacagt ggctcaggtc    105360
tgtaattcca ggactttggg aggctgaggc gggcagatca cctgaggtca ggatttcaag    105420
accagcctgg ccaacatggc aaaaccctgt ctctaaaaaa atagaaaaat tagctgggtg    105480
tggcggtggg tgcctgtaat tccagctact caggaggctg aggcaggaga atcgtttgaa    105540
cctgggaggt ggaggttgca gtgagcaaag atcacgccac tttactccaa cttgaatgac    105600
agagcaagac tctgcctcag gaccgccatg gcccctggg  ttctaggtca gagtttctcc    105660
gccacagcac tgatgacttt gggggctgca ttattagctc caaatggga  gctatcctgt    105720 gcactgcctc aacttacttg atgccagtag cgcccgcgcc ccagttgtga gaaccaaaaa    105780
tgtctccaca cattgccaaa tgtcccctgg gaggtgaaat caccctggt  tgagagtcac    105840 tgttctagat tgttaaatat tatcttacac tctagcacaa gtccaaggca aactgactta    105900
gaaattacca accttgcaaa aaatagaaga tttcttaaag tcagtgagca tgatggtggc    105960
aagctgctga aatcacaccc ccagacatta gcagatggga tctggacagt attcatctag    106020
ttaaaaattg acaaggactg ggacactgca ggctcttcaa aagagaatca tttgaataac    106080
aaggggtcaa gacagggta  attggtgaaa gccctgctc  ataatttgaa aatataaata    106140
ggcatcatga aaattcatcc tgcaaaagtc aaaagtcgaa tgtgcagtgt tatacatgat    106200
cagttgattt gggaggggaa attgcatgca cacacatgag agcttgcaca cccacacaca    106260
cacacctgtt caagtgtgtg tgccagtgct cagtgaggac catctcccca acctgtctga    106320
tcatcttgct ttggggtgac cctatgggtg aggcagaaat tcttggatca tagttttcta    106380
atgaatatta taattgttaa cttctgatgg gtgctgactt tttcatcttt gcaacactgc    106440
gtaggtattt ttactctccc catttttacag atgagacaac tgaggctcag aaagattgat    106500
tagctctaca cgaagccagg atccaggctt agcctggctc caggaatcat gttttgagtt    106560
```

```
acgtagcttc cctgattctg agggacctcc ccacttctga atcttctac tgttactccc    106620
catggccctt tcctattgac cggaggcacc ccagctcctc actcgtccct tatcttatga    106680
aacatgacca tgatgtctga attcaaagga gagcctgggc tttgtgggga aaacgaagca    106740
gaaaaagaaa ggtggaggtt ggtggttgtt tttggcatgg tgaggagcct gtcgttgctt    106800
gaggaaagca agaaaggaga ttgctggggc ttggatccat ctctgggtgc ctgtgggtct    106860
gtctgtaaaa atgagaactg gtcgtgctca ttagaggatt tgaccgttag gccttgggat    106920
agcgatttgg gaactttttt ctgctaagac aaagaataat atggttcagg ttcattttgc    106980
tcctgctttc ccaagcccta catctcttct gggctttttt ttttttcctt ttctctcctt    107040
cttcttcttc ttcttcttct tcttctcatt tttggatctg gacttctgct gactcatctc    107100
tctgagcaag gaaggaggga ggaagtcaga attgctcatt aaccgttttc tttagtgact    107160
cagctgtgat tcacatttta attaatggag gagaaaaacc tgatcagtcc taaggcatct    107220
gcccaatcac gcataactcc aggctggtga taataataat acttgaaaaa agtggggtgt    107280
cctgaattaa actatggctc attccccaca ttagtcttga ggactccacc aggccctcta    107340
agttccaggt ctcaatgggg ctccctgaac cagagcagct agtccaagcc ccgagcagca    107400
tttctgcaga gttagtctga ggtcaggaca agaaacagag gctcaagccc tcctgggatc    107460
gcaggaggat catgggaatg taatattgtt tcctgagctg gtctttggct ataatcccag    107520
gctcaagcct ggcctccctc ccctcggggc ctgaaatttg tcagagccta ttgcaggggc    107580
agcttctgtg cttttttgttt gcccagagaa tgagaaaagt ccagataatc atgaccgcta    107640
cttcctgagc acttactatg catcaggtgg tgtgctcagc acttctcatg aatgatcacg    107700
ttgaatcctc actctgtcca caaaaagaaa gagctttat ataattctcc aacctcccta    107760
tgaggaaact gaggcttggc aattgcccaa tgtagacaat tagtaaataa tcaggcagga    107820
tataaaccca acccttttccc acctgggagc cagagcttgc atctactata cttctctgct    107880
ttccagtcag ctgcaaagaa aaattggaag ctgatagctc attcaacaaa cacttattga    107940
acccttccac ctgctcagcc ctgttctaga caccagagat ccatcagtga accaaagagg    108000
caaatccatg gtctcatgaa actgacaatt tacctgccca agtgtattag ttactgttta    108060
taagttccta ttaagtgtat tagatatgct tgcagctgta acaaagaatc ccaacatgca    108120
taagggctca aaacaataaa aatttcgttc ttgcacagat aaagttcaaa aggtgtattc    108180
tttttttttt tttcttttgc gacggagttt tgctcttatc ctccaggcat gagtgcaatg    108240
gcccagtctc ggctcactgc aacctccacc tcctgggttc aagcattctc ctgactcagc    108300
ctccccagta gctggaatta caggtgcccg ccaccacacc tggctaattt tttgtatttt    108360
tagtataggt ggggtttcac catgttggtc aggctggtct taaactcctg acctcaggtg    108420
acccacctgc ctcggcctcc caaagtgctg ggattacagc cgtgagccac cgtgcctggc    108480
caaaaaaaaa atgtattctt aaacagcagg cacctctcct ctaagcagta agtcaggggc    108540
ccaggcttgt tccatattgt agctcctcat cttcaaccca tggcttccaa agtctccatg    108600
cttcttgata tcaagccaca gaagggaaaa gagcatgaga agggcacagg agaaatgttt    108660
ctgggacaga cccagaagta gtccatatga cttccatcta cctcccactg gctagagctt    108720
acatggcggc acccacttgc agagctggga aatggagtct aactgagcat ccaggaagga    108780
gagacagaca tgagtctttg cgtgggtcct cactgagaat caagctccac atttttgatcg    108840
atgtcaccag agcgtacatg gcggcgccca cttcagagcc tggaaacgg agtctaactg    108900
agcatccagg aaggagagac agacatcagt ctctgcgtgg gtcctcactg agaatcaagc    108960
```

-continued

```
ttcacatttt gatctgtgtc acctccttgc aagccctacc ttaggacaat tttaagggac   109020
attcctatct tcttccaccc ttaggacagt tttaagggac actcctgagt tcttccaccc   109080
acctcctctg tttcttgggc ttccagctct caggatttgc ctttgcctta caatggggtg   109140
aagcaagaat ctggaagaat gtctctcccc acaatttgaa gtcttatttg aaaaaaagca   109200
gtagagcatc cctccctctt gaggtaggga aatctagaat caaatcctgc ttctccagac   109260
tttgacctca gaaactgggg ggacttcaag gtcttcaggt gggcagcttt catgaaccat   109320
tcattcctcc cacctcatac caatcagggt cctaacagga aaagaatta acttctagat   109380
ggttcaaaag aagaccatgc catgaagaga ctccttaaag ataggaac aggtgagaga   109440
aatagataac ggctgtttga ggtcctcaga gagaagccat cgcgagccct acatttcctg   109500
gaacccagtg gaggcagagc tgtgcagaag ggactactgt cagaaccagg gagggagcag   109560
ggaagcaata ttccaatctc tttccctccc ctcatcttct gccagcgctt cccctcagcc   109620
aaaccaaacc ggaaacggag caaagcattc tgggagttgt agtcttcaag ggtccgcctc   109680
gagggcacag agcccgctgg agcattgacc tagagggcac cagggaatg actagtttgc   109740
accatcatgt gacggactgc acgccctcga ttatgtaatc cactctataa ttcaactgca   109800
gagctgcatg gtacagcagg atagccacta gccacacgag gctatttaaa tataaatgta   109860
cattcattaa aatttaacca aatgaaaatt ttagccactg agccccattt caaatgctca   109920
ttagccacac gtggctcttg gctaccatat tggacagatc agaatagaac atttccatca   109980
tcccagaaaa ttctaggggc cggcgcagct gtggtgtaac ctgagcccat gcatgttatg   110040
gaatggagaa gagagaaaac agcacaagag gcagttttga agggagacag agagctgtgg   110100
atcagtaggg aggagactct ctaggcaaag gagcagttga gaagcaagaa agttgagtga   110160
gctgctttgc tgcgatggag gcttccctca cggggaagag tagagtcaga aagctttagt   110220
tcaagttcag ctctgaaatg aaccaatgag tgttctgaca agacacctgg ccttccggaa   110280
ccttggtttt gtagtggcca agggcttgac cctctgaagg ttcactgaaa aaaatcaact   110340
cacaaggcat attaattgga gaaaaggcag gcagatttat ttaatgtgtt tgcacgagag   110400
ccttcagaat gaagacccaa agctgcaggg gaaattgtcc gtttttaag cttaggttca   110460
acaaagtatg gacagcggtg tagaaatatg attgaacaaa aagtgtacaa tgtaaatgct   110520
aatagactga gtggggaaac ccaaaaaggg ctgtcttgat tctccttggt ctctctgagc   110580
atgcatttct tccgggtatg ggacaagacc ctctctggaa tggagggggg gctctcttgg   110640
ttctccttgg tctctctcag catgcattcc ttccgggtat ggggcaggac cctctctgga   110700
ataaggggc tgtcttgatt cttcttggtc tctcagagca tgcattcctt ctgggtatgg   110760
ggcaggaccc tctctggaat gggatcctta taacctacgg tcaaataacg taagttagat   110820
aatttctttt ttttttttt ctttttttg agacagagtc tgattctgtt gcccaggcta   110880
gagtacagtg gcacaatctc ggctcactgc agcctctgcc ttctgggttc aaatgattct   110940
cctgcctcag cctcccaagt agctgggact acaggtaagc accaccatgc ccagctaatt   111000
tttgtatttt ttagtagaga cagggtttca ccatgttggc caggctggtc tcaaactgct   111060
gacctcaagt gatccaccac ctgggcctcc caaagtcctg ggatttgtaa tcccagcatg   111120
agccactgtg cccagccaga tcatttcttt ttctttttct ttttcttttc ttttttttt   111180
tttttttgag atggagtctc actctgttgc ccaggctgga gtgctgtggt gcaaactcag   111240
ctcactgcag cctctgcctc ctgggttcaa gcaattctcc tgcctcagcc ttccaagtag   111300
```

```
ctgggactag aggtgcgcgc caccatgccc agctaatttt tgtattttta gtagagacag 111360
tgttttgcca tgttggccag gctggtctta aactcctgac ctcaagtgat ccacccacgt 111420
cggcctccca aagtcccggg atttgtaatc ccagcatgag ctaccacagc tggccagata 111480
atttttttat aactagtttt tacaaagaaa ggtggaggga aagttagagt aacattttta 111540
ggtgttaggg ctgactttgg ggaaaagagg tctggtttct acgacccgcc ttagggaaga 111600
gggattctag tttttgtggc tagcccagg ggagaatggg actaagagat agaagggcag 111660
gagaaggtca gagaaaaact tttgcttctg tggctgcttc ggagaacttc attttggggt 111720
attgttttct gagccccaac agtttgctta tcagtgaagt gggtataggc gcccacctcc 111780
cacagtgacg atgctgtgaa cagggctttg gaagagtaga actatgaaat atttgttgtt 111840
gccttgtggg gaaatggtcg ttaaagccaa aattgttcaa gagaagaagc aggaagagtt 111900
cctttctttc ctgcaggtat cctcttaagc tgagtcttca gaatccctg acaacgttta 111960
atcaacactt tattaaattc accccaaccc tgcttcaaac cttcacctgg tcctcgagat 112020
cttccaactg tttcttgatg aagttagcag gcaattgtat ggcgggatca tcatctcatg 112080
ttttgttttg ttttttttcct ttttaccctc tgactttgag aaatccttgt cctttactt 112140
ttccaaacct gagagcattg cagagaagtt agaattgagc aggacatggg cttaagaccc 112200
agcccagcca tgtgctagct gtgtgaactc gaagcagtga ccccacctct ctgacctgga 112260
aagtagaggg aatgatagga cccaccaccg ccacacttgt agggtcatca tggggattga 112320
ataaaataat gcataagact tggcccacag caagcactca gaaatgtta gctacttcct 112380
aaatatattt ttaaccttt attgaatata acatacatac agaaaagcac atgtatcata 112440
caagtagagc ttgagtgatt ttcaaaaact gagcccagtc atgtaaccag cgcctagttc 112500
aagaaacaga acatagccga gtgaggctga ggcaggagaa tcacttgaat ctgggaggca 112560
gaggttgcag tgagcagaga tcatgctatc gctccccagc gtgggcaatg ggggcggagg 112620
ggaagagaga gagagagaga gagagagaga ggaaggaggg agggaaggaa ggaaggaagg 112680
agggagggag ggagggaagg gaaggaaggg gagagagaga aaaggaaaga aagaggaag 112740
acagaaagag agagagaaag gtaaagaaag aaaaggaaag aaagagaaag aaagaaaga 112800
ggaagacaga gaaagaaaga gaaagctaaa gaaagaaaaa aaggaaggaa ggaaaatagg 112860
gagggaagag gaggaggaag aagaagaaga aggggggag ggagggaaca gctgcagctt 112920
cgaggaagga aggagggagg gaaggaagga aggaaaggaa ggaaggaaaa aaaaacagca 112980
ccaacgttta gaaaccccct tgtgcctctg aggtcaccag taactccatc ctgacttcaa 113040
acagtctaga ttagttttgc ttgttttga actttaagca catgggtca tacagcatgc 113100
atgcattgac ttctttccct tgacgttgta tgtgtgagat tcatctgtgc tgttgctgtt 113160
catttgttct catcgctgtg tgtgctgaac cacctgttca tttactctac taatggtggg 113220
cagtttggtg ctttctactt tgggctatt ccagagaaag ctactttgaa cacactcaga 113280
tatgtctgtg ggtgaccact cttcatattt ctatgggaga tattcctagg accggaacat 113340
ctgagtcaga gggaggaatt ggtttagctt tggtaggaac tgcctaacaa ttggccgggc 113400
acagtggctc atgcctgtaa tcccagcact ttggaggct gaggggggca aatcacttga 113460
gctcaggagt tcgagaccag cctggccaat gtggcaaaac ccctggccaa catggcaaaa 113520
ccccgtctcc gcaaaaaaat acaaagatta gccgagcatg gtggcgtgtg cctgtaatct 113580
cagctactca ggaaactgag gcaggagaat tgcttgaacc tgggaggcag aggttgcagt 113640
gagcagagat tgcactactg tactccagcc tgggtggcag aatacatgaa actccatctc 113700
```

```
aaaaagaaga aaggaaggaa ggaagggaag gaaggaaagg aaactgccca acagttttcc  113760
caagtgtttg ggatggaagg aaggaaggaa ggaaggaaaa gaaactgcct aacagttttc  113820
ccaagtggtt ggaccagtta aaactcccac cacctgtgaa tgagagtttg tttttatttt  113880
gctcctggag tgcctctcct gtagcaggtt cccactgaat gtctgggaat tcaaatgtaa  113940
tgcacttgtt catttcctca agagcttcac tccatcaatt ggattcatcc attggctctc  114000
ccatctccac tgacactatg ttctcacctc tatttggaag acatcctgcc tccacctgcc  114060
caagtcacat tatcttctca ttccagcctc tcaaggagag ttttctcttt caccacctcc  114120
tctagccctg gtgattggca aggtctcgca acagtaccct tcaaaacact catgactgtg  114180
aatgcactgg ccttcactaa gtttcccatt cttctctttc tttcttttt cttttctttt  114240 cttttttttt gaacagagtt tcactcttgt tgaccaggct cgagtgcagt ggcacaaaca  114300
cagctcactg tagcctcaac ctcctgagct caaggtatcg tcctgcctca gcctccttag  114360
tagctgggac cacagacatg caacgttgtg cccagctgat tttctttttt ttcttttttt  114420 ttttttttt gagacatggt ctcaccctgt caaccaagtg cagtagcatg atcacagctc  114480
actgcagcct tgacctcccg ggctcatgcg attctcccac ctcagcctcc cgagtagctg  114540
gggctacagg cacaagccac catgcctggc taattttgt acttcttgta gagaccaggt  114600
ttcaccatgt tgcccaggct ggtcttgaac tctgggctc aagcagtcct cctgcctcag  114660
cctcccaaaa tgctgggatt acaggtgtga gccagcacgc ccggccatgg ctaatttctt  114720 cattttggt aaagacaggt ctcactttgt tgcctaggct ggtcttgaac tcctggactc  114780
aagcaatcct cctgtctcag cctcccaaag tgctaggact accgatgtga gccaccgcac  114840
ccggcaattt ccccttcttg acttctccag agctctcatc cctctcgagc tcctgtctct  114900
tctagaatca cttacctcac caccttatgg ggttttgcc tctgttccta ctcctctta  114960 tttaagaaaa cactgtactt taagagggct tcagaaacca cccgaaatag aaacatgtcc  115020
ttttgttcaa tccttactt taaaagacaa ataaaatgaa gaattgctct ccatgtagaa  115080
ggttaaggag cttgggagga ccttctgtga gtggggagaa ctttacatta aaggaaaaaa  115140
aatgctggag aatagctgtg aacccaggaa gggagaagga cttcctccac tgaacttgta  115200
aagcacaaac tctaaggcaa aaaaagacat gattacatga aaactaagat atttgttcaa  115260
ataaagatgc aattggggcc aggtgcggtg gctcacgcct gtaatcccag cactttggga  115320
ggccgaggca ggcgaatcac gaggtcagga gatcgagacc atcttggtca catggtgaa  115380 accccatctc tactaaaata caaaaaatta gccaggaatg tgtcacgtg cctgtaatcc  115440 cagctacttg ggaggcttag gcaggggaat tgcttgaacc agggaggtgg aggttgcagt  115500
gagctgaaat cacgccactg cactccagtc tagcgacaaa gcaagactcc gtccaaaaaa  115560
aaaagatgca atagcaggtg gttcgggaac caaaccttac atccagatgc tggttgtccc  115620
atttcctgtg aatccttggg tgagttatca acctctctga gcctcagttt cctcgtcaat  115680
aaaatggaga aaatagtatc tacctatgga attgttgtga gttttgaatg agttaatatt  115740
tataaatcat ttagaatagg aattagcaca tggtaaatag tggatagaat cataaaaaaa  115800
aaattgatca ggggttaact tctaactgct gtttgttata gaggtcccta gcactgtgtg  115860
gtcattttaa atttagatga tttagaatta aatgaaattt aaaactcagt tcttcattca  115920
cactagccac attttaagtg ctcaaaaccc acaggtgact agtggctacc atatttggca  115980
gcacagattg agaacagatt tatcatccag aaagttctgt cagacagtgt tgatcaaggc  116040
```

```
tacatgaggg tctgggtgca gtggctcaca cctgtaatcc cagtgctttg gaaggccaag   116100
gtgggaggat cactggaggc caggggtttg agaccagcct gggaaacaga gagacctcat   116160
ctctaccaac attttaagaa ttagccaggc aaagtgttgc atgcctgtag tcccagctac   116220
tcaggaggct gagacaggat tgcttgagcc caggaatttg aggctgcagt gaactatgag   116280
cgcaccgctg cactccagtc tgggtgacag agtgagacct gtctctaaac ataaaaaata   116340
aaaatgtagg tggggcatag tggctcccgc ctgtaatccc agcactttgg gaagccgaga   116400
tgggcagatt gtgaggtcag gagatcgaga ccaccctggc taacatggta aaaccgcgtc   116460
cgtactaaaa ataaaaaaaa attagccagg catggtggcg catgcctgta gtcccagcta   116520
ctcgagaggc tgaggcagga gaattgcttg aacctgggaa gcagaggttg cagtgagctg   116580
agattgcgcc actgcactcc ggcctgggcg acagagcgag actctgtctc aaaataaata   116640
aataaataaa taataataaa gtaaaaataa aaatgcaaag actacctgag ggaatgtctg   116700
caagtcaacc agaataacac agcaacccca ataggaaaac aggccgaaaa tgtgaacagg   116760
cggatcaggg aagtgaagtc tgaaaagcta atcagcctat gacatggtac tcaaagtcat   116820
ttgtaaccag aaagatggaa atgaaagcag tatctctgta cacctttaat attgggaaa    116880 aaatatgtga ataagccaag ggtttccagc gatgcgggca cagaggaaag tcttgcacca   116940
ctcaaagggg tgtggcccag ggaggccact ctggagacat atcggtagta ctcagtccag   117000
tgaggtccag caccatcagc gcttatgtcc ccaggcatcc atcccaggga cattcttacc   117060
aggtctgtta ggggcaggta cgagaatgct tactccagca ccatctatat aaggggagct   117120
gaaggccacc tggtgtccct cctggagacc aggaggcggc atgtgacagc ggcacccatg   117180
gagcaccaga atgagtgaga gctccagacc gcatatccga cagatactac gggatggggc   117240
ttttagaaat atggttgttg ccgggcacgg tggctcatgc gtgtcatccc agcactctgg   117300
caggccaagg cgggtggatc acctgaggtc aggagttcga ccagcctg gccaacatgg    117360 tgaaaccctg tctctattaa agatacaaaa attagctgga cgtggtggcg ggtgcctgta   117420
atcccaacta ctcgggaggc tgaggcaaga gaatcgcttg aacccaggag gcagaggttg   117480
cagtgagccg acatcgtgcc actgcactcc agcctgggtg acaagagcaa aactctgtct   117540
caaaaatttt aaaaaacaaa aataaaaat atggttctgg gtgaaaacag gaaacaacag    117600
aatgtgtcta acttcatcct gcttatgtca gttaaaaata gacacactca aaatatcgca   117660 cgtgttttg cgagaatgca ctcctataag gccaaattaa acattctctc agttgtctct    117720
gggagggaga agaatgaaag tagggtatag agagatatag gggaattaat gcatgaatga   117780
atgaaggtat aaacaagaga caggcgtcat acagaccaaa ggtaaagata tcccgtaacc   117840
tgaggagagc aaagaacttg actctgcatt tgaagattca gaaatgaat ttcagaaata    117900 gttttctcgc caggggtgg ctcacgcctg taaccccacc actttgcgag ggcgaggcag    117960
gtggatcact taaggtcagg agttcgagac cagcctggcc aacatgatga accctgtct    118020 ctactaaaaa tacaaaaatt agccaggcat ggtggcatgt gcctgtaatc ccagctactc   118080
aggaggctga ggcaggaaaa tcacttgaac ccgggaggca gaggttgcat tgagctgaga   118140
tcacaccatt gcactccagc ctgggtgaca gagcaagact tgtctcaaa aaaaaaaaa    118200 aaaaaaaaa aaaagaaga ggaagaaatc gttttttcaa gaagggaaa gctgggtgat    118260 ttaagaatga acttgaagag gatcactcag tcctcaacct aggagtggca agaatataga   118320
ctgtatggga agtggttctg ctccttggta cccatcttag aaatatttgg cctgagtctg   118380
taagaggcag gtactttatc taacctgagg ttaggggcc actacatccc catccctcc    118440
```

-continued

```
cctgctttct aaccatgcta acatcttctc actctcctgt ctcctctcct tctcactccc   118500
ctaatctgcc tattcacatt ttgggcctgt tttcctattg gggttgctgt gttattctca   118560
ctgatttgca gacattcctc tgtgtcatct ttttaatttt gttttaattt ttagaggcag   118620
gatgtcattc tgttgcactg gctgtagtga cgtagctcac tgcagcctca aactcttggg   118680
ctcaaactcc tgtcctctgc ctccacttct caactggtaa cctcacttct cttcatgagg   118740
tctctccagc cccagggcct ttgcacatgt tcccctctct tctgagtggc atatggtagt   118800
tgctcctctg taaatattta ttgacatcct gacttccaac cagcagagaa ttgacctcct   118860
tcccatgctc aggctagtga aggcatgagt ttggctgagg tcccagtggg gaaggtgagt   118920
ggggtggcag agttaaccag gagcagcatg gtagaatggg taaaaccaga cgtagcacgc   118980
aggcaccaca tgttagctgg acaagtagtt taaccccatg ggtctcaatt tccccatcaa   119040
tgaaagggag aatagaacaa gtccctggta agcagcataa aatgagctct cagaatgtaa   119100
agtaacaagc acacaacctg gaagagaata catttagtga atattggctc ctttaatcag   119160
caggttctga tatgacttag ctacaattaa gaaaataaaa atggaggccg gcgcagtgg   119220
ctcatgcctg taatcccagc actttgggag gccaagacgg gtgggtgga tcacctgagg   119280
tcaggagttt gagaacaggc tggccaacat ggtgaacccc atctctacta aaaatacaaa   119340
aattagccag gcgtggtggc gcacgcctgt agtcccagct actcgggagg ctgaggcagg   119400
agaaacattt gaacccagga ggtggaagtt gcagtgagcc cagattgcac cactgaactc   119460
cagcctgggc gacagagtga gatttgtctc aaaaacaaaa gaagtctgga ggccaggagg   119520
ttggttgcag ggttggttcc ttggctcaac aatgtctcca aagagtcctt ccatctttcc   119580
actctaacat cgtcactgta aggactttt ttaacattta ccactcacag ccccaagacg   119640
actgcgtcag ttctttcttt ttttccttca gacagagtcc cgctctgtcg cccaggctgg   119700
agtgcagtgg catgatctcg gctcactgca acctctgcct cctgggttca agcgattctc   119760
ctgtctcagc ctcccgagta gctgggatta caggtgcctg ccactgcatc cggctaattt   119820
tttgtatttt ttttagtaga gatagggttt caccatattg gtcaggctgg tctcaaactc   119880
ctgacctcag gtgatgcacc tgcctcggcc tcccaaaggg ctgggattac aggcgtgagc   119940
cactgtgccc ggccgatgac tgcctcagtt ctaaggtact tacccagcca tccacgtaga   120000
cagacacaaa agcatccggc caaagaagag ggagaggaag ggctgtctct taccatgtga   120060
ctcatctcac ggggaaaaaa tccttttcca gaagcaccca gcagatttt cacccagatc    120120
ctgttaggcc tacgaatggg tcatgtgaca agtgctctta ttgcaaggaa tcttgggaaa   120180
aagagactat taggcatttt ctgcctcttt gatgggaggt gggctctgcc agtaaggcgg   120240
gtagtggtgg tggctcttgg atggacaact gtgtcttcca ttcttcttct tctttttttt   120300
ttttttttaa gagacaaggt ctcactctgt tgcccaggca gaaatgcagt ggcacaatca   120360
cagctcactg ctgcctcgac ctgccaggct caggtgatcc gcccaccta gcctcacgag   120420
cagctggagg agtgtaccac catggccggc taatttttat atttttgta gagatgggt   120480
ctctttatgt tgcccaggct ggtcttgaac tcctgagctc aaacaatcct cctgcctcag   120540
cctcccaaag tgctgggatt acaggcataa gccaccacgc ctggactctc ttctttaaat   120600
actgagcctt ccacctcttc tagaatatac tctgttaatt atcaaccaca cttttctaca   120660
tttttgcttc attattcatt cagtaaacat ttattgagtg cctactgtat gccaggcaca   120720
gctttaggtg ctggagatgc tatgaacaaa acagatgaaa atttctaaaa aataaaataa   120780
```

```
aaaataaaaa taaattttgc aaagccaggc acagtggctt aggcctatag ttccacctac  120840
tcaggagtcc aaggcagtag gatctcatga gactgggagt ttgagtccag cctgggcagc  120900
atactaggac tctgtctcta aaaagaaaa gaaggccggg cgcagtggct cacgcctgta   120960
atcccagcac tttgggaggc cgaggcaggt gaatcgcaag gtcaggagtt tgagatcagc  121020
ctgaccaaca tggtgaaacc ccgtctctac taaaaatgta aaaattagcc aggcatggtg  121080
gcaagtgcct gtaatcccag ctacttggga ggctgaggca ggagaatcgc ttgaacctgg  121140
gaagcggagg atgcaataag ccgagatcgt gccactgcac tccagcctgg gcaacagaat  121200
gagaccctgt ctcaaaaaaa aaaaaaaaa gaaagaaaga atagaaaata tctgccctac  121260
ggggatggac atgctagaac atcaaagtcc aatggaactt tctgcactga tgaagtatgt  121320
atgtatgcac cagccacatg tggcttggga gcacttaaaa cgtgactggt acaagcgaat  121380
ttttcattta atttaaatga atttaaatct gtatttaaat agccatgtgt ggctagtggt  121440
tactttattg ggcggtgcag ctctctaaag gccaagagat acatcatcaa cttctctccc  121500
ttgacccata ttcagttctc tcccaccctg aaaatctcct ctcctaccca ggctcacatt  121560
tccagttctt ctcctcttgt tctccctcaa ccatcagccc ccgcaagact gacgtgaccc  121620
tgatgccgta tgaaatgcat tcttcatcct ttactcttac tcacctctgt gcggccctgg  121680
agaccagtga cctctccttt ctcaaaatac tttatttctg tgtgttttg ttgttgctat   121740 tgttttggg gggttttctt gagatggagt ttcactctca tcacctaggc tggagtgcag  121800
tggtgcgatc tcagcttact gcaacctctg cctcccaggt tcaagcgatt ctcctgcctc  121860
agcctcccaa gtagctggga ttacaggctc ccgccaccac ggctggctaa ttttcttgta  121920
tttttggtag agacggagtt ttgccatgtt ggccaggctg atctcgaact cctaacctca  121980
ggggatccac ctgcctcggc cttttcaaagt gctgagatta caggcatgag ccaccgcacc 122040
cagcctcaaa atgcttttga acttgactgt caggtatgcc attctccaca ccagtctcct  122100
cccatgtctg tgtcttctcc ctctccactg gggaccctgg gctttttcca cttcactcat  122160
ctaccctggg ttatctggtc ttccataacc ctgtcctctg ccacacctca cttattcacc  122220
caccacaata tttattgagt actcactagg ccatgaaaga tgctatacaa aaaaagcccc  122280
tgtcctcgtg gagctgacat tctagaagaa agcatgaata ataaatacga cttaataaac  122340
agtacggcca ggcatggtgg ctcacgccta tcatccaaac actaagagac caagatgaga  122400
ggatcacttg aatccaggag tttgagacca ccttgggaaa cgtactggga ccctgtctct  122460
acaaaaaaaa tattaaaaat tagctggata gggtaatgca tgcctgtagt tccagctact  122520
tgggaggaca aggtggaagg attgcttgag cctgagaggt caagtccgca gtgagctgtg  122580
actgtgcact gcacgccagc ctgggtgaca gagtgagatc ctgtcttaaa aataaataaa  122640
taaacaaaca aacaaacaat ataattccag agagtgaaga ggcaggatct ctttagctag  122700
gaagttgagg gatgttctct ctgagaaggc agaatctgag tttcaacctg aagaattcga  122760
agaggccagc taggcaaaag atgagagttg aaggaatggg gacggcagag gagacagcca  122820
atatagtaat tctcaataaa gcagaaagtg agcttttcct gctggcagaa cagaaaggaa  122880
gtcggagtgg ccagggtgtt gtgggacaag gtggtcagca ggagtcacat cacgcaaggt  122940
catgtggtca tggtagactt taaattttac tccaagcctg atggaagcca ttggaagatt  123000
ttaactaagg agtgacggaa aactggcatc tcaaactcaa catgtctaca acccagttct  123060 tgatcttga aaccttcttc ctccatcttc cccatctcca ttgacagcaa cttcatcctt   123120
cagttagctc aggccaaaac cctggagtca cccttgatac ctctctcctg ctccacactc  123180
```

```
agtctttcca ttggaagccc tagggctgc catattgttc tccatagcac ttcacaccgt   123240
ctgacatact atatctttc ccactattgc tttgtccttg gtagcatctt taggcactct    123300
ctgaatatct ggcacatagt acgtgctcac taaatccttg ttgaataaat gaatgaacat   123360
cactccgtgg tcctttcaga accagagcca ttcttctctt tcttcaccac cgttgcccct   123420
caccccgccc aactagtcac aggagttgaa ggatgacaca gtagagaact gggattctgg   123480
agtcctgtgg ctggtctggg gttcgagttc ttactcagtg gtaggaacct ccatgtggga   123540
ttaacttatc tggtctttag tttcctcctc tgtaaaatgg gcctcaaact gccaaccgct   123600
gggatgcagg gaggatttga tgagcccagg caggctccct ggagcacagc aatcaatggc   123660
agctatatat aaaccggggc ctcttttgta ctcccactgc ctttgtccta gttccagccc   123720
tcattacacc agcctgctct tgcggctccc tcctaacttc tgctccatca ccaccaatct   123780
gtcctttcag ctgtcaggct tgtcttctga acgccaaccc taatcacatc ccttcctgct   123840
ccaaaacctt acatgactct cactgtccac aggacaagac ccagcctcta gttgacagcc   123900
tccactgtcc agcttaccca acctctcccc taccacatac cctgagtgga gccttctgcc   123960
tccatagggc tttcttagcc agagaagcct cccttatctt cctgttctcc tcctaattcc   124020
ttcttatcct tccagggagg aggctgtgag gtaatgcatc ttgggagcca gctgggattg   124080
cacagggtgg tgagattatc tgcatttccg aggcttgaac aagttaaggc aatgggaaag   124140
gtcacacaat gagaaaatgc agggccagga tttaacccgt ctgagatgtt ctgactgtgc   124200
tatgctgcct ccccggacat gagctctgcg ataatgctgt ccccaggctg taatcattcc   124260
ctctttcatc cctgcctcct ctatccctgg ggtcagaggg acttgtagtt gaatctctca   124320
ctcactcatt ggtgtggtct ctccctaaag cagggtggag tttgtcttag cgttatcact   124380
gcatccagca caacctccct ggtccaggct tatcagcgtt caactgcgtc aatgcagttg   124440
cctcctcctc aatctcccag cttccggcct tgcccctag agagatcata ttttaataca    124500
agtcagatta catccctcct cccctcagaa ccctccatgg ctcacacctt actcagagaa   124560
aaagccaaag tcctctccac aacccacaaa gccctgcacc atccatcacc tcactgcctt   124620
cgtcccctca caccctcccc cttgctcgct ctgcttcagc cacaccaact catctctgtt   124680
tctcaaatac accaggcatg gcctagctat taaatgcacg gtccagcctg gtgcatttga   124740
agaacacgga tgaattggtg tggctggaac agagtgagtg aggggagag cgggaggagg    124800 acctttgcac cagctggacc tttgcaccgg ctgttccatt tgcctagagt tttccctgac   124860
atattcatat ggctcactct cttgcttccc ttgctttctc ccagtctttta ttcaaatgtc   124920 tatttctctg cacttgtgct gtttgataca gtcaccgctg gccacatgtg gcctttgagc   124980
acttcagttg aaacacatga agtgtagaa tattgaccag attccaagga aaaccatgtg    125040
caaaatatct tttatctctt aagatacagg gtctcgctct gtcttccagc ctggaatgca   125100
gtggcacgat cacagctcac tgcagcctca aaatcccaaa ctcaagtggt cctcccacca   125160
acagcctccc gagtagctgg gattacaggc acacaccaca atgccccgcc catttttta    125220 attgttatta tttttttaa tagcgacaag gtcttgccat gttgctcagg ctggtctgga    125280
actcctggcc tcaagcgatc ctcctgcctc agcctcccga gtagctgaga ttacaggcag   125340
gagcttttgt gcccagcagg tctacgatct tcttagaatg cttcaggctg ggcatagtgg   125400
ctcatgcctc aaataccagc actttgggag gccaaagcag gcagattgct tgagctcagg   125460
agttcgagac cagcctgggc aatatggtaa aaccctgtct ctccaaaaaa aatacaaaaa   125520
```

```
ttagctgggc ttggtggctc ccacctgtag tcccagctac ttaggaggct gaggaaggaa   125580
gatcacctga gcccaggagg cggaggttgc agtgagccaa gattgagcca ctgcactcca   125640
gcctagacaa cagggagacc ctgtctcaaa ataaataaat aaataaataa ataaataaat   125700
aaataaataa acaaacaaac aaacaaacca ataaatgaat tttacctgtt tcttttttact  125760
tttttaatgt ggctactagc aaattttaat tttttttttt tttttttttt tttttgagac   125820
agagtcacgc tctgtcaccc aggctggagt gcagtggtgt gatcttggct cactgcaacc   125880
tccacctcat gggttcaagc agttcgcctg cctctgcctc tgagtagctg ggattacaga   125940
tgcccaccgc cacgcccagc taatttttg catttttagt agagatggag tttcgccatg    126000
ttggccaggc tggtctcgaa ctcctggcct caagtgatct gcctgcgtcg gcctcccaaa   126060
gtgctgggat tacaggcatg agccaccgcg cctggctata aaatttcata agtagctctt   126120
aatagatttc tcctgggcag tgctggtcta aacactttt tttttttttt ttttttttga   126180
gacggcatct tgctctgtca ccaggctgga gtgcagtggc gcgatctctg ctcactgcat   126240
cctctgtcac ccgggttcaa gctattctcc tgccttagcc tcccaagtag ctgggactac   126300
agacacccgc caccacgccc agctaatttt tgtatttta gtagagacgg ttttcacca    126360
tattggccag gctggtctcg aactcctgac cttgtgatcc gccagccttg gcctcccaaa   126420
gtgctgggat tacaggcatg agccaccgca cctggctata aaatttcata agtagctctt   126480
aatagatttc tcctgggcag tgctggtcta aacactttt tttttttttt ttttttttga   126540
gacggcatct tgctctgtca ccaggctgga gtgcagtggc gcgatctctg ctcactgcat   126600
cctctgtcac ccgggttcaa gctattctcc tgccttagcc tcccaagtag ctgggactac   126660
agacacccgc caccacgccc agctaatttt tgtatttta gtagagacgg ttttcacca    126720
tattggccag gctggtctcg aactcctgac cttgtgatcc gccagccttg gcctcccaaa   126780
gtgttgggat tacaggtgtg agccaccgcg cccggccctg taacactttt aacactgaac   126840
tgtttgcctt ccaggtggta aagagcaggt gcctttactg atagaaatgt caccactccc   126900
ttcatcccgc cagccccatg tcactgacgc gtcctttccc cttgctctgt ggtaactttc   126960
tcctaagcac tcatcgccct aacatctgtc atacaggtat acctcagaga cactgctggt   127020
ttggttccag gtcgccataa caaagcgaat attgcaataa agggagtcgt gcctttttg    127080
gtttcccagt gcacataaaa gttatgctta cactatagtc tgttaagtgc atgatagcat   127140
tatgtctaaa aaaaatgta cataccttaa ttttaaaatc catcaaggct gagcacagtg    127200
gcttgtaatc ccaacacttt gggaggccaa ggcaggagga ttgcttgagc ccagggattt   127260
gaaaccaggc aacaaagtga gaccccgttt ctacaaaaaa attctttta aaaatagctg    127320
ggtatggtga cgcatgcctg tggtcccagc tacatgagag gctgaggtgg gaggctcact   127380
tgagcctgag agattgagac tgcagtgagc tgtgatcaca ccactgcact ctagcctggg   127440
ggacagagtg agaccgtatc tctcaacaaa aattaaaaaa aaaaaaaaaa aaggctgggc   127500
acagtggctc atgcctgtaa tcccaacagt tgtgaggcc aagtgggtg gatcacttga    127560
ggtcaggagt tcaaaccag cccagccaac atggtgaaac cccgtctcta tgaaaaatac   127620
aaaaaaatag ccgggtgtgg tggtgcacac ctataagccc agctactcgg gaggctgagg   127680
cacgagaatt gcttgaacct gggaggcggg ggggagattg cagtgagccg agattgcact   127740
gctgcactcc agcctgggtg acagactgag actctgtctc aaaaaataaa taaataaata   127800
aataaataaa taaatgtttt attactaaaa aagttaacaa tcatctgagc cttcagtgag   127860
tcctcatctt gctggtgaag ggtcactggc tcagtgttga tgggtgctga ctgatcgtgg   127920
```

```
gggtggttgc tgaagattgg ggtgcctgtg acattttctt aaaataagac aagaaagttt  127980
tccgcatcca tcgactcttc ctttcacgaa agatttctct agcatgagat gcttgttgac  128040
agcaatttta cccacagtag aacttttttc aaaattggag tcagttcttt caaaccctgc  128100
cactgctttg tcaactaagt ttatgtcata ttctaaatct catgttgtca ttttaacagt  128160
gttcacagaa ttttcaccag gagtagaatc catctcaaga aatcactttc tttgctcttc  128220
cataacaagt aacgcctcat gcattgaagt ttgatcatga ggctgcagca attcagtcac  128280
atcttcaggc tccacttcta actctagttc tcttgctagt tccatcactt ctgcagtgtc  128340
ttcctccagt gaagtcttga actcctcaaa gtcatccatg aggatcggaa ttgacttcct  128400
caaaattcct attaatgttg atattttgac ctgttcccac gaatcacaaa tgttctttt   128460 gttgtttgtt tgttgtggat tgttttttta tttttaattg agttgaggtc tcactatgtt  128520
gcccagactg gtcttgaact cttggcctca agtgatcctc ctgccttgat ctccctaagt  128580
gctgggatta caggcatgag ccactggaac agccacaaat gttcctaatg gtatctagaa  128640
tggtgaatgc ttttcagaaa gttttcaatt tcctttgccc agatgcatca aaggaattta  128700
tctatggcag ctatagcctt atgaaatgta tcccttaaat cataagactt gaaatagaga  128760
attacttctt gatccatggg ctacagaatg aatgttgtgg ctgggcatgg tggctcacac  128820
ctgtaatccc agcactttgg gaggctgagg caggtgggta acttgaggtc aggagttcaa  128880
gaccagcctg gtcaatatgg tgaaacccca tcactactaa aaatacaaaa attagctggg  128940
catggtggcg tatgactgta atcccagcca cttgggaggc tgaggcagga gaattgcttg  129000
aaccctcttg aagacagagg ttgcagtgag ccaagatcac accactgcag cgacagagtg  129060
agactctgtc tcaaaaaaaa aaaaaaatgt tgtgttagaa gtcataaaaa caacattcat  129120
cttcttgtac atgcccatta gaggtcctgg ataaccagtg cattgtcagc agtaaatttt  129180
tgaaagaaat cttttttctg gctgggtaca gtggctcgca cctgtaatcc caccactttg  129240
ggaggccgag gcgtgtggat cacctgaggt cgggagttca agaccagcct ggccaacatg  129300
gtgaaacccc aactctacta aaaatacaaa aaaattagcc aggcatggta gcaggtgcct  129360
gtaatcccag ctaccctgga ggctgaggca ggagaatcgc ttgaacctgg gagtcagagg  129420
ttgcagtgag ctgaggtcgt gccattgcac tccagcctgg gcaacaagag tgcgacttca  129480
tctaaaatac atatatatat ataacatgtt atatgtaata taaattatat atataacata  129540
tatgtaatat aaattatata tcacatataa catatatcat gtgttatata tatcacatat  129600
aacatatgtg ttatatatca catataacat gtgttatata tcacacataa catatattat  129660
gtgtatatat gtcacatata ttatgtgtta tatatgtcac atataacata ttgtgttata  129720
tatatcatat ataacatata ttatgtgtag tgtatcatat gtaacatata ttatgtgtag  129780
tgtatcatat ataacatata ttatgtgtag tgtatcatat ataacatatg tgtagtgtgt  129840
tatatataac atatattatg tgttatatat ctcatatgtt atatataaca tatattgtgt  129900
gttatatatt atatatatat ttttttctga gtagatctca acagtgggct taaaatatca  129960
gttatccatg ctataaacag acgggctgtc attcagtctt cattgttcca tttatagagc  130020
acaggcagag tagattcagc ataattctta agaccttagg actttaggaa tggtaagtga  130080
gcattggttt caacttaaag tcaccaggag cactagctcc taacaagaga gtcagcctgt  130140
cctttgaagc tttgaagcca ggcattgact tctcctctct agctatgaaa gtcctagatg  130200
gcaacttctt ccaatagggc atttcatcta cattaaaaat ctattattca gtgttgccag  130260
```

```
cttcattaat aatctcagct agatcttctg gataacttac tgcagcttct ccatcagcac    130320
ttatcacttc accttgcact tttatattat ggggacacct tctttcctta aacctcatga    130380
accaagatct tctagcttca gattttctt ctgcacttcc ccacctctct cagtcttgct    130440
gtgggcttgc tgtggattag gctttggctt aagggaatgt tgtggctggt ttgatcttct    130500
atccagacca ctaaaacttt ctccatgtca gcaagaagcc tgtcttactt tcttatcatt    130560
catgtgttta ctagagtagc ccttttaatt tccttcagta attttccctt tgcattcaca    130620
acttggctaa cctctagctt atggcctttt gtttgtttgt ttgttttgtt tttgagacag    130680
ggtctcactc cgttgcccag gctggagtgc agtggtgcaa tcaccgctca ctgcagcctt    130740
gacttcctgg gaccaagtga tcctcccacc tcagcctcct aagtagctga ccacaggt     130800 gtgcaccacc acacccagct aattttttta ttttctgtag atatagggtc tccctatttt    130860
gcccaagcta gtctcaaact cctaggctca agccatcctc tcacctcagc ctcccaaaat    130920
gctcggatta caggcatgag ccaccatccc tggccctatc tcagcttttg acacgccttc    130980
ctcactgtgt ttaatcattt ctagctttta atttaaagtg agagacgtgc aactcttctt    131040
ttcacttgag cacttaaagg ccattgtaca gttatacact gacctaattt caatattgtt    131100
atgtctcggg gaataggaag gcccaaggaa agcgggagag atggggaaat ggccagttgg    131160
tagagcagtc agaacacaca caatatttat cgatcaagtt tgccatcttc tatggatgtg    131220
gttcgtggca ccccaaaca atgactatag tcacatcaaa gatcactgat cacagaccac    131280
cataacagat gtaataatta tgtaaaagtt tgaaataccg taagaattac cagagtgtga    131340
cacagagacg caaagtgagc acacgctgtt ggaaaaaaaa tggccctgat agacctcctt    131400
gacacagggt tgccacaaat cttcaatttg taagaaacac aatatctaca aattgcaata    131460
aagcaaagca caatgaaatg aagtcttcct cggccggtgt ggtggctcac gtccataatc    131520
ccagcacttt gggaggccaa ggcaagagga tcccttgagc ccaggagttg gaggccagcc    131580
tgggcaacac agggagactc catctctaga acaaaacaaa acaaagcctg cttatattta    131640
ttgggtttac tctcagtctc ccccacacag agatagggcc tggcttgtta ttagtgctca    131700
gttgatgttt gtgaagtgaa atactaagga cttaaccact gcctgttctt tgctgttcat    131760
gccctgacag cttttatgtg ccagcacaga agaaacaag gtgcaagaag agaatagtga    131820
tctctaagtc agaatttgag gaacccaaat tagtaccaga aagctgggag gagaagagaa    131880
aaataaagta aatcaaatta aaagttgaat gggccaagtg cagtagctca tacctataat    131940
cccagcactt tgggaggctg aggtgagagg atcacttgag gccaggagtt ctagaccagc    132000
ctgggcaata tagcaagacc ccatctctac aaaaaaaatt ttttaatttt ctgaatatgt    132060
tgttgtacac ctgtagtccc agctgcttag gaggcagagg tgggaggatc gcttgagccc    132120
aggaggttga ggctgcagtg agctgttgtt gcaccactat actcaagcct gggtgacaga    132180
ataagtccct gtctccaaaa ataaaaataa ataaattcat tttttgtaaa gttgtatgtc    132240
atggcccctg cctactctgg cttcatgact tgctgcttga acctcaccat ccaaatccca    132300
gtggtgacac catgtcattt cttgaatttg ccaagccctc tttcagtccc aagctctctg    132360
tcatggccac tctcagcctg gaaagttctt tccccactgg ccagatttct cccctcatc    132420 tatgggaact tgacttgaag taggggtat cccaggccct ggactagtta acacgacctg    132480
ctgtgtgccc ctcaaagcca ttgtcttcct agctgagaag gcatcacacc tgcaacagat    132540
tcactcattg tgtgcatgtt tttcttaacc acttctcttc tgcatcagct ccatgggca    132600 gggatagtct catatgtcac tctacccagc acataggata cgctcagacg cccacttgtg    132660
```

```
gatggtggaa aaggtcagcc caacctaata tgcccatctc tcctctaggg gtaatcttga 132720 gaaaaaagt tgggaacttg ctttgtgtta gtttaggatg acccagaata gatcctgaaa 132780
caagaattta gggcaatcct tgtgcaagta gttcatctga gaggtgaccc cagaagggtt 132840
ggagaaggag aggggaggtg gggcaaggaa gggtgagttg tcctgtaggc aactgagctc 132900
cgtcctactg ggagcccacg tggaactcac ctcttaagtg atccagaatg aagggtgagg 132960
gagctgcggt attgatccac caactcccag caatctttgg ttgagggctg ctcccttaaa 133020
gttcattccc tgggcctgcc ccagatttgg agacagccct aaggcaagag gtacagatac 133080
cagttggcca cagactgaag tgttaagacc caagccctg gataaaactg aaaaatcaag 133140
ccagatgtgg tggttcccac ctgtaatccc agctactcag taggctaagg caggaggatt 133200
gcttgagccc aggagttcaa tgctgtagcg agctatgatt gcaccactgc attccagcct 133260
gggcatcaga gcaagacccc atgtctaaaa taaaataaaa ctgaaaaatc cccaagttat 133320
ttgctgtgac caaccttcca ttaaccacag accctctggt attcagcatt tcttgtccat 133380
tatatgaagt tctgatgaca gtctcttta ttgtattgtg ccttgaccac gcactgtaca 133440
tcacttagct ctgaaatgga catgttcagg aaacagggcc aggtgggacc ctgtgtttca 133500
acagcaatac ttttacaaat gaggtctcat gacagggtct tgctcggagg gtttctatgg 133560
aagcctcatc ccacctactg ctatcatcct tactaacttg catttacaaa agggactctt 133620
tttgaccaga ggcttggggt ctgtagctgc cttctagcca gctgatgctg gctggtccac 133680
acaagcagga tcacacccat ttttttgttt tcttatttat ttctgaatag gttagcatac 133740
cggtaacctg tgtgcctggc attgtgctga ccacttttg tcaacttact gaatcctcac 133800
aacccttgga ggtattgata ctattgttat ccaggttata caaaaggggg aaactgaggc 133860
acagagcagg gatgtcccct gcccaaggtt acccaactgg aaagtggcag atctgggatc 133920
tgaacccatg caggctgggc tcttaacact gaactacttt cctgccattt gttaaagagc 133980
cacaaaccag gccaggcacc atggctcacg cctgtaatcc cagcactttg ggaggccgag 134040
gcgggtggat cacctgaggt caggagttca agaccagcct ggccaacatg gtgaaaccct 134100
gtctctacaa aaatacaaaa aaaagtaccc gggcatgatg gcgggtgcgt agtaatccca 134160
gctactcggg aggctgaggc aggagaatcc cttgaacccg ggaggcagag gttgcagtga 134220
gctgagatca caccattgga gatcgcactc cagcctgggc aacagagtga gactctgtct 134280 caaaaaata aaataaaata aaataaagag ccacaaaccc cgaaaggtct gccattcccc 134340
cagggcccca ggccacccca caatctattg tcattgtagg ttgtgaaata tactgaatgt 134400 cacccccaacc ttgagccatg gggaagattc catttctctc attgcaacat ttgtgcaaca 134460
tgaaccatct gttgggggtc ttcgtaaatc accttttatc ccgtgaggca ggtactgtta 134520
agaccatttt acaggtgaca aaactgaggc cagtggtgtc gagtcacctg cctgtggtca 134580
cccaaccaat acaggacagc ttggaatccc aagcaccccc gccctgctgt ctgaccccca 134640
aaacccaccc tctgttctcc attctggctt ctttctttca gcatcttggc gacagttggg 134700
acggagtttg acctacggac gctgagggca gttcgagtgc tgcggccgct caagctggtg 134760
tctggaatcc caagtgcgtg agtttccgac cctgacaagg ggtttgctca cgggcccag 134820 gagccctcag tttcccctat gcagagcatc tcaggaggcc acatcctgcc accagcctgt 134880
gtgagggcag tctcttcttt gggactccct atagggaacc ccctaggaat atgactgtag 134940 ctcccccatga gctcctgaaa gcaaactagg agccacaccc atttattgag cacctactgt 135000
```

```
ctatcgggag ccatgctaag caccacgtgt gatctcattc agtactcaca gccctatgaa 135060
gttgatagga ctgatgtctc tattttatgg aggggggaaac tgaggctcag agtggctgaa 135120
acattggagc agggttttgt ggctgagaag tggcagaact aggagtgagc aagtgtgact 135180
ccaagcctgg gccgtaccac tggtggcaat gaccattccc atttaatgag tgcctgctgc 135240
gtgcagggca ctacagaagg actttacatg aattaccttt tttcatcctc acagtcaccc 135300
agcgaacacc cattttacag atgagacggt tgaggcttaa ggaggttaaa ttactcacct 135360
gaattcttag agtggacagt aatgagctct aaaattcata ctcattcctt gctgctttct 135420
cattctccac agatacatct agtccccgtt taagggtggc tgccatatgc agggtcaaga 135480
ttaagtgtag gttgagccaa aaaaaaatgt aaaaagcaaa aataaaacag ggctgtcctt 135540
tttctatctt cttgtcttgg ttaataataa taatttagcc aggcatggtg gctcatgcct 135600
gtaattccag cactttggga ggatcacttg aggccacaag ttcgagacca gcctgggcaa 135660
cattgtgagg aacaccaccc ccaccccccc gccaatatct acaaattttt tttttttttt 135720
tagaaattag ccaggttgac tgggcacagt ggctcacacc tggaatccca gcactttggg 135780
agaccgaagc gggcagatag agcgagctca ggagttttaa gaccagcctg gcaacatgg  135840
cgaaaccctg tctcaaaaaa aaaaaaaaat tagcaggcat gatggtgcac acctgtagtc 135900
ccagctactt aaaaggctga ggcaggagga tctgagccca ggaggtcaag gctgcagtga 135960
gctgtgatag caccactgca ctccagcctg acaacagag tgagaccttg tctcaaaaaa 136020
acagacaaca aaaagtttaa aaacaaacaa tttataggct gggtgcagtg gctcatgcct 136080
ataatcctag cactttggga ggccaaggtg gatgggtgga tcacctgagg tcaggagttc 136140
gagacctgcc tggccaaaat ggggaaaccc cgtctctact aaaaatacaa aacttagccg 136200
ggcgtggtgg cgggcatcta taatcccagc tactcgggag gctgaggcag gagaatcact 136260
tgaacccggg gggcggaggt tgcagtgagc tgaaatcacg ccactgcact ccagcctgga 136320
tgaaagagtg aaactccgtc tcaaaaaaag aaaaaaaaaa attaaaaagc acttactatg 136380
tgccagacat tattctaagt atttccattt ttttaaagtc ctttatcctc ccaacaagcc 136440
tgtgaagtag tctcttttat tatcaccatt ttacatttta ttggcttcgt tcttccggtt 136500
cattgctacc caggttttaaa gagtaagatt tcccagagga tcaccagcag gatcttttg  136560
tagaaagaag acacttctat ccaaggtctc tgcaagatcc cagcagatgc ctgcatcata 136620
ttaaattaag ggccatccca aatctaatag tcaaagagc caggtgcagt ggctcacacc 136680
tgtaatccca gcactttggg aggccaaggc aggacgattg cctgaggcta ggagttcaac 136740
accagcctgg gcaacaaagt gtgaccctgt ctcaaaaaat atatgtatat tataatagca 136800
gtagtaacaa gagtctctgt ttaatgacca cctatgactt accaggtact tcactgtgtg 136860
tgaactctct catctaatcg tatgagggag gtactattgc agtccccatt tacagatgga 136920
gaagctgagg tttggaattc actagtaagt ggatgactag gtcaggttcc cttgaagcgg 136980
atacttaggt gggtgttcag atgcacctgc tttattgggg acggctctt gggagagaca 137040
gcaggagatc agcagggtgg ggctgggaa tggatagagc agggacgcaa tttcagctgg 137100
agtgtgtgtg acaccagagt tgtcctccaa tgcatggcaa ggatgccggc cttttgtact 137160
tctatagtca gtcactgtgg atgggaggta gagacgcagt agctcccagg tgagatagct 137220
tttgatcacc aagggcaatt ctactaagaa gagaggcagc tgggaggcat tagcaaccaa 137280
catccatagc agctgagggg cgggtacacc agaaagaaaa tgggatcttg ccagacacc  137340
aagagtatcc agcaccttaa ccactgcacc acactgcatc tgttagcacc cacattacat 137400
```

```
ttttttttttt tttttttttt tttgagacgg agtctcgctc tgtcgcccag gctggagtgc 137460
agtggcgaga tctcggctca ctgcaagctc cgcctcccgg gttcacgcca ttctcctgcc 137520
tcagcctccc gagtagctgg gactacaggc gcccgctacc acgcccggct aattttttgt 137580 attttttagta gagacggggt ttcaccgtgt tagccaggat ggtctcgatc tcctgacctc 137640
gtgatccgcc cgcctcggcc tcccaaagtg ctgggattac aggcgtgagc caccgcgccc 137700
ggccagcacc cacattacat ttttaagccc ttggagtggc atggcccctc gagctatcct 137760
gacagcttcc ctctcttact gtggtctcca cccatcaaga gccatgggaa gttcctgcaa 137820
tcaagaagca aagcctcagg ctatatgttt gaaccttcat tttgatcata gactttccta 137880
gtagatacca tagtggttac aaacatagga tgttgtcatc gttcagacct gagttaatag 137940
cctcaagaaa aaaatggtag tggaaccagg tatggtgaag tgtgcctgta gtcccaccta 138000
ctcgggaggc tgaggcagga ggctcgcttg tgcccaggag gtcaaggctg cagtgagccg 138060
tgatcatgcc actgtattcc agcctgggtg acagagcaag cccatctcaa aaaaaaaaa 138120 aagccaatga taggcagaga aatactaact aaggctcttg ctctgtcgcc aggctggagt 138180
gcagtggtgc aatcacagct cagtacagcc tcaacctccc cagactcaag caatcctacc 138240
atctcagcct cccaaatagc tgggactcca ggcacacagc accatgccca gttaatttt 138300 ttgtattttg tagagacagg gtttcaccac gctgctcagg ctggtctcaa actcctgagt 138360
tcaagtgatc cacccgcctc agcctcccaa agtgctggga ttacaggtgt gagccaccac 138420
gcttggccag ctattattat tattaacatt cttcgagtct tacaacagtg gaactttag 138480 tgcaggatgc gaatttcagt attaacccct tcctctccca aaaggatttg aagcccagag 138540
taattcagcc gccatgaatg aaccatttgt tagatgagag gctactggag gctgagcttg 138600
gtaggataag agcttgcatg gggtccctga ttgatgacaa taccccaga tttaggtctt 138660 cagatgccca gttgggtgtg tcttctgttc cactgtgtcc cttcggggac tgttccctgc 138720
cttctttctt tttgagatgg aatctcgcac tttcacccag gctggagtgc aatggcgtga 138780
tctcagctca ctgcaagctc cacctcccgg gttcacacca ttctcctgcc tcagcctccc 138840
gagtagccag gactacaggt gcccgccacc acgcccagct aattttttg tattttagt 138900 agagacgggg tttcaccata ttagccagga tggtctcgat ctcctgacct cgtgatctgc 138960
ccgcctcggc ctcccaaagt gctgggatta caggcgtgag ccaccacacc tggcccctg 139020 ccttcttatt caccaccatc tttctgaatt gggttgctca gaacagagaa agcaacatca 139080
gcacatgggc aaacatgggg cttcatttca gatggacctg ggttcaaatc ctagttctgc 139140 ctttttttt tttttttttt tttttgaga cagagtcttg ctctgtcacc cagactggag 139200
tacagtggcg tcatcttggc tcactgcaac ctctgcctcc caagttcaag caattctcct 139260
tcctcagcct cccaagtagc tgggattaca ggcgctggcc accatgccca gataatttt 139320 tgtattttta gtagagatgg gtttcacca tgttggccag acttgtcttg aactcctgac 139380
ctcgttaatc cgctggcctc ggcttcccaa agtgctggga ttagaggcgt gaaccgccgc 139440
cgcgccctgc ctagttctgc catttctcat gcattctctg ggtgaatcac agcatctctg 139500
ttagccttgc ttcccacttc tgtaaaatga gagtgacttt acatgtatgg ccacctcagg 139560
ggcttgtcac tagaagccag tgaaataatg ttgagtctgg ttccttgggg ttgaaattgg 139620
gaccgccaac cgctttccta cccagagcag caactagcct atatgcggc cttttatgaa 139680 tgaggaaaag acaccgcctc ttggcagaaa aaaaaaatta agaaaatggc tccctcttct 139740
```

-continued

```
gggtgcaagt tgcccaacac ccaggaatat ggctccaaaa gcaatggact cccacccctt 139800
tcttgcccaa aagatcatca aatgaacag catgtcaaat acctttatta agtactttaa 139860
agttggctgg gctctgtggc tcatgcctgt aatcccagaa ctttgggagg cagaggctgg 139920
aagatcgctt gaggtcagga gttcgagacc agcctggata acatagtgag accctgtctc 139980
tataaaatat atatatagat ttatttgaga cagcgtcttg ctctgccact caggctgggg 140040
cgcagtggca caatcatagc tcactgcagc cttaacgatc ctcctgcctc agtccctaga 140100
gtagctagga ctacaggcat gcaccatcat gcctggctaa ttaaaataaa taaataaata 140160
aatactttaa agttaaaagt gcttttaaa aaataataag gccaggcgtg gagactcacg 140220
tctgtaatcc cagaactttg aagaccgag gcgggtggat cacgaggtca ggagatcgag 140280
accatcctgg ctaacacggt gaaaccctgt ctccactaaa aatatgaaaa attagctggg 140340
cctactcggg aggctgaggc aggagaatgg cgtaaacctg ggaggcggag cttgcagtga 140400
gccgagatgg caccactgca ctccagcctg ggcgatataa caagactctg tctcaaaaaa 140460
aataaataaa ataataata ataataatag gggccaggta tggtggctca cacctataat 140520
cctagcactt taggaggctg aggagtttga gtccttggag accaggggtt caggccagc 140580 ctgggcaaca tagcaagacc ccatctctac aaacaagttt taaaacttag ccaggcatgg 140640
tggtgcatgc ctgtagtcct agctattgca gggactgagg caggaggatc acctgagccc 140700
aggaggttga ggctgcagtg agctgtgatt gtgccactgc actccagcct gggcagcagt 140760
gcaaaaccct gtctcaaagg aaaaaaaaaa cctaggaagt gttgttccca tgataaggat 140820
cagcctccgt gtggtgcttc cttccaccatt gcccaatccc caggctcctg ggtgcttaat 140880
attccctcag gaacacacct gctttgtctg ggagagacct gggcgtcttg gtggcggggt 140940
ttgggggtac ttgctcatgg gcttatgggg cctctctctg tgtcccccca ggtttacaag 141000
tcgtcctgaa gtcgatcatg aaggcgatga tccctttgct gcagatcggc ctcctcctat 141060
tttttgcaat ccttattttt gcaatcatag ggttagaatt ttatatggga aaatttcata 141120
ccacctgctt tgaagagggg acaggtaggt ccacggagca tgatgcatct ttccagtttt 141180
ctccttcagg gacaagctct tgggaggatt aggcagggg gtgcttcttt ctcctggcag 141240
ctgggaggac cgtctccttc agagagcact acaggagagg cagtgagtga aatagcctct 141300
gagatcttag ctgttgaaag gggtgggtt ccacagaagg tgacccagca gagaaagagt 141360
ttatttggga atgatcccag gaagcaccat cgggggaatg aggaagtgag cagagaaaga 141420
agggatcttt taaagagtgt gctatcaagc gggttaccac ttaaaactgg gactggatcc 141480
ccctgggcac ctctgggaga cagcaaagaa cacacaactc agctggtcac ggtggctcac 141540
gcctgtaatc ccagcacttt gggggccaa ggcgggtgga tcacctgaga tcaggagtca 141600
gagaccatcc tggccaacat ggtgaaaccc catctgtact aaaaaataca aaaattagct 141660
gggtgtggtg gcaggcacct gtagtcccaa ttactcagga ggctgaggca ggagaatcac 141720
ttgaacccgg gaggcagaag ttgcagtgag ccaagatcac accactgcac tccagcctgg 141780
cgaaagagtg agactccatc tcaaataaat aaataaataa aatataaat aaaaaagaa 141840 cacacacctc agagccgtcc cagccaaggg gcaagggagc tggggtattt atacactggc 141900
ttctttttga cattggtgag gactgctcct agagtgggaa ttaatgcctg gcacatctgg 141960
ctgagtggaa caggtattct gggtgctttc agacctcgac cagtcctgac ttctaaagca 142020
agcaagaagt ggggagagtt gggccagaaa agggttattg cctcaatgca ttgtgagtgg 142080
taccttgtgg aaggtgagag acagagaaga ttccaggcac aggtgccatg ctaaacgata 142140
```

```
gttctcattt attataggaa cccatggatt tattttgttc tctgccctga gtgctgggtg   142200
agagtactgg atgagtcctc ctggtctccc ccaaccccca ggatgtacca gagataccccc  142260 aattgggagt cctggcacca accaatcaga acctagcact cagcagcatt ctgcccctcc   142320
ctgactatgc ccacattaac ccttcagtgg ctgggtctgg gggtagggtg agccccggaa   142380
aagccaggca gcgcagagac actctcccag ggctcagctc tgaaccagca gtgtggaagc   142440
agtgtgtcca ccacgatcca cactcaggaa ccaaatagcc cttggatacg ttttcagtta   142500
aatctttgcc atccaaactc tagctgcttg ctctctaaag ctccagaatg aaatggaatc   142560
aagtaggaag ggatgccttc agtatttcag tatttggacc actggccatc tgggtgcaga   142620
cagactgaat agcagttctg gttctgatga tttgggtcaa gggagctgtg aattgaagga   142680
gtggatagaa ggaatcaaga agcccaaagg ggaacccagg tgggcagaga aagaggtttc   142740
aggcccctta tttgggaaag gcagccacag aagaagattc tgtctgggag tggatttcca   142800
cccaccctct ccacccagtg accccaagt ggatccgcag aggcagcccc tgagccctcc    142860
ctccccactc ctccccacgg ggagggaaaa cccactgggg aaggtttatt tgcaatggtt   142920
ggaggtttgg gttttttttgt gggttttggt ttgttggttt ttttttttcct cttttctctct  142980 tgctcctcct gtctctttct ctcctgggct tgtgaagttt gctcaatatg gaatgtccta   143040
attatttctt tccccgatga agaaggtgtt aattgaggca gagctatttc tgctcctggc   143100
ctcgtcaccc aggcggaaat gcgagagaga gagagagaga gagagagaat gaatatgggg   143160
cagggcctct tggaaaaatc agccgtgagc agagaaacca ggactcctgg atcctaggtt   143220
tctgtgaagt tttattttat gtttttctac cctagactag ctaaaggaga agaggccatg   143280
gggttggctt gggtccgagt ggggttttga ggggacagat gtgggtggtg ccaccagagg   143340
ggaggaagcc tcgatttagg agaaagactg aaaagctagc tcacgattaa aaatataaga   143400
cgtgtgagta agagacagat atatacagac acccaggcag tgggttaatt ttaaaatgta   143460
tttataaccg aattcctcag acactctgga cgcttgtttt tctagaagca acgctcagag   143520
tgtttcgtgt cggtggttgg ggggttgagg gggattgcaa agctgctaaa gatagacccg   143580
ttttcagtag cattcctcag tgtcgggagc ccagttcctg tgtgcccagc accgtgccaa   143640
tcgcttagaa ggaagcaaag ataaagtgga aggcttcctg ctttctaaga gcttccaaaa   143700
tagttagagg aaacaagacc cctcatttgc agccattttt aacagtgaag gctaatgtgt   143760
gattataccc acgccccct aaatatgaaa attcagtagc tattgtatgc ctgaaagggg    143820
ccaggtgcag tggctcacac ctgtaatccc agcactttga gaggctgagg tgggagtatc   143880
ccttgaggcc gttagtttga accagccta ggcaacatag ccagaccctg tctctgctaa    143940
aataaaaatt taaaattgg ccgggtgcag tggctcacgc ctgtaatccc agcactttgg    144000
gaggccgagg caggcggatc aaaaggtcag gagttcaaga ccagcctggc caacatagtg   144060 aaacccgtc tctactaaaa atacaaaaaa aataaattag ccgggcatgg tggcgtgtgc    144120
ctgtagtacc acatacttga gaggctgagg caggagaatc acttgaacct gggacataga   144180
ggttacagtg agccgagatc acgctactgc actccagctt gggcaacaga gtgagatttt   144240
gtctcaaaat aaaaaaattt aaaaattagc catgagtggt ggtacatgcc tatagtccta   144300
gctactcagg aggctgagga agaaggatca cttgagccca ggaattggag gctgcaaggc   144360
tgcagtaagc tatgatggtg cccgcactcc agcctgggtg acaaagtgag accctgtctc   144420
aaaaaaaaaa aaaaaagag agagaggaag gaaagaagga aggaagggag ggagggaggg    144480
```

```
actgggctg  tgttaactgg  gctacacaaa  gaggctacat  ggagggtggg  aattgagcca  144540
gacttggaca  tggcgtggag  acagagaaga  ttccaggcac  aggtgccatg  ctaaacgata  144600
gttctcattt  attataggaa  cccatggatt  tattttgttc  tctgccctga  gccttatgtt  144660
taaaagattt  ttgccttcca  acctgtattt  atcaaataat  agttcatgta  ccaagtccag  144720
cataagtgag  gaaggcgttt  ccaacaactt  aagttcatgg  cgaggctaga  cttggagttt  144780
ctattcagcc  agagcttgaa  aggccaacaa  gattcattca  ttcagcattg  gtttatttcc  144840
ctctgctgtg  tgctcagtca  agggagcaga  gaattggtgc  tgcgaagtct  gtagcacata  144900
cattgagaga  tattttttgtt  gagtaggaag  cttgagttta  cacacactca  gctgtttgtt  144960
ttcttgtccg  acaatgccac  ggtcgtcttt  gaaaaccttc  aaaagcatcg  ctcacagaat  145020
aaggtcctct  cagacccgct  gtgctggtaa  aatgaggaca  ctcccagatg  tgagctttcc  145080
tgcctcccta  ccccatcaat  accttaagat  ttggactgac  ctttagcgtt  cagcctgact  145140
gccacctccc  caggaagctg  tctttggttt  ccagcaaaag  gggtgtctgt  tggcacgttt  145200
ctctctcctt  gtggcatttt  cacagcctgc  ctcctgctat  ttggggagaa  agctcagctc  145260
ctgttcctta  cccttaggca  agggtaggaa  ctgtgtgtac  tggtgtccct  cacccccaga  145320
acagctccct  gagcccagta  catcccaaga  agaaaaaaat  cagcaaggct  tataggaaaa  145380
taacacaatg  cgcttgacaa  atttgtccta  atggatgtcg  gaagaaggct  gcacttacca  145440
gctacaccat  gcacacggca  catttactaa  aactgactat  attatggacc  ataaagtttg  145500
tctcaacaga  ggtcaaaaag  ctgaaaaaaa  tacaaataca  aaacatattt  tctgaccgta  145560
atgcaattaa  gctggaaatc  agtaacaaaa  agagaactct  aaaagtgttt  gcagattaac  145620
agacatgcct  ctcatttatg  gatgaaatga  tatgatgtct  gagctttgct  ttaaaaatat  145680
tctaggctgg  gtgcagtggc  tcacgcctgt  aatcccagca  cttggaggc  cgaggcgggc  145740 ggatcacttg  aggtcaggag  ttcgagacca  gcctggccaa  catggtgaaa  ccccatctcc  145800
actaaaaata  caaagattat  ccaggtgtgg  tggtggccac  ctataatccc  agctacttgg  145860
gagcctgagg  caggagaatc  ccttgaacct  gggagtcgga  gattgtagtg  aggtgagatc  145920
atgccattgc  actccagcct  gggtgacaga  atgagactcc  gtctcaaaaa  aaaaaaaaa  145980 aaaaaattct  agtggcaagg  caaagtgttt  ggagggggata  cagaggaata  gatgaaacaa  146040
aatttgccag  aagtaaatag  gtaagtgtct  aaattggtga  taggtacatg  gtgaatcatt  146100
atattgtttt  atacttctct  ctcgctctct  ctctccccc  gttctctccc  tgtcttcctc  146160 tccctctgt  cttcatatat  atatatatat  atatacacac  acacacacac  agacacctaa  146220
taagtttttt  taaaaacaa  atacatctaa  attacccata  ggtcaaagaa  gaaataataa  146280
tggaaattag  aaaatatttt  acttgaacaa  taatgataat  gcatgacaaa  atgttgagat  146340
gcaggtaaag  ccacacttaa  aggcaattta  tagccttaaa  ggcagttaat  ccatccatct  146400
caaaagttta  ggaaaagaat  agaaaaaaaa  aaaaaactca  tggaaaacat  aaagagaaaa  146460
gtagtaaagc  tcagagaaga  aattaatcaa  tagaaaacca  ataatagacc  cccaaagcca  146520
aacattgatc  tctttgaaga  ctgatcacgt  ttgtcccaaa  agttattcgt  tccaacagca  146580
ttatagagtc  actggtccct  atttctcaga  gctggttttc  cctgctcctt  ccctgactt  146640 ttctccccctt  cccttttgta  gatgacattc  agggtgagtc  tccggctcca  tgtgggacag  146700
aagagcccgc  ccgcacctgc  cccaatggga  ccaaatgtca  gccctactgg  gaagggccca  146760
acaacgggat  cactcagttc  gacaaacatcc  tgtttgcagt  gctgactgtt  ttccagtgca  146820
taaccatgga  agggtggact  gatctcctct  acaatgtaag  tgatgctggg  acagtgtgtg  146880
```

```
tggacaatca gagtctcagg gaggtggcct cctgggacca gtgagactcc aaggctgcaa  146940
tggagggacc ctgagctggg aaaggcagcc caaggacaac acagccccac tgaagctggc  147000
ctgaggctca ggcttttgaa gattacaggg gctcatgagc agaactctaa ctatagggca  147060
tagaagtctg gagggccccc agatgcaaca tcattttca ttgtgcaagt gtttagatat  147120
aattttagat ttttgaatac ggaaaggtta tgtgatccaa aaccaacac agataaaaga  147180 tagagtaata tctttggacg taggcgaggg gtccctgccc tgaggctcac ccagtccttc  147240
tccagccata ccactccccg tgggatgaga agttcctgga gccaagggga tgtgtctacc  147300
aagagcttgt gccccacttt gtaggccatg ttttaagtta ccaggatcct ggaattccct  147360
gcccatggcc agattccatg aacttgcgtg caattctcat atggatctgt tcgtaaccca  147420
actgagggcc aaggacatcc gagggtggc tgttaacaca aatgtggcca gagcttggat  147480
gtacaagctg gaatgcccac acatatgtgt ggagcccctc tggcaggaca gagccatgac  147540
taagaagaga aagggacagg acagggctgg ctctccccac accttgaccc agtgcagata  147600
tccggattct aaattccacc ctgaccttcc aaagtgtaaa ggaaggtata tttgcaaagt  147660
agaagcacac agcatgtttt atttagttac cttttcaata tttccccgta gtatgtggtc  147720
tgcttttgta ctcttgccct agatcttaaa aatgttaggg atgtttctgg aaagatgtat  147780
ccctgccccc acttgcatgc tacttcctct tcccacaata tgcaacccct ttagttcctc  147840
agaatatcct tccaatgttt atttatgcaa ttataattat aagcataatc gaatctatgt  147900 cctccccct ctttcttatc ccaaggagta gcattctata catgctgttc aattctgtga  147960
tttttgtttt ctcataacca cacgttctag agatctttcc actgcaggac atggacagtc  148020
tcttcacggg tgcacactag tatgcccagc taatttttgt agagacaggg ttcttccgtg  148080
ttgcccaggc aggtctggaa ctcctgggct caagcaatcc tcccgcctct gcctcccaaa  148140
gtgctgggat tacaggcgtg agccaccacg cctggcctc tttattcttt tgcacagctg  148200
catagcattc tattgtgtgg ctgcccatag ttttatttgt ttgccattaa gagaaatgct  148260
tgactggctt cctgtccact gacatggaac atgatgctgc tctgccagga gcatgttgca  148320
cgtacctctt catactttg cagatatagc tagggggttg gagggtctcc attcccagaa  148380
gtgggattgc aggatcaaag actaaatgca tttataattt tattttggg gaagattttt  148440 gttttgtttt tttggagaca aggtctccct ctgtcgtcca ggctggagcg cagtggtgta  148500
atcatagctc actgcagcct taaactcctg ggctcaggtg atcctcccac cccagcctcc  148560
tgagtagctg ggaccacagg cacacaccac catacctagc taattttaa gaacaatttt  148620 atagagatgg ggtctcacta tgtttcccag gctgctctca gactcctggc ctcaagcaat  148680
cctcctgcct cagcctccca aagtgctagg attacaggtg tgagccactg cacccagcct  148740
aaatgcattt ataattttga tagatattta ggtgtgcaag ttttaaaccc cactctgtcc  148800
tcaccacagt tcaccttccc tcacctacta tgcaggtaag cagtcccag gcaggtcact  148860 tgtcagcagc tggagtgggg cagagccaag gattcaggat caaacacaag gatgccacaa  148920
ctgtagtgac cccatagagc accctggggc tgctccatac acacagctct gttgaccagt  148980
ggaggtctcc tcttcacctg ccctaagggc tgaaattacc attgaagttt aggccagcgg  149040
ttggcctgac ccgggagcaa tacctggctt cctcctcctg tacatagaga agctgaactt  149100
tcctcttggt cctagtgtat gttccttaac aacccattta tgcctagtgt tccattattg  149160
gaatgctaat cctgtgggag ttatttacat cctgctgctc aaggtcatca ctaaggtcgg  149220
```

```
atttttcaca cacacaaaaa ttgcaacctc cggcataaat gggttaagga atttccccac  149280
ttgtgggtgg agggagattt gcaaaaactc atccttgtaa tcctgatcaa caaaggcccg  149340
ttttagttgg gagtaggcag caaaaggagc cacatgaaca gttgcgcctg tcacgcactg  149400
cacaagaatg tcattcatat catagacaac atacgatttc tactgttatc ctgataattt  149460
attgacagaa aaaaggatgt ggggaaggga catggtgttc taatttgcat gaaaacctcg  149520
tctgagtgta gcatctctgg gaacatgcag cagatccgag ctcaggccct ctcttggccg  149580
tcacctgcaa acagcttgga caaagggtca gcccaattgg ccaaaactca ctggggaatt  149640
tttgtgggtt ctaggttttt actttgcaag gctggtgtga gaggaggttc cagcaggaaa  149700
tgaaccctcc tgagagggaa agagactggg aaatggagaa ggctgggaac tcaggagag  149760
aatgggagtg gggaatggga gctgaaaaaa attgtgagca taaaaaaggg atatgtcaca  149820
gggttggatg accagagaaa gcgtctgggg gttcagatta agatgctggg ggcgtgccca  149880
gtggtgggac aggaagcatg aatttccaga gggctcggtt ataaacatca ttgtccaatg  149940
ggtgtttccc ttggaagcct ctaagcttag agctaagcca cctctgggga cacaaactga  150000
gtggttaaga gcagagactc aggtgtcagc ctgtctgggt tccttccgac tcttccactt  150060
ccttgctgtg cagccttcgg caaggtgctt ggcctctctg tgccactatt tccacatgtg  150120
caaaacgaag agaagcatag tcccacctca caaggcacga ggactaagta aggtggattc  150180
gcatgaagtg tttagaactg atcctggccc ggggtgacct ccgtgtaagt caaattcccc  150240
accctgcatg gtgttccttt tagaaatgtg catgaatttt tcattagaac agctccagca  150300
gtgcctgagg aagtggagtg aggtgtgaga ggtcttactt tattcccctc gctggccctg  150360
ctattaacca ctaactcaga gtagctttct agcactttcc acacatttac atcccaccct  150420
cgtcctttgg ttagcagccc atgcaatgat ttggccttaa tgtgaaccta gaacacagct  150480
tctcgcccag ggatgatttc tgccccagg ggacacttgg cagtggctgc agacattttt  150540
ggttgtcaca actggatggg aagaaggagg atgctattgg catcaagtgg gtaaaggcca  150600
cggatgctac tcaacattct acaatgcaca gcatccccca cctctgcccc accatagaga  150660
atgatccagc cccaaatgtc agtaaggttt ctgtcaggaa accctgggtc agaagaccaa  150720
ggttccttga ggacggggat gccttatact gcaatcagct gtcactctct gcctctctct  150780
ggggctgctg tgatcacctg gcctgcatgg acaaccccta ggagcagccc ccatccagtg  150840
cctggagaag tcagtggata aatacccag ctccctccct gtcgggcgtt ttgctctgcc  150900
ctgcatctct ccagtgggat caggctctgg ttgcccgcag ggttaacctg gtcacgtaca  150960
caccttcac ttgccacctt cccttccctg tctggtattt cctgggatga acttttagat  151020
ttatttcctg gggctgctat aatgaagcac cacagactga gtagcttaaa acaacaggaa  151080
tttatggtct gacagttctg gaagccagaa gtccaaccc aagatgttag cagagctgac  151140
aacacgcccc tcaaaagcct ccgggggagg atccttcttt gcttcttcct ggcttttgct  151200
ggtttcccac aatctttggg attccttggc ttctagagcc ttcattctcc attccagtct  151260
tctgtcatct aatagcatcc tcccagcccg ggcacagtgg ctcacgcctg taatcccagc  151320
actttgggag gccgaggcag gcagatcact tgaggtcagg agtttgagac cagcctggcc  151380
aacatggtga acccccatct ctactaaaga tacaaaaatt agccaggcgt ggtgggcggg  151440
tgcctgtaat cccagccact tgggaggctg aggcaggaga atcacttgaa cccgggagat  151500
ggaggttgca gtgagccaag atcatgccac tgcactccag cctgggtgac agaatgagac  151560
tccgtctcaa aaaaaaaaaa aaaaaaaaa agaaaaagaa aagcatcctc ccttcgtgtg  151620
```

-continued

```
tctgtgtgtg ttctcctctt cttagaagga catcagttgt attggatcag aacctaccct 151680
actccagtcc aacctaattt taactaatta cgtctgcaat taccctattt ccaaataaga 151740
tcacattctg aggtaccagg gggttaggac ttaaacattt tgtgtgtgt agcaggagga 151800
cgtaattcca tttataactc ctcctaaata aaacgacttg catgtgaact cttgtctggg 151860
gcttcccaaa gtgagataac ccctctctct accnctaaaa caacgagtag cgtctgtcaa 151920
tgccagggtg caggggctaa ggtgcccatc tttgagtttc tgctgaggag gacacagctg 151980
ctacgttgga gcactcttgg gttctgcctt cgtgcccagc catctccctt gggctagccc 152040
tgccctgggt ctatcctaga atgagcctcg atctgtttgg ccataggcaa gcagagtgtc 152100
tggaaatctt tgtcctccat gactggtgct ggagccgaag ccagtgggtg tggccttgcc 152160
agccaactcc atttacccag ctctgaacaa gctagtagtt gagatcaacg agagtccag 152220
acagtcgctc caagcatctt ggaatccatg acacaggtg taccgcagag gcttcccacc 152280
tgggtaggca gcccttttgta agatcctggc accacattta ttctcttaac atcctttcag 152340
ttatccagta atcatttatt gagcacctac tgtgtgccag gcaatgatta ggtgattgga 152400
gacactgcaa cgaagaagac agactaaaat ctccaccctg gtaggagaga cagatgcaaa 152460
tggtaaacat gataaataat caatcaccca gaaagcagga gacactaagc aaatgtgtat 152520
gtactatggg aagcccaata ggaacgaaag ctacacaaga gaacaagtga tgggtggttc 152580
cttagtctag gtcaggcaat cagggagggc ttctcagagg aggtgatgtt tgagcagaga 152640
aggagggagc caggcagatg tttttggaaac agcattctca gcatggagaa cagtggcagc 152700
tcacctacag gatgtgtttg attcccttcc agattttgta ttcgtttctt gttttttctcc 152760
cttggcttcc tggtttaaat gccttttgaa gaaatctaag ctcaactaat cagcgatgct 152820
gttgaaggtt tatatcagga tatgcatccc agagttattt acaaaattag aacaaaactg 152880
gaagcaattg aaagcctgac aataggagat cagttaaata ccgtatggtc cttccgtatg 152940
atggcatatt atgtcatcat taaaaatcgt ctgctgggag aatattaagg atacagggga 153000
aaggctcacc atataatgat gagtgggggt gctgggcgca gtggttcatg cctgtaattc 153060
cagcaatttg ggagtctgag atgggtggat cacttgagcc caagagtttg aggccagcct 153120
gggcaacaca gtgaaaccca atctctacaa aaaaaaaaa acaaaaatac aaaaatcagc 153180
caggcatagt ggcgtacatc tgtagtccca gctactcagg aggctgagac aggaggatag 153240
gatcacttga gccctggagt cagaggtggc aataagccgt gatcacgcca ctgcactcca 153300
gcctgggcaa cagagtgaaa ccctgtcaaa aaacaaaaca aaaaaatga tgagtgggag 153360
aaacaagttt ttaaacaggg atcaaggagg ccaggcatgg tggctcacac ctataatccc 153420
agcactttgg gaggccaagg caggcagatc acctgaggtc aggagtttga ccagcctg 153480
gccaacatgg cgaaaccctca tctctactaa aaatacaaaa attagccagg catggtggcg 153540
ggcgcctgta atcccagcta cttgggaggc tgaggcagga aaatcgattg agcccaggag 153600
gtggaggttg cagtgagctg tgatcatgcc actgcactcc agcctgggca acagagcgaa 153660
agctgcacga gagaagaagt gatgcatggt tccctagtct aggtcagcca atcagggagg 153720
gttcctaaga ggaggtgatg tttgagcaga aaggaggaa gccaggcaga tgttttgaa 153780
acagcattcc cagcatggag aacagtggca gctcaccctg tctagaaaag aagaaatgat 153840
aagaggggaa aatgagtttt taaaaggaa tcaggggga gtaaaccta tgatctcaaa 153900
ggtacaaata tgaaaatata agtaaagaaa aactggagga cactgtacca agctgacctt 153960
```

```
cgggtggtgg gatttgggaa tcttgatatt ctcaatactt ctttgtatct tcaaatttct   154020
ctatgatgat cacagtttac ttttttttt tttttttgag atggagtctc actctgttgc   154080
ccaggctgga gtgcagtggt gcgatcttgg ctcacttggc tcacctctgg ggttcaagca   154140
attctcctac ctcttcctcc caagtagctg ggactatagg catgcaccag catggtcagc   154200 taatttttg tattttagt aaaaatgggg tttcatcatg ttggccaggc tggtctcgaa    154260
ctcgtaagtt caagtgatcc accaacctca gcctcccaaa ttggcttgag ccaattaaac   154320
ttgtcttgct aaatggttag cggggagaaa gaagaaggtc tcgggtcatt cctagaccag   154380
gaggcaggga gaaagggagg agaatgaacc tttcttaggc aaacagtgtc ctaggtgtcc   154440
ttatcttaca taatctgtcg agagagtcac actaaaataa atcattgatt gattgattga   154500
tacatcaata ataaatggcc agccttggtg gctcacatct gtaatcccag ctacttagga   154560
agctgaggtg ggaggattgt tgagacaag gagttcaaga ccagcctggg aaacacagca    154620
agactcatct taaaaaaatt ttttttttta attagccaga tgcggtggct cacgcctgta   154680
atcccagcac tttgggaggc cgaggcgggt ggatcacgag gtcaggaatt cgagaccagc   154740
ctggccaaca gggtgaaacc ccgtctctac taaaaataca aaaattagcc aggcgtggtg   154800
gcacacgcct gtagtcccag ctacgcagga ggctgaggca gaagaatcat atgaacctgg   154860
gaaacagagg ttgcagtgag ctgagatcac gccattacac tccagcctgg gcaacaagag   154920
caaaactaca tctcaaaaaa aatgtttttt aattagccgg gtgtggtggt ccatgtctgt   154980
agttccagct acttgggagg ctgaggcagg aggattgctt gagcccagca gttcaaggct   155040
gcagtgagct atgatcccgc cactgcactc cagcctgggc aacagcaaga ccccatctct   155100
taaataaaca cataagtaaa taaatgatca ttttttatttt attattaaat acacaagata   155160
aatgaaaaac aggcaaatct ttcttacaaa agaattccat ttaaagtatg taaacttcac   155220
tccccactgc cccaggaggt ggagactaat ctcccctact ttgagagtgg gctggattta   155280
gtgactcatt tccgaagaat agagtaggta aaggggaaaa tagaagtttt atagcggagg   155340
aacagataga taccacttta accaaatgat gaagattagt atccccagg atgtggata     155400 ttatgtaacc cttgatttta tgcctatata gcgttcttcc caaaaactcc taatcccagt   155460 tttttgggt tttgctctgt cttctaagct ggagtgcgat gatgcaatca tagctcactg    155520
cagctcaaac tcctggtctc aagcgatcct cccacctcaa cctcctgaat agctagggct   155580
gtaagcacat accatcatgc ccagctaatt gtattttttt ggtagagaca tgttctcaca   155640
cattgcccac gctgtcctcg agctactggc ctctagtgat cctcccaccc cagcctccag   155700
agtcactggg attataggca tgagccactg tgaccagccc agaatttttt tttaaggagt   155760
tgtgatgtcg tttaagagat gtgattcttc ataacacatc aacaacaagt cccagcgatg   155820
ggttggataa gtcttgggat ttcatgggag tattaagctt aaaagacttt gcatgatatc   155880
tgtgaactat atgtgatttc tgttggtaat gggggtcact gattctgcgg tttgccacct   155940
ccaatcatca tggaagaaaa tgttccactt ccagtgaaag taagaggaag taagggta     156000 attattttct atctaaattc acgaactcct tgaattctgt ccacagaccc ctaagtgttt   156060 cctcccaag gtgaaactga gagaatcttg ccagtgcctt ccgcagtcac tgtggctaga    156120 aaaccctca gaagaggtga tagtttagca ggtaactgga gttctcacca tccgtgtctg    156180
gctcagcccc catcacaacc agttaccag cccaaaatgt cagtagtact gaggttgaga    156240
ggctctgctc taggaggcca ggcctctcag aggaaggagg attggggtac tggctgggcc   156300
tcaagatgaa cctaccccct aagagctttg ggatggcgtg agtttctgtc catacccaag   156360
```

```
gactacaaat gcaggtttac tggaaattct gtgccaaaag tgaggtccaa ctcacttcta 156420
actgctacaa aacaaacctc catcaacata gcccatctct gttcttgacc tggaagctcc 156480
aaggtatcca catggctccc atgcccacta gacgggcctc ttccctggac cttcctgggc 156540
cagagaaggc tctgggtagc cttgtggaat caagatgggt gatcagccac ttcctctgtg 156600
ccaccctgtt ttggctactt ccctaggcat cagcctggga ttccttgatg gtaaaaatat 156660
aaaactctct gagctagggc ctttaatatc cccattttac agatgaagaa actgagtccc 156720
agagctgtgc acagcgattg agagtcagaa ttcagctctg tctcactcag tgtcaacatc 156780
ctcagattct gccatttata gcctcccaca gcaaatagga ttgagggctg cttctctgag 156840
ctcaagggga tagaatgggg aaccccatga gtactgcaac aaaactgttt gctggagaca 156900
agagctggtg gctctgtgtt gttctagtga caggtggcct catttcacag gaccccctc 156960 accctatgtg ccccatgtgg ctcagaaaag ccagaaattg tctccactct cacaggggaa 157020
ggtccctgac cccctctttg ccagctgggc caaggcaaat tggggtcact tcatgggta 157080 caggacctac cctctcttgg ttgcccccaa ggaggggatg tggagggggct ggggacctgg 157140 caggaccagg gtgtcttgag ttaatttggg gctgccttta gccgagggct tctgtgtgcc 157200
tggcatcagc tttacattgt gtcttgatcc gtaaaacagc cctgtgagga aagatatttt 157260
taaccccatc ttccagatga ggaaacggag gcccacaggg tgacgtgacc tgccaaggtc 157320
ccctagccaa gagtgacaaa gccagggttc acacacagct ctggacacaa ttcatcaccc 157380
ttcatccgtc tctctctgac tcttttcttt tccctctctc tctttgtctc tcttttttt 157440 ttttttttt tttgagacag cgtctcactc tgtcacccag gctagagtgc agtggcgcaa 157500
tctcggctca ctacaacctc catctcctgg gttcaagcga ttcttgtgcc tcaacctccc 157560
aagtagctgg gattacaggt gcgtgccacc acacccagct aattttgggg ggttttgttt 157620
tgttttgaga tggagtcttg ctctgtcgcc aggctggagt acagtggcgt gatctcggct 157680
cactgcagcc tctgactccc aggttcaagt gattcccctg cctcagcctc ctgagtagct 157740
gggactacag gcatgcacca acacgcccag ctaatttttt gtatttagt aaagacgggg 157800 tttcaccatg ttggccagga tggtctcgat ctcctgagct catgattcgc ccgccttggc 157860
ctcccaaagt gccgggatta caggcgtgag ccactgtgcc tgccaatttt ttgtattttt 157920
aacagagact gggtttcaac atgttggccg ggctggtctc gagctcctga cctcaagtga 157980
tctgcctgcc ttggcctccc aaagtgctgg tattacaggc atgagccacc atgcccagcc 158040
tttgtctctt ttattcttgt gttctctctc tctcttcctt ctctttctcc acctcctct 158100 ccttctctcc cttctcctca cccttctttg tgcttttctc tgtgagtttc tcttcttctc 158160
tatttctctc ctttggtgaa tgtcaattag aaaagcagaa aaactgcgtt taatttgtga 158220
tcataaatgc atgtccctgg ccaggcgtgg tggctcacgc ctggaatccc agccctttga 158280
gaagctgagg caggaagatt gcttgagacc gggagttcaa accagcctg gtcaaaaagc 158340 aagaccccat ctttaaaaaa gaaaataat taattagctg ggcatggtgg tgtgtacctg 158400
tagtcccagc tactcgggag gctgaggaag gaggattgcc tgagcccaag ggtttgaagc 158460
tgcaccgagc tgtgattaca cccctgcact ccagcctggg tgacagaacc agaccctgtc 158520
tcaaaaaaaa cctaataatt aaaaataaat aaataaataa atgcgtgtcc cctggccagt 158580
ggttgctaat gtttggaatc acctttgacc catgcccttt ttcattcata gatgtttgtc 158640
ttgaccaaaa tcaaagcatt agactttgga ctataaatca ctggttcatt caacaaccat 158700
```

```
cattgaatgc ctactgtatg cagacactct tctggacaca gaggagttga cgtgttggtg   158760
gggaaagcca gtgatcagtt gggataaaaa gggcagacag cagacattaa atagtttagg   158820
ctttgtgggc cagatggtct ccatcgcaac gactcaatct gctcctgtag cgtgaaagta   158880
acgacagata aagcgcgtaa gtgaatgagc atggctgtgg gccaattaaa cgttaaccta   158940
taaaaacagg tggctggccc gcgggctgta gtttgtggat cactgcctta gagatagtgt   159000
tagagggtgg tgagaggtcc gggatagaat aaaacagtag agagtttgtg cattgtcaag   159060
atgagaggtt gcagttcttc ttatacaccc cgaatggccg ggcaccgtgg ccattatgat   159120
ctataattct aacactttgg gaggctgagg caggaggatc ccttgagccc tagagtttaa   159180
gaccagccta ggcacatagt gagaccccat ctctacaaaa aaaaaatttt aaaaattagc   159240
tggacatggt ggagcatgcc tgtaggccca gctacttgag aggctgagat gggaggactg   159300
cttgagcctg ggaggttggg gctgcagtga gccgatcatg ccactgcact ccagcccgga   159360
tgacagagca agaactgtct caaaaaaaaa aaacaaaaaa acaaaaaaaa cagacctgaa   159420
ggaacaaatc atatgaatgc attaaagtat cacatgtatc caaaaaatat atacatctat   159480
cagcctggca cggtggctca tgcctgtaat cctagcacat tgggaggcca aggcaggcag   159540
attgcctgag ctcaggagtg caagaccacc ctaggctaca tggtgaaacc ccgtctctac   159600
taaaatacaa aaaattagct gggcatggtg gcaggcgcct gtagtcccag ctacttggga   159660
ggctgaggca caagaattgc ttgaacccag gagacagagg ttacagttag ccgagatcgt   159720
gccactgcac tccagcctgg acaacagagc aagactctgt ctcaaaaaaa aaaaaaaaaa   159780
aaaaaaaaaa aaaatatata tatatatata tatatatata tatatatata tatatatata   159840
tataatcaat taaaaatttt ccttaataaa taaacatttc tctccttctc tcccttggtg   159900
aatgtcaatt aataaagcaa caaaactatg tttagttagt gatcattaat gtatgtccct   159960
ggctgggtgt gatggctcac acttgtaatc ccagcacttt gggaggctga ggcaggagag   160020
gatagtttga ggccagcaat tgcttgaggc ttttgaaag acatgaagga gatgaaggga   160080
gccatggaga tatctcaggg aacagcagcc gaggtagatg gaacagccag tgcaaaggtc   160140
ctgaggcagg atgttcctgg catttgtgag gacatgtagc tgcccagatg tccagtgggg   160200
agtgagtgag gatgaaggaa ggagctgatg aaggaagatg ataaaatact tcatggatca   160260
gccaggcatg gtggctcccg cctgtaatcc cagcactttg ggaggccaag gcgggtggat   160320
cacaaggtca gagttccag accagcctgg ccaacatggc gaaacccccgt ctctactaaa   160380 aaatacaaaa aagttagcca ggcgtggtca tgcacgcgtg tactctcagc tacttgggag   160440
actgagactc gagaatcgct tgaacccagg agatggaggt tgcagtgagt tgagatcacc   160500
ccactgcact ccagcctagg tgacagagcg agactctgtc tcaaaaaaaa aaaaaaaaa   160560 aaaagactt cgtgaacaga cagcctatat aatttatgat ccaaaccagg acagttttga   160620
gagtgaaagg ggaaaagag cactgaaaaa ataattagca ggcctggcat gatctataac   160680
gggtataaag tgggacacac agcctctctc acggtcactg tcagacttca gcttttttcac   160740 actcaaatcc accccccatgt ttatcccata tactggagaa acgggtgttc tcctgagctg   160800
agttttgggg tttttttcctt ttgtttttgtt ttgtttttgt tttttaaca tcctgtatac   160860 tttttctcaa tgaaccatgc tcaaaaaaat tagaggaaaa taaaccataa aacagaaggc   160920
actgaaggat tttgctggga ctcagccatt agtttgtttg atgagtattt atggagcgct   160980
ttctaagcac caggcaccac cagcgatact gggatgaatc agtaacatcc ctcacccttg   161040
aagctctctt gggcccattg ttatttactt aaaatactat gcaagtacgg agaagggtg   161100
```

```
aagtgggaaa aaatcagttg gttgtaaagg ccagaatgac gggtctagtc ccacccatgc 161160
catctgcacc ctgtgtgatc caggcacatc atgttgcctc tctcagcttc agtttctcca 161220
tccaccaggc acagagatgg cgggaatcga ggaagatgtg gggagtattt catcagccca 161280
aaaagacttg gctaatgcga ccataattct gccttctgcc tctcctttcc cagaaaaata 161340
gcttaatcat ttggatttgg gataaacaca tttcctgtgt ttattattta aatgatccac 161400
caagctgggc atggtggctc acccctgtaa tcccaactct tgggaggct gaggagggcg 161460 gattgcttga gcccaggagt tcaagaccag cctggccaac atggcgaaac cccatcttta 161520
ctaaaaaaat acaaaaaaat tagctgagcg tggtggtgcg tgcctgtaat cccagctact 161580
tgggaggccg aggcacaaga atcacttgaa cctgggaggc agaggttgca gtgagcctag 161640
atcgtgccat cacactccag tctgggcgac agagtgagat tctgtcccta aataaataaa 161700
taaataaata aataaataaa taaaataaat gatccaccaa caggaacccc aggaacattt 161760
gtattgacta tgcaactaat gcttagtgag cacctactat gtccctggtg ctgatctgga 161820
cactgggatt tagacaggaa aaatctctac cctggaggag ctgatgatca agatgacaat 161880
cttgaaatgc ataagttgac aagatgattc agacagtgga acgtgctggg aagagaatga 161940
gatgtctggc tgagctgcag gaaggggcaa gtccttttga ttgagaggtc caagaaggct 162000
tctctgatgg gggcacaatg gatctaaggt tgagtgataa aagaaattg gccaagccaa 162060 gacctaaagg cagagttgct ccaggcatag gttcagagaa tggaaataat tggctgattg 162120
tgatcttgaa cttgaccttt cttttcttct gctaacttg ggtttggttt gttcttgctt 162180
ttctggctcc ttgaggtacg tgttgggttc ttaatttgta attttttttt tttttttttg 162240
cttttttgag acagagtctc actgtggtgc ccaggctgga gtacagcagc atgatcttga 162300
ctcactgcaa cctctgcctc ctaggctcaa gtgaacctcc cacttcagca tccccagtag 162360
ctgggactac tggtgcacag caccacaccc agctaatttt tttattttta tttttagag 162420 atgggtctc actgtgttgc ccaggctggt ctcaaacccc tagctcaagc gatcctcctg 162480 ccttagccccc ccaaagtgct gggatgagag gcgtgagcca ccacatctgg cctctgtttt 162540
ttgtgatgta ggtatttgat gctataaact tccctcttag ttgcttcttg gccctttagc 162600
taaggtcaag tgtaaacttc cctcagcact gcttctgctg catctcacag gtgttggtgt 162660
gttgtgtctc tattttcatt catttccaaa atttttaag tctccatctt aatttctgca 162720
ttgacccaat ggttgttcag gagcatgttg cgtaatatcc atatatttgc atcatttctg 162780
aaattcttct tggtattgat ttctagtttt atcccacggt agtctgagaa gatgcttgac 162840
agaattccag tattttaaaa tttgttgaga gttgttttgt ggcctaacat gtggtctgtc 162900
ttggagaatg tccatgtgct gatgagaaga atgtatgttc tccatcagac atgcaagaga 162960
cagacacttt ctcacctgcc tcatgggatc cataaaagag tcaatcagaa gttggcattt 163020
aagaaagacc agaaggaggc tgggtgcagt ggctcatgcc tgtaatccca gcactttggg 163080
aggctgaagt gggtggatca cctgaggtca ggagttcaag accagcctga ccaacaaggt 163140
gaaatcttgt ctctatttta aaaaatacaa aaattagcta ggtgtggtgg cgggcacctg 163200
taatcccagc tactctggag gctgaggcag agaatcactt ggaccagga ggtggaggtt 163260 gcagtgagct gagatcacac cattgcactc cagcctgggc aacagagcaa gaccccatct 163320
caaaaaaaaa aagaaagaaa aaaagaaag aagaccaga aagaggtgaa ggagcaagct 163380
acagagatat caaactgtat caatctggct gggcgtggtg gctcatgcct gaaatcccag 163440
```

```
cactttggga ggctgaagca ggaggatcac ttgagcccag gagttcgaga ccagcctggg   163500
caacagagac cccctctcta caaaatataa aaatttaatt aaaaagatgt attggtcagg   163560
gcagccaagt tatgctgcag taacaaacat ccccaaagcc tccatgactt tgacaacag   163620 atgtatttcc tgctcatgct acatgtccag tgcaggttgg cagtggggaa gaaggggct   163680 ctgttcagtg cagtcacttg agcctagct aatcacctag aacattgcca cttgctattc   163740
cagaaggaaa aaaggaatgc tagaaggtcc cacactgaaa gttcaatgct ctggctccaa   163800
aatgacagct atttccactc actcctcatt ggccagcact tagcatgtgg tcctcagcca   163860
accccaaagg gactcaggaa ggaccatccc accatattgc tggaaatatt tgatggcagc   163920
attaatgggg aacagtgttc caggcagtgg aagtctttga gcccttggaa gaaagacaag   163980
gcgatctcta gagcacatcc ttcccaatat taatgaattt aacaaatgag caagccatcc   164040
tcccccactc tccttcccga attcagactt gtgcatatcc ctcccttaac ttgaactgcc   164100
aaagaagaga tgagaaccag gagaagagat ctgtgacccc atctttgctg atgaactacc   164160
acagaacagc catggcatct ccagtccttg tgcttgtaaa atgtacttt cattttgctc   164220 ctgaacgaaa tccacccacc cccacccca aaccagggaa agctcatctc ctaatccaaa   164280
actgcaccca gccttccacc accttcttcc ctgggaattg ttgattccag agtatggaat   164340
tgaataattg gatgagtttg aagagaaaa agtgtctcta aaatcaggca gcagaagccc   164400 actcccaga gaggatggtg cagatgagag ttcaggaggg gcttggctt ggggttgacg   164460 atctgagcta tgcagggaac ttggacacac ctctcaatca gtcattcaac agacaccact   164520
tattgagcac cgactgtgtg ccagatgttg tcctaggggg ctgggaatac aggaatacag   164580
cagggaacaa aaaggacaaa gcccctccct cttgtcgaat ggacattcca gccaggaaga   164640
cgagagaaca agagaaataa gtaaagtata taggcggtga aatgcaaatg ggaaaaaaga   164700
aacaatgggg accagaaatg aggggtgcaa ttgtaaaggg ccatcagggg aggcctccct   164760
cagaaggtgg catttgagta aaaaacctga aggaggtgag gggaaaccat gtagcaatct   164820
caggaaagag cattccaggc agggagggac agcctgtgca agggccgagg taggactgtg   164880
cttggcgtgg ttgagaaact gcaaggaagc caggtggctg gaaccgaatg agcgagggaa   164940
aaggggagga gataaaagca aggagatggg agggttggag gcccctctg ccattcagta   165000 actgagtaac ttcatttatt tcctgtagct tgaaccacaa agaaccacaa atagagtagc   165060
tgaaaacaac agaaatttat ttattctctc gcagttcagg aggccaggag tccacagacc   165120
atcaaggtca gctgggccac agaccatcaa gatgtcagct gggccatggt gcctcctgag   165180
acttggtctg aaatcccttc ttgcctccct cctagcttct ggtggttgc caacagtgct   165240 tggtggtcct tgtcttgtag acgtatcacc ctgatcccgc cttcatctcc atttcacatg   165300
gccttctccc tctgtgcaag gttgtctctg tgcccaggtt tctcctttc ttattattta   165360 cttatttgtt tgtttgtttc tttattttag acacagggtc ttgctctgtc tcccaggctg   165420
gagtgcagtg gtgcgatcat agctcactac agcctcaaac tcctggcctc aagcaatcct   165480
cctacctcag cctcctgagt agctgggact gcagatgtga gccactgtgc tctgcccaga   165540
tgtcctcttt ttataaggaa accgtcatt taggatgagg ttccacccta atgacctgat   165600
cttaacttga ttccatctgc aaagaccta tttccaattc ataggtacca gggattagga   165660
cttcttcaat gcatcttttt ggagagaccc actgcaaccc acaacagaac tgtgggcatg   165720
taacttgacc tctcggccag gcgtgatggc tcacacctgt aatcccagca ctttgggagg   165780
ccgaggtgag tggatcgcct gaggtcggga gttcgagacc agcctggcca acatggtcaa   165840
```

-continued

```
accccgcctc tactaaaaat agaaaaatta gctgggcatg gtagcaagca cctgtaatcc 165900
caactacttg ggagggtgag gcaggagaat tgcttgaacc caggatgtag aggttgcagt 165960
gagccaagat agtgccattg cactccagcc tgggtgacag agtgagactc catctcaaaa 166020
aaaaaaaaaa aaaaaataga cctctctgtg cctcagcttt ctcacccggg aggatgggga 166080
taattatata cccactcctg gggttcatga gaggattaaa tgagctcaaa cagtccaagc 166140
ctccacgtgt gtctgttgtg gtgctgggta gcatgtcctg tggccagagg ttcccaagct 166200
tgtcgaggac ccaggcaagg gcagattcgg gtcttgttgg cagcacctga gatggacggg 166260
ctgccttggt atggaagggc ctcggctgtt tttccctttc agtcctgtcc ctctccccca 166320
tcctccaccc tgtccctgtc atctgagcct gctcctcgtg atggctcaga gtctccctac 166380
tggcggccgg tgcagagttt cgttccctgg gctatattta gccctgagaa atgggaacga 166440
gaaccctcag ccgccaaagt gatggagaga ggagcacaaa gccagtgctg ccttctgtcc 166500
agcaatgttc cgctgactcg gttctttctt ccagaacctt ccagaagcaa agcattggca 166560
tttctgagct cgttaaaaca aggatgtggg ctggtggctg gcacattcat tgtccccaga 166620
acctgtctgt gtccatgatt aaagctgact ttgttagttt tattttcagt gcttttttt 166680 ttttttaatc catggcaaaa cacacatgac ataaaattta ccatcctaat attttttta 166740 actttgtaac attttttaat tgacaagtaa ttgtacttat tcatgggta catagtgacg 166800 tttcaatgca tataatgcgt agtgctcaga tcagggtaat tagcatatcc atcttctcag 166860
acctttattg tttcttctg ttaggaacat tcaagctcct ccttctagct atttgaaacc 166920
attaatatat tgttgtcatc ctaaccattt ttaaggatac agtttcgtga aattaagtat 166980
aatacattca cattgttgtg caactgtcac caccatccat ctcccaaact tttccatctt 167040
ccaaatgtaa ctctgtcccc actaaacgcg aactccctgt tccccctccc ccagcccttg 167100
gcacccacca tgctactttc tgttttata aatctgacga ctctagggac ctcctataaa 167160
tggaatcata caggattttc cctttatga ctggtttatt tcacatagca taatgccctc 167220
aaggttcacc catgttgcag cacgtatcag cattttcttt cttttaagg taaagttgac 167280 tattaaaaaa aaacttctgc cgggctcagt ggctcacgcc tgtaattaca gcactttggg 167340
aggccaaggc aggcagatca ggaggtgagg agttcaagac cagcctgacc aacatggtga 167400
aaccccatct ctactaaaaa tacaaaaatt agccaggcat ggtggcgggc gcctgtaatc 167460
ccaactactc aggaggctga ggcaagagaa ttgcttgaac ccgggaggca gaggttgcag 167520
tgagctgaga tcatgccact gcactccagc ctcggcaaca gagtaagact ccgtctcaaa 167580
aaaaaacaac ttttaagaa ttgaagtaga ataaacatac agaaaaatcc gcggattata 167640
agtgaagagc ttgattaatt gtcacaaact aaacacatcc atgtaaccag cacacaaatg 167700
aggaaacaga aacttctcag ccccagaagc cccctcata tcctgttcct agtcactacc 167760
tccccgcaag ggtaccccta ccaggacttt gagcatcatt caccagttta gcctgttttg 167820
tattttgcat aaatgaagtc tggcttcttt tgcttgacgt taacttttta agatctcatg 167880
tgacctgtgg cattgttcat tgcatgtatc ctctctctcc tattgataac agtgtggatt 167940
gtttgcaatt tggagctatg atgaatacca ttgctatgaa tgttcttgtg tgtgctttct 168000
gttgtgtaat tattcagaat tactatttcg gaattactat ctaattgtag tgatcttgga 168060
tcagtaacta tccaagaatt actgggtgtt ggcaaaggta catacagtta tacactgcac 168120
aatggcattt tggtcaacaa cagatcaaat atgtaacagt ggtcccataa tggaccgaat 168180
```

```
acataacagt gattatcata cagtattttt actatagctt ttctgttttt agattctttt   168240
tttttttgaga cgaagtctcg ctctgttgcc caggctggag tgcagtggtg tgatctccgc   168300
tcactgcaag ctccgccttc tgggttcacg ccattctcct gcctcagcct cccaggtagc   168360
tacaggcgcc cgtcaccagg cccggctaat ttttttgta tttttagtag agacggggtt    168420
tcaccatgtt agccaggatg gcctcgatct cctgacctca tgatctgccc gcctcggcct   168480
cccaaagtgc tgggattgca ggcgtgagcc accgcaccg gcctgttttt agatattttt    168540
agatacacta tagagttaca attgcctaca gtattccata gaataacatg ctgtatgggt   168600
ttgtagccta ggagcaatag gcgagaccat gcagcctagg tgtgtagtag gctataccat   168660
ctaggtttgt gtaagtacac tccatgatgt ttgcacaaca aaatgaccta gtgacacatt   168720
tttcagaatg tatgcccatt gttaagcatg acttaatttt agcatagaaa ctctcaacca   168780
atttttcaag tagttgtacc atgtgttatg ggttttattg tctcaccca aaattcatat    168840
gttgaagtcc taaccccag tacctcagaa tgtgaccta tttggaaata gattcattgc     168900
acatgtaaag gttttgccat tggcaaaact gccgttattt ttgcaccaac catagcagtt   168960
aagatgagat cattagggtg ggtcctaatc taatacgatg gtgtccatat aaaaagggga   169020
gattttggca cagagacagg cacactcaca ggaagaatgc catgtttaaa caaaggcaga   169080
gctcaggatg atgcctctac aagccaagaa tcagcaaaga ttgccagcaa accgccagaa   169140
gctaggagag aggcataaaa cagattctgt ctcacagctc tcagaaggaa ccagcccttc   169200
tgacaccttg agcttggatt tttggcctct ataactgtaa gacaataaat ctttgttgtt   169260
taagccacct aggttgtggt tccttgttac agcagccaca ggagatgaat acagcatggt   169320
gccctcccat tggcagatta tgagggttcc agttgctcca cagcttcaca gacacctggt   169380
agtaatgacc tcatcttaac ttctttctca ttttagcctt tcttccaggc agcagcagtg   169440
tcatacatgc ttttaaaggt gggcttttaa agccacactt gagagccctg cattctgcag   169500
gtgtcacagg gtgatcaact attcaaaggc taccccctgcc ctgacagctg gaggcaaggc  169560
ttcccagcac agaggttaag cccatggact ctggggccag gtggttagtg caaatcccat   169620
gtccactagt gaataactct gtgatcttgg gctgatgatt ttgtctttct aagcctcagt   169680
ttcctcaata gtaacatggg cattataaca tagaggcatc atgaggatta aatgactaag   169740
tgagctaaca tacataatgt gcttaggaag gtgccagcac accataaata ctctgtaagt   169800
gctggctttt atcattcttt tctctctctc tctctctctc tctctctctc tctctctctc   169860
tctctccctc tctctctctg tctctctttc tctctccacc ccccaacctc ctctccttga   169920
ttttcttccc ctcatcttac ttccttcttg ctatagtgtt ctattttctg tttcagagag   169980
tattctatttt gtggactttt ttcctcttga aaattgagct gaaacttctg agaatttttt   170040
gtgattggca ttaaggctgc agggaatgga gcagggagac acttgaggaa agggctcatg   170100
gaccatctgt ctggcttggt gatttcacca ggccatcaga ctctgtggtc atgcatctcc   170160
tctaaggga gtctatgact gtgttgggag aagagaagga accaggggatt aattaatcca   170220
tttcaatagg ttttgtgttt tgtttggttt acttttttcct tctccttctg gactgtggtc   170280
tgggaagtcc tcttgtgttt cttactccat tcccaggtca attatgttat gtgaggagaa   170340
cataattaag agagagcttt accctttgga tgttttcttc agaaaacgtt cctccatttc   170400
cccctctggg atgccagagc cccagaactc cacaagccaa gaacatttaa gacagagcca   170460
caagagaacc gagcttcccc ttccctcacc tgtcaggttc tatctgagtc ccagtcaact   170520
ctcacctgct ttccctcctc acaccctaca gagcaacgat gcctcaggga acacttggaa   170580
```

```
ctggttgtac ttcatccccc tcatcatcat cggctccttt tttatgctga accttgtgct    170640
gggtgtgctg tcagggtaag tttctgctac tccccacccc atcccactca ctcctctttg    170700
ctaacttctt tccaagtaga ggccattgaa gctttgtttt cattcactag acagagaaaa    170760
ggcttcttcc cttgtttggg ttaccagact gttattagca agccatgcac aggtgcagag    170820
gttgtgtact gctaggggta cccagtgaga gggttcatat gggctttact ttctttacat    170880 ttttttaaa aaccaatagt ttgggtttac ttctccccca ttttccaaat ataaaatcat    170940
agcatatgct ctaacggtgt attttcctga cccatattgt cctctatccc caagattttt    171000
ttggcttaat cataaatggg cttcattttt cttaccataa gaagtctggg cacttgtatg    171060
gtggctctat ggcaccatca gcaaccccag attcttccag ctttccattc tgacatcttt    171120
accagaggct tccaatctcg tggataccte atggtcttaa gatggctgcc tcacgccctc    171180
cggatggcca cttcatgttc caaacaggaa aaggaagaag ggaaacagga agaggtggga    171240
cctatggcag agaagccaac ctgctgcaga aatctttcat tcatggctta ttggtctaac    171300
ttaaaagagg gctgaaataa ttattagcca aaagtatgaa gagaatgaga atgaggtatg    171360
cagccagtgg tggttggcat ggcatggttt tatccttttcg gttttttct tttttattgt    171420 ttttttttga dacggtgtct agctttatta cccagactgg agtgtagggg gcgatcatag    171480
ctcactgtaa cctagaactc ctaggcacaa gcgatcctcc tgcctcagcc tcctgagtag    171540
ctaaggcaac aagtgtatgc caccatgccc agctacattt tttattttttc atagagatgg    171600 ggcccactgt gttgtccagg ctggtctcaa attcctggcc ttaaatgata ctcccatctc    171660
agcctcacaa agtgctggga ttacagacat gagccactgt gcctggcctt tttctttacc    171720
taggcacagt tgtcgggaaa tgtgtgaagc tggcagaagc acccatcact ataatatccc    171780
agtcttttcc cagaagtcct gactcctcct gttgaaaact cctgacctcc agggacttct    171840
gaatccccaa acacacacac acacacaaac acacacacac acacacacac acacacacaa    171900
acacacacac aaacgtttcc taacattttc aaaacagcca tactctggct tttctatgct    171960
tctccaggga gtttgccaaa gaaagggaac gggtggagaa ccggcgggct tttctgaagc    172020
tgaggcggca acaacagatt gaacgtgagc tcaatgggta catggagtgg atctcaaaag    172080
caggtgaggc cctttcatcc tggggcccag ggatggagat cccaggccac ggagtacaaa    172140
gagagtcatg cagtttggag aaggctaagc tgggagggtt atgatgggag gagaaagaga    172200
acctgaattg gtagtcccaa attttatcaa caagaatcca gagtctgata tgaagaagtc    172260
taagatgaag ccaggatctg acatcacgta acttgaattc tgaaatcaga cgctggttta    172320
catcccggcc ctgccacttt ttacccatgc accacacatc cctgtacctc cgtttcctca    172380
gctgttacat ggaggcgatg gtagtgccta agtcatagta ctattggagt atttagtaaa    172440
ataatctcag ctgagtcact tggggagaga agtgcctgat acacggtagg cacatattta    172500
tttgttcagc catttaacaa acatttaggg agcacctgct gtgtgccagg cactgatcta    172560
agcactgagg atatgggagt aaacaataca caccaaatcc ctgccctcag agctctgata    172620
ttctaatgag agagataaag caaacaaata catgtcatgt tgggaactcc caaattcaga    172680
gaaggaagat aaaacagact aggaagataa acagagtag gaagttggcc gggcgcggtg    172740
gctcacgcct gtaatcccag cactttggga ggctaaggcg gcagatttc ctgaggtcag    172800 gcattcgaga ccagcctggc caacatggtg aaaccctgtc tctactaaaa atacaaaaat    172860
tagccaggca tggtggcgca cgcctgtaat cccagctact cgggaggctg aggcaggaga    172920
```

```
attgcttgaa cccaggaggc agaggttaca gtgagctgag gtcgcaccac tgcactccag  172980
cctgggcaac agagtgagac tctgtgtcag agaaaaaaaa aagagtagga agttagaggc  173040
agggtggtca gggaaggctt ctctaaggaa gtaccctctg agcagagaga cctgaaggac  173100
gtgaagaagg aagctgtggg gatgtcaagg gaagggcat tccaggcaga dacagcaagt  173160
gcaaaggccc tgagctagga acgtatttga dacacagcaa ggaagccagt gcagctgaaa  173220
cagagtgaga ggtggggaca gctggaggag aggaagacag gaaggtgatg gagatcagat  173280
caagcagggg cttataggct gtggtgtgga cattggtttt tattttgcgc gaggtgggga  173340
gaatgttggc tattgctact gttgcggagg tggggcttga agtcacaaac cacccagcag  173400
catgtttttt ggtcggttga gctgtcacca tcagtcagca gagaatgggg gtggccgggc  173460
agacccttct tcctggtcca agggagaact catcctccaa atgcaggagc ttaactctgt  173520
gctcttcctc ttcagaagag gtgatcctcg ccgaggatga aactgacggg gagcagaggc  173580
atccctttga tggtaactgc tctaaaccca cctcaggggt gggtcccagg ggagaaggga  173640
gaagctgtgg tggggagtcg ggggagagca ggtgactggt tctaaggatc ttgcagaggg  173700
tagacgttcc tcttggagga attttaggac ttccatgcag agtttcccta ttctggcctc  173760 cactttttg ttttaaccat ggacctggtt ttttctgctt tgtgccttgg tttttctcat  173820
ctgcaaaatg ggtatgatat aaacaatacc ctagctcacg agattgtttc tcagaatgat  173880
attcgttatg gcaaatagaa cacctgggat agtgcctggc atgggtcag cacgtttctg  173940 tttgctaaat aagtaataat tccaccaata atccagttta ctgtgaacgg ctgctgtctc  174000
ccatgttaga aacttaacga gacagaacca tgacttcttt tcttttcttt ttttttaat  174060 tgagacagag tctcgctctg tcacccaggc tggagtgcag tcacacgatc tcacctcact  174120
gcaacctctg gctcccaggt tcaagcaatt ctctgcctca gcctcatgag aagctgagat  174180
tacaagcatg agccaccatg cctggctaat ttttatattg ttgatagaga tggggtttcg  174240
ccatgttggc cgggctggtc ttgaactcct tgcctcaaat gatctgcaca ccttggcctc  174300
ccaaaatgct gggagtgtag atgtcaattc atggtcccct ggaaacctga atatgaaagg  174360
agggaccatt aaaaggtgt ccaaaagccc aacctcccca gcatagctgg gagtcagggg  174420
acagactgta agagtcactg tgtatccaac ctgaggcttc atgaaagtaa agtttcctag  174480
aatttagaga tagggttgga tgcggtctgt ctgtggctca catctgtaat cccaacactt  174540
tgggaggcca agacaggagg aacacttgag cctgggagtt caagaccagc ctgggcaaca  174600
taatgaggtt ccgtctctac aaaaaataaa cttagccaga tgtggggca cacgcaccta  174660 tggtcccagc tactcaggag gctgaggtgg gaggatcact tgagcccaag aggtcgaggt  174720
tgcagtgggc accactccac tccagcctgg gtgacagagt gagaccctgt ttcaaaagaa  174780
aaaaaaagaa tttagagata ggccagaata atatgtctgc aatataataa taacagcaat  174840
aagaaaaata atagtactcc ctgaaaaatg caacttcttg cttgagattt atcttctcat  174900
actttagaaa actggttaga caggggctgg gcgtggtggc tcatgcctgt aatcccagca  174960
ctttgggagg ccaaggcggg tggatcactt gaggccagga gttcaagacc ggcctggcca  175020
tcatggcgaa accccatctc tactaaaaat acaaaaatta gctaggtgtc atggcacacg  175080
cctgtaatcc cagctactca ggaggctaaa ctacgagaat tgcttgaacc tgggagacgg  175140
aagttgcggt gagccgagat cacaccactg cactccagcc taggcgacag agcaagactc  175200
tgtctcaaaa aaagaaaga aagctggtta gacagggtga tgacttttga ttaaaaatct  175260
gagagatttg agggaaataa aagaactggc actgcgtccc agaaggttat aaaatgaatt  175320
```

```
ttattatctt agttggggag gggagattac ctaactcccc taaatgagtt aggtaatcta   175380
actcatttag ggtacctaaa tcttttfatt ggaagtctac acctgaactt gtctgctgtg   175440
gagcccctgg ggtgtatagc ttgaatatgg gggcagaatc ccaaaattgc agcctgccta   175500
gcgagtatgc tacaggtcaa ggggtggact gttttcataa gaaagtgagg tttcttagaa   175560
tttaaaaata gaggctgagt ggggcggctc acgcctgtaa tcctagcact tttggaggcc   175620
aaggcaggca aatcacttga ggtcaagagt ttgaccagcc tggccaacat ggcaaaaccc   175680
catctctact aataatacaa aaattagcca ggcgtggtgg tgcatgcctg tagtctcagc   175740
tactcaggag gctgagggag gagaatcgct tgaactcagg aggcagaggt tgcagtaagc   175800
caagatcaca ccactctctg ggtgacagag caagattctg tctcaaaata aataaacaaa   175860
taaataaata aaccagaagg aaaatagtgg ctgagggccc agacctggag tcggactgaa   175920
cccgacttga ttcttgtctt tacccctttt agcaaagtga tagtgccacc ttgaacctca   175980
gtttacacat ctgaaaaatg gtatactat tagttcccgt gagaacagtt gccgtgagag   176040
ttaaatccaa ggacacactg tgtccatatg gtctgtgttg caaaagggt aacgtctttt   176100 tctcttgcca tgtttccatt gttggagctc tgcggagaac caccataaag aaaagcaaga   176160
cagatttgct caaccccgaa gaggctgagg atcagctggc tgatatagcc tctgtgggtg   176220 agtccettcc tctgccacct atcagttgtt catcacctat cgcccaagag acatggtggg   176280
gtgggggcag agggcttgca aaccgtgctg cctggatttg ggtctcagct ccacccttc   176340 ccacctgtgc gtgtgtcctg ggcagattac atcattatgg gaataacatc cgtgcctagc   176400
ttctcattat tttgtgggaa ttcaactaaa tgatccccat gaagcatggc aaaccagcac   176460
ctggcaggga cgaagctccc agtcaagttg gtgaatgttt gtgactcatt cgggaagtat   176520
tcatggggga cctgcttata ttaggtgctt ggttgcaaac aagacaaggc agtcacgagg   176580
ctgagctggg aggatcactt gagcctggga agtggaggct gcaataagcc attattgtgt   176640
tactgcactc cagcctgggc acagaaaaaa aaaaaaagac acaaactgag ccaggcacag   176700
tggctcacgc ctgtaatccc aacactttgg gaagctgaga tgagcggatc acctgatgtc   176760
gggagttcga gaccagcctg gccaacatgg tgaaaccctg gctctactaa aaatacgaaa   176820
aaaattagcc tgtagttcca gctactctgg aggctgaggc gggagcatca cttgaacctg   176880
ggaagcagag gttgcagtga gctgagatct catcactgcc ctccagcctg gcaacagag   176940 caagatcctg tctcaaaaaa aaaaaaaaa aaaagacaca aaccaaatcc ctacctacat   177000
ggagctcaca gtccagtgca ggaaatagaa attaaacaga gaattacaca aataaacctg   177060
taatggtaat ggcacttcag ggagaggctc tgggcttagc ttgctctaga aggatgggga   177120
gcagtcaggg aaggctacct ggaggaagtg acgttaagc tgggaactga aggatgggta   177180
ggagatcact gtggtggtga tagcagaagg aacagtgtga gaggcagggc tcagaccttt   177240
gccaccacaa gggccagagt tcgagggagg agggaacatt tattctttcc cttctcactc   177300
ctctgtccta ttgattcatt ggctgtgatg atgttgattt tgaccttcta aagtgagaat   177360
gtattgttat tgttgttgtt gttctttaat gggttttgt ttttaatgga aggaagcagca   177420 tccaggcaga ggaaataaga ctggaataag attgaggga gaaggaattt aggctgcttg   177480
ggaaactgtg tggccgcagt ttagaggaag aaaggatggc aagagaaaga ggaagggagg   177540
aagagaagga gggagagaag tgaaggaagg agggaagtta gtacatccat gtgtttctga   177600
tccatagttt ctgatccact atttcgtatt cccctttat cgctcgcccc tagtttataa   177660
```

```
ccttattgct gagtttaggc ataatttcca ttgcgatcac atatctcgta gggtggatac   177720
actatggttt gtttagccat agctctatta tagggtgttt gagttgtttc caataatttc   177780
tcttacgaag aacactgctg tgcacattta cgtacaatga ctcccccac cctttgggcg    177840 tatttccttg gggataatta taggatcaaa gatattaaca gcttttcaac tcattattca   177900
aagagccatt ctgagtttca aaaacatgga acccatttat aaacctgcca agtatgcata   177960
tgttcatgga ttccccaccc aggccatcga atattaccaa tttaatttcc tttcccagtt   178020
aagtgggttt gtaatgaaac cttaaagctt gttttcattt gcattttaa tttccagcca    178080 aaacacgctt ttctttgtaa tggagaactc attctgcttc cactcgtgtg tgcatctgtt   178140
taatttcctg taagcaaatg tcaagaattg gagcgctcag taggtgtctt gagtatttga   178200
tcaattatgt ctgtctcacg tgttacgtta cctccattgt ttaaaatctg ttttatgacg   178260
aggtacagtg gttcacgcct gtaatcccac tgctttggga ggccagtgca ggaggatctc   178320
ctaagatcag ccgttcaaga ccagcctggg caacataaca aggctccatc tctgaaaaac   178380
aaaatgttga aaaacttagc caggcattat ggcacacacc tatagtccca tctatttagg   178440
aagctaaggc aggaggattt cttgaaccca ggaattcaag gttgcagtga gctatgattg   178500
tgccactgca ctgcaacgtg ggcaacagag tgagaacctg tctcttaaaa aaataaaata   178560
acatacattc ttaaaaatct actttgctgg ccgggcgcgg tggctcacgc ctgtaatccc   178620
agcactttgg gaggctgagg cgggtagatc gcttaaggtc aggagtagga gaccagcctg   178680
gccaacatgg tgaaaccgtg tctgtactaa aaattcaaca attagctggg tgtggtggcg   178740
tgagcctgta atcccagcta ctcaggaggc tgaggcacaa aatcacttga acccgggagg   178800
cggaggctgc agtgagctga gatggcgcca ttgccctcca gcctgggcat caagagtgaa   178860
actccatcaa aaaaataaaa aatctgcata tacatatata tgtatatata tttttaattt   178920
ttttaatttt tttttttttt tctgagatgg agtcttgctc tagcacccag gctggagagc   178980
aatggtgcca tctcggctca ctgcagcctc cgcctctgtt aacaaggcag gtgacattgc   179040
agctttctaa acagacccaa aacccaggcc agtggcttgt tctttcatag ccacgtttgc   179100
tacaggcaaa tccaccaaaa cccacctcat cagcctgatt actcaaaaag acaaagaaag   179160
gagcccccaa tctagccagt ggttttctag accaccccaa aagagatctc tggaattcca   179220
ggattctggc aaggaatcac atttagcttt atttatttat gtaaagaatg caacaataca   179280
ggctgggtgt ggtggctcac gcctgtaatc ccaacatttt gggaagctga ggtgggagga   179340
tcgtttgagg tcaggagttt cagaccagcc taggcaacat agtgagaccc tgtctctatc   179400
aaatattagc tgggcattgt ggcacacgcc agtagtccca gctactcgtg aggctgaggt   179460
ggatcacctg agcccaggag gtcaaggctg cggtgagcca cagcatgccc ctgcactcca   179520
gcctgcgtga cagagacttc atctcaaaaa aaaaacaaa aaaagtaat aatacagtaa     179580 tgcatatttc aaagtaaggt gggagctatg tggtatttgc gttcacgttc acattatacc   179640
acagtatgca cagtcctttt tttttttttt ttgagacagt gtcttgctct gatgttcagg   179700
ctggagtgca gtggtgcagg catagctcac tgcagcctca aacccctgga ctcaagtgat   179760
cctcccacct cagcctccca gtagctggg actataggtg tacactgcta cactcagcta   179820
agttttttat atttttttact agagatggga tctcaatatg ttgcctaggc tggtctcaaa   179880
ctcctggcct caaacaatcc tcctacctcc acctcccaaa gcagtgggat tacaggcgtg   179940
agccaccaca cctggcccac atgcagtctt atataattgg tgattctact gcgctgttga   180000
atcagttgat aaacgcacta taaagcaggt tcattcctaa ttgatgaact tactgctgaa   180060
```

```
ataaggaact tgaatcattt acatgaaaag ttgagccatg ttgctgaaag gatatcaatt    180120 ttttttctt ttttttcttt tttttgaga tggagtctta ctctgtcgcc caggtgggag    180180
tgcagtggtg cgatctcggc tcactgcaac ctccaccttc caggttcaag cgattctccc    180240
acctcagcct ccaagtagct gggactacag gtgcacacca ccacgccctg ccaatttttg    180300
tactgttagt agagatgggg tttcaccatg ttggccaggc tggtctcaaa ctcctgacct    180360
caagtgatct gcccacctca gcctccgaaa gtgctgggat tacaggtgtt agccaccgcg    180420
cctgacagga tatcaaattt catttagact gcaggaatac gttcaagaga tctatttgt    180480 acagcctggc gactgtatta ataacaatgt attatatact tgaaaattgc tcagagagta    180540
ggttttaagc attctcaccg tgagaaaagt gataagcata tgtaataatg catatgttaa    180600
ctagctcaac tgagccactc catagtgtat acatatggtc aaaatatcat gttatgcact    180660
ataaatagat acagcctgta tctgtcaatt taaaataaat gaataataac tttaaaaaga    180720
aaaataacag tatggctggg cacggtggct cacacctgta atcccagcac tttgggatgc    180780
caagacaggc ttgaggccag gagtttgaga ccagcctggc caacatggcg aaactttgtc    180840
tctaataaat atacaaaaat cggctgggca tggaggcggg cgcctgtaat cccaactact    180900
tgggaggcag aggcatcact taacctggga gatggaggtt gcagtgagcc aagatctgca    180960
ctccagcctg ggtgatagag tgagccttta tttattctg taaagaatgc aataatacag    181020
gcctggtgcg gtggctcatg cctataatcc caatgttttg gaaggccaag gtgagaggat    181080
catttgaggc tacaggcgca tgccacagtg cccagctaat acttgataga gacacggtct    181140
cgctatgttg cccaggctgg tctcaaaacc ctggcttcaa atgagcctcc caccttggcc    181200
tcccagagtg ttgtgattac aggtgtgaga cactgtacct ggcctgtatt aaaaaaaaa    181260 aaagaagaa gaagaagaag aggaggaaag aagaagaagg aagaaggaag aagaagaaga    181320
ggaggaggag gaggaatggg aaggggaagg ggaagaagaa gaggaggaag gggaagggga    181380
agaagaagag gaggaggaag gggaaggga agaggaagaa gaagaggaag aagaagacga    181440
agaagaagca caatgataaa taagtaaaat gtggagcata tgaaaacaaa acaaaaaaaa    181500
gttgatccat tatgaatgga agctgccatt gtaactctgc ttttttagga aaaccagacc    181560
ccatttagat gatttattt gttttttaaag gcaggttctt gctctgtcac tcaggctgga    181620
gtgcagtgat atgatcatag ctctctgcag cctggagctc ctgggctcag gcgatcctcc    181680
cagcttagcc tcccaagtag ctgggactac aggcaccacc acacccagct aatttgttgt    181740
tgttgttgat gttgttgttg agatggggtc tggctatgtt gcccaggctg gtctcaaact    181800
cctggcctca agtgatcctc ctgccctggc ttcccaaagt tctgggatta caggcatgat    181860 ttttattaa tttatttgca gctgacaaat ggtaattgtg tatgtttatg gagtgcagtg    181920
tgatgtttta atctatgtat acatcataga atgattcagt catgctaatt aacacatcca    181980
tcgcctcacc acctcaccgt tttttgtgtg tggggaaggc attaaaaatc tcttagcaat    182040
tttgaaatat gcaacacatt actatttatt aataatgcaa tataaataca caataatgta    182100
ttaatgcatc actaaatgcg atgcaatgca atgcaatgca atagatcact aaaacttact    182160
cctccagtct aactgcaact tatacccttt gatcaacatc ttctccttct caatccctcc    182220
tcctcccctg cagcctccag gaaccacctt cctgctcttt ctatgagatc aatttttttt    182280
agttttaagc tcccacatgt gagatcatac tgtaattgtc tttctgtgcc agcttatttt    182340
actcagtata atgtcctcca gttctgtccc tgttgtcaca cattacagaa tttctttctt    182400
```

```
ttagggctgt atagtattct atttgtatac ataccacatt ttctttatcc attcatccat   182460
tgtgggacac ttagtttgct tccatatttt ggctattgtg aataatgctg aagtgaacgt   182520
gggagtgcag atgttctgaa aagacttaaa tgtcagacct gaaatggtaa agatgctcca   182580
agaaaacata aggagaaagc tccatggcat tggtctcggg aatgattttt tggacaggac   182640
ctcaaaagca caggcaacag aagccaaaat ggacaaatgg gatcgtatca aactaaaaaa   182700
tttgtgcaca gcaaaggaag cgttcagcag aggaaagaga caacctaagg aatgtgagaa   182760
aacgtttgca aacaatacat ctgataagga gctaatatcc aaaatatata aggaactcaa   182820
acaactcaac agcaagaaaa caacccaatt aaaaatgggc aaagacagct actcgggagg   182880
ctaagatgtg acgatccctt gagcccggga ggaggaggtt gcagtgagct gacattgcat   182940
cactgcactc caccctgggc gacagaagga gaccgagacc ctgtctcaaa ataaaaaata   183000
aaaatgtgca aaggatctga acatacatat cccaaaagaa aagacataca agtggccaac   183060
aggtatatga ataaaatgct gaacatcact catcatcagg gaaatgcaaa tcaaaaccac   183120
cattagctat caccctcacac ctgttagagt agctattatc ttttgtttg tttgtttgtt   183180 ttttgttttt tgtttgttt ttgagaggga gtctcactct gtcacccaag ctggagcgca   183240
gtgttgtgat ctcagctcac tgcaacctct gcctcctggg ttcaagggat tctcctgcct   183300
cagcctcccg agtaactgaa attacaggca cacgccacca tgcccagcta acttttgtat   183360 ttagttttcac tatgttggtc aggctggtct tgaattcctg acctcaaatg atctgccctc   183420
cttggcctcc caaagtgctg ggattacagg tgtgagacac tgtgcccagc ctagagtagc   183480
tattatcaaa aagacaaatg aggtttgttg aagttctaac ccctggtacc tgcaaatgtg   183540
gccttacatg aaaataggt ctttgcaggt ggtaatcaag ttaagatgag atcaaactta   183600
attagggtgg gtcctaaatc caatgactgc tgtctttata agaggagaag caggctgacc   183660
aacatggtga aaccccatct ctactaaaaa tacaaaaatt agctgggtgc agtagtgcac   183720
acctgtagtc ccagctactc aggaggctga ggcaggagaa ttgcttaaac ccaggaggtg   183780
gaggttgcag tgagcagacg tcatgccact gcactccagc ctgggtgaca gagtgagact   183840
ccatcttaca agaaaaaaaa aaagacaaa tcataacaag tgctggcaag gatgtgggga   183900
aacggggatc catttacatc attttaataa cacaggctct atatgggtgg tattgagttc   183960
ccagagttgc cattacaaaa tgtcacaaac ccagtggctt aaaacaacag aaatttcttc   184020
tctcacagtt ctagaggcca gaagtccaaa ctgaaatcaa ggtgtcagca gagccaccac   184080
gttccctcag aaggttttag gggagaatct gttccatggt attttcttag tttctggtgc   184140
tgccagcgat acttggtgtt cctcagttca tagatgcata attccagtct ctgcctctgt   184200
tgtcatatgg tcttctttct gtgtttctgt atgcgatttc ttttttttt tttttttct   184260 gagacaagtc tcactccatc acccaggctg gagtgcaatg gcacgatcac agctcactac   184320
aaccccaacc tcacaggctc atgccgtcct cccacctcag cctcccgagt agctgggatt   184380
acaggcgtgt gccaccatgc ccggctaatt tttgtatttt tagtagatac ggggtttcac   184440
catgttggcc aggctggtct cgaactcctg accttacgat ctgcccatct cggcctccca   184500
aagtgttggg attacgggca cgagccaccg cacctggcc taattactt tattttttg   184560 taaattttt tttgtaaatt tcatgtagcc tgagcataca gtgtttataa tatatacagg   184620
agtgtacaat aatatcctag gccttcacat tcactcacca ctcaactcac tccctcacca   184680
agagcaactt ccagtcctgc aagctccatt catgccaagt accctatgca gctgaaccac   184740
cttttctctt ttatactgtg tttttactgt acctttctta tgtttagata tgttcagaca   184800
```

```
cacaaatact atgatgttac agttgcctac agtattaagt acagtaacat gctgggcagg    184860
tttgtagccg aggagctaca aaccacgtag cctgggtgtg gagtaggcta caacatctag    184920
gtttatgtaa gttcacttta agatgctcac acaaggacaa aattgcctaa caatgcattt    184980
ctcagaacac gtctccctca ttaagccaca catggctgta ttacaattta catataattt    185040
taagcgtata taaattgcca gaaatcacca gatgaatcct tggcggtgac atacccctte    185100 ccccaccata gaacattgca gactggcccg gacgcccagt atctcatgcc tgtaatgcca    185160
gcactttggg aggctgcagc gggcagatca cttgaggtta ggagttcgag accagcctga    185220
ccaacatggc aaaacaccat ctttactaaa aatacaaaaa ttattcggac gtggtagtgg    185280
gcacctgtag ttccagctac ttgggaggct gaggcaggag agtcacttga acttgggagg    185340
cagaggttgc aatgagccaa gatcgtgcca ctgcactcca gcccgggtga cagaatgaga    185400
ctctatctca aaaaaaaag aaaaaaaaa aaaaggaaa agaacatttc agactggtac    185460
cagttacacc ggctcttgat cccttgaatg tggctgaccc tgaactagga tgtacttcat    185520
aataacacgt ccggctggga atacttagta caaagaaag agtataaaat atcttttgaa    185580
tccaccttga tattgattcc atgttgaaat ggtaatattt tggatgtatt gggttgaata    185640
aaacatctca tgaaagtgat ttttaaaaat ctagaaattg tctgcaatta taattccaga    185700
ccacagagaa aaacgagaga caggaatgta tagaaaaagg gaacgtggga caaagtgagt    185760
atgaaattca actaacagaa gtgacagtgc ctagcatggg gtccagcact tagtaggtgt    185820
tcaattaata ttcatttccc tctcccttac cagtgaaggg tatgcctgtc gtggggaatg    185880
tgtcttcagg ctgagtgatc aggaaggact ttctcaatgg ctggcacgtg aacctagtca    185940
tgatttcagc tcttgaggtt gtactagaag atttatatcc aataatcgta aggtaccact    186000
tagcatcacg ctaagatgta ttaattcatt tatgcctttg gatggccctt tgaggtagga    186060
agtgtggttg tctccagttt accaaggtgg cttgcccaag gtcatctgct ggttggtgat    186120
taagccaggt tttcagtgtg gctccagcag gagtgggggc tggggacctt ctacctgctg    186180
tggtttctct ctctctctct ctctctctct ctctctctct ctcgatctgt ggaacatccc    186240
ccctgtcccc caaggtccca agggtcttat ttcttttggc caagcccttt ggagacctgc    186300
agatctggac acatctttga gagtttcagg aactagggcc agaaatgctg ggcagggtca    186360
tgaggagctg ccactgggt tgagaaggtg atggacatga ggggaagggt ctttgcagaa    186420
aggagaggcg tccctgtaag caggtcacag ccactgggcc tggccaactg cagccgagtg    186480
gaatgtgccc ctgccccatg accatatgcc ccaggtgtgc aatgtggcgg cccagagcac    186540
acactctgaa ccatcttgac acatcttcac tggttactag accccctca gcctgtttcc    186600 ttggctgtaa aatggggatg acgctggtcc tacttccta gggctctgag caggagtaag    186660
tagcttgtcg tataaaacat gttccctgca gtgcctggtg cctgctaaat gttccataaa    186720
cgtcagctgt tattttcatt caggggaagc tgaaatccat attttcatgg aaaatctccc    186780 agttttaaa tgtggaccaa taatttcagc tttcacaaac ccagtatgag tcggtatggc    186840
ccctagggtg ccaactcaaa atctctgttg agaattttgc tgataggaag tggcctcctt    186900
ggaggtgttt gctgtgtcct gtgtctggca agtggggtgg ttttgataaa cgtgctggat    186960
ggatgtatgg gtgaatggat aaatggagga atgaatggag aaacaaatga gcaaatgaat    187020
aatgaatgga tggatgaatg gatgagcgaa tggatggatg aatggatgag caaatgaatg    187080
atgtacacac aaaggaatgg ataaatgatg aatgtgctaa tgaatttaag aatgatgaaa    187140
```

```
gaatgaatga ataaatgaac aaatggatgg atgaaagaat gaatgaatgt actaatgaat 187200
gaatcaatca atgaagaacc atttaaaaat gaatgcaact gagggtttat aagaaaaggt 187260
atcttaagcc tgggcatggt aattcatgct ggaatcccaa tgcttaggga cgctgaggcg 187320
ggaggatcgc ttgaacccag gagttcaaga ccagcctggg caacacaggg agacctcatt 187380
gctaccaaaa acaaaattgt tttaattaag cgggcatggt ggtacgtgcc tgtagtcata 187440
gctacttggg aggctgaggt gggaggatcg cttgaaccca ggagttcaag gctgcagtga 187500
gctaggatca agccactgca ttccagcctg ggcaacaaag caagatcctg tctcaaaaaa 187560
aaaaaaaaaa gatgtatttt agaaggtaaa ttcaatctgt ccaaaactga gctctgacct 187620 tccccctaaac ctgtgcccat tcagtggatg agagctccat cccttaaggg gttcaccaat 187680
tcatccattc ctttgtatgt acatcattca ttcaccttgg ctcatccctc tctcttacat 187740
ccacaccgtt ccatcagcaa atgttgaatc tgtcttaaat gattcatccc aaatcctccc 187800
cgcttaacta ccacccaact ccagccccca tccatcatca tcatcacttg cctggatggg 187860
ttcagtcacc tccagcctgg tctcccagct cccgtcctca cctctcactg tctactctcc 187920
cactcggcag ccagagggtg cctgtgaaca cccaaatcag gttccatccc tcctctactc 187980
agaaccctcc acggctcccc cctcactcag ggtaaaagcc aaagtcctcc ttgtggtcca 188040
ccaggccatg catgatctgc ctgtcacctc cctgccttca ccaccttcct cttttcccct 188100
caaccactcc actccagcca cactgacttc cttgtgctct tccccaaaaa tgtcgggcag 188160
acacattcat gcttcaggac cttaaatttg ctgtttcctc tacctaagat actaaagtga 188220
caagtcaaca cactcacctt gaccatgcaa tttaatgttg cagcctaccc tgtggactct 188280
ccaagggctc ccagtccctc tgtgatgctt tactttttct cttaaaaaaa aaattgttat 188340
ttaaaagaac ttgtctcgct gtgttgccca ggctggtgtc aaactcctgg cctcatacag 188400
tcctcccatt ccagcttccc aaagtactgg gattagaggc atgtgccact gcacccatcc 188460
caactttttt tttcccatag cacttttcat tttccatccc actgtaatt tacttattac 188520 gtccactgtc tgtctcctcc ccttagaggg tcagaccccg gaagtccagg ctctgttgcc 188580
taatgtatcc tgagccctg gaacagagcc tggcacaaaa taggtactca ataaatgcat 188640
aagagcaaaa ctatatgtag gcagaggaca cacccagctt attcctcagt gatcacttct 188700
aaagttaaat gtccatggaa aacagtctca tccacatctc tttctggagg ccttccaagc 188760
gtgctccatg cagctctgtt gcctgcccct gcatcaggga atggaggctc tgctttatcc 188820
tgccctgtgg tgtgactccc agaggcatca gatgtggctg ggagtgggag acatggaaaa 188880
ttggctcctg caacagagaa ctatcagcct tccatcaat tggttacttc taattctgtt 188940 attttttcagg ggcactgtct tctcataagc tccatctatg caaaactaag cccatgggtc 189000
atgatggttc cctcaggcca gaggcttgct ggagagacta atggatcccc tggctaaaat 189060
ctgtgcttgg gctgcacatt ggttaatttc ttctgaagga acagcctgag cctgacattc 189120
tccatctttt ccctggcagg ttctcccttc gcccgagcca gcattaaaag tgccaagctg 189180
gagaactcga cctttttttca caaaaaggag aggaggatgc gtttctacat ccgccgcatg 189240
gtcaaaactc aggccttcta ctggactgta ctcagtttgg tagctctcaa cacgctgtgt 189300
gttgctattg ttcactacaa ccagcccgag tggctctccg acttcctttg tgagtatcac 189360
ccagccccac ccctgccaac tccctgatcc ctccctcaca ccctttttcc acttctcttt 189420
ctctggtagt atgtgtatct tctttggtcc tcattgaatc tgccctttcc tttagccatt 189480
tctataactg tcactgggc caatgttact gttgctatga caatggaacc catctccctt 189540
```

```
agacctgaga gctggaagct ggaattcaga ccaacaaatg ctcctgtgat tcctttctaa   189600
gagagaggga cagagggggtg ctggtgaagg ggatgttgga agagagacag agaaagacgg   189660
agctcataag atagacagat agaaacagaa acatacatgt attaataatt tttatgtaca   189720
tctctggaaa tgttcataac ttatggttaa gagaggatgc cttagaaata aggagtggct   189780
tatatgttgc cctcattttc tctacttatt tctgactcta cttctctctt ctttcaaacc   189840
ttctgcttct ttcctgttag gttggtgcaa aattaattgc gttttttgcc ttttttttttt   189900
ttttttttaa ccacagttac ttttgcacca acctaatact tcctcccctg ccctttttgg   189960
cttccttatt cattcataga acatcccctc cagtatctgc gagagcgttt tgctccctca   190020
aggtacaagg cccactaagg ctttgccctc tgggcctatt cccagattct atgtgagtta   190080
gcatgagata gtatcaaaat tgagggccaa gtgagggtga ggaaaagcag caaaagatgg   190140
ggagatgtct gagcaggatt taaaaagtaa agagctcgag gaatcaacaa gagcagcgac   190200
tgggggccagg catggtggct cacacctgta atcccagcat tttgggaggc tgaggtgggt   190260
ggatcacttg aggccaggag ttcaagacca gcctggccaa tatggtgaaa ccctgtcttt   190320
acaaaaaata caaaaattag ccagatgtga tggtgcacac ctgtaatccc agctactcag   190380
gaggctgagg cactagaact gcttgaatcc aggaggcaga ggttgcagtg agccaagatc   190440
atgccactgc actccagcct gagcaacaga gagagtgtct gtctcaaaaa ataaagtaaa   190500
ataaaataaa ataaaataaa gagtagtgat tgggcagtga ggggggcagg tggatgccct   190560
ggctttggct cacaggcccc aagtaaggac ttctcaaaac gtcttttgcc tactggctgt   190620
ctaatttatt cactgacctt ctgacctggt tcagaattga cttaggacag caagaagaga   190680
cagtctagtc tttgacctag aaaggcccgt gagcctagtc caggccattg tcttcttata   190740
accctccttg ttcccagtca cgttggctga ccccccagga caccccctcag gaaccagttc   190800
tccttcccag ggccctgacc tagttttcaaa cttagtaatt gttttttagtc cctctggagt   190860
ctcttataaa tgaggactct acttcgtgtt ttaacttcct ctaatactct atttttaatc   190920
tcctatattc tctctactaa tcatcttgta cagtctgtcc tggttcagga acaagggact   190980
gagacttcct gcctgggtcc tcagtgtcta taaaggtcct ttactcattc ccactttccc   191040
tttgagaaaa ctgagacaca gagaggttaa gtagattgcc caggatcaca cattagcttg   191100
gcatgatggc gggcgcctgt aatcccagct acttgggagg ctgaggcagg agaatcgctt   191160
gaacctggga ggcagaggtt gcagtgagcc cagatcatgc cactgcactc tagcctgggc   191220
aacagagcta gacgccatct caaaaaaaaa aaaaaaaaaa aaaagataca cattaatttc   191280
agagatgtca aaatataaac aaaaatgtat atcttggcat cagtgaagtg tagttgtttc   191340
tctggatctc agactccaca tctatgtggt agaaaccgga tttgatggtc ctgaaagttc   191400
ttccagatgc aacaatgcta aggataagta attctttcaa gtcttgtgca tcacctgcta   191460
tcatgttttcc atggtaactg aggaacaaga tctcagaaac tcttcagtcc tcccagagtt   191520
acttctggtg ggtctaggaa tgtgtcagat gttacaaaca gacttcctct gctgatattt   191580
tggtcctagg aaccctagag ttcccctcag acactaagat ctccttagcg tcctataaat   191640
aaggagaaat tttggtgata aatactgtga aggactttga cggtcagttc aaaacacctc   191700
ttaaaagcat gacatagcaa acacccttgg caaatatctt agttcatttg tactgctata   191760
acaaattacc cgagactggg taatttgata agaacagaaa tttatttcct cacagttctg   191820
gaggctggga agcccaagat caaggcattg gcaggtttcc ctgtctggcg aaagctactc   191880
```

```
tctgcttcca agattgcacc ttgaacactg tatcctctgg aagggaggaa cactgggtcc  191940
ttacatggca gaaggtggag gagcaagagg gacaaacttc ctctgtcaac ctcttttata  192000
agggcaccta atcccattca tgagagctct accgtaatga cttaatcacc tcctgaaggc  192060
cccacctctt aatactgtta cattggcaat taagtttcaa cgtgaatttt ggaggggaca  192120
caaacattta aaccatcaca accaccaaac acaattagct ttgtggcctt aattagctat  192180
atgaaattca tggaagttag tttcagtcct ctgtctcttt cctttctgta tgctttctgc  192240
tcctcagaaa ccctcctcat ctctcctttc tatccattaa gtacccacgc ccttcctaac  192300
tcctcatctt cctaccctac caagaaagcc ctctcagaaa aggatctgat gtcagccatt  192360
tatttgctgg agcaaatgca tatccatgtt ttaccctcc ctgaggcatt tgcaatttta  192420
tgcttgctca tcaaagaaca aaaggctttg tcttactcaa gacttttag gtcactcaca  192480 acacaggatt tctagggac ataagacaag ttttctgagt taggagaaaa gccatacctt  192540
aggtgggttg cctgtgtcgc tccaactaag tacttaactt caggattaca aataggatat  192600
cattatgatt tctatttcct tttatccttt ggagctcagt cacgtagaag tagattaaat  192660
ataattgtta gatcacagca ccctggcatt atggggccgt tatggtccat tgttattatg  192720
tgaattattc agttaattag tttatttttt aaatgtgata acacccagg aacccaccag  192780 tcaacacaaa agtccttggc aataatctat atccgatcct tctcatcgaa ccagggcaaa  192840
aactacaaga tggagaccca ctgatatttt tctcattcct tttaaaatcg gcctaaggtt  192900
ggttagcttg ttggttggag ggtagggcat aattgttgct tttttttttt ttttttttt  192960 ttagacaagg tcttgctctg tcacccaggc tacagtaggg tggcccaatc ttggctcact  193020
gcaacctcca cctcccaggt ttaagtgatt ctcatgcctc agcctcccaa gtagctgggt  193080
ttacaggcat gtgtcaccac actggctaat ttttgtattt ttagtagagg cggggtttgc  193140
catgttagcc aggctggtct caaactcctg acctcagttg atctgaccgc ctaggcctcc  193200
caaagtgctg ggattacaga cgtgagccac catgcccagc cagctcttcc tttttaacag  193260
aggggaaact gaggcccatg ggaaggacac cttggacagg gcgtggccac agtgggtcat  193320
gtatataatc ccagcacttt gggaggctgt gctgggagga tcacttgagg ccaggagttc  193380
aagaccagcc agggcaacat agtgagaccc ccatctccac ataaaaattt taaaaagaaa  193440
aaagataagt cagaagttgg gtgtggtgac acatgcctgt agttctagca tgttggaggc  193500
caaatcaggg aaactgtttg aggccaggag tttgaaacca gcctaacagc atagcaagac  193560
ctcatctcta caaaaaataa aaagtttaaa aatgataata aaaggaaagt cagagccacc  193620
tggaacccct accctcagca agcctaacct cctctctgtt tcctccttct cccttctaga  193680
ctatgcagaa ttcattttct taggactctt tatgtccgaa atgtttataa aaatgtacgg  193740
gcttgggacg cggccttact tccactcttc cttcaactgc tttgactgtg gggtaagtgc  193800
tcttgtttct aagagttcat ttctccagct cttgcctgga atgacagata cctggacaca  193860
ttaaagggag aaaggtaaag tcacccctga atatgagaga ctcagatgga tgcagaagga  193920
atgagaaaac aatcccaaac actggcaagg atacagtgta cccagaaccc tcaaccaccg  193980
ccagtgggag gaaaacgtat agacccccctt tggaaagcta gtgggggac ataagacaag  194040 ttttccaagt tgggagaaaa gccatgcctt aggtgggttg cctgtgtcgc tccaactaag  194100
tacccaactt caggattaca aacaggacat caatatgatt tctatttctt cttttccttt  194160
gtagctcagt catgtggagg tagatgaagt ataattgtta gattcaaaca ccctggcatt  194220
atggagccat tatggtcctt tgttattttg tgaattactc agttaattaa tttattttt  194280
```

```
aaatgtgatt aacacccagt aacccactag tccacacaaa acctaagtcc tggagaataa   194340
tctacgtcca atccttctca tcgaaccagg gcaaaaacta caagatggag atatgaccca   194400
gcattccatt gctaggaatt catcctagaa aatctcaccc agatacctag gagacacagg   194460
ccagaatgtc cctgcagctg gaagtgaaat taaggttgtt cgcaaataag tggagaatgc   194520
ctggcccagg gcagccctaa tcatttacca tagtcctgtt ggtctcagaa aggcttaata   194580
atttatttat ttttttttat tttttgtttt tatttttttgt ttttgagatg gagtctcgtt   194640
ctgtcaccca ggctggagtg cggtggcgcc atctcggctc actgcaagct ccgcctccca   194700
ggttcactcc attctcctgc ctcagcctcc cgagtagctg gactacagg tgcccgccat    194760
catacctggc taattttttg tattttttagt agagatgggg tttcaccgtg ttagccagga   194820
tggtcttgat ctcctgacct cgtgatccac ccgccttggc ctcccaaagt gctgggatta   194880
caggcgtgag ccaccacacc cagccagctt aataatttat aataactgaa tgttgtactg   194940
ttttctgcca ttatagaaaa ttatgttgtt ggagaaaaca aaatacatac aaacaagcaa   195000
accttcccta cataaatgac ccaagtagtt aaagaataaa accaatttct ttccattaaa   195060
aagaaaagaa agccgggtgt gatgcctcat gcctatagcc tcagctattc aggaggctga   195120
ggcagcagaa ttgcttgagc ccaggagttg aaaaccagcc caggcaacat agcaagaccc   195180
tgtctctaca aaaattaata ataattagcc aggtgtggtg gtgcacacct gtagcccag    195240
ctactcagaa ggctaaggtg ggaggattgc ttgagcccag cagtttgagg ctgcagtgag   195300
ctatgatcac accactgccc tccagcctgg acaagagagt gagacccat ctctaagaaa    195360
taaaagtagg ccaggcacag tggctcacac ctataatccc agcactttga gaggcggagg   195420
caggtggatc acctgaagtc aggagttcaa gaccagcctg gccaacatgg cgaaaccccg   195480
tctatactaa aaaaatacaa aaattagcca ggcgtcgtgg cacatgcctg taatcccagc   195540
tacttgggag gctgaggaag gagaatcact tgaactgggg aggcagaggt tgcagtaagc   195600
tgagattgca ccactgcact ccagcctggg tgacagaatg agactccgtc tcaaaaaaa    195660
aaaaagaaaa atttttaaaat gtcctgagca accttgtttg taatagttcc aagtctcaat   195720
atccgtgtat cccttttgctg tagaacagat aaatattttg tggcatatct atataatgaa   195780
atactctgtg acaatcaaag tccaccaaca gcagccacat gcccaacaac aggaatgaat   195840
ctcacccatg taacatggca cagaaggagg caggagctag caacgtaagt ccatacagtt   195900
catgcaaagt tcaagtggac aaaattaaac tctctctctc tctctacata tatatatata   195960
tatatatata tttttttttt ttttttttttt ttttttttttt tttttgaga cagagtctca   196020
ctctattgcc caggctggag tgcagtggcg caatcttggc tcactacaac ctccacctcc   196080
cgggttcaag ccattctccc gcctcagcct cccaagtagc tgggattaga ggcatgcacc   196140
accaccccg gctaattttg tattttttgt agagaccggg attcagcaat tgcccaggc    196200
tggtctcgaa atcctgatct caggtgatcc acctgccctg gcctcccaaa gtgctggat    196260
tacaagcgtg agccaccacg ccccgcctta aactgtattt tttaaggatg atacttgaat   196320
acgttaaaaa ggcgaggacc ttgaaaacac aacgctcggt aaaagaaacc aaacacaaaa   196380
ggtcaagtat tgcataattc catttgtatg aaatgtccag agcaggcaaa tccatagaga   196440
cagaaagtag attagtggtt gctagggtct gggtgaggga gagtggggag taactgctca   196500
tggggacagg gcctccttttg ggggtgatga aaatgttttg gaacttgata gaggtgatag   196560
ttgcagaata ttgtgcatgt acctaaaggc actgaattgt gtaattcaaa gtgtgaattt   196620
```

```
tatgttatgt gaatttcacc tcagttttt ttaaggtaag aaaatggtta ttacaaaatt  196680
caggatggta gttatatcac agtgtctctg gaaacttcca gggtatccac atgtcccttt  196740 ttatttatt ttatttttta ttttatttga gatagggtct tgctctgttg cccaggctag  196800
agtgcagtgg caggatcatg accctctcct gtctcaaatt cctaggctca agctatcctc  196860
cctcctcagc ctcctaagta gctgggacta taggcacatg ccaccatgct tgactaattt  196920 ttttttttt tgtaaagtca gggtttccct gtgttaccca ggctggtctt gaactcctgg  196980
gctcaagtga tctgcccacc tcggcctccc aaagttccag aattacaggc atgagccact  197040
gccctagcct tctcctaatt gttgacatag gtagtagttg catgacattc actttgtaat  197100
tatgtgtttc aggaattctc aggcctgtgg gagctcttaa taaataaaaa agaggccagg  197160
tgtggtggct cacgcctgta atcccagcac tttgggaggc cgaggcaggc ggatcacgag  197220
gtcaggagtt cgagactagc ctggccaaca cagtgaaacc ccgtctctac taaaaataca  197280
aaaaattagc cgggcgtggt ggcgggtgcc tgtaatccca gttacttggg aggctgaggc  197340
aggagaatcg cttgaacctg ggaggcggag gttgcagtaa gctgagatcg cgccactgca  197400
caccagcctg ggtgataaga gcaagactcc atctcaaaat aaatgaataa ataaaaataa  197460
ataaataaat aagaggccgg gtgcagtggc tcaatgcttt ggaaagtgga ggccaacagt  197520
tggagagacc aaagcaggag gatggcttca gcccagaagt ttgaggccag cctgggcaat  197580
actagcgaga cactatctct ataaaaatgt tttaaaatta gccagatgtg gtggggcaca  197640
cctgtaatcc cagctactca agaggctgag gtgggaggat cacttaagcc caggaggaca  197700
gtgctgcagt gagctatgat tgcgccactg cactccagcc tgggtgacac agtgagaccc  197760
ggtctctata gataaatgaa tggatgaatg aggggggtcaa ggatcctcac ccggcttcca  197820
tttggaggga ggagttttggt tgagttcttg caaggttggt acctaggaaa tgcttgccag  197880
ttctggagcc cagacactgt ccctggacat gagaccaggt tctctgccct aggttatcat  197940
tgggagcatc ttcgaggtca tctgggctgt cataaaacct ggcacatcct ttggaatcag  198000
cgtgttacga gccctcaggt tattgcgtat tttcaaagtc acaaagtaag tctttggggt  198060
tcctggacat ttgtacaggg ggtggggatg gggacatgg tggggccgcc tccagaaagt  198120
tgggaaagtg agcctcgtgt ttcgagggct gactccgggg ccctgcctcc cccgcctggc  198180
ctgagtcctc gcctggcctc tgtcggcagg tactgggcat ctctcagaaa cctggtcgtc  198240
tctctcctca actccatgaa gtccatcatc agcctgttgt ttctccttt cctgttcatt  198300 gtcgtcttcg ccctttgggg aatgcaactc ttcggcggcc agtaagtcct tcacaggaat  198360
tccaactcct ggttccctgg ggtcaggctc agggaacaca cagtcccctc caccgtgcag  198420
gctgccttcc tcgtagccca gacacccatt gcggtcaccc aaatgggcag ggccctgggt  198480
accactcagg gtttcctggg gacagagatg atggagacgt tcgtttcctt ggagatgaga  198540
tactgagcca caccctcaga gcaccccggg tggggccaac gtgaaatgtc tgtgtcctcc  198600
ctgcaggttt aatttcgatg aagggactcc tcccaccaac ttcgatactt ttccagcagc  198660
aataatgacg gtgtttcagg tacagcctcc acctggcccc acgggccaac acctctcagt  198720
gtcacagatg aaagtgcctg ctccacatcc aaggggcttc cctgaactcc tccttctcta  198780
cctggccttt tcacaccact ttgaaacaca gattttatgg ttatcattat tcaattatgg  198840
tgaggccaac agatcaggag atgaatgtca ttggaaagat agtttgtggc tgggcacggt  198900
ggctcacacc cataatccca gcactttggc caggtacggg ggctcacacc tgtaatccca  198960
acgctttggg aagcccaggt gggcggatca cttgagatca ggaattcgag accagcctgg  199020
```

```
ccaacatggt gaaaccccat ctctactaaa aatacaaaaa ttagccgggc gtggtagcac    199080
atgcctgtaa tcccagctac tcgggagatg aggcacaaga attgcttgaa cctgggaggc    199140
agaggttgca gtgagccaag atcgcgccac tgcactccag cctgggcaac agagtgagac    199200
tccatctcaa aaagaaaaa  gaaaaaaaaa accactttgg gaggtcaaga tgggaggact    199260
acttgaggcc aggagtttga dacaagtctg gcaacatag  tgagactccg tctctgcaaa    199320
aaaataataa taataattag ctgggcatgg tgatacatac ctcctagcta ctagggcagc    199380
tgaagtggaa ggattgcttg agcccaggag gttgaggctg cagtaagcta caatcacacc    199440
actatactcc agcctgggcg agagagcaaa gccctgtctc aaaaacgaaa agaaagtttg    199500
ttatactcac agatcctcag agaaggagca caccatgcag gaccaagcag agaagcaaca    199560
gggtcaagca ggaagagaag gaaaatgtgg gcaagaggct tgattgtggt ttccatggga    199620
cggaatgggt gaggcagagt aaacagctcg agactggcta gtttggatca tttcagtggg    199680
ctctggggca gaggagctgt tcctacttgt ctaggacctg gccttgggt  gattaggca     199740
ggtggatagt gctgggaaga taaaggaggt ggttgggata tgggctggtt gggatattgt    199800
ttggtttgct tttaaaaagc ctgctcaggg ctaaattgtt tactacctct agggactggc    199860
tagtgctgga ccgggcagtc cctccagagt cagcaagacc ccagatgcat cagaataaag    199920
aaaataaaat gcgtggccag gccaatgagg tggttcatgc ctgtaatctc agcactttgg    199980
gagaccaagg cggaggatt  gcttgagccc aggagttcaa ggctgccgtg agctccagcc    200040
tgcaccacag agcaaggccc tgtctcttaa aaaaaggca  gagaaaaaaa atggctaata    200100
cacccatcaa atctgaagat accttggtct catattccag ggtgatcaac ccaaagcaac    200160
ttctgcaccc atgtgggcgc attccctgag gcttgggact ggcccagccg ggaccttcag    200220
agcatctttg gtggattctt tctctttgag ggactgagag tgtatagaaa atgtgacttc    200280
actctctcct tctcctgggg aggtagtttc taaatgagac cccaagacag ggagttgaag    200340
aggaaacctt ccatgaaggg aagttctgag cccccacata agcgattttt ttttttttt     200400
tgagatggag tctcgctctg ttgcccaggc tggagtgcga cggcacgttc ttggctcact    200460
acaacctctg cctcctgggt tcaagcgatt ctccgcctc  agcctcccga gtagctgaga    200520
ctacaggtgc atactaccat gcctggctaa ttttgtatt  tttagtagag acagggtttc    200580
actatgttgg ccaggctggt ctcgaactcc tggcctcgtg atctgcctgc ctcggcctcc    200640
caaagtgctg ggattacagg catgagccac cacacctggc ccataagcga ttattaatag    200700
cactgatcgc tagtcatgta tctttagctc agaggttctc acccaaggac aagtctgtcc    200760
tccaaggaca tgtagcaatg tctgcaagca ttgttggttg tcacagctag ggagagggtg    200820
ctactggcat ctggtgggtg gagactagga atgctgctca atatcctaca atgcacagga    200880
cagccccaaa tagaataatc tggccccaaa tatcagcagt gctgaggctt agaaaccctg    200940
ttttagcaga ttcatgtttt tggagttctt taacatttac tttatcctca tggggatatg    201000
gatagaagga aggaagttgg atctttttta aaggagcatg taggtgctgt ttgaatatcc    201060
ccttggttct ttcagtatgc atcagcacaa cttgcgtctg tcaacaccta atcctttgcc    201120
ttggtctttc tctggtcccc tgctctgccc ccaaggaact gcagtccagc agtactgtga    201180
attttttgtg ccacaccta aaaggagcag ccgttggtgg ataaataccc cagctccctc     201240
accctcaggt gggatgaccc ctagagctcc ccagcaagac caagccccgg ttacctacag    201300
tggaaactcg cttgatcaca tactgtttac gttccaccct cttttccctt ttctcacttc    201360
```

```
tcctctcccc tactggtgct tcctgagatc acctcccaga caaaccactt gcacccgaac 201420
ccttgttcca gggtctgcct caggcagggg gaccccaaac gtgtccttgt gctacatttg 201480
tgctatccac gtagtagctt gtttaatcat caccatgacc acatgaggaa cacaggtaaa 201540
tattaaaatc ctgtcttagt ctgctcaggc agccataaca aaataccaca cactgggtgg 201600
cttatacagg aaacatttat tctctcatag ttctggaggc cgggaagtcc aagatcaaag 201660
tgttagcagg gttagttagt tcctggtgag ggccctcttc ctagcttgca gatagccacc 201720
ttcttgctgt gtcctcatat gtcaaagaga gagagagaga gttgtgatgt tcttcctgt 201780 tctttttttt tttttttttt tgagacaaaa atctcaaaaa aaaatctatt ttttttttag 201840
gcaaatcaca tttttttgtc acccagcctg gagtgcagtg gcacaatcat agctcactgc 201900
agcctcaaac tcctaggttc aaacgatcct cccacctcag cccttgagt agctgggact 201960 acagatgggc accagctaat ttttttaaat tttttgtaaa gatgggtct tgctatattg 202020 cccaggctaa tcttgaactc ctgggctcaa gtgatcctcc caccttggcc tcccaaagtg 202080
ctgggattac aggcatgagc catggcatgc ggtctcttcc tgttcttata agggcactaa 202140
taccatcatg aagtccccca tgacctcatc taaccctagt tacctcttaa aggccccatc 202200
tccaaatacc atcccatcat aggttagggc ttcaactcat gaatttggag gcgggcacaa 202260
tttagtccat aacaaatccc cttaatcaca tcaagtaaga cagagttaca ggagggtctg 202320
tgactcctcc agggtcccat tttcctagaa gccaggctaa gagccccacg acgcaggaac 202380
ggccctttct actcgcaaac aaagagaaaa gccaaggaga agccaacacg gagtctggct 202440
ctgcaaaccg ggcaggattg ttaaagacct cctgggctcg gggatggggt gggcggattc 202500
cggctccaca gctgcatctc caaggggccc gtggctgaga gggggttgg ctgtgtgttt 202560 cttcctcccc tttcagatcc tgacgggcga agactggaac gaggtcatgt acgacgggat 202620
caagtctcag gggggcgtgc agggcggcat ggtgttctcc atctatttca ttgtactgac 202680
gctctttggg aactgtatcc ttcatggaga gagagaaggg gacaggcctg gacctctggc 202740
agaggagagg ttgcaggggc tcagggagg gtactgagag acccagatac ccagggccca 202800
agtggtgtcc caccagtggt tgcttttcct gactcagaca tttgcagaca ccctcctgaa 202860
tgtgttcttg gccatcgctg tggacaatct ggccaacgcc caggagctca ccaaggtgga 202920
ggcggtggga gaatgtttct ctggcaaagt taccacctgc ccatggcaga tcaggacggg 202980
ggtgggggtg ggggtggggg tggggtgggg ggcatgggaa cagggttaga acttttgccg 203040
gggatgcacc atgcaaagag aaggcgcctc tcccccact cccagaaaca gactgtccct 203100
catcaagcaa attctacagc caagagggtg ggaagggga aggcagtgag gtcgctgcag 203160 gaaacgatg gcaaactcaa ccaaaaggcc gtttacaggg agtaagcagg gtttccaagg 203220
aatggtgtag ccccaggct agtggatggg agagggagtg ctgttatggg gacccagtca 203280
gagctggggc caaggaaaaa gggctgccac cagccctggg accttagaga acccagaacc 203340
atggcaaggc acagatggag tggccaataa atgtccccac cttctctctt cctctggctt 203400
cccgctggag cctcccctta gccaaacgca gcatgttaag agctagcctc cgtccagcct 203460
aagcctctcc ccaaggaccc tattaagtta agattacatg taacaggtac agggtcttcc 203520
tctcagccct ggggtctccc tcagcattgc agccccacct ccagtgcctc gaggtattca 203580
ggacatgttt gtgaaattga accaaaccaa gcagacgttg ccaacgctcc atctgccggc 203640
cctggcagga gggagagaga gtttcccggc cccagctccc agtggaggga agcggaagtc 203700
tctgccatcc caagcacacg gccacaagcc tggccactgt ggagctggct ggcatggctg 203760
```

```
agccgagggc tgatccagcc atgagctcat ccaagttcca agagtccatc cttaggggct    203820
ggtgcaggag ggtagcagaa ggggagggag aaaggccagt tcgtttatct cctgggaggt    203880
gtggacattc ctctccagat ccacattctt tctttcattg atcctacaag catttcttgg    203940
tcatttaata cgtgttttta atcctattca gtcctcatgg aaaccttagg agccaagttc    204000
tctgagcccc attttacaga tttcatcatt cagtaagcac ttaatgagca cctactgtgt    204060
gaccaaggcc ctggtctagg acttagggat taagcagtga acaaaaaaag gcaaaaatcc    204120
ctgcctccgt ggagcaggga ttcaagaggg gagacagaca agaaacaaga taaatttgta    204180
aacatacgta gcttgtcagt tggtgataaa cacaacagag aaaaattcag tagggaaagt    204240
cagggagagt tggaattta dgatgagatgt gtgtcgcaca gagaggttga gagacttgcc    204300
caaggccaca cagcagtaag ttgtggagct gggatttgaa cccaggccgt ctgggtctgc    204360
agcttgtgct cttaactgct gtgtaccagt tgcttgaatt tgggcatgtt ttatgctcac    204420
ttgggaacct gtgggaaatg cagattccag ggcccagcac tggttctata gattatttgg    204480
ggagcctgag gatctgcatt ttaggtgttt ctgaggcaga tggtccagag acctagctct    204540
gaaaaatgct gggaatggtg ccaggagggg tggggtggc cctatgagag cagggtggcc    204600
agccagatcc catctccatg ttgtctctga cagtgtcctg atctgaccat ttccaaggtg    204660
gtaaggttgc tccccgttcc agtgattcgg agcacagcgg gagagctgcc tgcaatggca    204720
tgacttttct tatgggcggg ttcatttctg gccatttctt tctcgttgcc ttttctttgc    204780
tttttctttg ttggcttttc tgttttacga atgaggccct gcatgaaggc tgaagaagga    204840
tttaaagtcc aaaaacgtct ttttctgtat gtatttttaa aacctcttcc cccattctcc    204900
tcctctctga acctaaccac cagtgagcag cagcaccctg ggcagttggc tgtagcccaa    204960
gtgccctgct ctcctctccc caccgccttc ctgtcatggg ggctgggaat ataaattcct    205020
ctcctcattc tccttctggg ggctgttgac agtgcatggc aggggccatc ggatgccagg    205080
ctcttctgtg tgtgagggta gttggtgttt tttgaaagtt ggttcagaga gttcacatgg    205140
ctcagaaagc ctagtgagag gaaaatcttt gcactgcttt ccagctcatt aagacaggat    205200
gcaggggcca ggcatggtgg cacatgcctg gaatcccagc actttgggag gccgaaatgg    205260
gaggatcatt tgaggccaga agttcaagac cagcctgggc aacatagtga gaccctgtct    205320
ctacaaaaaa aaaaaaaaaa ttaaatgtat acaggcatag tggcatgcac ctgtagtccc    205380
agttgcttgg gaggctgagg tgggaggatt gcttgagccc aggagttcaa ggttacagtg    205440
agctatgatt gtgccactgc actccaggct gggcaaccaa gggagactct gtctctgaaa    205500
acaaacaaaa gaaaaaaaaa taggctgcag gaaagtcttc attgtaggaa gagaagggac    205560 attttttattt tttgttatct ggctgtgtgt taaaataggc ttcataatga gttagatgtc    205620
aaacttatac acagagggga tagcaataca cttaaccaat agcaggtacc cattccaatt    205680
ggggagcctt ggttctgatt ggtcgaaata tttcaaatgt tgcccctggt cagcaacagg    205740
gtcagaagtg agtccccaag gcctagttca tgttttgtga acaaagattc cacgtgcctt    205800
ttaggacgag caagaggaag aagaagcagc gaaccagaaa cttgccctac agaaagccaa    205860
ggaggtggca gaagtgagtc ctctgtccgc ggccaacatg tctatagctg tgtaagtgcc    205920
cctaatccct gggatgctac cctggctcct gaacgtccac actatcccag gcacagattt    205980
gggaagcagt gggggtggtc cttgacagaa ctgagcttta ggaagagaca cttcttgtcc    206040
ttccacccac tttcactcaa taaatatttg gttagcagct gttatgtacc cagcactgtt    206100
```

```
ctaacttctg gggatacagc attaacaagg aggaaaaaaa aaatcccacc tgtgtgtagc    206160
cattctagca agggaaggag tcaataaatt agataaataa gtaaattata tattgtgtta    206220
gaaggcgatg gaactacaga gaaagtaggg gagggaaata gcaaatgctg ggagtgaaga    206280
gagttgtgat tttaaacgaa gttgtcaggg aaggcatcac ctagaatagg ggtccccagt    206340
cccggggctg tggactggta ccaggccgag gcctattagg aacggggctg cacagcagga    206400
ggtgaacagt gagcaagcaa gcattaccgc ctgagctcca cctgccgtca gatcagcagg    206460
cagcattaga ttctcatagg aacacaaaca ctattgtgaa cggtgcatct gagggatcta    206520
ggttgcgtgc tccttttaag aatcgaatgc ctgatgatct caggtgaaac agtttcatcc    206580
caaaaccacc ccccacacct aggtctgtgg aaaaactgtc ttccacaaaa ctggcccctg    206640
gtgccaaaaa ggttggggac tgctcaccta gaaggttaca tggcctgaag gaggtgaggg    206700
aggagccact ggggggcctg gggaagggca tcccaggcag agggaacagc ataggcaatg    206760
gccctgaggc aggaacatgc ctgatgtgaa ggaggcctgt gtgactagaa tcgaatagta    206820
agtgtgagga ggtgaaggca aggaggtgac aagcagatta cacagggcct tctgggtcag    206880
gggggaggac ttgggctttt gcccctagcc aggtgggagc catggagggt tcttgagcag    206940
aggaggctgg gacctgactc agatgctcac agactcctag cattcagtgg ggagtagagg    207000
gtggagagca ggagtgggag gctgagatgt gggttggttc gcctgggtca tccatccaag    207060
ctacagtgcc tagcaatgct ctaagtcctg tgaccatgcc actgcaggaa agagcaacag    207120
aagaatcaaa agccagccaa gtccgtgtgg gagcagcgga ccagtgagat gcgaaagcag    207180
aacttgctgg ccagccggga ggccctgtat aacgaaatgg acccgacga gcgctggaag    207240 gctgcctaca cgcggcacct gcggccagac atgaagacgc acttggaccg gccgctggtg    207300
gtggacccgc aggagaaccg caacaacaac accaacaaga gccgggcggc cgagcccacc    207360
gtggaccagc gcctcggcca gcagcgcgcc gaggacttcc tcaggaaaca ggcccgctac    207420
cacgatcggg cccgggaccc cagcggctcg gcgggcctgg acgcacggag gccctgggcg    207480
ggaagccagg aggccgagct gagccgggag ggaccctacg gccgcgagtc ggaccaccac    207540
gcccgggagg gcagcctgga gcaacccggg ttctgggagg gcgaggccga gcgaggcaag    207600
gccggggacc cccaccggag gcacgtgcac cggcagggggg gcagcaggga gagccgcagc    207660
gggtccccgc gcacgggcgc ggacggggag catcgacgtc atcgcgcgca ccgcaggccc    207720
ggggaggagg gtccggagga caaggcggag cggagggcgc ggcaccgcga gggcagccgg    207780
ccggcccggg gcggcgaggg cgagggcgag ggccccgacg ggggcgagcg caggagaagg    207840
caccggcatg gcgctccagc cacgtacgag ggggacgcgc ggagggagga caaggagcgg    207900
aggcatcgga ggaggaagta agtggaggtg acctcgaatc cgcagaatga cggtaacatt    207960
aataatgaca acagccaaag tagcacgtgc tgtgtatttg tttataaaaa tatattataa    208020
aatgctgtat ttggccaggc gcagtggctc acgcctgtaa tcccagcact ttgggaggcc    208080
gaggcggatg gatcacgagg tcaggagttc aagaccagcc tggccaagat ggtgaaaccc    208140
cacctctaat aaaaatacaa aaattagccg ggcacggtgg caggcgcctg tagccccagc    208200
tactcaggag gctgaggcag gagaatcgcc tgaaaacagg gggcggaggt tgcaatgagc    208260
cgagatcaca ccaccgcact ccagcctggg cgacagagtg agactctgtc tcaaaaaaaa    208320 aaaaaagtg ctgtatttgg ccaggagcag tggctcatgc ctgtaatccc agcactttga    208380
gaggccgagg cgggcggatc acttgaggtc aggagttgga gacaggctg ccaacatag    208440 tgaaacccg tctctactaa aaatacaaaa attagtggtg gtgcccacct gtattcccac    208500
```

```
tactcaggag gctgaggcgg gagaatcagt tgaacctggg aggtggaggt aggttgcagt 208560
gagctgagat cgtgccatca cactccagcc tgggcaacag agcaagactc tgtctcaaaa 208620
aaaaaaaaat gctgtatgtt tttgttttt tgacacaggg tctcgcctgt tgcccaggct 208680
ggagtgcagt ggcagtcata gctcagtgca gcctctacct cccgggctca agccatccgc 208740
ctcagcctca caagtagctg ggaccacaga catgtgccac atgcctggct aattttgta 208800 gagacagtgt tttgtagaga cagggtttca ctgtgtttcc caggctggtc tcaaactcct 208860
gaactcaagc attccgcctg ccttagcctc cctaaagtgc tgggactaca gggttgagcc 208920
accacactca gcctaattt tttacccttta gtagaaatga ggcctggctc tgttgcccag 208980
gctggtcccc aactcctggc ctcaagcaat catcccacct cagtctccca aagtgttcgg 209040
attagaggct tcacagatgg ggaaactgag agattgagtg agctcctcaa ggtcattcct 209100
ctaaccagtg tccttgaacc caggctctct ggcaccagag gccttgagca tttcagggaa 209160
actattaaga gaagcccac tgtcgtccag aattatatag tcttctgtgt tcttgctgtg 209220
tgacttttgc aaagtgactt catatctctg ggcctcacac aatggaaata gtgggatcta 209280
attgggtcat tgccaggatt gaatgaggta atgtatgcaa agggcctgga agagcagctg 209340
acacataata agtgctcggt aaatttagag cattttggc cattttcagc caactctatt 209400
tacctaatgc tattctttgg aagtttgaaa agccactctg ttgggaggcc aaggtgggag 209460
gatcacttga taccaggagt tggagaccag tctgggcaat agaggcagac cccatctcta 209520
taaaatataa aaaattaaac agatgtggtg gcatgcacct gcagtcccaa ctacttggga 209580
ggctgaggca ggagggtcac tggagcccag gatgtctagg ctatgatgag ctatgattgc 209640
accactgcac ttcagcctgg gcgacagagc aaggctttgt ctcaaaaaat aaaataaaaa 209700
ataaagaaaa agaaaaggca ctttgggccg ttagaattga agggagagca gagtttcaaa 209760
gctttggatg cagcgggatg tggtggctca tgcctgtagt cccagcactt tgggaggcca 209820
aggtgggagg atccacttga gccccggagt tcaagaccag cctgcgcaac atagtgagac 209880
ctcacctttt aaaataaat aaaaatgtta gaaagctttt gaggcatctt ccaggccagc 209940
aacttatcca ttcagaacca gcatcctctt tttcataacg acattttgta atactttcta 210000
gcagatgcta tagtgattct gcatataggg actcaacaac ttacccatta aaatagacat 210060
cgtagacatt gtcctattac aaattaacct gctcttagtc ctcttttata ttaccatcag 210120
ggcataatat tgatttttt aatgatgggt ttaagtgatc ctgttgtatg acatatgagg 210180
taggccagca cttctcaaaa tctaatgtgt atgtgaatcc ccagggatct tgttaaaaca 210240
caaattgtaa ttccgtaggg ctaaggactc agtggagcct gagattctgc atttgcaacg 210300
agctcccaga tgaggctgat actactggtc cagggaccac attttgagta atgagactct 210360
ggaggacata gtgaagtaat tctgatatgt acaccataca caaaatcacc atgaagtgac 210420
aggcacaaat gatggctaac tctgggttgt gtggacaatt caaccacat gagggggagtt 210480 gccagcagtg tcaagatgtt ccacaatgtt gaacacctct tggcaaagtt ccatatacaa 210540
aagagtctag tctttcttcc atttatttaa tagttgcatt gcaggaaaat gcaatgtata 210600
ttaaaaacat acaaaaaata tgttgtgttc ttatgtaaaa gagttaggtt taaactaaaa 210660
gcacaggatc aggtgcagtg gctcccacct gtaatcccag tgcattggga ggctgaggaa 210720
ggagaatcgc ttgaggccag gagttcgaga ccaacctggg cgacataagg agacctcgat 210780
ctctacaaaa gaagtttttt aattagccag gtgtggcggc aggtgcctgt agttctagct 210840
```

```
acttggaagg ctgaagcagg aggattgctt gagcccagga gttcaagatt acagtgagct    210900
atgattatgc cattgcattc caacctgggc aacagaacaa gtccttgtct caaaaaaaaa    210960 aaaagaaag aaagaaagaa aaacccaaa caaacaagca aactaaaagc acaggtaatt       211020
acaagcaaga tttttcacct ctttgaggga cattagaaag tcatgaagag gaaaagataa    211080
gtctttccca tatgggactg tcatgtacat ggtagggtat ttagtataac tgcctaccat    211140
tctctaagtg cctgcagtgc ccctcaatca ttatgttatt aggtttccac gtagttctac    211200 aacagtttc tgaaaaccat tgttctaggt cattctttcg cttcaatctt ctcctatggg     211260
tttatgcatt cattcagtta gtatttacta agtgcctact atattctaag ctcatgctgt    211320
gagttcagtc acacaactgc aagtgaagtg gtctgagaca ttctgagaaa tacgaccaag    211380
aaactgctcc cagggtctca gggcaggttt ccagaggagc aatctgagaa gggagtagag    211440
tgtttcagtc taacaacagc atgtgcaaag gccctggggt ggaccagaag gaggccagtt    211500
tgcaggacat gactagtgac gagaaagtga caaagaaatt gaaggtgcat tgatgagact    211560
ctggggctgt cagtcactca ggggaatgag agatcaaaac gggagtttag gtggaataaa    211620
gtgtttacca cagcactctc tgtatagtaa agaccaatga agagccaggt acaggccagt    211680
gtgatggttc acgcctgtaa tcccagcact ttggggaggca gagacaggtg gatcacctga   211740
ggtcaggggt tcagaaccag cttggccaac atggcaaaac cctgtctcta ctaaaaatac    211800
aaaaaattag ccaggcgtgg tggtggacgc ctataatccc agctactcag gaggctgagg    211860
cacaagaatt gtcctgcgag gcagaggtta cagtgagctg agatcacacc actgcactcc    211920
agcctgggca acagaacaag actctgtctc aaaaaaaaaa aaaaaaaaaa aaagccaggt    211980
acagtggtat gcacctgtaa tcccagctac tcaggaggct gaggcaaagg attgcttgag    212040
cccaggagtt cgagaccagc ctgagcattt agagaatggg aggccagtat actaaatacc    212100
ctaccatgta caagacagtc tcatatggaa aagaattatc cttttcctctt catgactttc    212160 tagtgctcct cacacaggtg aaaaatcttg cttataatta tctgtgcctt tagttttgttg   212220 gtttatttag ggttttgttt gttttttttt tttttttgag gcagggtctt gctctgttgc    212280
ccaggttgga ttgcagtagc attgctcatt ttagagatga gcaagacctc atgtctaaaa    212340 aaaaagaaa gaccaatgat tattaattac tcttgctatt attactaata ttactgttat     212400
tatcagcctt attaacagat ctactgttat tgaaggaggc agagtgacag ggacaaaatg    212460
tctctcccta acaatatgcc aggaagagtt tttgaaagac aacagtaaac attggaaact    212520
acaagagcag caaagcctgg ttgtgaaagg caaggacttt ggggcaggca gtcacattcc    212580
tgccctatca cttccaggct gtgtgacttt cagaatttca ctcctctctg ggcctccatt    212640
tcctcatcta taaatgaag ataagaatag tagctacctc cttctctggg tataagattt      212700
aactgagccg ggcgcggtgg ctcatgcctg taatcccagc actttgggag gccgaggtga    212760
gcggatcaca aggtcatgag ttcaagacca cctggctaa tatggtgaaa ccccatctct      212820
actaaaaata ccaaaaaaaa aaaaaattag ccgggcgtag gtggtgcacg cctgtagtcc    212880
cagctactcg ggaggctgag gtaggagaat ggtgtaaaac ccgggaggcg gagcttgcag    212940
tgagccgaga tcgcaccact gcactccagc cgggagaca gagcgagact ccatctcaaa     213000 aaaaaaaaa aaaaaaaaa agatttaact gagttagtac gtgtaaaatg ctttgagtgg       213060
ttcctggctt ataccaagag ctcaataaat gttagcaatt ttttgtagca ttttggggtc    213120
tcactatgtt gcccaggctg gtgtcaaact cctggcctca agaaattctc ccactttggc    213180
ctcccaaagt gctggattta cagacatgag acaccatgcc tggccatgtt agctattatt    213240
```

```
aatatgaata ttattaagta ctcaatgaat gctatttta gcagtaatag taagcactca 213300
ggaagtgtca gctaatactg ttagtaatac tctcatcaat aaacataaaa agcaataagg 213360
acccagcttg cccaaatccc acagatggtt cctgctccct ctcttcttca gaggaagaaa 213420
ctatctcccc actttcaccc ccatagcctc agctggccag accccattc tgaaccaggg 213480 gagtactgct aattccatta ttaatagaca catcaaacaa tctggccggg agagacatta 213540
ttcatttggc tgataaagag gttctaaggc tctttggaaa taaaagttca tgaagattca 213600
tgcactttaa gagaaaaaaa ttcaagatca gtcattcatc tgctttaaaa aaagtggcaa 213660
agataaaact ttatttgaga atataaaata ataaaaagac attttcgttc tctgttgtga 213720
caaagccagt ggccttcgga ggtctgcctt gtacattttt cctcttcttc agtcattcct 213780
tgaggctttt tgcaaacgta ccctgtgttt ttcattctcc agcatattga taatttttt 213840 tttttgagac atggtctcgc tttgtcatcc aggccccgga gtacagtggt acaatcatgg 213900
ctcactgcag ccttgacttc ctgagctcag gtgattctcc cacctcagcc tcccgagcag 213960
ctgggactac aggtgtgcat gaccatgcct agctaatctt ttgtatttt tgtagacaca 214020 gggttttgcc acattgccaa ggctggtctc caactcctgg gttcaagcga tcctcccacc 214080
tcagcctccc aaagtgctgg gattacagga gcgagctacc ttgccaggcc gatcatattt 214140
ttttcctttt tattcacttt gtcttctcct cattcctacc ttcatctgtc tttcagtggc 214200
tcactccagt gaaaagtgga ctgacgcaca ttctatttca tataattcaa tggctgctgg 214260
ccccagatcc cccataccag gtggccgagc ccagtggccc tgcagggtgg acaaaatgag 214320
ggtggaactt tcccagactg tcagtaaaaa tctatggagg acagagcttc tgcctctccc 214380
ttgcaaccag gcagtgcctt ctcccaggcc tatctgcttg caaagggaac ttttgccaag 214440
acctgctcca ctctagaatt cttatctctg ctgttcgcat cctaattcca cctgcatctg 214500
tcaccatgac aacctgctcc ccaaaaggaa caggaagaga gatgctggac ttttgagctc 214560
cacagtttat cctgcatggg ggtagggagt ggttaattac ttagcactct aattcttacg 214620
gtacccccaa tgggcccaag ttggttttt taaaaaaaaa cagtcttgct ctgttaccca 214680
ggctggagtg cagtggcaca atcatagctc actgtagcct caaactcctg gactcaaatg 214740
atcttcccac ctcagcctcc caagtaactg gaacaacagt ctcgtgcaac tacgcccagc 214800
taattttttt tttttttt tttttttaga gatggggtct cactatgttc cccagactga 214860
tctcaaactc ctgggctcaa gcgatcttcc ttcctcagcc tcccaaagtg ctaggattac 214920
aggcgtaagc cactgtacca agctgcccca ttaaagcttt gaacaccaga gagcccagct 214980
cagctgtttt ccagctgggt aactctgggt aactttgcct ctctgaacct cagtctcctc 215040
ctgtgtgaaa tggggctgat cactataccc atctcggatg gtggtagttg cagggattaa 215100
atgagttaat acgtgaggtc cttaggacag ggggtgggga cacgagataa gcaataaaca 215160
ggaactgctg ttattatcac ccccacataa tccgatctca gggtctgagt gtgccccagg 215220
caaggtgtcc acagccctct gcagaaggat gcccaagtga tcagctggca caagaacgcc 215280
acgcacagca ggtgttatgc aactggccac ctattccagg cagaggatgc cagatcccca 215340
gggagaaggg ggtaggggtg cagcttcaaa gttttctgcc ccttttgagt tctccttgga 215400
gacactttgg aaatgaaacc tcccggaaat tgatattagg cctctgcagg ctgagcttgt 215460
taaaatttcc caacaaacag agccaacaga cgctctacaa ggaagcaaaa acaagacaaa 215520
acacattggc agaccctttt ccatctgctc ttggtagatg gtattcctct aagaaaatgc 215580
```

```
cgccacgagt ttctccatgg cttcttgagc tggtggccaa aggatttagg ttctctttga 215640
aattataact taactgggcc tgctttatgg cagggatatc actctctgaa atgtgtatat 215700
atatgtgtat gtatatatat acacatatat acacatatac atacacaggg ccaggcgtgg 215760
tggctcacac ctgtaatccc agcactttgg gcggccaagg caggtggatc tcttgagccc 215820
caggagttca ataccagcct gaacaacata gtgagaccct gtctctacaa aaattaataa 215880
aaataaccag gcatggcagt gtgtgcctgc aatcccagct acccagggtg ggaagatcgc 215940
ttgagcccag gagttaaaag ttgcagtgag ctatggtcat accactgcac ttcagcctgg 216000
gcaacagagc aagaccctgt ctcttaaaaa tatattatta ttattataca cacacagaca 216060
cacacagaca cacacacaca ttacagatga tgagaaaata ctctcagcca ggttttcatg 216120
atacacaact tctcaaaaag catcacaagc aggttagaat tagggatttc tttgtggact 216180
gtccaagatg ttgaggaaat attggtttag aatttacctc atttaggcca gaaatggtgg 216240
ctcacgcctg taatcctaac actttgggag gccaaggcca atggatctct tgaagccagg 216300
agttttagcc tggccaacat ggcaaaatcc tgtctctact aaaactacag aaaaaaaaaa 216360
aaaaattagc cgggtgtggt ggcacaggcc tgtagtccca gctactctgg aggctgaggc 216420
aggagaatca cttgaacctg ggaggcagag gttgcagtga gccgagatcg tgcattacac 216480
ttcagcctgg gtgacagagc aagactccat ctcaaaaaat aagatagata agataaaatat 216540
atataatata tatgttatat atataatata gaaactacag aacaagtgat ctttgtatgt 216600
ttccagaata taacagcggg acaggcatag gatagacgtt cccattgcaa aagggagaaa 216660
ttggaaggga taaagaggtc accagtccta agcaagtgct aaatccagca agacaaatcc 216720
cattaggttt caaggcctga gaataatcct cggtgactct cagctcatta acatacttag 216780
ttctcagagc cagactcaat gaggttacgg cccgcatgtt atgggtcagg aactgaggct 216840
aagtaactca ctggagatta tgtggtaaag aaggtccagg atcattgctt cagtctccag 216900
gatatgggga aggttctact cctgttatcc caaattttaa aatgtgggaa ctaaggctca 216960
gagaggttaa gcaaatcaca cagggttgca cagctagtga tgttgctgag atttccctgt 217020
gtgtagtggc tcatgcctat aatcccagca ttttgggagg ctgaggcaag agggtcgctt 217080
gatcccagga gtttgagacc agcctgggca atatagtgag acctcatctc tacaaaaaga 217140
aaaattaaaa agttagccag gcgtggtggc aggcacctga agtcccagct actgggaagg 217200
ctgaggtggg aggattgcct gagcctggga ggtggcgatt acagtgagct gagatcgcgc 217260
cactgcacta caacctgggc gacagagtga gaccctgtct caaaaaaaaa aaaaaaaaa 217320
gacattgccg agattcaaac ccaggtcagc ctgtcttctg aaatgtccct ctatgaccca 217380
ctcacaaaac tgagaaggca gaaagttgct tggacctgtc tatttcccct gtgcagtctc 217440
agagaaacag tggaactgcc tcggtttctc cttccgggaa gtattcatag aagcatccca 217500
cttacctact ttggtctgaa aataaattag cttgtctctc ttccacttac taaaaacacc 217560
gtgggttttt gcaagttaaa atgcaaaaat aaaatgagga gaatggtgct ggtagtttag 217620
ccagtgggaa gccctctggg gaaagccagc cttttattta ttacttattt atttatttat 217680
tctttctaga tagatttatg ggaaaccagg gctgtgttgt ccaggggtct gtagtccaga 217740
aggcatcaga tgggctacta agtgagtctt tgtccacctg tagatggcaa gaggcagggc 217800
ccaggtgtcc atggcttgga gaggcagggg ttgatgggag gtttgaggct gtgggatctc 217860
tcctggggcc tcagtatcct catctggata atgggggacat tctggccagg cacggtggct 217920
ctatatatcc agcacttagg gaggcctata atcccagcac tttgggaggc tgaggtgggt 217980
```

```
ggatcactgt aggccacgag ttcaagcagc ctgggcaaca tggcgaagcc ctgtctctac 218040
tgaaaataga aaaactagct gggtattgtg gtgcacgctg gtaatcccag ctattcggga 218100
ggctgaggca cgaggatcac ttgaatccac gaggcagagg ttgcagtgag ccaagatcct 218160
gccactgcac tccagcctgg gcaacagagt gaggctctgt ctcagttaaa aaaaaaaga 218220 aaaaagaaaa agaagaaag aaaaagaaaa tgggggtatt catttatcat ttgacagtaa 218280
gtttacccag cattgactgt gtgagaggcc ctgtactagg cagtgaaaac tcagctaaga 218340
ataagaaagt taaaaacaag ctgggcattg tggtttacgc ctgtaatccc aacattttag 218400
gaggccgagg aggaagaatc acttgaggcc aggagtttga ccacccctg gcaacatag 218460 tgagacgcca gtctctacaa aaaattgtaa aattagccag acatggtggc gtgagcctgt 218520
agcctcagct acctggaggc tgagatggga ggatcactgg agcccagaag ttcaaggctg 218580
cagtaagcta tgatcctgcc actgctctcc agcctgggca acagagtaag accctgtctg 218640
aaaaaaaaaa aaaaaagag ccaggtgca gtggctcaca cctgtaatct cagcactttg 218700
ggaggctgag gtgggtggat cacttgaggt caggaattcg agaccagcct ggccaaaatg 218760 gtgaaaccc atctctactg aaatacaaaa aattagccgg tcgtagtggt gggcacctgt 218820
aatcccagct actcaggagg ctgaggcaag agaatcgctt gaacctggga gccagaggtt 218880
gcagtgagcc gagatcacgc cactgtacga cagagcaaga aaaagaaag aagaaagaa 218940 aagaaataag atgatgggga gttgtggaaa cctgtccatg ggcacgtgaa ggtcttgacc 219000
tctgaccaag aagtgaacag gctcctctca attccaggca ctgcagggat ctgggacatg 219060
acttctccat gaccaaactg tacccttttcc ttttcttttt tgttttttg gtgacagggt 219120 ctcactctgt cacccagact ggagtgcagt ggggcgatca cggctcactg cagcctcaac 219180
ctcccaggct caagcaatcc tcccacttcg gcctcccaag tagctagaac tacaggcaca 219240
cagcgccacg cccgtcaatt tacacatttt ttgtagaaat agggtctcac tatgttgccc 219300
aagctggtct tgaactcctg gccttaagca atcctcctgc ctccgcttcc caaagtgctg 219360
ggattacagg cgtgagccac tgcgcccagc ccaaattgta ctcttgaaag atggaatctt 219420
agctaggatc ctgaactgtt gccttttatc ctaaatcagt tgttggttct ttttcattca 219480
cttgccttcc tcagagagaa ccagggctcc ggggtccctg tgtcgggccc caacctgtca 219540
accacccggc caatccagca ggacctgggc cgccaagacc cacccctggc agaggatatt 219600
gacaacatga agaacaacaa gctggccacc gcggagtcgg ccgctcccca cggcagcctt 219660
ggccacgccg gcctgcccca gagcccagcc aagatgggaa acagcaccga ccccggcccc 219720
atgctggcca tccctgccat ggccaccaac cccagaacg ccgccagccg ccggacgccc 219780
aacaacccgg ggaacccatc caatcccggc ccccccaaga ccccgagaa tagccttatc 219840 gtcaccaacc ccagcggcac ccagaccaat tcagctaaga ctgccaggaa acccgaccac 219900
accacagtgg acatccccc agcctgccca cccccctca accacaccgt cgtacaaggt 219960
gagaccctct gctctcacat cactgggcag gggacctggc gtccctggag ccagaggctc 220020
tgctgagtga ccctggactg tgaccccatc tctctggcct cagtctcctc ccctggaaaa 220080
tgggcatagg cgtagtttcc taccccacag ggctgtggag ggttcagtga gataatttgt 220140
gcacagtgcc tggcacgggg ttgtgttcag tcgggttagc aatatcttct acgtccttcc 220200
ttcccaaggg gagccaggaa gccaccccat ttgaggagca atagggtcct ctgatgaag 220260 cttgaggggg tcagatgatt gattctctcg gcccagcact gtccaaaaga aatgtaacac 220320
```

```
aggccacatg caaatgtcag tttaaactct ctagtcgcca cattaaaaaa ggggccagat    220380
gtactggctc atgcctgtaa tcccagtact tcaggaggcc gaggtagagt gagccaagat    220440
ggcacctctg tactgcagcc tgggtgacaa agcgagactg tctcaaaaaa aaaaaaaaaa    220500 aaaaaaatg gtgaactgct gggtggatta tgtcttaagt tcatctagtg tcagttctat     220560
gtgagagatt ttcatgagtt tgctggataa aggctttcca tggtcctgag acctaagatc    220620
ctaaggtctt gtcactgtgc ccattttata gatgtaggga ctgaggctca gagaggctca    220680
gcctgcccgt gggcacataa gcaggctggg ctgcagaatg gaagctccag aggctgatgg    220740
ctcctccccc tgagtcaaga gagggtgctg aatgggggca tgccatgcag tttatgggag    220800
gtctcagtat ttctatctgt tcagtgggtc tcttggcact ctccctacct gcctgcaagt    220860
gagggtgtga aggtccaacg aggataggg caggtctgtg ttaatatccc atgagggccc     220920
caccgcactc aaggctatag agtggttgag agcaggctct cggggccag gccgcctggg     220980 ttccaaatgc cagctctgcc acttcctgct gtgtgacctt agacaagtca ctttacttct    221040
ctgtgcctca atttcctcat ctgtaaacag agatcagaa tatatcaacc tcagggctat     221100
acaagggttc agtgatgtca taagatgcct ggtatataca gcaggcactt tagaaatgtc    221160
agccgcttct tgcctgccct gggagtacac aggagttccc agagacttgt gggaaattgt    221220
ggagggagcc ctgtgttggt tcttgtccca acagtgaaca aaaacgccaa cccagaccca    221280
ctgccaaaaa agaggaaga gaagaaggag gaggaggaag acgaccgtgg ggaagacggc     221340
cctaagccaa tgcctcccta tagctccatg ttcatcctgt ccacgaccaa cccgtgagta    221400
tggcccccag caagggcagg gggggcctgg ggctcccacc agggtggcgg aagtcaggcc    221460
agatagaggg caatgagtga gtgttgacca ccatgagtcc agggatacct ttgaacaagt    221520
tgaaaatgga tgctccttcc gtaagtcagg taagatgatt tgtcacaata tactttgttg    221580
gaagagaccc ctgtcctgcc atccactaga aaatcattgt tatttatgac aataaataaa    221640
caaatttgtc ataaataaac aaataaattt gtcctaaaca acaaataaat ttgtcataaa    221700
taaacaaatc ttcactgtga tgtaagaggc acccccttag aaatggctgc cttgtgcagt    221760
acacagcctg aacaactgca cgtggcagcc ctaggacctg aactctgttt ctaacctaga    221820
ctctgtaagg gtttagattc tgggcggata gtgtctgagt tccatggcct tctgtcttgg    221880
gcatctttga aatggataga ctatttaggg gagaaattta tcccatgaat gtcgtagtgg    221940
ctcggaggtt gttttagaat tgaatgtctc ccagggatat ttcttgaaag cctgaccgct    222000
caaaatgctt cttgacaatg aaggatcatg tcagataaga tggggagaa gctgctttct     222060 ataatctgcc tcttggcaac tcaccctggg tagtaataaa taaaagtacc tttaaagtac    222120 tttttttattt agttgactta tcgattttac taaggaaaca cttatgtggt atctactcag   222180
tgccaggcac tgttctgagt gccttaaaat tttttttaat ttctctgagg ttgttactat    222240
gcttagctcc atttgacaga tgaaaaaact gaggtccaga gacgtgaatt cacctgccca    222300
aggtcacaca gcaagccagt gggagagctg gagtttgagc ccagacactg gctctagcct    222360
ccttgttctt aaccactcag ctctgctgcc attcacacaa ccttatgaac tatttattat    222420
tggctccact tattaagagg ttaactggca catcccattg gcacattcaa ggctctgata    222480
aggcctgcaa ttcataattt caataactaa cttttggag ccctatcat gagccaggca     222540 taaattaagt cttgggtctc atgatttgt gaagtaagca ctagtattac ggctatttta    222600
cagatgaggg caccaaggca cagagggac aagtaacttg cccaaggtca cacagctaat    222660
ttttaaaaag aaagaaagaa atctacttaa cccatagatt cacaatattg tttggccctg    222720
```

```
ggacatttaa tatcgaaaag ccttttate tcctacagaa ttaaggaccg tatttcttca 222780
acctagcttg gggatcaaga tacttcaaga gggtcgtttg ggagtgatag gaactttgct 222840
aaacagggca tgtgaatgtc ttctctcacc gaggtcccct ctgccttctt ggggttccag 222900
gacccagaga gggcccccac ctggaggagt ttaatagttt gttgtgtagg aggccttggg 222960
ggttggagat ctcagtagtg gtaggtaaca tgagattatg gaagaaaagg gtttgtgagc 223020
ctgtggtctg agtggacctc tgcacgccca tctgtctcca acagccttcg ccgcctgtgc 223080
cattacatcc tgaacctgcg ctactttgag atgtgcatcc tcatggtcat tgccatgagc 223140
agcatcgccc tggccgccga ggaccctgtg cagcccaacg cacctcggaa caacgtgagt 223200
cccacagagc acaccccttc ctagcctggc tgctctgcct caggccactt tctcctgcat 223260
ccaaaatgct cataggtagg gtgggatgtt gggtcaccc ctaggcatag cccttatggc 223320
tgctggttga gaggggaagc tctgattcct tggggatgct cttgggagca agacattcct 223380
tgaggcagtt tctctgtgag cctggtgggg tggaggtggc ccagagtgac tggggctgaa 223440
aattgctgga ttctctaatg gaggcgtgag actagcagga tatggatgtt gcacattctc 223500
tacatggaat agggggggtta ctggggcagg ggcggtgctc agaggtggtc ccctccgcag 223560
tagacatttc ccttttgtaca cgaagctttg aaagaaacaa ctatttggct cagaaacaca 223620
gcctaagctt ttggttttta tgaaagcaag ccccctttgcg gatggtgggt ctgttgacaa 223680
cccctgttaa ttgagcactt gctgtgtccc aggaagaaac tcagcatgca gtatctcatt 223740
taatcctcac aatgcgcccc cccaaccccc cgcccaggca tccccatttg acagatggga 223800
aaactgaggc tcaggggaat gagagagtgg taagtggcct gtccagggtc acacagcaga 223860
attccaactc tgcatccccc aaagctccca ctgcttcccc caactgtctg catttactaa 223920
tcacctactg tatgctacgg atgggtgtgc atagcccctt tgagtcctga caagcaggaa 223980
tgagtgcatg cttgtggttg agatggggaa accgaggcac caacaggcaa gggcgtgcct 224040
cagtcatggg ctgcgggcag aggcttgacc ccagggcctg gtagagggtg gactggtggc 224100 tcctgttttcc ctccccagct ccctccccca acccttccct cccaacccag agccaaaaaa 224160
gtgtgttttc tgctggtcca aggctctgct gccctggcta agtaggttag gacccaggca 224220
aagctggcga gccccatccc tcaagcccgc ccacagctta ccatgcactt tcccttcctt 224280
cccaggcctg gcaggccccc ctggggacct gatggggggag atggaaggaa ataattagaa 224340
cgcagctcct ggaggaagct agagccagtg ctcagcctcc tcacagtccg cttagttgct 224400
tcccgcagcc tggtttcccc caggggcctc caggagccag gcgtggggag gaggtgtccc 224460
tggaggggtc cacaaacccc ctgctgacgc gaggatgctg aagaaggcgt tgccttcggc 224520
agggagggca caggcatgga tgatccaggg ggcacggcag ctcccagggc tgaagggaat 224580
ctaggcagtg ctcagaccag gccccaggga ctgtttgcaa agagcgttca gctccccggc 224640
cccctccctc gtccatctcg cagtcgaaac ttctctacaa gaacactgtg gccccataac 224700
gttcacacca cgtaaccacc atccagggca agaaatagaa caaaaacgcc ccacgcggca 224760
tgtgcctcct cgatccccca cccccaccgc cttctttccc tctagagctg ctggggacac 224820
tgtctggaga cattttttggt tgtcacgaca ggaggggggga ggtgctcctg gcatctggtg 224880
ggtggaggcc agggatgttg ctcagcaccc gccgatgccc aggacagccc ccactctaga 224940
ggatgatcca gacccaaatg tccacagagc ccagcttgag aaaccctgcc ttaccggtaa 225000
ccacgacccc agcttctgga atgagcgttt ttggcttctc tcttttttccc acctgcacag 225060
```

```
gcttttttttt tttttttttt taagagacaa tgtctctctc tgtcgcccag gttggggtgc   225120
agtaacgtga tcatggctca ctgcagcctc aacgtcccgg gctcaagtga tcctcccacc   225180 tcagccccccc aggtagctag gaccacaggc atgcaccacc acacccagct aattttttaaa  225240 tgcttgtaga acgggcctc gctatgttgc caggctggtc tcgaactctt gacctcaagc   225300
aatcctccct cctcagattc ccagagctct ggaattacag gcatgtaatt ccaattctta   225360
catgcctgta attggccaac actgccaat tcttaaaaac tgaatttatg tttgctcttc    225420
tgtaacattc aataaatgag acacttctat gcttcgcatt aaatgagtac atgttgcttt   225480
tgcaggattg atgggcattc tttttttttt tttttttttt gagatggagt cttgctctgt   225540
cacccaggct ggagtgcagt ggtgcaatct tggctcactg caacctccgc ctcccgggtt   225600
taagcgattc tcctgcctca gcctccagag tagctgggac tacaggcagg cgccaccaca   225660
cccggctaat ttttgtattt ttagtagaga cggggtttca cactatcagc cagactggtc   225720
tcaaactcct gacctcaagt gatccgcccg ccttggcctc ccaaagtgct gggattacag   225780
gcgtgagcca ccacgcccgg tcaatgagca ttctttatga tgctgttttg agatttactg   225840
tgtggcatgg gatgtgttat ccatcccctg ttgacagatg tttgggttgt ttctaagtgt   225900
gaatactgtc cccatgccac gcccctcaac atgtttcctg agtcacctgg acagtaattt   225960
ctccaggagg ccagatgcag tggctcacgc ctataatccc agcacttcga gaggccaagg   226020
tgggagcaat gcttgaggcc aggagttcaa gaccagcttg gcaacatag tgagaccccc    226080 acctctacca aaaaaaaaaa aaattttttt ttttttaatt aaccgagcgt ggtggtgcac   226140
acctgtggtc ccagccactt gggaggctga ggtgggagga tcacttgggt ctggaaggtc   226200
aaggctgtag tgatccatgt tcataccact gcactccaac ctgggtgaca gagcgagacc   226260
ctgtctcaat aaataagaat tcctccaggg tataaaccaa aagcgaagtt tctagagcat   226320
ataatttgca agtggttggc ctcagtaaat gcagcttgaa tgtttattgg acaataaaca   226380
cagtgaccct ttgggaggcc aaggcgggtg gatcacctga ggtcaggagt ttgagaccag   226440
cctggccaac atggtgaaac cccgtctcta ccaaaaatac aaaaattatc tgggcgtggt   226500
aacacacaac tgtaatccca gctactcggg aggctgaagc acaagaatca cttgaaccca   226560
ggaggtggag gttgcagtga gccaagatgg cgtcactgca ctctagcctt ggcgacagag   226620
cgagaccctg tctccaaaat atatataaat aaataaaaat aaacacagtg ggccgggcac   226680
agtgggccgg gctcgcacct gtaatcccag cactttggga ggccaaggtg ggtagatcac   226740
gtgaggtcag gagttcgaga ccagactggc caatatggta aaacctggtc tctactaaaa   226800
atacaaaaat tagccgggcg tggtagcatg cgcctgtaat cccagacact tggaggctga   226860
ggcagaagaa ttgcttgaac ccgggaggca gaggttccag tgagccaaga ttgtgccact   226920
gcactccagc ctgggtgaca gagtgagaca ccatctcaaa aaaaaattaa aaaataaatg   226980
aacgcagtgg cccttgcacc agtagctcat gggaactcct gttcttccac atccttgtca   227040
acacttggta ctgtcgactg tttcatttgg ccgatctgct gggtgtggag tgagatctta   227100
ttggggttgt gcttggcatt tccctgtaat gaatgagatc aagcactttt ttggattaga   227160
ctgagccaca ggaaataaca ttttcaaata gatgaaaaag atctaagtat taggaatact   227220
tgaacctaat ttattggtct tttgatttcc tcttgcacag cttattaaga gctccagaat   227280
tagattcacc tgaccccac ggcctgccct ttcccagctc cctctcttcc ttctttcctt    227340
ccattcattc ctttagtaag tatttgataa gcaactacta tgtgccaggt actgagcgag   227400
ccagggagga ttgacagggt atgagatggt ccctgcactc ccagagccca caaaccacca   227460
```

```
ggcctttgac caggctgtgc ccactgcctc gtgcacctga aatactctcc caccaccatc 227520
ccctctgccc acccaggtct ttcaagccaa tccccttgca ccagcccctc cctccaggaa 227580
gtcacctcac cctgacccca ggcactctgg tctctgattc ctcttcaagc accacatata 227640
acaggaatat aagttataac cacacagatc acagagccca gctcctccag gacccagtac 227700
agccccaact gttgatgcat tcattcaaca aacatttctt gagcacctac tgtattcctg 227760
accctgtatt ataagctgga gacgccatgg tgacagacag acatccctgt ccttgtgggg 227820
ctgacatttg ggtgggggag atggacaatg agattatcag taactacaac aaatgttcag 227880
ggagtgataa gtgccggggg gtgtggtggg cagagggaag gagagacttc gtaaagagga 227940
tctcaagcac caggagatgg aatttaaaca gccggtcagg ggagtcctca ctgggaaagt 228000
gttatttgag ctaagtcata aaggaggaga aagacggaat caaatgggat gtgggggaaa 228060
gcattccaga gagacagaac agcctgtgca aaggccctga ggtggaagca tcttggggaa 228120
caaaaggaag tgagcaaggg agagaatgag aggaagtgag ggcagggagc tgaatggtca 228180
gatcgtgcag gggcttgagg gcctcgggga ggactttgac ttttatccct gaatgaggtg 228240
ggagccacgg aggattgtaa gcaggggaag gatgtgcctg acttctttgg tgttcacagc 228300
gccctctggt ggccatgttc agtaatgctc agcccttgca gcttctgggt ggatctgatt 228360
tttttttttt tttttttttt agacagtctc tgtctcccag gctggagtgc agtggcacga 228420
tctcggctca ctgcaacctc cgcctcccac gttcaagtga ctgtcacgcc ttggcctccc 228480
aagtagctgg aattacaggc acacgccacc atgcccagct aattttttat attttttagta 228540 gacacggggt tttgccattt ggttaggctg gtctcgaact cctgacctca gtgatctgc 228600 ctgcctcagc ctcccaaagt gctgggatta caggctcgag ccaccgtgcc cagccggtgt 228660
ccaccccatg tctagcacca gccagacact gtgccggcgc accctcatct tcaggcctgg 228720
gtgacaccag aggtgtgcta tggtgtgtcc tggacagggg ctgggccaga ggacattgct 228780
cgtccaggca gaaacatcag gcctggggag gggcacagga aaaatcaacc taccctggca 228840
ggggcctggc cttgaagcag gaagagatgc cgtggcagga agttggcccc agtgtttaaa 228900
aaaaccacgt agcaactatt tctcgcccag gatgcccagg aaagcaaggg tactggggga 228960
ttagatccat caccaagaag gatacagtca gccctgaact tctctggggc cgcttctaat 229020
ccactacagg gcttgggggca aattttaaaa ggtacccttc ccgtgggtta gcgaactggc 229080
ctagtacagt gattttttg ttaggatttg ctgccatctg ctggacaatt tcattcacaa 229140
catacaaatc tgcagtatga aaagagatgg gaggggccct tgtgcagtgc acgccctgcg 229200
caactgtata tagcagctgt gtttcctctt ctgggtagaa actctgctcc ccagtaggcg 229260
atcgttagtt ttaccggggc tctgctggaa caggccagtg atccactgct ctcttgcttt 229320
tatcccttac aggtgctgcg atactttgac tacgttttta caggcgtctt tacctttgag 229380
atggtgatca aggtgagtgc agattataag tgagaacaca cggtaatttt tttttttaag 229440
caagtgcagg gctgggcaca gtggatcatg cctgtaatcc cagcactttg ggaggctgag 229500
gcaggcagat cacttgagat caggaggttg aggccagcct ggccaacatg gtgaaacccc 229560
atctctacta aaaatacaaa aattagccgg gcatggtggc acatgtctgt aatcccagct 229620
actcgggagg ctgaggcagg agaatcactt gaaccctagg ctgcaatgag ccgatgtgga 229680
ggctgcagtg agccgagatc ttgccactgc attccagcct gggtgacaca gcgagactct 229740
gtcaaaaaaa aaaaaaaaaa aaagagctgg gattccagga gatcctgagc ctccaagaat 229800
```

```
gcccccttg agaggatgag tctcccagag gattagaaat gcctggtgtg tttgaagagc 229860
agcaaggaag ctggtgtggc tgggcggagt gagagaacag tggggaaacg aaggacagag 229920
agatgagtgg ggaggtgagg gggcaccttg tgccggggat cacagagagg gctcttcggc 229980
tcttactttg agtgaggtga gggccataga gtgttctgag cagaggaggg acttgatcca 230040
ggtgttcaca ggtgcccttt ggcatctgtg ggaagccaga ggacctgtga gcaggtgatc 230100
acactggtcc ccatgggcga tgacggggac aggatcaggc tggtgaccaa agaagaggtg 230160
agaagtggac agattcttgg aaggttctgg aaatagagcc agtgagtttt gctgatagag 230220
ccaccaatga gggatttggg acaaagaggc atcaaagagg atcccaaagt ttggatctaa 230280
gagccggcaa gccagagctg cttccatca ggcaaggggg ggccgcctca tggggcaggg 230340
gctccccact cctccctgga gtcctctggc cactgcccat ccctgcaaga tgaggtggcc 230400
tcattggctt ccctgcctct ccccgagagg ctagagagtg ggtggcagca cccagggtg 230460 gggatcaggt gggggttctg agcaccctct cttctccccc acagatgatt gacctgggcc 230520
tcgtcctgca tcagggtgcc tacttccgtg acctctggaa tattctcgac ttcatagtgg 230580 tcagtgggc cctggtagcc tttgccttca cgtaagtctc ctcgcaaggg ttcctcttgc 230640
ctcttttccc ccaaccccca gcctgggcca cacatcggat tacaggacat gttctcaggg 230700
tctagggatg gggtgtgtgg gctccgggga cgtgggagat atcagcatgc caccaggaag 230760
agcttcgatg cttttttgca tgatgtccat ggaggaagaa ggagaaggga cccccctcc 230820 tgccaacctt ctacctcctc acacagcaac gggcctcagc cacatcactg gccccttgct 230880
gtgcagcttc ctgtagacta gcctcgccgg aacatctcat cccctacta ctccacaagc 230940 gccgcccaaa ccgctgtctc tttggaaagt ccctaaagag acaatcagga aacgaatgtg 231000
catgagaatt ctgacccccct ccctatgcct gaaggccccg tagttgtaga cctggtgact 231060 cccttgtgt gtcttcact tctcctggca gtcctaggat tctctgccct ctgaaaggcc 231120
atgtgtcatc ctgcagctcc aagatggcgc cccagttgta ggcagccatt tcaggatggc 231180
acccaagctc ttagtagtca tcccaagatg gcatccaagt tctgggtggc cattccaaga 231240
tggcccctga gttctgagct atcattccaa gatggcctct gaatttgggg tggtcattct 231300
tagatggtcc ctgagttcca aggtgacctt caagttctgg gtagccattc caggatggtc 231360
cccaagctct gggtggctat tccaagatgg cccaagttc taggcagcca ttgcaagatg 231420
gcccctgagt tccagggtgg ccccaagtt ctgggcaacc attccaaggt ggcatccaag 231480
ttctgggtgg ctattccaag atggcctctg atttctgggc taccatgcta agatggcctc 231540
tggattcttg gtggccattc ttacatggtc cctgagttcc aaggtggcct tcaagttctg 231600
ggtagccatt ccaagacggt ccccaagtct tggatggcta ctcgaaggtg acccccaagt 231660
tctgggcagc catctcaagg tggcacccta gttctgggta accattccaa aatggcaccc 231720
aagttctagg gcaaccattt caaaatggcc cccaagttct gggtgactat ttcaagatgg 231780
tacccaacag gtgagtggcc attagccctt agggccctga tagcagactt agcagtacat 231840
tcctgaagtt gtagacattt ggagcgggat gaaaaatatc taatcagtct ttaatcaaga 231900
aacaaatctt ggggaccctg gctgtgccca tcatggtgaa tgattccctg acaggttttg 231960
aaaggatctt gacacattca ctcccatcgt gagagaatca ggggcttcct cctgtgcctc 232020
tgcctctagg ctcccctcctg agccaatctg gagggcccct tgaatggtct ccctcaccaa 232080
acaatgagga cttggtttgt caggaggccc aaaaatagtgg cccatttcca gtagaagggc 232140
tgttaagtag gccacactta gattcttctc tgggaacaca atgaggtcaa gttgtgttag 232200
```

```
aacaaaaaat ctccagagtt tttggatgcc tcagagctgg agatgtatca tgaaggttgg   232260
gaggctgatt atacttcttt ctctttctct ttcactcctt cctcctcttt ctcctctctt   232320
tttgttcgtt tactcttttc tttttctctt ctcctctccc tccccacatc cttccctctc   232380
ctcaaagctt ttcagtgtct atttgactac tagagcaatg cacggtggct tacacctgca   232440
atcccagcac tttgggaggc tgagacaggc agattgcttg agcccaggag gccaagacca   232500
gcctgggtaa catagggaga ccccatctct aaaaaaaaaa aaaacaatt agccaggcat    232560 ggtagtatgc ctgcactagc agctacacgg gaggctgagg tgggagaatt gcttgagccc   232620
aggaggttca aggctgcagt gagccgaaat cgcaccactg cacccagtc tggggaacac    232680 aggaagaact tgtctcaaaa aaataaaaag tttaaaaaat taaaaatcaa tgaatttgct   232740
atttagaata ttatgcttta tatggttact gaataatttt aatagtgatg agtacaaaaa   232800
aaacaggttt agcaagctgt tctgtaggtt aaaaagtaaa taaataaata attaattaaa   232860
caaaatacaa tgcacatcaa attaggggac aaagattgtg acgaataaga caaggagtcc   232920
atgtctttaa aatatgaaaa gcagttacaa atcaataaga aacactactt ctcaatggat   232980
aaatgggcaa aggacataaa cagaaatctg atagaatgct ggcaactagt aaaaatggag   233040
gtaaatcaac ccttggaatt cagagaaatg taaaataaaa acgagataca attcattccc   233100
tatcaagtta gcactgttcc cgccgcaccc ccacacacac acaaaaaatg attttttag    233160 ctaataaaca gcatatataa gaatgtatta taataggctg ggcacagtgg ctcacgcctg   233220
taaccctagc attttgggag gccaagggag ggggatcacc tgaggtcagc agttcgagac   233280
cagcctggcc gacatgacaa aaccctgtct ctactaaaaa atacaaaaat tagccaggca   233340
tggtggcgga tgcctgtaat cccagctact caggtgggta aggcaggaga attgcttgga   233400
cccaggagat ggagactgca gtgagccgag atcatgccac tgcactccag cctgggtgag   233460
aaagcaagat tttgtctcaa aaataaaaaa aggaatgtat tataataaaa tatactttc    233520 tccccctcta tcacctattt aagcaggtcc ttcaagttgt caggtagaca tcatgctatg   233580
agaaaattta aatcctgaaa agccagaatg ttttaccacc ctcagcctgg aatgaatcct   233640
tctcctatgg aaataaccta cgggtttctc caccctctc tgccttcag cccctccct    233700 ccctctcccc tcctttttctt tctccctctt tctcttcctc cttcccctc tcttccctct   233760 ctcttcttcc ctctctctgt ctctttctgt tcgtcttct ccttttaccc cctctcagtt    233820
tctatctttt tattttcctc tttctctctc tctctccctc tctttctctc tcactccctg   233880
cactgttgat gacctatgtc cttgggtgat gtgggcctcc cctggaccgt gtagcttgga   233940
gaaagctgac cctctgtcat cggtctggca acagggactt ggccccccta ccctgcattc   234000
tgatgaggaa tggtattcag acaaaggcag atcccaggac acaggaggac atgctcaggc   234060
agggaccccc gcccctttcc tctggggcaa ggtctgctca gcagcctcca agattcctag   234120
ggctcaagag gtggcaggta gctcagggca ctagggcagg cagtgggtg aatatgtcac    234180 tcatatccac ctgtccacac acaatgctta ccttggccac ctgtgcccag gggaatgggt   234240
tttatcctgt gaatcctccc agtgaccacc actgagtgtg gcacagataa atggtaccaa   234300
gcccaagctg ttcaggtctc caatgtcact ttcctctcag acctctgttg tagctgacat   234360
actgtaatgc tgaggagggc cgggcacagt ggctcatgcc tgtaatccta gctctttcgg   234420
aggccaaggc agatggatca cctggggtca ggagttcaag accagcctgg gcaacatggt   234480
gaaaccccag gcaacatggt aaaccctgt ctctactaaa aatacaaata ttagccaagc    234540
```

```
gtgatagcag gcgcctgtaa tctcagctac tcgggaggct gaggcagaag aattgcttga   234600
acctgggaag tggaggttgc agtgagccaa gattgcacca ctgcactcca gcctgggcaa   234660
cagagcaaga ctctgtctca aaaaaaaaaa aaaatgctga ggaggtgact gtcccacctc   234720
catcctccga gttgaccatc acaatttagg gaggggaatg acctacaaag gacccagaag   234780
caagcctttc aattgttgag cttttgccat tatgggccat cgtttacaac atgctgtttc   234840
taggttctct ggaggtaaaa ttagcctcct cttttaaaca aagctaatct gcaaaagcga   234900
accaaaaatt cttttccacc agagatcaat tagcagaatg agctgggtgc gatggctcac   234960
acctgtaatc ccagcacttg gggaggccga ggcaggtgga tcacttgagg tcaggggtcc   235020
aagaccagca tggccaacat ggtgaaaccc catctctact aaaaatacaa aaactagctg   235080
ggtgtggtgg ggagggcctg tagtcccagc tactcgggag ggtgaggcag gagaattgct   235140
tgaacccagg aggtgaaggt tgcagtgagc caagattgtg ccactgcact ccagcctggg   235200
tgacggagca agactccatc tcaaaaaaaa aaaaaaaaaa aaaaaacagc agaatgattc   235260
ttttggggag ttgactttt ttttaatttc tgagttttct ttttaaatat caagttatac   235320
aagggcattc aaattggcct acaactcaca ggaatttggc agcctgtttg cagagtcaag   235380
cttttacatt gttctcatga aattggtaca ggcataaagc cacccttcac tcttgaaaat   235440
ccattttgaa tgttgttgtt ttaattctta tgcaagaaaa ggatctggat agggatttca   235500
ggccatcctg tcaaccctgg caggcttgta gatcatgcag gaactgggag gtgtgagatt   235560
ttgccagtag gatcctggca agtgcctggg actctcccag ggttttggaa gagccgacgg   235620
acatgagtcc aacagggagc atctttatat catggccgaa gggatgagag aggagaccct   235680
caaacctcac gcctaccaca ccctccccac cccactgtca agagtccatc tggtactgct   235740
gttcctcccc cagggcaggg ctgcaggccc agcacagctg gccaggtgcc ttgatcaagc   235800
cattcctgca cacctaagag ccaaactgct agaaaaccag aataggagct actgctttt   235860
tccctaaaaa gttttggaat cttctcccg ttacaggttt ctggcctctt tgcctgaga    235920
aggtctctca ccctatgagg actttgctta ttgtcttcc ttgttatcgg atagttggca   235980
cattggaagg agcatggatg ctctgaggtt ctcagcctga gcgctgaact ctccacccgc   236040
ccccacccc ccaccccagg gtcctctgct tatttccttt ctggtctttt aacttgcttt    236100
gtctgtcctc tgtgcatatc ccctcataga caaggctgag agcccacaa gtattagatt     236160
gaccttattg ttttaagaaa ttgtccctcc aggtctgttt gatttctctc tagatgtgca   236220
agtccttag cctctctgtg cctcagtttt tcccatctag atgaggaaac tgcggcccag    236280
agggactgtg gagggaagta agtccgacaa gatcactgag gttgggttca gctgtcagat   236340
gctacccatc tcccagccct gaatacggag gctcacagtg agcagaatga tgctcagcag   236400
cctggccagc ctgggttctt tgaggcctgg cagggctgcg agatccaggg gaagggaata   236460
ggggaaggga gcataaggtt attcccttcc ttgttgaaag gaaccttgcc attctggcct   236520
gttggggtca agcaaggat tcttccccca gtgctgtgat tgtggcctcg tctccgatat    236580
gggagaaaac tatccctgtg gtcccaccaa gggatgtatt gaagctcttc tgaagatgtc   236640
cacccctcct gcacctcacc caaatatctg tgtgtgtgtg tcctgctcaa ttcactgact   236700
gtgtcccttg tatccatgcg tctaccataa acaccccatt tcatgagcca tcacacgtgg   236760
tatcacgctc tgtgcccatg catcagggcg gccaactgac atttctcagc agctggcaga   236820
tcatgatcct gccctcaccg ccaagagtcc atctggcgcg gctgttcttc ccccaaaggc   236880
aggaccgcaa ctggcagagc gccttgatca agctgctcct gcatacccag gagccaaact   236940
```

```
gtcaggaagc caaagatgga gccctcaggc tgctatctct tgatcctcat cttcaaaaca 237000
gcccccaccc ctgaaggcat tattttcctt gtgtatgatg aaatggaaag aagattagag 237060
tgcgagatac ccacacctgg gtttgaatct tagtctgtct tcccagctgt gtgcctgccc 237120
ttgggcaggt cactcttttt ctctaggcct cagcttcctc atctggaaaa tggtcataat 237180
ggtgctgtct tcccataggc aaatgcagtg atgtccagaa gactcccata ttaaacctaa 237240
agtcagcaga ttaggcaaaa atcactgtca ttgaaaactc cctcaatcat ccgtaaagaa 237300
gctgggtgtg gtgtctctca cctgtagtcc cagctacttg ggaggctgag gtgggagaat 237360
cacttgagcc agggagttca aggctgcggt aagctatgat tgtgctactg cactccagcc 237420
tgggcgacag agcaagacca cgtctctaaa aatataaaat aaagccgggt gcggtggctt 237480
acgcctgtaa tcccagcact ttggaaggct gaggcagcct ggcaacagag tgagaatcca 237540
tcaaaaaaaa aaaaaaaaa aaaaaagta gaatctatat gattctacgt atgcaataat 237600
tcctagatac actgaatttg agaaccccaa gtcagactac aggaaaagga gatgaggggg 237660
tgtggaggag aatccacttg gaatatttgt agacatttaa accattctgt gttttaaaaa 237720
atatcacagc cgggcgcggt ggctcacacc tgtaatccta gcactttggg aggccaaggt 237780
gggcggatca cgaggtcaag agatggagac catcctggct aacacggtga accccatct 237840 ctactaaaaa tacaaaaaaa attagctggg cgtggtggtg ggcgcctgta gtcccagcac 237900
tcgggaggct gaggaaggag aatggcgtga acctgggagg cggagcttgc agtgagccga 237960
gatcttgcca ctgcactcca gcctgggcga cagagcgaga ctccgtttca aaaaaaaaa 238020 aaaaaatcac taacttccag aggggtcgtg gatggaaaat tccatagagt ccgcttggcg 238080
acagggtttc cgccattctg atggcggtca agtctttcta acctggatct ccagtcattg 238140
ttgaaggcgc ctaatgagcc ccaagcctga ttccaatgaa tcacgagagg accagctgct 238200
aggtgctgat agctttcccc aggcccgcat ttgctcagag ggcttcagag ttgcttctaa 238260
ttccatccca agtcagaact ctttgctgac cccctccttc ataaagagca aagccaaggc 238320
catagctttt gttaatcaaa catcagaatt ccacagacct gagttggttg gttgtttgtt 238380
ttaagagaca gagtcttgcc caggatgcag tggctcacac ttgtaatccc agcgctctgg 238440
gaggcctagg caggaggatc acttgagccc aggagtttga gaccagcctg agcaacataa 238500
tgagaccccc gtctctacaa aaaatggaaa aatttgcctg tatttccagc tacttgggag 238560
gctaaggtgg gagaatcacc tgagccctgg aggttgaggc tacagtgagc caagatcccg 238620
ctactgcact gcagcctggg caacagaggg agacctgcc tcaaaaaaaa aggagagaag 238680
gagagagaca gggtctccct atgttgtcca ggctggtctc gaacttctgg cctcaagcaa 238740
tcttcccaac tcgtcctccc aaggtgctgg gattatagct gtgagccacg gcacccagtc 238800
tgggcctgtt ttgcagatga ggataacgag aggcagagtc aggattcaaa cccaggtccc 238860
ctcaacttca aagctcacaa ccttttagac attctaaaac cttgcagctc cacaacgcct 238920
ggagaagagg ggtttctccg gctcttggca gtgactttcc gtggtgaatt cacctttggt 238980
aactgacagc tttgcagctg tcctgctacc tggaaatttg gctttcttag tgctttcttg 239040
ggcagtgcca ggtgcctgcc aagggcgggg gactgaatgg aggtgggggc ggcttccaga 239100
tggaaggatg gacatcggcc agcgccatga gcctgaggct cccccaactg ctgcccgggc 239160
gggactcggg ggtgctcagg ggtgcgtgtg tgtacgtgcg tgttctgtgt tcttttttct 239220
gaggccactt acgatctgtc tctccctccg atgccacatc accaggagca gtacacggta 239280
```

```
aagtctctct ctatctttct ctctctctct ctttctctct ctctctctct catattctgt 239340
ctctcgtgat ctgtcccctg gtgcagcctc gttagttctg ggcctgtttc tgtggccttg 239400
tgtccttgct gccgctgtcc tgtcgcttca aatgaccaga actcactccc tgcgaaggag 239460
gcatcccaaa gggtcttgcc aatgcctccg cccatgcccc accagttctt gcagagaaca 239520
gaaggggcag aggttcagtt tcaataggca agctgggtgg agcagttatc agaagcaatg 239580
aaagtgggcc agacacggtg gctcacgcct ctaatcccag cattttggga ggccgaggcg 239640
ggtagatcac ttgaggtcag gagtttcaga ccagcctggt caacatggtg aaaccccatc 239700
tctactaaaa atgcaaaaaa ttatctgggc ttggtggtgc acacctgtaa tcccagctac 239760
ataggaagct gaggcaggag aatcacttaa acctgggagg tggaggttgc agtgagctga 239820
gattgcacca ctgcactcca ccctgggtga cagagtgaga ctctgtctca aaaaaatata 239880
taaaataaat tgaacaataa aaaaataaaa tggccatgga atcgttttca gatgaggaga 239940
tgcagaatgc ccatggagac atgctcccaa ttgtcacttg tttgggacat caagatttta 240000
gccagttcca tgtgcaacct ggatgtacag ttccttgact ttttttctat caacatgtat 240060
tctaaagttc aatttcaaaa ggaaacttta gccaggtgca gtggtgcatg cctgcagtcc 240120
cagccatttg ggaggctgag actgaaggat cacttgagcc caggagttgg aggctgcggt 240180
gagctatgat cgtgccactg cactcccccc tgagattcca tctctttaat ttaaataaaa 240240
aaaaaggaaa ctatattatc cacttacaac cagcattgct aacctaagat aaatctgcaa 240300
ctgcaaaagt aaatgtaggc cagacatggt ggctcacacc tataatccca gcactttggg 240360
aggccgaggc aggtggatca cttgaggtcg ggagttcgag accagcctga ccaacatgga 240420
gaaaccccgt ctctactaaa aatacaaaat tagccggacg tgatggcaca tgcctgtaat 240480
cccagctact cgggaggctg aggcaaaaga atttcttgaa cccgggaggc agagactgct 240540
gtgagctgag atcacgccat tcactccagc ctgggtaaca agagagaaat gccatctcaa 240600 aaaaaaaaa aaaagtaaa tctaacagaa accagacaat gttgttgcct tcaagctggg 240660
ctctttgtta aaaggaaaat tactaagtgt tagggaggtg ttaaaggcct attagcatct 240720
acctgaggct tcctttctcg caaaagcaga gcgtctgaaa gatacgtgga aaagaaactt 240780
aaagtataat aaaaaagaaa gaaagaaaaa gaaatgatta tgcccctctg agatccaatt 240840
atttaatctg tgcccctgtt ctgcctaaaa ttatctcagt gactgtccaa cgtgtgtctc 240900
acacttgggg gcacagcctt gagatgataa tgatgatgtt agttttaaaa agaaaaaaaa 240960
aggttcagag ttctgaatcc tggagtatat ctctgcctag caggctaaaa tacaattatc 241020
gtctttgttc cctgaaaaat gaaaaaaatg gagtcccttta aaaagcaaat ggtgtgaaga 241080
atgatgtttt tgcactggat actgagaccc atcgtgatgg gggtctctgg ggcagctctg 241140
ctcatgacct gggaggtcac tgtagggaga tgttttctag gtgacctccc cacccaaata 241200
ctccaaccgg aggcattcac gtgtcctgag accacgccc aggcgcaggc taggggctag 241260
gacaagaatc aagattaaag gggaaatggc caggtgcggt ggctcatgcc tgtaatccca 241320
gcactttggg agtcaaggcc agtggattac ttgaggtcgg gagttcgaga ccagcctggc 241380
caacacggtg aaaccctgtc tctactgaaa atacaaaaat tagccaggtg tggtgactca 241440
tgcctgtagt cccagctatt cgggaggctg aggtgggaga atcacttgaa cccaggaggc 241500
agaggttgca gtaagccaag atcatgccac tgcactccag cctgggcaat agagcaagac 241560
tccatctcaa aaaaaaaaa aaagattaaa gggaaatga acacagagaa gagtagatta 241620
cactgtaagc ctttgaagag ttttctgtct aaaaccagag accgaagaaa caaacaaaga 241680
```

```
ttaactccga aatagcacat aggagctggc aggagccaga ggtaggcagt caggaaatgc   241740
tgtcggaggg agcaacaggt aatttgggct ttgaggaccg ggtagttctg tgactggaga   241800
agtggaggaa gggcatttct agcagcggga acagtatatg cataagcaga cagaggcaaa   241860
agaatgtggc tggggcttga gatatgtagc cataaatggg aatgcaaagg tgaaggtaag   241920
ttggactaga ttttcaagag cattgaatgc catgcccaga agtttgcact tgctcttctg   241980
agaattcacg tgctccagaa gaattctgag caagagaaag agtgacaagg tcattggctt   242040
tagccactgt gtgcataaaa catggaagaa aaggcaggga atgaggagca agttgggaga   242100
cgggtgaggg gggatggcac ccaggaatgg atggcgggat gttaaggaag gtgacccact   242160
ggggatgggg atgggatag agggcaggca gttgaccatg actctcaggt ttctggtgtg   242220
gacaactgga tgggtcatga gtgccatgaa ccacaagcta ttcatggtcc cactcaatac   242280
cctcctcttg gggggcctga gtcatggttg gccaagggtg tcatggcatc tctgggtct    242340 gcattgctaa gctcagttcc aacagacctt ggactgaact tctgtgcagt cctctctggc   242400
aaagatgggc tcagagaccc ttggagcaat gcagcagaga ccatggcagc agccacatca   242460
gcatctgaaa acagcggcac ccggttattt tccctccttc agactcaggg aatatggtgt   242520
gggaggggag atttggtata agggccactt taagtatctt ccagaatccc attggaaggg   242580
ggagaaaatc ccattttttt aagagcccac tgataccacc tttaaaaaga atacacaggg   242640
ggccaggcgc agtggctcac acctgtaatc ccaacacttt gggaggccaa ggtgggtgga   242700
tcacctgagg tcaggagttc aagaccagcc tggccaacat ggtgaagccc catctctact   242760
aaaaatacaa aagttagctg ggcatggtgg cacgcacctg tagtcccagc tacttggaga   242820
ggctgaggca agagaatcac ttgaacctgg gaggtggagg ttgcagtgag ccaagatcat   242880
accattgcac tccagcctgg gcaacaagag tgaaactcca tctcaaaaaa aaaaagaat    242940 acataggggga ccactaaact cctagaccaa gggctttttt gaaaatagct gtgaccaggt   243000
gtagtggctc acacctgtaa tcccagcact ttgagagggt gaggagggca gattgcttga   243060
gctcaggagt ttgaaaccag cctgggcaac atggtgaaac ctcatctcta caaaagaca    243120 aaacaattag ccaggcgcag tggcgtgtgc ctgtagtccc agctacttgg gaggctgagg   243180
tgggaggatg gctttagccc aggaggcgga ggttgcagtg agccgagatc gtgccactgc   243240
actccagcct tggtgacaga gccagaccct gtctcaaaaa agaaaaaaga aaagctgtgc   243300
agaaatgggg gtggggaatc agccaacccc cttgtgctgg gtctcaggga cacccaatac   243360
agctgctcag gcccagccag atggcaaagg gccctcaacc aaccctggga ccagaaccac   243420
aaaaagccac gtacttactg gctcccgagc ccaagcttaa caggtgaaat ggaccactct   243480
tcaccaggaa gggcagggct gtgccaagct caccccagac ttctaggcct gggagggtag   243540
ggtcccatgg agctgtgggc tgcccccta c ccaacctgac ctctgcttcc tctcttccct   243600
tcttcccacc taaacattcc tccacagtgg caatagcaaa ggaaaagaca tcaacacgat   243660
taaatccctc cgagtcctcc gggtgctacg acctcttaaa accatcaagc ggctgccaaa   243720
gctcaaggtg agattgggag atggtggggt gcggtggggg ggactgtcag ggttatcatg   243780
tacagctgag caggttgtac actgctcaag gacaacacat taaaggaggt gctgataaca   243840
tcctagccat cgtgtatgga tatttgtatt attacaactt cccagcagat ggcagtaaag   243900
tgagctgacc taaaataatc tgtgtattat ggcagttttt cttttagatga agtgtcttgg   243960 ggttaagatc ctttttccta attcgcatga aggcatcata tggatttaaa agggtataac   244020
```

```
cgtgatctgg gaagcaggaa ctagatttct tgttccataa aattttgact tttcatctac    244080
ctattctagg ctctagtatc tcccattcca aaatagcatg aaccagcatt tcccaaaagc    244140
ctgtcattca aaaacatata tatatattaa gggaaataaa atccagtcat tagagcaccc    244200
actttcactc tatgcttcac ctgggggtcc ccagtattat ctcttatgta atatgtttct    244260
ttaaatcaag tcacacccgt aatccctgca ttttgaaaga ccaaggcagg agtgttgctt    244320
gagcccagga gaatgagacc agcctgggca acatagttag actctgtctc tactaaaaat    244380
taaagacaga aaacagatac tgttatggaa atctaaccaa atatggctgc ctgcctaagg    244440
ctttgtgcat tgacaactgc tcttctcttgg ttaaagaggg aaaatgtcaa tggtaggtgt    244500
taacatggta gcaactaagt aaaaatttct ccttcactca aaaggattga gagagttgga    244560
aaggaagtaa ctttgttacc ttgttttttct gtgttgggct cctgtatcac ttaaaagcat    244620
ctctggtatc ccatctggga gttttagatc catagaatgc caggattgag tccaactcct    244680
ccaacgctta tttctgaaag ctgggggggac cttaccctag tgacttgact tatgaccttg    244740
cctgtaaaat gggaatgatc atggcagtat tttggtatga tgggccactg gaggcagaag    244800
gttgggcagg tccccagccc ctcatgctct ctgtcaactc caccccacag gctgtgtttg    244860
actgtgtggt gaactcactt aaaaacgtct tcaacatcct catcgtctac atgctattca    244920
tgttcatctt cgccgtggtg gctgtgcagc tcttcaaggg gaaattcttc cactgcactg    244980
acgagtccaa agagtttgag aaagattgtc ggtgggtctc cactttccag cacattccca    245040
ttggaaccag caggtgggca ggggggaagt ggctagaggc attggccact tgggctcaga    245100
gactggagaa gtgatgagcc ttggaagtga ctcagttgca accagcttgg atcttgggta    245160
gaaagaaaac cggttttaga atttgagtca ccacccagag ccacagaatg agtcataagc    245220
aaattgattg accctttcagc caccgccttt gtcatgtgag ggatattaat acacatccac    245280
agttccttac ttgaaatcgt tacaggcaga tgtgtttcaa agttgagaat attttgagat    245340
tcccatgtgg gacatgacac cctcagctgg gtctaaggca gccctataat caaacacaat    245400
atttctgcca taaaatgtgt aactatttac atcaaatggg gtaaataaca agtataaaga    245460
gcttcatgtc caatcagatc aggtttcatt accaaataag ttaggtaaga ggccaggtgc    245520
agtggctcac acctgtaatt ccaacacttt gggaggctga ggtgggagga tcacttgagg    245580
ccaggagttg gagaccaggt tgggcaacat aatgagagcc catcctacaa aataaatttt    245640
aaaagttagc ggggcatggt agcacacacc tgtagtccca gctacccggg aggctgaggc    245700
gggaggattg tttaaacaca ggagttcaag gctgcaatgc actatgatgg taccactgca    245760
ctccagcctg cgtgacagag tgagaccctg cctctcaaaa atatatacat ataggccggg    245820
cgcagtggct catgcttata atctcagcac tttaggaggc cgaggcgggc ggatcatgag    245880
gtcaggagat cgagaccatc ctggctaaca cggtgaaacc ctgtctctac taaaaataca    245940
aaaacctagc tgggcatggt ggcagacgcc tgtagtccca gctacttggg aggctgagac    246000
aggagaatgg cgtgaacccg ggaggcggag cttgcagtga gccagattg gccactgta    246060 ctccagtctg ggcaacagag ccagactcca tctcaaacaa acaaacaaac aaacaacaac    246120
aacaaaaata tatatatata tatatgtata tatatatatg tacacgcaca cacacatatg    246180
tattatatgt gtgtgtgtat atatatgtat gtgtatatat agtgatattg ttaccagtgt    246240
aaagtggcat tttgcaacac atggtagcct gttgttatct tgatggctat ttattgaaat    246300
taggaggatg ccagatgtct ggataggagt ctggaactaa cccttgtttc ctgccttgaa    246360
aaggagtagc aacctcccctt agcctgatga acctctaaat gtccctatg tctctctgcc    246420
```

```
tcctcctaaa ctccctccac cccaccccca gcaagcctga ggctctcacc ctgaggacta  246480
gaagttatca cgttggaaga gggtgctgga ccctgggtca gctctcccac caggagtaag  246540
gttgtgccat cacccatgga tttatctcaa agtagatgca cacgtcatcc cctatgaagc  246600
acaggaacac atggtggcag gatggggagt cactgcttcc caagcagtct aggctggtgg  246660
accactcttc ctttccctcc cctgtctct  gataaccaaa gacaagtgca agacagcccc  246720
tctttcccat ttactaacag tccccactct ctgtggcaga ggcaaatacc tcctctacga  246780
gaagaatgag gtgaaggcgc gagaccggga gtggaagaag tatgaattcc attacgacaa  246840
tgtgctgtgg gctctgctga ccctcttcac cgtgtccacg ggagaaggct ggccacagta  246900
agtggcccga ctggaaatct atccaggagg agccctgggg agcaggagga taaagggcct  246960
gagagcttag caataagaaa ggtcttggag gccgggcatg gtggctcacg cctgtaatcc  247020
caacacttta ggaggccaag gcagatgtat cacttgaggc caggagtttg agatcagcct  247080
ggccatcatg gcaaaactcc atttctacta aaaatcccaa aaaaaaaaa aaaaaaaaa   247140 aaaaaaagc tgccaggcat ggtggctcac acctgtggtc ccggctactc aggaggctga   247200
gacacgagaa tcacttgaac ccaggaggca gaggttgcag tgagccgaga ttgcaccact  247260
gcacttcatc ctgagtgaca gagcaagact atggcctccc cgccttcaaa aaaaaaaaa   247320 agtgaggctg aatcatggac ttagtcttta tttaaaattt tgagccactt gtggtggctc  247380
atacctgtta tcccagctac tcaggaggct gaggtgggag gatcgcttga gcccaagagt  247440
tcaaggctgc agtgagctgt gattatgcca ttgtactcca gcctagacaa cagaaggaga  247500
cccctatccc tgaaaaaaaa aagaagaag aaattgatat ttgttcatca tggactttt   247560 gcattaattt tgatttttta aaatattgga gcaaagatt atcttgatta ctgagatttt   247620
cagtaccccc ttaatttgca cccaaaacaa atgcctccct ccctcacctc gtccaagtaa  247680
tggtctttct ctcagaggtc ttggaaatgc caggctggaa gcttggtaga ttccagcatg  247740
tgccctcagc atcctcacct ccctccctct ctcagcaaat atgccaacct gaacatgccc  247800
tactacccac tctcagacac atccagtact cacacatgtg ggaataatgc taacccacaa  247860
ggcacctttg agcaaagttt ttttaaacac ctttctcaac agacttcatt tccatctgtc  247920
tgaaaatcat cgcaatagac ttaaatgatt ttgttcaaac aaggcactga aggaccacct  247980
gccaaaaaat tgtcatcatg aatacacaaa tctatcatgc ctatcatgtg aaggtatcgc  248040
ttagacacag agcctttgag cagtgtgcaa cctgcactac tgtacagagc tgctgtgcac  248100
ttacccactc tcatatatat ccccattgta cctcctgagc acccagcacc acctgtgctc  248160
aaatacccac tctacatgca tacacccacc tctactccct ccattgccac aacctgtctt  248220
taaatcccaa cttggccact tataagtggg tggtcttcag cacgtccctt taaattgctg  248280
aacctcaagt tcctcatgtg caaagtggag ccagtaataa cctccctggg agggttgctg  248340
agccggtggg gatgaattgt tgaatattgt ttccagcaca cagcaagccc ttcatgcaca  248400
gcagtagaaa tgactgacat tggccaggcg tggtggctca cacctgtaat ctcaacagtt  248460
tgggagaccg aggcaggtgg atcacctgag gtcaggagtt caagaccagc ctggccaaca  248520
tggtgaaacc ccgtctctac taaaaataca aaaaaattag ccaggcttgg tggcgcatgt  248580
ctgtaatccc agctacttgg gaggctgagg caggagaatc atttgaaccc gggaggcgga  248640
ggttgtagtg acccaagatc acgccgttgc actccagcct gggcaacgag agcgaaactc  248700
catctcaaaa aattaaaatt aaattaaga aataactgac attgttgtca gccttcaaa   248760
```

```
aaacagcgac tacttaaatt tcttttcat ttccctctgt tcctgttctg ccatctcact    248820
tccaccctct ctccaccttc ctcatcaccc cttgggtccc tgtctctctc cttcctgccc    248880
cttccctctc cctgccccat tccttgcagg gtcctcaagc attcggtgga cgccacctt    248940
gagaaccagg gccccagccc cgggtaccgc atggagatgt ccattttcta cgtcgtctac    249000
tttgtggtgt tccccttctt ctttgtcaat atctttgtgg ccttgatcat catcaccttc    249060
caggagcaag gggacaagat gatggaggaa tacagcctgg agaaaaatga ggtgccactt    249120
ccaattccat ctgtccttta aaactgggg acacacacaa actttaaaac acacacaaca    249180
cccaggaacc cctttctagg ggtacctggg ggagggaaca gaagcattgt cccaaccgaa    249240
tccagtcttc agggcagccc ttcatggagt ttccagagga aacacatcat atagtgtatg    249300
tatcagtcag tttagactag gttatgccgc agtaacaagc aacccagat ttcattgcca    249360
aatatccaca aagggactta ttttttgctc acactgcatg tcaacatcag ttgtggatct    249420
tgccatcttt attctggttc ccaggctggc agagcagcag agcagcctcc ctctgagatg    249480
ctccagatga aaagagagt atgtcagact gaggttcagt tcttcaggct tgtgctcaaa    249540
aattacacat gtcacttctg ctcacatttc atcagccaaa gcaagtcaca catccattct    249600
gacatcagtg gagtgggcaa atacaatctc ccctagcgaa gggtggtgaa tatttatgaa    249660
tgaaaagcca agccaggtgt ggtggctcac acctgtaatc ccaacatttt gggaagctga    249720
ggcaggagga tcacttgagc tcaggagttt gagaccagcc tggccaacat agcaagaccc    249780
catctctact acaaatcaaa aaaattagcc aggcaggatg gtgcacacct ttagccccag    249840
taacatggga ggctgaggtg ggaggatgct tgagcttggg agttcgaggc tgcagtgagc    249900
tatcattatg ccactgcact acagcctggg caacagagca gaccctctc tcaaaaaaag    249960
aaaaggaaag aaaatccagt cccctgtcta ccagagagta tagacatgac tctttgcctc    250020
tctggcatca tccaagctaa atagaggacc tagaatatat cctctgctcc cttgacccct    250080
aagacttaat aaccactatt cctccttctc tctccctcaa agagaaggag aagacgcagc    250140
aaagtattca gtaagaaaga atgggctggg cgcagtggct cacgcctgta atcttaacac    250200
tttaggaggc caaggcagga ggattgcttg agcccggaag ttcaagacca gcctgagcaa    250260
catagtgaga ccccatctct atgattaaaa aaaaaagtt ttaattagct gggtgtggtg    250320
gtgcacgcct gtagtcccag ctactcagga ggctgaagcg ggaggatcac ttgagtccag    250380
gaggtcaagg ctgcagtgag ctgtgattgc actgcactcc agcctgggtg acaaagcaag    250440
cccgtgtcaa agaaaaaaaa aaaaaagga aggaggagg gagggaggga aggaaggaaa    250500
tgagagagag aaagaaagga gggagggaag gaaggagata gggaagaagg aatgaagaag    250560
aaagaaaggg agcgaaggaa agaaggaaga agagagaaag gaaaggagaa aggggaaagg    250620
gtggaaggaa tgaagggaag gaaggaaaaa ggaaagtgaa ggagggaggg aggaaggaag    250680
gaaaggaggg agggaaggag gggggaaggg agggagggag ggaaggaggg agggagagaa    250740
ggagggaggg agggaaggaa ggagggagga aggaaggaag gagggagggg agcgagggagg    250800
gaggaagggg aagaaggatt aggcttcaat ttgatttggc acactcggta gctgtgtcac    250860
ctcaggcaag tggtttaacc tttctaagcc tctattttgg tgatctgcaa agtgaggcca    250920
ttgatagtac ccacttccca tgtttgtatt agccatgcaa taatgggaa atgtcagtgc    250980
aagttttggc agttggtgac atctcaagca actgtagctg ttgggataag aaagcaatgg    251040
tgagaaggaa gagagagccc aggaatcctg gctgggggca agagaggcag agactcaagc    251100
agaagcactt gagaaccgcg acgagttaga cagagggtgc ccggtgtaca gccaccttcc    251160
```

```
tcctgcctct gccgctctca ccactggcct ctctcccgca gagggcctgc attgatttcg   251220
ccatcagcgc caagccgctg acccgacaca tgccgcagaa caagcagagc ttccagtacc   251280
gcatgtggca gttcgtggtg tctccgcctt tcgagtacac gatcatggcc atgatcgccc   251340
tcaacaccat cgtgcttatg atgaaggtaa gtgccccaca ccagccccca gcactactta   251400
acccccacct cgttcctgcc tctaccctga taaaatgaaa ccatctgcag tttcccagac   251460
agaccacact ctggatcacc tctgagattt tgttcctgct gttccctcta cctgacacac   251520
tgttcccacc actcccccgg ccagcttctt cttcccagct gtacctgcag acctcttcct   251580
ccagaaagcc ttccctgacc acccaagact gcttgaggtg cccatcttag caggcatcct   251640
atctttatgt cgcctgccac aaaaatctgc gtcaggttgc atgacagtgt cccccaccca   251700
tttatgatga cctcagccct gaattcctag aggccaacaa ggatctggct cagacggaac   251760
aagaagctct ctataaatgt ttgattaatg aaatgagggg gctgggcgcg gtggctcatg   251820
cctgtaatcc cagaactttg ggaggccgag gcgggcggat cacctgaggt cacgagttcg   251880
agaccagcct gaccaacacg gagaaaccgc atctctacta aaaatacaaa attagccagg   251940
cgtggtggtg cgcatctgta atcccagcta ctcgggaggc tgaggcagga gaattgcttg   252000
aacccgggag gcggaggttg ccatgagccg agatagcgca attgcactct agcctgggca   252060
acaagagcaa gactccatct caaaaaaaaa aagaaaagaa aagaaagaa atgagggaga   252120 aggggtaggt gaggaccta aaatccccag ggctaaggag cggcttccaa aaaaaaactc   252180
tgaaaacctt tcaccctgtg ctttggactc caaagcgtgg attcaagccc agctcttcca   252240
tttaattcat ttacctttgt acaagcaacc agtgactttc tggggactca gtttccctgt   252300
caataaaatg ggaatgataa taagagcaca tttgccccct ccagaggagg tgagaggatt   252360
gaatgagaaa gttcatgcaa ggaccttagc tccttctcgg cacttcaaaa acgatcaata   252420
gtggccgggc aaggtggctc acacctgtaa tcccagcact ttgggaggtc gaggcaggcg   252480
gatcacttga ggccaggtgt tcgggaccaa ctggccaaca tggtgaaatc ccgtctctac   252540
taaaaataca aaaattagct gggcgtggtg gcgcatgcct ataataccag ctgcgtgaga   252600
ggctgaggca tgagaatcgc ttgaacccag ggggcggaag ttgcagtgag ctgagatcac   252660
accactgcac tccagcctgg gtaacagagt gagactccgt ctcaaaaaaa ataaggaagc   252720
cggggacggt ggctcacgcc tgtaatccca gcactttggg aggccgagga gggcgatcac   252780
aaggttagga gatcaagacc atcctggcta cacggtgaaa cgctgtctc tactaaaaat   252840 acaaaaagtt agctgggcat ggtggtgggc acctgtagtc ccagctactt gggaggctga   252900
ggcaggggaa tggcatgaac ccaggaggtg gagcttgcag tgagccgaga tcgcgccact   252960
gcactccagc ccgggtgaca gagtgagact cctcaaaaaa aaaaaaaaa aaaaagtata   253020 attcagccaa gcacaatggc gtatgcctat agtcccgact atcaggaggc taaggtagga   253080
ttgtgagttc aagcccagcc tgggcaaaat aggaagaccc cgtctaccaa aaaaaaaaa   253140 aaaaggttgg gggaggtttt tgtttttttg gatgtgaaaa gaagagccta gtccggcgga   253200
gagcggggct ttcctgaact gtgcctccta ccagtgaggt tgctcagacc ttgcctgggg   253260
ctggagtgtt gcctggagaa cagccatgaa gctgcctccc cacttcccac ttcccacccc   253320
tgctcgctga cccctgctac tcctgcttct ttccctagt tctatgggc ttctgttgct   253380 tatgaaaatg ccctgcgggt gttcaacatc gtcttcacct ccctcttctc tctgaatgt   253440 gtgctgaaag tcatggcttt tgggattctg gtaagtacca ccttggggct acagctatgg   253500
```

```
gcttgggaga agcccaaggg ggaacaatgg gtcctggatg atggtctccc aacgtggccc    253560
caagaacccc aacctcaagg gtggcttcag tatcctgcca gtggccacag atcctactta    253620
ggcattcttg tgtttgccaa ggagtcccag ggagacccaa cctgtgagtg ttaccatatg    253680
gctgcttatg tatccagttc ctcaaaatga tgggagtcat catggctggg agtctttagc    253740 atccattta gagataagaa aactgaaatc aggctgggcg aggtgtctca tggctgtaat    253800
tccagcactt tgggaggcca aggtgggcgg atcacctgag gtcgggagtt cgagaccagc    253860
ctgaccaaca tggagaaact ctgtctctac taaaaataca aaattagccg ggtgtggtgg    253920
cgcatgcctg taatcccagc tactcgggag gctgaggcag gagaatcgct tgaacctggg    253980
aggcagaggt tgtggtgagc cgagatcaca tcactgcact ccagcctggg caacaagagt    254040
gaaactctgt ctcaaaaaaa agaaagaaag aaagaaaact gaaatcaggc tgagcacagt    254100
ggctcatgcc tgtaatccta gcacttcagg aggccaaggc aggaggatcg cttgaagcta    254160
ggagttctca accagcctgg gcagcaaagc aagcccctgt ccctacaaaa aaaaaaaaa    254220 tttttttta attagccagg catggtaact cgtgcctgta gtgccagtta ctcaggaggc    254280
tgaggtggga agatattttg agcccaggag gtggaggttg cagtgagcta tgatcatgcc    254340
actgcacccc agcctgggca acagcaagac tccatcttta aaaacaaac acagaggtca    254400 ggcacagtga ctcacacctg taatcccagc actttgggag gcagaggcag gcaaatcact    254460
tgagcctagg agttcgagac caccctggcc aacatggcaa acccccatct ctactaaaac    254520
tacaaaaaat tagcctggcg tgcttgtggg tgcccatgat cccagctact caggaggctg    254580
aggcaggaga atcgcttgaa cccacaaagt ggaggttaca gtgagctgag atcacaccac    254640
tgcactccag cctgagcaac agagcaagtc tcaaaaaaat aataataata aaaataaata    254700
tgtctttatt tttcaccagc cactaactaa attttaacat ttccttccat cttaaaggga    254760
gataacaaac ccttagtatt agtattatca acccttaata ttatcaacat gacctgtgtc    254820
acttataaac atcagatatt ttcatactgc attataagag ctgcagatac cttaacattt    254880
aatttgcatt catcattgct ttaaaatgtt gcttgtgatt aaacctacag ctagaatttg    254940
ttactcagtg tttttttgtt gttgttctgt tttgtttttgt ttgagacagt ctcgctgttg    255000
cccaggctgg agtgcagtgg cgcaatctcg gctcactgaa agctccaccc cctgggttca    255060
cgccattctc ctgcctcagc ctcccgagta gctgggacta caggtgcctg ccaccacacc    255120
tggctaattg tttgtatttt tagtagagat ggggtttcac catgttggcc aggatggtct    255180
tgatttcctg acctcatgat ccgcccgcct cggcctccca aagtgctggg attacaggcg    255240
ggagccaccg cacccggcct actcagtgtg ttaatggaga agtatattca ttgttagatc    255300
gccattttta aaactttttt ttttttttg agacacagtc ttgctctgtt gcccaagctg    255360
gagtaccgtg gcacaatctt ggctcactga aacctccacc tcctgggttc aagcgattct    255420
cccatctcag ccttctgagt agctgggact acagatgcac accagcatgc caggctaatt    255480
tttatatttt tagtagagac ggggtttcac catgttggcc aggctggtct cgaactcctg    255540
gcatcaagca atctgcctgc ttcagcctcc caaaatgctg ggattacagg catgagacac    255600
tgtgcctagc cttaaaaaat attttgatag ctattttatt acaaaggta accttgaagc    255660 ccttgctatt ttgttatgca tttacaagcc tttatgcata aaataaaata gccagcacta    255720
ttctcacatg gccaaggttc atagcacaca cacaaaagta tagttggctg agtgcggtgg    255780
ctcacacctg taatcccaac actttgggag acagaggtgg gtggatcatg aggtcaagag    255840
atccagacca cccttgccaa catggtgaaa ccccatctct actaaaaagt acaaaaatta    255900
```

```
gctgggtgtg gtggcgcatg cctgtagtct cagctactcg ggaggctgag gcaggagaat   255960
catttgaacg tgggaggcgg aggttgcagt gagccgagat cttgccactg cactccagcc   256020
tgggtgacag agtgagactc catctcaata aataaataaa ttaaattaaa ttaaattaaa   256080 attattttt aaaaaattgg gggctgagtg tgatggctca cacctgtaat cccggcagtt   256140
tgggagcttg aggagggcag atcccttgag gtcaggagtt caagaccagc ctggacaaca   256200
tggtgaaacc ccgtctctac taaaaataca aaaattagcc aggcatggtg gcgtgtgcct   256260
gtaatcccag ctactcgtga ggctgaggcc caagcatcgc ttgaacctgt gaggcggagg   256320
ttgcagtgag ccaagatggc accagtgcac tccagcctgg gtgacagagt gagactttgt   256380
ctcaaaaaaa aaaaaaaatt aaggtgaaga aggcttatac tagtgggctg ggacttgaag   256440
tgaagtgaat tcttgaaggt ccccagtgag tggccaaggt gggacttgaa ccaggacatc   256500
tgttctcttg accaccagct tagtccatcc ctttgaagag agtgacctac agtctgggtc   256560
tcagccaggg tctcaggaaa ccaggttccc accttggctc acggaggtgg ttaggggcat   256620
cagctttagc accagagttc agatcttgcc tcgtcctata taagctttgt cacctcccca   256680
tcattaaaag gagccatcct cccctccac ctcagcagag ccctggtaaa cagcaaatgg   256740
actaacgtgc atctagaggg ttgaggatga agcctggcct ggcatgggca ctcaataaat   256800
gctaggggcc aggcacggtg gctgacacct gtaatcgcag cactttggga ggctgaggca   256860
ggtggatcgc ttgagcccag gagtctgaga ccaacctgga caacatagtg agattctgtc   256920
tctacaaaaa gtacaaaatt agcctggtgt ggtggcgtgc acctgcagtc ccatctactt   256980
aggaggctga ggtgagagga tggattcagc ccaggatgtc agggctgcag tgagtcgtga   257040
ttgagccgct gcaccccacc ctgggtgaca gagcaagacc ctgtatcaaa ataaataaat   257100
aaatgctagg aaagggatcc tactaatgga ccttttttcct ccaaaacagt ggctttcatt   257160
tggtggagat gctacttatt agaagcactt gaggccaggt gtggtggctc atgcctgtag   257220
tcccagcact ttgggacttc tgccaaggca gaagaattgc ttgaacccag gcgtttcaga   257280
ccagcctggg caacatagca agacctcatc tctagaaaac attgaaaaat tagccagcat   257340
agtggcacat gactgttgtc ctaactactt aggcgaaggc aggaggatta cttgagctca   257400
ggagttcaag gctgcagtga gctgcgatca catcactgcc ctccagcctg agcaacaaca   257460
caagacccgg actctaaaaa tcaaaaaaga agcacttagg gaaatttctt aaaattaaat   257520
gataccctga gcaaacccct agatgttctg attcatttgg tttggtgagg tgggagggaa   257580
tcactgaatc tgtaatttat tattatttt ttttttttga gatggattct cactctgttg   257640
cccaggctgg agtgcagtgg tgcaatcttg gctcactgca acctctgctt cccgggttca   257700
agcaattgtc ctgcctcagc ctcccgacta gttgggatta caggcgccca ccatcacgcc   257760
cggctaattt ttgtatttt agcagagacg gggattcacc acgtcagcca ggttggtctc   257820
caactcctga cctcaggtga tccgcctgcc tcggcctccc aaagtgctgg gattataggc   257880
atgagccacc gtacctagcc tgcagttatt ttattctgag ttgatcttct gctggtgaag   257940
tgagtcttcc actggggcct ggagctgcat ctccctcacc ctgccaatcc tgcaagagcc   258000
agcactgagc ttcccctctg cttctctttt tttttttt tttttttttt tgagatggga   258060
tcttactctg ttgcccagcc tgttcttgaa ctcgtggcct caagcagttc tccctccttg   258120
gcctcccaaa gtgctggaat taggcatg agccaccacg cctggtctcc ctttcagtt   258180 ttaaatgaag ccacaagttc cctgtataac atttgggaga tagaggggag ctctctagcc   258240
```

-continued

```
tagggggttga ggtctgtgac caaacgccta taaagttgtc tttgtttgga ctccccccaga 258300
agcagagcct gagacaagga ttgagtgcaa ggaatttatc tgggatgcag ggcagtaagg 258360
gagagaggaa gtgacacagg gacagaaagg caaccaggaa agagtgtatt attaagccag 258420
ttcctgctgt gaacaaatgg ggctcagttt cagtggatac ctccaggagg caacagagag 258480
cacataccac agagtcatcc cacctcacag ggagggaatt ggagtattta tcctccagtg 258540
cccatcagac ataatcacag gccactccca ggggagctat taattcccta acacttgtgc 258600
agccacagag agaccctggg caaagtagtg tacctcaggt gtgtagttga gctatgggca 258660
gggcccagc aacacctgcc aaaatgccaa aagtgccagt gggacctgaa ttcctttta 258720
tttatttatt tatttattta tttatttta tttatttatt tttgacggag tctcgctctg 258780
tggcccaggc tggagtgcag tggtgcaatc tctgctcact gcaagctctg cctcccaggt 258840
tcacgccatt ctcctgcctc agcctccgga gtagctggga ctacaggcgc gcaccaccac 258900
gcctgcctga ttttgtgtg cgtgtattt tagtagagat ggggattcac catgttatcc 258960
aggatggtct tgatctcctg acctcgtgat ccgcccacat cggcctccca aagtgctggg 259020
attgcaggcg tgagccaccg cgccggccc cctgaattcc ttttttaggc agttgtgaaa 259080
caacaacatc ccatctgttg ggcacctact gtatattcca tgctcagcga cgcacattca 259140
ttgtctgatt gctgtgttac cactgccttc cagagaaggg cgcagaggcc ccaggcactt 259200
cgcctaggag ggaagcacag ctctaaggtc aggctccttc tctgtaaggt agagggggcta 259260
cttcagggtc acactgaccg cccccaaccccc tgacctggcc tctgcttctg cgaagatgct 259320
gagaaggccc tgtgttttgt gttttgggtc ccactgaccc cagaggggag ggccatctct 259380
ttgacccaga ctcttggatc caaactgggg tgccacccat caccatgtca gtacccggtt 259440
gaggggagtc agagatagca ggagaccttg tgggacttga ggctgtgact gttctccaaa 259500
caatgtggag tatttccata ttttaacaaa agagaggcca ggcgtggtgg ctcacgcctg 259560
taatcccagc actttgggag gccgaggcgg atggatcaca acgtcaggag atcaagatca 259620
tcctggctaa catggtgaaa ccccgtctct actaaaaaat acaaaaaatt agccaggcgt 259680
ggtggtgggc gcctgtagtc ccagctactc aggagactga agcaggagaa tggtgtgaac 259740
ccgggaggca gagcttgtag tgagccgaga acgtgccact gcactccagc ctgggcgaca 259800
gagtgagact ctgtctcaaa aaaaaaaaac aaacagagag gttatgcttg tgtttcccct 259860
tgagccagca cccagcccag gaatgcagca gtcaggatag atcaagtgaa gctgcagtaa 259920
caaacagccc ccacatctca gtgacttaaa ttgatgggaa gggtttttta cattcagcag 259980
ggaagctgtt tgcctcatag ttacccaggg acccaggctc acagagtagc tgccattcaa 260040
aatgttactg gtcgccaagc ccagggttga gaggctagag agtccaacac tgaccagaaa 260100
gtgaccacac tgcttccaca cacagcacat cactgcacct agacacacat ggccccatct 260160
aaacacaagg ggaccaggaa gtgcgtgtgc ctgaaaggcc ccaaagcccc gtccagtgcc 260220
tgttctgcac cctgttactg tccgcctcca gatcaggaaa tggaggccca gagaggttaa 260280
gccacttgcc catagccaca cagctgtggt agcagagctg ggatttgaac ccagagtctc 260340
ctttctttgc gagtatgctg ccaacctagt ggggacctga acacagactg tgggctctct 260400
gaggcctggg ttcaaatcct ggctttacat ctctgtgctg ctagcctcag gcagatgagt 260460
ggcttggtta cctcctagaa aatgggtata cctgggagtg gtggctcacg cctataatcc 260520
caacactttg gaaggccaaa gtgagcagat cacttgaggt cagaagttcg agaccagcct 260580
gaccaacatg gtgaaacccc gtctctacta aaaatacaaa aattagctgg gtgtggtggc 260640
```

```
atgcacctgt ggtcctacct acttgggagg ctgaggcagg agaatcgctt gaacccagga    260700
ggcagaggtt acagtgagcc gagatcgtgc cactgcactc cagcctggat gactgagcga    260760
gactccatct caaaaaaaaa aaaaaaaaag agaagaaag aaaagaaaa tgggtgataa     260820 cccttccctc caggatcttc atgaggagct cagtgatgtc atttataaag ccctgggggt    260880
ctcgggagcc ctcaaaaatg ctggagagac aggccacagc tctgaagagc agcccagcc    260940 ctgtggagct gaagcagggt ctggaggccc cctctgggc caggccaatc atgggaaggc    261000
ccccaggagt tcccagggag ggagactcag cacagatgat gtcgaacagc ctttaccgca    261060
gcccttcgaa caaccataac tgtcccgggc actccgctga tgggcaactg tgcctctaac    261120
atgcacccgg ccagcctagg gggccgggaa ccaagccctc tgttggcatc tctgtcttgt    261180
gggtccccat tctagaatta tttccgcgat gcctggaaca tcttcgactt tgtgactgtt    261240
ctgggcagca tcaccgatat cctcgtgact gagtttgggg taagtctccc tccagcttct    261300
ctctgggtga ctctgggctg gacgaggcag gcggcagggg gcggggagc ggtcccagag     261360 gcagtgtgtc ccggaagcca tagctgcttg agccagcact tggccatgac cagagaggga    261420
gaactggggc cccggggaca agggcagccc ctcaggaggg cattgtgggg agatgggggt    261480
aaccaaagct tggctgtagg gccagcactg aggggtgggc tttcctgcat cctggcctag    261540
gaattaataa tgcagatgag tacactgagg gaactgagac actcaaaagc tctgaaagct    261600
gagccggctc ccaaacacca ccctatgtca ggagcccaga aagaatgggt ttcaagtcaa    261660
ttctgtttga accaaccctc tcctagttag tgggcaggag agagccacag ccctcaggcc    261720
agtgtgggga caccactccc agggccatag aggggtcccc agggtgtctt ccctcctcta    261780
gccccgggcc tggagactc tcaacatggg agtctctgga cctctctgtg gtggcccac      261840 aggccacatt gcccttctcc ttttctggaa gactcagggc cccagaggtc ctgtcctaga    261900
ccctctcctt ggccatctgc caatgagccc aggcttgggg tccctcagga gattgggggg    261960
agggtagaag atccttgcag ggggaagcaa tggtcaaaaa agggtgtcaa agccaagggt    262020
caagggtgat accaatgtca tcttactaac aataaaaata acaatagctc acgagaatcg    262080
cagccttgct gtgtgccagg gaactgtgcc aagtggttta cgtggattgg ctcagggtag    262140
aggtcttggt ctcagctcgt aagagaattc cctcggaggg ttcaactgaa ggcacccaaa    262200
tgcagacctc actggtggag gggaagggaa gggtacccac aagggtggca aggtgtccag    262260
cgaccaccca ccgtggggag ctgtcacctg cccaggtgct gaagtgggga gggaacctga    262320
gccggaggcc aggagaagcc accaagtggg agctgtcctg tcaatgtgga gagacagaga    262380
ccagggccca agcaggcaga gagcaatagg ggagaaacac cccaacctt ctctccctc      262440 atcccttatc tcctgccaga gcctcccatg gcccaaagta aaccggaagc aagctgaata    262500
tgatgctcag agcaggcagg gaagtcagga gaatagatct gggtgtggtc gggcctgagg    262560
aagagggtgt tgcctcattt cacagatggg aaaactgacc tcagctgggc acggtggctc    262620
atgcctgtaa tcccagcact ttgggaggcc gaagccggcg gatcacctga ggccaggagt    262680
tcaagaccag cctggccaac atggtgaaac cccatctcta ctgacaatac aaaaaattta    262740
gccaggtgtg gtggtcatg cctgtaatcc cagctactcg ggaggctgag gcaggaaaat     262800
tgcttgaacc cggaaggcgg aggttgcagt gagcgacggt cataccattg cactccagcc    262860
tgggtgacaa gagcgaaaac tccatctcaa aaaaaaaag aaagaaagaa aactgatctt     262920
caatgcctgg ggaagtgaga gacactccca aggtcacaaa gccaggcctg ggtgactcct    262980
```

```
gagagtacac tgacagctcc tggggtgtcc cagtcagatc cccctacaga aaaggatctg   263040
tttgcctgct cttccgtcct agaaggccag gagggctgg ggaactacac aaagagggg    263100 gccattcttt gatatgtcct acggcacccg cacccaagtg atacacactt atttgccttc   263160
agctccagtg agccagaatt ttccccttcc cctcaccta tccctgaaac cttcctctag    263220
agggttcttg cccacatggg ggctctctcc actggggtgc ccccacctgg tcattctccc   263280
ctgtcctgag tttctagaga gggctggagc tccagctggc aatcaaaata tcttgccatc   263340
cggctacata caagacagcc ttgaaccaat gtccctttgg gtcaagaggt tagaaggatg   263400
gtccagctcc ccagaagggc aggtggggtg gaggaagtta gctgaaacct tcaatcacca   263460
gtaagagagc tgtagggaca gactccaaca gcctgttctc ctggctggca ggaagatggg   263520
gcatggggtg ttcatgggac atcaggaccc ttgcagtagc caaacagccc ccagccctcc   263580
ctaccagctg tttgatcttg gacaacttgc gctatctctt tcatgtaga gtggggctaa    263640 ccattgcaac caacctcaga cacttgcaag actcacagtg atgcatgcac tcaaaagaca   263700
ttcattgagc acctactgtg tgcctggtgt gattataagt gctggagaca gaacgagaag    263760
gaggggtgcc aaacaaaaca gaccaagaat acagagtgtc tgctcccata gagctgacat   263820
tctaaggaga gagacgggaa cttttttacaa gtaaaagcat caacaggccg ggcatggtgg   263880
ctcacgcctg taatctcagc actttgggag accaaggcag gtggatcact tgaggtcagg   263940
agttcgagac cagcctggcc aacatggtga aactctgtcc ctactaaaaa tacaaaaatt   264000
agccgggcac ggtggcaggt gcctgtaatc ccagctactc aggaggctga ggcaagagaa   264060
tcacttgatt ctcaggaggc gagaggttgt agtaagccaa gattgtgcca ctgccctcca   264120
gcctgggcga cagagtgaaa ctctgtctca aaagaaaag gaagaaaaag aaagaaagaa    264180
acgtgaagtc cttggcacag aacctgccag gaaaccagga gttgaaaat ggtggttgtt    264240 aactattact gctgttgtta ttgttattgt gaatgggtgt gtagttttgt tagccagccc   264300
tgagttacag tcaatttgag ggaaagatag ggggtgggtg tttgggtcct tctgggacaa   264360
ttaactccca acctggagta gggagaggca tgtcctggca ggcaaggagg tctcagttgc   264420 cccttctgc ctcccaggta agcccactag ttctgaggcc agggcttggc caggctgaga    264480
caggaaatgc cagatgcttg ggcgggcagg tccctggggt ttaggggca gagggcatgc    264540 ggcagtacta accagtgctg tctcagctgc tgccccaag tggctggggt gatgtgggtt    264600
tgccctgtgt gcaatggata atgactgtgt ttcttgtctt gtctcttttc atgcctgctc   264660
ttaaaactgt atattggcgc aacgccgtct gaaaaactca tccaatcaaa atgcactatg   264720
aaattcattt gttcatccat gacatggtct gtgtgttcat acaccaatga cttatctccc   264780
aacccaccgc caccaccacc cccactcccc gcccgggaac cgaaacccat tggtttttg    264840 gcactggtta caaatcaacc taaaaaatgc tgaacacgcc tccccaactg ccccgcccg    264900 cccgctcccc ctcatcttca acatctgcat ctagaatccg gttggtctta cttctttctg   264960
aagtctaaat gccttacatt aactgtgaac gcatctcctc gcgtcggcat tgcatgccac   265020
accctgcctc tccaacgtgg gatgcctgac gctctcctca accctccgct ctcctctgtc   265080
tgtctgtcct cccgccccca gccctgtgc ctcccacttc ctgtagactc tgtctctctg    265140
tttttatcgg gttctgaatg ggggttttct gtttggggtg gtttgcgtct tttgcagaga   265200
aagggatggg ttttcccagc gcagcacctc tctcttgccc catccgcac acacatcccc    265260 tacactcaga gacaatagag gcaaatccac tcccagccac ctctcaccac tcctgtcccc   265320
cattcagctc catggacccc aggccccagg aaagctgcca actgtctcct cgcccctcca   265380
```

```
gctctctcca tcctgctgtc cccaatcctc catctcaagc ccacaagatc tttggccttg   265440
accagcagag acttgactct ccaagtctga taaaggagac ctgaaggcca ggcagtgtgc   265500
cggcaaagac tctcaggcag aggaactcag aagtgccaga cttggatctg gtagcttcat   265560
gtggggctgg cccactgagg ccctctcctg gagccttgaa ctgtacgtgc acacgcagtc   265620
acacagtcac tgcacacaga cactgcacac acagtcactg tgcacacact cagtcactgc   265680
gcacacactg tgcacacagt cactgcacac agacgctgca cgcagtcact gcagtcactg   265740
cacacagtca ctatgcacac acagtcactg cacacagaca ctgcacacac agtcactatc   265800
cacacacaca gtcactgcgc agacactgca cacacactgc acacacacaa tcactgcgca   265860
cacacagtca ctgcacgcag aaactggaca cacagtcact atgcacacac tgcacacacc   265920
actatgcaca cacactgtgc acagtcacta tgtacacaca ctggcactgc atgtagtcac   265980
tatggacaca cactgcacag tcactgtgca cacatacact gcacacactg tcactatgca   266040
aacacagtca ctgcacacag tcactatgca cacacactgc acacacagtc actgcacaca   266100
gagccactat gcatgcacac acagtctgca ttcacacatt gaacacacag tcgctataca   266160
cacacagtca ctgcacacac agtctatgca cccacacact gaacacacag tcactgcatg   266220
tacagacact gcacatagtc atgacctctt ctcttttct cactcattct ccaattctct    266280
ctctctctcg ctcttttttt tttttttttt tagacagagt ctcgctctgt cacccaggct   266340
ggcgtgcagt ggcacaatgt cagctaactg caacctctgc ctccccgttt caagcaatta   266400
tgatgcctca gcctcctgag tacctgggat tacaagcatg taccaccacg ccaggccact   266460
tcttgtattt ttagtagaga cagggtttca ccatgttggc caggctggtc tcgaactcct   266520
gacctcaagt gatgcacccg cctcagcctc ccaaagtgtt gggattacag gtgtgagcca   266580
ctacacctgg cctctaatcc tcattcactg ttcctgtctc tgtgtctctc acatacagtc   266640
atgcatgcat gcacgcatgc acacacacac acactggccc tctctgctac atctacccac   266700
cctgtacccc cactccagta catactgcac acatctctct ccctccccca cttctcagcc   266760
ccttgcacac cccttgttct gttaaatctc aactgcctct gccctctcc tacccaccaa    266820 tgaggccctt agagggacgc cccaatggca tctttgccct ggaatcatcc cttccctgct   266880
ggcaatacac atgcattcac ccaccaaaca tttaatgagc ccctatttgg tgccacagat   266940
ggaattatgg gcagaagcag acaccattac tgtcccctct taccacatac agtcaggtgg   267000
gggaggcagg catcggtcaa ataacccctt gactccactt aaaattatac ctgcactgcg   267060
agctgaagga tgagcagcat taacaaggca gagagagatg cacagagcat tccaggccca   267120
ggacagcaca tgcaaaggcc ctgtggtggg acggaacctg tgagggtca ggatctgcaa    267180 gcgagggaat gtggctgatg caaagacagc cgagaaaggc tggcctggag acagccgaag   267240
aaggcagaag gggacaggac ccggggctgg ggagggcggg gctatattgt ggaatatggg   267300
ctttctccta agcaccagga agggcctggg aggataggaa gcaggggagg cgcgactggt   267360
catgtgacta gacaagctcg ctctggttgc agggcaggga acagcttgac aggaggctgg   267420
gctggaggtg ggcaccagga atcgcagcaa gagatgacag tggaggagag agaacagtgg   267480
gagggttgtc ctctgcagga cccagggaaa gatcaggtct gaactgagat gaggtgcctg   267540
ggagcagtcg ggtctggctt aaaactggga gataggctga gcacggtgac tcaagcctct   267600
aatcccagca ctttgggagg ctgaggcagg aagatcacct gaggtcagga gttcgagacc   267660
agcctgacca acatggtgaa accccatctc tcctaaaaaa tacaaaaatt agccaggcgt   267720
```

```
ggtggcaggt gcctgtaatc ccagatcctc aggaggccga gacaggagaa tcacttaaac   267780
ctgggaggtg gaggttgcag tgagccgagg tcgtgccatt gcactccagc ctgggcaaca   267840
gagtgagact ctcttaaaaa aaaaatactg ggtgatagag gtgagcgagt gcaaggaaag   267900
gaccaggttg ggggaagaga ataggtgtgg gcatagcaag tttgaggtgc ctttaggaca   267960
tcccgaaata agtcagatag gcaggtgttg tgggggctgc agcttggagc tgaggtctac   268020
aagtagtagg acttttctgg agcccttagg tgggtggtct ccatatcctt ctgagcactt   268080
gaggaacatc tgagcacagc actggaaaag aaaagaccac aaggacgctg tcctcatgtc   268140
ttccaggggc tgtgtcccac ccccatcaca ttctagccag gaagttcagg ggaggtgttg   268200
aagagaggaa gctgcacctc ccaagccatg gattgaaatg tggaaggcag gaagagggaa   268260
cttgtcagaa gttctggggg cagtggaaag aattggtact gatgcaggaa gagatggagg   268320
gtggatgagg gcagactagt acccttcccc cactgcccca aacccttccc gtctccaccc   268380
ctacctgcct catgtgtctc ctcccccact tggctccaag aagggaagca tgttttctgc   268440
acgcatctcc ctgccagatc cctggctttt ttgcatggtt gcaagcttcc cctgctctcc   268500
tccaaacccc cctcctgagg ctgcttccag ggtccgcctg ccttcgcatg cctggccgag   268560
tccacatgtt atgatccgcc ccatgaaagg gatggcttgt actctggggt tgaacggag   268620 ggggctgggg atacctgagc catcggcccc atccccaggt ggagctgggt ggccaggcag   268680
ggatgggggt cagggcagca gggcacagag agtgactctg ttagccaagc tgggtttggg   268740
gcttgttcga ggcactggag acattctcac agcacttgag cccagtgtgg tcagggtagg   268800
atcccccagc ccccttcccc atcctagagg cctaaggacg cactgatgtg tcccagagag   268860
catcctagac attgccatca aacccagagg cctcagaaat tccttgaact ccagtccttg   268920
cctctcagct cccaggccaa agccagcaca agacacagat ctggcagcca gaaagccctc   268980
tggaagccac caagtaggat gcccatgtca cccaaactag dacacttttg aaacaggagg   269040
gaggctgtga ctgtatggtc accctgtgcc atttgggggg tgaaggttag accaagttaa   269100
atcttgctac gtggcctgta gcaaatccta caaatcccat agaacaagtc tgattaagcc   269160 ccttcccta gtgtggagag accctctact cctcctgcct tcaccctgct gggtactggc   269220
cagcgaagga gggtttccat gtctgcctga ggctggggtc tcaaactcaa atgcctctgg   269280
gggccaggca gacaccagtc aaccaggaaa gcaagtgcca tttctaaaac gtgaggaccc   269340
tggaaaactg gagatcatgt ggcctgcttc cagggagcaa tcgcagcagg cctggggttg   269400
ccagaaagcc agattggtgg gcaaaatctc ttgatttta acaatggca ataattttta   269460 attaaaaaca aggacaaatg aaaaaacact gctcgggccc aacaaaacag ttttattagc   269520
tagatttggc ccactcgtga cttcgagagt cccacccccc ccaccaaggt cccttgaagc   269580
cccacaatgg ccacttaact ctagctggtc tcctccctga ctctccaact ctctggcccc   269640
ctggttcttc tagcttgggt gggaggaggc agaggcagtg actagacagg gggttttga   269700 gcagaggcag tggccaccca gggaggtcct ggggcaggg atgccccac ctcccggccc   269760 ccagcacccg cccccttggtg ggccggggct gatttctgag ctcacccacc catgggagct   269820
gagtgcttcc tgcttcctgc aggcctggtc ccgtgctact ccaccagcc ccagaagctg   269880 agaagccatc cctgagaggg gggaaaggg ccccaaatgc atcttctccg actcagcggg   269940
cagcgaggac tcaccctgca gccgaacagt cccagctccc tcccgtcctc cccattcccg   270000
ctcgccaagg gggtaagaaa agatgctctt ccgcttctcc caattggctc gagccgctgc   270060
tcctcttggc cgtgggggtga ggtcagggcg ggcaggagcg ggtgggcagc tcggcagggc   270120
```

```
agggcagggc agggtgcccg gtgagtcccg tgacagatgc atttctggcc cggagcgtaa 270180
catgccctcg gaacccgcac atgtccacca ggcctgactg tgctggcgac ctccaccccc 270240
accccgccc  tggtgtttgt gcatcgtaca cgtatgatag attccgcaac ttgaccggct 270300
tgtgtccttt cgtctcagtg catttggttg ttgggagaaa caaaaaccat ctcgattttt 270360
ttcctgattg gatgattcgg atatattttc ttttcttgt  tcttttgtta tttcttcccc 270420
atccccgttc cttttttcctc ctttctttttt cttttctttt ccccattgtg ggtggggctg 270480
gcagggaggg cttatgcttt tgagttgatg cctttcctc cctcccaccc tctctctccc 270540
aacattattc cttttcgag  tttttcctct gcatcattgc attaatagtg ctttctctct 270600
ccctccttat ttggggtctg gcttgctttt ttcctgttgg ttggcttcat gtagggcct  270660
ctgtgagtgg tgacagctct gagccttttg gggtgggtgg atggtcaccc ctcttcctcc 270720
atctccccag aataacttca tcaacctgag ctttctccgc ctcttccgag ctgcccggct 270780
catcaaactt ctccgtcagg gttacaccat ccgcattctt ctctggacct ttgtgcagtc 270840
cttcaaggtg agtcctcgtc cctgctgctg gcccagggct gagaagacag gtgaccctca 270900
tgctctggct gaatgtagaa gtcagattgg aagtgcctct gtgatgtagt cgtgcagaga 270960
atctgttatc tccaaggctg ttgtcaaact tcctgtccct ggtgtgtctt cagagctgta 271020
agggcctcat cctagagccc ccagagatgc ccaccagccc tggaaggact ctggcacgtg 271080
gcatatggcc acccaaccca gtggggcaga gcactgggac aagggaggaa gacagtgcgg 271140
ctgagggacc cccagcactc ttcttcattg ccttttttcc caccaggccc tgccttatgt 271200
ctgtctgctg atcgccatgc tcttcttcat ctatgccatc attgggatgc aggtgagtgt 271260
cgtgtcccta aggttcccag agcctcccaa ggagggcagc cacccttaga aaggggtggg 271320
tcagaggagc ctggttcaca gaagcagcca tggaggttga gctgggtttc ccagaagcca 271380
ctggaggaat ggcagcccct ggtcgtcacc ctccaattcc acaggtgttt ggtaacattg 271440
gcatcgacgt ggaggacgag gacagtgatg aagatgagtt ccaaatcact gagcacaata 271500
acttccggac cttcttccag gccctcatgc ttctcttccg gtgagaaggg gacctgctct 271560
gataattctg tttccgtggg gtgggggtgcc tgccttcatc cttctgttcc catagaggat 271620
gtaccctcct cttccaatgc aagacgtgcc ctcctccttc tcttctggca ggggcgcgcc 271680
ctcacccttc ttttccggta gggggcgtgc ccttctcttc cggtagggga cgtgccggcc 271740
ttctcttccg atagggggcg tgccctcctc ctccttttct ggtgtggggg tggccagatg 271800
tgctcttatc cttctttttcc cgtgaggctg gaaatgggtg tcgtgggggg cccaggaatc 271860
ctagcagggc agaagcagag ggccctggga catagtcatc aaggtcattt tccaggcatt 271920
atctctgaat cttcctgacc accctgtgag gaagggattc ttggcagccc tatccgacaa 271980
ataagaaaac aggcttacag accgtgaggc ttgattcttt ggttcatcat cttggctgca 272040
cacaaaagtt ccttcactcg ttcagtgtag gtttttggg  ggggctttt  tttttttttt 272100
tttttttttt ggagatggag tctcgctctg ttcccaggc  tggagtacag tggcgcgatc 272160
tcggctcact gcaagctccg cctcccgggt tcacgccatt ctcctgcctc agcctcccga 272220
gtagctggga ctacaggcgc ccgccaccac gcccagataa ttttttttgta tttttagtag 272280
agtcggggtt tcaccatgtt agccaggatg gtctcgatct cctgacctcg tgatccgccc 272340
gcctcggcct cccaaagtgc tgggattaca ggcgtgagcc accgtgccca gccctttttt 272400
tttttttttt ttagatggag tctctctctg ttgcccaggc tggagtgcag tggcgccatc 272460
```

```
tcggctcact gcaagctcct cttgtggagg tgtattgagc acctacagca tgccaggcag   272520
ggctgaaaaa cgaggatgca ccaggaaata gagaaaagag acattttaag cactttggaa   272580
gctaacatcc ccatggggaa gacgaataat caggaaacaa attatagagg atgctggaaa   272640
aagataaaat tcaagaataa aggggaatag ggccaggtgc agtgactcgt gcctgtaatc   272700
ctagcatttt gggaggccga ggtgggagga tcgctttagc ccaggagttt gagaccagcc   272760
tgggcaacat agtgagaccc cgtctctaca aaaaaattgt ttttaattaa ctgggcatag   272820
tgccacacac ctgtagtccc agctacttgg gaggctgagg caggaggatt gctcgagccc   272880
aggagttcca ggctacagta agctatgatt gtgccactgc actccagcct cggcaacaga   272940
gcgagactct gtctctaaaa agaaaaatat attttttttaa ttttaaaaa aagttacaga   273000 ggtagatagt ggtgatagtt gcataataat gtgagcttac ttaatgctac tgaattgtac   273060
acttcaaaat ggttaaattg ataaacttca tgctgtgtgt attttgccac agtaaaaaat   273120
aataatgttt ttaatctaac aacaaaaaaa gaatagaggg ccggcaggtt atgcctctct   273180
gaaagtgtga catttgagag aaattggcaa gggagggagt cagtgggtat atggggaagg   273240
gcaggccaag ccgaggggac tgcctgtgta aaggccctga ggcaggagta tggctggcat   273300
gtttgaggac tgtgaggagc ccagcatacc tagaacagag tgatctaggg agaatatagt   273360
atgagatgac tgtcaccttc atggaggggg gctttttttt tttttttaatc tgagacagag   273420 tttcggtctt gttgcccagg ctggagtgca gtggtgcgat ctcggctcgg cgcaacttct   273480
gcctcccagg ttcaagcagt tctcctgcct cagcctcccg agtagctgag attataggtg   273540
cccgtcacca cgcccagcta attttttgtat ttttagtaga cgggggttt tgccatgttg   273600 gtcaggccgt tctcaaactc ctgacctcag gtgatccacc cgcctcagcc acccaaagtg   273660
ctgggattac aggcatgagc cactgcaccc ggcctgaagg gagctttttt ttttttttgc   273720 tttttttga gacagaatct ccctctttgt cacccaggct ggagtgcagt ggcgcgatct   273780
cagctcactg caacctccgc ctcctgggtt caagcgattt cctgcctca gcctcccaag   273840 tagctgagac tacaggtgag cgccaccaca ccgagcaaat ttttggtatt tttagtagag   273900
atagggtttc accatgttag ccaggatggt ctcaatctcc tgacctcgtg atccacccac   273960
ctcagcctcc caaagtgctg ggattacagg tgtgagccac cgcgcccagc caagagggga   274020
gcttttaaag cataacagtg accagcctga gcaatgcagt gaaacccat ctctacaaaa   274080 aaaatagtt taaaaattag ccaggagtgg tggcgtgtgc ctgtagtccc cagctactca   274140
ggaggccgag gcgggaggat cacctgagcc tgggaagttg aggctgcagt gagcagtgat   274200
tgtgccacta cactccaacc tgggtaacag agcaagaccc tgtcaaaaaa aaaaaagaga   274260
gagagagaga aaagaaagga aaagaaagag agagagaagg aaaagaaaag aaaaaaacat   274320
atcagtgtcc tcaaatccca ccctagacca actgaatcca agtctgctgg ggtggggcac   274380
gggcattggt attttttcaa agctctctgt ggacttcagt gcacagccaa gaatgtgaat   274440
tcccttctct cagctcccag taaaaggagg tggtccacct ggggcttgcc tggccagctc   274500
cagagcccaa gtgctcaacg tgtgtgctcc acctcctggg gaggcgttgg tacccagtca   274560
gggctgggtg tccgagtctc tgatttctcc ctgtcctcag gagtgccacc ggggaagctt   274620
ggcacaacat catgctttcc tgcctcagcg ggaaaccgtg tgataagaac tctggcatcc   274680
tgactcgaga gtgtggcaat gaatttgctt atttttactt tgtttccttc atcttcctct   274740
gctcgtttct ggtgagtctg tggacactgt gagggccgtc tgggctccct aagcctggct   274800
tcctttcagg ggagtgggtt tctgtggaat gtggctgtgt cgaaggcttg ttccctccaa   274860
```

```
ggcttctctg aaccagcctg ggatcaggtg accctgagcg tctcaaactc agcactgttg   274920
acatttgggg gtggctgatt ctttggggtg gggccatcat gtgcactgca gtgtatggca   274980
gcatccctgt cctccccca ccagatgctg cagcacacg ccaccgttc ctcctgttgt   275040
gacaaccaaa aatgtctccg gacattgcca ggtgccccca gggggtgggg gtggggttgg   275100
gagtgggggc cagaattccc ccatttgaga ctcaatgaaa tatttcagct gggcgtagtg   275160
gccgatgcct gtaatcccaa cacttcggga ggctgaggtg ggagggtcac ttgagcccag   275220
gaatacaaga ccagcctgga cagcatggtg tgaaacccat ctctttaaaa aaaaaaaaa   275280
aaattgaatt agctgcacac gtggtgctgt gcacctgcag tcccagctac tcaggaggct   275340
gaggtgggag gatcacttga gccttggagg tcgaggctgc agtgagccat gatcacacca   275400
ctgcacccca gccagggcga cagaatgaga tcctgtctca aaacaaaca aaacaaaca   275460
aaaaaaaaa aaacattgcg agggaagaaa tacctcactt tggccttgtt gggggcagat   275520
gtgggaggat ttggggtcac agtggttctc ttggtgttgg tccctgtttc agaagcctcc   275580
cctccctctc actgactctg tttctttcca tcattcttgg tctttgtctc tctctctctt   275640
ttttttttt ctttgaaatg gagtctcact ctgttgccca ggctaaagtg cagtggcgag   275700
acctcagctc actgcagcct ccacctccca ggttcaaccg attcttcagc ttcaacctcc   275760
caagtagctg ggattacagg tgcacatgcc accacccca gctaattttt gtatttttag   275820
tagagacagt gtttcaccat gttgaccagg ctggtctcaa actcctgacc tcaagtgatc   275880
tgtccacctc ggcctcccaa agtgctggga ttacaggcgt gatccaccgt gcccggccag   275940
tctttgtctc tttgtatctc tctctctcca tctctctctg tttctctctt cctcttcccc   276000
atctctccac ttgatctctc tctcactgga cctccttgtg tgagtgagca tcacctctcc   276060
attccccagt ctcttctgt ctctgtctca tttcctttcc ccatcttctc tctatccctc   276120
tctccatctg ggcctctgtg tacatgtctt tgggtctgtc tgtccgtctg tctgtctgta   276180
tccttctcac tcactcattc attccctcgg tctctgcccc cattctctct tggtccccgg   276240
ggtccccaca gatgctgaat ctctttgtcg ccgtcatcat ggacaacttt gagtacctca   276300
cccgagactc ctccatcctg gccccccacc acctggatga gtacgtgcgt gtctgggccg   276360
agtatgaccc cgcagcttgg taagaagtca ccccgaatcc tccagccaca atactcacct   276420
ctccctggaa ctgaaacacg ggctaggtca ggccccagac tctggagcac tgaactcctg   276480
gggtcctagc aggggtctca caggttcagt caggagagaa gatataagaa tcatcaccct   276540
tgcataccc agattaaaca cgtagggtgc caaccctgcc caaaccctgg actttctggg   276600
aaatgaggga gggcgtcaac catgagatgt cctgaagagc cctctcctcc tacgagtctc   276660
tcctgtctct cactgtgaag tctccagatg gtgaggatgc attagccagg ctccaggag   276720
aaaaccaaca gcatcccagc ctcagttctc ttgagagtgt ggggaggagg gctggcctac   276780
ccttggcaga caggattggc agcaacatca gagtagcaga actcagctcc cactgggacc   276840
cgtgaacctg ggagtgagag gacatacagg ccaggggagg acgcagagcc tcaggggccc   276900
atgcatcttt gtggccacaa agggagtggg cgctcccatc tgggtagaca ccagagggt   276960
ccctctccac tgacgggcaa tggtttcaga gggtggttc caccttgtgc acgtgtattg   277020
agtgcccacc caacaccaag ccttgaagga cactcagagg ctttatctga atacctggaa   277080
cccaccagcc actaactgag gatttagttc aggctggtct tggggcctga agaagcatta   277140
ctgggggcc ctcagcagcc taagcccat cttcctctgg cctcagcacc agagaggagg   277200
```

```
ccgtcacgag gaaggtgggc aggaggtggt cttggctatt cccatagcct caaacaagta    277260
ctccatgaga ccgagaggct ggggagagcc gtgggtctgg ggctgggctt tggctggttc    277320
ctaactcttc ctcttttgat tttaggtcac agcaattgga tgctgtcccc aaggcctcta    277380
ttccacaagc ccccccccac ccctgtagcc catgtagact gtggaggagg cagatgcaga    277440
gagagcccca ggggaggtgc cctgcagtcc cgaactcgac tgacatccta caccccgggg    277500
tctccccagt gtctgggaat gtactgggga ccttcacttg tccccagtct ctcccactcc    277560
ttcaagccag ggacacccca gcctcgggca tcatgacctc gctgtgtgcc cagggagccc    277620
gtgtgaaccc attgcctgca ctaaccccct ttcttctcct ttcagcggtc ggattcatta    277680
taaggatatg tacagtttat tacgagtaat atctcccctc tcggcttag gcaagaaatg     277740 tcctcatagg gttgcttgca aggtttgact tccactaaaa cctgctagca tccatggaat    277800
gagtgtggct tggggttctt caatatatat atttcatata tatatatata tatatctctc    277860
tctctctcta aaaaacaga gccatctctc tttcttgcat taaactagaa aactctctta     277920
gccaacagaa tgcagtcatg tagactcgat aaagcatgga acatatttcc tccttcccctt   277980 cagccttcag ccatctttgc ttgctcttag ctgaagctgc ccatcctggg gtctccacgg    278040 cacccccaaat cagatacatc ccctggggga ttgtaaccttt gcatttctcc cccaaccatc   278100
acctccactc tctccccctc caccccctcac ctcccaaagc cctagccct cctcccctcc    278160 ctggcactgg cccctgctcc ccacctaggc cccctcagag accagcctca gccaaaccag    278220
agaacgtgac ccaactgtag aaataacagt gatggccggg cgcagtggct catgcctgta    278280
atcccagcac tttgggaggc caaagcagga ggatcgcttg agcccaggag tttgagacca    278340
gcctgggcaa catagcaaga accccccttct ctataaaaaa ttagccaggc attgtggcgc    278400
atgcctgtag tccagctac ttgggaggct gaggcagaag gattgcttga gcccaggagg     278460
tggaggctgc agtgagctat gatcacacca ctgcactcca acccaggcga cagagagaga    278520
ccctgtctct ttaaaaaaaa aaaaaaaaa aaaaaaggc aatgaacaaa agcatggctc       278580
tacgtcttcc aaagtgagaa ttctccctcc cctccgcatc cctccagaac tgtagctcag    278640
agcccacgct gaatctgact tttctctttt ctctctctct ccctgctccc gagcagtgaa    278700
gtaatctttt tttactgacc ttttcttcca tttttttcc tcctctttc cattgatttg      278760 aaatatctat tttatcattc tctgcatctt tctctctcta ttttttcggc tcgtgtggat    278820 ttctttttc tttcttctgt ttctccccac ctctcttcct ttggttctct gttcccattc     278880
ccgttttgtt tttttgtttt tgttttgtt ttttcatttt tcggtgctgc caggggccgc     278940
atgccttacc tggacatgta tcagatgctg agacacatgt ctccgcccct gggtctgggg    279000
aagaagtgtc cggccagagt ggcttacaag gtagactacc cttgccgacc accgacgtcc    279060
aggcactggg ttttttttc ttcttcttct tctttttttt tagtgctgac cagaaacacc     279120
cggccgactc tcttttttcca acgtttctct tcttttttgt ttttgattct tttttttctt   279180
ttctcgagtc aactgatcat gaccatccct tgattctaag cagcacactg tgtccgtcct    279240
ttctgatgag tgtcttcgtg tttttgagact ccattatggc cgacatgccg ggggagggg     279300 gagggggagcg cccaggtccc cttgcacctg gtctcccagg taccaaattg gaaacaaaca    279360
cgcttcttca gggagtcaaa accatgcttc ccacttctg cccacccaga gcggccccca     279420
tgcccaggct ggggcaggcg ccttgcagag aggggcttta gccccgaaa gcaggcgagg     279480 tcccgggtcc ccgcccctgc cacgcacacc tgaagctgat ctctgaccta gggccttggg    279540
gattcgagac cttccaagga gcaccaagaa cctctcttcc cctcccttcc ttcccctgga    279600
```

```
gtttcgtccc cagccccgt ccctaatccc cccaagacac cccaacatgc ctctccattg  279660
ttccagagtg ggcaggcggc cgcagctgga cccctggacg gtggcacact gatgcaggcc  279720
atgcacgctg ccttggcggg gcctggggcg ggcaggcacc atggccgacg ggggtggtg   279780 catgctggct gagagagcga gcgtcctgcc gccaagcggc tggcccgggc caccctcca   279840 gatccctgtc ctggaatctc ccttggtgcc caaggacaga tgctctgttc cctccattca  279900
tccacaagaa gttcagggat gacctttaaa gattctcccc acccaaaaag tattacccca  279960
tcatcctatt ctcccatcca ccttgatctt ccctgcgtcc ctatccatca atgctatttg  280020
tacctgcccc gtgttgccac ctcattcctt tccttcctct gtgcacccct cctcacctaa  280080
cctatatgtc tcccctcctt ctcaatcaaa gccggggaca aggttgtccc accagcatct  280140
cagacaatga gcctctcctg gcacctgtcg ctctgtgccc ctccctgccg cccccccccc  280200 ccccccggt tttcctcaag tcgcttctct cagtctctgc ttagatgaat gtgtgcgcat    280260
gtgcaagaga gggagggcga gcccttcctc tcctggtctt tgtgcaggac caccatgggt  280320
ccataagaca actttgtgca aatttgaaaa aggcacccct tccacagaac atgcctgttg  280380
gaaaattgtt gcaatctacc aatgtggtga aacaagaca ctttttttct atcacctggg   280440
aagctgttat atttaatata caaatcgggg ctgggcgtg gtggctcatg cctgtaatcc   280500
tagtgctttg ggaggctgag acgggaggat cacttgagcc cagttcgaga ctagcctggg  280560
caacatagcg agaccccatc tctacaaaaa gaaaaaatat tttaattaat aaataagtac   280620
ataaatctat catttccaag atgggagccc tttgtgcggt gtacaacctg cacaactgtg   280680
cacagtggcc cagtctatgt gtgtttctct atttcccacc tccttcccca ccctaccccc   280740
agtgtcccct ccagtgtcct gctctggatt taccataccc ctccccatct tcaactctgt    280800
gtttcctgcc cacttgtgtc tgaatcccca cccaagttgc cctcaccccc cttctctgtg   280860
ccacttcagc ctgggctggt gcacaccagc ccagcatcct ctcccatgcc accaagcatg    280920
gtggacagag cccctgcctg ggacatgggg aatctttct tccctgggct ggaagggagt    280980 gccctcacc ccttcccct gccattgcac agagagccaa gatctggaca tgccctgag    281040 atacacttcc cacggagcta tgaatgagtc tcgagattcc gtctgcatgc gccctgtct   281100 gtgctgttct gtgtcacagc ctcgctgcat gcctgcgagg ggcctgcccc gtcagtgggg   281160
ggctgcctgc ctgctgcttc tcagaggaat gatgtggtct gtgcccatct gctctgtcct  281220
ggtctgggcc aagccaggga ttgggtgtgg ggagccagtg gcaccccca ccagcggctg    281280 tggtcctggc cccctcagcc ttggctgttg catgcactgc tcaaatccag cttgtgctct   281340
ttttctttgg ggtcagactg aaacggggcc atccagaaga actctggggc agggcgggg   281400 tggggcaagg gttgaggcaa accctggaaa tgccagctct caggtcaagc aggtggggga  281460 aaaaggaga gggcagggga ccagaagtac aagagagcct tttgtgccct cctgcgggc    281520 caccaagaga aactgagtac tgggacaggt aacctaagta agagacacct cagccgccac   281580
agctttcaga gttcttcctg ggactccctg ggtaggggcg ggcgcggctc acgggagacc   281640
caggagggat gcctgggaat gactgcgctt gccttgggtt ttctgtagcg gcttctgcgg   281700
atggacctgc ccgtcgcaga tgacaacacc gtccacttca attccaccct catggctctg   281760
atccgcacag ccctggacat caagattgcc aagggtaagg aagggacagg ggcgggcaca   281820
gacaggcgtg acagggtgga accggggatc tccctcccta ccccaaacta gaggatctgc   281880
tgtcaccacc cggatcttca ttcactcttc cattcattcg ttccacaggg ttttttgggg   281940
```

```
tttgggttt  tggtgttttt  tttttttttt  ttttgagaca  gagtcttgct  ctgttgccca  282000
ggcagcagtg  cggtgacatg  atcgcaagtc  actgcagcct  tgacctccca  ggctcaagtg  282060
atccttccac  ctcagcctcc  ccagtagctg  ggactacagg  cacacaccac  catactcggc  282120
taattttttt  tttttttggtg  tgacaatttc  cctctgtcac  ccaggctgaa  gtgcagtggt  282180
gtgatcttgg  ctcattgcta  cctccgcctc  ccgggttcaa  gcgattctcc  tgcctcagcc  282240
tcccaagtag  ctgggattat  aggtacccac  cagcacaccc  ggctaatttt  ttatattttg  282300
ggtagagatg  gggtttcacc  atgttggcca  ggctggtctc  gaactcctga  cctctggtct  282360
caaactcctg  acctcaagtg  atccacctgc  ctcgacctct  caaagtgctg  gattacaggc  282420
gtgagccacc  atgcccaacc  taattttttta  tattttttat  agagatgggg  tttcatcagg  282480
ttgcccaggc  tggtctcaaa  ctcctgggct  caagcagtcc  tcccaccttg  gtctcccaaa  282540
atgctggtat  tacaggcatg  agccaccaca  cccggcccat  ttggcagata  tttagtgcac  282600
tccttcaatg  tgccagagac  ccgtccaagc  aggggaggac  ccagcagctt  acactttaga  282660
tggatgggga  ggccgccact  gaggaggtaa  ggcagtgtct  catggatccc  tgggggaag  282720 gtgctccagg  cagaaggact  ggcaaaggcc  ctgacagagg  ggtgaacaca  ggacacccgg  282780
ggcattgagc  tgactcacct  tctgagtgag  ggcacgccac  gcaggttcag  agcagaggag  282840
gaacctgacc  caactcacat  ttgaacaggt  tccctccggc  cactgagggg  atgggagacc  282900
gaaaggaggc  cagtgtgggg  gctgctgata  tcatctgggt  ggagacaggg  cggcagctta  282960
gatctagggg  taggctcgac  gtggtggctc  acgcctgtaa  tctcagcact  ttgggaggcc  283020
aaggtgggtg  gattacttga  ggtcaggatg  accagcctgg  ccaatgtggt  gaaaccccg  283080 tctctactaa  aaatacaaaa  tttagccaga  cgtggtggtg  ggtactgtag  tcccagctac  283140
tagggaggat  gaggcagaag  aatcgcttga  acctgggagg  cggaggttgc  agtgagccga  283200
gatcacgcca  ctgcactaca  gcctgggtga  cagagcaaga  ctctgtctca  aaaattaaat  283260
taaattaaat  taactggaca  tggtggcata  tgcctgtggt  cccagctact  caggaggcag  283320
agatgagagt  attgcttgaa  gccaggagtt  tgaggctgca  gtgagtcatg  atcgcaccac  283380
tgcactccag  cctgggcgac  agaacgagat  cctagctcaa  aacaacagaa  agaaaaagaa  283440
aaaaacattt  ttttttaaagc  tgagaagggg  ctgggcgcag  tggcttacgc  ctgtaatccc  283500
agcactttgg  gaggccaagg  tgggtggatc  acgaggtcag  gagttcaaga  ccagcctggc  283560
caacatggtg  aaaccccatc  tctaccaaaa  atacaaaaag  tagccgggtg  tcatggtggg  283620
cgcctgtaac  cccagctact  ccggaggctg  aggcaggaga  atcacttgaa  cctgggagac  283680
agaggttgca  gtgagccaag  atcgcgccac  tgaactccag  cctggatgac  agagcaagac  283740
gctgtctcaa  aaaaaaaaa  agctgaggcc  gggcacgctg  gctcacgcct  gtaatagcag  283800
cactttggga  ggccgaggcg  ggcagatcat  gaggtcaaga  aatcgagacc  atcctgggta  283860
acacggtgaa  accccttctc  tactaaaaat  acaaaaaatt  agctgggtgt  ggtggcacgc  283920
acctgtagtc  cctgctactc  agaaggctga  ggcaggagaa  ttgcttgaac  ccgagaggca  283980
gaggttgcag  cgagccgagc  ttgtgccact  gcactccagc  ctgggtgaca  gagtgagact  284040
tcatctgaaa  aaaaaaaaa  aaaaaagccg  agaaggctgg  acatggtggc  tcacacctgt  284100
aatctcagca  ttttgttgag  gccaggcaca  gtggttcacg  cctgtaatct  gagcacgctg  284160
ggaggccgag  gtgggtggat  catttgaggt  caggagttcg  agatcagcct  ggccaacgtg  284220
gcaaaaccct  gtctctacta  aaaatacaaa  aattagccgg  gtgtcgtggc  gtgtgcctgt  284280
aatcccagca  ctttgggagg  ctgaagcggg  tggatcactt  gaggtcagga  gttcaagacc  284340
```

```
agcctggtca acatggcaaa accctgtctc tactaaaaat acaaaaatta gccaggtgtg  284400
gtggcgggta cctgtaatcc cagttactag ggaggctgag gcagaagaat cacttgaacc  284460
cgggaggcag agattgcagt gagccgagat cacatcactg cactttagcc tgggcgacag  284520
agcaagactc catctcaaaa ataaaaataa aaataaaaaa taccgagaaa ttcccccaaa  284580
gacctagctc agggctcact ctccatcatt aggggaaag aagaagagga ggccagggag  284640
gcgggcagag accagggcag tgtgggctcc tggaggcagc ttctatgttt aaaagggcgg  284700
cttcaggagg aagggaccaa accgtgtcag gcactgccca gagaccaagg atgacaagga  284760
tcacaagtga ctggtcatca tggtcacttt gaccagtgca gctttggcgg aggggtcagg  284820
ggtcccctgt ctggagtgca tttcggaggc ccgaaagggg atgtgatgtg atttggcagc  284880
tgattaagga cagcagggca gagagacagg cgcacaattg ccagaagaaa cggggacctg  284940
aggctcacgc ctgtaatccc agcactttgg gaggctgagg aaggtggatc acttgaggcc  285000
aggaatttga ccagcctg gccaacatgg cgaaacccca tctccactaa aaatacaaaa  285060
attagccagg catggtggtg cacacctata atcccaacaa cttgggaagc tgagcacaag  285120
aattacttga acctgggagg cagaggttgc agtgagccga gatcaaacca ttgcactcca  285180
gcctggggga cacagcaaga ctctgtctca aaaaaaaaa aaaaagaaa gaaagaaaga  285240 aaagaaaaaa caaatgggac cagaaaaaag gagtgggtgg gagaggagca ggtggatagt  285300
cccacacatg ggaaggtgct gagcccagct gaaaccacta gtaagtcagg aggagggaag  285360
actgagcctc gagacatatg tgccttccag ggtcttgagg gaaagaaggg aggaagagcc  285420
aaggccacgt ggcaagactc aaggaggaag tggcagggaa ggtgggggac tggaggggtg  285480
gaggacagat attgttaatg ccaggaacaa agtgaaggta aagagagcac aaggaagttg  285540
ggagcagtgg ctcacacctg taatcccagc actttgggaa gccaaggcag gaggatcact  285600
tgaggccagg agttcaagat cagcctggcc aacacagaga gaccccatct ctacagaaaa  285660 tttttaaaatt agccaggtgt ggtgatgtgc acctgtagtc ccaactactt gggaggctgg  285720
agtgggagga tcactgggga ctgggatgtc aaggctgcag tgagctatat gatgaccaca  285780
gacatagcag cttaagacac acctatttgt cagctcacag tcctgtaggt cagaagtcca  285840
aaaagctgga ctgggctgtc tgctgagggt ctcacgaggc tgaaatcaag gtgtcagcca  285900
agctgggctc ctctctggag gatctggggg agaatctact tccaggttca ttcaggtgtt  285960
ggcagaattg aagtccttgt ggctgtagga ctgaggtctt gttttatcac tggcttttta  286020 gcttttgct cctggaagtg catgtaatcc tccatgtgct ctcattctct ctgacttccc  286080
catctgccac ccagcagaga caatactgtg cttttcaagg gctcacctga ttggggcagg  286140
cctaccctga tcatctctgt attttgaggt cagctgactt gatatttttt ttttttcttg  286200
agacagaatt tcactcttgt tgccaaggct ggagtataat agtgtgatct cagttcactg  286260
caatctccgc ctcccaggtt caagcaattc tcctgcctca gcctcctgag tagctgagat  286320
tacaggtgcc caccaccacg cccagctaaa ttttttgta tttttagtag agatgggtt  286380 tcacaaggtt ggccaggctg gttttgaact cctgacctca ggtgatccac ccgcctcagc  286440
ctcccaaagt gctgggatta caggagtgag ccaccatgcc cagcattttc tttctttttt  286500 ttttttttt tgaaacggag tcttgttctg tcacccaggc tggagtgcag tggcgcaatc  286560
tcggctcact gcaacctcca tctcccgggt tcaagtgatt ctgcctcagc ctcccaagta  286620
ggtgggacta cagatgcgtg ccaccacgcc cggataattt tttgtatttt tagtagaaac  286680
```

```
ggggtttcac catgatagca ggatggtctc gatctcccaa cctcgtgatc tgcccacctc 286740
ggcctcccaa agtgctggga ttacaggcgt gagccaccgc accgggcctc cggtatttta 286800
attatatctg caaagtccct tcatagcctg ggcaatggtc cctagattag tgtttgaata 286860
aacagaatct tggcagaagg gcagcttttg aattctgcct accacagttc cttcgtttgt 286920
acaacgggtc taacaacacc cccactcttt gtatgtaatg ccatcgtaac tcagcttctg 286980
tggcactctg agaatctgtg ttcaggggtc ccaaaaccac ccacaggttc agtgattccc 287040
tggaagaact cagaactgag aaaagttttt atactcacag tttattacag tgaaagaata 287100
tagattaaaa tctgcaaagg gccgggcacg gtggctcacg cctgtaatcc cagcactttg 287160
ggagggcgag gtaggcagat cacttgaggt cacgagttca agaccagcct gaccaacatg 287220
gtgaaaccct gtctctacta aaaatacaaa aattagccag gcgtggtggc tggcgccagt 287280
aatcccagct acttggaagg ctaaggtagg agaatcactt gagcccagga ggcagaggtt 287340
gcagtgagcc gagatcccgc cacttcactc caggctggac agagtgagac tctattagaa 287400
aaaaaaaaaa aaaaaaaatc tgcaaagggc ctggcatggt ggcttacgcc tgtaatcctg 287460
gcactttggg agggcaaggc gggcagatca cttgaggtca caagtttgag accagcctgg 287520
ccaacatggc gaaaccccgt ctctaccaaa aatacaaaaa ttaggcatgg tgccagaccc 287580
ctgtaatccc aactactcag gaggctgagg caggagaatc gcttgaccct gggaggcaga 287640
ggttgcagtg agctgagact gtgccattgc actccagcct gtgtgacaag atcaaaactc 287700
tgtccaaaaa gaaaattagc caggtgtggt ggcatacacc tgtagtccca gctactccag 287760
aggctgaggc acaagaatcc tttcaaccca ggagatagag ctacattaag ccaagatcac 287820
gccactgcac tccagcctgg gcaacagagc aagactctgt ctcaaacaaa caaacaaatt 287880
ccaaaaacat aaaatgcgca aaggaagggc atctggggaa gggtccagga gacaccaggt 287940
gcgagcttcc agttgtctgc ctccagtgga gttgcacaga caacgcttaa ttctccctgc 288000
agtgtgtgac aacacgcacc gtgtactgcc aaccagggaa gctcacctga gccttggtgc 288060
cccagggttt ttattgaggg tttgtcatat aggcagggct gacgtagtta ctcagtctcc 288120
agtccctcca gaggtcaaac tgataccacg tggcccaaga ccccaacgat aaatcgcatt 288180
gttagaatga actgtatgga aaattatcca ggcgtggcgg cgggcggctg taatcccagc 288240
tactggggaa gctgaggcag gagaatcact tgaaactagg aggccgaggt tgcagtgagc 288300
caagatcgca ccattgcact ccagcctggg caatagagca aaaacaccat ctcaaaataa 288360
ataaataaat agaatgaact gtattggccg ggtacagtga ctcatgccta taatcccagc 288420
actttgggag gctgaggctg gaggatcgtt tgaggccagg agttcgagac cagcctaggc 288480
aacatagtga gaccctatct ctttttttta aaaaaaaaaa aaaaaaaaa aaagaatgaa 288540
ctatacagtg tgcccaaggg cccctgcta aataaagaca ctcttcaggc aggacatttc 288600
aaaggcttag agatcacctc ccaggagcaa gtcaatgggc cagtccttc atcggaatgt 288660
gcagggtttg gacaacacta gcctactgag ctagtcctta ctgcttagca ccccagcttc 288720
tatgacacct actggattcc cttcctgagg gtttcaaaga ctcctggaga tgtctctgaa 288780
tttggctgtc acagttgtta cttgtacccc agatgccact cagttccctg aagacaatga 288840
tcccccagat ttctcagcca ggagcccctc cacctcttgt cctcagtggg tgccaggcct 288900
catcctggag ttccacagct gagccaggct ctcggggtta cggaaggtca agagggtgtg 288960
gggacaacaa tggaagagtg ataacagtgg cagcccttg agcagatgcg ggtctcagga 289020
gaacataacg cgctttcttt tcatagttca gctcactttc taagcacact gagcttcctt 289080
```

```
tccagcaggc taaggggctg caaaggggt  acagattaac ctcattcttc agattctcaa  289140
aaatggtgtc accattcatt gctggagact gggagaaagg gggcaagtcc atctcattct  289200
ctctgtctct gtctctctct ctctcttccc tgtccatctg tttctctctc ccacccaccc  289260
ctctgttctc tctgcccaga agaatctcta ttttggtttt ggttttgttt gttttgtatt  289320
gttttgagac ggagtctcgt tctgtcgccc aggctggagt gcagtggcgc agtctcaact  289380
caccactgca gcctccacct cccaggttca agcgattctc atgcctcagc ctcccgagta  289440
gttgggatta caggcgcacg ccaccacgcc cagctaattt ttgcattttt actagagact  289500
ggtttcacca tgttgaccag gctggaccct atcctctttc aagcccccca ccccaggcat  289560
tgagggcaga gccaactacc tgcctgaacc aattagcata ttaaacgtaa acccagttag  289620
catatccaaa tagcagccca cagtgacatt ctgactgtca gaatgtggat tgcttgagcc  289680
caggagctca aggcttcggt gaacaaagat tgtgccacag cctgggcaac agagtaagtc  289740
cctgtcgatc gatagataga tgatagatag atagatagat agatagatag atagatagat  289800
agatagatag ataaatttt  aaaaaaata  ataggccagg cacagtggct catgcctgta  289860
atcccagcac tttgggaggc cgaggcaggc agatcacctg aggtcaggag ttcgagacca  289920
gcctggccaa catggtgaaa ccctgtctct acaaaaatat aaaaatagcc aggcagatgt  289980
ctgtaatccc agctactcag gaggctgagg taggagaatc gcttgaactc tgaaggtgga  290040
ggttgcagtg agccgagatc atgccattgc actccagcct gagtgacaga gcgagactcc  290100
atctcaaaaa taataacaat aataaaaata ataataaatg ctctggcccc aaagtggcac  290160
attacatggt gcacacccca ttagcaagga ctcatcacat ggccctgcca accacaggag  290220
gaaccccccc atgtactcag gtaggagggc caggaaacac cgtcagagag ctttaatgac  290280
tcaccccatg actggggtga gggacgaggg actggctgca ggccaagggc atgtccgtgg  290340
cagtggagac ttgggaaagg ggaaaagacc tcctctgagc cacgcacagt ggctttcatc  290400
tgtaattcca gcactttggg aggctgaggt gggaggatct tgagcccagg aggtcgagac  290460
tgcagtgagc tatgtttgtg ccacggcact ctagcctggg cgacagagca aaaccctgtc  290520
tcaaaaatca aaataaaacc aaaaccaaaa cttcctctgt tggggatgct ccagggcgtc  290580
ccagccttga acagatgggt cactgcagta ataatcctat ggcagacact gtcccaaggc  290640
tgcacgcacg ttactttgat catcaaacaa ccaggtgata gccaggcatg gtggtgcgtg  290700
cctgtagtcc cagctactca ggaagctgaa gcgggagaat ctcttgaacc tgggaggcgg  290760
aggtaacagt gagtcgagat cacatgactg cacttcagcc tgggaacaga gagagactct  290820
gtcaaaaaaa aaaaaaaaac aggccagacg cggtggctca cgcatgtaat cgccagcact  290880
ttgggaggct gaggagggtg gatcacctga ggtcaggagt tgagaccag cctggccaac  290940 atggtgaaac cccgtctcta ctaaaaatac aaaattagtt gggcgtggtg gtgcacacct  291000
gtaatcccag ctactcggga ggctgaggca ggagaatcgc ttgaacccag gaggcagagg  291060
ttgcagtgag ctgagattgc accattgcac tccagcctgg caacaagag tgaaactcca  291120 tctcaaaaaa aaacaaaaa  aaaacaacc  agcaggcgc  ggtggcttac gcctgtaatc  291180
ccagcacttt gggaggccga ggcgtgtgga tcacgagg  ttaggagttc gagaccagct  291240
tgaccaacat ggtgaaactc cgtctctact aaaaatacaa aaattagcc aggcatggtg  291300 gtgcatgtct gtaatcccag ctactcggga agctgagaca ggagaattgc ttgaacccag  291360
gagtcggagg ttgcagtgag ccaagctcgt gccactgcac tccagcctgg gcaacagagc  291420
```

```
aagactctgt ctaaaaaaaa aaaaaaaaca cacacacaca cacacaacaa ccaggtgagg   291480
caagtactct tgctatcatc tccatttcac agatggagaa actgagttac taagtggtag   291540
agtaacctaa gtcatgcagc cgataactgg gagacaagat tgggacccag gtcgcccagc   291600
tgttctccat gccgggctgt ctcctgcaca gctgctccat ggtcctggcc ccaccgaaaa   291660
ccagagccca caaggtcatt ccagcagcac tgcccagggc ctcctctggg ccaggccgtt   291720
ggggaactgg agaccccatg gggaccagaa agattgggt ctcgttctcg ggagcctatg    291780
gctttgcagc tgacccagag tccagctgac acccaggcag gcagtcaggg tctgtctaca   291840
cccccattgc aggaggagcc gacaaacagc agatggacgc tgagctgcgg aaggagatga   291900
tggcgatttg gcccaatctg tcccagaaga cgctagacct gctggtcaca cctcacaagt   291960
gtaagagctg agcccagccc tgggatccaa tccaccagga cagatggagg gggagggaaa   292020
ggggaggcct ggggagagtg ttggcctggg ctggtataca cagggaccca ggacaagggc   292080
cccaaagagg cctgcccttg gtgagctcac cgtgtgtgtg cccccagcca cggacctcac   292140
cgtggggaag atctacgcag ccatgatgat catgagtac taccggcaga gcaaggccaa    292200
gaagctgcag gccatgcgcg aggagcaggt gcgctgttcg ccgctctggg gacatctggg   292260
ctggggacag tggcttgcat gtcaccacgg gaaccaactg gaatatgagg gtggctgagc   292320 cccaggcag gtccctgaaa agtaggggct gtgcacagca gctcacacct gcaatctcag    292380
tgctttgaga ggcagggca gagggatcgt ttgagaccag gatgagacca ccctgggcaa    292440
cacagtgaga ctccatctct acaaaataaa acattagcca ggcatggtgg tgcacacctg   292500
tagtcccagc tatttaggag gccaagatgg gaggatcact tgaggccagg agtgggagac   292560
cagtctgggc aacatagaaa gacccatatc tctacaaaaa aaaaataaaa ttagctgcat   292620
gtggcgccat gcacctgtgg tcccagctac ttgggaggct gaggcaggag aatcacttga   292680
acctgggagg tggaggttgc agcaagccaa gatcaagcca ctgcactcca gcccgggtga   292740
taagagcagg actctatctc aaaaaaaaaa aaaaaaaaa aaaaaaagt tcttgccaag     292800 gacacatcat gtggattcat tcttcattca gctgctccac caacacttat tgagtattac   292860
tgtgtgcagg gcgctgttct cagtcctcgg ggatgcaccc atggggaaaa taggccagaa   292920
tccctgccct cagggagcag acattccaag tggggaaatg ccaatggtag caaatgactg   292980
aatcgtgcaa catccagcaa agagaaagaa agtgtcgtgg gggaaagtgg agaagaatcc   293040
agaagatagg agtatccagg ggaggagggg atgcggtggg aaatgggtag ttggggagcc   293100
tccctgagaa agtgacatgt gagcaaaggc ttgaaggaaa aggggagagg gagtgagcta   293160
agcaatacct ggaagggtgt tccaggcaga ggaaacagcc agtgcaaagg ctctgaggct   293220
ggaccgtgcc tgggttgttt gggtaacagc aaagaggcca gtgtggtgga aaagagcagg   293280
gaggagacaa gggcaaggag gtgacagggc agatccttca gggccatggg agctgcagga   293340
aggactctgg cttttccc aagcaagtgg gagccatgga gggttctaag caaaggaggg    293400
ataggacctg actcaagtgc tcatgggcgc cctctggtgg ctcttgtgga acagtggggt   293460
tgaaggtagg agcgggagac ctgggagaag gtgcctgcag tgagagatga ggacgtggga   293520
ccaggctggg gctatgactt gggtggagga gtgagaagtg gtccagttct gcgtggaatt   293580
ggaagggtct agatggatga gacctgagag agtgtgtgtg tgtgtgtgtg tgtatactgg   293640
ggatgtcgca atgccttctg ggtaccaccg tcccaccacc ccaccccttgt ccacacactg   293700 ctctctgccc cattccccag gaccggacac ccctcatgtt ccagcgcatg gagccccgt    293760 ccccaacgca ggaaggggga cctggccaga acgccctccc ctccacccag ctggacccag   293820
```

```
gaggagccct gtgagtgtca cccctgccag ggaggtggag tgtgggggtg ccgtggtccc  293880
cacgttctgg aagctgccca agcgcccact gctaccccgg cctctgtccc ccatgcagga  293940
tggctcacga aagcggcctc aaggagagcc cgtcctgggt gacccagcgt gcccaggaga  294000
tgttccagaa gacgggcaca tggagtccgg aacaaggccc ccctaccgac atgcccaaca  294060
gccagcctaa ctctcaggtg cctctgtccc ccaactcccc aatggctccc agggcccggg  294120
tggttcaggt ggaagggatc tgggcccccc acacacacac acctgcagct ccctccctct  294180
gcagacacca gggatctgga ggtcaggccc cagagctcat ctggctttgc catctgctcc  294240
gcagtccgtg gagatgcgag agatgggcag agatggctac tccgacagcg agcactacct  294300
ccccatggaa ggccagggcc gggctgcctc catgccccgc ctccctgcag agaaccaggt  294360
gagggctttc accactgccc tggggctgga cccctcactc tgcactgggt agggccaggc  294420 cccccacaa gcagcccagt gcatcccctc cctgccggac tcaggcctgg gtagggactc  294480
cttcagtctc tgaagcagtc tgcaggcccc acccaccacc tggtcacacc tggagcacct  294540
gcagaccctc ctccctcaca gaggacagag aggaaagtgc tcccctgggg cagagggca  294600 gtggccactg caaaatggtc tctggctgcc ctggttggag gctgcagaca ggggaggttg  294660
tggaagattt gtgggtgcag cagggttcaa cagggccagc tgagacctgc cacgaagatc  294720
acccctacac aaacacacac acacatgctc aacatacatg cacacacatg tgcagctgtg  294780
cgcctactca gatgcttgca tacacacacg tgtgtgcacg tgggcatata cacactgcac  294840
atgtactcac acatgcacac atgtacgtgc acacgtgtct gcatatggga acttggcagg  294900
tcctaggata cagtagcaga gtctgggtg ggtctggggg cagctgggct cgtattttct  294960
gtctggtctc tgtgggagtc attgggggc acagggtgt gtgcttgatg tgtgtctgtg  295020
tgtggccgct tcacccagct gccaggccca cctgcaggtg atcccgttgc cttggactca  295080
tgggacagag ggcccagagg catagctggc tgcccacccg gcctgaacag cgggggccca  295140
tgcacgcagc ccgcctctgg aggagaacag ggcatggctg tgagagcctg gcccgggtgc  295200
gtggcatgtg tggctgtggc gagctttccg tgtgccgtgt gtggcgtctg cacggggcag  295260
gaggctgtgc tgtgcctggc tggaccaggg tcacctgagg gcctggcctc tggctgctgg  295320
gaacgtgggt tggggagcac ccagcgtgca tgctgctgct ccctcaggac cgagctgctg  295380
ggccccagga gagggttggg acaagcccag ctgacggcca ccacatggaa gctttgagca  295440
tcggccggag ccaggggttg gggtgtgcat cgcatgaggc agagcccagg gccaggggct  295500
cgaggctgcg ccgtcctgtc tttcggtccc atgcctctgc catttgtctg tctgcatctc  295560
ctgtctgtct cctctgtacc catgggaata gaggacgccc agccccgggg gcctgggaca  295620
cccacccgcc aggactttaa cttttctttt cctccctgcc ttctccctcc gatttctctt  295680
gatgccagtg ccactcccct ccttggcttc ttctccatgc accacctcct cactctccct  295740
cttgcctttt atatttattt tcttctttct gttttttctg tgtgcaccat cccatgggc  295800 tgtgacagag gagaaggggc cggccacgtg ggaataacct cagtgtatgt accgcgcctg  295860
cccagcgccc agcagggctc cggcccccte ttcctcccca ccccccctcc agggagtccc  295920
gtcatctctc accgtccccg gaccccaccc tttctttggc aatcgcaccc tctcccctcc  295980
atggagccca atccttgtgt gtggtgtcct gtgtgtgccc ctcacccata gccctggtg  296040 ggcggggcca tccccatcct caccccctacc cccttttctt cagggccccc cacgccgag  296100 gacactggct ctccaagagc ctggcccact ctgcacctct ttctgggggg cttcttctcc  296160
```

```
tgacaccacc accaacccct ggtcctgcag ctcctacctg gagcagggcc accagcgctc  296220
agctgggctg gaccctggga ggcgggcgtc tgcccatct ccctccttcc ctcctctgcc   296280
tgctgcagag aaacctgtgt gtcagggctt gacccaggga tgaagcacca gggaaaagag  296340
tgggccccca gagcctccag tgcctgggta tccccaccc ccacccagag ctccctagct   296400
tgggcctcac cagaaggact cagacttgtg ggggcagcga gcacagcccc gttagccggg  296460
aggacccaaa gctgccatgc cgggcacctg gtcctgagcc cataggtcag ccagccacag  296520
tcggaggctt ctcaccctcc caggagagca agctggggca gggatgagtg cggcagtcca  296580
gggctcccag gtttgcaccc tggatgtgga gagggcttcc ctctggccag cctgagcctg  296640
cccaactgtg gctgggcccc caggactgga gagtgaggat cagatctttc tggtcagaac  296700
ccaggatggg ctcaaaagga gcagtcctgt ctctgaggga cagaggaatc ctcaggctcc  296760
accctcagag gcctggccac acccagagcc ctgattgatc aggggagcc aaggcccat    296820
ggcatcccct ggcccctgcc ccaggatggt cacaccgcag tcaccgaagg ccaccaccag  296880
gctgccacaa tggggcagga aggaccggga ccacttggtg ctagctgctg accccagccc  296940
accggcctgt cccctccccc agaccatctc agacaccagc ccatgaagc gttcagcctc   297000
cgtgctgggc ccaaggccc gacgcctgga cgattactcg ctggagcggg tcccgcccga   297060
ggagaaccag cggcaccacc agcggcgccg cgaccgcagc caccgcgcct ctgagcgctc  297120
cctgggccgc tacaccgatg tggacacagg tgggcagccc tgtggtgctc agggacaagc  297180
agaacagagg agaggagagg ggaggagaag gcagggcgga ggagacacta aggaagaaga  297240
aagggagagg cctccatgga gagggacag aggggggccag gcagcagctg caggaacctg   297300
ggtactaccc cctcccccca acccactgac ctgcctcggt tcagggatc tctagggccc   297360
ccacaccttc caggtggcct cctgtgtgtg catctgcccc acctctccct cacgaccacc  297420
tgtgtgtctg tctgaccctc accggcccca ggcttgggga cagacctgag catgaccacc  297480
caatccgggg acctgccgtc gaaggagcgg gaccaggagc ggggccggcc caaggatcgg  297540
aagcatcgac agcaccacca ccaccaccac caccaccacc atccccgcc ccgacaag     297600
gaccgctatg cccaggaacg gccggaccac ggccgggcac gggctcggga ccagcgctgg  297660
tcccgctcgc ccagcgaggg ccgagagcac atggcgcacc ggcaggtggg tgcggctgca  297720
agtgacccca ggctgggctc ggccgggagg cgggaggag agaaggggat accccatcca   297780
acagccactc taggcaaagg tccccggatc ccggctgtga ccacctccca tcctgccccc  297840
aagccaccgg ggtgcccggc ggccggagcg gacacggatc cccaccacac cagctgccta  297900
tgctgtcccc ccagccccct tgcccacccg ccgccccctc ccgccgcccc gcagctgctt  297960
gctcctcggt tgtggatcat atttgagttc tgggccgtgc cgcccgacct ttcactttcc  298020
tttaacccgg cttctgtttt tgtttcaatt atgatttctg tcctctggac gctgtgagt   298080
aattttttgaa acttctgcta tttttaaccc cgaaacttac aaaactccat ttctcatttc  298140
tcttttcact ttgttgtgtt ggttttcgac tcctcccctc cctgtctcac tcccctcct   298200
cccctccctc ctccctgtgg ctgttgcttt tttccattca atgtcctgtg tcccccctct  298260
cctcctcctc ctcctcctcc cctcccccct cctccctctc ctcccggccc ctctcccttc  298320
gctcccctct cttcctccca atcccgtgtc tcctttgatt tgttgtatc tttttttttg    298380
atttcctttg tttcaatttt cgtgtagggc agtagttccg taagtggaag cccagccccc  298440
tcaacatctg gtaccagcac tccgcggcgg ggccgccgcc agctccccca gaccccctcc  298500
acccccggc cacacgtgtc ctattcccct gtgatccgta aggccggcgg ctcggggccc   298560
```

-continued

```
ccgcagcagc agcagcagca gcagcagcag cagcagcagc aggcggtggc caggccgggc   298620
cgggcggcca ccagcggccc tcggaggtac ccaggcccca cggccgagcc tctgccggga   298680
gatcggccgc ccacgggggg ccacagcagc ggccgctcgc ccaggatgga gaggcgggtc   298740
ccaggcccgg cccggagcga gtcccccagg gcctgtcgac acggcgggc ccggtggccg    298800
gcatctggcc cgcacgtgtc cgaggggccc ccgggtcccc ggcaccatgg ctactaccgg   298860
ggctccgact acgacgaggc cgatggcccg ggcagcgggg gcggcgagga ggccatggcc   298920
ggggcctacg acgcgccacc ccccgtacga cacgcgtcct cgggcgccac cgggcgctcg   298980
cccaggactc cccgggcctc gggcccggcc tgcgcctcgc cttctcggca cggccggcga   299040
ctccccaacg gctactaccc ggcgcacgga ctggccaggc cccgcgggcc gggctccagg   299100
aagggcctgc acgaacccta cagcgagagt gacgatgatt ggtgctaagc ccgggcgagg   299160
tggcgcccgc ccggccccc acgcacccca cgcacacacc ccacccgagg agccgcgcag    299220
aggccgcggg ggcccagcac agagggcccg ggagagggcc agccgggaga ccccagactc   299280
tggagaggcc agggctgggc cacaagggtg tcccgcagag accctcggcc aaaagagacc   299340
ctcctgggca gccacggcgc cccccaacca gccccgatcc ccccacccac gacagggggct  299400
ctcgggtggg aggcagggag cagacaaacc acacagccaa gggatttgaa ttaactcagc   299460
cattttggga gaactttggg gaacatgaaa aaaaaaaaa aaaaaaaaa aaaaaacatt    299520
tttaaagaa aaaacgggga gaaaaaaata gcttctattg atgagttta tcatctcaat    299580
tgaatctttc ctttccctga tgaagacagc tggtggccga gtgcggcaaa gaagccagaa   299640
ggaaccagaa tcccagtgcc ctacacccac caccagacac actcacaccc acacgttc    299700
tcagacacac acaagagtgc ttgccggtta taccaaaccc tactattact gcctgcagaa   299760
atcaatttaa aaaataata ataacaataa acaattttaa aaaggacaaa aaaattaatg    299820
attgagaaaa gaggcatttt tttctgacat ttggtcctgc ttgaaacaac aaaagaagaa   299880
gaaaaaccca ccatcaccac cgattccttt gcttcttttt tccttttttc ctaccttgtt   299940
tgaaaaccgt gggcttggga ctgtgaatta ttgcatgaca ttcaaaaaga aaaaaaaat    300000
aaaaaaaagt tgaatcaaa                                                300019
```

<210> SEQ ID NO 44
<211> LENGTH: 1000
<212> TYPE: DNA
<213> ORGANISM: Artificial Sequence
<220> FEATURE:
<223> OTHER INFORMATION: Construct

<400> SEQUENCE: 44

```
atttcattta tcaggtgttc agtgaatgct tactatgtaa cagcacagtt atcagcactg     60
gggaaataga tgagtaagat aagatttgca ctttcattag cttacatgcc ataaagaggg    120
aaataaagag aacaccagat gatgataagt ttatgctgag aattaaaatg aagtgatgaa    180
ataatgggaa tgtcaggtgg ctacttttgg tgggatggtc aggaaaggca tctctgggga    240
gataaatttt aagctcagac ctgagtgaaa agaatgagcc agccatggaa acattatgtt    300
aactcacatg gtagtttgaa atgctttatc tgatcaaagg tacttatttt tggtgacttt    360
caacaatatt aagggtctat aaaccaacac tcatttgcat aagaataact accagtgaat    420
cttttgtat gataggtttt ttgtttgttg ttttttgag acagagtctc gctctgtcgc      480
ccaggctgga gtgcagtggc gcgatcttgg ctcactgcaa cctctacctc cccggttcaa    540
```

```
gtgattctcc tgcctcagcc tcccaaagta gctgggatta caggtgcctg ccaccacgcc    600
tggctaattt ttgtattttt agtagagatg gggtttcacc gtgttgtcca ggctcgtgtc    660
aaacttctga cctcaagcca tccacccgcc tcggcctccc aaagtgctgg gattacaggt    720
gtgagccacc actcctggcc atgataggtt attttgtgat gaaaatacct acctcttaat    780
ttgtctgata aatttaaatt ttatgtctag atttcctaag atcagcactt ccatattta    840 aagtaatctg tatcagacta actgctcttg cattctttta ataccagtga ctactttgat    900
tcgtgaaaca atgtattttc cttatgaata gttttctca tggtgtattt attcttttaa    960
gttttgtttt ttaaatatac ttcacttttg aatgtttcag                         1000

<210> SEQ ID NO 45
<211> LENGTH: 214
<212> TYPE: DNA
<213> ORGANISM: Artificial Sequence
<220> FEATURE:
<223> OTHER INFORMATION: Construct

<400> SEQUENCE: 45
acagcagcaa aagcagcaac agcagcagca gcagcagcag caggggggacc tatcaggaca    60 gagttcacat ccatgtgaaa ggccagccac cagttcagga gcacttggga gtgatctagg    120
tgatgctatg agtgaagaag acatgcttca ggcagctgtg accatgtctt tagaaactgt    180
cagaaatgat ttgaaaacag aaggaaaaaa ataa                                214

<210> SEQ ID NO 46
<211> LENGTH: 135
<212> TYPE: DNA
<213> ORGANISM: Artificial Sequence
<220> FEATURE:
<223> OTHER INFORMATION: Construct

<400> SEQUENCE: 46
aacttgttta ttgcagctta taatggttac aaataaagca atagcatcac aaatttcaca    60
aataaagcat ttttttcact gcattctagt tgtggtttgt ccaaactcat caatgtatct    120
tatcatgtct ggatc                                                    135

<210> SEQ ID NO 47
<211> LENGTH: 208
<212> TYPE: DNA
<213> ORGANISM: Artificial Sequence
<220> FEATURE:
<223> OTHER INFORMATION: Construct

<400> SEQUENCE: 47
tccccagcat gcctgctatt ctcttcccaa tcctccccct tgctgtcctg ccccaccca    60 ccccccagaa tagaatgaca cctactcaga caatgcgatg caatttcctc attttattag    120
gaaaggacag tgggagtggc accttccagg gtcaaggaag gcacggggga ggggcaaaca    180
acagatggct ggcaactaga aggcacag                                      208

<210> SEQ ID NO 48
<211> LENGTH: 214
<212> TYPE: DNA
<213> ORGANISM: Artificial Sequence
<220> FEATURE:
<223> OTHER INFORMATION: Construct

<400> SEQUENCE: 48
ctacttcttg ccctcggtct tcaggtcgtt gcgcacggtc tccaggctca tggtcacggc    60
```

```
ggcctgcagc atgtcctcct cgctcatggc gtcgcccagg tcgctgccca gggcgccgct    120
gctggtggcg gggcgctcgc aggggtggct gctctggccg ctcaggtcgc cctgctgctg    180
ctgctgctgc tgctgctgct gcttctgctg ctgt                                214

<210> SEQ ID NO 49
<211> LENGTH: 110
<212> TYPE: DNA
<213> ORGANISM: Artificial Sequence
<220> FEATURE:
<223> OTHER INFORMATION: Construct

<400> SEQUENCE: 49
ctgtaaatga atgagaaaac cggtttagaa agtgcacagc tgtcagggaa gtcaacactt     60
cagtgagcat gtgaccatgt ggagtcagct tcctgtttcg tgctgcaatc                110

<210> SEQ ID NO 50
<211> LENGTH: 374
<212> TYPE: DNA
<213> ORGANISM: Artificial Sequence
<220> FEATURE:
<223> OTHER INFORMATION: Construct

<400> SEQUENCE: 50
gtaaggcctg ctcaccattc atcatgttcg ctaccttcac actttatctg acatacgagc     60
tccatgtgat ttttgcttta cattattctt cattccctct ttaatcatat taagaatctt    120
aagtaaattt gtaatctact aaatttccct ggattaagga gcagttacca aaagaaaaaa    180
aaaaaaaaaa gctagatgtg gtggctcaca tctgtaatcc cagcactttg ggaaaccaag    240
gcaggagagg attgctagaa catttaatga atactttaac ataataattt aaacttcaca    300
gtaatttgta cagtctccaa aaattcctta gacatcatgg atatttttct tttttttgaga    360 tggagtcttg ctct                                                      374

<210> SEQ ID NO 51
<211> LENGTH: 136
<212> TYPE: DNA
<213> ORGANISM: Artificial Sequence
<220> FEATURE:
<223> OTHER INFORMATION: Target site

<400> SEQUENCE: 51
tttaagctca gacctgagtg aaaagaattt gagacagagt ctcgctctgt cgcctttcct     60
aagatcagca cttccatatt tggtgacttt caacaatatt aagggtctat aaaccaacac    120
tcatttgcat aagaat                                                    136
```

METHODS FOR TARGETED INSERTION OF DNA IN GENES

REFERENCE TO RELATED APPLICATIONS

This application is a continuation of previously filed and application U.S. Ser. No. 17/590,613, filed Feb. 1, 2022, now U.S. Pat. No. 11,365,407, which is a continuation of U.S. Ser. No. 17/366,290 filed Jul. 2, 2021, now U.S. Pat. No. 11,254,930, which is a continuation of U.S. Ser. No. 16/800,444 filed Feb. 25, 2020, now U.S. Pat. No. 11,091,756, which is a continuation of U.S. Ser. No. 16/601,144 filed Oct. 14, 2019, which claims the benefit of previously filed applications U.S. Ser. No. 62/746,497 filed Oct. 16, 2018, U.S. Ser. No. 62/830,654 filed Apr. 8, 2019, and U.S. Ser. No. 62/864,432 filed Jun. 20, 2019, the contents of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Oct. 14, 2019 is named 2019-10-14_BALTES_P12987US03_SEQUENCE_LISTING_BA2018 4WO.txt and is 517,077 bytes in size.

TECHNICAL FIELD

The present document is in the field of genome editing. More specifically, this document relates to the targeted modification of endogenous genes using rare-cutting endonucleases or transposases.

BACKGROUND

Monogenic disorders are caused by one or more mutations in a single gene, examples of which include sickle cell disease (hemoglobin-beta gene), cystic fibrosis (cystic fibrosis transmembrane conductance regulator gene), and Tay-Sachs disease (beta-hexosaminidase A gene). Monogenic disorders have been an interest for gene therapy, as replacement of the defective gene with a functional copy could provide therapeutic benefits. However, one bottleneck for generating effective therapies includes the size of the functional copy of the gene. Many delivery methods, including those that use viruses, have size limitations which hinder the delivery of large transgenes. Further, many genes have alternative splicing patterns resulting in a single gene coding for multiple proteins. Methods to correct partial regions of a defective gene may provide an alternative means to treat monogenic disorders.

SUMMARY

Gene editing holds promise for correcting mutations found in genetic disorders; however, many challenges remain for creating effective therapies for individual disorders, including those that are caused by gain-of-function mutations, or where precise repair is required. These challenges are seen with disorders such as spinocerebellar ataxia 3 and spinocerebellar ataxia 6, wherein the disorder is caused by gain-of-function mutations (expanded trinucleotide repeat) at the 3' end of the genes.

The methods described herein provide novel approaches for correcting mutations found at the 3' end of genes. The disclosure herein is based at least in part on the design of bimodule transgenes compatible with integration through multiple repair pathways. The transgenes described herein can be integrated into genes by the homologous recombination pathway, the non-homologous end joining pathway, or both the homologous recombination and non-homologous end joining pathway, or through transposition. Further, the outcome of integration in any case (HR, NHEJ forward, NHEJ reverse; transposition forward, or transposition reverse) can result in precise correction/alteration of the target gene's protein product. The transgenes described herein can be used to fix or introduce mutations in the 3' region of genes-of-interest. The methods are particularly useful in cases where precise editing of genes is necessary, or where the mutated endogenous gene being targeted cannot be 'replaced' by a synthetic copy because it exceeds the size capacity of standard vectors or viral vectors. The methods described herein can be used for applied research (e.g., gene therapy) or basic research (e.g., creation of animal models, or understanding gene function).

The methods described herein are compatible with current in vivo delivery vehicles (e.g., adeno-associated virus vectors and lipid nanoparticles), and they address several challenges with achieving precise alteration of gene products.

In one embodiment, this document features a method for integrating a transgene into an endogenous gene. The method can include delivery of a transgene, where the transgene harbors a first and second splice acceptor sequence, a first and second partial coding sequence, and a first and second terminator. In some embodiments, the first and second terminators can be replaced with a single bidirectional terminator. The method further includes administering one or more rare-cutting endonucleases targeted to a site within the endogenous gene, where the transgene is then integrated into the endogenous gene. The transgene can be targeted to a site within an intron or at an intron-exon junction. The first and second partial coding sequences can be oriented in a tail-to-tail orientation, such that integration of the transgene in either direction (i.e., forward or reverse) by NHEJ can result in precise alteration of the gene's protein product. In other embodiments, the transgene can include a left and right homology arm to enable integration by HR. These transgenes can be harbored within an adeno-associated virus vector (AAV), wherein the transgene can be integrated via HR (through the homology arms) or by NHEJ forward direction or NHEJ reverse direction (through direct integration of the AAV vector within a targeted double-strand break). In an embodiment, vectors with a first and second coding sequence and a left and right homology arm can further include a first and second site for cleavage by one or more rare-cutting endonucleases. Cleavage by the one or more rare-cutting endonucleases can result in liberation of a linear transgene with homology arms, capable of integrating into the genome through HR or NHEJ. In another embodiment, vectors with a first and second coding sequence can be flanked by a first and second site for cleavage by one or more rare-cutting endonucleases. Cleavage by the one or more rare-cutting endonucleases can result in liberation of a linear transgene, capable of integrating into the genome through NHEJ. In another embodiment, vectors with a first and second coding sequence can be flanked by a left and right transposon end. Delivery of a CRISPR-associated transposase (e.g., Cas6/7/8 along with TniQ, TnsA, TnsB, and TnsC) can result in integration of the transgene through transposition.

The methods can be used to alter the C-terminus of proteins produced by endogenous genes. In some embodiments, the endogenous gene can include the ATXN3 gene or CACNA1A gene. ATXN3 is a gene that encodes the enzyme ataxin-3. Ataxin-3 is a member in the ubiquitin-proteasome system which facilitates the destruction of excess or damaged proteins. Spinocerebellar ataxia type 3 is a genetic disorder caused by a trinucleotide repeat expansion within the 3' end of the ATXN3 gene. CACNA1A is a gene that encodes proteins involved in the formation of calcium channels. Spinocerebellar ataxia type 6 is a genetic disorder caused by mutations in the CACNA1A gene. The mutations which cause SCA6 include a trinucleotide repeat expansion in the 3' end of the CACNA1A gene. In some embodiments, the methods provided herein can be used to alter the 3' end of the endogenous ATXN3 gene or CACNA1A gene. In specific embodiments, the target for integration of the transgenes described herein can be intron 9 of the ATXN3 gene or intron 46 of the CACNA1A gene.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety for all purposes. In case of conflict, the present specification, including definitions, will control. In addition, the materials, methods, and examples are illustrative only and not intended to be limiting.

The details of one or more embodiments of the invention are set forth in the description below. Other features, objects, and advantages of the invention will be apparent from the description and from the claims.

DETAILED DESCRIPTION

Figure 1:
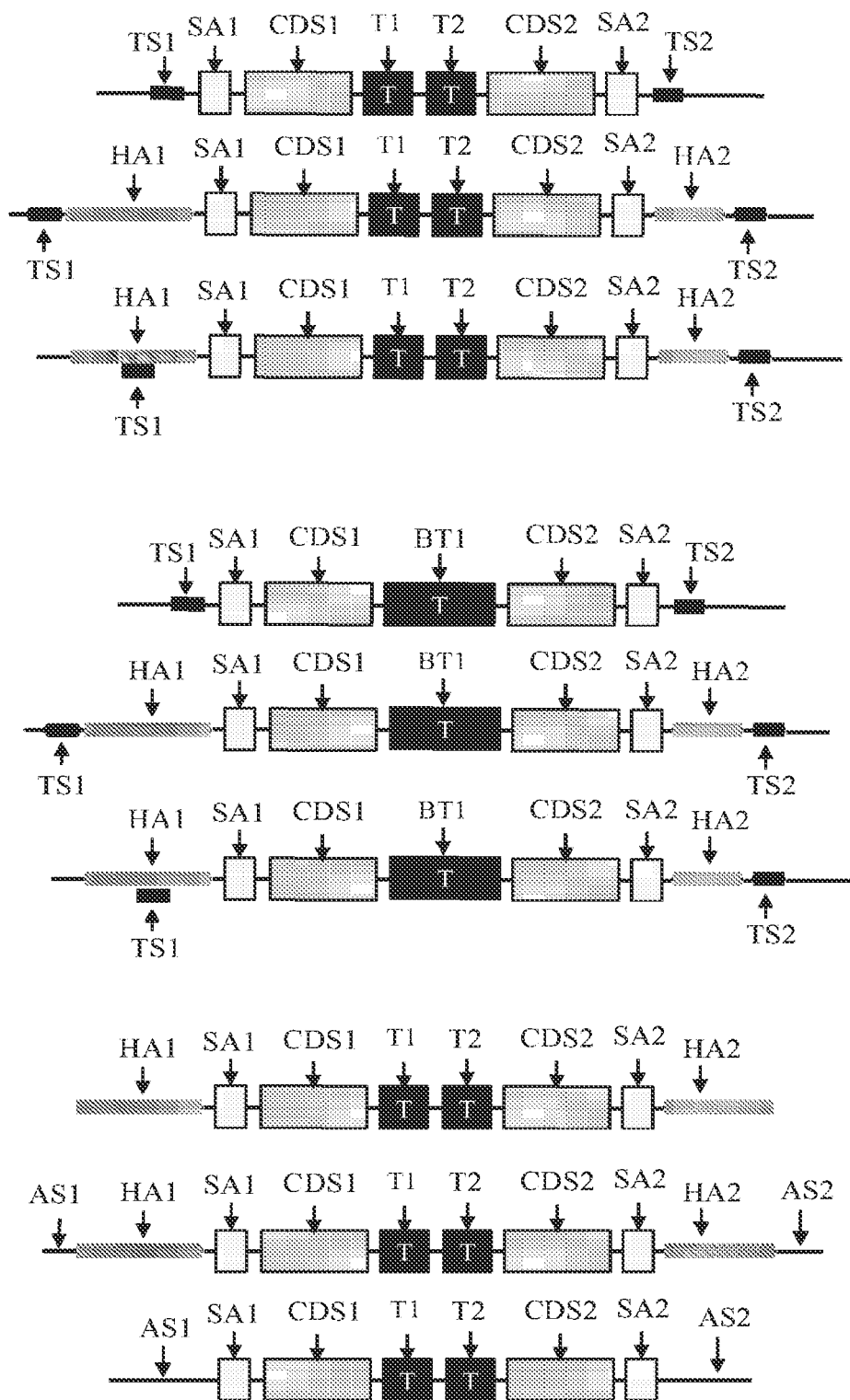
FIG. 1 is an illustration of the transgenes for the targeted insertion into endogenous genes. TS1, target site 1; SA1, splice acceptor site 1, CDS1, coding sequence 1; T1, terminator 1, TS2, target site 2; SA2, splice acceptor site 2, CDS2, coding sequence 2; T2, terminator 2; HA1, homology arm 1; HA2, homology arm 2; BT1, bidirectional terminator 1; AS1, additional sequence 1; AS2, additional sequence 2.

Disclosed herein are methods and compositions for modifying the coding sequence of endogenous genes. In some embodiments, the methods include inserting a transgene into an endogenous gene, wherein the transgene provides a partial coding sequence which substitutes for the endogenous gene's coding sequence.

In one embodiment, this document features a method of integrating a transgene into an endogenous gene, the method including administering a transgene, wherein the transgene comprises a first and second splice acceptor sequence, a first and second partial coding sequence, and one bidirectional terminator or a first and second terminator, and administering one or more rare-cutting endonuclease targeted to a site within the endogenous gene, wherein the transgene is integrated within the endogenous gene. The method can include designing the transgene to have the first splice acceptor operably linked to the first partial coding sequence and the second splice acceptor operably linked to the second partial coding sequence. The arrangement can also include having the first partial coding sequence operably linked to the first terminator, and the second partial coding sequence operably linked to the second terminator. In an embodiment, the two terminators can be replaced with a single bidirectional terminator. In an embodiment, transgenes with first and second splice acceptors, first and second partial coding sequences, and first and second terminators can be oriented in a tail-to-tail orientation. The transgenes with a tail-to-tail orientation of sequences can further comprise a first and second target site for one or more rare-cutting endonucleases, wherein the target sites flank the first and second splice acceptors. In another embodiment, the transgenes can comprise a left and right homology arm which flank the first and second splice acceptors. In this embodiment, the transgene can be harbored within an adeno-associated viral vector. In another embodiment, the transgene can further comprise a first and second target site for the one or more rare-cutting endonucleases, wherein the target sites flank the first and second splice acceptors. The first and second target sites can flank the first and second homology arms. In embodiments, the transgenes described herein can be integrated within an intron of the endogenous gene or at an intron-exon junction. The transgenes can be integrated within an intron, or at the intron-exon junction of the ATXN3 gene or CACNA1A gene. The transgene can comprise a first and second partial coding sequence encoding the peptide produced by exon 10 of a non-pathogenic ATXN3 gene and can be targeted to intron 9, or the intron 9 exon 10 junction, of a pathogenic ATXN3 gene. The transgene can comprise a first and second partial coding sequence encoding the peptide produced by exon 47 of a non-pathogenic CACNA1A gene and can be targeted to intron 46, or the intron 46 exon 47 junction, of a pathogenic CACNA1A gene. In certain embodiments, the rare-cutting endonuclease can be a CRISPR/Cas12a nuclease or a CRISPR/Cas9 nuclease. The first and second partial coding sequences encode the same amino acids. In an embodiment, the first and second coding sequences can differ in nucleic acid sequence but encode the same amino acids. The transgene can be harbored on a vector, wherein the vector format is selected from double-stranded linear DNA, double-stranded circular DNA, or a viral vector. The viral vector can include an adenovirus vector, an adeno-associated virus vector, or a lentivirus vector. The methods described here can be used with a transgene equal to or less than 4.7 kb. The transgene can comprise a first and second partial coding sequence that encode a partial peptide from a functional protein produced by the target endogenous gene. The target endogenous gene can be aberrant.

In another embodiment, this document provides DNA polynucleotides with a first and second splice acceptor sequence, a first and second partial coding sequence, one bidirectional terminator or a first and second terminator, optionally, a first and second homology arm, and, optionally, a first and second rare-cutting endonuclease target site. The DNA polynucleotides can include a design having the first splice acceptor operably linked to the first partial coding sequence and the second splice acceptor operably linked to the second coding sequence. The arrangement can also include having the first partial coding sequence operably linked to the first terminator, and the second partial coding sequence operably linked to the second terminator. In an embodiment, the two terminators can be replaced with a single bidirectional terminator. In an embodiment, DNA polynucleotides with first and second splice acceptors, first and second coding sequences, and first and second terminators can be oriented in a tail-to-tail orientation. The DNA polynucleotides with a tail-to-tail orientation of sequences can further comprise a first and second target site for one or more rare-cutting endonucleases, wherein the target sites flank the first and second splice acceptors. In another embodiment, the DNA polynucleotides can comprise a left and right homology arm which flank the first and second splice acceptors. In this embodiment, the DNA polynucleotide can be harbored within an adeno-associated viral vector. In another embodiment, the DNA polynucleotides can further comprise a first and second target site for one or more rare-cutting endonucleases, wherein the target sites flank the first and second splice acceptors. The first and second target sites can flank the first and second homology arms. In embodiments, the DNA polynucleotides described herein can be integrated within an intron of the endogenous gene or at an intron-exon junction. The DNA polynucleotides can be integrated within an intron, or at the intron-exon junction of the ATXN3 gene or CACNA1A gene. The DNA polynucleotide can comprise a first and second partial coding sequence encoding the peptide produced by exon 10 of a non-pathogenic ATXN3 gene. The DNA polynucleotide can comprise a first and second partial coding sequence encoding the peptide produced by exon 47 of a non-pathogenic CACNA1A gene. The first and second partial coding sequences encode the same amino acids. In an embodiment, the first and second coding sequences can differ in nucleic acid sequence but encode the same amino acids. The DNA polynucleotides can be harbored on a vector, wherein the vector format is selected from double-stranded linear DNA, double-stranded circular DNA, or a viral vector. The viral vector can be selected from an adenovirus vector, an adeno-associated virus vector, or a lentivirus vector. The DNA polynucleotides described here can be equal to or less than 4.7 kb.

In one embodiment, this document features a method of integrating a transgene into an endogenous gene, the method including administering a transgene, wherein the transgene comprises a left and right transposon end, a first and second splice acceptor sequence, a first and second partial coding sequence, and one bidirectional terminator or a first and second terminator, and administering a transposase targeted to the endogenous gene, where the transgene is integrated in the endogenous gene. The method can include designing the transgene to have the first splice acceptor operably linked to the first partial coding sequence and the second splice acceptor operably linked to the second coding sequence. The arrangement can also include having the first partial coding sequence operably linked to the first terminator, and the second partial coding sequence operably linked to the second terminator. In an embodiment, the two terminators can be replaced with a single bidirectional terminator. In an embodiment, transgenes with first and second splice acceptors, first and second coding sequences, and first and second terminators can be oriented in a tail-to-tail orientation. The transgenes with a tail-to-tail orientation of sequences can further comprise a left and right transposon end flanking the first and second splice acceptors. In embodiments, the transgenes described herein can be integrated within an intron of the endogenous gene or at an intron-exon junction. The transgenes can be integrated within an intron, or at the intron-exon junction of the ATXN3 gene or CACNA1A gene. The transgene can comprise a first and second partial coding sequence encoding the peptide produced by exon 10 of a non-pathogenic ATXN3 gene and can be targeted to intron 9, or the intron 9 exon 10 junction, of a pathogenic ATXN3 gene. The transgene can comprise a first and second partial coding sequence encoding the peptide produced by exon 47 of a non-pathogenic CACNA1A gene and can be targeted to intron 46, or the intron 46 exon 47 junction, of a pathogenic CACNA1A gene. The transposase can be a CRISPR transposase, where the CRISPR transposase comprises the Cas12k or Cas6 protein. The first and second partial coding sequences encode the same amino acids. In an embodiment, the first and second coding sequences can differ in nucleic acid sequence but encode the same amino acids. The transgene can be harbored on a vector, wherein the vector format is selected from double-stranded linear DNA, double-stranded circular DNA, or a viral vector. The viral vector iscan include an adenovirus vector, an adeno-associated virus vector, or a lentivirus vector. The methods described here can be used with a transgene equal to or less than 4.7 kb. The left end can comprise the sequence shown in SEQ ID NO:41, and the right end can comprise the sequence shown in SEQ ID NO:13.

In another embodiment, this document provides DNA polynucleotides with a first and second splice acceptor sequence, a first and second partial coding sequence, one bidirectional terminator or a first and second terminator, and a left and right transposon end. The DNA polynucleotides can include a design having the first splice acceptor operably linked to the first partial coding sequence and the second splice acceptor operably linked to the second coding sequence. The arrangement can also include having the first partial coding sequence operably linked to the first terminator, and the second partial coding sequence operably linked to the second terminator. In an embodiment, the two terminators can be replaced with a single bidirectional terminator. In an embodiment, DNA polynucleotides with first and second splice acceptors, first and second coding sequences, and first and second terminators can be oriented in a tail-to-tail orientation. The DNA polynucleotides with a tail-to-tail orientation of sequences can further comprise a left and right transposon end which flank the first and second splice acceptors. In embodiments, the DNA polynucleotides described herein can be integrated within an intron of the endogenous gene or at an intron-exon junction. The DNA polynucleotides can be integrated within an intron, or at the intron-exon junction of the ATXN3 gene or CACNA1A gene. The DNA polynucleotide can comprise a first and second partial coding sequence encoding the peptide produced by exon 10 of a non-pathogenic ATXN3 gene. The DNA polynucleotide can comprise a first and second partial coding sequence encoding the peptide produced by exon 47 of a non-pathogenic CACNA1A gene. The first and second partial coding sequences encode the same amino acids. In an embodiment, the first and second coding sequences can differ in nucleic acid sequence but encode the same amino acids. The DNA polynucleotides can be harbored on a vector, wherein the vector format is selected from double-stranded linear DNA, double-stranded circular DNA, or a viral vector. The viral vector can be selected from an adenovirus vector, an adeno-associated virus vector, or a lentivirus vector. The DNA polynucleotides described here can be equal to or less than 4.7 kb. The left end can comprise the sequence shown in SEQ ID NO:41, and the right end can comprise the sequence shown in SEQ ID NO: 13.

In one embodiment, this document features a method of integrating a transgene into an endogenous gene, the method including administering a transgene, wherein the transgene comprises a first and second splice acceptor sequence, a first and second coding sequence, one bidirectional terminator or a first and second terminator, and a first and second homology arm, wherein the transgene is integrated within the endogenous gene. The method can include designing the transgene to have the first splice acceptor operably linked to the first partial coding sequence and the second splice acceptor operably linked to the second coding sequence. The arrangement can also include having the first partial coding sequence operably linked to the first terminator, and the second partial coding sequence operably linked to the second terminator. In an embodiment, the two terminators can be replaced with a single bidirectional terminator. The homology arms can flank the first and second splice acceptor sequence, the first and second coding sequence, the one bidirectional terminator or the first and second terminator. The coding sequence can encode a full coding sequence or a partial coding sequence. In an embodiment, transgenes with first and second splice acceptors, first and second coding sequences, and first and second terminators can be oriented in a tail-to-tail orientation. The transgenes with a tail-to-tail orientation of sequences can further comprise a first and second target site for one or more rare-cutting endonucleases, wherein the target sites flank the first and second splice acceptors. In another embodiment, the transgenes can comprise a left and right homology arm which flank the first and second splice acceptors. In this embodiment, the transgene can be harbored within an adeno-associated viral vector. In another embodiment, the transgene can further comprise a first and second target site for the one or more rare-cutting endonucleases, wherein the target sites flank the first and second splice acceptors. The first and second target sites can flank the first and second homology arms. In embodiments, the transgenes described herein can be integrated within an intron of the endogenous gene or at an intron-exon junction.

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

As used herein, the terms "nucleic acid" and "polynucleotide," can be used interchangeably. Nucleic acid and polynucleotide can refer to a deoxyribonucleotide or ribonucleotide polymer, in linear or circular conformation, and in either single- or double-stranded form. These terms are not to be construed as limiting with respect to the length of a polymer. The terms can encompass known analogues of natural nucleotides, as well as nucleotides that are modified in the base, sugar and/or phosphate moieties.

The terms "polypeptide," "peptide" and "protein" can be used interchangeably to refer to amino acid residues covalently linked together. The term also applies to proteins in which one or more amino acids are chemical analogues or modified derivatives of corresponding naturally occurring amino acids.

The terms "operatively linked" or "operably linked" are used interchangeably and refer to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence but need not be directly adjacent to it. For example, an enhancer is a transcriptional regulatory sequence that is operatively linked to a coding sequence, even though they are not contiguous. Further, by way of example, a splice acceptor can be operably linked to a partial coding sequence if the splice acceptor enables delineation of an intron's 3' boundary, and if translation of the resulting mature mRNA results in incorporation of the peptide sequence encoded by the partial coding sequence into the final protein product.

As used herein, the term "cleavage" refers to the breakage of the covalent backbone of a nucleic acid molecule. Cleavage can be initiated by a variety of methods including, but not limited to, enzymatic or chemical hydrolysis of a phosphodiester bond. Cleavage can refer to both a single-stranded nick and a double-stranded break. A double-stranded break can occur as a result of two distinct single-stranded nicks. Nucleic acid cleavage can result in the production of either blunt ends or staggered ends. In certain embodiments, rare-cutting endonucleases are used for targeted double-stranded or single-stranded DNA cleavage.

An "exogenous" molecule can refer to a small molecule (e.g., sugars, lipids, amino acids, fatty acids, phenolic compounds, alkaloids), or a macromolecule (e.g., protein, nucleic acid, carbohydrate, lipid, glycoprotein, lipoprotein, polysaccharide), or any modified derivative of the above molecules, or any complex comprising one or more of the above molecules, generated or present outside of a cell, or not normally present in a cell. Exogenous molecules can be introduced into cells. Methods for the introduction or "administering" of exogenous molecules into cells can include lipid-mediated transfer, electroporation, direct injection, cell fusion, particle bombardment, calcium phosphate co-precipitation, DEAE-dextran-mediated transfer and viral vector-mediated transfer. As defined herein, "administering" can refer to the delivery, the providing, or the introduction of exogenous molecules into a cell. If a transgene or a rare-cutting endonuclease is administered to a cell, then the transgene or rare-cutting endonuclease is delivered to, provided, or introduced into the cell. The rare-cutting endonuclease can be administered as purified protein, nucleic acid, or a mixture of purified protein and nucleic acid. The nucleic acid (i.e., RNA or DNA), can encode for the rare-cutting endonuclease, or a part of a rare-cutting endonuclease (e.g., a gRNA). The administering can be achieved though methods such as lipid-mediated transfer, electroporation, direct injection, cell fusion, particle bombardment, calcium phosphate co-precipitation, DEAE-dextran-mediated transfer, viral vector-mediated transfer, or any means suitable of delivering purified protein or nucleic acids, or a mixture of purified protein and nucleic acids, to a cell.

An "endogenous" molecule is a molecule that is present in a particular cell at a particular developmental stage under particular environmental conditions. An endogenous molecule can be a nucleic acid, a chromosome, the genome of a mitochondrion, chloroplast or other organelle, or a naturally occurring episomal nucleic acid. Additional endogenous molecules can include proteins, for example, transcription factors and enzymes.

As used herein, a "gene," refers to a DNA region encoding that encodes a gene product, including all DNA regions which regulate the production of the gene product. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. As used herein, a "wild type gene" refers to a form of the gene that is present at the highest frequency in a particular population.

An "endogenous gene" refers to a DNA region normally present in a particular cell that encodes a gene product as well as all DNA regions which regulate the production of the gene product.

"Gene expression" refers to the conversion of the information, contained in a gene, into a gene product. A gene product can be the direct transcriptional product of a gene. For example, the gene product can be, but not limited to, mRNA, tRNA, rRNA, antisense RNA, ribozyme, structural RNA, or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Encoding" refers to the conversion of the information contained in a nucleic acid, into a product, wherein the product can result from the direct transcriptional product of a nucleic acid sequence. For example, the product can be, but not limited to, mRNA, tRNA, RNA, antisense RNA, ribozyme, structural RNA, or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

A "target site" or "target sequence" defines a portion of a nucleic acid to which a rare-cutting endonuclease or CRISPR-associated transposase will bind, provided sufficient conditions for binding exist.

As used herein, the term "recombination" refers to a process of exchange of genetic information between two polynucleotides. The term "homologous recombination (HR)" refers to a specialized form of recombination that can take place, for example, during the repair of double-strand breaks. Homologous recombination requires nucleotide sequence homology present on a "donor" molecule. The donor molecule can be used by the cell as a template for repair of a double-strand break. Information within the donor molecule that differs from the genomic sequence at or near the double-strand break can be stably incorporated into the cell's genomic DNA.

The term "integrating" as used herein refers to the process of adding DNA to a target region of DNA. As described herein, integration can be facilitated by several different means, including non-homologous end joining, homologous recombination, or targeted transposition. By way of example, integration of a user-supplied DNA molecule into a target gene can be facilitated by non-homologous end joining. Here, a targeted-double strand break is made within the target gene and a user-supplied DNA molecule is administered. The user-supplied DNA molecule can comprise exposed DNA ends to facilitate capture during repair of the target gene by non-homologous end joining. The exposed ends can be present on the DNA molecule upon administration (i.e., administration of a linear DNA molecule) or created upon administration to the cell (i.e., a rare-cutting endonuclease cleaves the user-supplied DNA molecule within the cell to expose the ends). Additionally, the user-supplied DNA molecule can be harbored on a viral vector, including an adeno-associated virus vector. In another example, integration occurs though homologous recombination. Here, the user-supplied DNA can harbor a left and right homology arm. In another example, integration occurs through transposition. Here, the user-supplied DNA harbors a transposon left and right end.

The term "transgene" as used herein refers to a sequence of nucleic acids that can be transferred to an organism or cell. The transgene may comprise a gene or sequence of nucleic acids not normally present in the target organism or cell. Additionally, the transgene may comprise a copy of a gene or sequence of nucleic acids that is normally present in the target organism or cell. A transgene can be an exogenous DNA sequence introduced into the cytoplasm or nucleus of a target cell. In one embodiment, the transgenes described herein contain partial coding sequences, wherein the partial coding sequences encodes a portion of a protein produced by a gene in the host cell.

As used herein, the term "pathogenic" refers to anything that can cause disease. A pathogenic mutation can refer to a modification in a gene which causes disease. A pathogenic gene refers to a gene comprising a modification which causes disease. By means of example, a pathogenic ATXN3 gene in patients with spinocerebellar ataxia 3 refers to an ATXN3 gene with an expanded CAG trinucleotide repeat, wherein the expanded CAG trinucleotide repeat causes the disease.

As used herein, the term "tail-to-tail" refers to an orientation of two units in opposite and reverse directions. The two units can be two sequences on a single nucleic acid molecule, where the 3' end of each sequence are placed adjacent to each other. For example, a first nucleic acid having the elements, in a 5' to 3' direction, [splice acceptor 1]-[partial coding sequence 1]-[terminator 1] and a second nucleic acid having the elements [splice acceptor 2]-[partial coding sequence 2]-[terminator 2] can be placed in tail-to-tail orientation resulting in [splice acceptor 1]-[partial coding sequence 1]-[terminator 1]-[terminator 2 RC]-[partial coding sequence 2 RC]-[splice acceptor 2 RC], where RC refers to reverse complement.

The term "intron-exon junction" refers to a specific location within a gene. The specific location is between the last nucleotide in an intron and the first nucleotide of the following exon. When integrating a transgene described herein, the transgene can be integrated within the "intron-exon junction." If the transgene comprises cargo, the cargo will be integrated immediately following the last nucleotide in the intron. In some cases, integrating a transgene within the intron-exon junction can result in removal of sequence within the exon (e.g., integration via HR and replacement of sequence within the exon with the cargo within the transgene).

The term "homologous" as used herein refers to a sequence of nucleic acids or amino acids having similarity to a second sequence of nucleic acids or amino acids. In some embodiments, the homologous sequences can have at least 80% sequence identity (e.g., 81%, 85%, 90%, 95%, 96%, 97%, 98%, or 99% sequence identity) to one another.

The term "partial coding sequence" as used herein refers to a sequence of nucleic acids that encodes a partial protein. The partial coding sequence can encode a protein that comprises one or less amino acids as compared to the wild type protein or functional protein. The partial coding sequence can encode a partial protein with homology to the wild type protein or functional protein. The term "partial coding sequence" when referring to ATXN3 refers to a sequence of nucleic acids that encodes a partial ATXN3 protein. The partial ATXN3 protein has one or less amino acids compared to a wild type ATXN3 protein. If modifying the 3' end of the gene, the one or less amino acids can be from the N-terminus end of the protein. If the ATXN3 gene has 11 exons, then the partial coding sequence can comprise sequence encoding the peptide produced by exons 2-11, or 3-11 or 4-11, or 5-11, or 6-11, or 7-11, or 8-11, or 9-11, or 10-11, or 11.

The methods and compositions described in this document can use transgenes having a cargo sequence. The term "cargo" can refer to elements such as the complete or partial coding sequence of a gene, a partial sequence of a gene harboring single-nucleotide polymorphisms relative to the WT or altered target, a splice acceptor, a terminator, a transcriptional regulatory element, purification tags (e.g., glutathione-S-transferase, poly(His), maltose binding protein, Strep-tag, Myc-tag, AviTag, HA-tag, or chitin binding protein) or reporter genes (e.g., GFP, RFP, lacZ, cat, luciferase, puro, neomycin). As defined herein, "cargo" can refer to the sequence within a transgene that is integrated at a target site. For example, "cargo" can refer to the sequence on a transgene between two homology arms, two rare-cutting endonuclease target sites, or a left and right transposon end.

The term "homology sequence" refers to a sequence of nucleic acids that comprises homology to a second nucleic acid. Homology sequence, for example, can be present on a donor molecule as an "arm of homology" or "homology arm." A homology arm can be a sequence of nucleic acids within a donor molecule that facilitates homologous recombination with the second nucleic acid. As defined herein, a homology arm can also be referred to as an "arm". In a donor molecule with two homology arms, the homology arms can be referred to as "arm 1" and "arm 2." In one aspect, a cargo sequence can be flanked with first and second homology arm.

The term "bidirectional terminator" refers to a terminator that can terminate RNA polymerase transcription in either the sense or antisense direction. In contrast to two unidirectional terminators in tail-to-tail orientation, a bidirectional terminator can comprise a non-chimeric sequence of DNA. Examples of bidirectional terminators include the ARO4, TRP1, TRP4, ADH1, CYC1, GAL1, GAL7, and GAL10 terminator.

A 5' or 3' end of a nucleic acid molecule references the directionality and chemical orientation of the nucleic acid. As defined herein, the "5' end of a gene" can comprise the exon with the start codon, but not the exon with the stop codon. As defined herein, the "3' end of a gene" can comprise the exon with the stop codon, but not the exon with the start codon.

The term "ATXN3" gene refers to a gene that encodes the enzyme ataxin-3. A representative sequence of the ATXN3 gene can be found with NCBI Reference Sequence: NG_008198.2 and corresponding SEQ ID NO:42. The exon and intron boundaries can be defined with the sequence provided in SEQ ID NO:42. Specifically, exon 1 includes the sequence from 1 to 54. Exon 2 includes the sequence from 9745 to 9909. Exon 3 includes the sequence from 10446 to 10490. Exon 4 includes the sequence from 12752 to 12837. Exon 5 includes the sequence from 13265 to 13331. Exon 6 includes the sequence from 17766 to 17853. Exon 7 includes the sequence from 23325 to 23457. Exon 8 includes the sequence from 24117 to 24283. Exon 9 includes the sequence from 25522 to 25618. Exon 10 includes the sequence from 35530 to 35648. Exon 11 includes the sequence from 42169 to 48031. Intron 1 includes the sequence from 55 to 9744. Intron 2 includes the sequence from 9910 to 10445. Intron 3 includes the sequence from 10491 to 12751. Intron 4 includes the sequence from 12838 to 13264. Intron 5 includes the sequence from 13332 to 17765. Intron 6 includes the sequence from 17854 to 23324. Intron 7 includes the sequence from 23458 to 24116. Intron 8 includes the sequence from 24284 to 25521. Intron 9 includes the sequence from 25619 to 35529. Intron 10 includes the sequence from 35649 to 42168.

The term "CACNA1A" gene refers to a gene that encodes the calcium voltage-gated channel subunit alpha1A protein. A representative sequence of the CACNA1A gene can be found with NCBI Reference Sequence: NG_011569.1 and corresponding SEQ ID NO:43. The exon and intron boundaries can be defined with the sequence provided in SEQ ID NO:43. Specifically, exon 1 includes the sequence from 1 to 529. Exon 2 includes the sequence from 51249 to 51354. Exon 3 includes the sequence from 53446 to 53585. Exon 4 includes the sequence from 134682 to 134773. Exon 5 includes the sequence from 140992 to 141144. Exon 6 includes the sequence from 146662 to 146855. Exon 7 includes the sequence from 170552 to 170655. Exon 8 includes the sequence from 171968 to 172083. Exon 9 includes the sequence from 173536 to 173592. Exon 10 includes the sequence from 176125 to 176217. Exon 11 includes the sequence from 189140 to 189349. Exon 12 includes the sequence from 193680 to 193792. Exon 13 includes the sequence from 197933 to 198045. Exon 14 includes the sequence from 198210 to 198341. Exon 15 includes the sequence from 198607 to 198679. Exon 16 includes the sequence from 202577 to 202694. Exon 17 includes the sequence from 202848 to 202915. Exon 18 includes the sequence from 205805 to 205911. Exon 19 includes the sequence from 207108 to 207917. Exon 20 includes the sequence from 219495 to 219958. Exon 21 includes the sequence from 221255 to 221393. Exon 22 includes the sequence from 223065 to 223194. Exon 23 includes the sequence from 229333 to 229392. Exon 24 includes the sequence from 230505 to 230611. Exon 25 includes the sequence from 243628 to 243727. Exon 26 includes the sequence from 244851 to 245011. Exon 27 includes the sequence from 246760 to 246897. Exon 28 includes the sequence from 248910 to 249111. Exon 29 includes the sequence from 251202 to 251366. Exon 30 includes the sequence from 253360 to 253470. Exon 31 includes the sequence from 261196 to 261279. Exon 32 includes the sequence from 270731 to 270847. Exon 33 includes the sequence from 271187 to 271252. Exon 34 includes the sequence from 271425 to 271540. Exon 35 includes the sequence from 274601 to 274751. Exon 36 includes the sequence from 276252 to 276379. Exon 37 includes the sequence from 277666 to 277762. Exon 38 includes the sequence from 281689 to 281794. Exon 39 includes the sequence from 291853 to 291960. Exon 40 includes the sequence from 292128 to 292228. Exon 41 includes the sequence from 293721 to 293830. Exon 42 includes the sequence from 293939 to 294077. Exon 43 includes the sequence from 294245 to 294358. Exon 44 includes the sequence from 295809 to 295844. Exon 45 includes the sequence from 296963 to 297149. Exon 46 includes the sequence from 297452 to 297705. Exon 47 includes the sequence from 298413 to 300019. Intron 1 includes the sequence from 530 to 51248. Intron 2 includes the sequence from 51355 to 53445. Intron 3 includes the sequence from 53586 to 134681. Intron 4 includes the sequence from 134774 to 140991. Intron 5 includes the sequence from 141145 to 146661. Intron 6 includes the sequence from 146856 to 170551. Intron 7 includes the sequence from 170656 to 171967. Intron 8 includes the sequence from 172084 to 173535. Intron 9 includes the sequence from 173593 to 176124. Intron 10 includes the sequence from 176218 to 189139. Intron 11 includes the sequence from 189350 to 193679. Intron 12 includes the sequence from 193793 to 197932. Intron 13 includes the sequence from 198046 to 198209. Intron 14 includes the sequence from 198342 to 198606. Intron 15 includes the sequence from 198680 to 202576. Intron 16 includes the sequence from 202695 to 202847. Intron 17 includes the sequence from 202916 to 205804. Intron 18 includes the sequence from 205912 to 207107. Intron 19 includes the sequence from 207918 to 219494. Intron 20 includes the sequence from 219959 to 221254. Intron 21 includes the sequence from 221394 to 223064. Intron 22 includes the sequence from 223195 to 229332. Intron 23 includes the sequence from 229393 to 230504. Intron 24 includes the sequence from 230612 to 243627. Intron 25 includes the sequence from 243728 to 244850. Intron 26 includes the sequence from 245012 to 246759. Intron 27 includes the sequence from 246898 to 248909. Intron 28 includes the sequence from 249112 to 251201. Intron 29 includes the sequence from 251367 to 253359. Intron 30 includes the sequence from 253471 to 261195. Intron 31 includes the sequence from 261280 to 270730. Intron 32 includes the sequence from 270848 to 271186. Intron 33 includes the sequence from 271253 to 271424. Intron 34 includes the sequence from 271541 to 274600. Intron 35 includes the sequence from 274752 to 276251. Intron 36 includes the sequence from 276380 to 277665. Intron 37 includes the sequence from 277763 to 281688. Intron 38 includes the sequence from 281795 to 291852. Intron 39 includes the sequence from 291961 to 292127. Intron 40 includes the sequence from 292229 to 293720. Intron 41 includes the sequence from 293831 to 293938. Intron 42 includes the sequence from 294078 to 294244. Intron 43 includes the sequence from 294359 to 295808. Intron 44 includes the sequence from 295845 to 296962. Intron 45 includes the sequence from 297150 to 297451. Intron 46 includes the sequence from 297706 to 298412.

The percent sequence identity between a particular nucleic acid or amino acid sequence and a sequence referenced by a particular sequence identification number is determined as follows. First, a nucleic acid or amino acid sequence is compared to the sequence set forth in a particular sequence identification number using the BLAST 2 Sequences (Bl2seq) program from the stand-alone version of BLASTZ containing BLASTN version 2.0.14 and BLASTP version 2.0.14. This stand-alone version of BLASTZ can be obtained online at fr.com/blast or at ncbi.nlm.nih.gov. Instructions explaining how to use the Bl2seq program can be found in the readme file accompanying BLASTZ. Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. For example, the following command can be used to generate an output file containing a comparison between two sequences: C:\Bl2seq -i c:\seq1.txt -j c:\seq2.txt -p blastn -o c:\output.txt -q -1 -r 2. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (e.g., 100 consecutive nucleotides or amino acid residues from a sequence set forth in an identified sequence), followed by multiplying the resulting value by 100. The percent sequence identity value is rounded to the nearest tenth.

In one embodiment, this document features methods for modifying the 3' end of endogenous genes, where endogenous genes have at least one intron between two coding exons. The intron can be any intron which is removed from precursor messenger RNA by normal messenger RNA processing machinery. The intron can be between 20 bp and >500 kb and comprise elements including a splice donor site, branch sequence, and acceptor site. The transgenes disclosed herein for the modification of the 3' end of endogenous genes can comprise multiple functional elements, including target sites for rare-cutting endonucleases, homology arms, splice acceptor sequences, coding sequences, and transcription terminators (FIG. 1).

In one embodiment, the transgene comprises two target sites for one or more rare-cutting endonucleases. The target sites can be a suitable sequence and length for cleavage by a rare-cutting endonuclease. The target site can be amenable to cleavage by CRISPR systems, TAL effector nucleases, zinc-finger nucleases or meganucleases, or a combination of CRISPR systems, TALE nucleases, zinc finger nucleases or meganucleases, or any other site-specific nuclease. The target sites can be positioned such that cleavage by the rare-cutting endonuclease results in liberation of a transgene from a vector. The vector can include viral vectors (e.g., adeno-associated vectors) or non-viral vectors (e.g., plasmids, minicircle vectors). If the transgene comprises two target sites, the target sites can be the same sequence (i.e., targeted by the same rare-cutting endonuclease) or they can be different sequences (i.e., targeted by two or more different rare-cutting endonucleases).

In one embodiment, the transgene comprises a first and second target site for one or more rare-cutting endonucleases along with a first and second homology arm. The first and second homology arms can include sequence that is homologous to a genomic sequence at or near the desired site of integration. The homology arms can be a suitable length for participating in homologous recombination with sequence at or near the desired site of integration. The length of each homology arm can be between 20 nt and 10,000 nt (e.g., 20 nt, 30 nt, 40 nt, 50 nt, 100 nt, 200 nt, 300 nt, 400 nt, 500 nt, 600 nt, 700 nt, 800 nt, 900 nt, 1,000 nt, 2,000 nt, 3,000 nt, 4,000 nt, 5,000 nt, 6,000 nt, 7,000 nt, 8,000 nt, 9,000 nt, 10,000 nt). In one embodiment, a homology arms can comprise functional elements, including a target site for a rare-cutting endonuclease and/or a splice acceptor sequence. In one embodiment, a first homology arm (e.g., a left homology arm) can comprise sequence homologous to the intron being targeted, which includes the splice acceptor site of the intron being targeted. In another embodiment, a second homology arm can comprise sequence homologous to genomic sequence downstream of the intron being targeted (e.g., exon sequence, 3' UTR sequence). However, the second homology arm must not possess splice acceptor functions in the reverse complement direction. To determine if a sequence comprises splice acceptor functions, several steps can be taken, including in silico analysis and experimental tests. To determine if there is potential for splice acceptor functions, the sequence desired for second homology arm can be searched for consensus branch sequences (e.g., YTRAC) and splice acceptor sites (e.g., Y-rich NCAGG). If branch or splice acceptor sequences are present, single nucleotide polymorphisms can be introduced to destroy function, or a different but adjacent sequence not comprising such sequences can be selected. Preferably, the window of sequence that can be used for a second homology arm extends from 1 bp to 10 kb downstream of the intron being targeted for integration. To experimentally determine if the second homology possesses splice acceptor function, a synthetic construct comprising the second homology arm within an intron within a reporter gene can be constructed. The construct can then be administered to an appropriate cell type and monitored for splicing function.

In one embodiment, the transgene comprises two splice acceptor sequences, referred to herein as the first and second splice acceptor sequence. The first and second splice acceptor sequences are positioned within the transgene in opposite directions (i.e., in tail-to-tail orientations) and flanking internal sequences (i.e., coding sequences and terminators). When the transgene is integrated into an intron in forward or reverse directions, the splice acceptor sequences facilitate the removal of the adjacent/upstream intron sequence during mRNA processing. The first and second splice acceptor sequences can be the same sequences or different sequences. One or both splice acceptor sequences can be the splice acceptor sequence of the intron where the transgene is to be integrated. One or both splice acceptor sequences can be a synthetic splice acceptor sequence or a splice acceptor sequence from an intron from a different gene.

In one embodiment, the transgene comprises a first and second coding sequence operably linked to the first and second splice acceptor sequences. The first and second coding sequences are positioned within the transgene in opposite directions (i.e., in tail-to-tail orientations). When the transgene is integrated into an endogenous gene in forward or reverse directions, the first or second coding sequence is transcribed into mRNA by the endogenous gene's promoter. The coding sequences can be designed to correct defective coding sequences, introduce mutations, or introduce novel peptide sequences. The first and second coding sequence can be the same nucleic acid sequence and code for the same protein. Alternatively, the first and second coding sequence can be different nucleic acid sequences and code for the same protein (i.e., using the degeneracy of codons). The coding sequence can encode purification tags (e.g., glutathione-S-transferase, poly(His), maltose binding protein, Strep-tag, Myc-tag, AviTag, HA-tag, or chitin binding protein) or reporter proteins (e.g., GFP, RFP, lacZ, cat, luciferase, puro, neomycin). In one embodiment, the transgene comprises a first and second partial coding sequence operably linked to a first and second splice acceptor sequence, and the transgene does not comprise a promoter.

In one embodiment, the transgene can comprise a bidirectional terminator, or a first and second terminator, operably linked to a first and second coding sequence. The bidirectional terminator, or the first and second terminators are positioned within the transgene in opposite directions (i.e., in tail-to-tail orientations). When the transgene is integrated into an endogenous gene in forward or reverse directions, the bidirectional terminator, or first and second terminators, terminate transcription from the endogenous gene's promoter. The first and second terminators can be the same terminators or different terminators.

Figure 2:
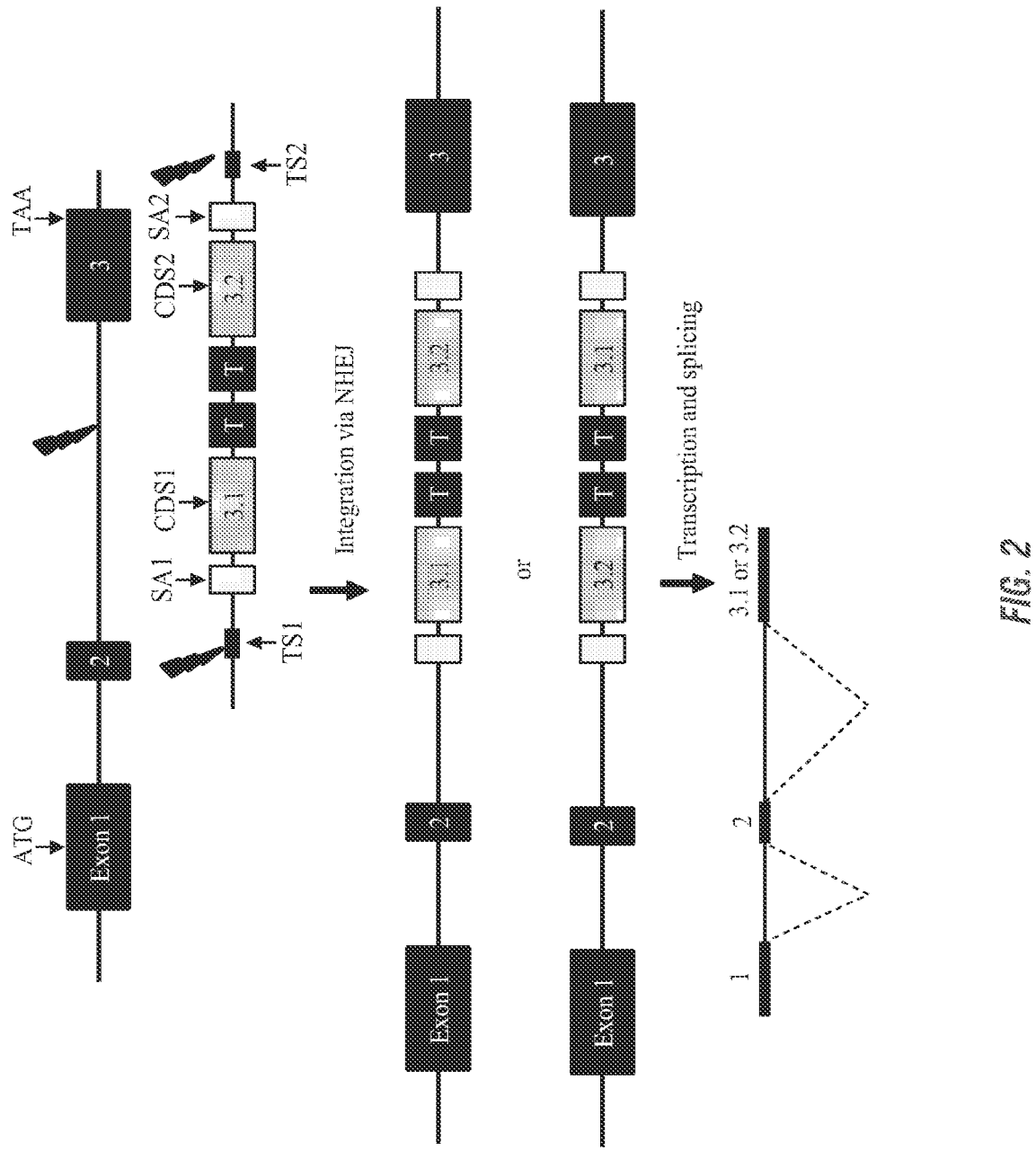
FIG. 2 is an illustration showing integration of a transgene into an exemplary gene. The transgene comprises two target sites for one or more rare-cutting endonucleases, two splice acceptor sequences, two coding sequences (3.1 and 3.2) and two terminators (T). Integration proceeds through non-homologous end joining (NHEJ).

In one embodiment, this document provides a transgene comprising a first and second rare-cutting endonuclease target site, a first and second splice acceptor sequence, a first and second coding sequence, and one bidirectional terminator or a first and second terminator. The transgene can be integrated in endogenous genes via non-homology dependent methods, including non-homologous end joining and alternative non-homologous end joining or by microhomology-mediated end joining. In one aspect, the transgene is integrated into an intron within the endogenous gene (FIG. 2).

Figure 3:
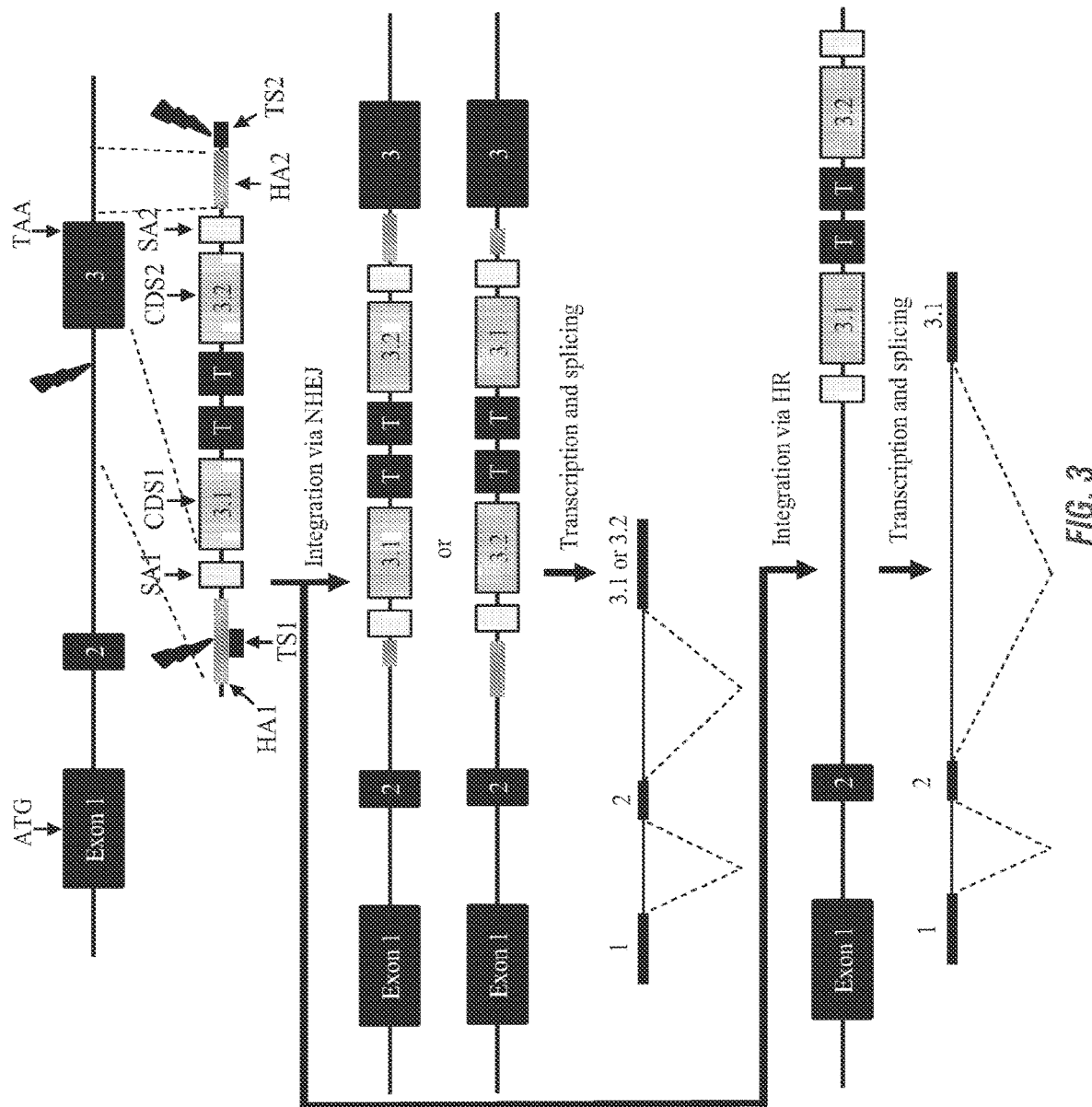
FIG. 3 is an illustration showing integration of a transgene into an exemplary gene. The transgene comprises two homology arms, two target sites for one or more rare-cutting endonucleases, two splice acceptor sequences, two coding sequences (3.1 and 3.2) and two terminators. Integration proceeds through either homologous recombination (HR) or non-homologous end joining (NHEJ).

In another embodiment, this document provides a transgene comprising a first and second homology arm, a first and second rare-cutting endonuclease target site, a first and second splice acceptor sequence, a first and second coding sequence, and one bidirectional terminator or a first and second terminator. The transgene can be integrated in endogenous genes via both homology dependent methods (e.g., synthesis dependent strand annealing and microhomology-mediated end joining) and non-homology dependent methods (e.g., non-homologous end joining and alternative non-homologous end joining). In one aspect, the transgene is integrated into an intron within the endogenous gene (FIG. 3). In another aspect, the transgene is integrated at the end of the intron or the starting of the downstream exon (FIG. 3).

In another embodiment, this document provides a transgene comprising a first and second homology arm, a first and second coding sequence, a first and second splice acceptor sequence, and one bidirectional terminator or a first and second terminator (FIG. 1). In another embodiment, this document provides a transgene comprising, a first and second coding sequence, a first and second splice acceptor sequence, and one bidirectional terminator or a first and second terminator.

In another embodiment, this document provides a transgene comprising a first and second homology arm, a first and second coding sequence, a first and second splice acceptor sequence, one bidirectional terminator or a first and second terminator, and a first and second additional sequence (FIG. 1). In certain embodiments, the additional sequence can be any additional sequence that is present on the transgene at the 5' and 3' ends, however, the additional sequence should not comprise any element that functions as a splice acceptor. The additional sequence can be, for example, inverted terminal repeats of a virus genome. The additional sequence can be present on a transgene having a linear format. The linear format permits integration by NHEJ. For example, a transgene harbored in an adeno-associated virus vector, wherein the additional sequence is the inverted terminal repeats, can be directly integrated by NHEJ at a target site after cleavage by a rare-cutting endonuclease (i.e., no processing of the transgene is required). In another example, the additional sequence is a left and right transposon end.

In another embodiment, this document provides transgenes within viral vectors, including adeno-associated viruses and adenoviruses, where the transgene comprises a first and second splice acceptor sequence, a first and second coding sequence, and one bidirectional terminator or a first and second terminator. Due to the inverted terminal repeats of the viral vectors, the transgenes also comprise a first and second additional sequence.

In another embodiment, this document provides transgenes within viral vectors, including adeno-associated viruses and adenoviruses, where the transgene comprises a first and second homology arm, a first and second splice acceptor sequence, a first and second coding sequence, and one bidirectional terminator or a first and second terminator. Due to the inverted terminal repeats of the viral vectors, the transgenes also comprise a first and second additional sequence.

In some embodiments, the transgenes provided herein can be integrated with transposases. The transposases can include CRISPR transposases (Strecker et al., Science 10.1126/science.aax9181, 2019; Klompe et al., Nature, 10.1038/s41586-019-1323-z, 2019). The transposases can be used in combination with a transgene comprising, a first and second splice acceptor sequence, a first and second coding sequence, one bidirectional terminator or a first and second terminator (FIG. 1), and a transposon left end and right end. The CRISPR transposases can include the TypeV-U5, C2C5 CRISPR protein, Cas12k, along with proteins tnsB, tnsC, and tniQ. In some embodiments, the Cas12k can be from *Scytonema hofmanni* (SEQ ID NO:30) or *Anabaena cylindrica* (SEQ ID NO:31). In one embodiment, the transgenes described herein comprising a left (SEQ ID NO:32) and right transposon end (SEQ ID NO:33) can be delivered to cells along with ShCas12k, tnsB, tnsC, TniQ and a gRNA (SEQ ID NO:14). Alternatively, the CRISPR transposase can include the Cas6 protein, along with helper proteins including Cas7, Cas8 and TniQ. In one embodiment, the transgenes described herein comprising a left (SEQ ID NO:41) and right transposon end (SEQ ID NO:13) can be delivered to eukaryotic cells along with Cas6 (SEQ ID NO:37), Cas7 (SEQ ID NO:37), Cas8 (SEQ ID NO:37), TniQ (SEQ ID NO:37), TnsA (SEQ ID NO:37), TnsB (SEQ ID NO:37), TnsC (SEQ ID NO:37) and a gRNA (SEQ ID NO:12). The proteins can be administered to cells directly as purified protein or encoded on RNA or DNA. If encoded on RNA or DNA, the sequence can be codon optimized for expression in eukaryotic cells. The gRNA (SEQ ID NO:12) can be placed downstream of an RNA polIII promoter and terminated with a poly(T) terminator.

In some embodiments, the transgenes described herein can have a combination of elements including splice acceptors, partial coding sequences, terminators, homology arms, left and right transposase ends, and sites for cleavage by rare-cutting endonucleases. In one embodiment, the combination can be, from 5' to 3', [splice acceptor 1]-[partial coding sequence 1]-[terminator 1]-[terminator 2 RC]-[partial coding sequence 2 RC]-[splice acceptor 2 RC], where RC stands for reverse complement. This combination can be harbored on a linear DNA molecule or AAV molecule and can be integrated by NHEJ through a targeted break in the target gene. In another embodiment, the combination can be, from 5' to 3', [rare-cutting endonuclease cleavage site 1]-[splice acceptor 1]-[partial coding sequence 1]-[terminator 1]-[terminator 2 RC]-[partial coding sequence 2 RC]-[splice acceptor 2 RC]-[rare-cutting endonuclease cleavage site 1]. In another embodiment, the combination can be, from 5' to 3', [rare-cutting endonuclease cleavage site 1]-[homology arm 1]-[splice acceptor 1]-[partial coding sequence 1]-[terminator 1]-[terminator 2 RC]-[partial coding sequence 2 RC]-[splice acceptor 2 RC]-[homology arm 2]-[rare-cutting endonuclease cleavage site 2]. In this combination one or more rare-cutting endonucleases can be used to facilitate HR and NHEJ. For example, a single rare-cutting nuclease can cleave the target gene (i.e., a desired intron) and the cleavage sites flanking the homology arms can be designed to be the same target sequence within the intron. In another embodiment, the combination can be, from 5' to 3', [homology arm 1+rare-cutting endonuclease cleavage site 1]-[splice acceptor 1]-[partial coding sequence 1]-[terminator 1]-[terminator 2 RC]-[partial coding sequence 2 RC]-[splice acceptor 2 RC]-[homology arm 2]-[rare-cutting endonuclease cleavage site 1]. In this combination, one or more rare-cutting endonucleases can facilitate HR and NHEJ. For example, a single-rare cutting nuclease can cleave within homology arm 1, downstream of homology arm 2, and at the genomic target site (i.e., at the site with homology to the sequence in the homology arm 1). In another embodiment, the combination can be from 5' to 3', [left end for a transposase]-[splice acceptor 1]-[partial coding sequence 1]-[terminator 1]-[terminator 2 RC]-[partial coding sequence 2 RC]-[splice acceptor 2 RC]-[right end for a transposase]. In all embodiments, the splice acceptor 1 and splice acceptor 2 can be the same or different sequences; the partial coding sequence 1 and partial coding sequence 2 can be the same or different sequences; the terminator 1 and terminator 2 can be the same or different sequences.

In embodiments, a transgene comprising the structure [rare-cutting endonuclease cleavage site 1]-[homology arm 1]-[splice acceptor 1]-[partial coding sequence 1]-[terminator 1]-[terminator 2 RC]-[partial coding sequence 2 RC]-[splice acceptor 2 RC]-[homology arm 2]-[rare-cutting endonuclease cleavage site 2] can be integrated into the DNA through delivery of one or more rare-cutting endonucleases. If one rare-cutting endonuclease is delivered, the rare-cutting endonuclease can liberate the transgene by cleavage at the rare-cutting endonuclease cleavage site 1 and 2. Further, the same rare-cutting endonuclease can create a break within the target gene, simulating insertion through HR or NHEJ.

In other embodiments, a transgene comprising the structure [homology arm 1+rare-cutting endonuclease cleavage site 1]-[splice acceptor 1]-[partial coding sequence 1]-[terminator 1]-[terminator 2 RC]-[partial coding sequence 2 RC]-[splice acceptor 2 RC]-[homology arm 2]-[rare-cutting endonuclease cleavage site 1] can be integrated into the DNA thorough delivery of one or more rare-cutting endonucleases. If one rare-cutting endonuclease is delivered, the rare-cutting endonuclease can liberate the transgene by cleavage at the rare-cutting endonuclease cleavage site 1 and 2. Further, the same rare-cutting endonuclease can create a break within the target gene, simulating insertion through HR or NHEJ. Integration by HR can occur when cleavage is upstream of the site of integration (i.e., within a homology arm).

In embodiments, the location for integration of transgenes can be an intron or an intron-exon junction. When targeting an intron, the partial coding sequence can comprise sequence encoding the peptide produced by the following exons within the endogenous gene. For example, if the transgene is designed to be integrated in intron 9 of an endogenous gene with 11 exons, then the partial coding sequence can comprise sequence encoding the peptide produced by exons 10 and 11 of the endogenous gene. When targeting an intron-exon junction, the transgene can be designed to comprise homology arms with sequence homologous to the 3' of said intron.

In some embodiments, the partial coding sequences can be full coding sequences. The full coding sequence can encode an endogenous gene (e.g., Factor VIII, Factor IX, or INS), or reporter genes (e.g., RFP, GFP, cat, lacZ, luciferase). The full coding sequences can be operably linked to splice acceptors and terminators and placed in a transgene in a tail-to-tail orientation.

The methods and compositions provided herein can be used within to modify endogenous genes within cells. The endogenous genes can include, fibrinogen, prothrombin, tissue factor, Factor V, Factor VII, Factor VIII, Factor IX, Factor X, Factor XI, Factor XII (Hageman factor), Factor XIII (fibrin-stabilizing factor), von Willebrand factor, prekallikrein, high molecular weight kininogen (Fitzgerald factor), fibronectin, antithrombin III, heparin cofactor II, protein C, protein S, protein Z, protein Z-related protease inhibitor, plasminogen, alpha 2-antiplasmin, tissue plasminogen activator, urokinase, plasminogen activator inhibitor-1, plasminogen activator inhibitor-2, glucocerebrosidase (GBA), α-galactosidase A (GLA), iduronate sulfatase (IDS), iduronidase (IDUA), acid sphingomyelinase (SMPD1), MMAA, MMAB, MMACHC, MMADHC (C2orf25), MTRR, LMBRD1, MTR, propionyl-CoA carboxylase (PCC) (PCCA and/or PCCB subunits), a glucose-6-phosphate transporter (G6PT) protein or glucose-6-phosphatase (G6Pase), an LDL receptor (LDLR), ApoB, LDLRAP-1, a PCSK9, a mitochondrial protein such as NAGS (N-acetylglutamate synthetase), CPS1 (carbamoyl phosphate synthetase I), and OTC (ornithine transcarbamylase), ASS (argininosuccinic acid synthetase), ASL (argininosuccinase acid lyase) and/or ARG1 (arginase), and/or a solute carrier family 25 (SLC25A13, an aspartate/glutamate carrier) protein, a UGT1A1 or UDP glucuronsyltransferase polypeptide A1, a fumarylacetoacetate hydrolyase (FAH), an alanine-glyoxylate aminotransferase (AGXT) protein, a glyoxylate reductase/hydroxypyruvate reductase (GRHPR) protein, a transthyretin gene (TTR) protein, an ATP7B protein, a phenylalanine hydroxylase (PAH) protein, an USH2A protein, an ATXN protein, and a lipoprotein lyase (LPL) protein.

The transgene may include sequence for modifying the sequence encoding a polypeptide that is lacking or non-functional or having a gain-of-function mutation in the subject having a genetic disease, including but not limited to the following genetic diseases: achondroplasia, achromatopsia, acid maltase deficiency, adenosine deaminase deficiency, adrenoleukodystrophy, aicardi syndrome, alpha-1 antitrypsin deficiency, alpha-thalassemia, androgen insensitivity syndrome, pert syndrome, arrhythmogenic right ventricular dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the 6th codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency, leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, *porphyria*, Prader-Willi syndrome, progeria, *Proteus* syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome, lysosomal storage diseases (e.g., Gaucher's disease, GM1, Fabry disease and Tay-Sachs disease), mucopolysaccahidosis (e.g. Hunter's disease, Hurler's disease), hemoglobinopathies (e.g., sickle cell diseases, HbC, α-thalassemia, β-thalassemia) and hemophilias.

Additional diseases that can be treated by targeted integration include von Willebrand disease, usher syndrome, polycystic kidney disease, spinocerebellar ataxia type 3, and spinocerebellar ataxia type 6.

In one embodiment, the genomic modification is the insertion of a transgene in the endogenous CACNA1A genomic sequence. The transgene can include a synthetic and partial coding sequence for the CACNA1A protein. The partial coding sequence can be homologous to coding sequence within a wild type CACNA1A gene, or a functional variant of the wild type CACNA1A gene, or a mutant of the wild type CACNA1A gene. In one embodiment, the transgene encoding the partial CACNA1A protein is inserted into intron 46 or the beginning of exon 47.

In another embodiment, the genomic modification is the insertion of a transgene in the endogenous ATXN3 genomic sequence. The transgene can include a synthetic and partial coding sequence for the ATXN3 protein. The partial coding sequence can be homologous to coding sequence within a wild type ATXN3 gene, or a functional variant of the wild type ATXN3 gene, or a mutant of the wild type ATXN3 gene. In one embodiment, the transgene encoding the partial ATXN3 protein is inserted into intron 9 or the beginning of exon 10.

In one embodiment, the methods and compositions described herein can be used to modify the 3' end of an endogenous gene, thereby resulting in modification of the C-terminus of the protein encoded by the endogenous gene. The modification of the 3' end of the endogenous gene's coding sequence can include the replacement of the final coding exon (i.e., the exon comprising the stop codon), up to an exon that is between the exon with the start coding and the final exon. As defined herein "replacement" refers to the insertion of DNA in a gene, wherein the inserted DNA provides the information for producing the mRNA and protein of 1 or more exons. Replacement can occur by integrating a transgene into the endogenous gene, wherein the transgene comprises one or more coding sequences operably linked to a splice acceptor. The insertion may or may not result in the deletion of sequence within the endogenous gene (e.g., deletion of introns and exons). For example, if a gene comprises 72 exons, and the start codon is within exon 1, the modification can include replacement of exons 2-72, 3-72, 4-72, 5-72, 6-72, 7-72, 8-72, 9-72, 10-72, 11-72, 12-72, 13-72, 14-72, 15-72, 16-72, 17-72, 18-72, 19-72, 20-72, 21-72, 22-72, or 23-72, or 24-72, or 25-72, or 26-72, or 27-72, or 28-72, or 29-72, or 30-72, or 31-72, or 32-72, or 33-72, or 34-72, or 35-72, or 36-72, or 37-72, or 38-72, or 39-72, or 40-72, or 41-72, or 42-72, or 43-72, or 44-72, or 45-72, or 46-72, or 47-72, or 48-72, or 49-72, or 50-72, or 51-72, or 52-72, or 53-72, or 54-72, or 55-72, or 56-72, or 57-72, or 58-72, or 59-72, or 60-72, or 61-72, or 62-72, or 63-72, or 64-72, or 65-72, or 66-72, or 67-72, or 68-72, or 69-72, or 70-72, or 71-72 or 72. In one embodiment, the endogenous gene's exons can be replaced by integrating a transgene into the endogenous gene, wherein the transgene comprises a first and second partial coding sequence, wherein the first and second partial coding sequence encodes a peptide produced by the endogenous genes exons. For example, the transgene's first and second coding sequence can encode a peptide that is produced by the endogenous gene's exons 2-72, 3-72, 4-72, 5-72, 6-72, 7-72, 8-72, 9-72, 10-72, 11-72, 12-72, 13-72, 14-72, 15-72, 16-72, 17-72, 18-72, 19-72, 20-72, 21-72, 22-72, or 23-72, or 24-72, or 25-72, or 26-72, or 27-72, or 28-72, or 29-72, or 30-72, or 31-72, or 32-72, or 33-72, or 34-72, or 35-72, or 36-72, or 37-72, or 38-72, or 39-72, or 40-72, or 41-72, or 42-72, or 43-72, or 44-72, or 45-72, or 46-72, or 47-72, or 48-72, or 49-72, or 50-72, or 51-72, or 52-72, or 53-72, or 54-72, or 55-72, or 56-72, or 57-72, or 58-72, or 59-72, or 60-72, or 61-72, or 62-72, or 63-72, or 64-72, or 65-72, or 66-72, or 67-72, or 68-72, or 69-72, or 70-72, or 71-72 or 72. The transgene can be integrated within the endogenous gene in the upstream intron or at the beginning of the exon corresponding to the first exon within the transgene's partial coding sequence (FIG. 2). The transgene can be designed to be 4.7 kb or less, and incorporated into an AAV vector and particle, and delivered in vivo to target cells.

In an embodiment, the transgene is a sequence of DNA that harbors a first and second partial coding sequence, wherein the partial coding sequences encode a partial protein, wherein the partial protein is homologous to a corresponding region in a functional protein produced from a wild type gene. The host gene or endogenous gene is one in which expression of the protein is aberrant, in other words, is not expressed, is expressed at low levels, or is expressed but the mRNA or protein product or portion thereof is non-functional, has reduced function, or has a gain-of-function, resulting in a disorder in the host.

As described herein, the donor molecule can be in a viral or non-viral vector. The vectors can be in the form of circular or linear double-stranded or single stranded DNA. The donor molecule can be conjugated or associated with a reagent that facilitates stability or cellular update. The reagent can be lipids, calcium phosphate, cationic polymers, DEAE-dextran, dendrimers, polyethylene glycol (PEG) cell penetrating peptides, gas-encapsulated microbubbles or magnetic beads. The donor molecule can be incorporated into a viral particle. The virus can be retroviral, adenoviral, adeno-associated vectors (AAV), herpes simplex, pox virus, hybrid adenoviral vector, epstein-bar virus, lentivirus, or herpes simplex virus.

In certain embodiments, the AAV vectors as described herein can be derived from any AAV. In certain embodiments, the AAV vector is derived from the defective and nonpathogenic parvovirus adeno-associated type 2 virus. All such vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., Lancet 351:9117 1702-3, 1998; Kearns et al., Gene Ther. 9:748-55, 1996). Other AAV serotypes, including AAV1, AAV2, AAV3, AAV4, AAV5, AAV6, AAV7, AAV8, AAV9 and AAVrh.10 and any novel AAV serotype can also be used in accordance with the present invention. In some embodiments, chimeric AAV is used where the viral origins of the long terminal repeat (LTR) sequences of the viral nucleic acid are heterologous to the viral origin of the capsid sequences. Non-limiting examples include chimeric virus with LTRs derived from AAV2 and capsids derived from AAV5, AAV6, AAV8 or AAV9 (i.e. AAV2/5, AAV2/6, AAV2/8 and AAV2/9, respectively).

The constructs described herein may also be incorporated into an adenoviral vector system. Adenoviral based vectors are capable of very high transduction efficiency in many cell types and do not require cell division. With such vectors, high titer and high levels of expression can been obtained.

The methods and compositions described herein are applicable to any eukaryotic organism in which it is desired to alter the organism through genomic modification. The eukaryotic organisms include plants, algae, animals, fungi and protists. The eukaryotic organisms can also include plant cells, algae cells, animal cells, fungal cells and protist cells.

Exemplary mammalian cells include, but are not limited to, oocytes, K562 cells, CHO (Chinese hamster ovary) cells, HEP-G2 cells, BaF-3 cells, Schneider cells, COS cells (monkey kidney cells expressing SV40 T-antigen), CV-1 cells, HuTu80 cells, NTERA2 cells, NB4 cells, HL-60 cells and HeLa cells, 293 cells (see, e.g., Graham et al. (1977) J. Gen. Virol. 36:59), and myeloma cells like SP2 or NS0 (see, e.g., Galfre and Milstein (1981) Meth. Enzymol. 73(B):3 46). Peripheral blood mononucleocytes (PBMCs) or T-cells can also be used, as can embryonic and adult stem cells. For example, stem cells that can be used include embryonic stem cells (ES), induced pluripotent stem cells (iPSC), mesenchymal stem cells, hematopoietic stem cells, liver stem cells, skin stem cells and neuronal stem cells.

The methods and compositions of the invention can be used in the production of modified organisms. The modified organisms can be small mammals, companion animals, livestock, and primates. Non-limiting examples of rodents may include mice, rats, hamsters, gerbils, and guinea pigs. Non-limiting examples of companion animals may include cats, dogs, rabbits, hedgehogs, and ferrets. Non-limiting examples of livestock may include horses, goats, sheep, swine, llamas, alpacas, and cattle. Non-limiting examples of primates may include capuchin monkeys, chimpanzees, lemurs, macaques, marmosets, tamarins, spider monkeys, squirrel monkeys, and vervet monkeys. The methods and compositions of the invention can be used in humans.

Exemplary plants and plant cells which can be modified using the methods described herein include, but are not limited to, monocotyledonous plants (e.g., wheat, maize, rice, millet, barley, sugarcane), dicotyledonous plants (e.g., soybean, potato, tomato, alfalfa), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); vegetative crops for consumption (e.g. soybean and other legumes, squash, peppers, eggplant, celery etc.), flowering plants (e.g., *petunia*, rose, *chrysanthemum*), conifers and pine trees (e.g., pine fir, spruce); poplar trees (e.g. *P. tremula×P. alba*); fiber crops (cotton, jute, flax, bamboo) plants used in phytoremediation (e.g., heavy metal accumulating plants); oil crops (e.g., sunflower, rape seed) and plants used for experimental purposes (e.g., *Arabidopsis*). The methods disclosed herein can be used within the genera Asparagus, *Avena, Brassica, Citrus, Citrullus, Capsicum, Cucurbita, Daucus, Erigeron, Glycine, Gossypium, Hordeum, Lactuca, Lolium, Lycopersicon, Malus, Manihot, Nicotiana, Orychophragmus, Oryza, Persea, Phaseolus, Pisum, Pyrus, Prunus, Raphanus, Secale, Solanum, Sorghum, Triticum, Vitis, Vigna*, and *Zea*. The term plant cells include isolated plant cells as well as whole plants or portions of whole plants such as seeds, callus, leaves, and roots. The present disclosure also encompasses seeds of the plants described above wherein the seed has the has been modified using the compositions and/or methods described herein. The present disclosure further encompasses the progeny, clones, cell lines or cells of the transgenic plants described above wherein said progeny, clone, cell line or cell has the transgene or gene construct. Exemplary algae species include microalgae, diatoms, *Botryococcus braunii, Chlorella, Dunaliella tertiolecta, Gracileria, Pleurochrysis carterae, Sorgassum* and *Ulva*.

The methods described in this document can include the use of rare-cutting endonucleases for stimulating homologous recombination or non-homologous integration of a transgene molecule into an endogenous gene. The rare-cutting endonuclease can include CRISPR, TALENs, or zinc-finger nucleases (ZFNs). The CRISPR system can include CRISPR/Cas9 or CRISPR/Cas12a (Cpf1). The CRISPR system can include variants which display broad PAM capability (Hu et al., *Nature* 556, 57-63, 2018; Nishimasu et al., *Science* DOI: 10.1126, 2018) or higher on-target binding or cleavage activity (Kleinstiver et al., *Nature* 529:490-495, 2016). The gene editing reagent can be in the format of a nuclease (Mali et al., *Science* 339:823-826, 2013; Christian et al., *Genetics* 186:757-761, 2010), nickase (Cong et al., *Science* 339:819-823, 2013; Wu et al., *Biochemical and Biophysical Research Communications* 1:261-266, 2014), CRISPR-FokI dimers (Tsai et al., *Nature Biotechnology* 32:569-576, 2014), or paired CRISPR nickases (Ran et al., *Cell* 154:1380-1389, 2013).

The methods and compositions described in this document can be used in a circumstance where it is desired to modify the 3' end of the coding sequence of an endogenous gene. For example, patients with SCA3 or SCA6 have expanded CAG repeats in exons 10 (second to last exon) and exon 47 (last exon), respectively. Patients with SCA3 or SCA6 may benefit from replacement of exons 10-11 and exon 47, respectively. In other examples, patients with genetic disorders due to loss of function mutations within the 3' end of an endogenous gene could benefit from replacement of the final exons of said gene.

The invention will be further described in the following examples, which do not limit the scope of the invention described in the claims.

EXAMPLES

Example 1: Targeted Integration of DNA in the ATXN3 Gene

Three plasmids were constructed with transgenes designed to integrate into the ATXN3 gene in human cells. All transgenes were designed to be inserted within intron 9 or the junction of intron 9 and exon 10 of the ATXN3 gene and all transgenes were designed to insert at least one splice acceptor and at least one functional coding sequence for exons 10 and 11 of the ATXN3 gene. The first plasmid, designated pBA1135, comprised a left and right homology arm with sequence homologous to the 3' end of intron 9 and 5' end of intron 10 (i.e., successful gene targeting would result in removal of exon 10 and replacement with the cargo sequence within pBA1135). Between the homology arms, from 5' to 3', was a splice acceptor (splice acceptor from ATXN3 intron 9), coding sequence for exons 10 and 11 of ATXN3, SV40 terminator, reverse BGH terminator, reverse coding sequence for exons 10 and 11 (codon adjusted), and reverse splice acceptor. The sequence for the pBA1135 transgene is shown in SEQ ID NO:17. A corresponding Cas9 nuclease was designed to cleave i) within intron 9 of the ATXN3 gene, ii) within the left homology arm of pBA1135, and iii) at the 3' end of the right homology arm of pBA1135. Successful cleavage of the plasmid was expected to liberate the transgene, thereby enabling the sequence to be used as a template for HR or for integration via NHEJ. The Cas9 gRNA target site is shown in SEQ ID NO:18. The individual elements within pBA1135 are shown in SEQ ID NOS:44-51. SEQ ID NO:44 comprises the left homology arm, nuclease target site, and splice acceptor. SEQ ID NO:45 comprises the partial coding sequence (exon 10 and 11) of a non-pathogenic ATXN3 gene. SEQ ID NO:46 comprises the SV40 p(A) terminator sequence. SEQ ID NO:47 comprises the BGH terminator in reverse complement. SEQ ID NO:48 comprises the reverse complement, codon adjusted partial coding sequence (exon 10 and 11) of a non-pathogenic ATXN3 gene. SEQ ID NO:49 comprises the sequence for the splice acceptor. SEQ ID NO:50 comprises the sequence for the right homology arm. SEQ ID NO:51 comprises the target site sequence for the nuclease. The second plasmid, designated pBA1136, comprised the same cargo as pBA1135, however, the homology arms were removed. Nuclease target sites were kept to facilitate liberation of the transgene from the plasmid. Successful cleavage of the plasmid was expected to liberate the transgene, thereby enabling the sequence to be used for integration by NHEJ into the ATXN3 gene. The sequence of pBA1136 is shown in SEQ ID NO:19. The third plasmid, designated pBA1137, comprised the same sequence as pBA1135, except for the reverse sequences and nuclease target site (i.e., reverse terminator, reverse coding sequence and reverse splice acceptor). Plasmid pBA1137 was used as a control for conventional HR based methods. The sequence of pBA1137 is shown in SEQ ID NO:20.

Transfection was performed using HEK293T cells. HEK293T cells were maintained at 37° C. and 5% CO2 in DMEM high supplemented with 10% fetal bovine serum (FBS). HEK293T cells were transfected with 2 ug of donor, 2 ug of guide RNA (RNA format) and 2 ug of Cas9 (RNA format). Transfections were performed using electroporation. Genomic DNA was isolated 72 hours post transfection and assessed for integration events. A list of primers used to detect integration or genomic DNA is shown in Table 1.

TABLE 1

Primers for detecting integration of transgenes in ATXN3.

| Primer Name | Sequence (5' to 3') | SEQ ID NO: |
| --- | --- | --- |
| oNJB043 | CAAAGGTGCCCTTGAGGTT | 21 |
| oNJB044 | AGGAGAAGTCTGCCGTTACT | 22 |
| oNJB113 | GGACAAACCACAACTAGAATGC | 23 |
| oNJB114 | TAGGAAAGGACAGTGGGAGT | 24 |
| oNJB116 | CCATTATGTCTCAGTTGTTCAGTG | 25 |
| oNJB156 | CCAGACCATCTCAGACACC | 26 |
| oNJB162 | GGCTGGGCTTCCACTTAC | 27 |
| oNJB167 | GTGGTTTGTCCAAACTCATCAA | 28 |
| oNJB170 | AGTAACTCTGCACTTCCCATTG | 29 |

Figure 8:
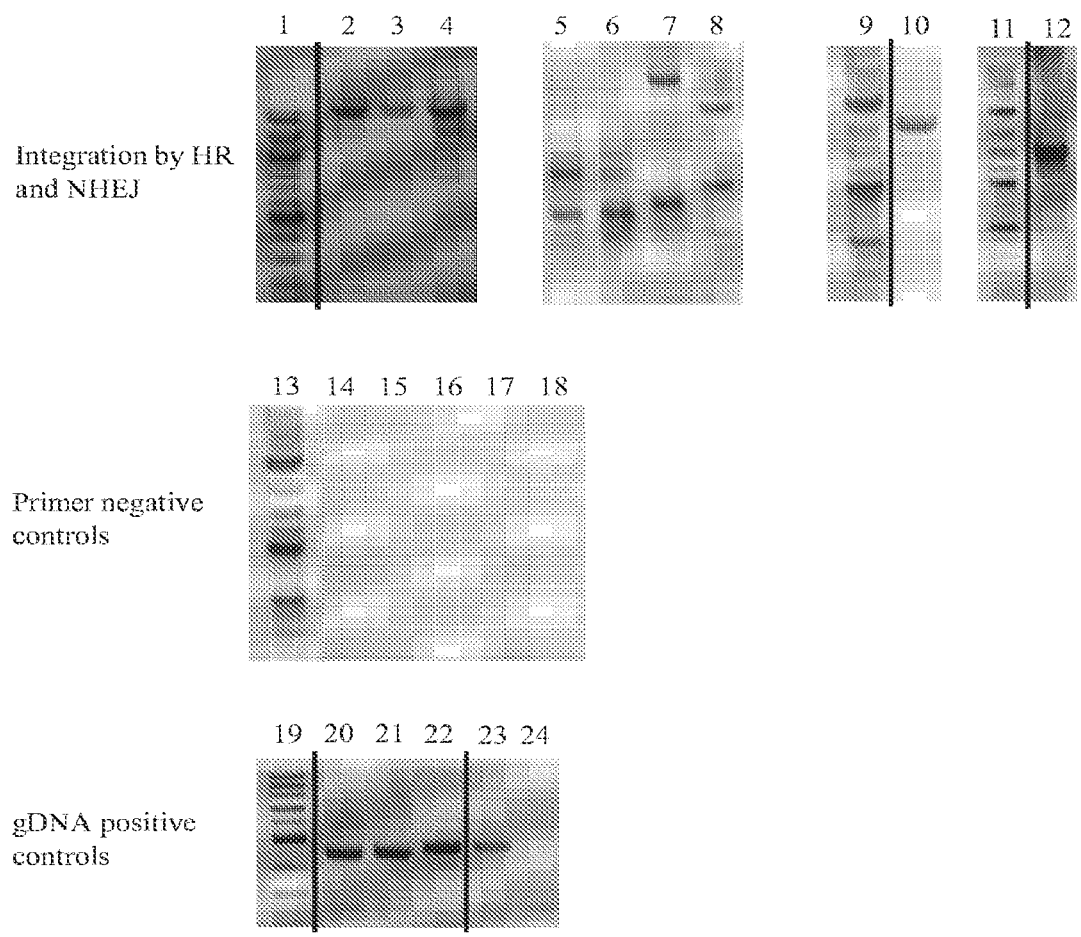
FIG. 8 are images of gels detecting integration of transgenes into the ATXN3 gene. 1, 100 bp ladder with top band running at 1,517 bp; 2, pBA1135 5' junction; 3, pBA1136 5' junction; 4, pBA1137 5' junction; 5, pBA1135 3' junction; 6, pBA1136 3' junction; 7, pBA1137 3' junction; 8, 1 kb ladder with darker bands running at 500 bp, 1,000 bp and 3,000 bp; 9, 1 kb ladder with darker bands running at 500 bp, 1,000 bp and 3,000 bp; 10, pBA1135 inverted 5' junction; 11, 1 kb ladder with darker bands running at 500 bp, 1,000 bp and 3,000 bp; 12, pBA1136 inverted 5' junction; 13, 1 kb ladder with darker bands running at 500 bp, 1,000 bp and 3,000 bp; 14, primer pair oNJB156+oNJB113; 15, primer pair 114+162; 16, primer pair oNJB116+oNJB113; 17, primer pair oNJB114+oNJB170; 18, primer pair oNJB167+oNJB170; 19, 100 bp ladder with the dark band running at 500 bp; 20, genomic DNA from transfection with pBA1135 and nuclease; 21, genomic DNA from transfection with pBA1136 and nuclease; 22, genomic DNA from transfection with pBA1137 and nuclease; 23, genomic DNA from transfection with water; 24, no DNA control.

To detect the integration of pBA1135, pBA1136 and pBA1137, PCRs were performed on the genomic DNA. Regarding pBA1137, the transgene was designed to be integrated precisely by HR. Accordingly, bands were detected in the 5' and 3' junction PCRs, which indicate precise insertion into exon 10 (FIG. 8 lanes 4 and 7). Expected band sizes were 1,520 bp for the 5' junction and 786 bp for the 3' junction. Primers oNJB113 and oNJB116 were used for the 5' junction PCR. Primers oNJB167 and oNJB170 were used for the 3' junction PCR. Regarding pBA1136, as no homology arms were present, the transgene was predicted to insert via NHEJ insertion. Appropriate size bands were observed for the transgene integrating in the forward and reverse directions. Integration in the forward direction can be seen in FIG. 8 lanes 3 (expected size approximately 1,520 bp) and 6 (expected size approximately 1,519 bp). Integrating in the reverse direction can be seen in FIG. 8 lane 12 (expected size approximately 1,520 bp). Primers oNJB113 and oNJB116 were used for the 5' junction PCR. Primers oNJB114 and oNJB170 were used for the 3' junction PCR. Primers oNJB116 and oNJB114 were used for the inverse 5' junction PCR. Regarding ppBA1135, both homology arms and nuclease cleavage sites were present on the transgene. Integration by HR was observed by detecting bands in the 5' and 3' junction PCRs (FIG. 8 lane 2 and 5). Further, integration by NHEJ was observed by detecting bands in an inverse 5' junction PCR (FIG. 8 lane 10). Expected size for the 5' junction PCR was 1,520 bp. Expected size for the 3' junction PCR was 1,157 bp. Expected size for the inverse 5' junction PCR was approximately 1,520 bp. Primers oNJB113 and oNJB116 were used for the 5' junction PCR. Primers oNJB114 and oNJB170 were used for the 3' junction PCR. Primers oNJB116 and oNJB114 were used for the inverse 5' junction PCR.

The results show that the described transgenes comprising bidirectional partial coding sequences can be integrated into genomic DNA through multiple different repair pathways.

Example 2: Targeted Integration of DNA in the CACNA1A Gene

Figure 4:
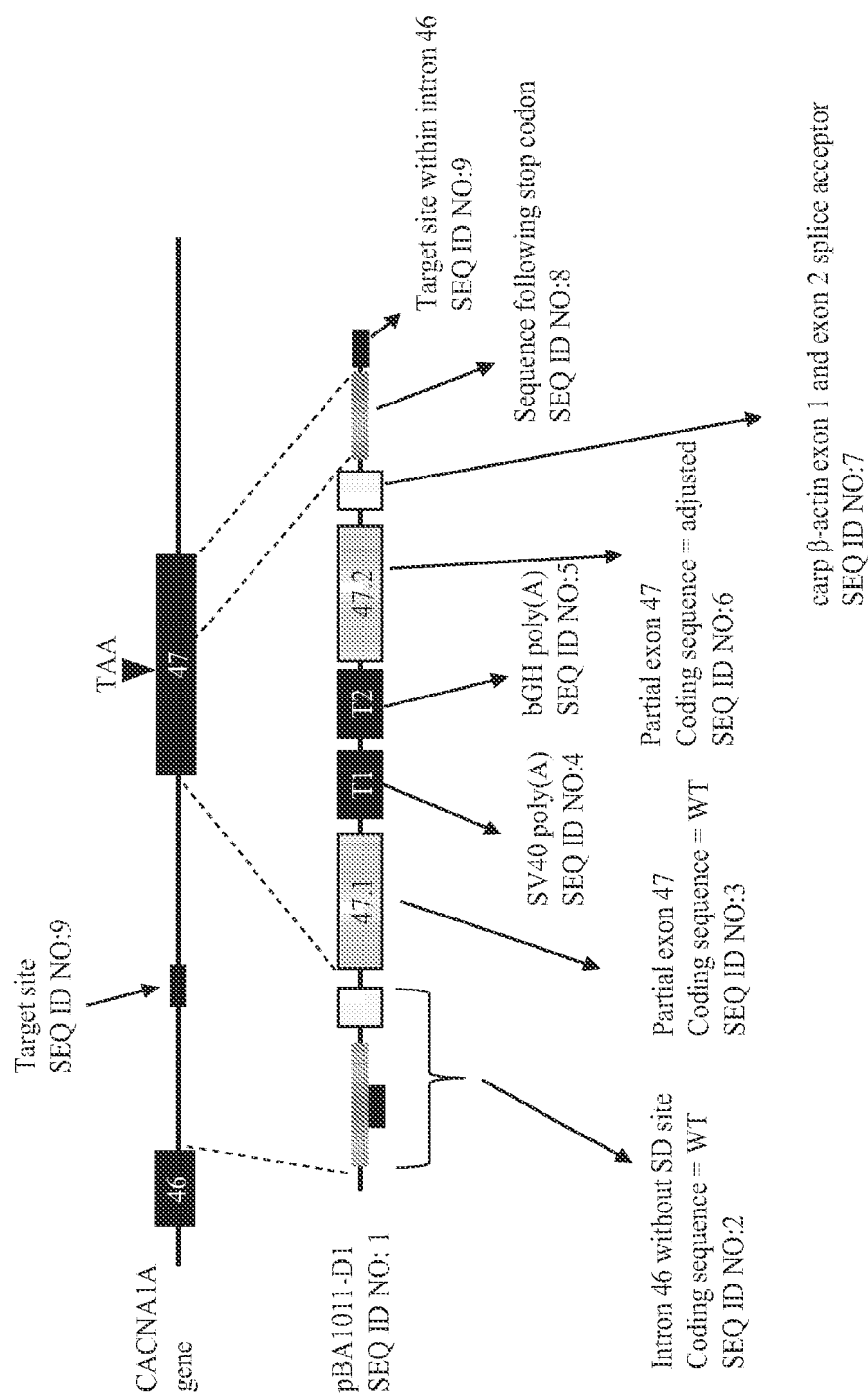
FIG. 4 is an illustration of exon 46, intron 46 and intron 47 of the CACNA1A gene. Also shown is the pB1011-D1 transgene for integration in the CACNA1A gene.

A CACNA1A-targeting transgene is designed to replace the 3' end of the CACNA1A coding sequence. A plasmid is constructed with a transgene designed to integrate WT coding sequence into intron 46 or the start of exon 47 (FIG. 4). The transgene comprises a first homology arm which is homologous to sequence immediately following the splice donor site in intron 46. The first homology arm also comprises the target site for a nuclease (SEQ ID NO:9) and a splice acceptor sequence. The first homology arm is followed by a first coding sequence comprising the CACNA1A exon 47 and a non-expanded CAG repeat sequence (SEQ ID NO:3). Following the first coding sequence is a SV40 poly(A) termination sequence (SEQ ID NO:4). In a tail-to-tail orientation, a second set of functional elements is present. The beginning of the second set of elements comprises a target site for the nuclease (SEQ ID NO:9) followed by a second homology arm. The second homology arm harbors 446 bp which is homologous to sequence immediately following the stop coding (SEQ ID NO:8). This sequence was determined to be free of consensus branch or splice acceptor sequences via in silico analysis. Following the second homology arm is a second splice acceptor from carp beta-actin intron 1 (SEQ ID NO:7). Following the splice acceptor is a codon optimized version of the CACNA1A exon 47 (SEQ ID NO:6) and a bGH poly(A) terminator (SEQ ID NO:5).

A corresponding Cas12a nuclease is designed to create three double-strand breaks following transfection of the plasmid: i) within intron 46 of the endogenous CACNA1A gene, 2) within the first homology arm in the pBA1011-D1 transgene, and 3) following the second homology arm in the pBA1011-D1 transgene. The target sequence for the Cas12a nuclease is shown in SEQ ID NO:9.

Figure 5:
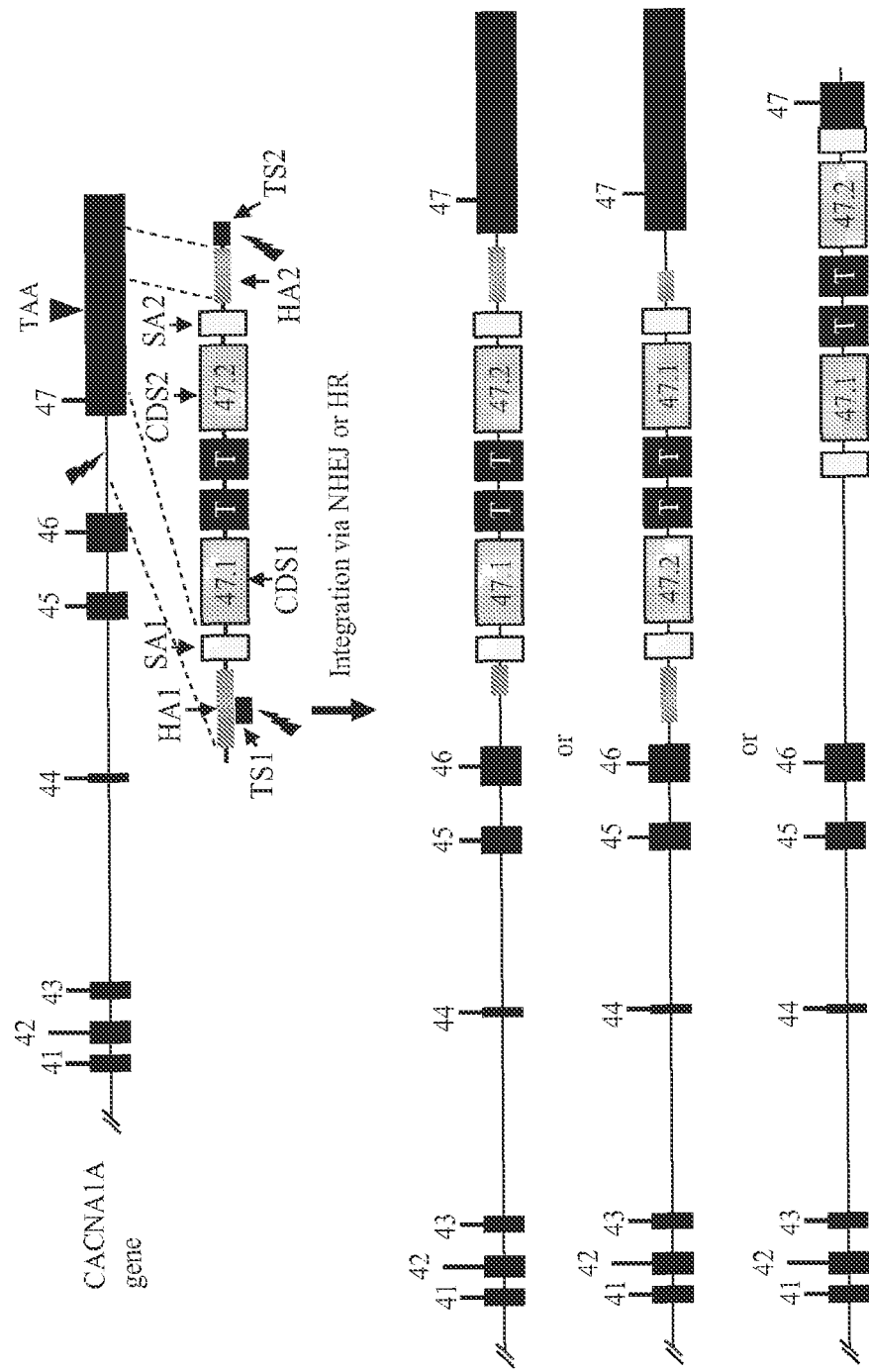
FIG. 5 is an illustration of the integration outcomes for the pB1011-D1 transgene within the CACNA1A gene.
Figure 6:
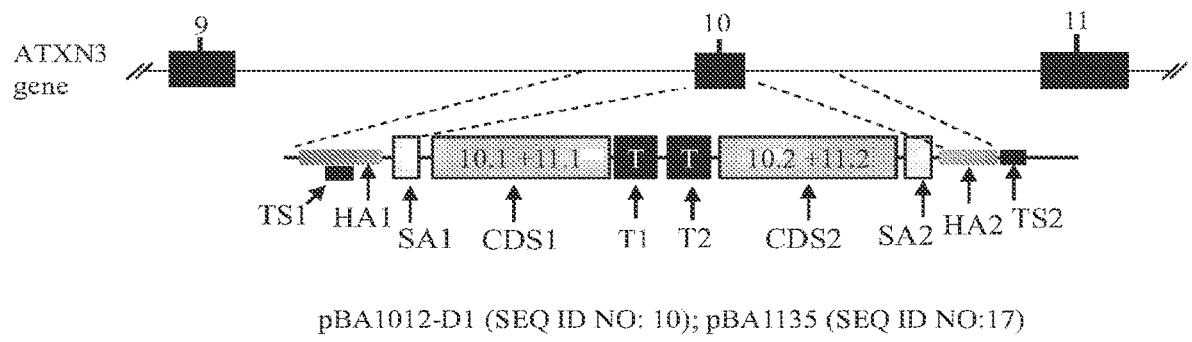
FIG. 6 is an illustration of exon 9, intron 9, exon 10, intron 10 and exon 11 of the ATXN3 gene. Also shown is the pB1012-D1 transgene for integration in the ATXN3 gene.

Confirmation of the function of the transgene and CRISPR vectors is achieved by transfection of HEK293 cells. HEK293 cells are maintained at 37° C. and 5% CO2 in DMEM high glucose without L-glutamine without sodium pyruvate medium supplemented with 10% fetal bovine serum (FBS) and 1% penicillin-streptomycin (PS) solution 100×. HEK293 cells are transfected with each of the plasmid constructs and combinations thereof using Lipofectamine 3000. Two days post transfection, DNA is extracted and assessed for mutations and targeted insertions within the CACNA1A gene. Nuclease activity is analyzed using the Cel-I assay or by deep sequencing of amplicons comprising the CRISPR/Cas12a target sequence. Successful integration of the transgene is analyzed using PCR (FIG. 5).

Example 3: Targeted Integration of DNA in the ATXN3 Gene

An ATXN3-targeting transgene is designed to replace the 3' end of the ATXN coding sequence (exons 10 and 11). A plasmid is constructed with a transgene designed to integrate WT coding sequence into intron 9 or the start of exon 10 (FIG. 5). The transgene comprises a first homology arm which is homologous to sequence intron 9 (SEQ ID NO:10). The first homology arm also comprises the target site for a Cas12a nuclease and a splice acceptor sequence. The first homology arm is followed by a first coding sequence comprising the ATXN3 exon 10 and 11 and a non-expanded CAG repeat sequence. Following the first coding sequence is a SV40 poly(A) termination sequence. In a tail-to-tail orientation, a second set of functional elements is present. The beginning of the second set of elements comprises a target site for the Cas12a nuclease followed by a second homology arm. The second homology arm harbors 379 bp which is homologous to sequence immediately following the end of exon 10 (i.e., the start of intron 10). This sequence was determined via in silico analysis to have a limited number of potential branch or splice acceptor sequences. Following the second homology arm is a second splice acceptor from carp beta-actin intron 1. Following the splice acceptor is a codon optimized version of the ATXN3 exons 10 and 11 and a bGH poly(A) terminator.

A corresponding Cas12a nuclease is designed to create three double-strand breaks following transfection of the plasmid: i) within intron 9 of the endogenous ATXN3 gene, 2) within the first homology arm in the pBA1012-D1 transgene, and 3) following the second homology arm in the pBA1012-D1 transgene. The target sequence for the Cas12a nuclease is shown in SEQ ID NO:11.

Figure 7:
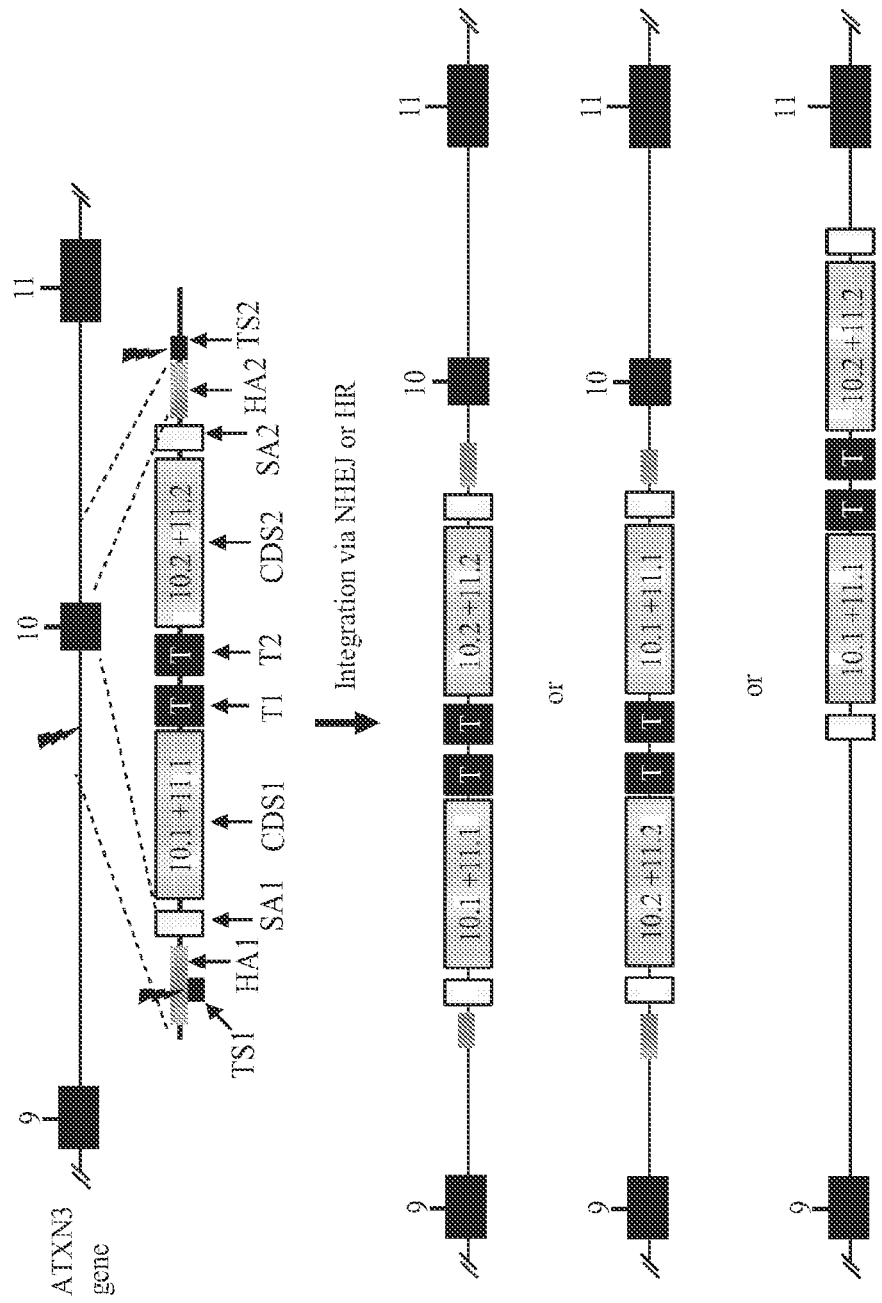
FIG. 7 is an illustration of the integration outcomes for the pB1012-D1 transgene within the ATXN3 gene.

Confirmation of the function of the transgene and CRISPR vectors is achieved by transfection of HEK293 cells. HEK293 cells are maintained at 37° C. and 5% CO2 in DMEM high glucose without L-glutamine without sodium pyruvate medium supplemented with 10% fetal bovine serum (FBS) and 1% penicillin-streptomycin (PS) solution 100×. HEK293 cells are transfected with each of the plasmid constructs and combinations thereof using Lipofectamine 3000. Two days post transfection, DNA is extracted and assessed for mutations and targeted insertions within the ATXN3 gene. Nuclease activity is analyzed using the Cel-I assay or by deep sequencing of amplicons comprising the CRISPR/Cas12a target sequence. Successful integration of the transgene is analyzed using PCR (FIG. 7).

Example 4: Targeted Integration of DNA in the ATXN3 Gene Using Cas12k Transposases An ATXN3-targeting transgene is designed to replace the 3' end of the ATXN coding sequence (exons 10 and 11). A plasmid is constructed with a transgene designed to integrate WT coding sequence into intron 9 or the start of exon 10. The transgene comprises a transposon right end and left end, a first and second splice acceptor, a first and second coding sequence (encoding amino acids from exons 10 and 11), and a first and second terminator. The sequence between the transposon right and left ends is shown in SEQ ID NO: 17.

Plasmids are engineered to express the *Scytonema hofmanni* tnsB, tnsC, tniQ and Cas12k (SEQ ID NO:30) using eukaryotic promoters. A second plasmid is engineered to express the corresponding Cas12k guide RNA (SEQ ID NO:14). The guide RNA targeted sequence CCGCCCGACCTTTCACTTTC (SEQ ID NO:15). The Cas12k transposon plasmids is cotransformed in HEK293 cells with a plasmid harboring the ATXN3-targeting transgene. HEK293 cells are maintained at 37° C. and 5% CO2 in DMEM high glucose without L-glutamine without sodium pyruvate medium supplemented with 10% fetal bovine serum (FBS) and 1% penicillin-streptomycin (PS) solution 100×. HEK293 cells are transfected with each of the plasmid constructs and combinations thereof using Lipofectamine 3000. Two days post transfection, DNA is extracted and assessed for targeted insertions within the ATXN3 gene. Integration of the transgene is analyzed using PCR.

Example 5: Targeted Integration of DNA in the CACNA1A Gene

A CACNA1A-targeting transgene is designed to replace the 3' end of the CACNA1A coding sequence. A plasmid is constructed with a transgene designed to integrate WT coding sequence into intron 46 or the start of exon 47. The transgene comprises a transposon right end and left end, a first and second splice acceptor, a first and second coding sequence (encoding amino acids from exon 47), and a first and second terminator.

Plasmids are engineered to express the *Scytonema hofmanni* tnsB, tnsC, tniQ and Cas12k (SEQ ID NO:30) using eukaryotic promoters. A second plasmid is engineered to express the corresponding Cas12k guide RNA (SEQ ID NO:14). The guide RNA is designed to target sequence CCCGGATCCCGGCTGTGACC (SEQ ID NO: 16). The Cas12k transposon plasmids are cotransformed in HEK293 cells with a plasmid harboring the ATXN3-targeting transgene. HEK293 cells are maintained at 37° C. and 5% CO2 in DMEM high glucose without L-glutamine without sodium pyruvate medium supplemented with 10% fetal bovine serum (FBS) and 1% penicillin-streptomycin (PS) solution 100×. HEK293 cells are transfected with each of the plasmid constructs and combinations thereof using Lipofectamine 3000. Two days post transfection, DNA is extracted and assessed for targeted insertions within the ATXN3 gene. Integration of the transgene is analyzed using PCR.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A vector comprising a transgene comprising from 5' to 3' orientation:
   a first splice acceptor, a first coding sequence, a first terminator, a second terminator reverse complement, a second coding sequence reverse complement, and a second splice acceptor reverse complement,
   wherein the first coding sequence is operably linked to the first splice acceptor and first terminator, and the second coding sequence is operably linked to the second splice acceptor and second terminator, wherein the first and second coding sequences differ in nucleic acid sequence but encode the same amino acids, wherein said amino acids encoded by the first and second coding sequences correspond to amino acids encoded by an endogenous Factor VIII gene, and
   wherein the transgene is equal to or less than 4.7 kb.

2. The vector of claim 1, wherein the first terminator is selected from an SV40 poly(A) or BGH poly(A).

3. The vector of claim 2, wherein the second terminator is selected from an SV40 poly(A) or BGH poly(A).

4. The vector of claim 3, wherein the amino acids encoded by the first and second coding sequences have at least 80% sequence identity to the amino acids encoded by the endogenous Factor VIII gene, wherein the percent sequence identity is calculated by matching amino acids encoded by the first and second coding sequence with amino acids encoded by an endogenous Factor VIII gene and dividing the number of matches by the length of the amino acids encoded by the first and second coding sequence, followed by multiplying the resulting value by 100.

5. The vector of claim 4, wherein the amino acids encoded by the first and second coding sequences have about 98% sequence identity to the amino acids encoded by an endogenous Factor VIII gene.

6. The vector of claim 4, wherein the amino acids encoded by the first and second coding sequences have about 99% sequence identity to the amino acids encoded by an endogenous Factor VIII gene.

7. The vector of claim 4, wherein the vector is a viral vector.

8. The vector of claim 7, wherein the viral vector is selected from the group consisting of an adenovirus vector, an adeno-associated virus vector, and a lentivirus vector.

9. The vector of claim 8, wherein the viral vector is an adeno-associated viral vector.

10. The vector of claim 9, wherein the first splice acceptor comprises a splice acceptor sequence from an intron of the endogenous Factor VIII gene.

* * * * *